(12) United States Patent
de Beer et al.

(10) Patent No.: US 11,634,742 B2
(45) Date of Patent: Apr. 25, 2023

(54) COMPOSITIONS OF DNA MOLECULES, METHODS OF MAKING THEREFOR, AND METHODS OF USE THEREOF

(71) Applicant: Anjarium Biosciences AG, Schlieren (CH)

(72) Inventors: Joel de Beer, Zollikon (CH); Monique Maurer, Zollikon (CH); Nicolas Meier, Thalwil (CH); Lavaniya Kunalingam, Zurich (CH); Marcello Clerici, Zurich (CH)

(73) Assignee: Anjarium Biosciences AG, Schlieren (CH)

( * ) Notice: Subject to any disclaimer, the term of this patent is extended or adjusted under 35 U.S.C. 154(b) by 0 days.

(21) Appl. No.: 17/404,249

(22) Filed: Aug. 17, 2021

(65) Prior Publication Data

US 2022/0098633 A1   Mar. 31, 2022

Related U.S. Application Data

(63) Continuation of application No. PCT/EP2021/070884, filed on Jul. 26, 2021.

(60) Provisional application No. 63/057,179, filed on Jul. 27, 2020, provisional application No. 63/139,486, filed on Jan. 20, 2021.

(51) Int. Cl.
| | |
|---|---|
| *C12P 19/34* | (2006.01) |
| *C12N 15/113* | (2010.01) |
| *C12Q 1/6853* | (2018.01) |
| *A61K 31/713* | (2006.01) |
| *C12N 15/11* | (2006.01) |

(52) U.S. Cl.
CPC ............ *C12P 19/34* (2013.01); *C12N 15/113* (2013.01); *C12Q 1/6853* (2013.01); *A61K 31/713* (2013.01); *C12N 15/111* (2013.01); *C12N 2310/531* (2013.01); *C12N 2750/14171* (2013.01)

(58) Field of Classification Search
CPC ..... C12N 15/86; C12N 15/111; C12N 15/113; C12N 2310/14; C12N 2310/351; C12N 2310/531
USPC .... 435/6.1, 91.1, 91.31, 455, 458; 536/23.1, 536/24.5
See application file for complete search history.

(56) References Cited

U.S. PATENT DOCUMENTS

| | | | |
|---|---|---|---|
| 6,867,028 B2 | 3/2005 | Janulaitis et al. | |
| 7,011,966 B2 | 3/2006 | Samuelson et al. | |
| 7,081,358 B2 | 7/2006 | Heiter et al. | |
| 7,820,424 B2 | 10/2010 | Xu et al. | |
| 7,943,303 B2 | 5/2011 | Xu et al. | |
| 8,709,778 B2 | 4/2014 | Danthinne | |
| 9,169,494 B2 | 10/2015 | Hewitt et al. | |
| 9,598,703 B2 | 3/2017 | Garcia et al. | |
| 9,873,893 B2 | 1/2018 | Sieving et al. | |
| 10,561,610 B2 | 2/2020 | De Beer | |
| 11,484,500 B2 | 11/2022 | De Beer | |
| 2003/0022317 A1 | 1/2003 | Jack et al. | |
| 2014/0107186 A1 | 4/2014 | Garcia et al. | |
| 2014/0271551 A1 | 9/2014 | Hirsch et al. | |
| 2016/0354313 A1 | 12/2016 | De Beer | |
| 2019/0203229 A1 | 7/2019 | Engelhardt et al. | |
| 2019/0284574 A1 | 9/2019 | Bovolenta et al. | |
| 2020/0222324 A1 | 7/2020 | De Beer | |
| 2020/0283794 A1 | 9/2020 | Kotin et al. | |
| 2021/0059953 A1 | 3/2021 | Kotin et al. | |
| 2021/0071197 A1 | 3/2021 | Alkan et al. | |
| 2021/0163986 A1 | 6/2021 | Seregin et al. | |

FOREIGN PATENT DOCUMENTS

| | | |
|---|---|---|
| EP | 2500434 A1 | 9/2012 |
| EP | 2606127 B1 | 3/2019 |
| EP | 2673286 B1 | 7/2019 |
| EP | 3792367 A1 | 3/2021 |
| WO | WO 2006130581 A2 | 12/2006 |
| WO | WO 2010021692 A1 | 2/2010 |
| WO | WO 2010050997 A1 | 5/2010 |
| WO | WO 2011088081 A1 | 7/2011 |
| WO | WO 2012024351 A2 | 2/2012 |
| WO | WO 2012028680 A1 | 3/2012 |
| WO | WO 2012109667 A1 | 8/2012 |
| WO | WO 2012123430 A1 | 9/2012 |
| WO | WO 2014127196 A1 | 8/2014 |
| WO | WO 2014197624 A1 | 12/2014 |
| WO | WO 2015/110957 | 7/2015 |
| WO | WO 2015110957 A2 | 7/2015 |
| WO | WO 2016008291 A1 | 1/2016 |
| WO | WO 2016033338 A1 | 3/2016 |
| WO | WO 2016077687 A1 | 5/2016 |
| WO | WO 2016094783 A1 | 6/2016 |
| WO | WO 2016115503 A1 | 7/2016 |
| WO | WO 2016132129 A1 | 8/2016 |
| WO | WO 2017066579 A1 | 4/2017 |

(Continued)

OTHER PUBLICATIONS

Hardee et al., 2017, "Advances in Non-Viral DNA Vectors for Gene Therapy," Genes, 8(2):65.
International Search Report and Written Opinion dated Jul. 7, 2021 for PCT/EP2021/070884 (14 pages).
Orefice, Nicola Salvatore, 2020, "Development of New Strategies Using Extracellular Vesicles Loaded with Exogenous Nucleic Acid," Pharmaceutics, 12(8):705.
International Search Report and Written Opinion dated Dec. 7, 2021 for PCT/EP2021/070884 (14 pages).
Shi et al., 2013, "An Enzyme-Catalyzed Multistep DNA Refolding Mechanism in Hairpin Telomere Formation," PLOS Biology, 11(1):e1001472.

(Continued)

*Primary Examiner* — Jane J Zara
(74) *Attorney, Agent, or Firm* — Jones Day

(57) ABSTRACT

Provided herein are double strand DNA molecules comprising inverted repeats, expression cassette and one or more restriction sites for nicking endonucleases, the methods of use thereof, and the methods of making therefor.

24 Claims, 18 Drawing Sheets

Specification includes a Sequence Listing.

(56) References Cited

FOREIGN PATENT DOCUMENTS

| | | | |
|---|---|---|---|
| WO | WO 2017127565 A1 | 7/2017 | |
| WO | WO 2017152149 A1 | 9/2017 | |
| WO | WO 2017201258 A1 | 11/2017 | |
| WO | WO 2018004514 A1 | 1/2018 | |
| WO | WO 2018089527 A1 | 5/2018 | |
| WO | WO 2018187552 A1 | 10/2018 | |
| WO | WO 2018191450 A2 | 10/2018 | |
| WO | WO 2018204797 A1 | 11/2018 | |
| WO | WO 2018/222926 | 12/2018 | |
| WO | WO-2019011310 A1 * | 1/2019 | ............ D06F 34/28 |
| WO | WO 2019028306 A2 | 2/2019 | |
| WO | WO 2019032102 A1 | 2/2019 | |
| WO | WO 2019032898 A1 | 2/2019 | |
| WO | WO 2019051255 A1 | 3/2019 | |
| WO | WO 2019051289 A1 | 3/2019 | |
| WO | WO 2019067540 A1 | 4/2019 | |
| WO | WO 2019092145 A1 | 5/2019 | |
| WO | WO 2019092287 A1 | 5/2019 | |
| WO | WO 2019113310 A1 | 6/2019 | |
| WO | WO 2019140353 A1 | 7/2019 | |
| WO | WO 2019141806 A1 | 7/2019 | |
| WO | WO 2019143885 A1 | 7/2019 | |
| WO | WO 2019161059 A1 | 8/2019 | |
| WO | WO 2019165050 A1 | 8/2019 | |
| WO | WO-2019169233 A1 * | 9/2019 | ............ C12N 15/10 |
| WO | WO 2019169233 A1 | 9/2019 | |
| WO | WO 2019200016 A1 | 10/2019 | |
| WO | WO 2019215644 A1 | 11/2019 | |
| WO | WO 2019222329 A1 | 11/2019 | |
| WO | WO 2019226650 A1 | 11/2019 | |
| WO | WO 2019246544 A2 | 12/2019 | |
| WO | WO-2019246544 A2 * | 12/2019 | ............ C12N 15/86 |
| WO | WO 2020018766 A1 | 1/2020 | |
| WO | WO 2020/030661 | 2/2020 | |
| WO | WO 2020033863 A1 | 2/2020 | |
| WO | WO 2020077165 A1 | 4/2020 | |
| WO | WO 2020079580 A1 | 4/2020 | |
| WO | WO 2020086844 A1 | 4/2020 | |
| WO | WO 2020097417 A1 | 5/2020 | |
| WO | WO 2020150143 A2 | 7/2020 | |
| WO | WO 2020154645 A1 | 7/2020 | |
| WO | WO 2020168222 A1 | 8/2020 | |
| WO | WO 2020168234 A1 | 8/2020 | |
| WO | WO 2020181168 A1 | 9/2020 | |
| WO | WO 2020181182 A1 | 9/2020 | |
| WO | WO 2020186150 A2 | 9/2020 | |
| WO | WO 2020186207 A2 | 9/2020 | |
| WO | WO-2020186207 A2 * | 9/2020 | ......... A61K 48/0041 |
| WO | WO 2020198233 A1 | 10/2020 | |
| WO | WO 2020214796 A1 | 10/2020 | |
| WO | WO 2020214797 A1 | 10/2020 | |
| WO | WO 2020214809 A2 | 10/2020 | |
| WO | WO 2020215010 A1 | 10/2020 | |
| WO | WO 2020219941 A1 | 10/2020 | |
| WO | WO 2020219990 A1 | 10/2020 | |
| WO | WO 2020236815 A1 | 11/2020 | |
| WO | WO 2020257590 A1 | 12/2020 | |
| WO | WO 2021003195 A1 | 1/2021 | |
| WO | WO 2021011840 A1 | 1/2021 | |
| WO | WO 2021011842 A1 | 1/2021 | |
| WO | WO 2021016075 A1 | 1/2021 | |
| WO | WO 2021030312 A1 | 2/2021 | |
| WO | WO 2021030678 A1 | 2/2021 | |
| WO | WO 2021030701 A1 | 2/2021 | |
| WO | WO 2021046265 A1 | 3/2021 | |
| WO | WO 2021048366 A1 | 3/2021 | |
| WO | WO 2021067448 A1 | 4/2021 | |
| WO | WO 2021072201 A1 | 4/2021 | |
| WO | WO 2021076566 A1 | 4/2021 | |
| WO | WO 2021076634 A | 4/2021 | |
| WO | WO 2021102182 A1 | 5/2021 | |
| WO | WO 2021102390 A1 | 5/2021 | |
| WO | WO 2021102411 A1 | 5/2021 | |
| WO | WO 2021108530 A1 | 6/2021 | |
| WO | WO 2022/023284 | 2/2022 | |

OTHER PUBLICATIONS

Hsu et al., Sep. 2013, DNA Targeting Specificity of RNA-Guided Cas9 Nucleases, Nature Biotechnology, 31(9), pp. 827-832.

Fuste et al., Jan. 2010, Mitochondrial RNA Polymerase Is Needed for Activation of the Origin of Light-Strand DNA Replication, Molecular Cell, 37, pp. 67-78.

Shen et al., 2019, A Nucleus-Targeting DNA Aptamer for Dead Cell Indication, ACS Sensors, 4, pp. 1612-1618.

Gleditzsch et al., Apr. 2019, PAM Identification by CRISPR-Cas Effector Complexes: Diversified Mechanisms and Structures, RNA Biology, 16(4): pp. 504-517.

Leenay et al., Apr. 2016, Identifying and Visualizing Functional PAM Diversity Across CRISPR-Cas Systems, Molecular Cell, 62(1), pp. 137-147.

Kluge et al., 2018, Inducible Promoters and Functional Genomic Approaches for the Genetic Engineering of Filamentous Fungi, Applied Microbiology and Biotechnology, 102, pp. 6357-6372.

Nordin et al., 2019, Tangential Flow Filtration With or Without Subsequent Bind-Elute Size Exclusion Chromatography for Purification of Extracellular Vesicles, Ch. 18 in Methods in Molecular Biology, vol. 1953, Humana Press, New York, NY, pp. 287-299.

Xu et al., 2019, Endonuclease Activity Inhibition of the NS1 Protein of Parvovirus B19 as a Novel Target for Antiviral Drug Development, Antimicrobial Agents and Chemotherapy, 63(3), e01879-18.

Song et al., 2020, Adeno-Associated Virus Vector Mobilization: Risk Versus Reality, Human Gene Therapy, 31(19-20), pp. 1054-1067.

Grieger et al., 2006, Production and Characterization of Adeno-Associated Viral Vectors, Nature Protocols, 1(3), pp. 1412-1428.

International Search Report and Written Opinion dated Aug. 24, 2022 for PCT/EP2022/060306 (16 pages).

Lin et al., 2001 "Inverted repeats as genetic elements for promoting DNA inverted duplication: implications in gene amplification," Nucleic Acids Research, 29(17):3529-3538.

McCarty, D, 2008, "Self-complementary AAV Vectors; Advances and Applications," Molecular Therapy, 16(10):1648-1656.

Third Party Observation dated Nov. 25, 2022 for PCT/EP2021/070884 (6 pages).

* cited by examiner

Structural Elements
1. Branched Hairpin
2. Bulge Loop
3. Internal Loop
4. 3-way Junction
5. Primary Stem
6. Apex

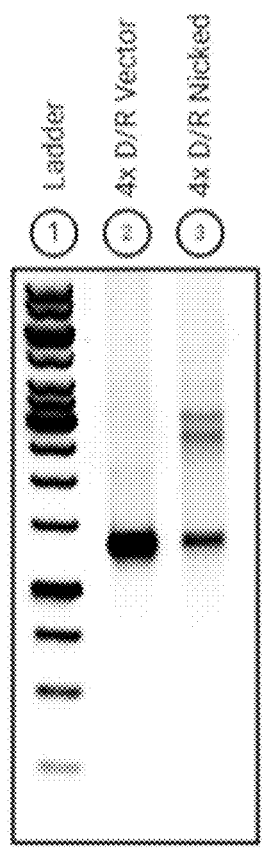
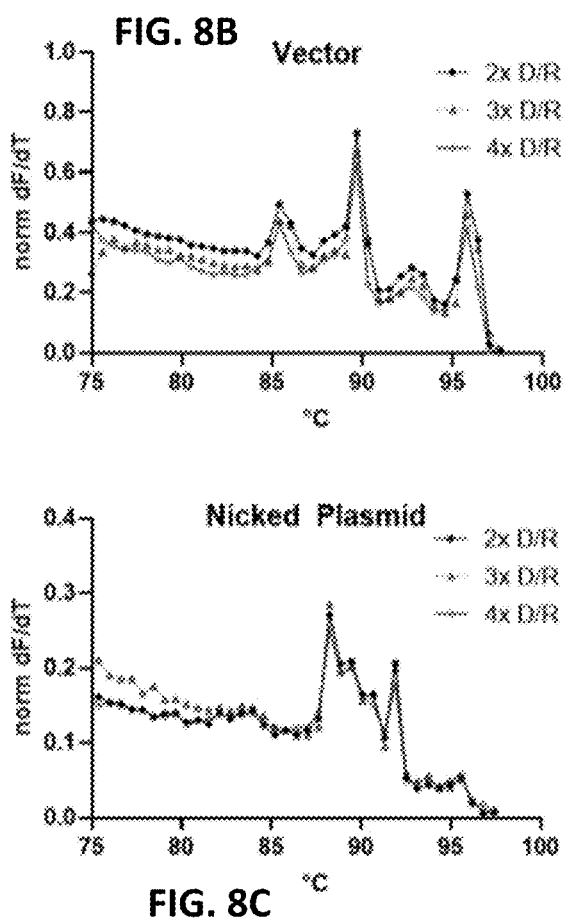
FIG. 8A
FIG. 8B
FIG. 8C
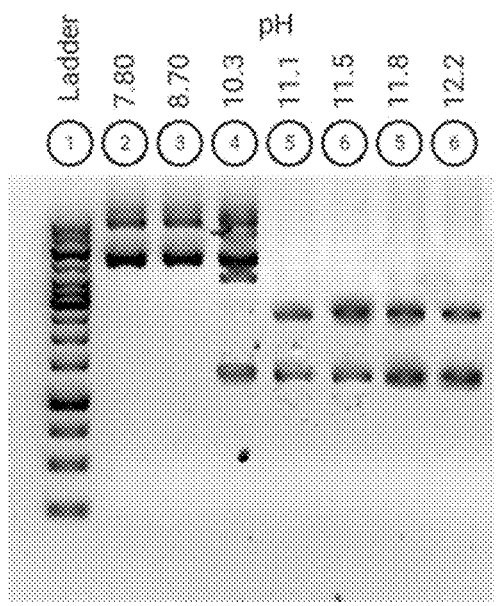
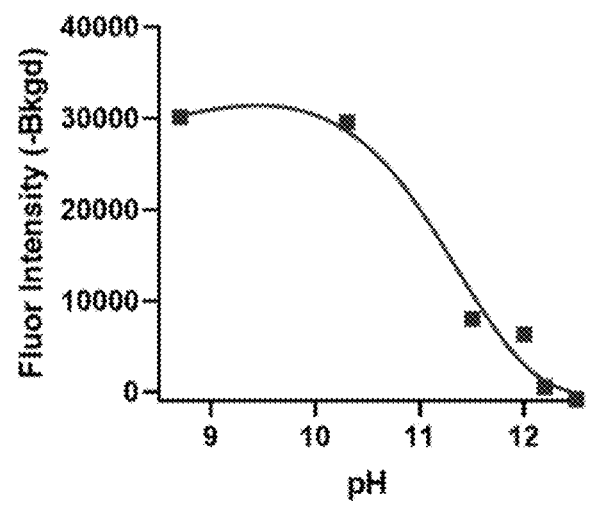
FIG. 9A
FIG. 9B

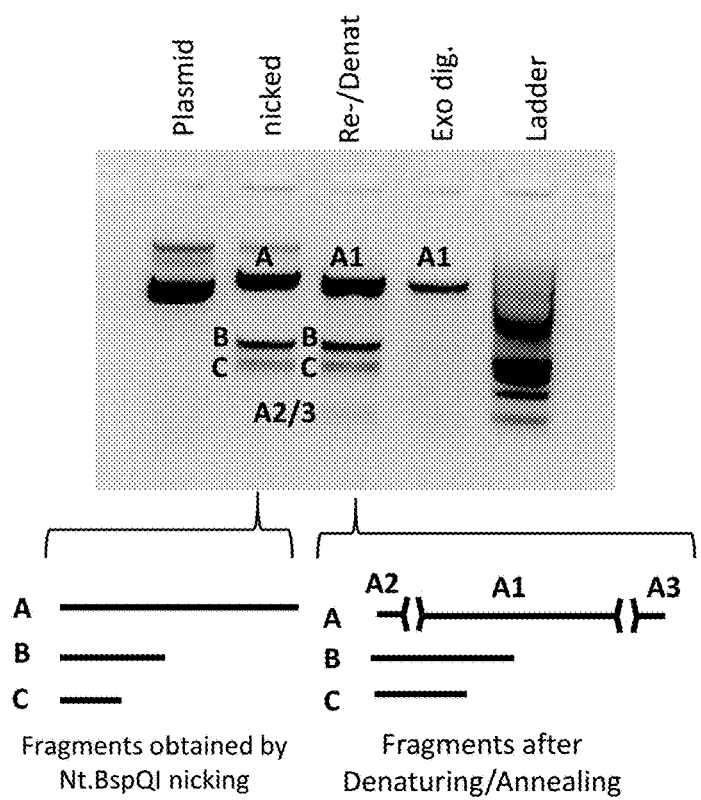# 
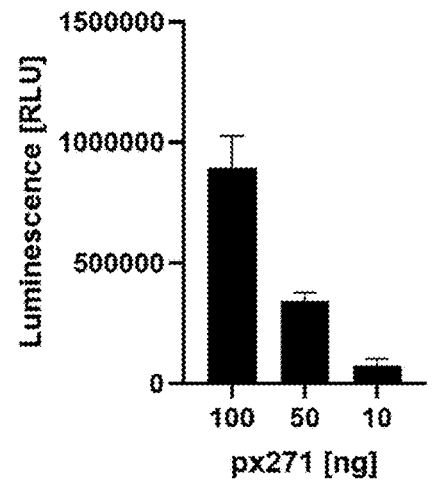
FIG. 25A
FIG. 25B
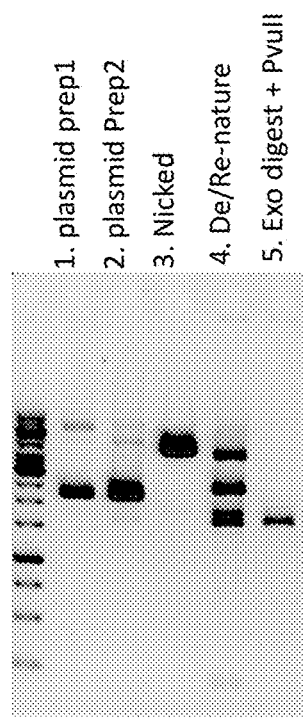
FIG. 26A
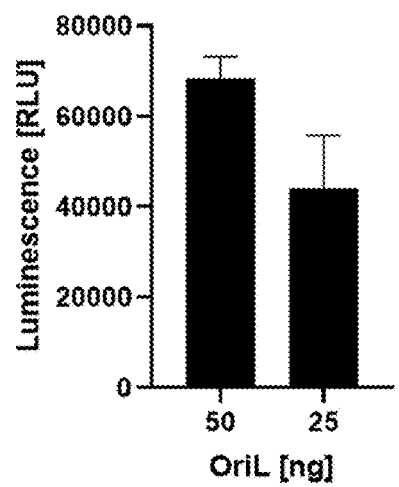
FIG. 26B

COMPOSITIONS OF DNA MOLECULES, METHODS OF MAKING THEREFOR, AND METHODS OF USE THEREOF

PRIORITY

This application is a continuation of International Patent Application No. PCT/EP2021/070884, filed Jul. 26, 2021, which claims the benefit of priority to U.S. Ser. No. 63/057,179 filed Jul. 27, 2020 and U.S. Ser. No. 63/139,486 filed Jan. 20, 2021, each of which is incorporated herein by reference in its entirety.

REFERENCE TO SEQUENCE LISTING SUBMITTED ELECTRONICALLY

This application incorporates by reference in its entirety the Computer Readable Form (CRF) of a Sequence Listing in ASCII text format submitted via EFS-Web. The Sequence Listing text file submitted via EFS-Web is entitled Substitute_Seqlisting_14497-010-999_08-19-21, was created on Aug. 19, 2021 and is 137,559 bytes in size.

1. FIELD

Provided herein are double-stranded DNA molecules comprising inverted repeats, expression cassette and one or more restriction sites for nicking endonucleases, the methods of use thereof, and the methods of making therefor.

2. BACKGROUND

Gene therapy aims to introduce genes into target cells to treat or prevent disease. By supplying a transcription cassette with an active gene product (sometimes referred to as a transgene), the application of gene therapy can improve clinical outcomes, as the gene product can result in a gain of positive function effect, a loss of negative function effect, or another outcome, such as in patients suffering from cancer, can have an oncolytic effect. Delivery and expression of a corrective gene in the patient's target cells can be carried out via numerous methods, including non-viral delivery (e.g. liposomal) or viral delivery methods that include the use engineered viruses and viral gene delivery vectors. Among the available virus-derived vectors, also known as viral particles, (e.g., recombinant retrovirus, recombinant lentivirus, recombinant adenovirus, and the like), AAV systems are gaining popularity as a versatile vector in gene therapy.

However, there are several major deficiencies in using viral particles as a gene delivery vector. One major drawback is the dependency on viral life cycle and viral proteins to package the transcription cassette into the viral particles. As a result, use of viral vectors has been limited in terms of size of transgenes (e.g. less than 150,000 Da protein coding capacity for AAV) or the requirement for specific viral sequences to be present to ensure efficient replication and packaging (e.g. Rep-Binding Element), which can in turn destabilize the expression cassette. Thus, more than one viral particle may be required to deliver large transgenes (e.g., transgenes encoding proteins larger than 150,000 Da, or transgenes longer than about 4.7 Kb). Use of two or more AAV constructs can increase the risk of re-activation of the AAV genome. Furthermore, use of a viral Rep or Nonstructural Protein 1 Binding Element may increase the risk of vector mobilization in the patient.

The second drawback is that viral particles used for gene therapy are often derived from wild-type viruses to which a subset of the population has been exposed during their lifetime. These patients are found to carry neutralizing antibodies which can in turn hinder gene therapy efficacy as further described in Snyder, Richard O., and Philippe Moullier. *Adeno-associated virus: methods and protocols.* Totowa, N.J.: Humana Press, 2011. For the remaining seronegative patients, the capsids of viral vectors are often immunogenic, preventing re-administration of the viral vector therapy to patients should an initial dose not be sufficient or should the therapy wear off.

As such, there is unmet need for non-viral, capsid-free AAV based gene therapies as an alternative to viral particles, particularly therapies that require the delivery of large transgenes. There is also a need for the capsid-free AAV vectors to confer greater stability in cell nuclei, allowing prolonged expression compared to circular plasmid DNA. Additionally, there is unmet need for methods to produce these capsid free vectors in host cells without the co-presences of a plasmid or DNA sequences that encode for the viral replication machinery (e.g. AAV Rep genes), because these viral proteins or the viral DNA sequences encoding for them can contaminate the isolated DNA of a capsid free viral vector. Furthermore, there remains an important unmet need for recombinant DNA vectors with improved production and/or expression properties. There is also an unmet need for DNA-based vectors that do not elicit an anti-viral (e.g. viral capsid, toll like receptor activation, etc.) immune response allow for repeat administration without loss of efficacy (due to e.g., neutralizing antibodies) or loss of transgene-expressing cells.

3. SUMMARY

In one aspect, provided herein is a double-stranded DNA molecule comprising in 5' to 3' direction of the top strand:
  a. a first inverted repeat, wherein a first and a second restriction site for nicking endonuclease are arranged on opposite strands in proximity of the first inverted repeat such that nicking results in a top strand 5' overhang comprising the first inverted repeat or a fragment thereof upon separation of the top from the bottom strand of the first inverted repeat;
  b. an expression cassette; and
  c. a second inverted repeat, wherein a third and a fourth restriction site for nicking endonuclease are arranged on opposite strands in proximity of the second inverted repeat such that nicking results in a top strand 3' overhang comprising the second inverted repeat or a fragment thereof upon separation of the top from the bottom strand of the second inverted repeat.

In certain embodiments of this aspect,
  a. the first nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the first inverted repeat;
  b. the second nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the first inverted repeat;
  c. the third nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the second inverted repeat; and/or
  d. the fourth nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the second inverted repeat;

wherein the first nick and the fourth nick are two resulting nicks on the top strand, with the first nick being the one closer to the 5' end of the top strand and the fourth nick being the one closer to the 3' end of the top strand, and wherein the second nick and the third nick are two resulting nicks on the bottom strand, with the third nick being the one closer to the 5' end of the bottom strand and the second nick being the one closer to the 3' end of the bottom strand.

In one aspect, provided herein is a double-stranded DNA molecule comprising in 5' to 3' direction of the top strand:
 a. a first inverted repeat, wherein a first and a second restriction site for nicking endonuclease are arranged on opposite strands in proximity of the first inverted repeat such that nicking results in a bottom strand 3' overhang comprising the first inverted repeat upon separation of the top from the bottom strand of the first inverted repeat;
 b. an expression cassette; and
 c. a second inverted repeat, wherein a third and a fourth restriction site for nicking endonuclease are arranged on opposite strands in proximity of the second inverted repeat such that nicking results in a bottom strand 5' overhang comprising the second inverted repeat upon separation of the top from the bottom strand of the second inverted repeat.

In certain embodiments of this aspect,
 a. the first nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the first inverted repeat;
 b. the second nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the first inverted repeat;
 c. the third nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the second inverted repeat; and/or
 d. the fourth nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the second inverted repeat;
wherein the first nick and the fourth nick are two resulting nicks on the top strand, with the first nick being the one closer to the 5' end of the top strand and the fourth nick being the one closer to the 3' end of the top strand, and wherein the second nick and the third nick are two resulting nicks on the bottom strand, with the third nick being the one closer to the 5' end of the bottom strand and the second nick being the one closer to the 3' end of the bottom strand.

In one aspect, provided herein is a double-stranded DNA molecule comprising in 5' to 3' direction of the top strand:
 a. a first inverted repeat, wherein a first and a second restriction site for nicking endonuclease are arranged on opposite strands in proximity of the first inverted repeat such that nicking results in a bottom strand 3' overhang comprising the first inverted repeat upon separation of the top from the bottom strand of the first inverted repeat;
 b. an expression cassette; and
 c. a second inverted repeat, wherein a third and a fourth restriction site for nicking endonuclease are arranged on opposite strands in proximity of the second inverted repeat such that nicking results in a top strand 3' overhang comprising the second inverted repeat upon separation of the top from the bottom strand of the second inverted repeat.

In certain embodiments of this aspect,
 a. the first nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the first inverted repeat;
 b. the second nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the first inverted repeat;
 c. the third nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the second inverted repeat; and/or
 d. the fourth nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the second inverted repeat;
wherein the first nick and the fourth nick are two resulting nicks on the top strand, with the first nick being the one closer to the 5' end of the top strand and the fourth nick being the one closer to the 3' end of the top strand, and wherein the second nick and the third nick are two resulting nicks on the bottom strand, with the third nick being the one closer to the 5' end of the bottom strand and the second nick being the one closer to the 3' end of the bottom strand.

In certain embodiments, the first nick, the second nick, third nick, and/or the fourth nick is inside the inverted repeat. In certain embodiments, the first nick, the second nick, the third nick, and/or the fourth nick is outside the inverted repeat.

In certain embodiments, the double-stranded DNA molecule is an isolated DNA molecule.

In certain embodiments, the first, second, third, and fourth restriction sites for nicking endonuclease are all restriction sites for the same nicking endonuclease.

In certain embodiments, the first and the second inverted repeats are the same. In certain embodiments, the first and/or the second inverted repeat is an ITR of a parvovirus. In certain embodiments, the first and/or the second inverted repeat is a modified ITR of a parvovirus. In specific embodiments, the parvovirus is a Dependoparvovirus, a Bocaparvovirus, an Erythroparvovirus, a Protoparvovirus, or a Tetraparvovirus. In specific embodiments, the nucleotide sequence of the modified ITR is at least 50%, 60%, 70%, 80%, 90%, 95%, 98%, or at least 99% identical to the ITR of the parvovirus.

In certain embodiments, the double-stranded DNA molecule is a plasmid.

In specific embodiments, the plasmid further comprises a bacterial origin of replication.

In specific embodiments, the plasmid further comprises a restriction enzyme site in the region 5' to the first inverted repeat and 3' to the second inverted repeat wherein the restriction enzyme site is not present in any of the first inverted repeat, second inverted repeat, and the region between the first and second inverted repeats. In a specific embodiment, the cleavage with the restriction enzyme results in single strand overhangs that do not anneal at detectable levels under conditions that favor annealing of the first and/or second inverted repeat. In specific embodiments, the plasmid further comprises an open reading frame encoding the restriction enzyme. In a specific embodiment, expression of the restriction enzyme is under the control of an inducible promoter.

In one aspect, provided herein is a method for preparing a hairpin-ended DNA, wherein the method comprises:
  a. culturing a host cell comprising the double-stranded DNA molecule described in the previous paragraph under conditions resulting in amplification of the double-stranded DNA molecule;
  b. releasing the double-stranded DNA molecule from the host cell;
  c. incubating the double-stranded DNA molecule with one or more nicking endonuclease recognizing the four restriction sites resulting in four nicks;
  d. denaturing and thereby creating a DNA fragment that comprises the expression cassette and is flanked by the two single strand DNA overhangs;
  e. annealing the single strand DNA overhangs intramolecularly and thereby creating a hairpinned inverted repeat on both ends of the DNA fragment resulting from step 77.d;
  f. incubating the double-stranded DNA molecule or the fragments resulting from step 77.d with the restriction enzyme and thereby cleaving the double-stranded DNA molecule or a fragment of the double-stranded DNA molecule; and
  g. incubating the fragments of the double-stranded DNA molecule with an exonuclease thereby digesting the fragments of the double-stranded DNA molecule except the fragment resulting from step 77.e.

In specific embodiments, the plasmid further comprises a fifth and a sixth restriction site for nicking endonuclease in the region 5' to the first inverted repeat and 3' to the second inverted repeat, wherein the fifth and sixth restriction sites for nicking endonuclease are: a. on opposite strands; and b. create a break in the double stranded DNA molecule such that the single strand overhangs of the break do not anneal at detectable levels inter- or intramolecularly under conditions that favor annealing of the first and/or second inverted repeat. In a specific embodiment, the fifth and the sixth nick are 1, 2, 3, 4, 5, 6, 7, 8, 9, 10, 11, 12, 13, 14, 15, 16, 17, 18, 19, or 20 nucleotides apart. In a specific embodiment, the first, second, third, fourth, fifth, and sixth restriction sites for nicking endonuclease are all target sequences for the same nicking endonuclease. In specific embodiment, the plasmid further comprises an open reading frame encoding a nicking endonuclease that recognizes the first, second, third, fourth, fifth, and/or sixth restriction site for nicking endonuclease. In a specific embodiment, expression of the nicking endonuclease is under the control of an inducible promoter. In certain embodiments, the nicking endonuclease that recognizes the fifth and sixth restriction site for nicking endonuclease Nt. BsmAI; Nt. BtsCI; N. ALwI; N. BstNBI; N. BspD6I; Nb. Mva1269I; Nb. BsrDI; Nt. BtsI; Nt. BsaI; Nt. Bpu10I; Nt. BsmBI; Nb. BbvCI; Nt. BbvCI; or Nt. BspQI.

In one aspect, provided herein is a method for preparing a hairpin-ended DNA, wherein the method comprises:
  a. culturing a host cell comprising the double-stranded DNA molecule described in the previous paragraph under conditions resulting in amplification of the double-stranded DNA molecule;
  b. releasing the double-stranded DNA molecule from the host cell;
  c. incubating the double-stranded DNA molecule with one or more nicking endonuclease recognizing the first, second, third, and fourth restriction sites resulting in four nicks;
  d. denaturing and thereby creating a DNA fragment that comprises the expression cassette and is flanked by the two single strand DNA overhangs;
  e. annealing the single strand DNA overhangs intramolecularly and thereby creating a hairpinned inverted repeat on both ends of the DNA fragment resulting from step 78.d;
  f. incubating the double-stranded DNA molecule or the fragments resulting from step 78.d with one or more nicking endonuclease recognizing the fifth and sixth restriction sites resulting in the break in the double stranded DNA molecule; and
  g. incubating the fragments of the double-stranded DNA molecule with an exonuclease thereby digesting the fragments of the double-stranded DNA molecule except the fragment resulting from step 78.e.

In certain embodiments, one or more of the nicking endonuclease site is a target sequence of an endogenous nicking endonuclease.

In certain embodiments, the nicking endonuclease that recognizes the first, second, third, and/or fourth restriction site for nicking endonuclease is Nt. BsmAI; Nt. BtsCI; N. ALwI; N. BstNBI; N. BspD6I; Nb. Mva1269I; Nb. BsrDI; Nt. BtsI; Nt. BsaI; Nt. Bpu10I; Nt. BsmBI; Nb. BbvCI; Nt. BbvCI; or Nt. BspQI.

In various embodiments, the expression cassette comprises a promoter operatively linked to a transcription unit. In certain embodiments, the transcription unit comprises an open reading frame. In certain embodiments, the expression cassette further comprises a posttranscriptional regulatory element. In certain embodiments, the expression cassette further comprises a polyadenylation and termination signal. In certain embodiments, the size of the expression cassette is at least 4 kb, at least 4.5 kb, at least 5 kb, at least 5.5 kb, at least 6 kb, at least 6.5 kb, at least 7 kb, at least 7.5 kb, at least 8 kb, at least 8.5 kb, at least 9 kb, at least 9.5 kb, or at least 10 kb.

In one aspect, provided herein is a method for preparing a hairpin-ended DNA molecule, wherein the method comprises:
a. culturing a host cell comprising the double-stranded DNA molecule described above under conditions resulting in amplification of the double-stranded DNA molecule;
b. releasing the double-stranded DNA molecule from the host cell;
c. incubating the double-stranded DNA molecule with one or more nicking endonuclease recognizing the four restriction sites resulting in four nicks;
d. denaturing and thereby creating a DNA fragment that comprises the expression cassette and is flanked by the two single strand DNA overhangs;
e. annealing the single strand DNA overhangs intramolecularly and thereby creating a hairpinned inverted repeat on both ends of the DNA fragment resulting from step 76.d.

In certain embodiments of the method for preparing a hairpin-ended DNA molecule described herein, the method further comprises: h. repairing the nicks with a ligase to form a circular DNA.

In certain embodiments of the method for preparing a hairpin-ended DNA molecule described herein, the steps are performed in the order in which they appear in the embodiment.

In certain embodiments of the method for preparing a hairpin-ended DNA molecule described herein, the hairpin-ended DNA consists of two hairpin ends.

In certain embodiments of the method for preparing a hairpin-ended DNA molecule described herein, the hairpin-ended DNA is a viral genome. In specific embodiments, the viral genome is parvovirus genome. In specific embodiments, the parvovirus is a Dependoparvovirus, a Bocaparvovirus, an Erythroparvovirus, a Protoparvovirus, or a Tetraparvovirus.

In one aspect, provided herein is a double-stranded DNA molecule, comprising in 5' to 3' direction of the top strand:
a. a first hairpinned inverted repeat;
b. a nick of the bottom strand;
c. an expression cassette;
d. a nick of the bottom strand; and
e. a second hairpinned inverted repeat.

In one aspect, provided herein is a double-stranded DNA molecule, comprising in 5' to 3' direction of the top strand:
a. a first hairpinned inverted repeat;
b. a nick of the top strand;
c. an expression cassette;
d. a nick of the top strand; and
e. a second hairpinned inverted repeat.

In one aspect, provided herein is a double-stranded DNA molecule, comprising in 5' to 3' direction of the top strand:
a. a first hairpinned inverted repeat;
b. a nick of the bottom strand;
c. an expression cassette;
d. a nick of the top strand; and
e. a second hairpinned inverted repeat.

In one aspect, provided herein is a double-stranded DNA molecule, comprising in 5' to 3' direction of the top strand:
a. a first hairpinned inverted repeat;
b. a nick of the top strand;
c. an expression cassette;
d. a nick of the bottom strand; and
e. a second hairpinned inverted repeat.

In certain embodiments, the double-stranded DNA molecule is an isolated DNA molecule.

In certain embodiments, the first and/or the second inverted repeat is the ITR of a parvovirus. In certain embodiments, the first and the second inverted repeats are the same. In certain embodiments, the first and/or the second inverted repeat is a modified ITR of a parvovirus. In specific embodiments, the parvovirus is a Dependoparvovirus, a Bocaparvovirus, an Erythroparvovirus, a Protoparvovirus, or a Tetraparvovirus. In specific embodiments, the nucleotide sequence of the modified ITR is at least 50%, 60%, 70%, 80%, 90%, 95%, 98%, or at least 99% identical to the ITR of the parvovirus.

In various embodiments, the expression cassette comprises a promoter operatively linked to a transcription unit. In certain embodiments, the transcription unit comprises an open reading frame. In certain embodiments, the expression cassette further comprises a posttranscriptional regulatory element. In certain embodiments, the expression cassette further comprises a polyadenylation and termination signal. In certain embodiments, the size of the expression cassette is at least 4 kb, at least 4.5 kb, at least 5 kb, at least 5.5 kb, at least 6 kb, at least 6.5 kb, at least 7 kb, at least 7.5 kb, at least 8 kb, at least 8.5 kb, at least 9 kb, at least 9.5 kb, or at least 10 kb.

In certain embodiments, the double-stranded DNA molecule is protected from an exonuclease. In specific embodiments, the exonuclease is RecBCD exonuclease.

In certain embodiments, the double-stranded DNA molecule lacks at least one replication-associated protein binding sequence ("RABS"). In certain embodiments, the double-stranded DNA molecule lacks a replication-associated protein ("RAP") encoding sequence. In certain embodiments, the double-stranded DNA molecule lacks a viral capsid protein encoding sequence. In specific embodiments, the first inverted repeat lacks at least one RABS. In specific embodiments, the second inverted repeat lacks at least one RABS. In specific embodiments, the DNA sequence between the ITR closing base pair of the first inverted repeat and the ITR closing base pair of the second inverted repeat lacks at least one RABS. In specific embodiments, the first inverted repeat lacks at least one RABS and the second inverted repeat lacks at least one RABS.

In certain embodiments, the double-stranded DNA molecule lacks a terminal resolution site (TRS). In specific embodiments, the first inverted repeat lacks a TRS. In specific embodiments, the second inverted repeat lacks a TRS. In specific embodiments, the DNA sequence between the ITR closing base pair of the first inverted repeat and the ITR closing base pair of the second inverted repeat lacks a TRS. In specific embodiments, the first inverted repeat lacks a TRS and the second inverted repeat lacks a TRS.

In certain embodiments, the mobilization risk of the double-stranded DNA molecule when administered to a host is lower than control DNA molecules with the at least one RABS and/or with the TRS by 100%, 95%, 90%, 85%, 80%, 75%, 70%, 65%, 60%, 55%, or 50%.

In certain embodiments, wherein the double-stranded DNA molecule lacks a TRS, the mobilization risk of the double-stranded DNA molecule when administered to a host is lower than control DNA molecules with the TRS by 100%, 95%, 90%, 85%, 80%, 75%, 70%, 65%, 60%, 55%, or 50%.

In certain embodiments, wherein the double-stranded DNA molecule lacks at least one RABS and lacks a TRS, the mobilization risk of the double-stranded DNA molecule when administered to a host is lower than control DNA molecules with the at least one RABS and the TRS by 100%, 95%, 90%, 85%, 80%, 75%, 70%, 65%, 60%, 55%, or 50%.

In one aspect, provided herein are isolated double-stranded DNA molecule described herein, wherein the isolated double-stranded DNA molecules are free of fragments of the double-stranded DNA molecule.

In one aspect, provided herein are isolated double-stranded DNA molecules described herein, wherein fragments of the double-stranded DNA molecules are no more than 1%, 2%, 3%, 4%, 5%, 6%, 7%, 8%, 9%, or 10% of the isolated double-stranded DNA molecules.

In one aspect, provided herein are isolated double-stranded DNA molecules described herein, wherein the isolated double-stranded DNA molecules are free of nucleic acid contaminants that are not fragments of the double-stranded DNA molecules.

In one aspect, provided herein are isolated double-stranded DNA molecules described herein, wherein nucleic acid contaminants that are not fragments of the double-stranded DNA molecules are less than 1%, 2%, 3%, 4%, 5%, 6%, 7%, 8%, 9%, or 10% of the isolated double-stranded DNA molecules.

In one aspect, provided herein are isolated double-stranded DNA molecules described herein, wherein the isolated double-stranded DNA molecules are free of baculoviral DNA.

In one aspect, provided herein are isolated double-stranded DNA molecules described herein, wherein the baculoviral DNA is less than 1%, 2%, 3%, 4%, 5%, 6%, 7%, 8%, 9%, or 10% of the isolated double-stranded DNA molecules.

In one aspect, provided herein is a delivery vehicle comprising the double-stranded DNA molecule described herein. In certain embodiments, the delivery vehicle comprises a hybridosome, a liposome, or a lipid nanoparticle.

3.1 Illustrative Embodiments Set 1

Embodiment 1. A double-stranded DNA molecule comprising in 5' to 3' direction of the top strand:
  a. a first inverted repeat, wherein a first and a second restriction site for nicking endonuclease are arranged on opposite strands in proximity of the first inverted repeat such that nicking results in a top strand 5' overhang comprising the first inverted repeat or a fragment thereof upon separation of the top from the bottom strand of the first inverted repeat;
  b. an expression cassette; and
  c. a second inverted repeat, wherein a third and a fourth restriction site for nicking endonuclease are arranged on opposite strands in proximity of the second inverted repeat such that nicking results in a top strand 3' overhang comprising the second inverted repeat or a fragment thereof upon separation of the top from the bottom strand of the second inverted repeat.

Embodiment 2. A double-stranded DNA molecule comprising in 5' to 3' direction of the top strand:
  a. a first inverted repeat, wherein a first and a second restriction site for nicking endonuclease are arranged on opposite strands in proximity of the first inverted repeat such that nicking results in a bottom strand 3' overhang comprising the first inverted repeat upon separation of the top from the bottom strand of the first inverted repeat;
  b. an expression cassette; and
  c. a second inverted repeat, wherein a third and a fourth restriction site for nicking endonuclease are arranged on opposite strands in proximity of the second inverted repeat such that nicking results in a bottom strand 5' overhang comprising the second inverted repeat upon separation of the top from the bottom strand of the second inverted repeat.

Embodiment 3. A double-stranded DNA molecule comprising in 5' to 3' direction of the top strand:
  a. a first inverted repeat, wherein a first and a second restriction site for nicking endonuclease are arranged on opposite strands in proximity of the first inverted repeat such that nicking results in a top strand 5' overhang comprising the first inverted repeat upon separation of the top from the bottom strand of the first inverted repeat;
  b. an expression cassette; and
  c. a second inverted repeat, wherein a third and a fourth restriction site for nicking endonuclease are arranged on opposite strands in proximity of the second inverted repeat such that nicking results in a bottom strand 5' overhang comprising the second inverted repeat upon separation of the top from the bottom strand of the second inverted repeat.

Embodiment 4. A double-stranded DNA molecule comprising in 5' to 3' direction of the top strand:
  a. a first inverted repeat, wherein a first and a second restriction site for nicking endonuclease are arranged on opposite strands in proximity of the first inverted repeat such that nicking results in a bottom strand 3' overhang comprising the first inverted repeat upon separation of the top from the bottom strand of the first inverted repeat;
  b. an expression cassette; and
  c. a second inverted repeat, wherein a third and a fourth restriction site for nicking endonuclease are arranged on opposite strands in proximity of the second inverted repeat such that nicking results in a top strand 3' overhang comprising the second inverted repeat upon separation of the top from the bottom strand of the second inverted repeat.

Embodiment 5. The double-stranded DNA molecule of any one of embodiments 1 to 4, wherein the double-stranded DNA molecule is an isolated DNA molecule.

Embodiment 6. The double-stranded DNA molecule of any one of embodiments 1 to 5, wherein the first, second, third, and fourth restriction sites for nicking endonuclease are all restriction sites for the same nicking endonuclease.

Embodiment 7. The double-stranded DNA molecule of any one of embodiments 1 to 5, wherein the first and the second inverted repeats are the same.

Embodiment 8. The double-stranded DNA molecule of any one of embodiments 1 to 5, wherein the first and/or the second inverted repeat is an ITR of a parvovirus.

Embodiment 9. The double-stranded DNA molecule of any one of embodiments 1 to 5, wherein the first and/or the second inverted repeat is a modified ITR of a parvovirus.

Embodiment 10. The double-stranded DNA molecule of embodiment 8 or 9, wherein the parvovirus is a Dependoparvovirus, a Bocaparvovirus, an Erythroparvovirus, a Protoparvovirus, or a Tetraparvovirus.

Embodiment 11. The double-stranded DNA molecule of embodiment 9 wherein the nucleotide sequence of the modified ITR is at least 50%, 60%, 70%, 80%, 90%, 95%, 98%, or at least 99% identical to the ITR of the parvovirus.

Embodiment 12. The double-stranded DNA molecule of embodiment 1 or 5, wherein the
- a. the first nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the first inverted repeat;
- b. the second nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the first inverted repeat;
- c. the third nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the second inverted repeat; and/or
- d. the fourth nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the second inverted repeat;

wherein the first nick and the fourth nick are two resulting nicks on the top strand, with the first nick being the one closer to the 5' end of the top strand and the fourth nick being the one closer to the 3' end of the top strand, and wherein the second nick and the third nick are two resulting nicks on the bottom strand, with the third nick being the one closer to the 5' end of the bottom strand and the second nick being the one closer to the 3' end of the bottom strand.

Embodiment 13. The double-stranded DNA molecule of embodiment 2 or 5, wherein the
- a. the first nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the first inverted repeat;
- b. the second nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the first inverted repeat;
- c. the third nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the second inverted repeat; and/or
- d. the fourth nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the second inverted repeat;

wherein the first nick and the fourth nick are two resulting nicks on the top strand, with the first nick being the one closer to the 5' end of the top strand and the fourth nick being the one closer to the 3' end of the top strand, and wherein the second nick and the third nick are two resulting nicks on the bottom strand, with the third nick being the one closer to the 5' end of the bottom strand and the second nick being the one closer to the 3' end of the bottom strand.

Embodiment 14. The double-stranded DNA molecule of embodiment 3 or 5, wherein the
- a. the first nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the first inverted repeat;
- b. the second nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the first inverted repeat;
- c. the third nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the second inverted repeat; and/or
- d. the fourth nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the second inverted repeat;

wherein the first nick and the fourth nick are two resulting nicks on the top strand, with the first nick being the one closer to the 5' end of the top strand and the fourth nick being the one closer to the 3' end of the top strand, and wherein the second nick and the third nick are two resulting nicks on the bottom strand, with the third nick being the one closer to the 5' end of the bottom strand and the second nick being the one closer to the 3' end of the bottom strand.

Embodiment 15. The double-stranded DNA molecule of embodiment 4 or 5, wherein the
- a. the first nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the first inverted repeat;
- b. the second nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the first inverted repeat;
- c. the third nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the second inverted repeat; and/or
- d. the fourth nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the second inverted repeat;

wherein the first nick and the fourth nick are two resulting nicks on the top strand, with the first nick being the one closer to the 5' end of the top strand and the fourth nick being the one closer to the 3' end of the top strand, and wherein the second nick and the third nick are two resulting nicks on the bottom strand, with the third nick being the one closer to the 5' end of the bottom strand and the second nick being the one closer to the 3' end of the bottom strand.

Embodiment 16. The double-stranded DNA molecule of any one of embodiments 12 to 15, wherein the first nick, the second nick, the third nick, and/or the fourth nick is inside the inverted repeat.

Embodiment 17. The double-stranded DNA molecule of any one of embodiments 12 to 15, wherein the first nick, the second nick, the third nick, and/or the fourth nick is outside the inverted repeat.

Embodiment 18. The double-stranded DNA molecule of any one of the preceding embodiments, wherein the double-stranded DNA molecule is a plasmid.

Embodiment 19. The double-stranded DNA molecule of embodiment 18, wherein the plasmid further comprises a bacterial origin of replication.

Embodiment 20. The double-stranded DNA molecule of embodiment 18, wherein the plasmid further comprises a restriction enzyme site in the region 5' to the first inverted repeat and 3' to the second inverted repeat wherein the restriction enzyme site is not present in any of the first inverted repeat, second inverted repeat, and the region between the first and second inverted repeats.

Embodiment 21. The double-stranded DNA molecule of embodiment 20, wherein the cleavage with the restriction enzyme results in single strand overhangs that do not anneal at detectable levels under conditions that favor annealing of the first and/or second inverted repeat.

Embodiment 22. The double-stranded DNA molecule of embodiment 20, wherein the plasmid further comprises an open reading frame encoding the restriction enzyme.

Embodiment 23. The double-stranded DNA molecule of embodiment 22, wherein expression of the restriction enzyme is under the control of an inducible promoter.

Embodiment 24. The double-stranded DNA molecule of embodiment 18, wherein the plasmid further comprises a fifth and a sixth restriction site for nicking endonuclease in the region 5' to the first inverted repeat and 3' to the second inverted repeat, wherein the fifth and sixth restriction sites for nicking endonuclease are:
  a. on opposite strands; and
  b. create a break in the double stranded DNA molecule such that the single strand overhangs of the break do not anneal at detectable levels inter- or intramolecularly under conditions that favor annealing of the first and/or second inverted repeat.

Embodiment 25. The double-stranded DNA molecule of embodiment 24, wherein the fifth and the sixth nick are 1, 2, 3, 4, 5, 6, 7, 8, 9, 10, 11, 12, 13, 14, 15, 16, 17, 18, 19, or 20 nucleotides apart.

Embodiment 26. The double-stranded DNA molecule of embodiment 24, wherein the first, second, third, fourth, fifth, and sixth restriction sites for nicking endonuclease are all target sequences for the same nicking endonuclease.

Embodiment 27. The double-stranded DNA molecule of any one of the preceding embodiments, wherein one or more of the nicking endonuclease site is a target sequence of an endogenous nicking endonuclease.

Embodiment 28. The double-stranded DNA molecule of any one of embodiments 24 to 27, wherein the plasmid further comprises an open reading frame encoding a nicking endonuclease that recognizes the first, second, third, fourth, fifth, and/or sixth restriction site for nicking endonuclease.

Embodiment 29. The double-stranded DNA molecule of embodiment 28, wherein expression of the nicking endonuclease is under the control of an inducible promoter.

Embodiment 30. The double-stranded DNA molecule of any one of embodiment 1 to 29 wherein the nicking endonuclease that recognizes the first, second, third, and/or fourth restriction site for nicking endonuclease is Nt. BsmAI; Nt. BtsCI; N. ALwI; N. BstNBI; N. BspD6I; Nb. Mva1269I; Nb. BsrDI; Nt. BtsI; Nt. BsaI; Nt. Bpu10I; Nt. BsmBI; Nb. BbvCI; Nt. BbvCI; or Nt. BspQI.

Embodiment 31. The double-stranded DNA molecule of embodiment 24 wherein the nicking endonuclease that recognizes the fifth and sixth restriction site for nicking endonuclease Nt. BsmAI; Nt. BtsCI; N. ALwI; N. BstNBI; N. BspD6I; Nb. Mva1269I; Nb. BsrDI; Nt. BtsI; Nt. BsaI; Nt. Bpu10I; Nt. BsmBI; Nb. BbvCI; Nt. BbvCI; or Nt. BspQI.

Embodiment 32. The double-stranded DNA molecule of any one of embodiment 1 to 31, wherein the expression cassette comprises a promoter operatively linked to a transcription unit.

Embodiment 33. The double-stranded DNA molecule of embodiment 32, wherein the transcription unit comprises an open reading frame.

Embodiment 34. The double-stranded DNA molecule of embodiment 32 or 33, wherein the expression cassette further comprises a posttranscriptional regulatory element.

Embodiment 35. The double-stranded DNA molecule of embodiment 32 or 33, wherein the expression cassette further comprises a polyadenylation and termination signal.

Embodiment 36. The double-stranded DNA molecule of any one of embodiments 32 to 35, wherein the size of the expression cassette is at least 4 kb, at least 4.5 kb, at least 5 kb, at least 5.5 kb, at least 6 kb, at least 6.5 kb, at least 7 kb, at least 7.5 kb, at least 8 kb, at least 8.5 kb, at least 9 kb, at least 9.5 kb, or at least 10 kb.

Embodiment 37. A double-stranded DNA molecule, comprising in 5' to 3' direction of the top strand:
  a. a first hairpinned inverted repeat;
  b. a nick of the bottom strand;
  c. an expression cassette;
  d. a nick of the bottom strand; and
  e. a second hairpinned inverted repeat.

Embodiment 38. A double-stranded DNA molecule, comprising in 5' to 3' direction of the top strand:
  a. a first hairpinned inverted repeat;
  b. a nick of the top strand;
  c. an expression cassette;
  d. a nick of the top strand; and
  e. a second hairpinned inverted repeat.

Embodiment 39. A double-stranded DNA molecule, comprising in 5' to 3' direction of the top strand:
  a. a first hairpinned inverted repeat;
  b. a nick of the bottom strand;
  c. an expression cassette;
  d. a nick of the top strand; and
  e. a second hairpinned inverted repeat.

Embodiment 40. A double-stranded DNA molecule, comprising in 5' to 3' direction of the top strand:
  a. a first hairpinned inverted repeat;
  b. a nick of the top strand;
  c. an expression cassette;
  d. a nick of the bottom strand; and
  e. a second hairpinned inverted repeat.

Embodiment 41. The double-stranded DNA molecule of any one of embodiments 37 to 40, which is an isolated DNA molecule.

Embodiment 42. The double-stranded DNA molecule of any one of embodiments 37 to 41, wherein the first and/or the second inverted repeat is the ITR of a parvovirus.

Embodiment 43. The double-stranded DNA molecule of any one of embodiments 37 to 41, wherein the first and the second inverted repeats are the same.

Embodiment 44. The double-stranded DNA molecule of any one of embodiments 37 to 41, wherein the first and/or the second inverted repeat is a modified ITR of a parvovirus.

Embodiment 45. The double-stranded DNA molecule of embodiment 42 or 44, wherein the parvovirus is a Dependoparvovirus, a Bocaparvovirus, an Erythroparvovirus, a Protoparvovirus, or a Tetraparvovirus.

Embodiment 46. The double-stranded DNA molecule of 45, wherein the nucleotide sequence of the modified ITR is at least 50%, 60%, 70%, 80%, 90%, 95%, 98%, or at least 99% identical to the ITR of the parvovirus.

Embodiment 47. The double-stranded DNA molecule of any one of embodiment 37 to 46, wherein the expression cassette comprises a promoter operatively linked to a transcription unit.

Embodiment 48. The double-stranded DNA molecule of embodiment 47, wherein the transcription unit comprises an open reading frame.

Embodiment 49. The double-stranded DNA molecule of embodiment 47 or 48, wherein the expression cassette further comprises a posttranscriptional regulatory element.

Embodiment 50. The double-stranded DNA molecule of embodiment 47 or 48, wherein the expression cassette further comprises a polyadenylation and termination signal.

Embodiment 51. The double-stranded DNA molecule of any one of embodiments 37 to 50, wherein the size of the expression cassette is at least 4 kb, at least 4.5 kb, at least 5 kb, at least 5.5 kb, at least 6 kb, at least 6.5 kb, at least 7 kb, at least 7.5 kb, at least 8 kb, at least 8.5 kb, at least 9 kb, at least 9.5 kb, or at least 10 kb.

Embodiment 52. The double-stranded DNA molecule of any one of embodiments 37 to 51, wherein the double-stranded DNA molecule is protected from an exonuclease.

Embodiment 53. The double-stranded DNA molecule of embodiment 52, wherein the exonuclease is RecBCD exonuclease.

Embodiment 54. The double-stranded DNA molecule of any one of the preceding embodiments, wherein the double-stranded DNA molecule lacks at least one replication-associated protein binding sequence ("RABS").

Embodiment 55. The double-stranded DNA molecule of any one of the preceding embodiments, wherein the double-stranded DNA molecule lacks a replication-associated protein ("RAP") encoding sequence.

Embodiment 56. The double-stranded DNA molecule of any one of the preceding embodiments, wherein the double-stranded DNA molecule lacks a viral capsid protein encoding sequence.

Embodiment 57. The double-stranded DNA molecule of any one of the preceding embodiments, wherein the first inverted repeat lacks at least one RABS.

Embodiment 58. The double-stranded DNA molecule of any one of the preceding embodiments, wherein the second inverted repeat lacks at least one RABS.

Embodiment 59. The double-stranded DNA molecule of any one of the preceding embodiments, wherein the DNA sequence between the ITR closing base pair of the first inverted repeat and the ITR closing base pair of the second inverted repeat lacks at least one RABS.

Embodiment 60. The double-stranded DNA molecule of any one of the preceding embodiments, wherein the first inverted repeat lacks at least one RABS and the second inverted repeat lacks at least one RABS.

Embodiment 61. The double-stranded DNA molecule of any one of the preceding embodiments, wherein the double-stranded DNA molecule lacks a terminal resolution site (TRS).

Embodiment 62. The double-stranded DNA molecule of any one of the preceding embodiments, wherein the first inverted repeat lacks a TRS.

Embodiment 63. The double-stranded DNA molecule of any one of the preceding embodiments, wherein the second inverted repeat lacks a TRS.

Embodiment 64. The double-stranded DNA molecule of any one of the preceding embodiments, wherein the DNA sequence between the ITR closing base pair of the first inverted repeat and the ITR closing base pair of the second inverted repeat lacks a TRS.

Embodiment 65. The double-stranded DNA molecule of any one of the preceding embodiments, wherein the first inverted repeat lacks a TRS and the second inverted repeat lacks a TRS.

Embodiment 66. The double-stranded DNA molecule of any one of embodiments 53 and 56 to 64, wherein the mobilization risk of the double-stranded DNA molecule when administered to a host is lower than control DNA molecules with the at least one RABS and/or with the TRS by 100%, 95%, 90%, 85%, 80%, 75%, 70%, 65%, 60%, 55%, or 50%.

Embodiment 67. The double-stranded DNA molecule of any one of embodiments 53 and 56 to 64, which lacks a TRS, wherein the mobilization risk of the double-stranded DNA molecule when administered to a host is lower than control DNA molecules with the TRS by 100%, 95%, 90%, 85%, 80%, 75%, 70%, 65%, 60%, 55%, or 50%.

Embodiment 68. The double-stranded DNA molecule of any one of embodiments 53 and 56 to 64, which lacks at least one RABS and lacks a TRS, wherein the mobilization risk of the double-stranded DNA molecule when administered to a host is lower than control DNA molecules with the at least one RABS and the TRS by 100%, 95%, 90%, 85%, 80%, 75%, 70%, 65%, 60%, 55%, or 50%.

Embodiment 69. Isolated double-stranded DNA molecules of any one of embodiments 5 to 67, wherein the isolated double-stranded DNA molecules are free of fragments of the double-stranded DNA molecule.

Embodiment 70. Isolated double-stranded DNA molecules of any one of embodiments 5 to 68, wherein fragments of the double-stranded DNA molecules are no more than 1%, 2%, 3%, 4%, 5%, 6%, 7%, 8%, 9%, or 10% of the isolated double-stranded DNA molecules.

Embodiment 71. Isolated double-stranded DNA molecules of any one of embodiments 5 to 69, wherein the isolated double-stranded DNA molecules are free of nucleic acid contaminants that are not fragments of the double-stranded DNA molecules.

Embodiment 72. Isolated double-stranded DNA molecule of any one of embodiments 5 to 70, wherein the nucleic acid contaminants that are not fragments of the double-stranded DNA molecules are less than 1%, 2%, 3%, 4%, 5%, 6%, 7%, 8%, 9%, or 10% of the isolated double-stranded DNA molecules.

Embodiment 73. Isolated double-stranded DNA molecule of any one of embodiments 5 to 71, wherein the isolated double-stranded DNA molecules are free of baculoviral DNA.

Embodiment 74. Isolated double-stranded DNA molecule of any one of embodiments 5 to 72, wherein the baculoviral DNA is less than 1%, 2%, 3%, 4%, 5%, 6%, 7%, 8%, 9%, or 10% of the isolated double-stranded DNA molecules.

Embodiment 75. A delivery vehicle comprising the double-stranded DNA molecule of any one of embodiments 37 to 73.

Embodiment 76. The delivery vehicle of embodiment 74, wherein the delivery vehicle comprises a hybridosome, a liposome, or a lipid nanoparticle.

Embodiment 77. A method for preparing a hairpin-ended DNA molecule, wherein the method comprises:
  a. culturing a host cell comprising the double-stranded DNA molecule of any one of embodiments 1 to 35 under conditions resulting in amplification of the double-stranded DNA molecule;
  b. releasing the double-stranded DNA molecule from the host cell;
  c. incubating the double-stranded DNA molecule with one or more nicking endonuclease recognizing the four restriction sites resulting in four nicks;
  d. denaturing and thereby creating a DNA fragment that comprises the expression cassette and is flanked by the two single strand DNA overhangs;

e. annealing the single strand DNA overhangs intramolecularly and thereby creating a hairpinned inverted repeat on both ends of the DNA fragment resulting from step 76.d.

Embodiment 78. A method for preparing a hairpin-ended DNA, wherein the method comprises:
 a. culturing a host cell comprising the double-stranded DNA molecule of embodiment 20 under conditions resulting in amplification of the double-stranded DNA molecule;
 b. releasing the double-stranded DNA molecule from the host cell;
 c. incubating the double-stranded DNA molecule with one or more nicking endonuclease recognizing the four restriction sites resulting in four nicks;
 d. denaturing and thereby creating a DNA fragment that comprises the expression cassette and is flanked by the two single strand DNA overhangs;
 e. annealing the single strand DNA overhangs intramolecularly and thereby creating a hairpinned inverted repeat on both ends of the DNA fragment resulting from step 77.d;
 f. incubating the double-stranded DNA molecule or the fragments resulting from step 77.d with the restriction enzyme and thereby cleaving the double-stranded DNA molecule or a fragment of the double-stranded DNA molecule; and
 g. incubating the fragments of the double-stranded DNA molecule with an exonuclease thereby digesting the fragments of the double-stranded DNA molecule except the fragment resulting from step 77.e.

Embodiment 79. A method for preparing a hairpin-ended DNA, wherein the method comprises:
 a. culturing a host cell comprising the double-stranded DNA molecule of embodiment 24 under conditions resulting in amplification of the double-stranded DNA molecule;
 b. releasing the double-stranded DNA molecule from the host cell;
 c. incubating the double-stranded DNA molecule with one or more nicking endonuclease recognizing the first, second, third, and fourth restriction sites resulting in four nicks;
 d. denaturing and thereby creating a DNA fragment that comprises the expression cassette and is flanked by the two single strand DNA overhangs;
 e. annealing the single strand DNA overhangs intramolecularly and thereby creating a hairpinned inverted repeat on both ends of the DNA fragment resulting from step 78.d;
 f. incubating the double-stranded DNA molecule or the fragments resulting from step 78.d with one or more nicking endonuclease recognizing the fifth and sixth restriction sites resulting in the break in the double stranded DNA molecule; and
 g. incubating the fragments of the double-stranded DNA molecule with an exonuclease thereby digesting the fragments of the double-stranded DNA molecule except the fragment resulting from step 78.e.

Embodiment 80. The method of embodiment 76, 77, or 78, further comprising: h. repairing the nicks with a ligase to form a circular DNA Embodiment 81. The method of any one of embodiments 76 to 79, wherein the steps are performed in the order in which they appear in the embodiment.

Embodiment 82. The method of any one of embodiments 76 to 80, wherein the hairpin-ended DNA consists of two hairpin ends.

Embodiment 83. The method of any one of embodiments 76 to 81, wherein the hairpin-ended DNA is a viral genome.

Embodiment 84. The method of embodiment 82, wherein the viral genome is parvovirus genome.

Embodiment 85. The method of embodiment 83, wherein the parvovirus is a Dependoparvovirus, a Bocaparvovirus, an Erythroparvovirus, a Protoparvovirus, or a Tetraparvovirus.

3.2 Illustrative Embodiments Set 2

Embodiment 1. A double-stranded DNA molecule comprising in 5' to 3' direction of the top strand:
 a. a first inverted repeat, wherein a first and a second restriction site for nicking endonuclease are arranged on opposite strands in proximity of the first inverted repeat such that nicking results in a top strand 5' overhang comprising the first inverted repeat upon separation of the top from the bottom strand of the first inverted repeat;
 b. an expression cassette; and
 c. a second inverted repeat, wherein a third and a fourth restriction site for nicking endonuclease are arranged on opposite strands in proximity of the second inverted repeat such that nicking results in a top strand 3' overhang comprising the second inverted repeat upon separation of the top from the bottom strand of the second inverted repeat.

Embodiment 2. A double strand DNA molecule comprising in 5' to 3' direction of the top strand:
 a. a first inverted repeat, wherein a first and a second restriction site for nicking endonuclease are arranged on opposite strands in proximity of the first inverted repeat such that nicking results in a bottom strand 3' overhang comprising the first inverted repeat upon separation of the top from the bottom strand of the first inverted repeat;
 b. an expression cassette; and
 c. a second inverted repeat, wherein a third and a fourth restriction site for nicking endonuclease are arranged on opposite strands in proximity of the second inverted repeat such that nicking results in a bottom strand 5' overhang comprising the second inverted repeat upon separation of the top from the bottom strand of the second inverted repeat.

Embodiment 3. A double-stranded DNA molecule comprising in 5' to 3' direction of the top strand:
 a. a first inverted repeat, wherein a first and a second restriction site for nicking endonuclease are arranged on opposite strands in proximity of the first inverted repeat such that nicking results in a top strand 5' overhang comprising the first inverted repeat upon separation of the top from the bottom strand of the first inverted repeat;
 b. an expression cassette; and
 c. a second inverted repeat, wherein a third and a fourth restriction site for nicking endonuclease are arranged on opposite strands in proximity of the second inverted repeat such that nicking results in a bottom strand 5' overhang comprising the second inverted repeat upon separation of the top from the bottom strand of the second inverted repeat.

Embodiment 4. A double strand DNA molecule comprising in 5' to 3' direction of the top strand:
 a. a first inverted repeat, wherein a first and a second restriction site for nicking endonuclease are arranged on opposite strands in proximity of the first inverted repeat such that nicking results in a bottom strand 3' overhang comprising the first inverted repeat upon separation of the top from the bottom strand of the first inverted repeat;

b. an expression cassette; and c. a second inverted repeat, wherein a third and a fourth restriction site for nicking endonuclease are arranged on opposite strands in proximity of the second inverted repeat such that nicking results in a top strand 3' overhang comprising the second inverted repeat upon separation of the top from the bottom strand of the second inverted repeat.

Embodiment 5. The DNA molecule of any one of embodiments 1 to 4, wherein the DNA molecule is an isolated DNA molecule.

Embodiment 6. The DNA molecule of any one of embodiments 1 to 5, wherein the first, second, third, and fourth restriction sites for nicking endonuclease are all restriction sites for the same nicking endonuclease.

Embodiment 7. The DNA molecule of any one of embodiments 1 to 5, wherein the first and the second inverted repeats are the same.

Embodiment 8. The DNA molecule of any one of embodiments 1 to 5, wherein the first and/or the second inverted repeat is an ITR of a parvovirus.

Embodiment 9. The DNA molecule of any one of embodiments 1 to 5, wherein the first and/or the second inverted repeat is a modified ITR of a parvovirus.

Embodiment 10. The DNA molecule of embodiment 8 or 9, wherein the parvovirus is a Dependoparvovirus, a Bocaparvovirus, an Erythroparvovirus, a Protoparvovirus, or a Tetraparvovirus.

Embodiment 11. The DNA molecule of embodiment 9 wherein the nucleotide sequence of the modified ITR is at least 50%, 60%, 70%, 80%, 90%, 95%, 98%, or at least 99% identical to the ITR of the parvovirus.

Embodiment 12. The DNA molecule of embodiment 1 or 5, wherein the
a. the first nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the first inverted repeat;
b. the second nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the first inverted repeat;
c. the third nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the second inverted repeat; and/or
d. the fourth nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the second inverted repeat.

Embodiment 13. The DNA molecule of embodiment 2 or 5, wherein the
a. the first nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the first inverted repeat;
b. the second nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the first inverted repeat;
c. the third nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the second inverted repeat; and/or
d. the fourth nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the second inverted repeat.

Embodiment 14. The DNA molecule of embodiment 3 or 5, wherein the
a. the first nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the first inverted repeat;
b. the second nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the first inverted repeat;
c. the third nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the second inverted repeat; and/or
d. the fourth nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the second inverted repeat.

Embodiment 15. The DNA molecule of embodiment 4 or 5, wherein the
a. the first nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the first inverted repeat;
b. the second nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the first inverted repeat;
c. the third nick is within 1, 2, 3, 4, 5, 6, 7, 8, 9, 10, 11, 12, 13, 14, 15, 16, 17, 18, 19, or 20 nucleotides from the 5' nucleotide of the ITR closing base pair of the second inverted repeat; and/or
d. the fourth nick is within 1, 2, 3, 4, 5, 6, 7, 8, 9, 10, 11, 12, 13, 14, 15, 16, 17, 18, 19, or 20 nucleotides from the 3' nucleotide of the ITR closing base pair of the second inverted repeat.

Embodiment 16. The DNA molecule of any one of embodiments 12 to 15, wherein the nick is inside the inverted repeat.

Embodiment 17. The DNA molecule of any one of embodiments 12 to 15, wherein the nick is outside the inverted repeat.

Embodiment 18. The DNA molecule of any one of the preceding embodiments, wherein the DNA molecule is a plasmid.

Embodiment 19. The DNA molecule of embodiment 18, wherein the plasmid further comprises a bacterial origin of replication.

Embodiment 20. The DNA molecule of embodiment 18, wherein the plasmid further comprises a restriction enzyme site in the region 5' to the first inverted repeat and 3' to the second inverted repeat wherein the restriction enzyme site is not present in any of the first inverted repeat, second inverted repeat, and the region between the first and second inverted repeats.

Embodiment 21. The DNA molecule of embodiment 20, wherein the cleavage with the restriction enzyme results in single strand overhangs that do not anneal at detectable levels under conditions that favor annealing of the first and/or second inverted repeat.

Embodiment 22. The DNA molecule of embodiment 20, wherein the plasmid further comprises an open reading frame encoding the restriction enzyme.

Embodiment 23. The DNA molecule of embodiment 22, wherein expression of the restriction enzyme is under the control of an inducible promoter.

Embodiment 24. The DNA molecule of embodiment 18, wherein the plasmid further comprises a fifth and a sixth restriction site for nicking endonuclease in the region 5' to the first inverted repeat and 3' to the second inverted repeat, wherein the fifth and sixth restriction sites for nicking endonuclease are:
  a. on opposite strands; and
  b. create a break in the double stranded DNA molecule such that the single strand overhangs of the break do not anneal at detectable levels inter- or intramolecularly under conditions that favor annealing of the first and/or second inverted repeat.

Embodiment 25. The DNA molecule of embodiment 24, wherein the fifth and the sixth nick are 1, 2, 3, 4, 5, 6, 7, 8, 9, 10, 11, 12, 13, 14, 15, 16, 17, 18, 19, or 20 nucleotides apart.

Embodiment 26. The DNA molecule of embodiment 24, wherein the first, second, third, fourth, fifth, and sixth restriction sites for nicking endonuclease are all target sequences for the same nicking endonuclease.

Embodiment 27. The DNA molecule of any one of the preceding embodiments, wherein one or more of the nicking endonuclease site is a target sequence of an endogenous nicking endonuclease.

Embodiment 28. The DNA molecule of any one of embodiments 24 to 27, wherein the plasmid further comprises an open reading frame encoding a nicking endonuclease that recognizes the first, second, third, fourth, fifth, and/or sixth restriction site for nicking endonuclease.

Embodiment 29. The DNA molecule of embodiment 28, wherein expression of the nicking endonuclease is under the control of an inducible promoter.

Embodiment 30. The DNA molecule of any one of embodiment 1 to 29 wherein the nicking endonuclease that recognizes the first, second, third, and/or fourth restriction site for nicking endonuclease is Nt. BsmAI; Nt. BtsCI; N. ALwI; N. BstNBI; N. BspD6I; Nb. Mva1269I; Nb. BsrDI; Nt. BtsI; Nt. BsaI; Nt. Bpu10I; Nt. BsmBI; Nb. BbvCI; Nt. BbvCI; or Nt. BspQI.

Embodiment 31. The DNA molecule of embodiment 24 wherein the nicking endonuclease that recognizes the fifth and sixth restriction site for nicking endonuclease Nt. BsmAI; Nt. BtsCI; N. ALwI; N. BstNBI; N. BspD6I; Nb. Mva1269I; Nb. BsrDI; Nt. BtsI; Nt. BsaI; Nt. Bpu10I; Nt. BsmBI; Nb. BbvCI; Nt. BbvCI; or Nt. BspQI.

Embodiment 32. The DNA molecule of any one of embodiment 1 to 26, wherein the expression cassette comprises a promoter operatively linked to a transcription unit.

Embodiment 33. The DNA molecule of embodiment 32, wherein the transcription unit comprises an open reading frame.

Embodiment 34. The DNA molecule of embodiment 32 or 33, wherein the expression cassette further comprises a posttranscriptional regulatory element.

Embodiment 35. The DNA molecule of embodiment 32 or 33, wherein the expression cassette further comprises a polyadenylation and termination signal.

Embodiment 36. The DNA molecule of any one of embodiments 32 to 35, wherein the size of the expression cassette is at least 4 kb, at least 4.5 kb, at least 5 kb, at least 5.5 kb, at least 6 kb, at least 6.5 kb, at least 7 kb, at least 7.5 kb, at least 8 kb, at least 8.5 kb, at least 9 kb, at least 9.5 kb, or at least 10 kb.

Embodiment 37. A double strand DNA molecule comprising in 5' to 3' direction of the top strand:
  a. a first hairpinned inverted repeat;
  b. a nick of the bottom strand;
  c. an expression cassette;
  d. a nick of the bottom strand; and
  e. a second hairpinned inverted repeat.

Embodiment 38. A double strand DNA molecule comprising in 5' to 3' direction of the top strand:
  a. a first hairpinned inverted repeat;
  b. a nick of the top strand;
  c. an expression cassette;
  d. a nick of the top strand; and
  e. a second hairpinned inverted repeat.

Embodiment 39. A double strand DNA molecule comprising in 5' to 3' direction of the top strand:
  a. a first hairpinned inverted repeat;
  b. a nick of the bottom strand;
  c. an expression cassette;
  d. a nick of the top strand; and
  e. a second hairpinned inverted repeat.

Embodiment 40. A double strand DNA molecule comprising in 5' to 3' direction of the top strand:
  a. a first hairpinned inverted repeat;
  b. a nick of the top strand;
  c. an expression cassette;
  d. a nick of the bottom strand; and
  e. a second hairpinned inverted repeat.

Embodiment 41. The double strand DNA molecule of any one of embodiments 37 to 40, wherein the double strand DNA molecule is an isolated DNA molecule.

Embodiment 42. The double strand DNA molecule of any one of embodiments 37 to 41, wherein the first and/or the second inverted repeat is the ITR of a parvovirus.

Embodiment 43. The double strand DNA molecule of any one of embodiments 37 to 41, wherein the first and the second inverted repeats are the same.

Embodiment 44. The DNA molecule of any one of embodiments 37 to 41, wherein the first and/or the second inverted repeat is a modified ITR of a parvovirus.

Embodiment 45. The DNA molecule of embodiment 42 or 44, wherein the parvovirus is a Dependoparvovirus, a Bocaparvovirus, an Erythroparvovirus, a Protoparvovirus, or a Tetraparvovirus.

Embodiment 46. The DNA molecule of 45, wherein the nucleotide sequence of the modified ITR is at least 50%, 60%, 70%, 80%, 90%, 95%, 98%, or at least 99% identical to the ITR of the parvovirus.

Embodiment 47. The DNA molecule of any one of embodiment 37 to 46, wherein the expression cassette comprises a promoter operatively linked to a transcription unit.

Embodiment 48. The DNA molecule of embodiment 47, wherein the transcription unit comprises an open reading frame.

Embodiment 49. The DNA molecule of embodiment 47 or 48, wherein the expression cassette further comprises a posttranscriptional regulatory element.

Embodiment 50. The DNA molecule of embodiment 47 or 48, wherein the expression cassette further comprises a polyadenylation and termination signal.

Embodiment 51. The DNA molecule of any one of embodiments 37 to 50, wherein the size of the expression cassette is at least 4 kb, at least 4.5 kb, at least 5 kb, at least 5.5 kb, at least 6 kb, at least 6.5 kb, at least 7 kb, at least 7.5 kb, at least 8 kb, at least 8.5 kb, at least 9 kb, at least 9.5 kb, or at least 10 kb.

Embodiment 52. The DNA molecule of any one of embodiments 37 to 51, wherein the DNA molecule is protected from an exonuclease.

Embodiment 53. The DNA molecule of embodiment 52, wherein the exonuclease is RecBCD exonuclease.

Embodiment 54. The DNA molecule of any one of the preceding embodiments, wherein the DNA molecule lacks replication (Rep) protein binding sites.

Embodiment 55. A delivery vehicle comprising the DNA molecule of any one of embodiments 37 to 51.

Embodiment 56. The delivery vehicle of embodiment 55, wherein the delivery vehicle comprises a hydridosome, a liposome, or a lipid nanoparticle.

Embodiment 57. A method for preparing a hairpin-ended DNA molecule, wherein the method comprises:
    a. culturing a host cell comprising the DNA molecule of any one of embodiments 1 to 35 under conditions resulting in amplification of the DNA molecule;
    b. releasing the DNA molecule from the host cell;
    c. incubating the DNA molecule with one or more nicking endonuclease recognizing the four restriction sites resulting in four nicks;
    d. denaturing and thereby creating a DNA fragment that comprises the expression cassette and is flanked by the two single strand DNA overhangs;
    e. annealing the single strand DNA overhangs intramolecularly and thereby creating a hairpinned inverted repeat on both ends of the DNA fragment resulting from step d.

Embodiment 58. A method for preparing a hairpin-ended DNA, wherein the method comprises:
    a. culturing a host cell comprising the plasmid of embodiment 20 under conditions resulting in amplification of the plasmid;
    b. releasing the plasmid from the host cell;
    c. incubating the DNA molecule with one or more nicking endonuclease recognizing the four restriction sites resulting in four nicks;
    d. denaturing and thereby creating a DNA fragment that comprises the expression cassette and is flanked by the two single strand DNA overhangs;
    e. annealing the single strand DNA overhangs intramolecularly and thereby creating a hairpinned inverted repeat on both ends of the DNA fragment resulting from step d;
    f. incubating the plasmid or the fragments resulting from step d with the restriction enzyme and thereby cleaving the plasmid or a fragment of the plasmid; and
    g. incubating the fragments of the plasmid with an exonuclease thereby digesting the fragments of the plasmid except the fragment resulting from step e.

Embodiment 59. A method for preparing a hairpin-ended DNA, wherein the method comprises:
    a. culturing a host cell comprising the plasmid of embodiment 24 under conditions resulting in amplification of the plasmid;
    b. releasing the plasmid from the host cell;
    c. incubating the DNA molecule with one or more nicking endonuclease recognizing the first, second, third, and fourth restriction sites resulting in four nicks;
    d. denaturing and thereby creating a DNA fragment that comprises the expression cassette and is flanked by the two single strand DNA overhangs;
    e. annealing the single strand DNA overhangs intramolecularly and thereby creating a hairpinned inverted repeat on both ends of the DNA fragment resulting from step d;
    f. incubating the plasmid or the fragments resulting from step d with one or more nicking endonuclease recognizing the fifth and sixth restriction sites resulting in the break in the double stranded DNA molecule; and
    g. incubating the fragments of the plasmid with an exonuclease thereby digesting the fragments of the plasmid except the fragment resulting from step e.

Embodiment 60. The method of embodiment 57, 58, or 59, further comprising: h. repairing the nicks with a ligase to form a circular DNA Embodiment 61. The method of any one of embodiments 57 to 60, wherein the steps are performed in the order in which they appear in the embodiment.

Embodiment 62. The method of any one of embodiments 57 to 61, wherein the hairpin-ended DNA consists of two hairpin ends.

Embodiment 63. The method of any one of embodiments 57 to 62, wherein the hairpin-ended DNA is a viral genome.

Embodiment 64. The method of embodiment 63, wherein the viral genome is parvovirus genome.

Embodiment 65. The method of embodiment 64, wherein the parvovirus is a Dependoparvovirus, a Bocaparvovirus, an Erythroparvovirus, a Protoparvovirus, or a Tetraparvovirus.

4. BRIEF DESCRIPTION OF THE DRAWINGS

FIGS. 8A-8C depict multiple re-/de-nature cycles as described in Example 2.

FIGS. 9A-9B depict isothermal denaturing of construct 1 as described in Example 3.

Figure 10:
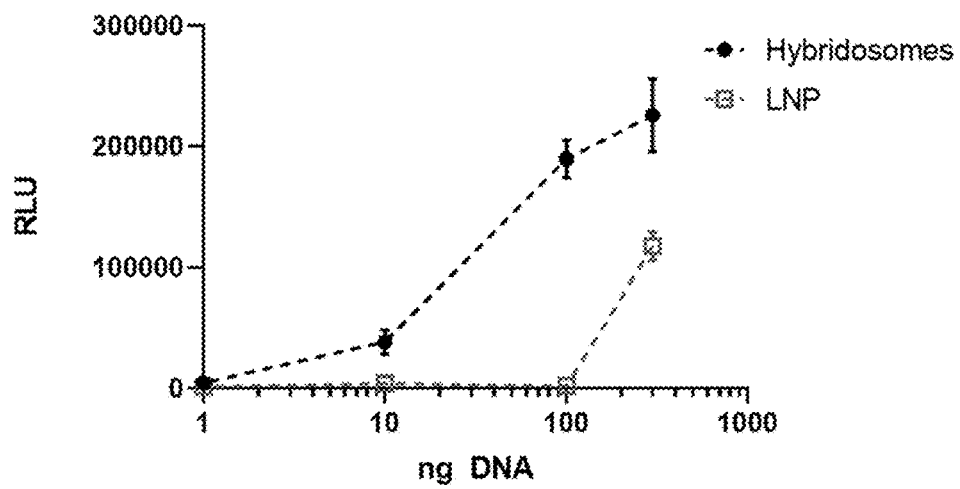

FIG. 10 depicts expression level of luciferase from various DNA vector amounts. Cells were transfected with different concentrations of DNA vector with either Hybridosomes or lipid nanoparticles. Luciferase activity was determined 48 h after transfection.

Figure 11A:
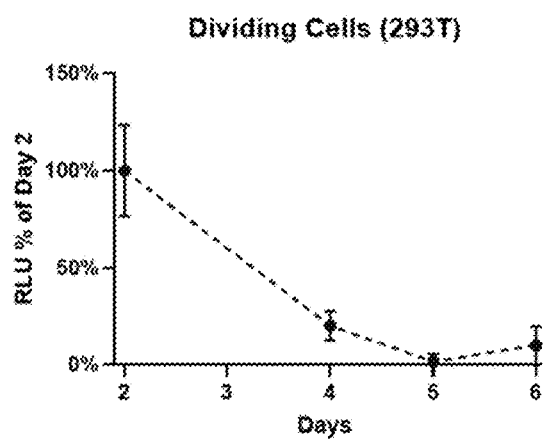
Figure 11B:
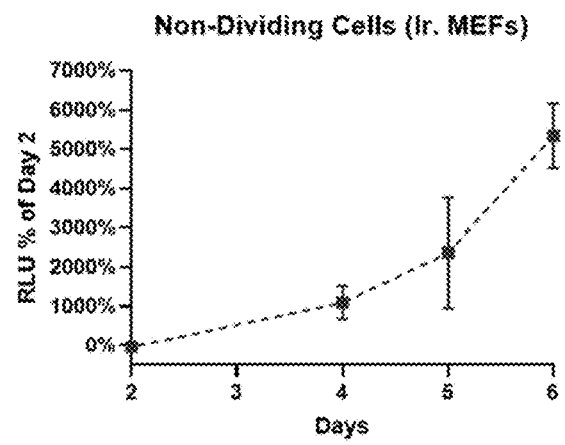
Figure 11C:
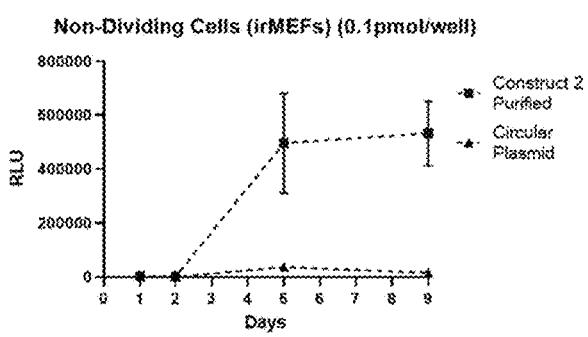
Figure 11D:
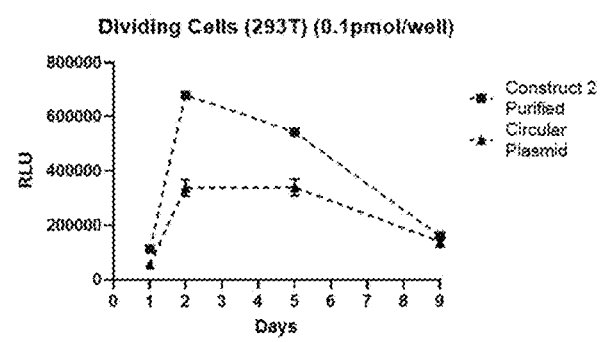

FIGS. 11A-11D depict luciferase expression in dividing and non-dividing cells as described in Section 6.5 (Example 5 Expression in dividing and non-dividing cells). FIGS. 11A and 11B depict expression of non-secreted Turboluc (construct 1) in dividing (11A) and non-dividing (11B) cells. For non-secreted Turboluc (construct 1), luciferase activity peaks in dividing cells on day 2, while in non-dividing cells the expression continues to increase. FIGS. 11C and 11D depict expression of secreted Turboluc (construct 2) in non-dividing (11C) and dividing cells (11D). For secreted Turboluc (construct 2), luciferase activity peaks in dividing cells on day 2, while in non-dividing cells the expression increases and then remains stable over 9 days. As a direct comparison, equimolar amounts of full circular plasmids encoding construct 2 were also transfected and as seen in FIGS. 11C and 11D, generally a lower luciferase activity was recorded, indicating improved nuclear delivery of the purified construct 2 with folded ITRs.

Figure 12:
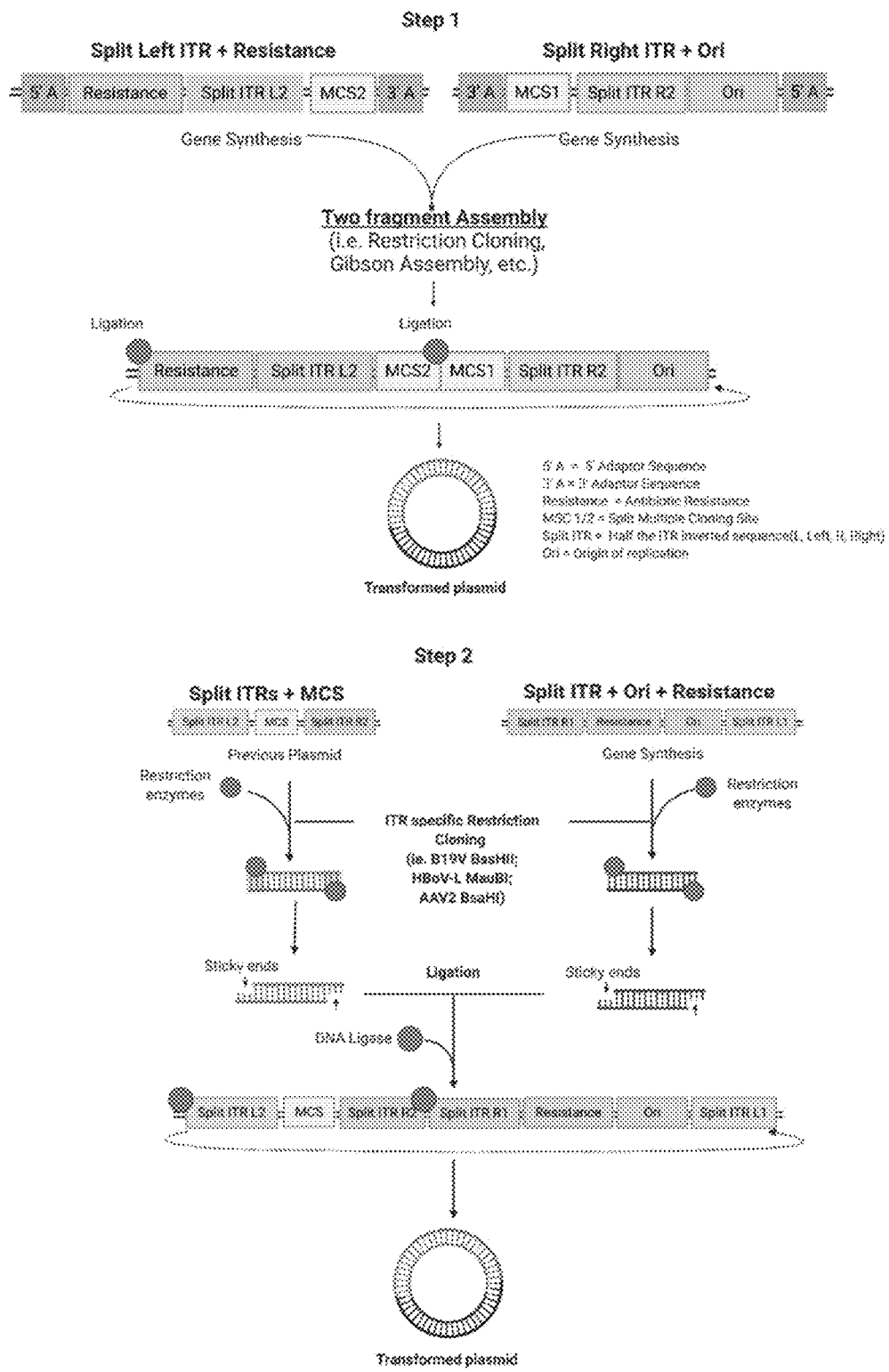

FIG. 12 depicts a vector construction strategy for the de novo synthesis of hairpin encoding plasmids.

Figure 13:
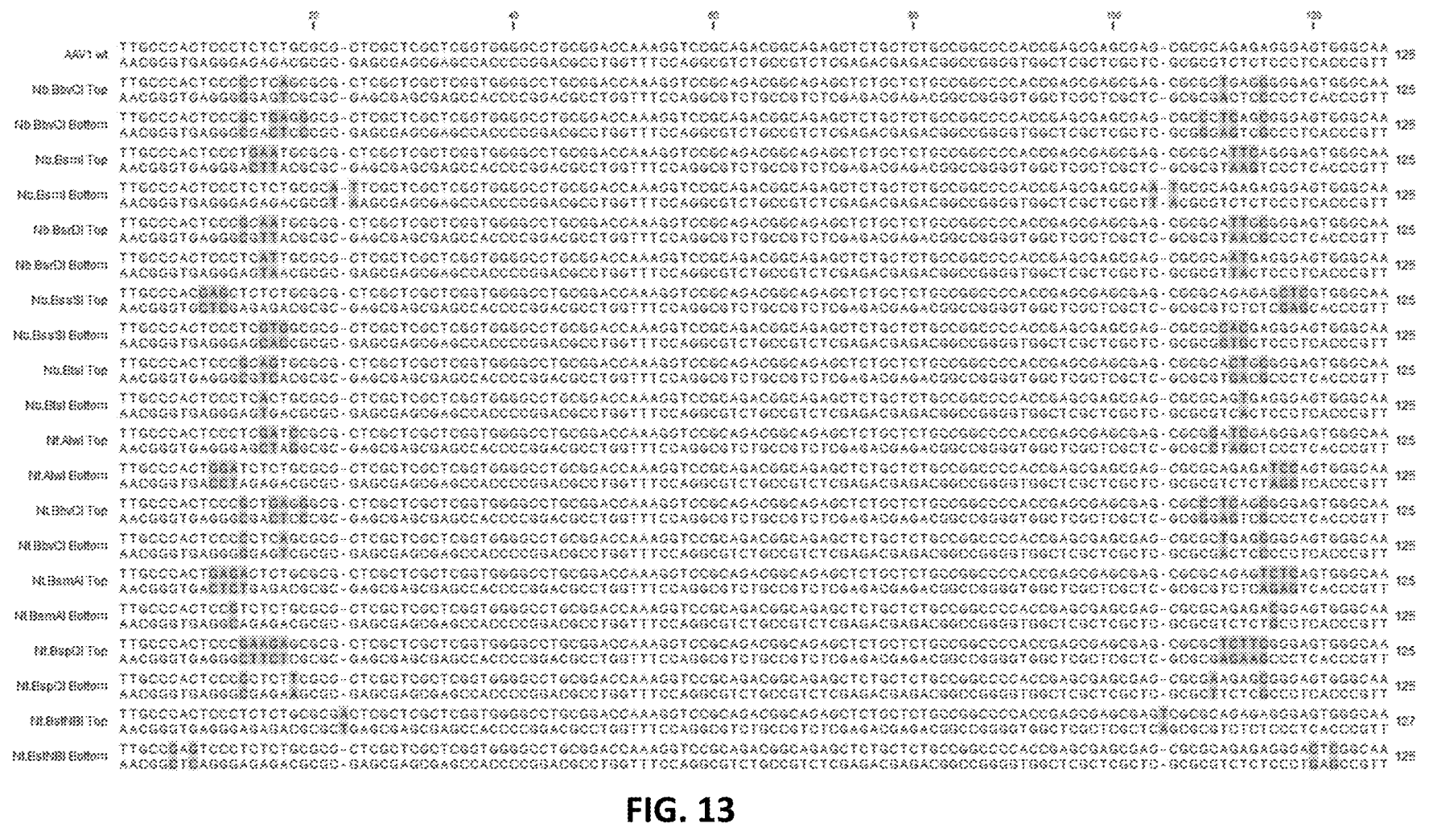

FIG. 13 depicts a sequence alignment of ITRs derived from AAV1 highlighting sequence modifications to generate recognition sites for different nicking endonucleases recognition sites.

Figure 14:
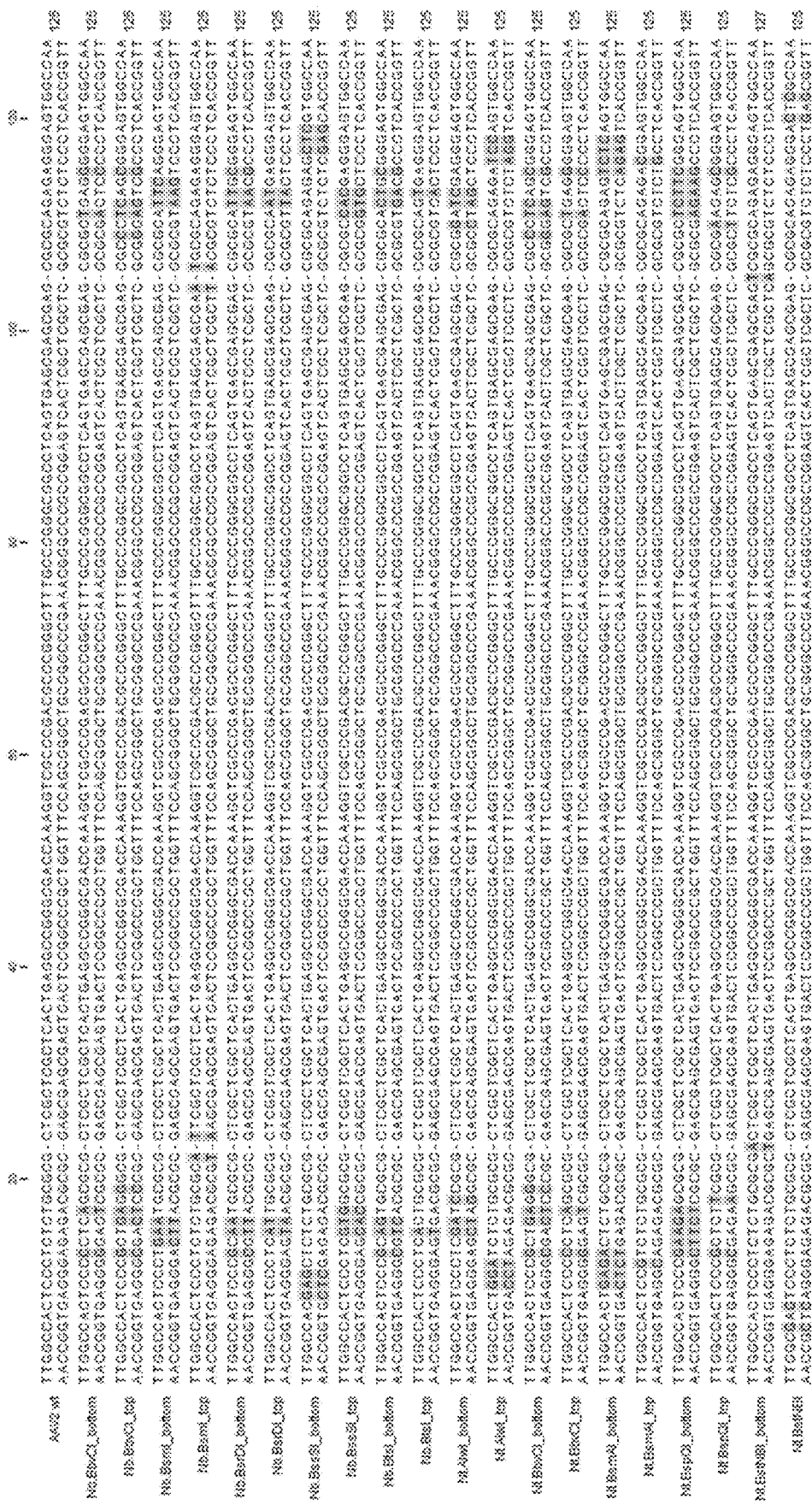

FIG. 14 depicts a sequence alignment of ITRs derived from AAV2 highlighting sequence modifications to generate recognition sites for different nicking endonucleases recognition sites.

Figure 15:
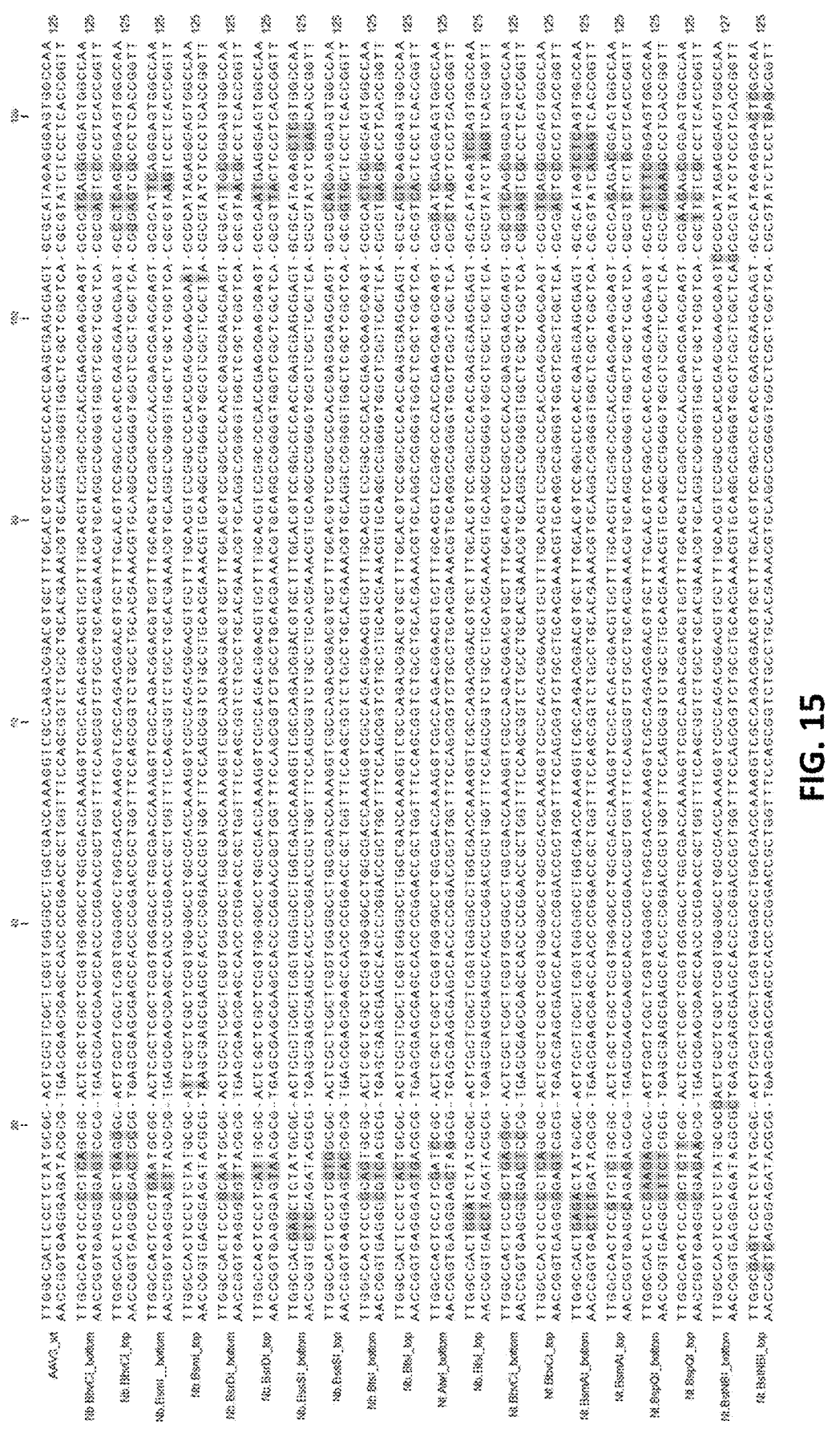

FIG. 15 depicts a sequence alignment of ITRs derived from AAV3 highlighting sequence modifications to generate recognition sites for different nicking endonucleases recognition sites.

Figure 16:
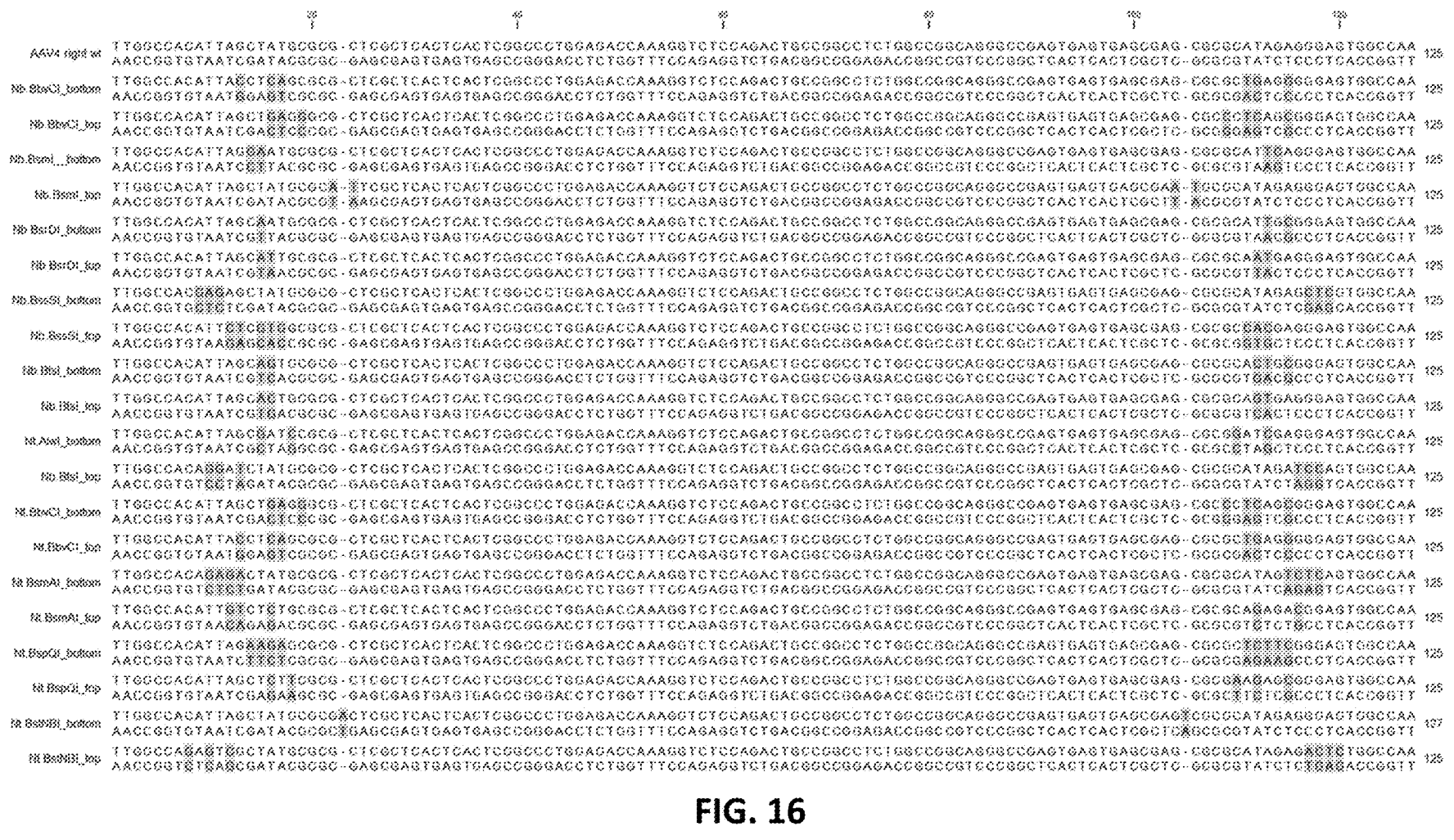

FIG. 16 depicts a sequence alignment of ITRs derived from AAV4 Left highlighting sequence modifications to generate recognition sites for different nicking endonucleases recognition sites.

Figure 17:
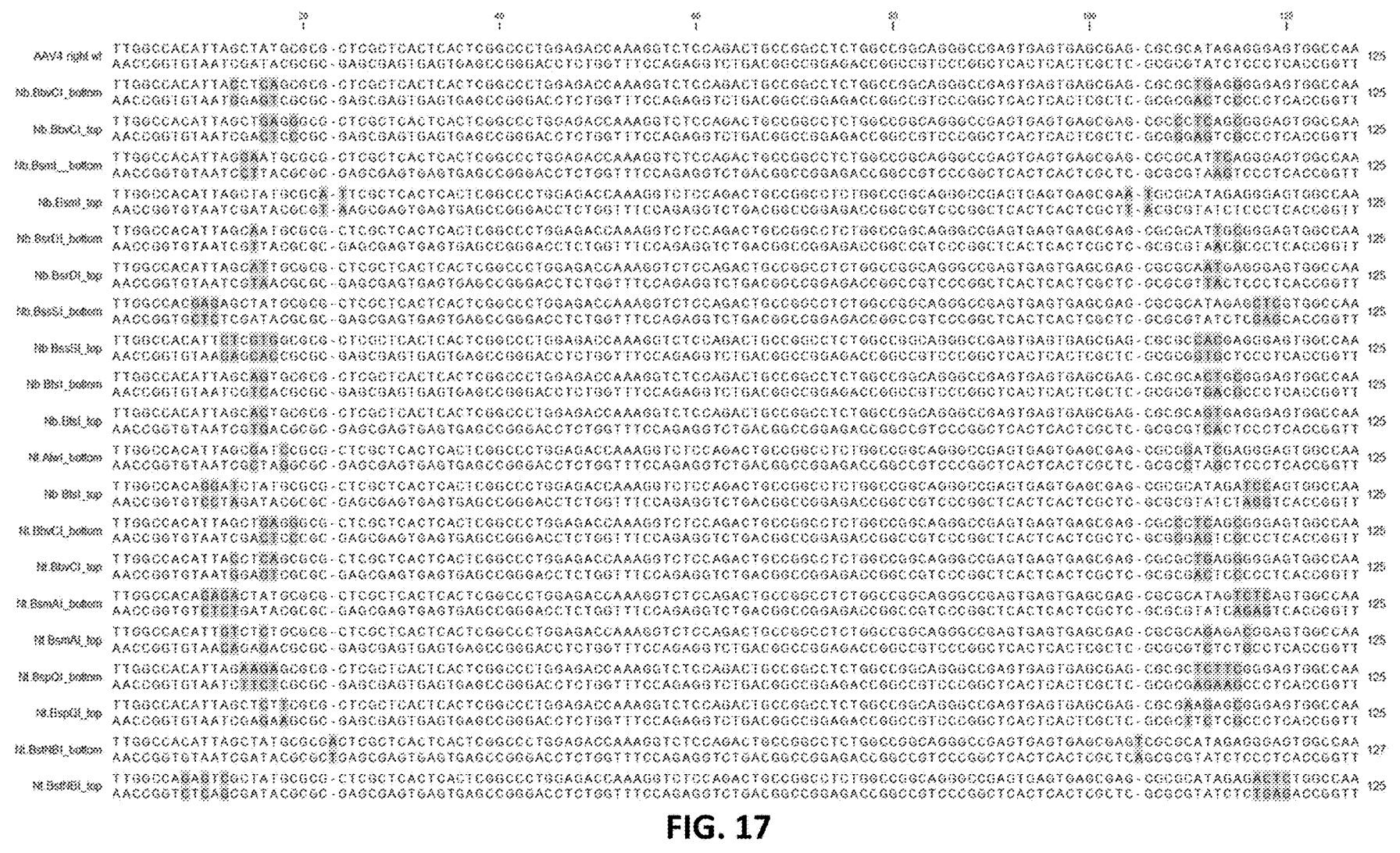

FIG. 17 depicts a sequence alignment of ITRs derived from AAV4 Right highlighting sequence modifications to generate recognition sites for different nicking endonucleases recognition sites.

Figure 18:
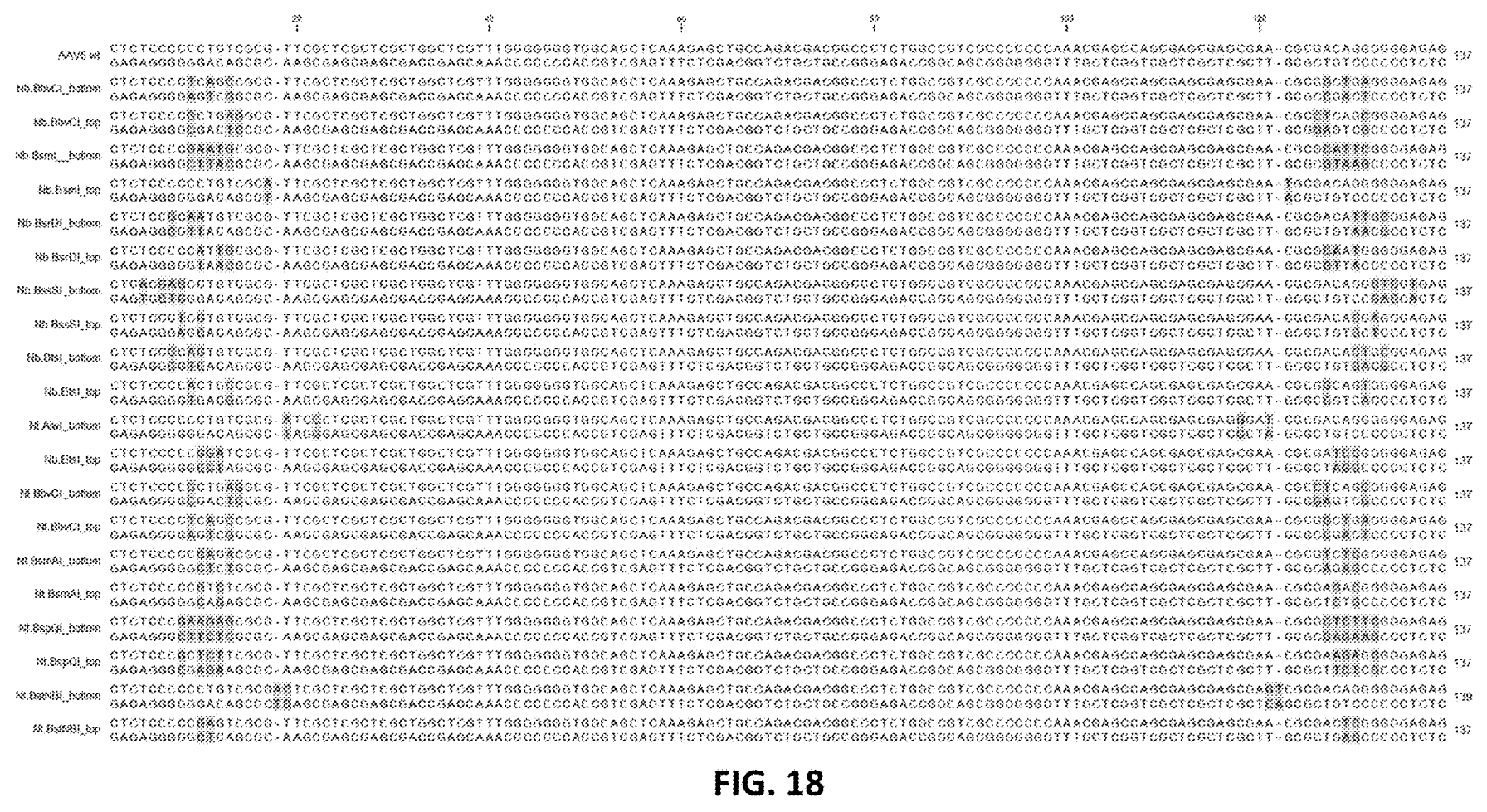

FIG. 18 depicts a sequence alignment of ITRs derived from AAV5 highlighting sequence modifications to generate recognition sites for different nicking endonucleases recognition sites.

Figure 19:
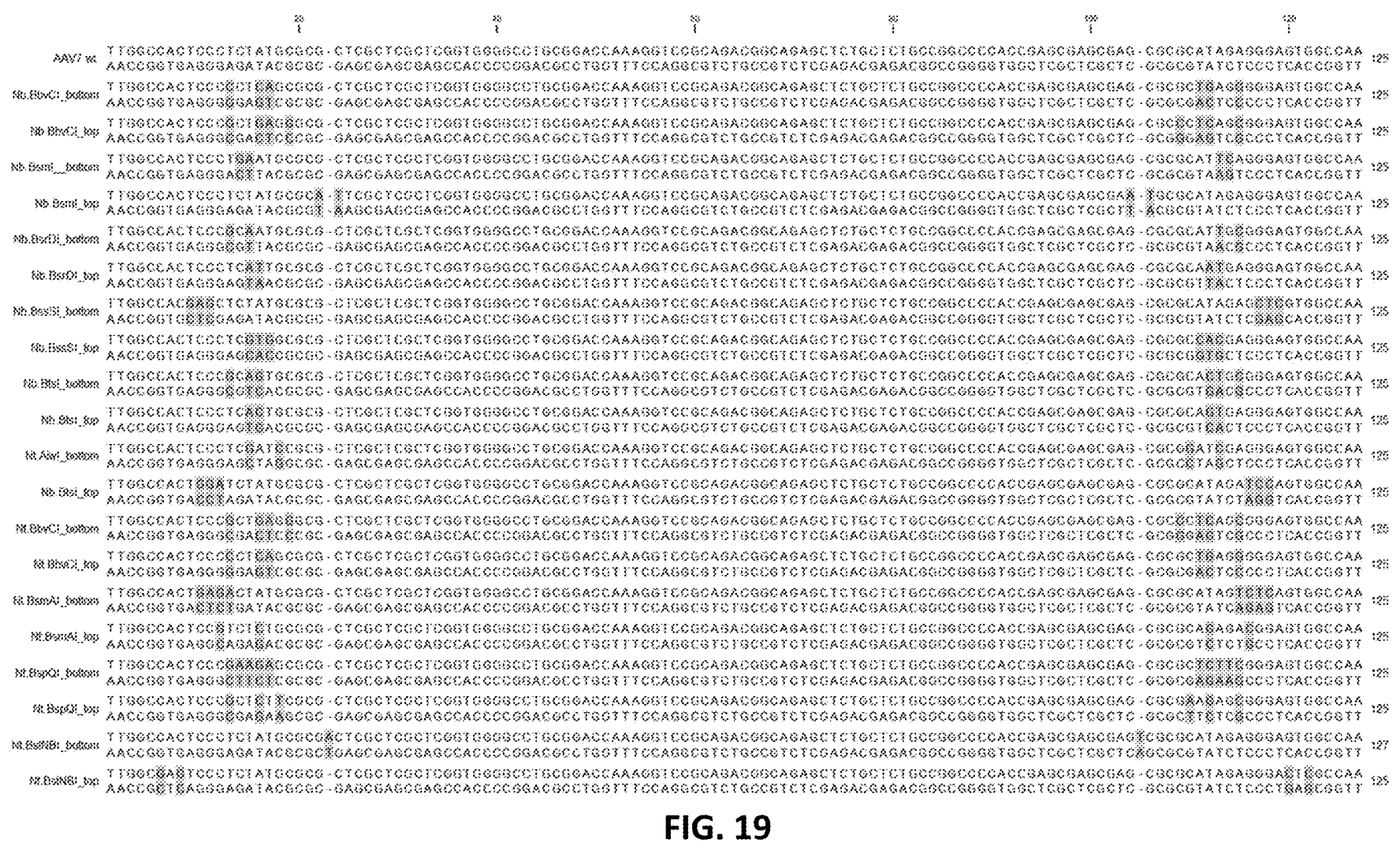

FIG. 19 depicts a sequence alignment of ITRs derived from AAV7 Left highlighting sequence modifications to generate recognition sites for different nicking endonucleases recognition sites.

Figure 20A:
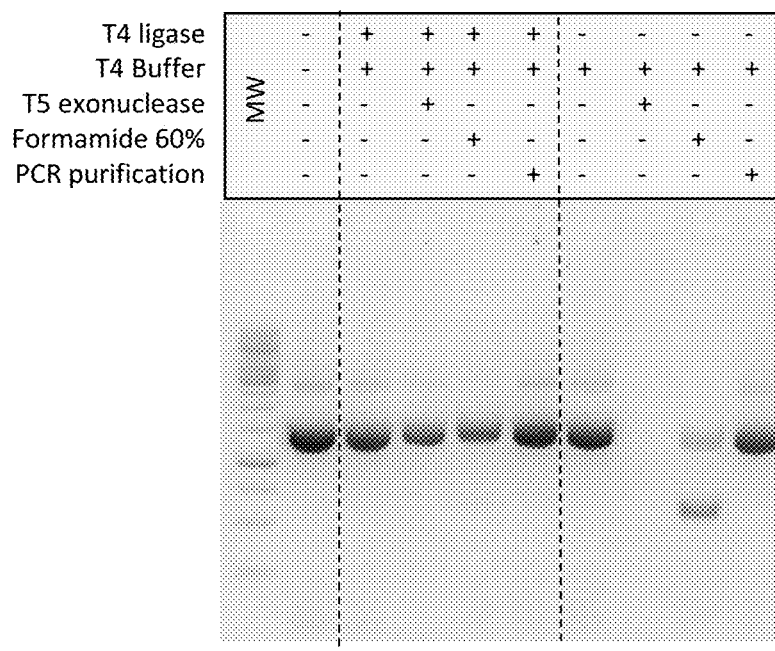
Figure 20B:
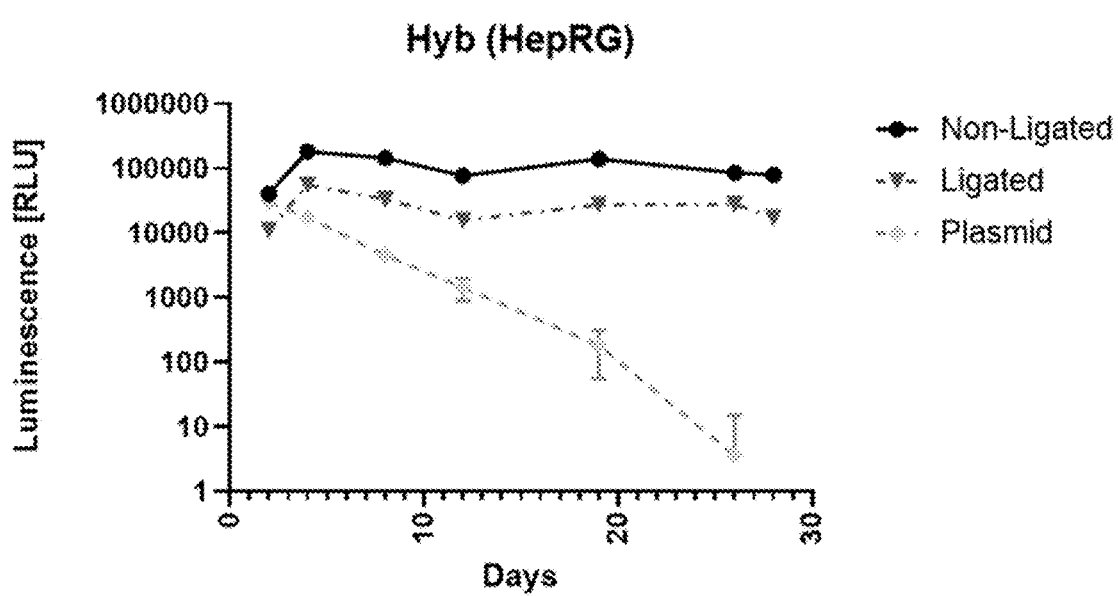

FIGS. 20A and 20B depict an agarose gel showing the successful ligation of the DNA construct and the corresponding luciferase expression in non-dividing hepatocytes transfected with hybridosomes encapsulating the ligated construct and non-ligated construct as well as parental plasmid, respectively.

Figure 21:
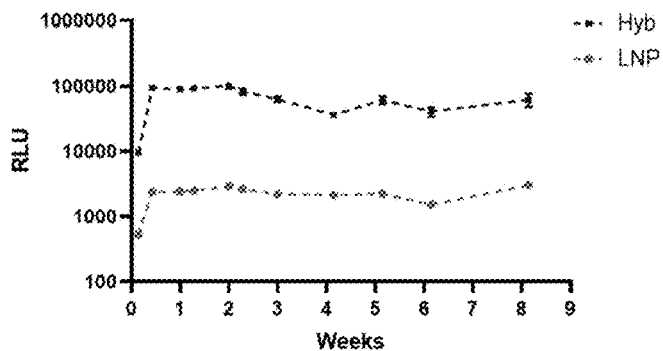

FIG. 21 depicts expression over time of luciferase by non-dividing cells transfected with equimolar amounts of hairpin-ended DNA molecules encoding a secreted luciferase encapsulated in LNPs or Hybridosomes.

Figure 22:
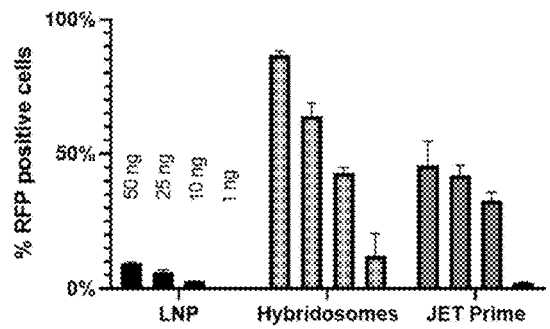

FIG. 22 depicts the percentage of RFP positive color switch HEK293 cells following 72 h of transfection of hairpin ended DNA encoding Cre recombinase delivered by lipid nanoparticles, hybridosomes and jetprime as described in Example 9.

Figure 23A:
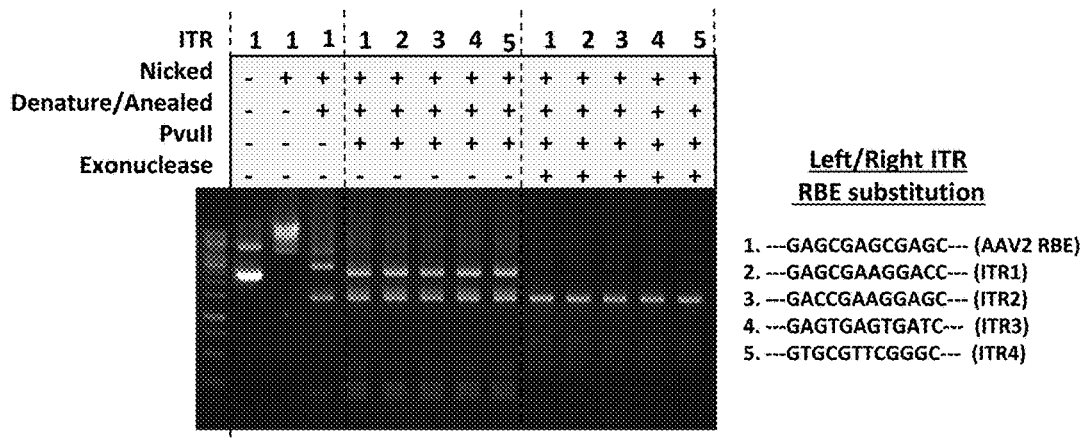
Figure 23B:
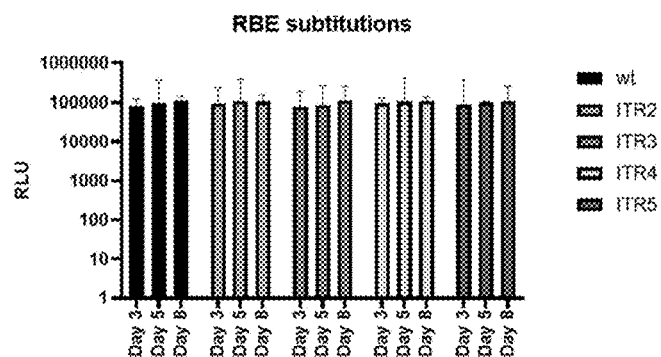

FIGS. 23A and 23B depict an agarose gel showing the successful formation of hairpin ended DNA from plasmids comprising right and left ITRs with a wild type AAV RBE compared to mutants in which the RBE was substituted to the corresponding sequences shown in the figure. The luciferase expression in non-dividing hepatocytes transfected with corresponding ITR sequences is shown in FIG. 23B.

Figure 24A:
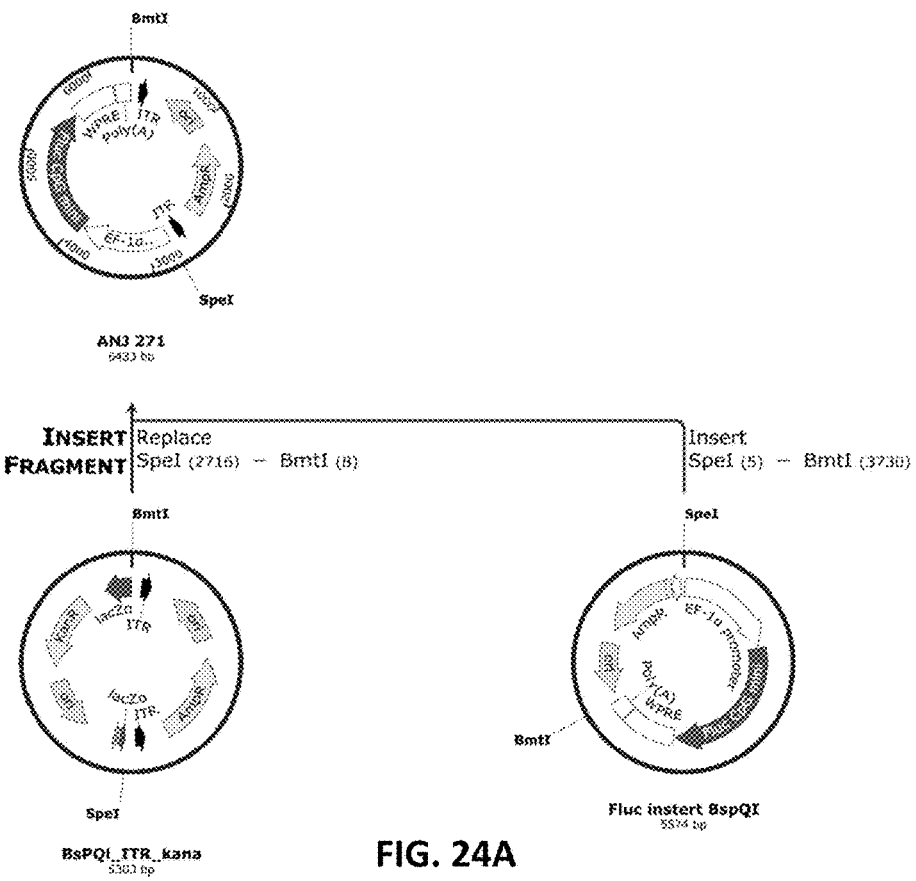
Figure 24B:
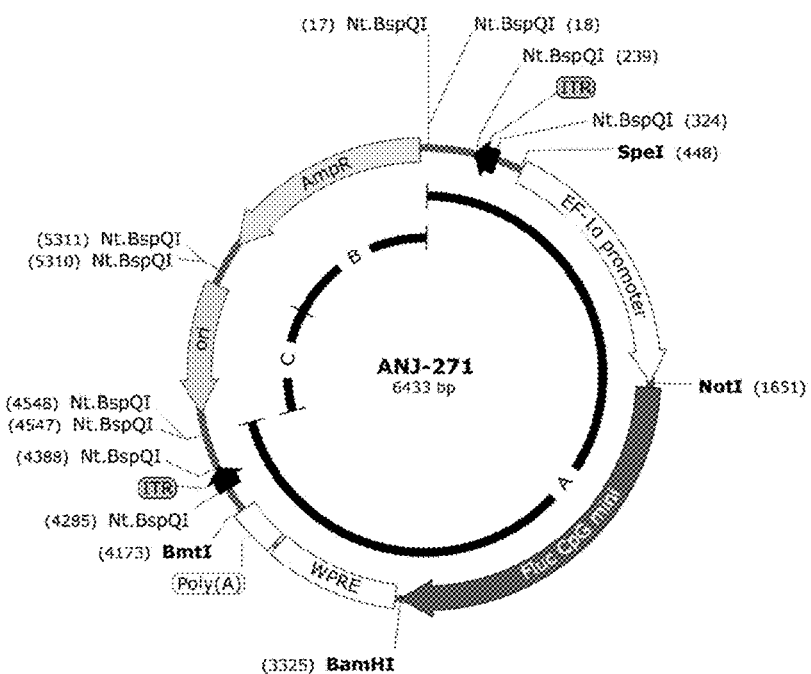

FIGS. 24A and 24B: illustrates a further exemplary cloning method (FIG. 24A) and the resulting map of a plasmid (FIG. 24B) from which hairpinned inverted repeat DNA molecules as disclosed herein can be prepared by performing method steps as described in Example 11. In this example, six restriction sites for nicking endonuclease are placed in the region 5' to the left ITR and 3' to the right ITR.

FIGS. 25A and 25B depicts and visualizes the products from nicking, denaturing/annealing and exonuclease digestions starting from the plasmid depicted in FIG. 24B on an agarose gel as well as the luminescence readout of said product transfected.

FIGS. 26A and 26B depict and visualizes the products from nicking, denaturing/annealing and exonuclease digestions of a construct with OriL derived ITRs as described in example 13 on an agarose gel as well as the luminescence readout of the secreted turboluc in the supernatant of Hek293 cells.

5. DETAILED DESCRIPTION

Provided herein are methods of making hairpin-ended DNA molecules. Also provided herein are methods of using hairpin-ended DNA molecules, including for example, using hairpin-ended DNA molecules for gene therapies. The various methods of making the hairpin-ended DNA molecules are further described in Section 5.2 below. The various methods of using hairpin-ended DNA molecules are described in Section 5.7 below. The hairpin-ended DNA made by these methods are provided in Section 5.4 below and include hairpinned inverted repeats at the two ends and an expression cassette, each of which are further described below. In some embodiments, the hairpin-ended DNA also include one or two nicks, as further provided below in Section 5.4 below. Hairpin, hairpinned inverted repeats, and the hairpinned ends are described in Section 5.4 below; the inverted repeats that form the hairpinned ends are described in Section 5.3.1 below; the nicks, nicking endonuclease, and restriction sites for nicking endonuclease are described in Sections 5.3.2 and 5.4 below; the expression cassette are described in Sections 5.3.3 and 5.4 below; and the functional properties of the hairpin-ended DNA molecules are described in Section 5.5 below. As such, the disclosure provides hairpin-ended DNA molecules, methods of making thereof, methods of using therefor, with any combination or permutation of the components provided herein.

Also provided herein are parent DNA molecules used in the methods to make the hairpin-ended DNA molecules, which parent DNA molecules include two inverted repeats, two or more restriction sites for nicking endonuclease, and an expression cassette, each of which are further described below. The restriction sites for nicking endonuclease are arranged such that, upon nicking by the nicking endonuclease and denaturing, single strand overhangs with inverted repeat sequences form, which then fold to form hairpins upon annealing, each step as described in Section 5.2. The inverted repeats are described in Section 5.3.1 below; the nicks, nicking endonuclease, and restriction sites for nicking endonuclease are described in Section 5.3.2 below; the expression cassette are described in Section 5.3.3 below. As such, the disclosure provides parent DNA molecules used in the methods of making, with any combination or permutation of the components provided herein.

5.1 Definitions

As used herein, the term "isolated" when used in reference to a DNA molecule is intended to mean that the referenced DNA molecule is free of at least one component as it is found in its natural, native, or synthetic environment. The term includes a DNA molecule that is removed from some or all other components as it is found in its natural, native, or synthetic environment. Components of a DNA molecule's natural, native, or synthetic environment include anything in natural native, or synthetic environment that are required for, are used in, or otherwise play a role in the replication and maintenance of the DNA molecule in that environment. Components of a DNA molecule's natural, native, or synthetic environment also include, for example, cells, cell debris, cell organelles, proteins, peptides, amino acids, lipids, polysaccharides, nucleic acids other than the referenced DNA molecule, salts, nutrients for cell culture, and/or chemicals used for DNA synthesis. A DNA molecule of the disclosure can be partly, completely, or substantially free from all of these components or any other components of its natural, native, or synthetic environment from which it is isolated, synthetically produced, naturally produced, or recombinantly produced. Specific examples of isolated DNA molecules include partially pure DNA molecules and substantially pure DNA molecules.

As used herein, the term "delivery vehicle" refers to substance that can be used to administer or deliver one or more agents to a cell, a tissue, or a subject, particular a human subject, with or without the agent(s) to be delivered. A delivery vehicle may preferentially deliver agent(s) to a particular subset or a particular type of cells. The selective or preferential delivery achieved by the delivery vehicle can be achieved the properties of the vehicle or by a moiety conjugated to, associated with, or contained in the delivery vehicle, which moiety specifically or preferentially binds to a particular subset of cells. A delivery vehicle can also increase the in vivo half-life of the agent to be delivered, the efficiency of the delivery of the agent comparing to the delivery without using the delivery vehicle, and/or the bioavailability of the agent to be delivered. Non-limiting examples of a delivery vehicle are hybridosomes, liposomes, lipid nanoparticles, polymersomes, mixtures of natural/synthetic lipids, membrane or lipid extracts, exosomes, viral particles, protein or protein complexes, peptides, and/or polysaccharides.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

5.2 Methods of Making the Hairpin-Ended DNA Molecules

In one aspect, provided herein is a method for preparing a hairpin-ended DNA molecule, wherein the method comprises: a. culturing a host cell comprising the DNA molecule as described in Section 5.3 under conditions resulting in amplification of the DNA molecule; b. releasing the DNA molecule from the host cell; c. incubating the DNA molecule with one or more nicking endonuclease recognizing the four restriction sites resulting in four nicks; d. denaturing and thereby creating a DNA fragment that comprises the expression cassette and is flanked by the two single strand DNA overhangs; e. annealing the single strand DNA overhangs intramolecularly and thereby creating a hairpinned inverted repeat on both ends of the DNA fragment resulting from step d.

In another aspect, provided herein is a method for preparing a hairpin-ended DNA, wherein the method comprises: a. culturing a host cell comprising the plasmid of Section 5.3.5 under conditions resulting in amplification of the plasmid; b. releasing the plasmid from the host cell; c. incubating the DNA molecule with one or more nicking endonuclease recognizing the four restriction sites resulting in four nicks; d. denaturing and thereby creating a DNA fragment that comprises the expression cassette and is flanked by the two single strand DNA overhangs; e. annealing the single strand DNA overhangs intramolecularly and thereby creating a hairpinned inverted repeat on both ends of the DNA fragment resulting from step d; f. incubating the plasmid or the fragments resulting from step d with the restriction enzyme and thereby cleaving the plasmid or a fragment of the plasmid; and g. incubating the fragments of the plasmid with an exonuclease thereby digesting the fragments of the plasmid except the fragment resulting from step e.

In a further aspect, provided herein is a method for preparing a hairpin-ended DNA, wherein the method comprises: a. culturing a host cell comprising the DNA molecule as described in Embodiment 24 of Section 3.1 under conditions resulting in amplification of the plasmid; b. releasing the plasmid from the host cell; c. incubating the DNA molecule with one or more nicking endonuclease recognizing the first, second, third, and fourth restriction sites resulting in four nicks; d. denaturing and thereby creating a DNA fragment that comprises the expression cassette and is flanked by the two single strand DNA overhangs; e. annealing the single strand DNA overhangs intramolecularly and thereby creating a hairpinned inverted repeat on both ends of the DNA fragment resulting from step d; f. incubating the plasmid or the fragments resulting from step d with one or more nicking endonuclease recognizing the fifth and sixth restriction sites resulting in the break in the double stranded DNA molecule; and g. incubating the fragments of the plasmid with an exonuclease thereby digesting the fragments of the plasmid except the fragment resulting from step e.

In one aspect, provided herein is a method for preparing a hairpin-ended DNA molecule, wherein the method comprises: a. culturing a host cell comprising the DNA molecule as described in Section 5.3 under conditions resulting in amplification of the DNA molecule; b. releasing the DNA molecule from the host cell; c. incubating the DNA molecule with one or more programmable nicking enzyme recognizing the four target sites for the guide nucleic acid resulting in four nicks; d. denaturing and thereby creating a DNA fragment that comprises the expression cassette and is flanked by the two single strand DNA overhangs; e. annealing the single strand DNA overhangs intramolecularly and thereby creating a hairpinned inverted repeat on both ends of the DNA fragment resulting from step d.

In another aspect, provided herein is a method for preparing a hairpin-ended DNA, wherein the method comprises: a. culturing a host cell comprising the plasmid of 5.3.5 under conditions resulting in amplification of the plasmid; b. releasing the plasmid from the host cell; c. incubating the DNA molecule with one or more programmable nicking enzyme recognizing the four target sites for the guide nucleic acid resulting in four nicks; d. denaturing and thereby creating a DNA fragment that comprises the expression cassette and is flanked by the two single strand DNA overhangs; e. annealing the single strand DNA overhangs intramolecularly and thereby creating a hairpinned inverted repeat on both ends of the DNA fragment resulting from step d; f. incubating the plasmid or the fragments resulting from step d with the restriction enzyme and thereby cleaving the plasmid or a fragment of the plasmid; and g. incubating the fragments of the plasmid with an exonuclease thereby digesting the fragments of the plasmid except the fragment resulting from step e.

In a further aspect, provided herein is a method for preparing a hairpin-ended DNA, wherein the method comprises: a. culturing a host cell comprising the DNA molecule as described in Embodiment 24 of Section 3.1 under conditions resulting in amplification of the plasmid; b. releasing the plasmid from the host cell; c. incubating the DNA molecule with one or more programmable nicking enzyme recognizing the first, second, third, and fourth target sites for the guide nucleic acids resulting in four nicks; d. denaturing and thereby creating a DNA fragment that comprises the expression cassette and is flanked by the two single strand DNA overhangs; e. annealing the single strand DNA overhangs intramolecularly and thereby creating a hairpinned inverted repeat on both ends of the DNA fragment resulting from step d; f. incubating the plasmid or the fragments resulting from step d with programmable nicking enzyme recognizing the fifth and sixth target sites for the guide nucleic acids resulting in the break in the double stranded DNA molecule; and g. incubating the fragments of the plasmid with an exonuclease thereby digesting the fragments of the plasmid except the fragment resulting from step e. In another embodiment, step f of the paragraph can be replaced with step f: incubating the plasmid or the fragments resulting from step d with one or more nicking endonuclease recognizing the two restriction sites resulting in the break in the double stranded DNA molecule.

In certain embodiments, the DNA molecule that comprise an expression cassette flanked by inverted repeats (as described in Section 5.3) can be provided by culturing host cells comprising the DNA molecules or the plasmids and releasing the DNA molecules or plasmid from the host cell as provided in the steps a and b in the preceding paragraphs. Alternatively, such DNA molecules can be synthesized in a cell-free system or in a combination of cell-free and host cell-based systems. For example, chemical synthesis of DNA fragments and plasmids of various size and sequences is known and widely used in the art; fragments can be chemically synthesized and then ligated by any means known in the art, or recombined in a host cell. In other embodiments, the DNA molecules or plasmids can be provided by in vitro replication. Various methods can be used for in vitro replication, including amplification by polymerase chain reaction (PCR). PCR methods for replicating DNA fragments or plasmids of various sizes are well known and widely used in the art, for example, as described in Molecular Cloning: A Laboratory Manual, 4th Edition, by Michael Green and Joseph Sambrook, ISBN 978-1-936113-42-2 (2012), which is incorporated herein in its entirety by reference. In some embodiments, the method of in vitro replication can be isothermal DNA amplification. In some embodiments, step a and b can be replaced by a step of providing DNA molecules by chemical synthesis or PCR. In other embodiments, step a, b, c, and d can be replaced by providing DNA molecules by chemical synthesis.

In one aspect, methods provided herein can be used to prepare hairpin ended DNA molecules comprising an expression cassette, whereby the methods comprise: a. providing a double stranded DNA molecule as described in Section 5.3; b. incubating the DNA molecule with at least one nicking enzyme in conditions resulting in nicking of the double stranded DNA molecule, thereby creating at least two stoichiometric DNA fragments; c. denaturing the DNA fragments; d. annealing the DNA fragments, whereby at least one DNA fragment comprises the expression cassette and single strand DNA overhangs that can be annealed intramolecularly and thereby creating a hairpinned inverted repeat on both ends of said DNA; e. incubating the DNA fragments with at least one exonuclease thereby digesting the stoichiometric DNA fragments of step b, except the hairpin ended fragment comprising the expression cassette resulting from step d. In specific embodiments, step b. of the method in the paragraph creates at least 2, at least 3, at least 4, at least 5, at least 6 or more stoichiometric fragments. In further embodiments, step b. of the method in the paragraph creates at least two stoichiometric DNA fragments, whereby the DNA fragment comprising the expression cassette is stoichiometrically equivalent to the DNA molecules provided in step a. In some embodiments, the digestion resistant hairpin ended fragment comprising the expression cassette resulting from step e in the paragraph can be approximately stochiometrically equivalent compared to the DNA molecules provided in step a.

In some embodiments, methods provided herein can be used to prepare hairpin ended DNA molecules comprising an expression cassette, whereby the methods comprise: a. providing a double stranded DNA molecule as described in Section 5.3; b. incubating the DNA molecule with at least one nicking enzyme in conditions resulting in nicking of the double stranded DNA molecule, thereby creating at least two stoichiometric DNA fragments; c. denaturing the DNA fragments into single stranded DNA; d. annealing the sense and antisense strand of a DNA fragment comprising the expression cassette, whereby the sense and/or antisense strand comprises single strand DNA overhangs that can be annealed intramolecularly and thereby creating a hairpinned inverted repeat on both ends of the DNA fragment comprising the expression cassette; e. incubating the DNA fragments with at least one exonuclease thereby digesting the stoichiometric DNA fragments of step b, except the hairpin ended fragment comprising the expression cassette resulting from step d.

In some embodiments, methods provided herein can be used to prepare hairpin ended DNA molecules comprising an expression cassette, whereby the methods comprise: a. providing a double stranded DNA molecule as described in Section 5.3; b. incubating the DNA molecule with at least one nicking enzyme in conditions resulting in nicking of the double stranded DNA molecule; c. denaturing the double stranded DNA into thereby creating at least two stoichiometric DNA fragments; d. annealing the DNA fragments, whereby at least one DNA fragment comprises the expression cassette and single strand DNA overhangs that can be annealed intramolecularly and thereby creating a hairpinned inverted repeat on both ends of said DNA fragment.

In a further aspect, the methods provided herein can be used to prepare hairpin ended DNA molecules, wherein the method comprises at least one pot (e.g., a container, vessel, well, tube, plate, or other receptacle) comprising the double stranded DNA molecule as described in Section 5.3 in an aqueous buffer to which sequentially (i) a nicking enzyme, (ii) a denaturing agent (e.g. a base), (iii) an annealing agent (e.g. an acid) and (iv) an exonuclease is added. The ability to perform the method provided herein as a one-pot reaction, may provide at least a further advantage, in that the method to produce hairpin ended DNA molecules can be completed without the need to purify any intermediates, contaminants (e.g. enzymes) or DNA digestion byproducts (i.e. nucleotides, oligos or single stranded DNA fragments) between the method steps (i) to (iv), thereby offering an favorable method in terms of costs and production failure risks (e.g. by minimizing purification losses, requiring less starting material, tighter control of process variables, etc.).

In further embodiments, methods provided herein can be used to produce hairpin ended DNA molecules, wherein the method comprises a. providing one pot (e.g., a container, vessel, well, tube, plate, or other receptacle) comprising a double stranded DNA molecule as described in Section 5.3 and at least one nicking enzyme in conditions resulting in nicking of the double stranded DNA molecule, b. denaturing and annealing the DNA (e.g. by changing the temperature, pH or buffer composition) and c. adding an exonuclease without needing to purify any intermediates (e.g. between step a and c). In a specific embodiment, the pot in the method of the paragraph; in step a. comprises at least one species of double stranded DNA molecule (e.g. a plasmid or derivative thereof), at least one species of nicking enzyme and an aqueous buffer and in step c. an aqueous buffer comprising at least one species of hairpin ended DNA, at least one species of nicking enzyme, at least one species of exonuclease and DNA digestion products (e.g. dNMPs, dinucleotides and/or short oligos).

In a further embodiment, the methods provided herein can be used to produce hairpin ended DNA molecules, whereby the methods comprises: a. providing a double stranded DNA molecule as described in Section 5.3 and at least one nicking enzyme in at least one pot (e.g., a container, vessel, well, tube, plate, or other receptacle) under conditions resulting in nicking of the double stranded DNA molecule, b. denaturing the DNA molecule and thereby creating a DNA fragment that comprises the expression cassette and is flanked by the two single strand DNA overhangs; c. annealing the single strand DNA overhangs intramolecularly and thereby creating a hairpinned inverted repeat on both ends of the DNA fragment resulting from step b; d. adding to the pot an exonuclease thereby digesting the DNA fragments of the DNA molecules in step b, except the fragment resulting from step c.

In some embodiments, methods provided herein can be used to prepare hairpin ended DNA molecules comprising an expression cassette, whereby the methods comprises: a. providing a double stranded DNA molecule as described in Section 5.3 and at least one nicking enzyme in at least one pot (e.g., a container, vessel, well, tube, plate, or other receptacle) under conditions resulting in nicking of the double stranded DNA molecule, thereby creating at least two stoichiometric DNA fragments, b. denaturing the DNA fragments; c. annealing the DNA fragments, whereby at least one DNA fragment comprises single strand DNA overhangs that can be annealed intramolecularly and thereby creating a hairpinned inverted repeat on both ends of the DNA fragment comprising the expression cassette; d. adding to the pot at least one exonuclease thereby digesting the DNA fragments of step a, except the hairpin ended DNA fragment comprising the expression cassette resulting from step c. In further embodiments, in step a. of the method in the paragraph creates at least 2, at least 3, at least 4, at least 5, at least 6 or more stoichiometric fragments.

In some embodiments, methods provided herein can be used to prepare hairpin ended DNA molecules comprising an expression cassette, whereby the methods comprises: a. providing a double stranded DNA molecule as described in Section 5.3 in at least one pot (e.g., a container, vessel, well, tube, plate, or other receptacle), b. adding at least one nicking enzyme to the pot in conditions resulting in nicking of the double stranded DNA molecule, thereby creating at least two stoichiometric DNA fragments, c. denaturing the DNA fragments; d. annealing the DNA fragments, whereby at least one DNA fragment comprises single strand DNA overhangs that can be annealed intramolecularly and thereby creating a hairpinned inverted repeat on both ends of the DNA fragment comprising the expression cassette; e. adding at least one exonuclease to the pot thereby digesting the stoichiometric DNA fragments of step b, except the hairpin ended fragment comprising the expression cassette resulting from step d. In specific embodiments, the pot of the method in the paragraph comprises, at step a. one species of DNA molecule and at step b. at least 2, at least 3, at least 4, at least 5, at least 6 or more stoichiometric fragments compared to the DNA molecule in step a, whereby the fragment comprising the expression cassette is stoichiometrically equivalent to the DNA molecules provided in step a. In specific embodiments, the pot at step b. of the method in the paragraph comprises, at least 2, at least 3, at least 4, at least 5, at least 6 or more stoichiometric fragments compared to the DNA molecule in step a, whereby the fragment comprising the expression cassette is stoichiometrically equivalent to the DNA molecules provided in step a. In a non-limiting example, the pot at step b. of the method in the paragraph comprises three stoichiometric DNA fragments; (i) two fragments devoid of the expression cassette and one fragment comprising the expression cassette, whereby the fragment comprising the expression cassette is stoichiometrically equivalent to the DNA molecule provided in step a. In further specific embodiments, the pot at step e. of the method in the paragraph comprises an amount of digestion resistant hairpin ended DNA molecule that is stoichiometrically equivalent compared to the DNA molecules provided in step a. In specific embodiments, the pot at step e. of the method in the paragraph comprises at most an amount of digestion resistant hairpin ended DNA molecule that is stoichiometrically approximately equivalent compared to the DNA molecules provided in step a. In some embodiments, the pot at step e. of the method in the paragraph comprises at most an amount of digestion resistant hairpin ended DNA molecule that is stoichiometrically approximately equivalent compared to the DNA molecules provided in step a, whereby the total mass of DNA molecules is reduced approximately by the ratio of nucleotides present in hairpin ended DNA molecule comprising the expression cassette divided by the nucleotides present in the DNA molecule provided in step a. In specific embodiments, the pot at step e. of the method in the paragraph comprises an amount of digestion resistant hairpin ended DNA molecule that is stoichiometrically approximately equivalent compared to the expression cassettes of the DNA molecules provided in step a.

In some embodiments, the methods provided herein can be used to prepare hairpin ended DNA molecules comprising an expression cassette, whereby the methods comprises: a. culturing a host cell comprising the DNA molecule as described in Section 5.3 under conditions resulting in amplification of the DNA molecule; b. releasing the DNA molecule from the host cell; c. adding the DNA molecule to least one pot (e.g., a container, vessel, well, tube, plate, or other receptacle); d. adding at least one nicking enzyme to the pot in conditions resulting in nicking of the double stranded DNA molecule, thereby creating at least two stoichiometric DNA fragment; e. denaturing the DNA fragments; f. annealing the DNA fragments, whereby at least one DNA fragment comprises the expression cassette and single strand DNA overhangs that can be annealed intramolecularly and thereby creating a hairpinned inverted repeat on both ends of the DNA fragment; g. adding at least one exonuclease to the pot thereby digesting the stoichiometric DNA fragments of step f, except the hairpin ended fragment comprising the expression cassette resulting from step f. In specific embodiments, the pot at step g. of the method in the paragraph comprises an amount of digestion resistant hairpin ended DNA molecule that is stoichiometrically approximately equivalent compared to the DNA molecules provided in step c.

In some embodiments, the methods provided herein can be used to prepare hairpin ended DNA molecules comprising an expression cassette, whereby the methods comprises: a. culturing a host cell comprising the plasmid as described in Section 5.3 under conditions resulting in amplification of the plasmid; b. releasing the plasmid from the host cell; c. adding the plasmid to least one pot (e.g., a container, vessel, well, tube, plate, or other receptacle); d. adding at least one nicking enzyme to the pot in conditions resulting in nicking of the plasmid, thereby creating at least two stoichiometric DNA fragment; e. denaturing the DNA fragments; f. annealing the DNA fragments, whereby at least one DNA fragment comprises the expression cassette and single strand DNA overhangs that can be annealed intramolecularly and thereby creating a hairpinned inverted repeat on both ends of the DNA fragment; g. adding at least one exonuclease to the pot thereby digesting the stoichiometric DNA fragments of step f, except the hairpin ended fragment comprising the expression cassette resulting from step f. In specific embodiments, the pot at step g. of the method in the paragraph comprises an amount of digestion resistant hairpin ended DNA molecule that is stochiometrically approximately equivalent compared to the plasmid provided in step c.

The order of the method steps are listed in the methods for illustrative purposes. In certain embodiments, the method steps are performed in the order in which they appear as described herein. In some embodiments, the method steps can be performed in an order different from which they appear as described herein. Specifically, in some embodiments, the steps of the methods of making the hairpin-ended DNA molecules can be performed in the order as they appeared or as alphabetically listed as described herein, from a to e, or from a to g. Alternatively, the steps of the methods of making the hairpin-ended DNA molecules can be performed not in the order as they appear as described herein. In one embodiment, the step c (incubating the DNA molecule with one or more nicking endonuclease recognizing the four restriction sites resulting in four nicks) can be performed before step b (releasing the plasmid from the host cell), when the host cells naturally express, are engineered to express, otherwise contain one or more nicking endonuclease. In another embodiment, step f (incubating the plasmid or the fragments resulting from step d with the restriction enzyme or incubating the plasmid or the fragments resulting from step d with one or more nicking endonuclease) can be performed before step d (denaturing and thereby creating a DNA fragment that comprises the expression cassette and is flanked by the two single strand DNA overhangs), or before step c (incubating the DNA molecule with one or more nicking endonuclease). Additionally, one or more steps can be combined into one step that perform all the actions of the separate step. In certain embodiments, the step a (culturing a host cell) can be combined with step c (incubating the DNA molecule with one or more nicking endonuclease), when the host cells naturally express, are engineered to express, otherwise contain one or more nicking endonuclease. In other embodiments, step f (incubating the plasmid or the fragments resulting from step d with the restriction enzyme or incubating the plasmid or the fragments resulting from step d with one or more nicking endonuclease) can be combined with step c (incubating the DNA molecule with one or more nicking endonuclease) by incubating with the nicking endonuclease or restriction enzyme recited in step f and c together. Therefore, the disclosure provides that the steps can be performed in various combinations and permutations according to the state of the art.

Additional steps can be added to the methods provided herein, before all the method steps, after all the method steps, or in between any of the method steps. In one embodiment, the methods provided herein further include a step h. repairing the nicks with a ligase to form a circular DNA. In another embodiment, the step h of repairing the nicks with a ligase to form a circular DNA is performed after all the other method steps described herein.

As is further described further below in Sections 5.3.1 and 5.4, the hairpins formed at the end of the DNA molecules is determined by properties the overhang between the restriction sites for nicking endonucleases. Therefore, by designing the properties including the sequence and structural properties of the overhang between the restriction sites for nicking endonucleases according to Sections 5.3.1 and 5.4, the methods can be used to produce 1, 2 or more hairpinned ends. In one embodiment, the methods produce hairpin-ended DNA comprising 1 hairpin end. In another embodiment, the methods produce hairpin-ended DNA consisting of 1 hairpin end. In yet another embodiment, the methods produce hairpin-ended DNA comprising two hairpin ends. In a further embodiment, the methods produce hairpin-ended DNA consisting of two hairpin ends.

The methods provided herein can be used to produce DNA molecules comprising artificial sequences, natural DNA sequences, or sequences having both natural DNA sequences and artificial sequences. In one embodiment, the methods produce hairpin-ended DNA molecules comprising artificial sequences. In another embodiment, the methods produce hairpin-ended DNA molecules comprising natural sequences. In yet another embodiment, the methods produce hairpin-ended DNA molecules comprising both natural sequences and artificial sequences. In certain embodiments, the methods produce hairpin-ended DNA molecules comprising viral inverted terminal repeat (ITR). In yet another embodiment, the methods produce a hairpin-ended DNA molecule comprising hairpinned inverted repeats lacking a RABS. In yet another embodiment, the methods produce a hairpin-ended DNA molecule comprising two hairpinned terminal repeats, wherein both hairpinned inverted repeats lack a RABS. In another embodiment, the methods produce a hairpin-ended DNA molecule comprising two hairpinned inverted repeat, wherein both hairpinned inverted repeats lack a TRS. In a further embodiment, the methods produce a hairpin-ended DNA molecule comprising two hairpinned inverted repeats, wherein both hairpinned inverted repeats lack a RABS and a TRS. In another embodiment, the methods produce a hairpin-ended DNA molecule comprising two hairpinned inverted repeats, wherein both hairpinned inverted repeats promoter activity (e.g. P5 promoter activity) and transcriptional activity (e.g. transcription start sites [TSS]). In another embodiment, the methods produce a hairpin-ended DNA molecule comprising two hairpinned inverted repeats, wherein both hairpinned inverted repeats lack a RABS, promoter activity (e.g. P5 promoter activity), transcriptional activity (e.g. transcription start sites [TSS]) and a TRS. In yet another embodiment, the methods produce a hairpin-ended DNA molecule comprising two hairpinned inverted repeats, wherein both hairpinned inverted repeats lack a RABS. In a further embodiment, the methods produce hairpin-ended DNA molecules comprising a viral genome. In some embodiments, the viral genome is an engineered viral genome comprising one or more non-viral genes in the expression cassette. In certain embodiments, the viral genome is an engineered viral genome wherein one or more viral genes have been knocked out. In some specific embodiments, the viral genome is an engineered viral genome wherein the replication-associated protein ("RAP," i.e., Rep or NS1) gene, capsid (Cap) gene, or both RAP and Cap genes are knocked out. In other embodiments, the viral genome is parvovirus genome. In yet other embodiments, the parvovirus is a Dependoparvovirus, a Bocaparvovirus, an Erythroparvovirus, a Protoparvovirus, or a Tetraparvovirus.

The steps performed in the various methods provided herein are described in further details below. The embodiments of host cells and culturing of the host cells are described in Section 5.2.1; the embodiments for the step of releasing the DNA molecules from the host cells are described in Section 5.2.2; the embodiments for the step of denaturing the DNA molecules are described in Section 5.2.3; the embodiments for the step of annealing are described in Section 5.2.5; the embodiments for the step of incubating the DNA molecules with nicking endonucleases or restriction enzymes are described in Section 5.2.4; the embodiments for the step of incubating with exonuclease are described in Section 5.2.6; and the embodiments for the step of ligation are described in Section 5.2.7. As such, the disclosure provides methods comprising permutations and combinations of the various embodiments of the steps described herein.

5.2.1 Host Cells and Culturing of the Host Cells

The disclosure provides that various host cells can be cultured to amplify the DNA molecules. A host cell for use in the methods provided herein can be a eukaryotic host cell, a prokaryotic host cell, or any transformable organism that is capable of replicating or amplifying recombinant DNA molecules. In some embodiments, the host cell can be a microbial host cell. In further embodiments, the host cell can be a host microbial cell selected from, bacteria, yeast, fungus or any of a variety of other microorganism cells applicable to replicating or amplifying DNA molecules. A bacterial host cell can be that of any species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida*. A yeast or fungus host cell can be that of any species selected from *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae,* and the like. *E. coli* is a particularly useful host cell since it is a well characterized microbial cell and widely used for molecular cloning. Other particularly useful host cells include yeast such as *Saccharomyces cerevisiae*. It is understood that any suitable microbial host cells can be used to amplify the DNA molecules as known in the art.

Similarly, a eukaryotic host cell for use in the methods provided herein can be any eukaryotic cell that is capable of replicating or amplifying recombinant DNA molecules, as known and used in the art. In some embodiments, a host cell for use in the methods provided herein can be a mammalian host cells. In further embodiments, a host cell can be a human or non-human mammalian host cell. In other embodiments, a host cell can be an insect host cells. Some widely used non-human mammalian host cells include CHO, mouse myeloma cell lines (e.g. NS0, SP2/0), rat myeloma cell line (e.g. YB2/0), and BHK. Some widely used human host cells include HEK293 and its derivatives, HT-1080, PER.C6, and Huh-7. In certain embodiments, the host cell is selected from the group consisting of HeLa, NIH3T3, Jurkat, HEK293, COS, CHO, Saos, SF9, SF21, High 5, NS0, SP2/0, PC12, YB2/0, BHK, HT-1080, PER.C6, and Huh-7.

A host cell can be cultured as each host cell is known and cultured in the art. The culturing conditions and culture media for different host cells can be different as is known and practiced in the art. For example, bacterial or other microbial host cells can be cultured at 37° C., at an agitation speed of up to 300 rpm, and with or without forced aeration. Some insect host cells can be optimally cultured generally at 25 to 30° C., with no agitation at an agitation speed of up to 150 rpm, and with or without forced aeration. Some mammalian host cells can be optimally cultured at 37° C., with no agitation or at an agitation speed of up to 150 rpm, and with or without forced aeration. Additionally, conditions for culturing the various host cells can be determined by examining the growth curve of the host cells under various conditions, as is known and practiced in the art. Some widely used host cell culturing media and culturing conditions are described in Molecular Cloning: A Laboratory Manual, 4th Edition, by Michael Green and Joseph Sambrook, ISBN 978-1-936113-42-2 (2012), which is incorporated herein in its entirety by reference.

5.2.2 Releasing the DNA Molecules from Host Cells

DNA molecules can be released from the host cells by various ways as known and practiced in the art. For example, the DNA molecules can be released by breaking up the host cells physically, mechanically, enzymatically, chemically, or by a combination of physical, mechanical, enzymatic and chemical actions. In some embodiments, the DNA molecules can be released from the host cells by subjecting the cells to a solution of cell lysis reagents. Cell lysis reagents include detergents, such as triton, SDS, Tween, NP-40, and/or CHAPS. In other embodiments, the DNA molecules can be released from the host cells by subjecting the host cells to difference in osmolarity, for example, subjecting the host cells to a hypotonic solution. In other embodiments, the DNA molecules can be released from the host cells by subjecting the host cells to a solution of high or low pH. In certain embodiments, the DNA molecules can be released from the host cells by subjecting the host cells to enzyme treatment, for example, treatment by lysozyme. In some further embodiments, the DNA molecules can be released from the host cells by subjecting the host cells to any combinations of detergent, osmolarity pressure, high or low pH, and/or enzymes (e.g. lysozyme).

Alternatively, the DNA molecules can be released from the host cells by exerting physical force on the host cells. In one embodiment, the DNA molecules can be released from the host cells by directly applying force to the host cells, e.g. by using the Waring blender and the Polytron. Waring blender uses high-speed rotating blades to break up the cells and the Polytron draws tissue into a long shaft containing rotating blades. In another embodiment, the DNA molecules can be released from the host cells by applying shear stress or shear force to the host cells. Various homogenizers can be used to force the host cells through a narrow space, thereby shearing the cell membranes. In some embodiments, the DNA molecules can be released from the host cells by liquid-based homogenization. In one specific embodiment, the DNA molecules can be released from the host cells by use a Dounce homogenizer. In another specific embodiment, the DNA molecules can be released from the host cells by use a Potter-Elvehjem homogenizer. In yet another specific embodiment, the DNA molecules can be released from the host cells by use a French press. Other physical forces to release the DNA molecules from host cells include manual grinding, e.g. with a mortar and pestle. In manual grinding, host cells are often frozen, e.g. in liquid nitrogen and then crushed using a mortar and pestle, during which process the tensile strength of the cellulose and other polysaccharides of the cell wall breaks up the host cells.

Additionally, the DNA molecules can be released from the host cells by subjecting the cells to freeze and thaw cycles. In some embodiments, a suspension of host cells are frozen and then thawed for a number of such freeze and thaw cycles. In some embodiments, the DNA molecules can be released from the host cells by applying 1, 2, 3, 4, 5, 6, 7, 8, 9, 10, 11, 12, 13, 14, 15, 16, 17, 18, 19, or 20 freeze and thaw cycles to the host cells.

The above described methods for releasing the DNA molecules from the host cells are not mutually exclusive. Therefore, the disclosure provides that the DNA molecules can be released from the host cells by any combinations of DNA releasing methods provide in this Section 5.2.2.

5.2.3 Denaturing the DNA Molecules

DNA molecules can be denatured by various ways as known and practiced in the art. The step of denaturing the DNA molecule can separate the DNA molecule from double strand DNA (dsDNA) into single strand DNA (ssDNA). In separating two DNA strands, the temperature can be increased until the DNA unwinds and the hydrogen bonds that hold the two strands together weaken and finally break. The process of breaking double-stranded DNA into single strands is known as DNA denaturation, or DNA denaturing.

In some embodiments, the step of denaturing the DNA molecule can separate the two DNA strands of one or more segments of the dsDNA molecule, while keeping the other segment(s) of the DNA molecule as dsDNA. In some embodiments, the step of denaturing the DNA molecule can separate all DNA strands of one or more segments of the dsDNA molecule into ssDNA strands. In some further embodiments, the step of denaturing the DNA molecules can separate the dsDNA into ssDNA at the segment between the first and second restriction sites for nicking endonuclease on the top and bottom strand of the DNA (e.g. DNA molecules described in Section 5.3), while keeping the other part of the DNA molecule as dsDNA, thereby creating an overhang between the first and second restriction sites. In certain embodiments, the step of denaturing the DNA molecules can separate the dsDNA into ssDNA at the segment between the third and fourth restriction sites for nicking endonuclease on the top and bottom strand of the DNA (e.g. DNA molecules described in Section 5.3), while keeping the other part of the DNA molecule as dsDNA, thereby creating an overhang between the third and fourth restriction sites. In other embodiment, the step of denaturing the DNA molecules can separate the dsDNA into ssDNA at the segments between the first and second restriction sites and between the third and fourth restriction sites for nicking endonuclease on the top and bottom strand of the DNA (e.g. DNA molecules described in Section 5.3), while keeping the other part of the DNA molecule as dsDNA, thereby (1) breaking the DNA molecule into two daughter DNA molecules and (2) creating an overhang between the first and second restriction sites and an overhang between the third and fourth restriction sites. In one embodiments, the overhang between the first and second restriction sites for nicking endonuclease can be a top strand 5' overhang. In another embodiment, the overhang between the first and second restriction sites for nicking endonuclease can be a bottom strand 3' overhang. In yet another embodiment, the overhang between the third and fourth restriction sites for nicking endonuclease can be a top strand 3' overhang. In a further embodiment, the overhang between the third and fourth restriction sites for nicking endonuclease can be a bottom strand 5' overhang. In some embodiments, step of denaturing the DNA molecule can separate the DNA molecules in any combinations of the embodiments provided herein.

The overhang can vary in length depending on the distance between the restriction sites for nicking endonuclease. In one embodiment, the overhangs can be identical in length and/or sequences. In another embodiment, the overhangs can be different in length and/or sequences. In some embodiments, a top strand 5' overhang can be at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, or at least 100 nucleotides in length. In other embodiments, a top strand 5' overhang can be about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, or more nucleotides in length. In certain embodiments, a bottom strand 3' overhang can be at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, or at least 100 nucleotides in length. In further embodiments, a bottom strand 3' overhang can be about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, or more nucleotides in length. In yet other embodiments, a top strand 3' overhang can be at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, or at least 100 nucleotides in length. In other embodiments, a top strand 3' overhang can be about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, or more nucleotides in length. In some embodiments, a bottom strand 5' overhang can be at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, or at least 100 nucleotides in length. In other embodiments, a bottom strand 5' overhang can be about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, or more nucleotides in length.

As is known and practiced in the art, the DNA molecules can be denatured by heat, by changing the pH in the environment of the DNA molecules, by increasing the salt concentration, or by any combination of these and other known means. The disclosure provides that the DNA molecules can be denatured in the methods by using a denaturing condition that selectively separates the dsDNA into ssDNA at the segments between the first and second restriction sites and/or between the third and fourth restriction sites on the top and bottom strand of the DNA, while keeping the other part of the DNA molecule as dsDNA. In some embodiment, the denaturing completely separates the dsDNA into ssDNA. Such selective separating of dsDNA to ssDNA can be performed by controlling the denaturing conditions and/or the time the DNA molecules are subjected to the denaturing conditions. In one embodiment, the DNA molecules are denatured at a temperature of at least 70° C., at least 71° C., at least 72° C., at least 73° C., at least 74° C., at least 75° C., at least 76° C., at least 77° C., at least 78° C., at least 79° C., at least 80° C., at least 81° C., at least 82° C., at least 83° C., at least 84° C., at least 85° C., at least 86° C., at least 87° C., at least 88° C., at least 89° C., at least 90° C., at least 91° C., at least 92° C., at least 93° C., at least 94° C., or at least 95° C. In another embodiment, the DNA molecules are denatured at a temperature of about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., or about 95° C. In one specific embodiment, the DNA molecules are denatured at a temperature of about 90° C.

Other than denaturation by heat, sections or all the DNA molecules provided herein can undergo the denaturation process by addition of various chemical agents such as guanidine, formamide, sodium salicylate, dimethyl sulfoxide, propylene glycol, and urea. These chemical denaturing agents lower the melting temperature by competing for hydrogen bond donors and acceptors with pre-existing nitrogenous base pairs and allow for isothermal denaturing. In some embodiments, chemical agents are able to induce denaturation at room temperature. In some specific embodiment, alkaline agents (e.g. NaOH) can be used to denature DNA by changing pH and removing hydrogen-bond contributing protons. In other embodiments, chemically denaturing the DNA molecules provided herein can be a gentler procedure for DNA stability compared to denaturation induced by heat. In other embodiments, chemically denaturing and renaturing the DNA molecules (e.g. changing the pH) provided herein can be a quicker than by heating. In some embodiments, the DNA of the disclosure can be replicated and nicked in bacteria and denatured simultaneously during the release (e.g. alkali lysis step) from bacteria.

In one embodiment, the DNA molecules are denatured at a pH of at least 10, at least 10.1, at least 10.2, at least 10.3, at least 10.4, at least 10.5, at least 10.6, at least 10.7, at least 10.8, at least 10.9, at least 11, at least 11.1, at least 11.2, at least 11.3, at least 11.4, at least 11.5, at least 11.6, at least 11.7, at least 11.8, at least 11.9, at least 12, at least 12.1, at least 12.2, at least 12.3, at least 12.4, at least 12.5, at least 13, at least 13.5, or at least 14. In another embodiment, the DNA molecules are denatured at a pH of about 10, about 10.1, about 10.2, about 10.3, about 10.4, about 10.5, about 10.6, about 10.7, about 10.8, about 10.9, about 11, about 11.1, about 11.2, about 11.3, about 11.4, about 11.5, about 11.6, about 11.7, about 11.8, about 11.9, about 12, about 12.1, about 12.2, about 12.3, about 12.4, about 12.5, about 13, about 13.5, or about 14. In yet another embodiment, the DNA molecules are denatured at a salt concentration of at least 1M, at least 1.5M, at least 2M, at least 2.5M, at least 3M, at least 3.5M, or at least 4M of salt. In a further embodiment, the DNA molecules are denatured at a salt concentration of about 1M, about 1.5M, about 2M, about 2.5M, about 3M, about 3.5M, or about 4M of salt. In certain embodiments, the DNA molecule is subject to the denaturing condition for at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 minutes. In other embodiments, the DNA molecule is subject to the denaturing condition for about 1, about 2, about 3, about 4, about 5, about 6, about 7, about 8, about 9, about 10, about 11, about 12, about 13, about 14, about 15, about 16, about 17, about 18, about 19, or about 20 minutes. In some embodiments, the DNA molecules can be denatured by any combination of denaturing conditions and duration of denaturing as provided herein.

The denaturing conditions can be determined for the method step to selectively denaturing the segments between the first and second restriction sites and between the third and fourth restriction sites on the top and bottom strand of the DNA, while keeping the other part of the DNA molecule as dsDNA. Such selective denaturing conditions can be determined according to the properties of the DNA segments to be selectively denatured. The stability of the DNA double helix correlates with the length of the DNA segments and the percentage of G/C content. The disclosure provides that the selective denaturing conditions can be determined by the sequence of the DNA segments to be selectively denatured or the resulting sequence of the overhang. For example, the temperature for selective denaturing can be approximately determined as Tm=2° C.×number of A-T pair+4° C.×number of G-C pair for a DNA sequence to be selectively denatured. Other more precise calculations of the Tm are also known and used in the art, for example, as described in Freier S M, et al., *Proc Natl Acad Sci,* 83, 9373-9377 (1986); Breslauer K J, et al., *Proc Natl Acad Sci,* 83, 3746-3750 (1986); Panjkovich, A. and Melo, F. *Bioinformatics* 21:711-722 (2005); Panjkovich, A., et al. *Nucleic Acids Res* 33:W570-W572 (2005), all of which are herein incorporated in their entireties by reference.

The overhang can comprise various DNA sequences. In one embodiment, the overhang comprises an inverted repeat or a fragment thereof (e.g., at least 50%, 60%, 70%, 75%, 80%, 85%, 90%, 95%, or 99% of an inverted repeat). In another embodiment, the overhang comprises a viral inverted repeat or a fragment thereof (e.g., at least 50%, 60%, 70%, 75%, 80%, 85%, 90%, 95%, or 99% of a viral inverted repeat). In yet another embodiment, the overhang comprises or consists of any embodiments of sequences described in Sections 5.3.1, 5.3.2, 5.3.3, and 5.4. In a further embodiment, the overhang comprises or consists of any one of the sequences as described in Sections 5.3.1 and 5.4. In some embodiments, the overhang does not comprise one or more viral replication related sequences (e.g. RABS, RBE or TRS) as described in Section 5.3.4. In some embodiments, the overhang does not comprise one or more transcriptional activity related sequences (e.g. TSSs or CpG motifs) as described in Section 5.3.4.

5.2.4 Incubating the DNA Molecules with One or More Nicking Endonucleases or Restriction Enzymes The disclosure provides one or more method steps for incubating the DNA molecules with one or more nicking endonucleases or restriction enzymes as described in Sections 3 and 5.2. Without being bound by the theory, a nicking endonuclease recognizes the restriction sites for the nicking endonuclease in the DNA molecule and cuts only on one strand (e.g. hydrolyzes the phosphodiester bond of a single DNA strand) of the dsDNA at a site that is either within or outside the restriction sites for the nicking endonuclease, thereby creating a nick in the dsDNA. A restriction enzyme, on the other hand, recognizes the restriction sites for the restriction enzyme and cuts both strands of the dsDNA, thereby cleaving DNA molecules at or near the specific restriction sites.

In the various embodiments of compositions and methods provided herein, nicking endonucleases can be methylation-dependent, methylation-sensitive, or methylation-insensitive. Various nicking endonucleases known and practiced in the art are provided herein. In some embodiments, the nicking endonucleases for the compositions and methods provided herein can be naturally occurring nicking endonucleases that are not 5-methylcytosine dependent, including Nb.BsmI, Nb.BbvCI, Nb.BsrDI, Nb.BtsI, Nt.BbvCI, Nt.Alwl, Nt. CviPII, Nt. BsmAI, Nt. Alwl and Nt.BstNBI. Nicking endonucleases for the compositions and methods provided herein can also be engineered from Type IIs restriction enzymes (e.g., Alwl, Bpu1OI, BbvCI, BsaI, BsmBI, BsmAI, BsmI, BspOJ, Mlyl, Mval2691 and Sapl, etc.) and methods of making nicking endonucleases can be found in references for example in, U.S. Pat. Nos. 7,081,358; 7,011,966; 7,943,303; 7,820,424, WO201804514, all of which are herein incorporated in their entirety by reference.

Alternatively, a programmable nicking enzyme can be used for the compositions and methods provided herein instead of nicking endonucleases. Such programmable nicking enzyme include, e.g., Cas9 or a functional equivalent thereof (such as *Pyrococcus furiosus* Argonaute (PfAgo) or Cpfl). Cas9 contains two catalytic domains, RuvC and HNH. Inactivating one of those domains will generate a programmable nicking enzyme that can replace a nicking endonuclease for the methods and compositions provided herein. In Cas9, the RuvC domain can be inactivated by an amino acid substitution at position D10 (e.g., D10A) and the HNH domain can be inactivated by an amino acid substitution at position H840 (e.g., H840A), or at a position corresponding to those amino acids in other Cas9 equivalent proteins. Such programmable nicking enzyme can also be Argonaute or Type II CRISPR/Cas endonucleases that comprise two components: a nicking enzyme (e.g., a D10A Cas9 nicking enzyme or variant or ortholog thereof) that cleaves the target DNA and a guide nucleic acid e.g., a guide DNA or RNA (gDNA or gRNA) that targets or programs the nicking enzyme to a specific site in the target DNA (see, e.g., Hsu, et al., Nature Biotechnology 2013 31: 827-832, which is herein incorporated in its entirety by reference). A programmable nicking enzyme can also be made by fusing a site specific DNA binding domain (targeting domain) such as the DNA binding domain of a DNA binding protein (e.g., a restriction endonuclease, a transcription factor, a zinc-finger or another domain in that binds to DNA at non-random positions) with a nicking endonuclease so that it acts on a specific, non-random site. As is clear from the foregoing, the programmable cleavage by a programmable nicking enzyme results from targeting domain within or fused to the nicking enzyme or from guide molecules (gDNA or gRNA) that direct the nicking enzyme to a specific, non-random site, which site can be programmed by changing the targeting domain or the guide molecule. Such programmable nicking enzymes can be found in references for example, U.S. Pat. No. 7,081,358 and WO2010021692A, which are herein incorporated in their entireties by reference.

Suitable guide nucleic acid (e.g. gDNA or gRNA) sequences and suitable target sites for the guide nucleic acid have been known and widely utilized in the art. The guide nucleic acid (e.g. gDNA or gRNA) is a specific nucleic acid (e.g. gDNA or gRNA) sequence that recognizes the target DNA region of interest and directs the programmable nicking enzyme (e.g. Cas nuclease) there for editing. The guide nucleic acid (e.g. gDNA or gRNA) is often made up of two parts: targeting nucleic acid, a 15-20 nucleotide sequence complementary to the target DNA, and a scaffold nucleic acid, which serves as a binding scaffold for the programmable nicking enzyme (e.g. Cas nuclease). The suitable target sites for the guide nucleic acid must have two components the complementary sequence to the targeting nucleic acid in the programmable nicking enzyme and an adjacent Protospacer Adjacent Motif (PAM). The PAM serves as a binding signal for the programmable nicking enzyme (e.g. Cas nuclease). Various PAMs have been known, characterized, and utilized in the art, for example as discussed in Daniel Gleditzsch et al., *RNA Biol.* 16(4): 504-517 (April 2019); Ryan T. Leenay et al., *Mol Cell.* 62(1): 137-147 (Apr. 7, 2016), both of which are herein incorporated in their entirety by reference. Exemplary gRNA and gDNA sequences targeting the primary stem sequence of AAV2 ITRs include such listed in Table 1.

TABLE 1

Exemplary Nicking Endonuclease and Their Corresponding Restriction Sites

| | |
|---|---|
| SEQ ID NO: 176<br>AAV2 wt gRNA for Nicking Cas9 | AGCGAGCGAGCGCGCAGAGAGGG |
| SEQ ID NO: 177<br>AAV2 wt gDNA for PfAgo | GCTCGCTCGCTCGGTG |

Various nicking endonucleases known and used in the art can be used in the methods provided herein. An exemplary list of nicking endonuclease provided as embodiments for the nicking endonuclease for use in the methods and the corresponding restriction sites for some of the nicking endonuclease are described in The Restriction Enzyme Database (known in the art as REBASE), which is available at www.rebase.neb.com/cgi-bin/azlist?nick and incorporated herein in its entirety by reference. In one embodiments, the nicking endonuclease that recognizes the first, second, third, and/or fourth restriction site are all for target sequences for the same nicking endonuclease. In another embodiment, the first, second, third, and fourth restriction sites for nicking endonucleases are target sequences for two different nicking endonucleases, including all possible combinations of arranging the four sites for two different nicking endonuclease target sequences (e.g. the first restriction site for the first nicking endonuclease and the rest for the second nicking endonuclease, the first and second restriction sites for the first nicking endonuclease and the rest for the second nicking endonuclease etc.). In yet another embodiment, the first, second, third, and fourth restriction sites for nicking endonucleases are target sequences for three different nicking endonucleases, including all possible combinations of arranging the four sites for three different endonuclease target sequences. In a further embodiment, the first, second, third, and fourth restriction sites for nicking endonucleases are target sequences for four different nicking endonucleases. In some embodiments, the nicking endonuclease can be any one selected from those listed in Table 2.

TABLE 2

Exemplary Nicking Endonuclease and Their Corresponding Restriction Sites:

| Nicking Endonuclease | Corresponding Restriction Sites for the Nicking Endonuclease and Position of Nick Relative to the Restriction Sites (Note: 1/none means the nick is 1 nucleotide 3' from the restriction sites on the top strand). |
|---|---|
| Nt. BsmAI | GTCTC (1/none) |
| Nt. BtsCI | GGATG (2/none) |
| N. ALwl | GGATC (4/none) |
| N. BstNBI | GAGTC (4/none) |
| N. BspD6I | GAGTC (4/none) |
| Nb. Mva1269I | GAATGC (none/-1) |
| Nb. BsrDI | GCAATG (none/0) |
| Nb. BtsI | GCAGTG (none/0) |
| Nt. BtsI | GCAGTG (2/none) |
| Nt. BsaI | GGTCTC (1/none) |
| Nt. Bpu10I | CCTNAGC (-5/none) |
| Nb. Bpu10I | CCTNAGC (none/-2) |
| Nt. BsmBI | CGTCTC (1/none) |
| Nb. BbvCI | CCTCAGC (none/-2) |
| Nt. BbvCI | CCTCAGC (-5/none) |
| Nt. BspQI | GCTCTTC (1/none) |

The conditions for the various nicking endonuclease to cut one strand of the dsDNA are known for the various nicking endonucleases provided herein, including the temperatures, the salt concentration, the pH, the buffering reagent, the presence or absence of certain detergent, and the duration of incubation to achieve the desired percentage of nicked DNA molecules. These conditions are readily available from the websites or catalogs of various vendors of the nicking endonucleases, e.g. New England BioLabs. The disclosure provides that the step of incubating the DNA molecule with one or more nicking endonuclease is performed according to the incubation conditions as known and practiced in the art. In some embodiments, the step of incubating the DNA molecule with one or more nicking endonuclease is according to the incubation conditions optimized by methods known in the art.

Various restriction enzymes known and used in the art can be used in the methods provided herein. An exemplary list of restriction enzymes provided as embodiments for the restriction enzymes for use in the methods and the corresponding restriction sites for the restriction enzymes are described in the catalog of New England Biolabs, which is available at neb.com/products/restriction-endonucleases and incorporated herein in its entirety by reference. The conditions for the various restriction enzymes to cleave the dsDNA are known for the various restriction enzymes provided herein, including the temperatures, the salt concentration, the pH, the buffering reagent, the presence or absence of certain detergent, and the duration of incubation to achieve the desired percentage of nicked DNA molecules. These conditions are readily available from the websites or catalogs of various vendors of the restriction enzymes, e.g. New England BioLabs. The disclosure provides that the step of incubating the DNA molecule with the restriction enzymes is performed according to the incubation conditions as known and practiced in the art.

5.2.5 Annealing

The step of annealing in the methods provided herein is performed to selectively anneal the ssDNA overhang intramolecularly and thereby creating a hairpinned inverted repeat on one end of the DNA fragment (e.g. from Sections 5.3 and 5.4) resulted from the step of denaturing as described above (Section 5.2.3). In certain embodiments, the step of annealing in the methods provided herein is performed to selectively anneal the ssDNA overhangs intramolecularly and thereby creating hairpinned inverted repeats on two ends the DNA fragment (e.g. from Sections 5.3 and 5.4) resulted from the step of denaturing as described above (Section 5.2.3). Without being bound or otherwise limited by the theory, such selective intramolecular annealing of the ssDNA overhangs is achieved because the intramolecular complementary sequences within the ssDNA overhangs make the intramolecular annealing of the ssDNA overhangs thermodynamically and/or kinetically favored over the intermolecular annealing of the ssDNA overhangs.

Figure 2A:
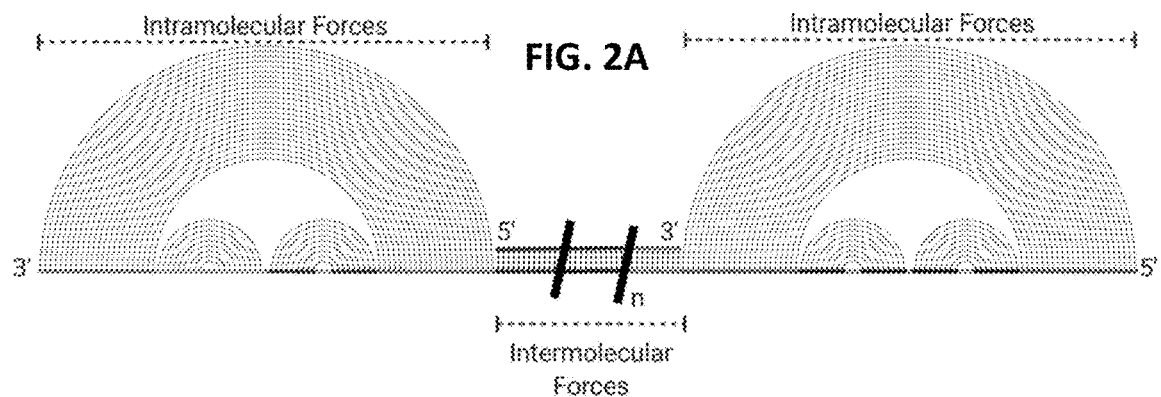
FIGS. 2A and 2B depict a linear interaction plot showing exemplary strand conformations and intramolecular forces within the overhang as well as intermolecular forces between the strands and FIG. 2C depicts the expected annealed structure of FIG. 2A and FIG. 2B.
Figure 2B:
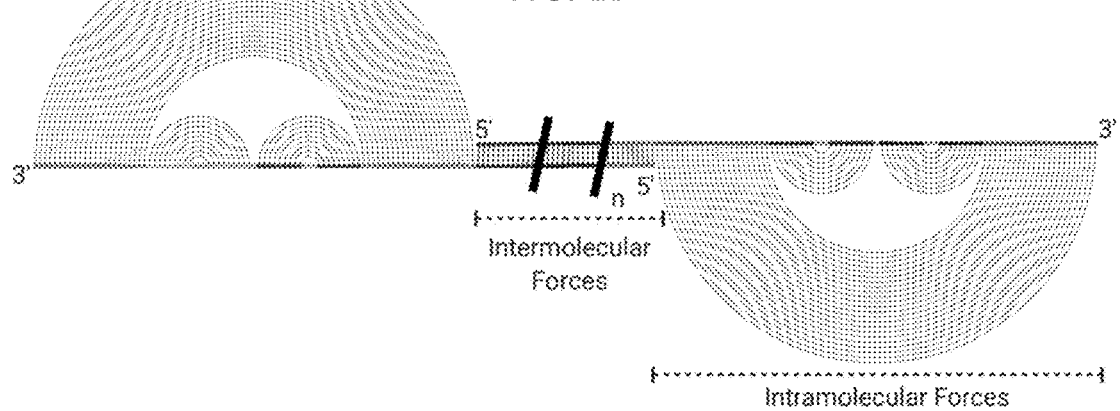
Figure 2C:
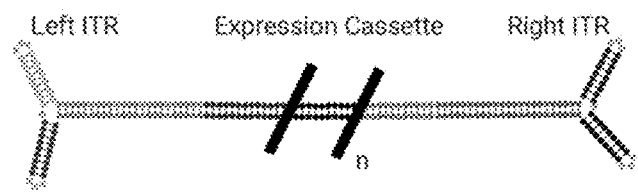

Without being bound or otherwise limited by the theory, it is recognized that certain lengths and/or the sequences of the overhang can make the intramolecular annealing of the ssDNA overhangs thermodynamically and/or kinetically favored over the intermolecular annealing of the ssDNA overhangs. For example, a linear interaction plot showing the intramolecular forces within the overhang and intermolecular forces between the strands as well as the resulting structure is depicted in FIG. 2A-C. The thermodynamics and the kinetics of the annealing of the ssDNA overhang is determined by the enthalpy (ΔH) and the entropy (ΔS), among other factors. The inventors recognize that, as the loss of movement freedom from a free ssDNA overhang to an intramolecularly annealed overhang is less than the loss of movement freedom from free ssDNA overhang to intermolecularly annealed overhang, the entropy loss in an intramolecular annealing is less than the entropy loss in an intramolecular annealing. On the other hand, as the number of complementary nucleotide pairs in an intramolecularly annealed overhang is less than number of complementary nucleotide pairs in an intermolecularly annealed overhang (hence less Watson-Crick and Hoogsteen-type hydrogen bonding), the enthalpy gain in an intramolecular annealing may be less than the enthalpy gain in an intramolecular annealing. The disclosure provides that the ssDNA overhang can be designed to have certain lengths, numbers of complementary nucleotide pairs, and percentage of G-C and A-T pairs, such that the free energy gain (ΔG=ΔH−TΔS) of intramolecular annealing of the overhang is bigger over that of intermolecular annealing, thereby making the intramolecular annealing thermodynamically favored over the intermolecular annealing. The inventors further recognize that, as the nucleotides within the ssDNA overhang have a higher probability of contacting each other than contacting the nucleotides of another ssDNA overhang in molecular motion, the kinetics of intramolecular annealing of the ssDNA overhang can be higher than that of intermolecular annealing. The disclosure provides that even if the intramolecular annealing is thermodynamically disfavored over the intermolecular annealing, the superior kinetics of intramolecular annealing of the ssDNA overhang can result in the formation of intramolecularly annealed overhang over intermolecularly annealed overhang.

The annealing step can be performed at various temperatures to favor the intramolecular annealing over intermolecular annealing. In one embodiment, the ssDNA overhang is annealed at a temperature of at least 15° C., at least 16° C., at least 17° C., at least 18° C., at least 19° C., at least 20° C., at least 21° C., at least 22° C., at least 23° C., at least 24° C., at least 25° C., at least 26° C., at least 27° C., at least 28° C., at least 29° C., at least 30° C., at least 31° C., at least 32° C., at least 33° C., at least 34° C., at least 35° C., at least 36° C., at least 37° C., at least 38° C., at least 39° C., at least 40° C., at least 41° C., at least 42° C., at least 43° C., at least 44° C., at least 45° C., at least 46° C., at least 47° C., at least 48° C., at least 49° C., at least 50° C., at least 51° C., at least 52° C., at least 53° C., at least 54° C., at least 55° C., at least 56° C., at least 57° C., at least 58° C., at least 59° C., or at least 60° C. In another embodiment, the ssDNA overhang is annealed at a temperature of about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., or about 60° C. In one specific embodiment, the ssDNA overhang is annealed at a temperature of at least 25° C. In another specific embodiment, the ssDNA overhang is annealed at a temperature of about 25° C. In yet another specific embodiment, the ssDNA overhang is annealed at room temperature.

Additionally, the annealing step can be performed for various durations of time to favor the intramolecular annealing over intermolecular annealing. In certain embodiments, the ssDNA overhang is annealed for at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, or at least 40 minutes. In other embodiments, the ssDNA overhang is annealed for about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, or about 40 minutes. In one specific embodiment, the ssDNA overhang is annealed for at least 20 minutes. In another specific embodiment, the ssDNA overhang is annealed for about 20 minutes.

In some embodiments, annealing can be accomplished by lowering the temperature below the calculated melting temperatures of the sense and antisense sequence pairs. The melting temperature is dependent upon the specific nucleotide base content and the characteristics of the solution being used, e.g., the salt concentration. Melting temperatures for any given sequence and solution combination are readily calculated as known and practiced in the art.

In some embodiments, annealing can be accomplished isothermally by reducing the amount of denaturing chemical agents to allow an interaction between the sense and antisense sequence pairs. The minimum concentration of denaturing chemical agents required to denature the DNA sequence can dependent upon the specific nucleotide base content and the characteristics of the solution being used, e.g., temperature or the salt concentration. The concentration of chemical denaturing agents that do not lead to denaturing for any given sequence and solution combination are readily identified as known and practiced in the art. The concentration of chemical denaturing agents can also be readily modified as known and practiced in the art. For example, the amount of urea can be lowered by dialysis or tangential flow filtration or the pH can be changed by the addition of acids or bases.

The annealing temperature and the annealing duration for intramolecular annealing correlate with the lengths of the ssDNA overhang, the number of complementary nucleotide pairs, and percentage of G-C and A-T pairs, and the sequence of the ssDNA overhang (the arrangement of the complementary nucleotide pairs). In certain embodiments, an ssDNA overhang provided for the methods provided herein comprises any number of nucleotides in length as described in Section 5.2.3. In certain embodiments, a ssDNA overhang provided for the methods provided herein comprises at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, or at least 50 intramolecularly complementary nucleotide pairs. In some embodiments, a ssDNA overhang provided for the methods provided herein comprises about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, or about 50 intramolecularly complementary nucleotide pairs. In some embodiments, a ssDNA overhang provided for the methods provided herein comprises at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, or at least 90% G-C pairs among intramolecularly complementary nucleotide pairs. In certain embodiments, a ssDNA overhang provided for the methods provided herein comprises about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, or about 90% G-C pairs among intramolecularly complementary nucleotide pairs.

Additionally, the inventors recognize that the concentration of the DNA molecules, which correlates with the concentration of the overhangs, can affect the equilibrium and kinetics of the intramolecular annealing and the intermolecular annealing of the overhangs. Without being bound or otherwise limited by the theory, when the concentration of the overhang is too high, the probability of the intermolecular contact among the overhangs increases and the kinetic advantage of the intramolecular contact over intermolecular contact seen at lower concentration as discussed above is then diminished.

As discussed above, in some embodiments, intramolecular interactions can occur at a faster rate while intermolecular interactions occur at a slower rate. In some embodiments, base pair interactions involving three or more molecules (e.g. three different strands) occur at the slowest rate. In some embodiments, the kinetic rate of intramolecular interactions versus intermolecular interactions is governed by the concentration of each molecule. In some embodiments, the intramolecular interactions are kinetically faster or intramolecular forces are larger when the concentration of DNA strands is lower.

Viewed individually, the absolute free energy of forming each complementary domain of IRs or ITRs, may be different, leading to regions of the IR or ITR that may locally fold earlier as the strand transitions from a denatured to annealed state. The presence of locally folded domains (e.g. a central hairpin or branched hairpin like in AAV2 ITRs as described in elsewhere in this Section (Section 5.3.1) and Section 5.4) can reduce the amount of bases available for pairing with other strands and thus can reduce the likelihood of intermolecular annealing or hybridization and shift the equilibrium from intermolecular annealing to intramolecular annealing or ITR formation.

Accordingly, the disclosure provides that the annealing step can be performed at various concentrations to favor the intramolecular annealing over intermolecular annealing. In some embodiments, the ssDNA overhang is annealed at a concentration of no more than 1, no more than 2, no more than 3, no more than 4, no more than 5, no more than 6, no more than 7, no more than 8, no more than 9, no more than 10, no more than 11, no more than 12, no more than 13, no more than 14, no more than 15, no more than 16, no more than 17, no more than 18, no more than 19, no more than 20, no more than 21, no more than 22, no more than 23, no more than 24, no more than 25, no more than 26, no more than 27, no more than 28, no more than 29, no more than 30, no more than 31, no more than 32, no more than 33, no more than 34, no more than 35, no more than 36, no more than 37, no more than 38, no more than 39, no more than 40, no more than 41, no more than 42, no more than 43, no more than 44, no more than 45, no more than 46, no more than 47, no more than 48, no more than 49, no more than 50, no more than 55, no more than 60, no more than 65, no more than 70, no more than 75, no more than 80, no more than 85, no more than 90, no more than 95, no more than 100, no more than 110, no more than 120, no more than 130, no more than 140, no more than 150, no more than 160, no more than 170, no more than 180, no more than 190, no more than 200, no more than 210, no more than 220, no more than 230, no more than 240, no more than 250, no more than 260, no more than 270, no more than 280, no more than 290, no more than 300, no more than 325, no more than 350, no more than 375, no more than 400, no more than 425, no more than 450, no more than 475, no more than 500, no more than 550, no more than 600, no more than 650, no more than 700, no more than 750, no more than 800, no more than 850, no more than 900, no more than 950, no more than 1000 ng/µl for the DNA molecules. In certain embodiments, the ssDNA overhang is annealed at a concentration of about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375, about 400, about 425, about 450, about 475, about 500, about 550, about 600, about 650, about 700, about 750, about 800, about 850, about 900, about 950, about 1000 ng/µl for the DNA molecules.

Similarly, the disclosure provides that the annealing step can be performed at various molar concentrations to favor the intramolecular annealing over intermolecular annealing. In some embodiments, the ssDNA overhang is annealed at a concentration of no more than 1, no more than 2, no more than 3, no more than 4, no more than 5, no more than 6, no more than 7, no more than 8, no more than 9, no more than 10, no more than 11, no more than 12, no more than 13, no more than 14, no more than 15, no more than 16, no more than 17, no more than 18, no more than 19, no more than 20, no more than 21, no more than 22, no more than 23, no more than 24, no more than 25, no more than 26, no more than 27, no more than 28, no more than 29, no more than 30, no more than 31, no more than 32, no more than 33, no more than 34, no more than 35, no more than 36, no more than 37, no more than 38, no more than 39, no more than 40, no more than 41, no more than 42, no more than 43, no more than 44, no more than 45, no more than 46, no more than 47, no more than 48, no more than 49, no more than 50, no more than 55, no more than 60, no more than 65, no more than 70, no more than 75, no more than 80, no more than 85, no more than 90, no more than 95, no more than 100, no more than 110, no more than 120, no more than 130, no more than 140, no more than 150, no more than 160, no more than 170, no more than 180, no more than 190, no more than 200, no more than 210, no more than 220, no more than 230, no more than 240, no more than 250, no more than 260, no more than 270, no more than 280, no more than 290, no more than 300, no more than 325, no more than 350, no more than 375, no more than 400, no more than 425, no more than 450, no more than 475, no more than 500, no more than 550, no more than 600, no more than 650, no more than 700, no more than 750, no more than 800, no more than 850, no more than 900, no more than 950, no more than 1000 nM for the DNA molecules. In certain embodiments, the ssDNA overhang is annealed at a concentration of about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 55, about 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, about 300, about 325, about 350, about 375, about 400, about 425, about 450, about 475, about 500, about 550, about 600, about 650, about 700, about 750, about 800, about 850, about 900, about 950, about 1000 nM for the DNA molecules. In some further embodiments, the ssDNA overhang is annealed at a concentration of no more than 1, no more than 2, no more than 3, no more than 4, no more than 5, no more than 6, no more than 7, no more than 8, no more than 9, no more than 10, no more than 11, no more than 12, no more than 13, no more than 14, no more than 15, no more than 16, no more than 17, no more than 18, no more than 19, no more than 20 µM. In yet other embodiments, the ssDNA overhang is annealed at a concentration of about 1, about 2, about 3, about 4, about 5, about 6, about 7, about 8, about 9, about 10, about 11, about 12, about 13, about 14, about 15, about 16, about 17, about 18, about 19, about 20 µM. In one specific embodiment, the ssDNA overhang is annealed at a concentration of about 10 nM for the DNA molecules. In another specific embodiment, the ssDNA overhang is annealed at a concentration of about 20 nM for the DNA molecules. In yet another specific embodiment, the ssDNA overhang is annealed at a concentration of about 30 nM for the DNA molecules. In a further specific embodiment, the ssDNA overhang is annealed at a concentration of about 40 nM for the DNA molecules. In still another specific embodiment, the ssDNA overhang is annealed at a concentration of about 50 nM for the DNA molecules. In another specific embodiment, the ssDNA overhang is annealed at a concentration of about 60 nM for the DNA molecules. In one specific embodiment, the ssDNA overhang is annealed at a concentration of about 10 ng/µl for the DNA molecules. In another specific embodiment, the ssDNA overhang is annealed at a concentration of about 20 ng/µl for the DNA molecules. In yet another specific embodiment, the ssDNA overhang is annealed at a concentration of about 30 ng/µl for the DNA molecules. In a further specific embodiment, the ssDNA overhang is annealed at a concentration of about 40 ng/µl for the DNA molecules. In one specific embodiment, the ssDNA overhang is annealed at a concentration of about 50 ng/µl for the DNA molecules. In another specific embodiment, the ssDNA overhang is annealed at a concentration of about 60 ng/µl for the DNA molecules. In yet another specific embodiment, the ssDNA overhang is annealed at a concentration of about 70 ng/µl for the DNA molecules. In one specific embodiment, the ssDNA overhang is annealed at a concentration of about 80 ng/µl for the DNA molecules. In another specific embodiment, the ssDNA overhang is annealed at a concentration of about 90 ng/µl for the DNA molecules. In yet another specific embodiment, the ssDNA overhang is annealed at a concentration of about 100 ng/µl for the DNA molecules.

In some embodiments, an ssDNA overhang provided for the methods provided herein comprises any sequences listed in Table 3.

TABLE 3

Sequences of ssDNA overhang and the corresponding structure after annealing.

Figure 1:
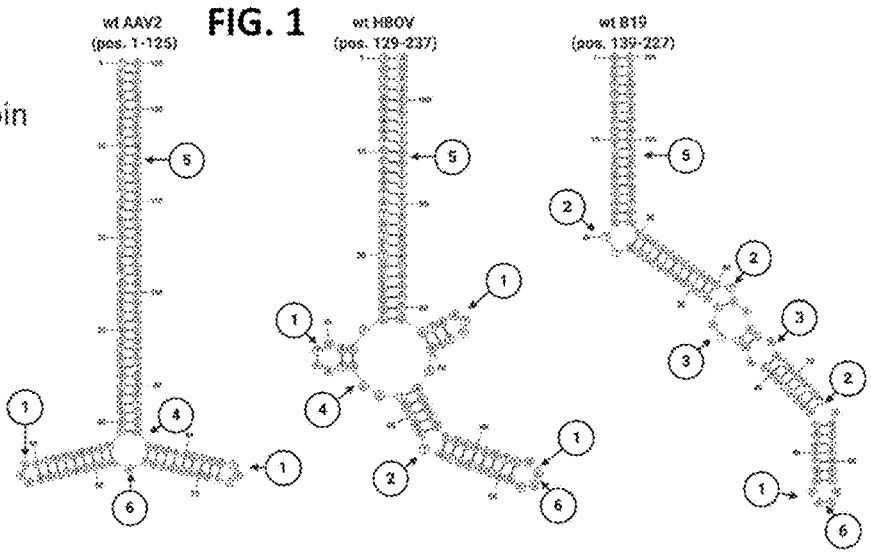
FIG. 1 depicts the structures of various exemplary hairpins and the structural elements of the hairpins.
Figure 3:
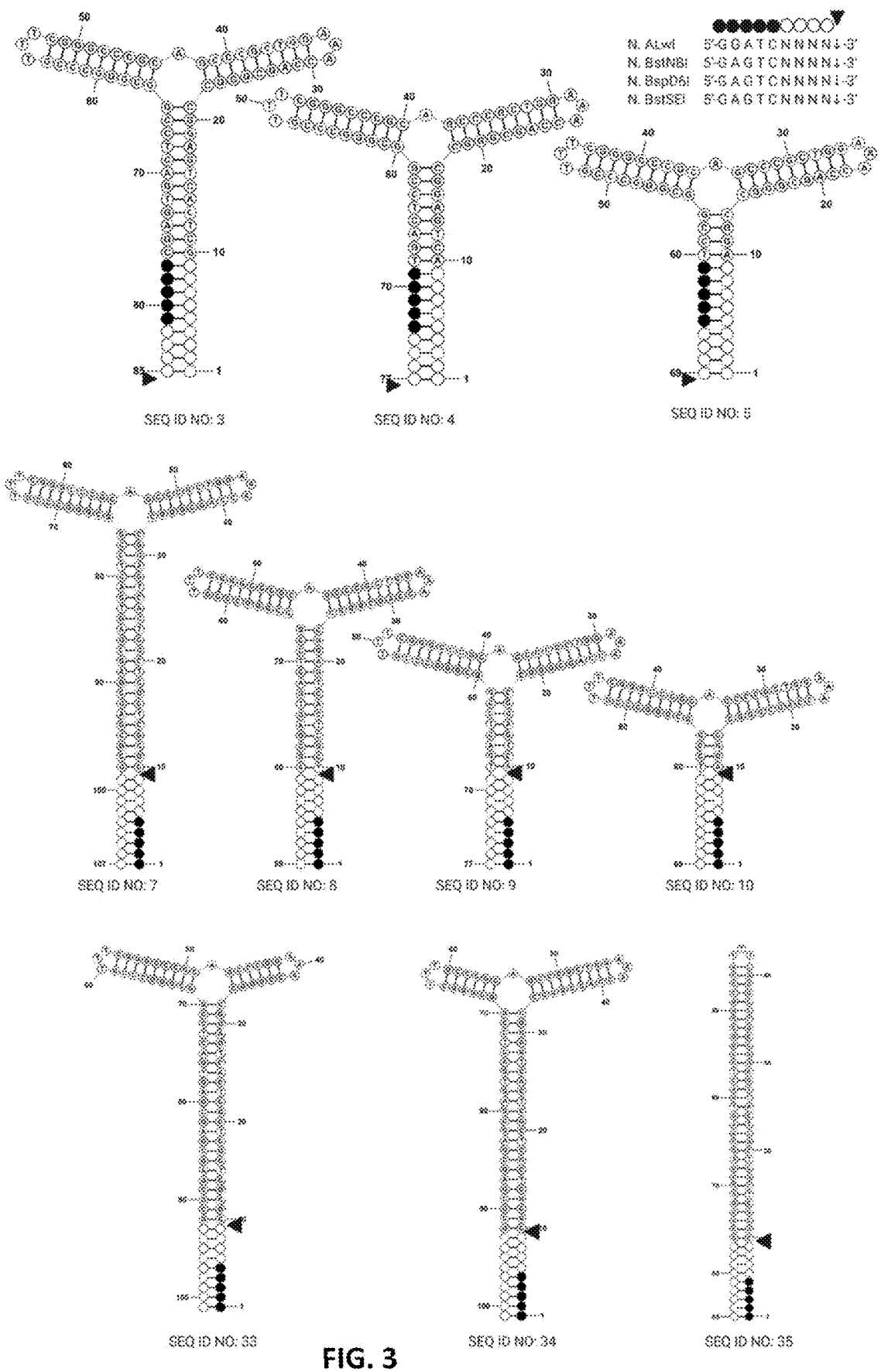
FIG. 3 depicts various exemplary arrangements of hairpins and the location of various restriction sites as well as restriction sites for type II nicking endonucleases in the primary stem of a hairpin
Figure 4:
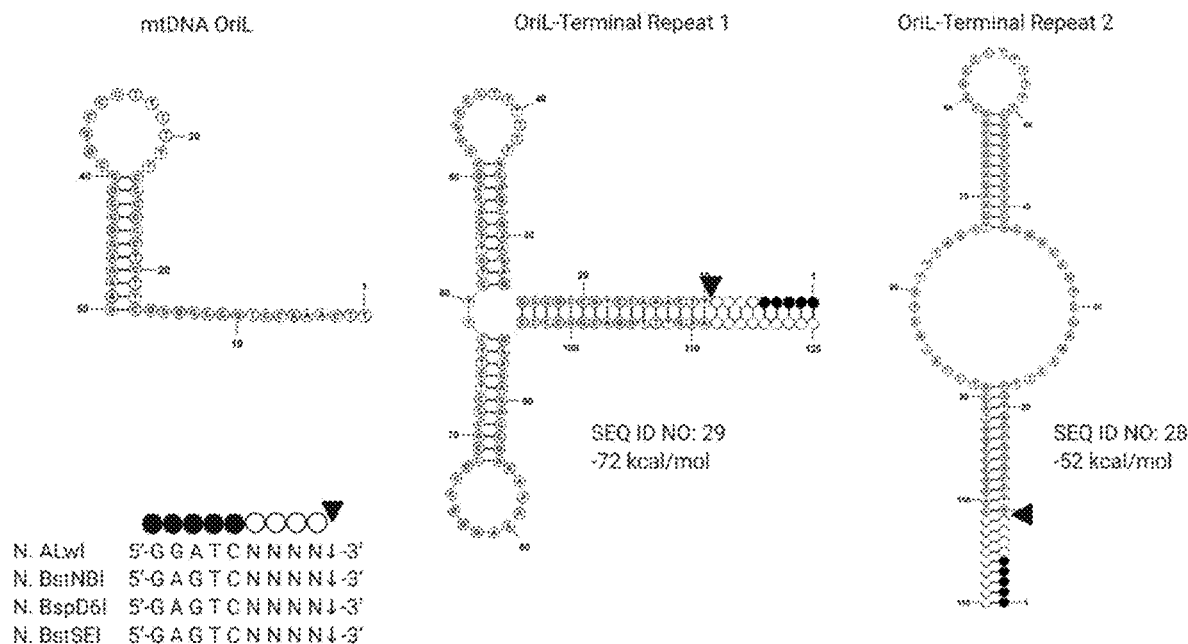
FIG. 4 depicts the structures of various exemplary hairpins and the structural elements of human mitochondrial DNA OriL and OriL derived ITRs.
Figure 5:
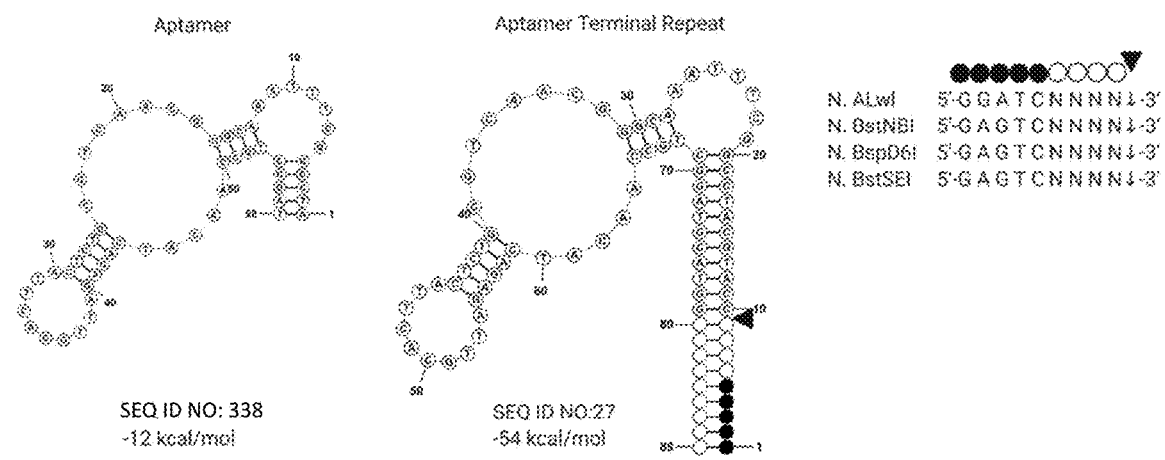
FIG. 5 depicts the structures of hairpins of an exemplary aptamer and aptamer ITR.

| ssDNA overhang sequences | Structures after annealing |
| --- | --- |
| SEQ ID NO: 3 | FIG. 3 |
| SEQ ID NO: 4 | FIG. 3 |
| SEQ ID NO: 5 | FIG. 3 |
| SEQ ID NO: 7 | FIG. 3 |
| SEQ ID NO: 8 | FIG. 3 |
| SEQ ID NO: 9 | FIG. 3 |
| SEQ ID NO: 10 | FIG. 3 |
| SEQ ID NO: 33 | FIG. 3 |
| SEQ ID NO: 34 | FIG. 3 |
| SEQ ID NO: 35 | FIG. 3 |
| SEQ ID NO: 27 | FIG. 5 |
| SEQ ID NO: 29 | FIG. 4 |
| SEQ ID NO: 28 | FIG. 4 |
| SEQ ID NO. 183 (HBOV (nucleotides 129-237 on wt genome)) | FIG. 1 |
| SEQ ID NO. 184 (B19 (nucleotides 139-227 on wt genome)) | FIG. 1 |

In some embodiments, the structure of the DNA molecules provided herein is the same after 2, 3, 4, 5, 10 or 20 cycles of denaturing/renaturing (e.g. denaturing as described in Section 5.2.3 and re-annealing as described in this Section (Section 5.2.5)). DNA structures can be described by an ensemble of structures at or around the energy minimum. In certain embodiments, the ensemble DNA structure is the same after 2, 3, 4, 5, 10 or 20 cycles of denaturing/renaturing. In one embodiment, the folded hairpin structure formed from the ITR or IR provided herein is the same after 2, 3, 4, 5, 10 or 20 cycles of denaturing/renaturing. In another embodiment, the ensemble structure of the folded hairpin is the same after 2, 3, 4, 5, 10 or 20 cycles of denaturing/renaturing.

5.2.6 Incubating with Exonuclease

The disclosure provides a step of incubating with an exonuclease as described in Section 3. Exonucleases cleaves nucleotides from the end (exo) of a DNA molecules. Exonucleases can cleave nucleotides along the 5' to 3' direction, along the 3' to 5' direction, or along both directions. In certain embodiments, an exonuclease for use in the methods provided herein cleaves nucleotides with no sequence specificity. In some embodiments, an exonuclease for use in the methods provided herein digests the DNA fragments comprising ends created by one or more nicking endonuclease recognizing and cutting the fifth and sixth restriction sites or by restriction enzyme cleaving the plasmid or a fragment of the plasmid, as provided in Section 3.

Various exonucleases known and used in the art can be used in the methods provided herein. An exemplary list of exonucleases provided as embodiments for the restriction enzymes for use in the methods are described in the catalog of New England Biolabs, which is available at neb.com/products/dna-modifying-enzymes-and-cloning-technologies/nucleases and incorporated herein in its entirety by reference. The conditions for the various exonucleases to digest the DNA molecules are known for the various exonucleases provided herein, including the temperatures, the salt concentration, the pH, the buffering reagent, the presence or absence of certain detergent, and the duration of incubation to achieve the desired percentage of digestion. These conditions are readily available from the websites or catalogs of various vendors of the restriction enzymes, e.g. New England BioLabs. The disclosure provides that the step of incubating the DNA molecule with the restriction enzymes is performed according to the incubation conditions as known and practiced in the art.

The step of incubating exonucleases selectively digests the DNA molecules with one or more ends, while leaving the hairpin-ended DNA molecules intact. As is clear from the description of Sections 5.2.5 and 5.4, the hairpin-ended DNA molecules comprise 0, 1, 2, or more nicks. In some embodiments, an exonuclease for use in the methods provided herein can be an exonuclease that selectively digests DNA molecules with one or more ends, while leaving intact the circular ssDNA/dsDNA molecules or DNA molecules comprising one or more nicks but no ends. In one embodiment, an exonuclease for use in the methods provided herein can be Exonuclease V (RecBCD). In one embodiment, an exonuclease for use in the methods provided herein can be Exonuclease VIII or truncated Exonuclease VIII. Exonuclease V (RecBCD), Exonuclease VIII, and truncated Exonuclease VIII comprise the selectivity described in this paragraph. In certain embodiments, an exonuclease for use in the methods provided herein can be an exonuclease that selectively digests linear segments of DNA molecules, initiating from one or more nicks, but which cannot progress through folded hairpins, terminating the digestion at the hairpin and leaving a ssDNA behind. In certain embodiments, an exonuclease for use to initiate at one or more nicks and/or double strand break can be a T7 exonuclease. Other suitable exonucleases are also known, used in the art, and provided herein, for example, as described on the websites or in the catalogs of various vendors of exonucleases including New England BioLabs.

In some embodiments, after exonuclease treatment, the DNA molecules of the present disclosure are substantially free of any prokaryotic backbone sequences. In some embodiments, the backbone refers to the plasmid sequence that is not part of the sequence encompassing the expression cassette in between the two ITRs. In some embodiments, the backbone refers to the vector sequence that is not part of the sequence encompassing the expression cassette in between the two ITRs. In some embodiments, the isolated DNA molecules of the disclosure are 100% free, 99% free, 98% free, 97% free, 96% free, 95% free, 94% free, 93% free, 92% free, 91% free, or 90% free of prokaryotic backbone sequence of the parental plasmid.

5.2.7 Repairing the Nicks with a Ligase

The disclosure provides an optional step of repairing the nicks with a ligase as described in Section 3. DNA ligases catalyze the joining of two ends of DNA molecules by forming one or more new covalent bonds. For example, commonly used T4 DNA ligase catalyzes the formation of a phosphodiester bond between juxtaposed 5' phosphate and 3' hydroxyl termini in DNA. The formation of new covalent bonds that are catalyzed by ligase to joint two DNA molecules is referred to as "ligation." In certain embodiments, a DNA ligase for use in the methods provided herein ligates nucleotides with no sequence specificity. In some embodiments, a DNA ligase for use in the methods provided herein ligates the two ends at one nick of the DNA molecule described in Section 5.4, thereby repairing said one nick. In some embodiments, a DNA ligase for use in the methods provided herein ligates each pair of two ends at the two nicks of the DNA molecule described in Section 5.4, thereby repairing the two nicks. In some embodiments, a DNA ligase for use in the methods provided herein ligates each pair of two ends at all nicks of the DNA molecule described in Section 5.4, thereby repairing all nicks of the DNA molecule. When the DNA molecule described in Section 5.4 forms a circular DNA after all nicks of the DNA molecule described in Section 5.4 have been repaired. As described in Section 5.4, in some embodiments, the DNA molecule described in Section 5.4 consists of two nicks. In certain embodiments, the DNA molecule described in Section 5.4 comprises two nicks. In other embodiments, the DNA molecule described in Section 5.4 consists of one nick. In yet other embodiments, the DNA molecule described in Section 5.4 comprises one nick.

In some embodiments, the step of repairing the nicks with a ligase can be performed according to the incubation conditions as known and practiced in the art.

Various ligases known and used in the art can be used in the methods provided herein. An exemplary list of ligases provided as embodiments for the ligases for use in the methods are described in the catalog of New England Biolabs, which is available at neb.com/products/dna-modifying-enzymes-and-cloning-technologies/dna-ligases/dna-ligases and incorporated herein in its entirety by reference. The conditions for the various ligases to digest the DNA molecules are known for the various ligases provided herein, including the temperatures, the salt concentration, the pH, the buffering reagent, the presence or absence of certain detergent, and the duration of incubation to achieve the desired percentage of digestion. These conditions are readily available from the websites or catalogs of various vendors of the restriction enzymes, e.g. New England BioLabs. The ligation conditions also correlates with the freedom of movement of the two DNA ends to be ligated. When the two DNA ends can be brought to proximity or can have a higher probability of coming to proximity of each other, for example by both ends annealing to a common DNA strand, ligation can be enhanced. In one embodiment, the method step provided in this Section (Section 5.2.7) repairs the nicks with a ligase to form a circular DNA, wherein the two DNA ends at any nick of the DNA molecule described in Section 5.4 have annealed to a common DNA strand. In some embodiments, the step of repairing the nicks with a ligase is performed according to the incubation conditions as known and practiced in the art.

In certain embodiments, the methods provided in this Section 5.2 can be used to generate the hairpin-ended DNA molecules described herein at high scale, high yield, and/or high purity. In certain embodiments, high scale, high yield, and/or high purity can be accomplished in a single reaction vessel. In certain embodiments, the high scale is at least 1 mg, 10 mg, 100 mg, 1 g, 10 g, 100 g, 1 kg, or at least 10 kg. In certain embodiment, the high yield is at least 50%, 60%, 70%, 80%, 90%, 95%, 98%, or at least 99% yield (comparing number of plasmid copies used as input and number of hairpin-ended DNA molecules as product). In certain embodiments, the high purity is at least 50%, 60%, 70%, 80%, 90%, 95%, 98%, or at least 99% purity of hairpin-ended DNA molecules as product as a result of a method provided herein.

5.3 DNA Molecules Used in the Methods

The disclosure provides various aspects and embodiments of the DNA molecules for use in the methods provided herein as described in Section 3 above. In one aspect, provided herein is a double-stranded DNA molecule comprising in 5' to 3' direction of the top strand: i) a first inverted repeat (e.g. as described in Section 5.3.1), wherein a first and a second restriction site for nicking endonuclease are arranged on opposite strands in proximity of the first inverted repeat such that nicking results in a top strand 5' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a third and a fourth restriction site for nicking endonuclease are arranged on opposite strands in proximity of the second inverted repeat such that nicking results in a top strand 3' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2). In certain embodiments, the top strand 5' overhang comprises the first inverted repeat. In certain embodiments, the top strand 3' overhang comprises the second inverted repeat. In certain embodiments, the top strand 5' overhang comprises the first inverted repeat and the top strand 3' overhang comprises the second inverted repeat.

In another aspect, provided herein is a double strand DNA molecule comprising in 5' to 3' direction of the top strand: i) a first inverted repeat (e.g. as described in Section 5.3.1), wherein a first and a second restriction site for nicking endonuclease are arranged on opposite strands in proximity of the first inverted repeat such that nicking results in a bottom strand 3' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a third and a fourth restriction site for nicking endonuclease are arranged on opposite strands in proximity of the second inverted repeat such that nicking results in a bottom strand 5' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2 or depicted in FIGS. 2A and 2C). In certain embodiments, the bottom strand 3' overhang comprises the first inverted repeat. In certain embodiments, the bottom strand 5' overhang comprises the second inverted repeat. In certain embodiments, the bottom strand 3' overhang comprises the first inverted repeat and the bottom strand 5' overhang comprises the second inverted repeat.

In yet another aspect, provided herein is a double-stranded DNA molecule comprising in 5' to 3' direction of the top strand: i) a first inverted repeat (e.g. as described in Section 5.3.1), wherein a first and a second restriction site for nicking endonuclease are arranged on opposite strands in proximity of the first inverted repeat such that nicking results in a top strand 5' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a third and a fourth restriction site for nicking endonuclease are arranged on opposite strands in proximity of the second inverted repeat such that nicking results in a bottom strand 5' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2). In certain embodiments, the top strand 5' overhang comprises the first inverted repeat. In certain embodiments, the bottom strand 5' overhang comprises the second inverted repeat. In certain embodiments, the top strand 5' overhang comprises the first inverted repeat and the bottom strand 5' overhang comprises the second inverted repeat.

In a further aspect, provide herein is a double strand DNA molecule comprising in 5' to 3' direction of the top strand: i) a first inverted repeat (e.g. as described in Section 5.3.1), wherein a first and a second restriction site for nicking endonuclease are arranged on opposite strands in proximity of the first inverted repeat such that nicking results in a bottom strand 3' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a third and a fourth restriction site for nicking endonuclease are arranged on opposite strands in proximity of the second inverted repeat or a fragment thereof (e.g., at least 50%, 60%, 70%, 75%, 80%, 85%, 90%, 95%, or 99% of the second inverted repeat) such that nicking results in a top strand 3' overhang comprising the second inverted repeat upon separation of the top from the bottom strand of the second inverted repeat (e.g. as described in Sections 5.2.3, 5.2.4 and 5.3.2 or depicted in FIGS. 2B and 2C). In certain embodiments, the bottom strand 3' overhang comprises the first inverted repeat. In certain embodiments, the top strand 3' overhang comprises the second inverted repeat. In certain embodiments, the bottom strand 3' overhang comprises the first inverted repeat and the top strand 3' overhang comprises the second inverted repeat.

In one aspect, provided herein is a double-stranded DNA molecule comprising in 5' to 3' direction of the top strand: i) a first inverted repeat (e.g. as described in Section 5.3.1), wherein a first and a second target site for the guide nucleic acids for programmable nicking enzyme are arranged on opposite strands in proximity of the first inverted repeat such that nicking by programmable nicking enzyme results in a top strand 5' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a third and a fourth target site for the guide nucleic acids for programmable nicking enzyme are arranged on opposite strands in proximity of the second inverted repeat such that nicking by programmable nicking enzyme results in a top strand 3' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2). In certain embodiments, the top strand 5' overhang comprises the first inverted repeat. In certain embodiments, the top strand 3' overhang comprises the second inverted repeat. In certain embodiments, the top strand 5' overhang comprises the first inverted repeat and the top strand 3' overhang comprises the second inverted repeat.

In another aspect, provided herein is a double strand DNA molecule comprising in 5' to 3' direction of the top strand: i) a first inverted repeat (e.g. as described in Section 5.3.1), wherein a first and a second target site for the guide nucleic acids for programmable nicking enzyme are arranged on opposite strands in proximity of the first inverted repeat such that nicking by programmable nicking enzyme results in a bottom strand 3' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a third and a fourth target site for the guide nucleic acids for programmable nicking enzyme are arranged on opposite strands in proximity of the second inverted repeat such that nicking by programmable nicking enzyme results in a bottom strand 5' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2 or depicted in FIGS. 2A and 2C). In certain embodiments, the bottom strand 3' overhang comprises the first inverted repeat. In certain embodiments, the bottom strand 5' overhang comprises the second inverted repeat. In certain embodiments, the bottom strand 3' overhang comprises the first inverted repeat and the bottom strand 5' overhang comprises the second inverted repeat.

In yet another aspect, provided herein is a double-stranded DNA molecule comprising in 5' to 3' direction of the top strand: i) a first inverted repeat (e.g. as described in Section 5.3.1), wherein a first and a second target site for the guide nucleic acids for programmable nicking enzyme are arranged on opposite strands in proximity of the first inverted repeat such that nicking by programmable nicking enzyme results in a top strand 5' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a third and a fourth target site for the guide nucleic acids for programmable nicking enzyme are arranged on opposite strands in proximity of the second inverted repeat such that nicking by programmable nicking enzyme results in a bottom strand 5' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2). In certain embodiments, the top strand 5' overhang comprises the first inverted repeat. In certain embodiments, the bottom strand 5' overhang comprises the second inverted repeat. In certain embodiments, the top strand 5' overhang comprises the first inverted repeat and the bottom strand 5' overhang comprises the second inverted repeat.

In a further aspect, provide herein is a double strand DNA molecule comprising in 5' to 3' direction of the top strand: i) a first inverted repeat (e.g. as described in Section 5.3.1), wherein a first and a second target site for the guide nucleic acids for programmable nicking enzyme are arranged on opposite strands in proximity of the first inverted repeat such that nicking by programmable nicking enzyme results in a bottom strand 3' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a third and a fourth target site for the guide nucleic acids for programmable nicking enzyme are arranged on opposite strands in proximity of the second inverted repeat such that nicking by programmable nicking enzyme results in a top strand 3' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2 or depicted in FIGS. 2B and 2C). In certain embodiments, the bottom strand 3' overhang comprises the first inverted repeat. In certain embodiments, the top strand 3' overhang comprises the second inverted repeat. In certain embodiments, the bottom strand 3' overhang comprises the first inverted repeat and the top strand 3' overhang comprises the second inverted repeat. In one embodiment, the first, second, third, and fourth target site for programmable nicking enzyme in this and the preceding three paragraphs are all the same. In another embodiment, three of the first, second, third, and fourth target site for programmable nicking enzyme in this and the preceding three paragraphs are the same. In yet another embodiment, two of the first, second, third, and fourth target site for programmable nicking enzyme in this and the preceding three paragraphs are the same. In a further embodiment, the first, second, third, and fourth target site for programmable nicking enzyme in this and the preceding three paragraphs are all different.

The DNA molecules provided herein comprise various features or have various embodiments as described in Section 3 and the preceding paragraphs of this Section (Section 5.3), which features and embodiments are further described in the various subsections below: the embodiments for the inverted repeats, including the first inverted repeat and/or the second inverted repeat, are described in Section 5.3.1, the embodiments for the restriction enzymes, nicking endonucleases, and their respective restriction sites are described in Sections 5.3.2 and 5.2.4, the embodiments for the programmable nicking enzymes and their targeting sites are described in Section 5.2.4, the embodiments for the expression cassette are described in Section 5.3.3, the embodiments for plasmids and vectors are described in Section 5.3.5, the embodiments for DNA molecules comprising less than 4 restriction site for nicking endonucleases are described in Section 5.3.6. As such, the disclosure provides DNA molecules comprising any permutations and combinations of the various embodiments of DNA molecules and embodiments of features of the DNA molecules described herein. In further embodiments, the arrangement among the ITR, the expression cassette, the restriction sites for nicking endonuclease or restriction enzymes, and the programmable nicking enzyme and their targeting sites can be any arrangement as described in Sections 5.2.3, 5.2.4, 5.2.5, 5.3.1, 5.3.2, 5.3.3 5.3.6, and 5.4.

In one aspect, provided herein is a double-stranded DNA molecule comprising in the 5' to 3' direction of the top strand: i) a first viral replication deficient inverted repeat (e.g. as described in Section 5.3.1 and Section 5.3.4), wherein a first and a second restriction site for nicking endonuclease are arranged on opposite strands in proximity of the first inverted repeat such that nicking results in a top strand 5' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4, 5.3.2 and 5.3.4); ii) an expression cassette (e.g. as described in Section 5.3.3); and iii) a second viral replication deficient inverted repeat (e.g. as described in Section 5.3.1 and Section 5.3.4), wherein a third and a fourth restriction site for nicking endonuclease are arranged on opposite strands in proximity of the second inverted repeat such that nicking results in a top strand 3' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2). In certain embodiments, the top strand 5' overhang comprises the first viral replication deficient inverted repeat. In certain embodiments, the top strand 3' overhang comprises the second viral replication deficient inverted repeat. In certain embodiments, the top strand 5' overhang comprises the first viral replication deficient inverted repeat and the top strand 3' overhang comprises the second viral replication deficient inverted repeat.

In another aspect, provided herein is a double strand DNA molecule comprising in the 5' to 3' direction of the top strand: i) a first viral replication deficient inverted repeat (e.g. as described in Section 5.3.1 and 5.3.4), wherein a first and a second restriction site for nicking endonuclease are arranged on opposite strands in proximity of the first inverted repeat such that nicking results in a as described in Sections 5.2.3, 5.2.4 and 5.3.2); ii) an expression cassette (e.g. as described in Section 5.3.3); and iii) a second viral replication deficient inverted repeat (e.g. as described in Section 5.3.1 and Section 5.3.4), wherein a third and a fourth restriction site for nicking endonuclease are arranged on opposite strands in proximity of the second inverted repeat such that nicking results in a bottom strand 5' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2 or depicted in FIGS. 2A and 2C). In certain embodiments, the bottom strand 3' overhang comprises the first viral replication deficient inverted repeat. In certain embodiments, the bottom strand 5' overhang comprises the second viral replication deficient inverted repeat. In certain embodiments, the bottom strand 3' overhang comprises the first viral replication deficient inverted repeat and the bottom strand 5' overhang comprises the second viral replication deficient inverted repeat.

In yet another aspect, provided herein is a double-stranded DNA molecule comprising in the 5' to 3' direction of the top strand: i) a first viral replication deficient inverted repeat (e.g. as described in Section 5.3.1 and 5.3.4), wherein a first and a second restriction site for nicking endonuclease are arranged on opposite strands in proximity of the first inverted repeat such that nicking results in a top strand 5' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second viral replication deficient inverted repeat (e.g. as described in Section 5.3.1 and 5.3.4), wherein a third and a fourth restriction site for nicking endonuclease are arranged on opposite strands in proximity of the second inverted repeat such that nicking results in a bottom strand 5' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2). In certain embodiments, the top strand 5' overhang comprises the first viral replication deficient inverted repeat. In certain embodiments, the bottom strand 5' overhang comprises the second viral replication deficient inverted repeat. In certain embodiments, the top strand 5' overhang comprises the first viral replication deficient inverted repeat and the bottom strand 5' overhang comprises the second viral replication deficient inverted repeat.

In a further aspect, provide herein is a double stranded DNA molecule comprising in 5' to 3' direction of the top strand: i) a first viral replication deficient inverted repeat (e.g. as described in Section 5.3.1 and 5.3.4), wherein a first and a second restriction site for nicking endonuclease are arranged on opposite strands in proximity of the first inverted repeat such that nicking results in a bottom strand as described in Sections 5.2.3, 5.2.4 and 5.3.2); ii) an expression cassette (e.g. as described in Section 5.3.3); and iii) a second viral replication deficient inverted repeat (e.g. as described in Section 5.3.1 and Section 5.3.4), wherein a third and a fourth restriction site for nicking endonuclease are arranged on opposite strands in proximity of the second inverted repeat or a fragment thereof (e.g., at least 50%, 60%, 70%, 75%, 80%, 85%, 90%, 95%, or 99% of the second inverted repeat) such that nicking results in a top strand 3' overhang comprising the second inverted repeat upon separation of the top from the bottom strand of the second inverted repeat (e.g. as described in Sections 5.2.3, 5.2.4 and 5.3.2 or depicted in FIGS. 2B and 2C). In certain embodiments, the bottom strand 3' overhang comprises the first viral replication deficient inverted repeat. In certain embodiments, the top strand 3' overhang comprises the second viral replication deficient inverted repeat. In certain embodiments, the bottom strand 3' overhang comprises the first viral replication deficient inverted repeat and the top strand 3' overhang comprises the second viral replication deficient inverted repeat.

The DNA molecule provided herein can be a DNA molecule in its native environment or an isolated DNA molecule. In certain embodiments, the DNA molecule is a DNA molecule in its native environment. In some embodiments, the DNA molecule is an isolated DNA molecule. In one embodiment, the isolated DNA molecule can be a DNA molecule of at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% purity. In another embodiment, the isolated DNA molecule can be a DNA molecule of about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% purity. Other embodiments of the isolated DNA molecules provided herein in terms of purities are further described in Section 5.3.7, which can be combined in any suitable combination with the embodiments provided in this paragraph.

As the DNA molecules can be fully engineered (e.g. synthetically produced or recombinantly produced), the DNA molecules provided herein including those of Sections 3 and this Section 5.3 can lack certain sequences or features as further described in Section 5.3.4.

5.3.1 Inverted Repeats

The ITRs or IRs provided in Sections 3 and this Section (Section 5.3.1) can form the hairpinned ITRs in the hairpin-ended DNA molecules provided in Section 5.4, for example upon performing the method steps described in Sections 3, 5.2.3, 5.2.4, and 5.2.5. Accordingly, in some embodiments, the ITRs or IRs provided in Sections 3 and this Section (Section 5.3.1) can comprise any embodiments of the IRs or ITRs provided in Sections 3 and Section 5.4 and additional embodiments provided in this Section (Section 5.3.1), in any combination.

The majority of DNA in the cells comprises two strands engaged in Watson-Crick base pairing, which sequesters most of the functional groups and limits structural and functional diversity. While this is a desirable property for a molecule whose function is to store genetic information, single stranded viruses have evolved to utilize the intramolecular interaction of linear single stranded DNA (ssDNA) to form secondary structures that add another layer of functional complexity. One major contributing factor is that the ssDNA viral genomes are composed of just one strand that folds back on itself to form hairpins.

The secondary structure of a single stranded DNA molecule can be a representation of the pattern, based on an initial DNA sequence, of complementary base-pairings that are formed between the constituent nucleotides. The sequence, represented as a string of four letters (one for each nucleotide species), is a single strand consisting of the nucleotides which are generally assumed to form different secondary structures with minimum free energies that are governed by thermodynamic interactions.

"Inverted repeat" or "IR" refers to a single stranded nucleic acid sequence that comprises a palindromic sequence region. This palindromic region comprises a sequence of nucleotides as well as its reverse complement, i.e., "palindromic sequence" as further described below, on the same strand as further described below. In a denatured state, meaning in conditions in which the hydrophobic stacking attractions between the bases are broken, the IR nucleic acid sequence is present in a random coil state (e.g. at high temperature, presence of chemical agents, high pH, etc.). As conditions become more physiological, said IR can fold into a secondary structure whose outermost regions are non-covalently held together by base pairing. In some embodiments, an IR can be an ITR. In certain embodiments, an IR comprise an ITR. In some embodiments an IR can be a hairpinned inverted repeat. In certain embodiments, an inverted repeat, once folded upon itself, can create a hairpin loop (also known as stem loop) in which an unpaired loop of single stranded DNA is created when the DNA strand folds and forms base pairs with another section of the same strand. Upon folding, an inverted repeat can comprise one, two, three, four, five, six, seven, eight, nine, or ten such hairpin loop structures.

"Inverted terminal repeat" "terminal repeat," "TR," or "ITR" refers to an inverted repeat region that is at or proximal to a terminal of a single strand DNA molecule or an inverted repeat that is at or in the single strand overhang of a dsDNA molecule. An ITR can fold onto itself as a result of the palindromic sequence in the ITR. In one embodiment, an ITR is at or proximal to one end of an ssDNA. In another embodiment, an ITR is at or proximal to one end of a dsDNA. In yet another embodiment, two ITRs are each at or proximal to the two respective ends of an ssDNA. In a further embodiment, two ITRs are each at or proximal to the two respective end of a dsDNA. In some embodiments, the non-ITR part of the ssDNA or dsDNA is heterologous to the ITR. In certain embodiments, the non-ITR part of the ssDNA or dsDNA is homologous to the ITR. In a denatured state, meaning in conditions in which the hydrophobic stacking attractions between the bases are broken, the ITR comprising nucleic acid sequence is present in a random coil state (e.g. at high temperature, presence of chemical agents, high pH, etc.). In some embodiments, as conditions become more suitable for annealing as described in Section 5.2.5, the ITR can fold on itself into a structure that is non-covalently held together by base pairing while the heterologous non-ITR part of the dsDNA remain intact or the heterologous non-ITR part of the ssDNA molecule can hybridize with a second ssDNA molecule comprising the reverse complement sequence of the heterologous DNA molecule. The resulting complex of two hybridized DNA strands encompass three distinct regions, a first folded single stranded ITR covalently linked to a double stranded DNA region that is in turn covalently linked to a second folded single stranded ITR. In certain embodiments, the ITR sequence can start at one of the restriction site for nicking endonuclease described in Sections 3, 5.2.4, and 5.3.2 and end at the last base before the dsDNA. In one embodiment, as opposed to a linear double stranded DNA molecule, the ITR present at the 5' and 3' termini of the top and bottom strand at either end of the DNA molecule can fold in and face each other (e.g. 3' to 5', 5' to 3' or vice versa) and therefore do not expose a free 5' or 3' terminus at either end of the nucleic acid duplex. When the ITR folds on itself, the dsDNA in the folded ITR can be immediately next to the dsDNA of the non-ITR part of the DNA molecule, creating a nick flanked by dsDNA in some embodiments, or the dsDNA in the folded ITR can be one or more nucleotide apart from the dsDNA of the non-ITR part of the DNA molecule, creating a "ssDNA gap" flanked by dsDNA in other embodiments. The two ITRs that flank the non-ITR DNA sequence are referred to an "ITR pair". In some embodiments, when the ITR assumes its folded state, it is resistant to exonuclease digestion (e.g. exonuclease V), e.g. for over an hour at 37° C.

The boundary between the terminal base of the ITR folded into its secondary structure and the terminal base of the DNA hybridized duplex can further be stabilized by stacking interactions (e.g. coaxial stacking) between base pairs flanking the nick or ssDNA gap and these interactions are sequence-dependent. In the case of a structure resembling a nick, an equilibrium between two conformations can exist wherein, the first conformation is very close to that of the intact double helix where stacking between the base pairs flanking the nick is conserved while the other conformation corresponds to complete loss of stacking at the nick site thus inducing a kink in DNA. Nicked molecules are known to move somewhat slower during polyacrylamide and agarose gel electrophoresis than intact molecules of the same size. In some cases, this retardation is enhanced at higher temperatures. It is thought that the fast equilibration between stacked/straight and unstacked/bent conformations of the nick directly affects the mobility of DNA molecule during gel electrophoreses, leading to differential retardation characteristic to a DNA molecule carrying the nick.

Without being bound by theory, it is thought that cellular proteins can recognize parallel 5' and 3' termini as double strand breaks and can engage as well as process these, which can adversely affect the fate of the DNA in a cell. Hence, the ITR can prevent premature, unwanted degradation of the expression cassette with ITRs at one or both of its two ends as provided in Sections 3 and 5.4 and this Section (Section 5.3.1).

By placing a first and a second restriction site for nicking endonucleases on opposite strands and in proximity of the inverted repeats and subsequent separation of the top from the bottom strand of the inverted repeat, the resulting overhang can fold back on itself and form a double stranded end that contains at least one restriction site for the nicking endonuclease. In some embodiments, the folded ITR resembles the secondary structure conformation of viral ITRs. In one embodiment, the ITR is located on both the 5' and 3' terminus of the bottom strand (e.g. a left ITR and right ITR). In another embodiment, the ITR is located on both the 5' and 3' terminus of the top strand. In yet another embodiment, one ITR is located at the 5' terminus of the top strand, and the other ITR is located at the opposite end of the bottom strand (e.g. the left ITR at the 5' terminus on the top strand and the right ITR at the 5' terminus of the bottom). In yet another embodiment, one ITR is located at the 3' terminus of the top strand, and the other ITR is located at the 3' terminus of the bottom strand.

In some aspects, the disclosure provides a DNA molecule comprising palindromic sequences. "Palindromic sequences" or "palindromes" are self-complimentary DNA sequences that can fold back to form a stretch of dsDNA in the self-complimentary region under a condition that favors intramolecular annealing. In some embodiments, a palindromic sequence comprises a contiguous stretch of polynucleotides that is identical when read forwards as when read backwards on the complementary strand. In one embodiment, a palindromic sequence comprises a stretch of polynucleotides that is identical when read forwards as when read backwards on the complementary strand, wherein such stretch is interrupted by one or more stretches of non-palindromic polynucleotides. In another embodiment, a palindromic sequence comprises a stretch of polynucleotides that is 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical when read forwards as when read backwards on the complementary strand. In yet another embodiment, a palindromic sequence comprises a stretch of polynucleotides that is 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical when read forwards as when read backwards on the complementary strand, wherein such stretch is interrupted by one or more stretches of non-palindromic polynucleotides. An ssDNA encoding one or more palindromic sequences can fold back upon itself, to form double stranded base pairs comprising a secondary structure (e.g., a hairpin loop, or a three-way junction).

Under appropriate conditions, for example as described in Sections 5.2.3, 5.2.4, and 5.2.5, An IR or an ITR provided in this Section (Section 5.3.1) can fold and form hairpin structures as described in this Section (Section 5.3.1) and Section 5.4, including stems, a primary stem, loops, turning points, bulges, branches, branch loops, internal loops, and/or any combination or permutation of the structural features described in Section 5.4.

In one embodiment, an IR or ITR for the methods and compositions provided herein comprises one or more palindromic sequences. In some embodiments, an IR or ITR described herein comprises palindromic sequences or domains that in addition to forming the primary stem domain can form branched hairpin structures. In some embodiments, an IR or ITR comprises palindromic sequences that can form any number of branched hairpins. In certain specific embodiments, an IR or ITR comprises palindromic sequences that can form 1 to 30, or any subranges of 1 to 30, branched hairpins. In some specific embodiments, an IR or ITR comprises palindromic sequences that can form 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 branched hairpins. In some embodiments, an IR or ITR comprises sequence that can form two branched hairpin structures that lead to a three-way junction domain (T-shaped). In some embodiments, an IR or ITR comprises sequence that can form three branched hairpin structures that lead to a four-way junction domain (or cruciform structure). In some embodiments, an IR or ITR comprises sequence that can form a non-T-shaped hairpin structure, e.g., a U-shaped hairpin structure. In some embodiments, an IR or ITR comprises sequence that can form interrupted U-shaped hairpin structure including a series of bulges and base pair mismatches. In some embodiments, the branched hairpins all have the same length of stem and/or loop. In some embodiments, one branched hairpin is smaller (e.g. truncated) than the other branched hairpins. Some exemplar embodiments of the hairpin structures and the structural elements of the hairpin structures are depicted in FIG. 1.

"Hairpin closing base pair" refers to the first base pair following the unpaired loop sequence. Certain stem loop sequences have preferred closing base pairs (e.g. GC in AAV2 ITRs). In one embodiment, the stem loop sequence comprises G-C pair as the closing base pair. In another embodiment, the stem loop sequence comprises C-G pair as the closing base pair.

"ITR closing base pair" refers to the first and last nucleotide that forms a base pair in a folded ITR. The terminal base pair is usually the pair of nucleotides of the primary stem domain that are most proximal to the non-ITR sequences (e.g. expression cassette) of the DNA molecule. The ITR closing base pair can be any type of base pair (e.g. CG, AT, GC or TA). In one embodiment, the ITR closing base pair is a G-C base pair. In another embodiment, the ITR closing base pair is an A-T base pair. In yet another embodiment, the ITR closing base pair is a C-G base pair. In a further embodiment, the ITR closing base pair is a T-A base pair.

The disclosure provides that the DNA secondary structure can be computationally predicted according as known and practiced in the art. DNA secondary structures can be represented in several ways: squiggle plot, graph representation, dot-bracket notation, circular plot, arc diagram, mountain plot, dot plot, etc. In circular plots, the backbone is represented by a circle, and the base pairs are symbolized by arcs in the interior of the circle. In arc diagrams, the DNA backbone is drawn as a straight line and the nucleotides of each base pair are connected by an arc. Both circular and arc plots allow for the identification of secondary structure similarities and differences.

One of the many methods for DNA secondary structure prediction uses the nearest-neighbor model and minimizes the total free energy associated with a DNA structure. The minimum free energy is estimated by summing individual energy contributions from base pair stacking, hairpins, bulges, internal loops and multi-branch loops. The energy contributions of these elements are sequence- and length-dependent and have been experimentally determined. The segregation of the sequence into a stem loop and sub-stems can be depicted, for example, by displaying the structure as graph plot. In a linear interaction plot, each residue is represented on the abscissa and semi-elliptical lines connect bases that pair with each other (e.g. FIGS. 2A and B).

In some embodiments, the ITR promotes the long-term survival of the nucleic acid molecule in the nucleus of a cell. In some embodiments, the ITR promotes the permanent survival of the nucleic acid molecule in the nucleus of a cell (e.g., for the entire life-span of the cell). In some embodiments, the ITR promotes the stability of the nucleic acid molecule in the nucleus of a cell. In some embodiments, the ITR inhibits or prevents the degradation of the nucleic acid molecule in the nucleus of a cell.

In certain embodiments, IRs or ITRs can comprise any viral ITR. In other embodiments, IRs or ITRs can comprise a synthetic palindromic sequence that can form a palindrome hairpin structure that does not expose a 5' or 3' terminus at the outmost apex or turning point of the repeat.

In some embodiments, the single stranded ITR sequence stretching from one nucleotide of the ITR closing base pair to the other nucleotide of the ITR closing base pair has a Gibbs free energy ($\Delta G$) of unfolding under physiological conditions in the range of −10 kcal/mol to −100 kcal/mol. In one embodiment, the Gibbs free energy ($\Delta G$) of unfolding referred to in the preceding sentence is no more than −10 (meaning ≤−10, including e.g. −20, −30, etc.), no more than −11, no more than −12, no more than −13, no more than −14, no more than −15, no more than −16, no more than −17, no more than −18, no more than −19, no more than −20, no more than −21, no more than −22, no more than −23, no more than −24, no more than −25, no more than −26, no more than −27, no more than −28, no more than −29, no more than −30, no more than −31, no more than −32, no more than −33, no more than −34, no more than −35, no more than −36, no more than −37, no more than −38, no more than −39, no more than −40, no more than −41, no more than −42, no more than −43, no more than −44, no more than −45, no more than −46, no more than −47, no more than −48, no more than −49, no more than −50, no more than −51, no more than −52, no more than −53, no more than −54, no more than −55, no more than −56, no more than −57, no more than −58, no more than −59, no more than −60, no more than −61, no more than −62, no more than −63, no more than −64, no more than −65, no more than −66, no more than −67, no more than −68, no more than −69, no more than −70, no more than −71, no more than −72, no more than −73, no more than −74, no more than −75, no more than −76, no more than −77, no more than −78, no more than −79, no more than −80, no more than −81, no more than −82, no more than −83, no more than −84, no more than −85, no more than −86, no more than −87, no more than −88, no more than −89, no more than −90, no more than −91, no more than −92, no more than −93, no more than −94, no more than −95, no more than −96, no more than −97, no more than −98, no more than −99, or no more than −100 kcal/mol. In another embodiment, the Gibbs free energy (ΔG) of unfolding referred to in the preceding sentence is about −10 (meaning ≤−10, including e.g. −20, −30, etc.), about −11, about −12, about −13, about −14, about −15, about −16, about −17, about −18, about −19, about −20, about −21, about −22, about −23, about −24, about −25, about −26, about −27, about −28, about −29, about −30, about −31, about −32, about −33, about −34, about −35, about −36, about −37, about −38, about −39, about −40, about −41, about −42, about −43, about −44, about −45, about −46, about −47, about −48, about −49, about −50, about −51, about −52, about −53, about −54, about −55, about −56, about −57, about −58, about −59, about −60, about −61, about −62, about −63, about −64, about −65, about −66, about −67, about −68, about −69, about −70, about −71, about −72, about −73, about −74, about −75, about −76, about −77, about −78, about −79, about −80, about −81, about −82, about −83, about −84, about −85, about −86, about −87, about −88, about −89, about −90, about −91, about −92, about −93, about −94, about −95, about −96, about −97, about −98, about −99, or about −100 kcal/mol. In some embodiments, the ITR sequence stretching from one nucleotide of the ITR closing base pair to the other nucleotide of the ITR closing base pair has a Gibbs free energy (ΔG) of unfolding under physiological conditions in the range of −26 kcal/mol to −95 kcal/mol. In some embodiments, the ITR sequence stretching from one nucleotide of the ITR closing base pair to the other nucleotide of the ITR closing base pair contribute to all of the Gibbs free energy (ΔG) of unfolding for the ITR sequence under physiological conditions.

In some embodiments, in the folded state, the single stranded IR or ITR has an overall Watson-Crick self-complementarity of approximately 50% to 98%. In one embodiment, in the folded state, the single stranded IR or ITR has an overall Watson-Crick self-complementarity of about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%. In another embodiment, in the folded state, the single stranded IR or ITR has an overall Watson-Crick self-complementarity of at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%. In some embodiments, in the folded state, IR or ITR has an overall Watson Crick complementarity of approximately 60% to 98%. In some embodiments, the single stranded IR or ITR has an overall GC content of approximately 60-95%. In certain embodiments, the single stranded IR or ITR has an overall GC content of at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, or at least 95%. In other embodiments, the single stranded IR or ITR has an overall GC content of about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, or about 95%. In some embodiments, the single stranded IR has an overall GC content of approximately 60-91%.

Table 4 lists the folding free energy, GC content, percent of complementation, length of exemplary ITRs and Table 5 lists the Sequences of the ITRs in Table 4.

TABLE

Folding free energy, GC content, percent of complementation, length of exemplary ITRs.

| ITR | Length | A-T | G-C | G-T | Paired Total | GC % | ΔG kcal/mol | Compl. % | Unpaired % |
|---|---|---|---|---|---|---|---|---|---|
| SEQ ID NO: 3 | 85 | 8 | 31 | | 39 | 79% | −83.0 | 92% | 8% |
| SEQ ID NO: 4 | 77 | 7 | 28 | | 35 | 80% | −72.7 | 91% | 9% |
| SEQ ID NO: 5 | 69 | 5 | 26 | | 31 | 84% | −63.6 | 90% | 10% |
| SEQ ID NO: 7 | 89 | 7 | 34 | | 41 | 83% | −90.0 | 92% | 8% |
| SEQ ID NO: 8 | 71 | 6 | 26 | | 32 | 81% | −65.2 | 90% | 10% |
| SEQ ID NO: 9 | 59 | 4 | 22 | | 26 | 85% | −50.7 | 88% | 12% |
| SEQ ID NO: 10 | 51 | 2 | 20 | | 22 | 91% | −41.9 | 86% | 14% |
| SEQ ID NO: 27 | 70 | 7 | 13 | | 20 | 65% | −26.6 | 57% | 43% |
| SEQ ID NO: 29 | 92 | 6 | 18 | 1 | 25 | 75% | −52.1 | 52% | 48% |
| SEQ ID NO: 28 | 102 | 12 | 26 | | 38 | 68% | −72.8 | 75% | 25% |
| SEQ ID NO: 31 | 87 | 13 | 23 | | 36 | 64% | −63.0 | 83% | 17% |
| SEQ ID NO: 32 | 113 | 18 | 31 | | 49 | 63% | −93.6 | 87% | 13% |
| SEQ ID NO: 33 | 83 | 6 | 32 | | 38 | 84% | −83.0 | 92% | 8% |
| SEQ ID NO: 34 | 83 | 7 | 31 | | 38 | 82% | −80.0 | 92% | 8% |
| SEQ ID NO: 35 | 67 | 6 | 26 | | 32 | 81% | −79.1 | 96% | 4% |

TABLE 5

Sequences of the ITRs in Table 4

| SEQ ID NO | Sequence |
| --- | --- |
| SEQ ID NO: 3 | GCTCGACTCGCTCACTGAGGCCGGGCGACCAAAGGTCGCCCGA CGCCCGGGCTTTGCCCGGGCGGCCTCAGTGAGCGAGTCGAGC |
| SEQ ID NO: 4 | GCTCGACTCACTGAGGCCGGGCGACCAAAGGTCGCCCGACGCC CGGGCTTTGCCCGGGCGGCCTCAGTGAGTCGAGC |
| SEQ ID NO: 5 | CGCTGACTCAGGCCGGGCGACCAAAGGTCGCCCGACGCCCGGG CTTTGCCCGGGCGGCCTGAGTCAGCG |
| SEQ ID NO: 7 | CGCGCTCGCTCGCTCACTGAGGCCGGGCGACCAAAGGTCGCCC GACGCCCGGGCTTTGCCCGGGCGGCCTCAGTGAGCGAGCGAGC GCG |
| SEQ ID NO: 8 | TCGCTCACTGAGGCCGGGCGACCAAAGGTCGCCCGACGCCCGG GCTTTGCCCGGGCGGCCTCAGTGAGCGA |
| SEQ ID NO: 9 | ACTGAGGCCGGGCGACCAAAGGTCGCCCGACGCCCGGGCTTTG CCCGGGCGGCCTCAGT |
| SEQ ID NO: 10 | AGGCCGGGCGACCAAAGGTCGCCCGACGCCCGGGCTTTGCCCG GGCGGCCT |
| SEQ ID NO: 27 | CCATGCATCCGGCTTTAAACGGGCAACTGCGTCTCATTCACGTT AGAGACTACAACCGTCGGATGCATGG |
| SEQ ID NO: 28 | TTCAAACCTGCCGGGGAGAAGCGGCGTTTTTTCCCGGCCGCCG CTTCTCTTCTTCTCCCGCCGCCGGGAAAAAAGGCGGGAGAAGC CCCGGCAGGTTTGAA |
| SEQ ID NO: 29 | GTCCGGGCCATGCTTCAAACCTGCCGGGGCTTCTCCCGCCTTTT TTCCCGGCGGCGGGAGAAGTAGATTTCTCGTACCTGCATGGCCC GGAC |
| SEQ ID NO: 31 | CCAGCGCTTGGGGTTGACGTGCCACTAAGATCAAGCGGCGCGC GCGCGCCGCTTGTCTTAGTGTCAAGGCAACCCCAAGCAAGCTG G |
| SEQ ID NO: 32 | GGTTGACTCTGGGCCAGCTTGCTTGGGGTTGCCTTGACACTAAG ACAAGCGGCGCGCGCGCCGCTTGATCTTAGTGGCACGTCAA CCCCAAGCGCTGGCCCAGAGTCAACC |
| SEQ ID NO: 33 | CGCGCTCGCTCGCTCACTGAGGCCGGGCCAAAGGCCCGACGCC CGGGCTTTGCCCGGGCGGCCTCAGTGAGCGAGCGAGCGCG |
| SEQ ID NO: 34 | CGCGCTCGCTCGCTCACTGAGGCCGGGCGACCAAAGGTCGCCC GACGCCCGTTTCGGGCGGCCTCAGTGAGCGAGCGAGCGCG |
| SEQ ID NO: 35 | CGCGCTCGCTCGCTCACTGAGGCCGCCCGGGCTTTGCCCGGGCG GCCTCAGTGAGCGAGCGAGCGCG |

The DNA molecules for the methods and compositions provided herein can comprise IR or ITRs of various origins. In one embodiment, the IR or ITR in the DNA molecule is a viral ITR. "Viral ITR" includes any viral terminal repeat or synthetic sequence that comprises at least one minimal required origin of replication and a region comprising a palindrome hairpin structure. In one embodiment, the viral ITR is derived from Parvoviridae. In another embodiment, the viral ITR derived from Parvoviridae comprises a "minimal required origin of replication" that comprises at least one viral replication-associated protein binding sequence ("RABS"). RABS refers to a DNA sequence to which a viral DNA replication-associated protein ("RAP") or an isoform thereof, encoded by the Parvoviridae gene Rep and/or NS1, can bind. In some embodiments, the RABS is a Rep binding sequence ("RBS"). In some embodiments the RABS comprises a Rep binding sequence ("RBS"), Rep can bind to two elements within the ITR. It can bind to a nucleotide sequence in the stem structure of the ITR (i.e., the nucleotide sequence recognized by a Rep protein for replication of viral nucleic acid molecules). Such an RBS is also referred to as RBE (Rep-binding element). Rep can also bind to a nucleotide sequence. which forms a small palindrome comprising a single tip of an internal hairpin within the ITR, thereby stabilizing the association between Rep and the ITR. Such an RBS is also referred to as RBE'. In another embodiment, the viral ITR derived from Parvoviridae comprises an RABS which comprises NS1-binding elements ("NSBEs") that replication-associated viral protein NS1 can bind. In another embodiment, the RABS is an NS1-binding element ("NSBE") to which replication-associated viral protein NS1 can bind. In some embodiments, viral ITR is derived from Parvoviridae and comprises a terminal resolution site ('TRS") at which the viral DNA replication-associated proteins NS1 and/or Rep can perform an endonucleolytic nick within a sequence at the TRS. In yet another embodiment, the viral ITR comprises at least one RBS or NSBE and at least one TRS. In the context of a virus or recombinant RAP (i.e. Rep or NS1) based production of viral genomes, the ITRs mediate replication and virus packaging. As unexpectedly found by the inventors and provided herein, duplex linear DNA vectors with ITRs similar to viral ITRs can be produced without the need for Rep or NS1 proteins and consequently independent of the RABS or TRS sequence for DNA replication. Accordingly, the RABS and TRS can optionally be encoded in the nucleotide sequence disclosed herein but are not required and offer flexibility with regard to designing the ITRs. In one embodiment, the ITR for the methods and compositions provided herein does not comprise at least one RABS (e.g., one RABS, two RABS, or more than two RABS). In another embodiment, the ITR for the methods and compositions provided herein does not comprise any RABS. In another embodiment, the ITR for the methods and compositions provided herein does not comprise at least one RBS. In another embodiment, the ITR for the methods and compositions provided herein does not comprise any RBS. In another embodiment, the ITR for the methods and compositions provided herein does not comprise RBE. In another embodiment, the ITR for the methods and compositions provided herein does not comprise RBE'. In another embodiment, the ITR for the methods and compositions provided herein does not comprise RBE and RBE'. In another embodiment, the ITR for the methods and compositions provided herein does not comprise NSBE. In yet another embodiment, the ITR for the methods and compositions provided herein does not comprise TRS. In a further embodiment, the ITR for the methods and compositions provided herein does not comprise at least one RABS (e.g., one RABS, two RABS, or more than two RABS) and does not comprise TRS. In a further embodiment, the ITR for the methods and compositions provided herein does not comprise any RABS and does not comprise TRS. In a further embodiment, the ITR for the methods and compositions provided herein comprises RBS (i.e., RBE and/or RBE'), TRS, or both RBS (i.e., RBE and/or RBE') and TRS. In a further embodiment, the ITR for the methods and compositions provided herein comprises NBSE, TRS, or both NBSE and TRS.

"An ITR pair" refers to two ITRs within a single DNA molecule. In some embodiments, the two ITRs in the ITR pair are both derived from wild type viral ITRs (e.g. AAV2 ITR) that have an inverse complement sequence across their entire length. An ITR can be considered to be a wild-type sequence, even if it has one or more nucleotides that deviate from the canonical naturally occurring sequence, so long as the changes do not affect the properties and overall three-dimensional structure of the sequence. The disclosure provides that, in some embodiments, the insertion, deletion or substitution of one or more nucleotides can provide the generation of a restriction site for nicking endonuclease without changing the overall three-dimensional structure of the viral ITR. In some aspects, the deviating nucleotides represent conservative sequence changes. In certain embodiments, the sequence of an ITR provided herein can have at least 95%, at least 96%, at least 97%, at least 98%, or at least 99% sequence identity to the canonical sequence (as measured, e.g., using BLAST at default settings), and also has a restriction site for nicking endonuclease, such that the 3D structures are the same shape in geometrical space. In other embodiments, the sequence of an ITR provided herein can have about 95%, about 96%, about 97%, about 98%, or about 99% sequence identity to the canonical sequence (as measured, e.g., using BLAST at default settings), and also has a restriction site for nicking endonuclease, such that the 3D structures are the same shape in geometrical space.

In some embodiments, a DNA molecule for the methods and compositions provided herein comprises a pair of wt-ITRs. In certain specific embodiments, a DNA molecule for the methods and compositions provided herein comprises a pair of wt-ITRs selected from the group shown in Table 6. Table 6 shows exemplary ITRs from the same serotype or different serotypes, or different parvoviruses, including AAV serotype 1 (AAV1), AAV serotype 2 (AAV2), AAV serotype 3 (AAV3), AAV serotype 4 (AAV4), AAV serotype 5 (AAV5), AAV serotype 6 (AAV6), AAV serotype 7 (AAV7), AAV serotype 8 (AAV8), AAV serotype 9 (AAV9), AAV serotype 10 (AAV10), AAV serotype 11 (AAV11), or AAV serotype 12 (AAV12); AAVrh8, AAVrh1O, AAV-DJ, and AAV-DJ8 genome (e.g., NCBI: NC 002077; NC 001401; NC001729; NC001829; NC006152; NC 006260; NC 006261), ITRs from warm-blooded animals (avian AAV (AAAV), bovine AAV (BAAV), canine, equine, and ovine AAV), ITRs from B19 parvovirus (GenBank Accession No: NC 000883), Minute Virus from Mouse (MVM) (GenBank Accession No. NC 001510); Goose: goose parvovirus (GenBank Accession No. NC 001701); snake: snake parvovirus 1 (GenBank Accession No. NC 006148).

TABLE 6

Exemplary ITR sequences

| Virus (accession number) | Left ITR | Right ITR |
|---|---|---|
| AAV1 | TTGCCCACTCCCTCTCTGCGCGC TCGCTCGCTCGGTGGGGCCTGC GGACCAAAGGTCCGCAGACGGC AGAGCTCTGCTCTGCCGGCCCC ACCGAGCGAGCGAGCGCGCAGA CCCCACCGAGCGAGCGAGCGC GAGGGAGTGGGCAA (SEQ ID NO: 11) | TTGCCCACTCCCTCTCTGCGCG CTCGCTCGCTCGGTGGGGCCT GCGGACCAAAGGTCCGCAGAC GGCAGAGCTCTGCTCTGCCGG GCAGAGAGGGAGTGGGCAA (SEQ ID NO: 12) |
| AAV2 | TTGGCCACTCCCTCTCTGCGCGC TCGCTCGCTCACTGAGGCCGGG CGACCAAAGGTCGCCCGACGCC CGGGCTTTGCCCGGGCGGCCTC AGTGAGCGAGCGAGCGCGCAGA GAGGGAGTGGCCAA (SEQ ID NO: 13) | TTGGCCACTCCCTCTCTGCGCG CTCGCTCGCTCACTGAGGCCG GGCGACCAAAGGTCGCCCGAC GCCCGGGCTTTGCCCGGGCGG CCTCAGTGAGCGAGCGAGCGC GCAGAGAGGGAGTGGCCAA (SEQ ID NO: 14) |
| AAV3 | TTGGCCACTCCCTCTATGCGCAC TCGCTCGCTCGGTGGGGCCTGG | TTGGCCACTCCCTCTATGCGCA CTCGCTCGCTCGGTGGGGCCT |

TABLE 6-continued

Exemplary ITR sequences

| Virus (accession number) | Left ITR | Right ITR |
|---|---|---|
| | CGACCAAAGGTCGCCAGACGGA CGTGCTTTGCACGTCCGGCCCCA CCGAGCGAGCGAGTGCGCATAG AGGGAGTGGCCAA (SEQ ID NO: 15) | GGCGACCAAAGGTCGCCAGAC GGACGTGCTTTGCACGTCCGG CCCCACCGAGCGAGCGAGTGC GCATAGAGGGAGTGGCCAA (SEQ ID NO: 16) |
| AAV4 | TTGGCCACTCCCTCTATGCGCGC TCGCTCACTCACTCGGCCCTGGA GACCAAAGGTCTCCAGACTGCC GGCCTCTGGCCGGCAGGGCCGA CCGGCAGGGCCGAGTGAGTGA GTGAGTGAGCGAGCGCGCATAG AGGGAGTGGCCAA (SEQ ID NO: 17) | CTATGCGCGCTCGCTCACTCAC TCGGCCCTGGAGACCAAAGGT CTCCAGACTGCCGGCCTCTGG GCGAGCGCGCATAGAGGGAGT GGCCAA (SEQ ID NO: 18) |
| AAV5 (NC_006152) | CTCTCCCCCCTGTCGCGTTCGCT CGCTCGCTGGCTCGTTTGGGGG GGTGGCAGCTCAAAGAGCTGCC AGACGACGGCCTCTGGCCGTC GCCCCCCCAAACGAGCCAGCGA GCGAGCGAACGCGACAGGGGG GAGAG (SEQ ID NO: 19) | CTCTCCCCCCTGTCGCGTTCGC TCGCTCGCTGGCTCGTTTGGGG GGGTGGCAGCTCAAAGAGCTG CCAGACGACGGCCCTCTGGCC GTCGCCCCCCCAAACGAGCCA GCGAGCGAGCGAACGCGACAG GGGGGAGAG (SEQ ID NO: 20) |
| AAV7 (NC_006260) | TTGGCCACTCCCTCTATGCGCGC TCGCTCGCTCGGTGGGGCCTGC GGACCAAAGGTCCGCAGACGGC AGAGCTCTGCTCTGCCGGCCCC ACCGAGCGAGCGAGCGCGCATA GAGGGAGTGGCCAA (SEQ ID NO: 21) | TTGGCCACTCCCTCTATGCGCG CTCGCTCGCTCGGTGGGGCCT GCGGACCAAAGGTCCGCAGAC GGCAGAGCTCTGCTCTGCCGG CCCCACCGAGCGAGCGAGCGC GCATAGAGGGAGTGGCCAA (SEQ ID NO: 22) |
| HBOV (JQ923422) | GTGGTTGTACAGACGCCATCTTG GAATCCAATATGTCTGCCGGCTC AGTCATGCCTGCGCTGCGCGCA GCGCGCTGCGCGCGCGCATGAT CTAATCGCCGGCAGACATATTG GATTCCAAGATGGCGTCTGTAC AACCAC (SEQ ID NO: 23) | TTGCTTATGCAATCGCGAAACT CTATATCTTTTAATGTGTTGTT GTTGTACATGCGCCATCTTAGT TTTATATCAGCTGGCGCCTTAG TTATATAACATGCATGTTATAT AACTAAGGCGCCAGCTGATAT AAAACTAAGATGGCGCATGTA CAACAACAACACATTAAAAGA TATAGAGTTTCGCGATTGCATA AGCAA (SEQ ID NO: 24) |
| hB19 (AY386330) | TGGGCCAGCTTGCTTGGGGTTGC CTTGACACTAAGACAAGCGGCG CGCCGCTTGATCTTAGTGGCACG TCAACCCCAAGCGCTGGCCCA (SEQ ID NO: 25) | TGGGCCAGCGCTTGGGGTTGA CGTGCCACTAAGATCAAGCGG CGCGCCGCTTGTCTTAGTGTCA AGGCAACCCCAAGCAAGCTGG CCCA (SEQ ID NO: 26) |

In some embodiments, the DNA molecules for the methods and compositions provided herein comprise whole or part of the parvoviral genome. The parvoviral genome is linear, 3.9-6.3 kb in size, and the coding region is bracketed by terminal repeats that can fold into hairpin-like structures, which are either different (heterotelomeric, e.g. HBoV) or identical (homotelomeric, e.g. AAV2). In one embodiment, a DNA molecule for the methods and compositions provided herein comprises 2 different ITRs at the 2 ends of the DNA molecule. In another embodiment, a DNA molecule for the methods and compositions provided herein comprises 2 identical ITRs at the 2 ends of the DNA molecule. In yet another embodiment, a DNA molecule for the methods and compositions provided herein comprises 2 different ITRs at the 2 ends of the DNA molecule corresponding to the 2 HBoV ITRs. In a further embodiment, a DNA molecule for the methods and compositions provided herein comprises 2 identical ITRs at the 2 ends of the DNA molecule corresponding to the AAV2 ITR.

In certain embodiments, the ITR in the DNA molecules provided herein can be an AAV ITR. In other embodiments, the ITR can be a non-AAV ITR. In one embodiment, the ITRs in the DNA molecules provided herein can be derived from an AAV ITR or a non-AAV TR. In some specific embodiments, the ITR can be derived from any one of the family Parvoviridae, which encompasses parvoviruses and dependoviruses (e.g., canine parvovirus, bovine parvovirus, mouse parvovirus, porcine parvovirus, human parvovirus B-19). In other specific embodiments, the ITR can be derived from the SV40 hairpin that serves as the origin of SV40 replication. Parvoviridae family viruses consist of two subfamilies: Parvovirinae, which infect vertebrates, and Densovirinae, which infect invertebrates. As such, in one embodiment, the ITR can be derived from any one of the subfamily Parvovirinae. In another embodiment, the ITR can be derived from any one of the subfamily Densovirinae.

In comparison to the T-shaped AAV ITRs, the human erythrovirus B19 has ITRs that terminate in imperfect, palindromes that can fold into long linear duplexes with a few unpaired nucleotides, creating a series of small, but highly conserved, mismatched bulges. In some embodiments, any parvovirus ITR can be used as an ITR for the DNA molecules provided herein (e.g. wild type or modified ITR) or can act as a template ITR for modification and then incorporation in the DNA molecules provided herein. In some specific embodiments, the parvovirus, from which the ITRs of the DNA molecules are derived, is a dependovirus, an erythroparvovirus, or a bocaparvovirus. In other specific embodiments, the ITRs of the DNA molecules provided herein are derived from AAV, B19 or HBoV. In certain embodiments, the serotype of AAV ITRs chosen for the DNA molecules provided herein can be based upon the tissue tropism of the serotype. AAV2 has a broad tissue tropism, AAV1 preferentially targets to neuronal and skeletal muscle, and AAV5 preferentially targets neuronal, retinal pigmented epithelia, and photoreceptors. AAV6 preferentially targets skeletal muscle and lung. AAV8 preferentially targets liver, skeletal muscle, heart, and pancreatic tissues. AAV9 preferentially targets liver, skeletal and lung tissue. In one embodiment, the ITR or modified ITR of the DNA molecules provided herein is based on an AAV2 ITR. In one embodiment, the ITR or modified ITR of the DNA molecules provided herein is based on an AAV1 ITR. In one embodiment, the ITR or modified ITR of the DNA molecules provided herein is based on an AAV5 ITR. In one embodiment, the ITR or modified ITR of the DNA molecules provided herein is based on an AAV6 ITR. In one embodiment, the ITR or modified ITR of the DNA molecules provided herein is based on an AAV8 ITR. In one embodiment, the ITR or modified ITR of the DNA molecules provided herein is based on an AAV9 ITR.

In one embodiment, the DNA molecules for the methods and compositions provided herein comprise one or more non-AAV ITR. In a further embodiment, such non-AAV ITR can be derived from hairpin sequences found in the mammalian genome. In one specific embodiment, such non-AAV ITR can be derived from the hairpin sequences found in the mitochondrial genome including the OriL hairpin sequence (SEQ ID NO:30: 5'CTTCTCCCGCCGCCGG-GAAAAAAGGCGGGAGAAGCCCCGGCAGGTTT-GAA'3), which adopts a stem-loop structure and is involved in initiating the DNA synthesis of mitochondrial DNA (see Fuste et al., Molecular Cell, 37, 67-78, Jan. 15, 2010, which is incorporated herein in its entirety by reference). In another specific embodiment, the DNA molecules for the methods and compositions provided herein comprise an ITR derived from the OriL sequence that is mirrored to form a T junction with two self-complimentary palindromic regions and a 12-nucleotide loop at either apex of the hairpin. In one embodiment the DNA molecules for the methods and compositions provided herein comprise an ITR derived from the OriL sequence that maintains OriL hairpin loop followed by an unpaired bulge and a GC-rich stem. Some exemplary embodiments of the ITRs derived from mitochondria OriL are depicted in FIG. 2.

In one embodiment, the DNA molecules for the methods and compositions provided herein comprise one or more non-AAV ITRs that are derived from aptamer. Similar to viral ITRs, aptamers are composed of ssDNA that folds into a three-dimensional structure and have the ability to recognize biological targets with high affinity and specificity. DNA aptamers can be generated by systematic evolution of ligands by exponential enrichment (SELEX). For example, it has previously been shown that some aptamers can target the nuclei of human cells (See Shen et al ACS Sens. 2019, 4, 6, 1612-1618, which is herein incorporated in its entirety by reference). In one embodiment, the DNA molecules for the methods and compositions provided herein comprise nucleus targeting aptamer ITRs or their derivatives, wherein the aptamer specifically binds nuclear protein. In some embodiments, the aptamer ITRs fold into a secondary structure that can contain such as hairpins as well as internal loops as well bulges and a stem region. Some exemplary embodiments of aptamers or the ITRs derived from are depicted in FIG. 3.

In some specific embodiments, the DNA molecules for the methods and compositions provided herein comprise one or more AAV2 ITR, human erythrovirus B19 ITR goose parvovirus ITR, and/or their derivatives in any combination. In other specific embodiments, the DNA molecules for the methods and compositions provided herein comprise two ITRs selected from AAV2 ITR, human erythrovirus B19 ITR goose parvovirus ITR, and their derivatives, in any combination. In some specific embodiments, the DNA molecules for the methods and compositions provided herein comprise one or more AAV2 ITR, human erythrovirus B19 ITR goose parvovirus ITR, and/or their derivatives, in any combination, wherein the ITRs remain functional regardless of whether the palindromic regions of their ITRs are in direct, reverse, or any possible combination of 5' and 3' ITR directionality with respect to the expression cassette (as described in WO2019143885, which is herein incorporated in its entirety by reference).

In some embodiments, a modified IR or ITR in the DNA molecules provided herein is a synthetic IR sequence that comprises a restriction site for endonuclease such as 5'-GAGTC-3' in addition to various palindromic sequence allowing for hairpin secondary structure formation as described in this Section (Section 5.3.1).

In certain embodiments, the IR or ITR in the DNA molecules provided herein can be an IR or ITR having various sequence homology with the IR or ITR sequences described in this Section (Section 5.3.1). In other embodiments, the IR or ITR in the DNA molecules provided herein can be an IR or ITR having various sequence homology with the known IR or ITR sequences of various ITR origins described in this Section (Section 5.3.1) (e.g. viral ITR, mitochondria ITR, artificial or synthetic ITR such as aptamers, etc.). In one embodiment, such homology provided in this paragraph can be a homology of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%. In another embodiment, such homology provided in this paragraph can be a homology of about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%.

In some embodiments, the IR or ITR in the DNA molecules provided herein can comprise any one or more features described in this Section (Section 5.3.1), in various permutations and combinations.

5.3.2 Restriction Enzymes, Nicking Endonucleases, and their Respective Restriction Sites; Programmable Nicking Enzymes and their Targeting Sites Various embodiments for the nicking endonucleases, restriction enzymes, and/or their respective restriction sites as describe in Section 5.2.4 are provided for the DNA molecules provided herein. In some embodiments, the first, second, third, and fourth restriction sites for nicking endonuclease provided for the DNA molecules as described in Section 3 and this Section (Section 5.3) can be all target sequences for the same nicking endonuclease. In some embodiments, the first, second, third, and fourth restriction sites for nicking endonuclease provided for the DNA molecules as described in Section 3 and this Section (Section 5.3) can be target sequences for four different nicking endonucleases. In other embodiments, the first, second, third, and fourth restriction sites for nicking endonucleases are target sequences for two different nicking endonucleases, including all possible combinations of arranging the four sites for two different nicking endonuclease target sequences (e.g. the first restriction site for the first nicking endonuclease and the rest for the second nicking endonuclease, the first and second restriction sites for the first nicking endonuclease and the rest for the second nicking endonuclease, etc.). In certain embodiments, the first, second, third, and fourth restriction sites for nicking endonucleases are target sequences for three different nicking endonucleases, including all possible combinations of arranging the four sites for three different nicking endonuclease target sequences. In some embodiments, the nicking endonuclease and restriction sites for the nicking endonuclease can be any one selected from those described in Section 5.2.4, including Table 2. In further embodiments, each of the first, second, third, and fourth restriction site for nicking endonuclease can be a site for any nicking endonuclease selected from those described in Section 5.2.4, including Table 2.

Table 7 to Table 16 show exemplary modified AAV ITR sequences that harbor two antiparallel recognition sites for the same nicking endonuclease, grouped by nicking endonuclease species. The corresponding alignments for modified sequences of ITRs and wild type of AAV1, AAV2, AAV3, AAV4 left, AAV4 Right, AAV5 and AAV7 are depicted in FIG. 13 to FIG. 19

TABLE 7

Exemplary AAV derived ITRs harboring antiparallel recognition sites for nicking endonuclease Nb.BvCI:

| SEQ ID No: | Name | Full Sequence |
|---|---|---|
| SEQ ID No: 1 | source: AAV1; Recogn. Site: Nb.BbvCI; Format: bl | TTGCCCACTCCCCCTCAGCGCGCTCGCTCGCT CGGTGGGGCCTGCGGACCAAAGGTCCGCAG ACGGCAGAGCTCTGCTCTGCCGGCCCCACCG AGCGAGCGAGCGCGCTGAGGGGGAGTGGGC AA |
| SEQ ID No: 2 | source: AAV1; Recogn. Site: Nb.BbvCI; Format: tl | TTGCCCACTCCCGCTGAGGGCGCTCGCTCGC TCGGTGGGGCCTGCGGACCAAAGGTCCGCAG ACGGCAGAGCTCTGCTCTGCCGGCCCCACCG AGCGAGCGAGCGCCCTCAGCGGGAGTGGGC AA |
| SEQ ID No: 36 | source: AAV2; Recogn. Site: Nb.BbvCI; Format: bl | TTGGCCACTCCCCCTCAGCGCGCTCGCTCGCT CACTGAGGCCGGGCGACCAAAGGTCGCCCG ACGCCCGGGCTTTGCCCGGGCGGCCTCAGTG AGCGAGCGAGCGCGCTGAGGGGGAGTGGCC AA |
| SEQ ID No: 37 | source: AAV2; Recogn. Site: Nb.BbvCI; Format: tl | TTGGCCACTCCCGCTGAGGGCGCTCGCTCGC TCACTGAGGCCGGGCGACCAAAGGTCGCCCG ACGCCCGGGCTTTGCCCGGGCGGCCTCAGTG AGCGAGCGAGCGCCCTCAGCGGGAGTGGCC AA |
| SEQ ID No: 38 | source: AAV3; Recogn. Site: Nb.BbvCI; Format: bl | TTGGCCACTCCCCCTCAGCGCACTCGCTCGCT CGGTGGGGCCTGGCGACCAAAGGTCGCCAG ACGGACGTGCTTTGCACGTCCGGCCCCACCG AGCGAGCGAGTGCGCTGAGGGGGAGTGGCC AA |
| SEQ ID No: 39 | source: AAV3; Recogn. Site: Nb.BbvCI; Format: tl | TTGGCCACTCCCGCTGAGGGCACTCGCTCGC TCGGTGGGGCCTGGCGACCAAAGGTCGCCAG ACGGACGTGCTTTGCACGTCCGGCCCCACCG AGCGAGCGAGTGCCCTCAGCGGGAGTGGCC AA |
| SEQ ID No: 40 | source: AAV4 left; Recogn. Site: Nb.BbvCI; Format: bl | TTGGCCACTCCCCCTCAGCGCGCTCGCTCACT CACTCGGCCCTGGAGACCAAAGGTCTCCAGA CTGCCGGCCTCTGGCCGGCAGGGCCGAGTGA GTGAGCGAGCGCGCTGAGGGGAGTGGCCA A |
| SEQ ID No: 41 | source: AAV4 left; Recogn. Site: Nb.BbvCI; Format: tl | TTGGCCACTCCCGCTGAGGGCGCTCGCTCAC TCACTCGGCCCTGGAGACCAAAGGTCTCCAG ACTGCCGGCCTCTGGCCGGCAGGGCCGAGTG AGTGAGCGAGCGCCCTCAGCGGGAGTGGCC AA |
| SEQ ID No: 42 | source: AAV4 right; Recogn. Site: Nb.BbvCI; Format: | TTGGCCACATTACCTCAGCGCGCTCGCTCACT CACTCGGCCCTGGAGACCAAAGGTCTCCAGA CTGCCGGCCTCTGGCCGGCAGGGCCGAGTGA |

TABLE 7-continued

Exemplary AAV derived ITRs harboring antiparallel recognition sites for nicking endonuclease Nb.BvCI:

| SEQ ID No: | Name | Full Sequence |
|---|---|---|
| | bl | GTGAGCGAGCGCGCTGAGGGGAGTGGCCAA |
| SEQ ID No: 43 | source: AAV4 right; Recogn. Site: Nb.BbvCI; Format: tl | TTGGCCACATTAGCTGAGGGCGCTCGCTCAC TCACTCGGCCCTGGAGACCAAAGGTCTCCAG ACTGCCGGCCTCTGGCCGGCAGGGCCGAGTG AGTGAGCGAGCGCCCTCAGCGGGAGTGGCC AA |
| SEQ ID No: 44 | source: AAV5; Recogn. Site: Nb.BbvCI; Format: bl | CTCTCCCCTCAGCCGCGTTCGCTCGCTCGCTG GCTCGTTTGGGGGGGTGGCAGCTCAAAGAGC TGCCAGACGACGGCCCTCTGGCCGTCGCCCC CCCAAACGAGCCAGCGAGCGAGCGAACGCG GCTGAGGGGAGAG |
| SEQ ID No: 45 | source: AAV5; Recogn. Site: Nb.BbvCI; Format: tl | CTCTCCCCGCTGAGGCGTTCGCTCGCTCGCTG GCTCGTTTGGGGGGGTGGCAGCTCAAAGAGC TGCCAGACGACGGCCCTCTGGCCCGTCGCCCC CCCAAACGAGCCAGCGAGCGAGCGAACGCC TCAGCGGGGAGAG |
| SEQ ID No: 46 | source: AAV7; Recogn. Site: Nb.BbvCI; Format: bl | TTGGCCACTCCCCCTCAGCGCGCTCGCTCGCT CGGTGGGGCCTGCGGACCAAAGGTCCGCAG ACGGCAGAGCTCTGCTCTGCCGGCCCCACCG AGCGAGCGAGCGCGCTGAGGGGGAGTGGCC AA |
| SEQ ID No: 47 | source: AAV7; Recogn. Site: Nb.BbvCI; Format: tl | TTGGCCACTCCCGCTGAGGGCGCTCGCTCGC TCGGTGGGGCCTGCGGACCAAAGGTCCGCAG ACGGCAGAGCTCTGCTCTGCCGGCCCCACCG AGCGAGCGAGCGCCCTCAGCGGGAGTGGCC AA |

TABLE 8

Exemplary AAV derived ITRs harboring antiparallel recognition sites for nicking endonuclease Nb.BsmI:

| SEQ ID No: | Name | Full Sequence |
|---|---|---|
| SEQ ID No: 48 | source: AAV1; Recogn. Site: Nb.BsmI; Format: bl | TTGCCCACTCCCTGAATGCGCGCTCGCTCGCT CGGTGGGGCCTGCGGACCAAAGGTCCGCAG ACGGCAGAGCTCTGCTCTGCCGGCCCCACCG AGCGAGCGAGCGCGCATTCAGGGAGTGGGC AA |
| SEQ ID No: 49 | source: AAV1; Recogn. Site: Nb.BsmI; Format: tl | TTGCCCACTCCCTCTCTGCGCATTCGCTCGCT CGGTGGGGCCTGCGGACCAAAGGTCCGCAG ACGGCAGAGCTCTGCTCTGCCGGCCCCACCG AGCGAGCGAATGCGCAGAGAGGGAGTGGGC AA |
| SEQ ID No: 50 | source: AAV2; Recogn. Site: Nb.BsmI; Format: bl | TTGGCCACTCCCTGAATGCGCGCTCGCTCGCT CACTGAGGCCGGGCGACCAAAGGTCGCCCG ACGCCCGGGCTTTGCCCGGGCGGCCTCAGTG AGCGAGCGAGCGCGCATTCAGGGAGTGGCC AA |
| SEQ ID No: 51 | source: AAV2; Recogn. Site: Nb.BsmI; Format: tl | TTGGCCACTCCCTCTCTGCGCATTCGCTCGCT CACTGAGGCCGGGCGACCAAAGGTCGCCCG ACGCCCGGGCTTTGCCCGGGCGGCCTCAGTG AGCGAGCGAATGCGCAGAGAGGGAGTGGCC AA |
| SEQ ID No: 52 | source: AAV3; Recogn. Site: Nb.BsmI; Format: bl | TTGGCCACTCCCTGAATGCGCACTCGCTCGCT CGGTGGGGCCTGGCGACCAAAGGTCGCCAG ACGGACGTGCTTTGCACGTCCGGCCCCACCG AGCGAGCGAGTGCGCATTCAGGGAGTGGCC AA |
| SEQ ID No: 53 | source: AAV3; Recogn. Site: | TTGGCCACTCCCTCTATGCGCATTCGCTCGCT CGGTGGGGCCTGGCGACCAAAGGTCGCCAG |

TABLE 8-continued

Exemplary AAV derived ITRs harboring antiparallel recognition sites for nicking endonuclease Nb.BsmI:

| SEQ ID No: | Name | Full Sequence |
|---|---|---|
| | Nb.BsmI; Format: tl | ACGGACGTGCTTTGCACGTCCGGCCCCACCG AGCGAGCGAATGCGCATAGAGGGAGTGGCC AA |
| SEQ ID No: 54 | source: AAV4 left; Recogn. Site: Nb.BsmI; Format: bl | TTGGCCACTCCCTGAATGCGCGCTCGCTCACT CACTCGGCCCTGGAGACCAAAGGTCTCCAGA CTGCCGGCCTCTGGCCGGCAGGGCCGAGTGA GTGAGCGAGCGCGCATTCAGGGAGTGGCCA A |
| SEQ ID No: 55 | source: AAV4 left; Recogn. Site: Nb.BsmI; Format: tl | TTGGCCACTCCCTCTATGCGCATTCGCTCACT CACTCGGCCCTGGAGACCAAAGGTCTCCAGA CTGCCGGCCTCTGGCCGGCAGGGCCGAGTGA GTGAGCGAATGCGCATAGAGGGAGTGGCCA A |
| SEQ ID No: 56 | source: AAV4 right; Recogn. Site: Nb.BsmI; Format: bl | TTGGCCACATTAGGAATGCGCGCTCGCTCAC TCACTCGGCCCTGGAGACCAAAGGTCTCCAG ACTGCCGGCCTCTGGCCGGCAGGGCCGAGTG AGTGAGCGAGCGCGCATTCAGGGAGTGGCC AA |
| SEQ ID No: 57 | source: AAV4 right; Recogn. Site: Nb.BsmI; Format: tl | TTGGCCACATTAGCTATGCGCATTCGCTCACT CACTCGGCCCTGGAGACCAAAGGTCTCCAGA CTGCCGGCCTCTGGCCGGCAGGGCCGAGTGA GTGAGCGAATGCGCATAGAGGGAGTGGCCA A |
| SEQ ID No: 58 | source: AAV5; Recogn. Site: Nb.BsmI; Format: bl | CTCTCCCCGAATGCGCGTTCGCTCGCTCGCTG GCTCGTTTGGGGGGGTGGCAGCTCAAAGAGC TGCCAGACGACGGCCCTCTGGCCGTCGCCCC CCCAAACGAGCCAGCGAGCGAGCGAACGCG CATTCGGGGAGAG |
| SEQ ID No: 59 | source: AAV5; Recogn. Site: Nb.BsmI; Format: tl | CTCTCCCCCCTGTCGCATTCGCTCGCTCGCTG GCTCGTTTGGGGGGGTGGCAGCTCAAAGAGC TGCCAGACGACGGCCCTCTGGCCGTCGCCCC CCCAAACGAGCCAGCGAGCGAGCGAATGCG ACAGGGGGGAGAG |
| SEQ ID No: 60 | source: AAV7; Recogn. Site: Nb.BsmI; Format: bl | TTGGCCACTCCCTGAATGCGCGCTCGCTCGCT CGGTGGGGCCTGCGGACCAAAGGTCCGCAG ACGGCAGAGCTCTGCTCTGCCGGCCCCACCG AGCGAGCGAGCGCGCATTCAGGGAGTGGCC AA |
| SEQ ID No: 61 | source: AAV7; Recogn. Site: Nb.BsmI; Format: tl | TTGGCCACTCCCTCTATGCGCATTCGCTCGCT CGGTGGGGCCTGCGGACCAAAGGTCCGCAG ACGGCAGAGCTCTGCTCTGCCGGCCCCACCG AGCGAGCGAATGCGCATAGAGGGAGTGGCC AA |

TABLE 9

Exemplary AAV derived ITRs harboring antiparallel recognition sites for nicking endonuclease Nb.BsrDI

| SEQ ID No: | Name | Full Sequence |
|---|---|---|
| SEQ ID No: 62 | source: AAV1; Recogn. Site: Nb.BsrDI; Format: bl | TTGCCCACTCCCGCAATGCGCGCTCGCTCGCT CGGTGGGGCCTGCGGACCAAAGGTCCGCAGA CGGCAGAGCTCTGCTCTGCCGGCCCCACCGAG CGAGCGAGCGCGCATTGCGGGAGTGGGCAA |
| SEQ ID No: 63 | source: AAV1; Recogn. Site: Nb.BsrDI; Format: tl | TTGCCCACTCCCTCATTGCGCGCTCGCTCGCT CGGTGGGGCCTGCGGACCAAAGGTCCGCAGA CGGCAGAGCTCTGCTCTGCCGGCCCCACCGAG CGAGCGAGCGCAATGAGGGAGTGGGCAA |
| SEQ ID No: 64 | source: AAV2; Recogn. Site: | TTGGCCACTCCCGCAATGCGCGCTCGCTCGCT CACTGAGGCCGGGCGACCAAAGGTCGCCCGA |

TABLE 9-continued

Exemplary AAV derived ITRs harboring antiparallel recognition sites for nicking endonuclease Nb.BsrDI

| SEQ ID No: | Name | Full Sequence |
|---|---|---|
| | Nb.BsrDI; Format: b1 | CGCCCGGGCTTTGCCCGGGCGGCCTCAGTGAG CGAGCGAGCGCGCATTGCGGGAGTGGCCAA |
| SEQ ID No: 65 | source: AAV2; Recogn. Site: Nb.BsrDI; Format: t1 | TTGGCCACTCCCTCATTGCGCGCTCGCTCGCT CACTGAGGCCGGGCGACCAAAGGTCGCCCGA CGCCCGGGCTTTGCCCGGGCGGCCTCAGTGAG CGAGCGAGCGCGCAATGAGGGAGTGGCCAA |
| SEQ ID No: 66 | source: AAV3; Recogn. Site: Nb.BsrDI; Format: b1 | TTGGCCACTCCCGCAATGCGCACTCGCTCGCT CGGTGGGGCCTGGCGACCAAAGGTCGCCAGA CGGACGTGCTTTGCACGTCCGGCCCCACCGAG CGAGCGAGTGCGCATTGCGGGAGTGGCCAA |
| SEQ ID No: 67 | source: AAV3; Recogn. Site: Nb.BsrDI; Format: t1 | TTGGCCACTCCCTCATTGCGCACTCGCTCGCT CGGTGGGGCCTGGCGACCAAAGGTCGCCAGA CGGACGTGCTTTGCACGTCCGGCCCCACCGAG CGAGCGAGTGCGCAATGAGGGAGTGGCCAA |
| SEQ ID No: 68 | source: AAV4 left; Recogn. Site: Nb.BsrDI; Format: b1 | TTGGCCACTCCCGCAATGCGCGCTCGCTCACT CACTCGGCCCTGGAGACCAAAGGTCTCCAGA CTGCCGGCCTCTGGCCGGCAGGGCCGAGTGA GTGAGCGAGCGCGCATTGCGGGAGTGGCCAA |
| SEQ ID No: 69 | source: AAV4 left; Recogn. Site: Nb.BsrDI; Format: t1 | TTGGCCACTCCCTCATTGCGCGCTCGCTCACT CACTCGGCCCTGGAGACCAAAGGTCTCCAGA CTGCCGGCCTCTGGCCGGCAGGGCCGAGTGA GTGAGCGAGCGCGCAATGAGGGAGTGGCCAA |
| SEQ ID No: 70 | source: AAV4 right; Recogn. Site: Nb.BsrDI; Format: b1 | TTGGCCACATTAGCAATGCGCGCTCGCTCACT CACTCGGCCCTGGAGACCAAAGGTCTCCAGA CTGCCGGCCTCTGGCCGGCAGGGCCGAGTGA GTGAGCGAGCGCGCATTGCGGGAGTGGCCAA |
| SEQ ID No: 71 | source: AAV4 right; Recogn. Site: Nb.BsrDI; Format: t1 | TTGGCCACATTAGCATTGCGCGCTCGCTCACT CACTCGGCCCTGGAGACCAAAGGTCTCCAGA CTGCCGGCCTCTGGCCGGCAGGGCCGAGTGA GTGAGCGAGCGCGCAATGAGGGAGTGGCCAA |
| SEQ ID No: 72 | source: AAV5; Recogn. Site: Nb.BsrDI; Format: b1 | CTCTCCGCAATGTCGCGTTCGCTCGCTCGCTG GCTCGTTTGGGGGGTGGCAGCTCAAAGAGC TGCCAGACGACGGCCCTCTGGCCGTCGCCCCC CCAAACGAGCCAGCGAGCGAGCGAACGCGAC ATTGCGGAGAG |
| SEQ ID No: 73 | source: AAV5; Recogn. Site: Nb.BsrDI; Format: t1 | CTCTCCCCCATTGCGCGTTCGCTCGCTCGCTG GCTCGTTTGGGGGGTGGCAGCTCAAAGAGC TGCCAGACGACGGCCCTCTGGCCGTCGCCCCC CCAAACGAGCCAGCGAGCGAGCGAACGCGCA ATGGGGAGAG |
| SEQ ID No: 74 | source: AAV7; Recogn. Site: Nb.BsrDI; Format: b1 | TTGGCCACTCCCGCAATGCGCGCTCGCTCGCT CGGTGGGGCCTGCGGACCAAAGGTCCGCAGA CGGCAGAGCTCTGCTCTGCCGGCCCCACCGAG CGAGCGAGCGCGCATTGCGGGAGTGGCCAA |
| SEQ ID No: 75 | source: AAV7; Recogn. Site: Nb.BsrDI; Format: t1 | TTGGCCACTCCCTCATTGCGCGCTCGCTCGCT CGGTGGGGCCTGCGGACCAAAGGTCCGCAGA CGGCAGAGCTCTGCTCTGCCGGCCCCACCGAG CGAGCGAGCGCGCAATGAGGGAGTGGCCAA |

TABLE 10

Exemplary AAV derived ITRs harboring antiparallel recognition sites for nicking endonuclease Nb.BssSi

| SEQ ID No: | Name | Full Sequence |
|---|---|---|
| SEQ ID No: 76 | source: AAV1; Recogn. Site: Nb.BssSI; Format: b1 | TTGCCCACGAGCTCTCTGCGCGCTCGCTCGCT CGGTGGGGCCTGCGGACCAAAGGTCCGCAGA CGGCAGAGCTCTGCTCTGCCGGCCCCACCGAG CGAGCGAGCGCGCAGAGAGCTCGTGGGCAA |

TABLE 10-continued

Exemplary AAV derived ITRs harboring antiparallel recognition sites for nicking endonuclease Nb.BssSi

| SEQ ID No: | Name | Full Sequence |
|---|---|---|
| SEQ ID No: 77 | source: AAV1; Recogn. Site: Nb.BssSI; Format: tl | TTGCCCACTCCCTCGTGGCGCGCTCGCTCGCT CGGTGGGGCCTGCGGACCAAAGGTCCGCAGA CGGCAGAGCTCTGCTCTGCCGGCCCCACCGAG CGAGCGAGCGCGCCACGAGGGAGTGGGCAA |
| SEQ ID No: 78 | source: AAV2; Recogn. Site: Nb.BssSI; Format: bl | TTGGCCACGAGCTCTCTGCGCGCTCGCTCGCT CACTGAGGCCGGGCGACCAAAGGTCGCCCGA CGCCCGGGCTTTGCCCGGGCGGCCTCAGTGAG CGAGCGAGCGCGCAGAGAGCTCGTGGCCAA |
| SEQ ID No: 79 | source: AAV2; Recogn. Site: Nb.BssSI; Format: tl | TTGGCCACTCCCTCGTGGCGCGCTCGCTCGCT CACTGAGGCCGGGCGACCAAAGGTCGCCCGA CGCCCGGGCTTTGCCCGGGCGGCCTCAGTGAG CGAGCGAGCGCGCCACGAGGGAGTGGCCAA |
| SEQ ID No: 80 | source: AAV3; Recogn. Site: Nb.BssSI; Format: bl | TTGGCCACGAGCTCTATGCGCACTCGCTCGCT CGGTGGGGCCTGGCGACCAAAGGTCGCCAGA CGGACGTGCTTTGCACGTCCGGCCCCACCGAG CGAGCGAGTGCGCATAGAGCTCGTGGCCAA |
| SEQ ID No: 81 | source: AAV3; Recogn. Site: Nb.BssSI; Format: tl | TTGGCCACTCCCTCGTGGCGCACTCGCTCGCT CGGTGGGGCCTGGCGACCAAAGGTCGCCAGA CGGACGTGCTTTGCACGTCCGGCCCCACCGAG CGAGCGAGTGCGCCACGAGGGAGTGGCCAA |
| SEQ ID No: 82 | source: AAV4 left; Recogn. Site: Nb.BssSI; Format: bl | TTGGCCACGAGCTCTATGCGCGCTCGCTCACT CACTCGGCCCTGGAGACCAAAGGTCTCCAGA CTGCCGGCCTCTGGCCGGCAGGGCCGAGTGA GTGAGCGAGCGCGCATAGAGCTCGTGGCCAA |
| SEQ ID No: 83 | source: AAV4 left; Recogn. Site: Nb.BssSI; Format: tl | TTGGCCACTCCCTCGTGGCGCGCTCGCTCACT CACTCGGCCCTGGAGACCAAAGGTCTCCAGA CTGCCGGCCTCTGGCCGGCAGGGCCGAGTGA GTGAGCGAGCGCGCCACGAGGGAGTGGCCAA |
| SEQ ID No: 84 | source: AAV4 right; Recogn. Site: Nb.BssSI; Format: bl | TTGGCCACGAGAGCTATGCGCGCTCGCTCACT CACTCGGCCCTGGAGACCAAAGGTCTCCAGA CTGCCGGCCTCTGGCCGGCAGGGCCGAGTGA GTGAGCGAGCGCGCATAGAGCTCGTGGCCAA |
| SEQ ID No: 85 | source: AAV4 right; Recogn. Site: Nb.BssSI; Format: tl | TTGGCCACATTCTCGTGGCGCGCTCGCTCACT CACTCGGCCCTGGAGACCAAAGGTCTCCAGA CTGCCGGCCTCTGGCCGGCAGGGCCGAGTGA GTGAGCGAGCGCGCCACGAGGGAGTGGCCAA |
| SEQ ID No: 86 | source: AAV5; Recogn. Site: Nb.BssSI; Format: bl | CTCACGAGCCTGTCGCGTTCGCTCGCTCGCTG GCTCGTTTGGGGGGGTGGCAGCTCAAAGAGC TGCCAGACGACGGCCCTCTGGCCGTCGCCCCC CCAAACGAGCCAGCGAGCGAGCGAACGCGAC AGGCTCGTGAG |
| SEQ ID No: 87 | source: AAV5; Recogn. Site: Nb.BssSI; Format: tl | CTCTCCCTCGTGTCGCGTTCGCTCGCTCGCTG GCTCGTTTGGGGGGGTGGCAGCTCAAAGAGC TGCCAGACGACGGCCCTCTGGCCGTCGCCCCC CCAAACGAGCCAGCGAGCGAGCGAACGCGAC ACGAGGGAGAG |
| SEQ ID No: 88 | source: AAV7; Recogn. Site: Nb.BssSI; Format: bl | TTGGCCACGAGCTCTATGCGCGCTCGCTCGCT CGGTGGGGCCTGCGGACCAAAGGTCCGCAGA CGGCAGAGCTCTGCTCTGCCGGCCCCACCGAG CGAGCGAGCGCGCATAGAGCTCGTGGCCAA |
| SEQ ID No: 89 | source: AAV7; Recogn. Site: Nb.BssSI; Format: tl | TTGGCCACTCCCTCGTGGCGCGCTCGCTCGCT CGGTGGGGCCTGCGGACCAAAGGTCCGCAGA CGGCAGAGCTCTGCTCTGCCGGCCCCACCGAG CGAGCGAGCGCGCCACGAGGGAGTGGCCAA |

TABLE 11

Exemplary AAV derived ITRs harboring antiparallel recognition sites for nicking endonuclease Nb.BtsI:

| SEQ ID No: | Name | Full Sequence |
|---|---|---|
| SEQ ID No: 90 | source: AAV1; Recogn. Site: Nb.BtsI; Format: bl | TTGCCCACTCCCGCAGTGCGCGCTCGCTCGCT CGGTGGGGCCTGCGGACCAAAGGTCCGCAGA CGGCAGAGCTCTGCTCTGCCGGCCCCACCGAG CGAGCGAGCGCGCACTGCGGGAGTGGGCAA |
| SEQ ID No: 91 | source: AAV1; Recogn. Site: Nb.BtsI; Format: tl | TTGCCCACTCCCTCACTGCGCGCTCGCTCGCT CGGTGGGGCCTGCGGACCAAAGGTCCGCAGA CGGCAGAGCTCTGCTCTGCCGGCCCCACCGAG CGAGCGAGCGCGCAGTGAGGGAGTGGGCAA |
| SEQ ID No: 92 | source: AAV2; Recogn. Site: Nb.BtsI; Format: bl | TTGGCCACTCCCGCAGTGCGCGCTCGCTCGCT CACTGAGGCCGGGCGACCAAAGGTCGCCCGA CGCCCGGGCTTTGCCCGGGCGGCCTCAGTGAG CGAGCGAGCGCGCACTGCGGGAGTGGCCAA |
| SEQ ID No: 93 | source: AAV2; Recogn. Site: Nb.BtsI; Format: tl | TTGGCCACTCCCTCACTGCGCGCTCGCTCGCT CACTGAGGCCGGGCGACCAAAGGTCGCCCGA CGCCCGGGCTTTGCCCGGGCGGCCTCAGTGAG CGAGCGAGCGCGCAGTGAGGGAGTGGCCAA |
| SEQ ID No: 94 | source: AAV3; Recogn. Site: Nb.BtsI; Format: bl | TTGGCCACTCCCGCAGTGCGCACTCGCTCGCT CGGTGGGGCCTGGCGACCAAAGGTCGCCAGA CGGACGTGCTTTGCACGTCCGGCCCCACCGAG CGAGCGAGTGCGCACTGCGGGAGTGGCCAA |
| SEQ ID No: 95 | source: AAV3; Recogn. Site: Nb.BtsI; Format: tl | TTGGCCACTCCCTCACTGCGCACTCGCTCGCT CGGTGGGGCCTGGCGACCAAAGGTCGCCAGA CGGACGTGCTTTGCACGTCCGGCCCCACCGAG CGAGCGAGTGCGCAGTGAGGGAGTGGCCAA |
| SEQ ID No: 96 | source: AAV4 left; Recogn. Site: Nb.BtsI; Format: bl | TTGGCCACTCCCGCAGTGCGCGCTCGCTCACT CACTCGGCCCTGGAGACCAAAGGTCTCCAGA CTGCCGGCCTCTGGCCGGCAGGGCCGAGTGA GTGAGCGAGCGCGCACTGCGGGAGTGGCCAA |
| SEQ ID No: 97 | source: AAV4 left; Recogn. Site: Nb.BtsI; Format: tl | TTGGCCACTCCCTCACTGCGCGCTCGCTCACT CACTCGGCCCTGGAGACCAAAGGTCTCCAGA CTGCCGGCCTCTGGCCGGCAGGGCCGAGTGA GTGAGCGAGCGCGCAGTGAGGGAGTGGCCAA |
| SEQ ID No: 98 | source: AAV4 right; Recogn. Site: Nb.BtsI; Format: bl | TTGGCCACATTAGCAGTGCGCGCTCGCTCACT CACTCGGCCCTGGAGACCAAAGGTCTCCAGA CTGCCGGCCTCTGGCCGGCAGGGCCGAGTGA GTGAGCGAGCGCGCACTGCGGGAGTGGCCAA |
| SEQ ID No: 99 | source: AAV4 right; Recogn. Site: Nb.BtsI; Format: tl | TTGGCCACATTAGCACTGCGCGCTCGCTCACT CACTCGGCCCTGGAGACCAAAGGTCTCCAGA CTGCCGGCCTCTGGCCGGCAGGGCCGAGTGA GTGAGCGAGCGCGCAGTGAGGGAGTGGCCAA |
| SEQ ID No: 100 | source: AAV5; Recogn. Site: Nb.BtsI; Format: bl | CTCTCCGCAGTGTCGCGTTCGCTCGCTCGCTG GCTCGTTTGGGGGGGTGGCAGCTCAAAGAGC TGCCAGACGACGGCCCTCTGGCCGTCGCCCCC CCAAACGAGCCAGCGAGCGAGCGAACGCGAC ACTGCGGAGAG |
| SEQ ID No: 101 | source: AAV5; Recogn. Site: Nb.BtsI; Format: tl | CTCTCCCCACTGCCGCGTTCGCTCGCTCGCTG GCTCGTTTGGGGGGGTGGCAGCTCAAAGAGC TGCCAGACGACGGCCCTCTGGCCGTCGCCCCC CCAAACGAGCCAGCGAGCGAGCGAACGCGGC AGTGGGGAGAG |
| SEQ ID No: 102 | source: AAV7; Recogn. Site: Nb.BtsI; Format: bl | TTGGCCACTCCCGCAGTGCGCGCTCGCTCGCT CGGTGGGGCCTGCGGACCAAAGGTCCGCAGA CGGCAGAGCTCTGCTCTGCCGGCCCCACCGAG CGAGCGAGCGCGCACTGCGGGAGTGGCCAA |
| SEQ ID No: 103 | source: AAV7; Recogn. Site: Nb.BtsI; Format: tl | TTGGCCACTCCCTCACTGCGCGCTCGCTCGCT CGGTGGGGCCTGCGGACCAAAGGTCCGCAGA CGGCAGAGCTCTGCTCTGCCGGCCCCACCGAG CGAGCGAGCGCGCAGTGAGGGAGTGGCCAA |

TABLE 12

Exemplary AAV derived ITRs harboring antiparallel recognition sites for nicking endonuclease Nt.AlwI:

| SEQ ID No: | Name | Full Sequence |
|---|---|---|
| SEQ ID No: 104 | source: AAV1; Recogn. Site: Nt.AlwI; Format: bl | TTGCCCACTCCCTCGATCCGCGCTCGCTCGCT CGGTGGGGCCTGCGGACCAAAGGTCCGCAGA CGGCAGAGCTCTGCTCTGCCGGCCCCACCGAG CGAGCGAGCGCGGATCGAGGGAGTGGGCAA |
| SEQ ID No: 105 | source: AAV1; Recogn. Site: Nt.AlwI; Format: tl | TTGCCCACTGGATCTCTGCGCGCTCGCTCGCT CGGTGGGGCCTGCGGACCAAAGGTCCGCAGA CGGCAGAGCTCTGCTCTGCCGGCCCCACCGAG CGAGCGAGCGCGCAGAGATCCAGTGGGCAA |
| SEQ ID No: 106 | source: AAV2; Recogn. Site: Nt.AlwI; Format: bl | TTGGCCACTCCCTCGATCCGCGCTCGCTCGCT CACTGAGGCCGGGCGACCAAAGGTCGCCCGA CGCCCGGGCTTTGCCCGGGCGGCCTCAGTGAG CGAGCGAGCGCGGATCGAGGGAGTGGCCAA |
| SEQ ID No: 107 | source: AAV2; Recogn. Site: Nt.AlwI; Format: tl | TTGGCCACTGGATCTCTGCGCGCTCGCTCGCT CACTGAGGCCGGGCGACCAAAGGTCGCCCGA CGCCCGGGCTTTGCCCGGGCGGCCTCAGTGAG CGAGCGAGCGCGCAGAGATCCAGTGGCCAA |
| SEQ ID No: 108 | source: AAV3; Recogn. Site: Nt.AlwI; Format: bl | TTGGCCACTCCCTCGATCCGCACTCGCTCGCT CGGTGGGGCCTGGCGACCAAAGGTCGCCAGA CGGACGTGCTTTGCACGTCCGGCCCCACCGAG CGAGCGAGTGCGGATCGAGGGAGTGGCCAA |
| SEQ ID No: 109 | source: AAV3; Recogn. Site: Nt.AlwI; Format: tl | TTGGCCACTGGATCTATGCGCACTCGCTCGCT CGGTGGGGCCTGGCGACCAAAGGTCGCCAGA CGGACGTGCTTTGCACGTCCGGCCCCACCGAG CGAGCGAGTGCGCATAGATCCAGTGGCCAA |
| SEQ ID No: 110 | source: AAV4 left; Recogn. Site: Nt.AlwI; Format: bl | TTGGCCACTCCCTCGATCCGCGCTCGCTCACT CACTCGGCCCTGGAGACCAAAGGTCTCCAGA CTGCCGGCCTCTGGCCGGCAGGGCCGAGTGA GTGAGCGAGCGCGGATCGAGGGAGTGGCCAA |
| SEQ ID No: 111 | source: AAV4 left; Recogn. Site: Nt.AlwI; Format: tl | TTGGCCACTGGATCTATGCGCGCTCGCTCACT CACTCGGCCCTGGAGACCAAAGGTCTCCAGA CTGCCGGCCTCTGGCCGGCAGGGCCGAGTGA GTGAGCGAGCGCGCATAGATCCAGTGGCCAA |
| SEQ ID No: 112 | source: AAV4 right; Recogn. Site: Nt.AlwI; Format: bl | TTGGCCACATTAGCGATCCGCGCTCGCTCACT CACTCGGCCCTGGAGACCAAAGGTCTCCAGA CTGCCGGCCTCTGGCCGGCAGGGCCGAGTGA GTGAGCGAGCGCGGATCGAGGGAGTGGCCAA |
| SEQ ID No: 113 | source: AAV4 right; Recogn. Site: Nt.AlwI; Format: tl | TTGGCCACAGGATCTATGCGCGCTCGCTCACT CACTCGGCCCTGGAGACCAAAGGTCTCCAGA CTGCCGGCCTCTGGCCGGCAGGGCCGAGTGA GTGAGCGAGCGCGCATAGATCCAGTGGCCAA |
| SEQ ID No: 114 | source: AAV5; Recogn. Site: Nt.AlwI; Format: bl | CTCTCCCCCCTGTCGCGATCCCTCGCTCGCTG GCTCGTTTGGGGGGTGGCAGCTCAAAGAGC TGCCAGACGACGGCCCTCTGGCCGTCGCCCCC CCAAACGAGCCAGCGAGCGAGGGATCGCGAC AGGGGGGAGAG |
| SEQ ID No: 115 | source: AAV5; Recogn. Site: Nt.AlwI; Format: tl | CTCTCCCCCGGATCGCGTTCGCTCGCTCGCTG GCTCGTTTGGGGGGTGGCAGCTCAAAGAGC TGCCAGACGACGGCCCTCTGGCCGTCGCCCCC CCAAACGAGCCAGCGAGCGAGCGAACGCGAT CCGGGGGAGAG |
| SEQ ID No: 116 | source: AAV7; Recogn. Site: Nt.AlwI; Format: bl | TTGGCCACTCCCTCGATCCGCGCTCGCTCGCT CGGTGGGGCCTGCGGACCAAAGGTCCGCAGA CGGCAGAGCTCTGCTCTGCCGGCCCCACCGAG CGAGCGAGCGCGGATCGAGGGAGTGGCCAA |
| SEQ ID No: 117 | source: AAV7; Recogn. Site: Nt.AlwI; Format: tl | TTGGCCACTGGATCTATGCGCGCTCGCTCGCT CGGTGGGGCCTGCGGACCAAAGGTCCGCAGA CGGCAGAGCTCTGCTCTGCCGGCCCCACCGAG CGAGCGAGCGCGCATAGATCCAGTGGCCAA |

TABLE 13

Exemplary AAV derived ITRs harboring antiparallel recognition sites for nicking endonuclease Nt.BbvCI:

| SEQ ID No: | Name | Full Sequence |
|---|---|---|
| SEQ ID No: 118 | source: AAV1; Recogn. Site: Nt.BbvCI; Format: bl | TTGCCCACTCCCGCTGAGGGCGCTCGCTCGCT CGGTGGGGCCTGCGGACCAAAGGTCCGCAGA CGGCAGAGCTCTGCTCTGCCGGCCCCACCGAG CGAGCGAGCGCCCTCAGCGGGAGTGGGCAA |
| SEQ ID No: 119 | source: AAV1; Recogn. Site: Nt.BbvCI; Format: tl | TTGCCCACTCCCCCTCAGCGCGCTCGCTCGCT CGGTGGGGCCTGCGGACCAAAGGTCCGCAGA CGGCAGAGCTCTGCTCTGCCGGCCCCACCGAG CGAGCGAGCGCGCTGAGGGGGAGTGGGCAA |
| SEQ ID No: 120 | source: AAV2; Recogn. Site: Nt.BbvCI; Format: bl | TTGGCCACTCCCGCTGAGGGCGCTCGCTCGCT CACTGAGGCCGGGCGACCAAAGGTCGCCCGA CGCCCGGGCTTTGCCCGGGCGGCCTCAGTGAG CGAGCGAGCGCCCTCAGCGGGAGTGGCCAA |
| SEQ ID No: 121 | source: AAV2; Recogn. Site: Nt.BbvCI; Format: tl | TTGGCCACTCCCCCTCAGCGCGCTCGCTCGCT CACTGAGGCCGGGCGACCAAAGGTCGCCCGA CGCCCGGGCTTTGCCCGGGCGGCCTCAGTGAG CGAGCGAGCGCGCTGAGGGGGAGTGGCCAA |
| SEQ ID No: 122 | source: AAV3; Recogn. Site: Nt.BbvCI; Format: bl | TTGGCCACTCCCGCTGAGGGCACTCGCTCGCT CGGTGGGGCCTGCGACCAAAGGTCGCCAGA CGGACGTGCTTTGCACGTCCGGCCCCACCGAG CGAGCGAGTGCCCTCAGCGGGAGTGGCCAA |
| SEQ ID No: 123 | source: AAV3; Recogn. Site: Nt.BbvCI; Format: tl | TTGGCCACTCCCCCTCAGCGCACTCGCTCGCT CGGTGGGGCCTGCGACCAAAGGTCGCCAGA CGGACGTGCTTTGCACGTCCGGCCCCACCGAG CGAGCGAGTGCGCTGAGGGGGAGTGGCCAA |
| SEQ ID No: 124 | source: AAV4 left; Recogn. Site: Nt.BbvCI; Format: bl | TTGGCCACTCCCGCTGAGGGCGCTCGCTCACT CACTCGGCCCTGGAGACCAAAGGTCTCCAGA CTGCCGGCCTCTGGCCGGCAGGGCCGAGTGA GTGAGCGAGCGCCCTCAGCGGGAGTGGCCAA |
| SEQ ID No: 125 | source: AAV4 left; Recogn. Site: Nt.BbvCI; Format: tl | TTGGCCACTCCCCCTCAGCGCGCTCGCTCACT CACTCGGCCCTGGAGACCAAAGGTCTCCAGA CTGCCGGCCTCTGGCCGGCAGGGCCGAGTGA GTGAGCGAGCGCGCTGAGGGGGAGTGGCCAA |
| SEQ ID No: 126 | source: AAV4 right; Recogn. Site: Nt.BbvCI; Format: bl | TTGGCCACATTAGCTGAGGGCGCTCGCTCACT CACTCGGCCCTGGAGACCAAAGGTCTCCAGA CTGCCGGCCTCTGGCCGGCAGGGCCGAGTGA GTGAGCGAGCGCCCTCAGCGGGAGTGGCCAA |
| SEQ ID No: 127 | source: AAV4 right; Recogn. Site: Nt.BbvCI; Format: tl | TTGGCCACATTACCTCAGCGCGCTCGCTCACT CACTCGGCCCTGGAGACCAAAGGTCTCCAGA CTGCCGGCCTCTGGCCGGCAGGGCCGAGTGA GTGAGCGAGCGCGCTGAGGGGGAGTGGCCAA |
| SEQ ID No: 128 | source: AAV5; Recogn. Site: Nt.BbvCI; Format: bl | CTCTCCCCGCTGAGGCGTTCGCTCGCTCGCTG GCTCGTTTGGGGGGGTGGCAGCTCAAAGAGC TGCCAGACGACGGCCCTCTGGCCGTCGCCCCC CCAAACGAGCCAGCGAGCGAGCGAACGCCTC AGCGGGGAGAG |
| SEQ ID No: 129 | source: AAV5; Recogn. Site: Nt.BbvCI; Format: tl | CTCTCCCCTCAGCCGCGTTCGCTCGCTCGCTG GCTCGTTTGGGGGGGTGGCAGCTCAAAGAGC TGCCAGACGACGGCCCTCTGGCCGTCGCCCCC CCAAACGAGCCAGCGAGCGAGCGAACGCGGC TGAGGGGAGAG |
| SEQ ID No: 130 | source: AAV7; Recogn. Site: Nt.BbvCI; Format: bl | TTGCCCACTCCCGCTGAGGGCGCTCGCTCGCT CGGTGGGGCCTGCGGACCAAAGGTCCGCAGA CGGCAGAGCTCTGCTCTGCCGGCCCCACCGAG CGAGCGAGCGCCCTCAGCGGGAGTGGCCAA |
| SEQ ID No: 131 | source: AAV7; Recogn. Site: Nt.BbvCI; Format: tl | TTGCCCACTCCCCCTCAGCGCGCTCGCTCGCT CGGTGGGGCCTGCGGACCAAAGGTCCGCAGA CGGCAGAGCTCTGCTCTGCCGGCCCCACCGAG CGAGCGAGCGCGCTGAGGGGGAGTGGCCAA |

TABLE 14

Exemplary AAV derived ITRs harboring antiparallel recognition sites for nicking endonuclease Nt.BsmAI:

| SEQ ID No: | Name | Full Sequence |
|---|---|---|
| SEQ ID No: 132 | source: AAV1; Recogn. Site: Nt.BsmAI; Format: bl | TTGCCCACTGAGACTCTGCGCGCTCGCTCGCT CGGTGGGGCCTGCGGACCAAAGGTCCGCAGA CGGCAGAGCTCTGCTCTGCCGGCCCCACCGAG CGAGCGAGCGCGCAGAGTCTCAGTGGGCAA |
| SEQ ID No: 133 | source: AAV1; Recogn. Site: Nt.BsmAI; Format: tl | TTGCCCACTCCGTCTCTGCGCGCTCGCTCGCT CGGTGGGGCCTGCGGACCAAAGGTCCGCAGA CGGCAGAGCTCTGCTCTGCCGGCCCCACCGAG CGAGCGAGCGCGCAGAGACGGAGTGGGCAA |
| SEQ ID No: 134 | source: AAV2; Recogn. Site: Nt.BsmAI; Format: bl | TTGGCCACTGAGACTCTGCGCGCTCGCTCGCT CACTGAGGCCGGGCGACCAAAGGTCGCCCGA CGCCCGGGCTTTGCCCGGGCGGCCTCAGTGAG CGAGCGAGCGCGCAGAGTCTCAGTGGCCAA |
| SEQ ID No: 135 | source: AAV2; Recogn. Site: Nt.BsmAI; Format: tl | TTGGCCACTCCGTCTCTGCGCGCTCGCTCGCT CACTGAGGCCGGGCGACCAAAGGTCGCCCGA CGCCCGGGCTTTGCCCGGGCGGCCTCAGTGAG CGAGCGAGCGCGCAGAGACGGAGTGGCCAA |
| SEQ ID No: 136 | source: AAV3; Recogn. Site: Nt.BsmAI; Format: bl | TTGGCCACTGAGACTATGCGCACTCGCTCGCT CGGTGGGGCCTGGCGACCAAAGGTCGCCAGA CGGACGTGCTTTGCACGTCCGGCCCCACCGAG CGAGCGAGTGCGCATAGTCTCAGTGGCCAA |
| SEQ ID No: 137 | source: AAV3; Recogn. Site: Nt.BsmAI; Format: tl | TTGGCCACTCCGTCTCTGCGCACTCGCTCGCT CGGTGGGGCCTGGCGACCAAAGGTCGCCAGA CGGACGTGCTTTGCACGTCCGGCCCCACCGAG CGAGCGAGTGCGCAGAGACGGAGTGGCCAA |
| SEQ ID No: 138 | source: AAV4 left; Recogn. Site: Nt.BsmAI; Format: bl | TTGGCCACTGAGACTATGCGCGCTCGCTCACT CACTCGGCCCTGGAGACCAAAGGTCTCCAGA CTGCCGGCCTCTGGCCGGCAGGGCCGAGTGA GTGAGCGAGCGCGCATAGTCTCAGTGGCCAA |
| SEQ ID No: 139 | source: AAV4 left; Recogn. Site: Nt.BsmAI; Format: tl | TTGGCCACTCCGTCTCTGCGCGCTCGCTCACT CACTCGGCCCTGGAGACCAAAGGTCTCCAGA CTGCCGGCCTCTGGCCGGCAGGGCCGAGTGA GTGAGCGAGCGCGCAGAGACGGAGTGGCCAA |
| SEQ ID No: 140 | source: AAV4 right; Recogn. Site: Nt.BsmAI; Format: bl | TTGGCCACAGAGACTATGCGCGCTCGCTCACT CACTCGGCCCTGGAGACCAAAGGTCTCCAGA CTGCCGGCCTCTGGCCGGCAGGGCCGAGTGA GTGAGCGAGCGCGCATAGTCTCAGTGGCCAA |
| SEQ ID No: 141 | source: AAV4 right; Recogn. Site: Nt.BsmAI; Format: tl | TTGGCCACATTGTCTCTGCGCGCTCGCTCACT CACTCGGCCCTGGAGACCAAAGGTCTCCAGA CTGCCGGCCTCTGGCCGGCAGGGCCGAGTGA GTGAGCGAGCGCGCAGAGACGGAGTGGCCAA |
| SEQ ID No: 142 | source: AAV5; Recogn. Site: Nt.BsmAI; Format: bl | CTCTCCCCGAGACGCGTTCGCTCGCTCGCTG GCTCGTTTGGGGGGGTGGCAGCTCAAAGAGC TGCCAGACGACGGCCCTCTGGCCGTCGCCCCC CCAAACGAGCCAGCGAGCGAGCGAACGCGTC TCGGGGAGAG |
| SEQ ID No: 143 | source: AAV5; Recogn. Site: Nt.BsmAI; Format: tl | CTCTCCCCGTCTCGCGTTCGCTCGCTCGCTG GCTCGTTTGGGGGGGTGGCAGCTCAAAGAGC TGCCAGACGACGGCCCTCTGGCCGTCGCCCCC CCAAACGAGCCAGCGAGCGAGCGAACGCGAG ACGGGGAGAG |
| SEQ ID No: 144 | source: AAV7; Recogn. Site: Nt.BsmAI; Format: bl | TTGGCCACTGAGACTATGCGCGCTCGCTCGCT CGGTGGGGCCTGCGGACCAAAGGTCCGCAGA CGGCAGAGCTCTGCTCTGCCGGCCCCACCGAG CGAGCGAGCGCGCATAGTCTCAGTGGCCAA |
| SEQ ID No: 145 | source: AAV7; Recogn. Site: Nt.BsmAI; Format: tl | TTGGCCACTCCGTCTCTGCGCGCTCGCTCGCT CGGTGGGGCCTGCGGACCAAAGGTCCGCAGA CGGCAGAGCTCTGCTCTGCCGGCCCCACCGAG CGAGCGAGCGCGCAGAGACGGAGTGGCCAA |

TABLE 15

Exemplary AAV derived ITRs harboring antiparallel recognition sites for nicking endonuclease Nt.BspQI:

| SEQ ID No: | Name | Full Sequence |
|---|---|---|
| SEQ ID No: 146 | source: AAV1; Recogn. Site: Nt.BspQI; Format: bl | TTGCCCACTCCCGAAGAGCGCGCTCGCTCGCT CGGTGGGGCCTGCGGACCAAAGGTCCGCAGA CGGCAGAGCTCTGCTCTGCCGGCCCCACCGAG CGAGCGAGCGCGCTCTTCGGGAGTGGGCAA |
| SEQ ID No: 147 | source: AAV1; Recogn. Site: Nt.BspQI; Format: tl | TTGCCCACTCCCGCTCTTCGCGCTCGCTCGCTC GGTGGGGCCTGCGGACCAAAGGTCCGCAGAC GGCAGAGCTCTGCTCTGCCGGCCCCACCGAGC GAGCGAGCGCGAAGAGCGGGAGTGGGCAA |
| SEQ ID No: 148 | source: AAV2; Recogn. Site: Nt.BspQI; Format: bl | TTGGCCACTCCCGAAGAGCGCGCTCGCTCGCT CACTGAGGCCGGGCGACCAAAGGTCGCCCGA CGCCCGGGCTTTGCCCGGGCGGCCTCAGTGAG CGAGCGAGCGCGCTCTTCGGGAGTGGCCAA |
| SEQ ID No: 149 | source: AAV2; Recogn. Site: Nt.BspQI; Format: tl | TTGGCCACTCCCGCTCTTCGCGCTCGCTCGCT CACTGAGGCCGGGCGACCAAAGGTCGCCCGA CGCCCGGGCTTTGCCCGGGCGGCCTCAGTGAG CGAGCGAGCGCGAAGAGCGGGAGTGGCCAA |
| SEQ ID No: 150 | source: AAV3; Recogn. Site: Nt.BspQI; Format: bl | TTGGCCACTCCCGAAGAGCGCACTCGCTCGCT CGGTGGGGCCTGGCGACCAAAGGTCGCCAGA CGGACGTGCTTTGCACGTCCGGCCCCACCGAG CGAGCGAGTGCGCTCTTCGGGAGTGGCCAA |
| SEQ ID No: 151 | source: AAV3; Recogn. Site: Nt.BspQI; Format: tl | TTGGCCACTCCCGCTCTTCGCACTCGCTCGCT CGGTGGGGCCTGGCGACCAAAGGTCGCCAGA CGGACGTGCTTTGCACGTCCGGCCCCACCGAG CGAGCGAGTGCGAAGAGCGGGAGTGGCCAA |
| SEQ ID No: 152 | source: AAV4 left; Recogn. Site: Nt.BspQI; Format: bl | TTGGCCACTCCCGAAGAGCGCGCTCGCTCACT CACTCGGCCCTGGAGACCAAAGGTCTCCAGA CTGCCGGCCTCTGGCCGGCAGGGCCGAGTGA GTGAGCGAGCGCGCTCTTCGGGAGTGGCCAA |
| SEQ ID No: 153 | source: AAV4 left; Recogn. Site: Nt.BspQI; Format: tl | TTGGCCACTCCCGCTCTTCGCGCTCGCTCACT CACTCGGCCCTGGAGACCAAAGGTCTCCAGA CTGCCGGCCTCTGGCCGGCAGGGCCGAGTGA GTGAGCGAGCGCGAAGAGCGGGAGTGGCCAA |
| SEQ ID No: 154 | source: AAV4 right; Recogn. Site: Nt.BspQI; Format: bl | TTGGCCACATTAGAAGAGCGCGCTCGCTCACT CACTCGGCCCTGGAGACCAAAGGTCTCCAGA CTGCCGGCCTCTGGCCGGCAGGGCCGAGTGA GTGAGCGAGCGCGCTCTTCGGGAGTGGCCAA |
| SEQ ID No: 155 | source: AAV4 right; Recogn. Site: Nt.BspQI; Format: tl | TTGGCCACATTAGCTCTTCGCGCTCGCTCACT CACTCGGCCCTGGAGACCAAAGGTCTCCAGA CTGCCGGCCTCTGGCCGGCAGGGCCGAGTGA GTGAGCGAGCGCGAAGAGCGGGAGTGGCCAA |
| SEQ ID No: 156 | source: AAV5; Recogn. Site: Nt.BspQI; Format: bl | CTCTCCCGAAGAGCGCGTTCGCTCGCTCGCTG GCTCGTTTGGGGGGGTGGCAGCTCAAAGAGC TGCCAGACGACGGCCCTCTGGCCGTCGCCCCC CCAAACGAGCCAGCGAGCGAGCGAACGCGCT CTTCGGGAGAG |
| SEQ ID No: 157 | source: AAV5; Recogn. Site: Nt.BspQI; Format: tl | CTCTCCCGCTCTTCGCGTTCGCTCGCTCGCTGG CTCGTTTGGGGGGGTGGCAGCTCAAAGAGCT GCCAGACGACGGCCCTCTGGCCGTCGCCCCCC CAAACGAGCCAGCGAGCGAGCGAACGCGAAG AGCGGGAGAG |
| SEQ ID No: 158 | source: AAV7; Recogn. Site: Nt.BspQI; Format: bl | TTGCCCACTCCCGAAGAGCGCGCTCGCTCGCT CGGTGGGGCCTGCGGACCAAAGGTCCGCAGA CGGCAGAGCTCTGCTCTGCCGGCCCCACCGAG CGAGCGAGCGCGCTCTTCGGGAGTGGCCAA |
| SEQ ID No: 159 | source: AAV7; Recogn. Site: Nt.BspQI; Format: tl | TTGGCCACTCCCGCTCTTCGCGCTCGCTCGCT CGGTGGGGCCTGCGGACCAAAGGTCCGCAGA CGGCAGAGCTCTGCTCTGCCGGCCCCACCGAG CGAGCGAGCGCGAAGAGCGGGAGTGGCCAA |

TABLE 16

Exemplary AAV derived ITRs harboring antiparallel recognition sites for nicking endonuclease Nt.BstNBI:

| SEQ ID No: | Name | Full Sequence |
| --- | --- | --- |
| SEQ ID No: 160 | source: AAV1; Recogn. Site: Nt.BstNBI; Format: bl | TTGCCCACTCCCTCTCTGCGCGACTCGCTCGC TCGGTGGGGCCTGCGGACCAAAGGTCCGCAG ACGGCAGAGCTCTGCTCTGCCGGCCCCACCGA GCGAGCGAGTCGCGCAGAGAGGGAGTGGGCA A |
| SEQ ID No: 161 | source: AAV1; Recogn. Site: Nt.BstNBI; Format: tl | TTGCCGAGTCCCTCTCTGCGCGCTCGCTCGCT CGGTGGGGCCTGCGGACCAAAGGTCCGCAGA CGGCAGAGCTCTGCTCTGCCGGCCCCACCGAG CGAGCGAGCGCGCAGAGAGGGACTCGGCAA |
| SEQ ID No: 162 | source: AAV2; Recogn. Site: Nt.BstNBI; Format: bl | TTGGCCACTCCCTCTCTGCGCGACTCGCTCGC TCACTGAGGCCGGGCGACCAAAGGTCGCCCG ACGCCCGGGCTTTGCCCGGGCGGCCTCAGTGA GCGAGCGAGTCGCGCAGAGAGGGAGTGGCCA A |
| SEQ ID No: 163 | source: AAV2; Recogn. Site: Nt.BstNBI; Format: tl | TTGGCGAGTCCCTCTCTGCGCGCTCGCTCGCT CACTGAGGCCGGGCGACCAAAGGTCGCCCGA CGCCCGGGCTTTGCCCGGGCGGCCTCAGTGAG CGAGCGAGCGCGCAGAGAGGGACTCGCCAA |
| SEQ ID No: 164 | source: AAV3; Recogn. Site: Nt.BstNBI; Format: bl | TTGGCCACTCCCTCTATGCGCGACTCGCTCGC TCGGTGGGGCCTGGCGACCAAAGGTCGCCAG ACGGACGTGCTTTGCACGTCCGGCCCCACCGA GCGAGCGAGTCGCGCATAGAGGGAGTGGCCA A |
| SEQ ID No: 165 | source: AAV3; Recogn. Site: Nt.BstNBI; Format: tl | TTGGCGAGTCCCTCTATGCGCACTCGCTCGCT CGGTGGGGCCTGGCGACCAAAGGTCGCCAGA CGGACGTGCTTTGCACGTCCGGCCCCACCGAG CGAGCGAGTGCGCATAGAGGGACTCGCCAA |
| SEQ ID No: 166 | source: AAV4 left; Recogn. Site: Nt.BstNBI; Format: bl | TTGGCCACTCCCTCTATGCGCGACTCGCTCAC TCACTCGGCCCTGGAGACCAAAGGTCTCCAG ACTGCCGGCCTCTGGCCGGCAGGGCCGAGTG AGTGAGCGAGTCGCGCATAGAGGGAGTGGCC AA |
| SEQ ID No: 167 | source: AAV4 left; Recogn. Site: Nt.BstNBI; Format: tl | TTGGCGAGTCCCTCTATGCGCGCTCGCTCACT CACTCGGCCCTGGAGACCAAAGGTCTCCAGA CTGCCGGCCTCTGGCCGGCAGGGCCGAGTGA GTGAGCGAGCGCGCATAGAGGGACTCGCCAA |
| SEQ ID No: 168 | source: AAV4 right; Recogn. Site: Nt.BstNBI; Format: bl | TTGGCCACATTAGCTATGCGCGACTCGCTCAC TCACTCGGCCCTGGAGACCAAAGGTCTCCAG ACTGCCGGCCTCTGGCCGGCAGGGCCGAGTG AGTGAGCGAGTCGCGCATAGAGGGAGTGGCC AA |
| SEQ ID No: 169 | source: AAV4 right; Recogn. Site: Nt.BstNBI; Format: tl | TTGGCCAGAGTGCGCTATGCGCGCTCGCTCACT CACTCGGCCCTGGAGACCAAAGGTCTCCAGA CTGCCGGCCTCTGGCCGGCAGGGCCGAGTGA GTGAGCGAGCGCGCATAGAGACTCTGGCCAA |
| SEQ ID No: 170 | source: AAV5; Recogn. Site: Nt.BstNBI; Format: bl | CTCTCCCCCCTGTCGCGACTCGCTCGCTCGCT GGCTCGTTTGGGGGGTGGCAGCTCAAAGAG CTGCCAGACGACGGCCCTCTGGCCGTCGCCCC CCCAAACGAGCCAGCGAGCGAGCGAGTCGCG ACAGGGGGGAGAG |
| SEQ ID No: 171 | source: AAV5; Recogn. Site: Nt.BstNBI; Format: tl | CTCTCCCCCGAGTCGCGTTCGCTCGCTCGCTG GCTCGTTTGGGGGGTGGCAGCTCAAAGAGC TGCCAGACGACGGCCCTCTGGCCGTCGCCCCC CCAAACGAGCCAGCGAGCGAGCGAACGCGAC TCGGGGGAGAG |
| SEQ ID No: 172 | source: AAV7; Recogn. Site: Nt.BstNBI; Format: bl | TTGGCCACTCCCTCTATGCGCGACTCGCTCGC TCGGTGGGGCCTGCGGACCAAAGGTCCGCAG ACGGCAGAGCTCTGCTCTGCCGGCCCCACCGA GCGAGCGAGTCGCGCATAGAGGGAGTGGCCA A |
| SEQ ID No: 173 | source: AAV7; Recogn. Site: | TTGGCGAGTCCCTCTATGCGCGCTCGCTCGCT CGGTGGGGCCTGCGGACCAAAGGTCCGCAGA |

TABLE 16-continued

Exemplary AAV derived ITRs harboring antiparallel recognition sites for nicking endonuclease Nt.BstNBI:

| SEQ ID No: | Name | Full Sequence |
|---|---|---|
| | Nt.BstNBI; Format: tl | CGGCAGAGCTCTGCTCTGCCGGCCCCACCGAG CGAGCGAGCGCGCATAGAGGGACTCGCCAA |

TABLE 17

Reverse Complement of Nicking Enzyme Targets

| SEQ ID: | Name | Sequence |
|---|---|---|
| SEQ ID No: 186 | wt_AAV1 | AACGGGTGAGGGAGAGACGCGCGAGCGAGCG AGCCACCCCGGACGCCTGGTTTCCAGGCGTCTG CCGTCTCGAGACGAGACGGCCGGGGTGGCTCG CTC |
| SEQ ID No: 187 | AAV1_Nb.BbvCI_BL | AACGGGTGAGGGGGAGTCGCGCGAGCGAGCGA GCCACCCCGGACGCCTGGTTTCCAGGCGTCTGC CGTCTCGAGACGAGACGGCCGGGGTGGCTCGC TC |
| SEQ ID No: 188 | AAV1_Nb.BbvCI_TL | AACGGGTGAGGGCGACTCCCGCGAGCGAGCGA GCCACCCCGGACGCCTGGTTTCCAGGCGTCTGC CGTCTCGAGACGAGACGGCCGGGGTGGCTCGC TC |
| SEQ ID No: 189 | AAV1_Nb.BsmI_BL | AACGGGTGAGGGACTTACGCGCGAGCGAGCGA GCCACCCCGGACGCCTGGTTTCCAGGCGTCTGC CGTCTCGAGACGAGACGGCCGGGGTGGCTCGC TC |
| SEQ ID No: 190 | AAV1_Nb.BsmI_TL | AACGGGTGAGGGAGAGACGCGTAAGCGAGCG AGCCACCCCGGACGCCTGGTTTCCAGGCGTCTG CCGTCTCGAGACGAGACGGCCGGGGTGGCTCG CTC |
| SEQ ID No: 191 | AAV1_Nb.BsrDI_BL | AACGGGTGAGGGCGTTACGCGCGAGCGAGCGA GCCACCCCGGACGCCTGGTTTCCAGGCGTCTGC CGTCTCGAGACGAGACGGCCGGGGTGGCTCGC TC |
| SEQ ID No: 192 | AAV1_Nb.BsrDI_TL | AACGGGTGAGGGAGTAACGCGCGAGCGAGCGA GCCACCCCGGACGCCTGGTTTCCAGGCGTCTGC CGTCTCGAGACGAGACGGCCGGGGTGGCTCGC TC |
| SEQ ID No: 193 | AAV1_Nb.BssSI_BL | AACGGGTGCTCGAGAGACGCGCGAGCGAGCGA GCCACCCCGGACGCCTGGTTTCCAGGCGTCTGC CGTCTCGAGACGAGACGGCCGGGGTGGCTCGC TC |
| SEQ ID No: 194 | AAV1_Nb.BssSI_TL | AACGGGTGAGGGAGCACCGCGCGAGCGAGCGA GCCACCCCGGACGCCTGGTTTCCAGGCGTCTGC CGTCTCGAGACGAGACGGCCGGGGTGGCTCGC TC |
| SEQ ID No: 195 | AAV1_Nb.BtsI_BL | AACGGGTGAGGGCGTCACGCGCGAGCGAGCGA GCCACCCCGGACGCCTGGTTTCCAGGCGTCTGC CGTCTCGAGACGAGACGGCCGGGGTGGCTCGC TC |
| SEQ ID No: 196 | AAV1_Nb.BtsI_TL | AACGGGTGAGGGAGTGACGCGCGAGCGAGCGA GCCACCCCGGACGCCTGGTTTCCAGGCGTCTGC CGTCTCGAGACGAGACGGCCGGGGTGGCTCGC TC |
| SEQ ID No: 197 | AAV1_Nt.AlwI_BL | AACGGGTGAGGGAGCTAGGCGCGAGCGAGCGA GCCACCCCGGACGCCTGGTTTCCAGGCGTCTGC CGTCTCGAGACGAGACGGCCGGGGTGGCTCGC TC |
| SEQ ID No: 198 | AAV1_Nt.AlwI_BL | AACGGGTGACCTAGAGACGCGCGAGCGAGCGA GCCACCCCGGACGCCTGGTTTCCAGGCGTCTG |

TABLE 17-continued

Reverse Complement of Nicking Enzyme Targets

| SEQ ID: | Name | Sequence |
|---|---|---|
| | | CGTCTCGAGACGAGACGGCCGGGGTGGCTCGC<br>TC |
| SEQ ID No: 199 | AAV1_Nt.BbvCI_TL | AACGGGTGAGGGCGACTCCCGCGAGCGAGCGA<br>GCCACCCCGGACGCCTGGTTTCCAGGCGTCTGC<br>CGTCTCGAGACGAGACGGCCGGGGTGGCTCGC<br>TC |
| SEQ ID No: 200 | AAV1_Nt.BbvCI_BL | AACGGGTGAGGGGGAGTCGCGCGAGCGAGCGA<br>GCCACCCCGGACGCCTGGTTTCCAGGCGTCTGC<br>CGTCTCGAGACGAGACGGCCGGGGTGGCTCGC<br>TC |
| SEQ ID No: 201 | AAV1_Nt.BsmAI_TL | AACGGGTGACTCTGAGACGCGCGAGCGAGCGA<br>GCCACCCCGGACGCCTGGTTTCCAGGCGTCTGC<br>CGTCTCGAGACGAGACGGCCGGGGTGGCTCGC<br>TC |
| SEQ ID No: 202 | AAV1_Nt.BsmAI_BL | AACGGGTGAGGCAGAGACGCGCGAGCGAGCG<br>AGCCACCCCGGACGCCTGGTTTCCAGGCGTCTG<br>CCGTCTCGAGACGAGACGGCCGGGGTGGCTCG<br>CTC |
| SEQ ID No: 203 | AAV1_Nt.BspQI_TL | AACGGGTGAGGGCTTCTCGCGCGAGCGAGCGA<br>GCCACCCCGGACGCCTGGTTTCCAGGCGTCTGC<br>CGTCTCGAGACGAGACGGCCGGGGTGGCTCGC<br>TC |
| SEQ ID No: 204 | AAV1_Nt.BspQI_BL | AACGGGTGAGGGCGAGAAGCGCGAGCGAGCG<br>AGCCACCCCGGACGCCTGGTTTCCAGGCGTCTG<br>CCGTCTCGAGACGAGACGGCCGGGGTGGCTCG<br>CTC |
| SEQ ID No: 205 | AAV1_Nt.BstNBI_TL | AACGGGTGAGGGAGAGACGCGCTGAGCGAGCG<br>AGCCACCCCGGACGCCTGGTTTCCAGGCGTCTG<br>CCGTCTCGAGACGAGACGGCCGGGGTGGCTCG<br>CTC |
| SEQ ID No: 206 | AAV1_Nt.BstNBI_BL | AACGGCTCAGGGAGAGACGCGCGAGCGAGCGA<br>GCCACCCCGGACGCCTGGTTTCCAGGCGTCTGC<br>CGTCTCGAGACGAGACGGCCGGGGTGGCTCGC<br>TC |
| SEQ ID No: 207 | wt_AAV2 | AACCGGTGAGGGAGAGACGCGCGAGCGAGCG<br>AGTGACTCCGGCCCGCTGGTTTCCAGCGGGCTG<br>CGGGGCCCGAAACGGGCCCGCCGGAGTCACTCG<br>CTC |
| SEQ ID No: 208 | AAV2_Nb.BbvCI_BL | AACCGGTGAGGGGGAGTCGCGCGAGCGAGCGA<br>GTGACTCCGGCCCGCTGGTTTCCAGCGGGCTGC<br>GGGCCCGAAACGGGCCCGCCGGAGTCACTCGC<br>TC |
| SEQ ID No: 209 | AAV2_Nb.BbvCI_TL | AACCGGTGAGGGCGACTCCCGCGAGCGAGCGA<br>GTGACTCCGGCCCGCTGGTTTCCAGCGGGCTGC<br>GGGCCCGAAACGGGCCCGCCGGAGTCACTCGC<br>TC |
| SEQ ID No: 210 | AAV2_Nb.BsmI_BL | AACCGGTGAGGGACTTACGCGCGAGCGAGCGA<br>GTGACTCCGGCCCGCTGGTTTCCAGCGGGCTGC<br>GGGCCCGAAACGGGCCCGCCGGAGTCACTCGC<br>TC |
| SEQ ID No: 211 | AAV2_Nb.BsmI_TL | AACCGGTGAGGGAGAGACGCGTAAGCGAGCGA<br>GTGACTCCGGCCCGCTGGTTTCCAGCGGGCTGC<br>GGGCCCGAAACGGGCCCGCCGGAGTCACTCGC<br>TC |
| SEQ ID No: 212 | AAV2_Nb.BsrDI_BL | AACCGGTGAGGGCGTTACGCGCGAGCGAGCGA<br>GTGACTCCGGCCCGCTGGTTTCCAGCGGGCTGC<br>GGGCCCGAAACGGGCCCGCCGGAGTCACTCGC<br>TC |
| SEQ ID No: 213 | AAV2_Nb.BsrDI_TL | AACCGGTGAGGGAGTAACGCGCGAGCGAGCGA<br>GTGACTCCGGCCCGCTGGTTTCCAGCGGGCTGC<br>GGGCCCGAAACGGGCCCGCCGGAGTCACTCGC<br>TC |

TABLE 17-continued

Reverse Complement of Nicking Enzyme Targets

| SEQ ID: | Name | Sequence |
| --- | --- | --- |
| SEQ ID No: 214 | AAV2_Nb.BssSI_BL | AACCGGTGCTCGAGAGACGCGCGAGCGAGCGAGTGACTCCGGCCCGCTGGTTTCCAGCGGGCTGCGGGCCCGAAACGGGCCCGCCGGAGTCACTCGCTC |
| SEQ ID No: 215 | AAV2_Nb.BssSI_TL | AACCGGTGAGGGAGCACCGCGCGAGCGAGCGAGTGACTCCGGCCCGCTGGTTTCCAGCGGGCTGCGGGCCCGAAACGGGCCCGCCGGAGTCACTCGCTC |
| SEQ ID No: 216 | AAV2_Nb.BtsI_BL | AACCGGTGAGGGCGTCACGCGCGAGCGAGCGAGTGACTCCGGCCCGCTGGTTTCCAGCGGGCTGCGGGCCCGAAACGGGCCCGCCGGAGTCACTCGCTC |
| SEQ ID No: 217 | AAV2_Nb.BtsI_TL | AACCGGTGAGGGAGTGACGCGCGAGCGAGCGAGTGACTCCGGCCCGCTGGTTTCCAGCGGGCTGCGGGCCCGAAACGGGCCCGCCGGAGTCACTCGCTC |
| SEQ ID No: 218 | AAV2_Nt.AlwI_BL | AACCGGTGAGGGAGCTAGGCGCGAGCGAGCGAGTGACTCCGGCCCGCTGGTTTCCAGCGGGCTGCGGGCCCGAAACGGGCCCGCCGGAGTCACTCGCTC |
| SEQ ID No: 219 | AAV2_Nt.AlwI_BL | AACCGGTGACCTAGAGACGCGCGAGCGAGCGAGTGACTCCGGCCCGCTGGTTTCCAGCGGGCTGCGGGCCCGAAACGGGCCCGCCGGAGTCACTCGCTC |
| SEQ ID No: 220 | AAV2_Nt.BbvCI_TL | AACCGGTGAGGGCGACTCCCGCGAGCGAGCGAGTGACTCCGGCCCGCTGGTTTCCAGCGGGCTGCGGGCCCGAAACGGGCCCGCCGGAGTCACTCGCTC |
| SEQ ID No: 221 | AAV2_Nt.BbvCI_BL | AACCGGTGAGGGGGAGTCGCGCGAGCGAGCGAGTGACTCCGGCCCGCTGGTTTCCAGCGGGCTGCGGGCCCGAAACGGGCCCGCCGGAGTCACTCGCTC |
| SEQ ID No: 222 | AAV2_Nt.BsmAI_TL | AACCGGTGACTCTGAGACGCGCGAGCGAGCGAGTGACTCCGGCCCGCTGGTTTCCAGCGGGCTGCGGGCCCGAAACGGGCCCGCCGGAGTCACTCGCTC |
| SEQ ID No: 223 | AAV2_Nt.BsmAI_BL | AACCGGTGAGGCAGAGACGCGCGAGCGAGCGAGTGACTCCGGCCCGCTGGTTTCCAGCGGGCTGCGGGCCCGAAACGGGCCCGCCGGAGTCACTCGCTC |
| SEQ ID No: 224 | AAV2_Nt.BspQI_TL | AACCGGTGAGGGCTTCTCGCGCGAGCGAGCGAGTGACTCCGGCCCGCTGGTTTCCAGCGGGCTGCGGGCCCGAAACGGGCCCGCCGGAGTCACTCGCTC |
| SEQ ID No: 225 | AAV2_Nt.BspQI_BL | AACCGGTGAGGGCGAGAAGCGCGAGCGAGCGAGTGACTCCGGCCCGCTGGTTTCCAGCGGGCTGCGGGCCCGAAACGGGCCCGCCGGAGTCACTCGCTC |
| SEQ ID No: 226 | AAV2_Nt.BstNBI_TL | AACCGGTGAGGGAGAGACGCGCTGAGCGAGCGAGTGACTCCGGCCCGCTGGTTTCCAGCGGGCTGCGGGCCCGAAACGGGCCCGCCGGAGTCACTCGCTC |
| SEQ ID No: 227 | AAV2_Nt.BstNBI_BL | AACCGCTCAGGGAGAGACGCGCGAGCGAGCGAGTGACTCCGGCCCGCTGGTTTCCAGCGGGCTGCGGGCCCGAAACGGGCCCGCCGGAGTCACTCGCTC |
| SEQ ID No: 228 | wt_AAV3 | AACCGGTGAGGGAGATACGCGTGAGCGAGCGAGCCACCCCGGACCGCTGGTTTCCAGCGGTCTGCCTGCACGAAACGTGCAGGCGGGGTGGCTCGCTC |

TABLE 17-continued

Reverse Complement of Nicking Enzyme Targets

| SEQ ID: | Name | Sequence |
| --- | --- | --- |
| SEQ ID No: 229 | AAV3_Nb.BbvCI_BL | AACCGGTGAGGGGGAGTCGCGTGAGCGAGCGAGCCACCCCGGACCGCTGGTTTCCAGCGGTCTGCCTGCACGAAACGTGCAGGCCGGGGTGGCTCGCTC |
| SEQ ID No: 230 | AAV3_Nb.BbvCI_TL | AACCGGTGAGGGCGACTCCCGTGAGCGAGCGAGCCACCCCGGACCGCTGGTTTCCAGCGGTCTGCCTGCACGAAACGTGCAGGCCGGGGTGGCTCGCTC |
| SEQ ID No: 231 | AAV3_Nb.BsmI_BL | AACCGGTGAGGGACTTACGCGTGAGCGAGCGAGCCACCCCGGACCGCTGGTTTCCAGCGGTCTGCCTGCACGAAACGTGCAGGCCGGGGTGGCTCGCTC |
| SEQ ID No: 232 | AAV3_Nb.BsmI_TL | AACCGGTGAGGGAGATACGCGTAAGCGAGCGAGCCACCCCGGACCGCTGGTTTCCAGCGGTCTGCCTGCACGAAACGTGCAGGCCGGGGTGGCTCGCTC |
| SEQ ID No: 233 | AAV3_Nb.BsrDI_BL | AACCGGTGAGGGCGTTACGCGTGAGCGAGCGAGCCACCCCGGACCGCTGGTTTCCAGCGGTCTGCCTGCACGAAACGTGCAGGCCGGGGTGGCTCGCTC |
| SEQ ID No: 234 | AAV3_Nb.BsrDI_TL | AACCGGTGAGGGAGTAACGCGTGAGCGAGCGAGCCACCCCGGACCGCTGGTTTCCAGCGGTCTGCCTGCACGAAACGTGCAGGCCGGGGTGGCTCGCTC |
| SEQ ID No: 235 | AAV3_Nb.BssSI_BL | AACCGGTGCTCGAGATACGCGTGAGCGAGCGAGCCACCCCGGACCGCTGGTTTCCAGCGGTCTGCCTGCACGAAACGTGCAGGCCGGGGTGGCTCGCTC |
| SEQ ID No: 236 | AAV3_Nb.BssSI_TL | AACCGGTGAGGGAGCACCGCGTGAGCGAGCGAGCCACCCCGGACCGCTGGTTTCCAGCGGTCTGCCTGCACGAAACGTGCAGGCCGGGGTGGCTCGCTC |
| SEQ ID No: 237 | AAV3_Nb.BtsI_BL | AACCGGTGAGGGCGTCACGCGTGAGCGAGCGAGCCACCCCGGACCGCTGGTTTCCAGCGGTCTGCCTGCACGAAACGTGCAGGCCGGGGTGGCTCGCTC |
| SEQ ID No: 238 | AAV3_Nb.BtsI_TL | AACCGGTGAGGGAGTGACGCGTGAGCGAGCGAGCCACCCCGGACCGCTGGTTTCCAGCGGTCTGCCTGCACGAAACGTGCAGGCCGGGGTGGCTCGCTC |
| SEQ ID No: 239 | AAV3_Nt.AlwI_BL | AACCGGTGAGGGAGCTAGGCGTGAGCGAGCGAGCCACCCCGGACCGCTGGTTTCCAGCGGTCTGCCTGCACGAAACGTGCAGGCCGGGGTGGCTCGCTC |
| SEQ ID No: 240 | AAV3_Nt.AlwI_BL | AACCGGTGACCTAGATACGCGTGAGCGAGCGAGCCACCCCGGACCGCTGGTTTCCAGCGGTCTGCCTGCACGAAACGTGCAGGCCGGGGTGGCTCGCTC |
| SEQ ID No: 241 | AAV3_Nt.BbvCI_TL | AACCGGTGAGGGCGACTCCCGTGAGCGAGCGAGCCACCCCGGACCGCTGGTTTCCAGCGGTCTGCCTGCACGAAACGTGCAGGCCGGGGTGGCTCGCTC |
| SEQ ID No: 242 | AAV3_Nt.BbvCI_BL | AACCGGTGAGGGGGAGTCGCGTGAGCGAGCGAGCCACCCCGGACCGCTGGTTTCCAGCGGTCTGCCTGCACGAAACGTGCAGGCCGGGGTGGCTCGCTC |
| SEQ ID No: 243 | AAV3_Nt.BsmAI_TL | AACCGGTGACTCTGATACGCGTGAGCGAGCGAGCCACCCCGGACCGCTGGTTTCCAGCGGTCTGCCTGCACGAAACGTGCAGGCCGGGGTGGCTCGCTC |

TABLE 17-continued

Reverse Complement of Nicking Enzyme Targets

| SEQ ID: | Name | Sequence |
| --- | --- | --- |
| SEQ ID No: 244 | AAV3_Nt.BsmAI_BL | AACCGGTGAGGCAGAGACGCGTGAGCGAGCGA GCCACCCCGGACCGCTGGTTTCCAGCGGTCTGC CTGCACGAAACGTGCAGGCCGGGGTGGCTCGC TC |
| SEQ ID No: 245 | AAV3_Nt.BspQI_TL | AACCGGTGAGGGCTTCTCGCGTGAGCGAGCGA GCCACCCCGGACCGCTGGTTTCCAGCGGTCTGC CTGCACGAAACGTGCAGGCCGGGGTGGCTCGC TC |
| SEQ ID No: 246 | AAV3_Nt.BspQI_BL | AACCGGTGAGGGCGAGAAGCGTGAGCGAGCGA GCCACCCCGGACCGCTGGTTTCCAGCGGTCTGC CTGCACGAAACGTGCAGGCCGGGGTGGCTCGC TC |
| SEQ ID No: 247 | AAV3_Nt.BstNBI_TL | AACCGGTGAGGGAGATACGCGCTGAGCGAGCG AGCCACCCCGGACCGCTGGTTTCCAGCGGTCTG CCTGCACGAAACGTGCAGGCCGGGGTGGCTCG CTC |
| SEQ ID No: 248 | AAV3_Nt.BstNBI_BL | AACCGCTCAGGGAGATACGCGTGAGCGAGCGA GCCACCCCGGACCGCTGGTTTCCAGCGGTCTGC CTGCACGAAACGTGCAGGCCGGGGTGGCTCGC TC |
| SEQ ID No: 249 | wt_AAV4_left | AACCGGTGAGGGAGATACGCGCGAGCGAGTGA GTGAGCCGGGACCTCTGGTTTCCAGAGGTCTGA CGGCCGGAGACCGGCCGTCCCGGCTCACTCACT CGCTCGCGCGTATCTCCCTCACCGGTT |
| SEQ ID No: 250 | AAV4_left_Nb.BbvCI_BL | AACCGGTGAGGGGGAGTCGCGCGAGCGAGTGA GTGAGCCGGGACCTCTGGTTTCCAGAGGTCTGA CGGCCGGAGACCGGCCGTCCCGGCTCACTCACT CGCTCGCGCGACTCCCCCTCACCGGTT |
| SEQ ID No: 251 | AAV4_left_Nb.BbvCI_TL | AACCGGTGAGGGCGACTCCCGCGAGCGAGTGA GTGAGCCGGGACCTCTGGTTTCCAGAGGTCTGA CGGCCGGAGACCGGCCGTCCCGGCTCACTCACT CGCTCGCGGGAGTCGCCCTCACCGGTT |
| SEQ ID No: 252 | AAV4_left_Nb.BsmI_BL | AACCGGTGAGGGACTTACGCGCGAGCGAGTGA GTGAGCCGGGACCTCTGGTTTCCAGAGGTCTGA CGGCCGGAGACCGGCCGTCCCGGCTCACTCACT CGCTCGCGCGTAAGTCCCTCACCGGTT |
| SEQ ID No: 253 | AAV4_left_Nb.BsmI_TL | AACCGGTGAGGGAGATACGCGTAAGCGAGTGA GTGAGCCGGGACCTCTGGTTTCCAGAGGTCTGA CGGCCGGAGACCGGCCGTCCCGGCTCACTCACT CGCTTACGCGTATCTCCCTCACCGGTT |
| SEQ ID No: 254 | AAV4_left_Nb.BsrDI_BL | AACCGGTGAGGGCGTTACGCGCGAGCGAGTGA GTGAGCCGGGACCTCTGGTTTCCAGAGGTCTGA CGGCCGGAGACCGGCCGTCCCGGCTCACTCACT CGCTCGCGCGTAACGCCCTCACCGGTT |
| SEQ ID No: 255 | AAV4_left_Nb.BsrDI_TL | AACCGGTGAGGGAGTAACGCGCGAGCGAGTGA GTGAGCCGGGACCTCTGGTTTCCAGAGGTCTGA CGGCCGGAGACCGGCCGTCCCGGCTCACTCACT CGCTCGCGCGTTACTCCCTCACCGGTT |
| SEQ ID No: 256 | AAV4_left_Nb.BssSI_BL | AACCGGTGCTCGAGATACGCGCGAGCGAGTGA GTGAGCCGGGACCTCTGGTTTCCAGAGGTCTGA CGGCCGGAGACCGGCCGTCCCGGCTCACTCACT CGCTCGCGCGTATCTCGAGCACCGGTT |
| SEQ ID No: 257 | AAV4_left_Nb.BssSI_TL | AACCGGTGAGGGAGCACCGCGCGAGCGAGTGA GTGAGCCGGGACCTCTGGTTTCCAGAGGTCTGA CGGCCGGAGACCGGCCGTCCCGGCTCACTCACT CGCTCGCGCGGTGCTCCCTCACCGGTT |
| SEQ ID No: 258 | AAV4_left_Nb.BtsI_BL | AACCGGTGAGGGCGTCACGCGCGAGCGAGTGA GTGAGCCGGGACCTCTGGTTTCCAGAGGTCTGA CGGCCGGAGACCGGCCGTCCCGGCTCACTCACT CGCTCGCGCGTGACGCCCTCACCGGTT |

TABLE 17-continued

Reverse Complement of Nicking Enzyme Targets

| SEQ ID: | Name | Sequence |
|---|---|---|
| SEQ ID No: 259 | AAV4_left_Nb.BtsI_TL | AACCGGTGAGGGAGTGACGCGCGAGCGAGTGAGTGAGCCGGGACCTCTGGTTTCCAGAGGTCTGACGGCCGGAGACCGGCCGTCCCGGCTCACTCACTCGCTCGCGCGTCACTCCCTCACCGGTT |
| SEQ ID No: 260 | AAV4_left_Nt.AlwI_BL | AACCGGTGAGGGAGCTAGGCGCGAGCGAGTGAGTGAGCCGGGACCTCTGGTTTCCAGAGGTCTGACGGCCGGAGACCGGCCGTCCCGGCTCACTCACTCGCTCGCGCCTAGCTCCCTCACCGGTT |
| SEQ ID No: 261 | AAV4_left_Nt.AlwI_BL | AACCGGTGACCTAGATACGCGCGAGCGAGTGAGTGAGCCGGGACCTCTGGTTTCCAGAGGTCTGACGGCCGGAGACCGGCCGTCCCGGCTCACTCACTCGCTCGCGCGTATCTAGGTCACCGGTT |
| SEQ ID No: 262 | AAV4_left_Nt.BbvCI_TL | AACCGGTGAGGGCGACTCCCGCGAGCGAGTGAGTGAGCCGGGACCTCTGGTTTCCAGAGGTCTGACGGCCGGAGACCGGCCGTCCCGGCTCACTCACTCGCTCGCGGGAGTCGCCCTCACCGGTT |
| SEQ ID No: 263 | AAV4_left_Nt.BbvCI_BL | AACCGGTGAGGGGGAGTCGCGCGAGCGAGTGAGTGAGCCGGGACCTCTGGTTTCCAGAGGTCTGACGGCCGGAGACCGGCCGTCCCGGCTCACTCACTCGCTCGCGCGACTCCCCCTCACCGGTT |
| SEQ ID No: 264 | AAV4_left_Nt.BsmAI_TL | AACCGGTGACTCTGATACGCGCGAGCGAGTGAGTGAGCCGGGACCTCTGGTTTCCAGAGGTCTGACGGCCGGAGACCGGCCGTCCCGGCTCACTCACTCGCTCGCGCGTATCAGAGTCACCGGTT |
| SEQ ID No: 265 | AAV4_left_Nt.BsmAI_BL | AACCGGTGAGGCAGAGACGCGCGAGCGAGTGAGTGAGCCGGGACCTCTGGTTTCCAGAGGTCTGACGGCCGGAGACCGGCCGTCCCGGCTCACTCACTCGCTCGCGCGTCTCTGCCTCACCGGTT |
| SEQ ID No: 266 | AAV4_left_Nt.BspQI_TL | AACCGGTGAGGGCTTCTCGCGCGAGCGAGTGAGTGAGCCGGGACCTCTGGTTTCCAGAGGTCTGACGGCCGGAGACCGGCCGTCCCGGCTCACTCACTCGCTCGCGCGAGAAGCCCTCACCGGTT |
| SEQ ID No: 267 | AAV4_left_Nt.BspQI_BL | AACCGGTGAGGGCGAGAAGCGCGAGCGAGTGAGTGAGCCGGGACCTCTGGTTTCCAGAGGTCTGACGGCCGGAGACCGGCCGTCCCGGCTCACTCACTCGCTCGCGCTTCTCGCCCTCACCGGTT |
| SEQ ID No: 268 | AAV4_left_Nt.BstNBI_TL | AACCGGTGAGGGAGATACGCGCTGAGCGAGTGAGTGAGCCGGGACCTCTGGTTTCCAGAGGTCTGACGGCCGGAGACCGGCCGTCCCGGCTCACTCACTCGCTCAGCGCGTATCTCCCTCACCGGTT |
| SEQ ID No: 269 | AAV4_left_Nt.BstNBI_BL | AACCGCTCAGGGAGATACGCGCGAGCGAGTGAGTGAGCCGGGACCTCTGGTTTCCAGAGGTCTGACGGCCGGAGACCGGCCGTCCCGGCTCACTCACTCGCTCGCGCGTATCTCCCTGAGCGGTT |
| SEQ ID No: 270 | wt_AAV4_Right | AACCGGTGTAATCGATACGCGCGAGCGAGTGAGTGAGCCGGGACCTCTGGTTTCCAGAGGTCTGACGGCCGGAGACCGGCCGTCCCGGCTCACTCACTCGCTCGCGCGTATCTCCCTCACCGGTT |
| SEQ ID No: 271 | AAV4_Right_Nb.BbvCI_BL | AACCGGTGTAATGGAGTCGCGCGAGCGAGTGAGTGAGCCGGGACCTCTGGTTTCCAGAGGTCTGACGGCCGGAGACCGGCCGTCCCGGCTCACTCACTCGCTCGCGCGACTCCCCCTCACCGGTT |
| SEQ ID No: 272 | AAV4_Right_Nb.BbvCI_TL | AACCGGTGTAATCGACTCCCGCGAGCGAGTGAGTGAGCCGGGACCTCTGGTTTCCAGAGGTCTGACGGCCGGAGACCGGCCGTCCCGGCTCACTCACTCGCTCGCGGGAGTCGCCCTCACCGGTT |
| SEQ ID No: 273 | AAV4_Right_Nb.BsmI_BL | AACCGGTGTAATCCTTACGCGCGAGCGAGTGAGTGAGCCGGGACCTCTGGTTTCCAGAGGTCTGACGGCCGGAGACCGGCCGTCCCGGCTCACTCACTCGCTCGCGCGTAAGTCCCTCACCGGTT |

TABLE 17-continued

Reverse Complement of Nicking Enzyme Targets

| SEQ ID: | Name | Sequence |
| --- | --- | --- |
| SEQ ID No: 274 | AAV4_Right_Nb.BsmI_TL | AACCGGTGTAATCGATACGCGTAAGCGAGTGAGTGAGCCGGGACCTCTGGTTTCCAGAGGTCTGACGGCCGGAGACCGGCCGTCCCGGCTCACTCACTCGCTTACGCGTATCTCCCTCACCGGTT |
| SEQ ID No: 275 | AAV4_Right_Nb.BsrDI_BL | AACCGGTGTAATCGTTACGCGCGAGCGAGTGAGTGAGCCGGGACCTCTGGTTTCCAGAGGTCTGACGGCCGGAGACCGGCCGTCCCGGCTCACTCACTCGCTCGCGCGTAACGCCCTCACCGGTT |
| SEQ ID No: 276 | AAV4_Right_Nb.BsrDI_TL | AACCGGTGTAATCGTAACGCGCGAGCGAGTGAGTGAGCCGGGACCTCTGGTTTCCAGAGGTCTGACGGCCGGAGACCGGCCGTCCCGGCTCACTCACTCGCTCGCGCGTTACTCCCTCACCGGTT |
| SEQ ID No: 277 | AAV4_Right_Nb.BssSI_BL | AACCGGTGCTCTCGATACGCGCGAGCGAGTGAGTGAGCCGGGACCTCTGGTTTCCAGAGGTCTGACGGCCGGAGACCGGCCGTCCCGGCTCACTCACTCGCTCGCGCGTATCTCGAGCACCGGTT |
| SEQ ID No: 278 | AAV4_Right_Nb.BssSI_TL | AACCGGTGTAAGAGCACCGCGCGAGCGAGTGAGTGAGCCGGGACCTCTGGTTTCCAGAGGTCTGACGGCCGGAGACCGGCCGTCCCGGCTCACTCACTCGCTCGCGCGGTGCTCCCTCACCGGTT |
| SEQ ID No: 279 | AAV4_Right_Nb.BtsI_BL | AACCGGTGTAATCGTCACGCGCGAGCGAGTGAGTGAGCCGGGACCTCTGGTTTCCAGAGGTCTGACGGCCGGAGACCGGCCGTCCCGGCTCACTCACTCGCTCGCGCGTGACGCCCTCACCGGTT |
| SEQ ID No: 280 | AAV4_Right_Nb.BtsI_TL | AACCGGTGTAATCGTGACGCGCGAGCGAGTGAGTGAGCCGGGACCTCTGGTTTCCAGAGGTCTGACGGCCGGAGACCGGCCGTCCCGGCTCACTCACTCGCTCGCGCGTCACTCCCTCACCGGTT |
| SEQ ID No: 281 | AAV4_Right_Nt.AlwI_BL | AACCGGTGTAATCGCTAGGCGCGAGCGAGTGAGTGAGCCGGGACCTCTGGTTTCCAGAGGTCTGACGGCCGGAGACCGGCCGTCCCGGCTCACTCACTCGCTCGCGCCTAGCTCCCTCACCGGTT |
| SEQ ID No: 282 | AAV4_Right_Nt.AlwI_BL | AACCGGTGTCCTAGATACGCGCGAGCGAGTGAGTGAGCCGGGACCTCTGGTTTCCAGAGGTCTGACGGCCGGAGACCGGCCGTCCCGGCTCACTCACTCGCTCGCGCGTATCTAGGTCACCGGTT |
| SEQ ID No: 283 | AAV4_Right_Nt.BbvCI_TL | AACCGGTGTAATCGACTCCCGCGAGCGAGTGAGTGAGCCGGGACCTCTGGTTTCCAGAGGTCTGACGGCCGGAGACCGGCCGTCCCGGCTCACTCACTCGCTCGCGGGAGTCGCCCTCACCGGTT |
| SEQ ID No: 284 | AAV4_Right_Nt.BbvCI_BL | AACCGGTGTAATGGAGTCGCGCGAGCGAGTGAGTGAGCCGGGACCTCTGGTTTCCAGAGGTCTGACGGCCGGAGACCGGCCGTCCCGGCTCACTCACTCGCTCGCGCGACTCCCCCTCACCGGTT |
| SEQ ID No: 285 | AAV4_Right_Nt.BsmAI_TL | AACCGGTGTCTCTGATACGCGCGAGCGAGTGAGTGAGCCGGGACCTCTGGTTTCCAGAGGTCTGACGGCCGGAGACCGGCCGTCCCGGCTCACTCACTCGCTCGCGCGTATCAGAGTCACCGGTT |
| SEQ ID No: 286 | AAV4_Right_Nt.BsmAI_BL | AACCGGTGTAACAGAGACGCGCGAGCGAGTGAGTGAGCCGGGACCTCTGGTTTCCAGAGGTCTGACGGCCGGAGACCGGCCGTCCCGGCTCACTCACTCGCTCGCGCGTCTCTGCCTCACCGGTT |
| SEQ ID No: 287 | AAV4_Right_Nt.BspQI_TL | AACCGGTGTAATCTTCTCGCGCGAGCGAGTGAGTGAGCCGGGACCTCTGGTTTCCAGAGGTCTGACGGCCGGAGACCGGCCGTCCCGGCTCACTCACTCGCTCGCGCGAGAAGCCCTCACCGGTT |
| SEQ ID No: 288 | AAV4_Right_Nt.BspQI_BL | AACCGGTGTAATCGAGAAGCGCGAGCGAGTGAGTGAGCCGGGACCTCTGGTTTCCAGAGGTCTGACGGCCGGAGACCGGCCGTCCCGGCTCACTCACTCGCTCGCGCTTCTCGCCCTCACCGGTT |

TABLE 17-continued

Reverse Complement of Nicking Enzyme Targets

| SEQ ID: | Name | Sequence |
|---|---|---|
| SEQ ID No: 289 | AAV4_Right_Nt.BstNBI_TL | AACCGGTGTAATCGATACGCGCTGAGCGAGTG<br>AGTGAGCCGGGACCTCTGGTTTCCAGAGGTCTG<br>ACGGCCGGAGACCGGCCGTCCCGGCTCACTCA<br>CTCGCTCAGCGCGTATCTCCCTCACCGGTT |
| SEQ ID No: 290 | AAV4_Right_Nt.BstNBI_BL | AACCGGTCTCAGCGATACGCGCGAGCGAGTGA<br>GTGAGCCGGGACCTCTGGTTTCCAGAGGTCTGA<br>CGGCCGGAGACCGGCCGTCCCGGCTCACTCACT<br>CGCTCGCGCGTATCTCTGAGACCGGTT |
| SEQ ID No: 291 | wt_AAV5 | GAGAGGGGGGACAGCGCAAGCGAGCGAGCGA<br>CCGAGCAAACCCCCCACCGTCGAGTTTCTCGA<br>CGGTCTGCTGCCGGGAGACCGGCAGCGGGGGG<br>GTTTGCTCGGTCGCTCGCTCGCTTGCGCTGTCC<br>CCCCTCTC |
| SEQ ID No: 292 | AAV5_Nb.BbvCI_BL | GAGAGGGGAGTCGGCGCAAGCGAGCGAGCGA<br>CCGAGCAAACCCCCCACCGTCGAGTTTCTCGA<br>CGGTCTGCTGCCGGGAGACCGGCAGCGGGGGG<br>GTTTGCTCGGTCGCTCGCTCGCTTGCGCCGACT<br>CCCCTCTC |
| SEQ ID No: 293 | AAV5_Nb.BbvCI_TL | GAGAGGGGCGACTCCGCAAGCGAGCGAGCGAC<br>CGAGCAAACCCCCCACCGTCGAGTTTCTCGAC<br>GGTCTGCTGCCGGGAGACCGGCAGCGGGGGGG<br>TTTGCTCGGTCGCTCGCTCGCTTGCGGAGTCGC<br>CCCTCTC |
| SEQ ID No: 294 | AAV5_Nb.BsmI_BL | GAGAGGGGCTTACGCGCAAGCGAGCGAGCGAC<br>CGAGCAAACCCCCCACCGTCGAGTTTCTCGAC<br>GGTCTGCTGCCGGGAGACCGGCAGCGGGGGGG<br>TTTGCTCGGTCGCTCGCTCGCTTGCGCGTAAGC<br>CCCTCTC |
| SEQ ID No: 295 | AAV5_Nb.BsmI_TL | GAGAGGGGGGACAGCGTAAGCGAGCGAGCGA<br>CCGAGCAAACCCCCCACCGTCGAGTTTCTCGA<br>CGGTCTGCTGCCGGGAGACCGGCAGCGGGGGG<br>GTTTGCTCGGTCGCTCGCTCGCTTACGCTGTCC<br>CCCCTCTC |
| SEQ ID No: 296 | AAV5_Nb.BsrDI_BL | GAGAGGCGTTACAGCGCAAGCGAGCGAGCGAC<br>CGAGCAAACCCCCCACCGTCGAGTTTCTCGAC<br>GGTCTGCTGCCGGGAGACCGGCAGCGGGGGGG<br>TTTGCTCGGTCGCTCGCTCGCTTGCGCTGTAAC<br>GCCTCTC |
| SEQ ID No: 297 | AAV5_Nb.BsrDI_TL | GAGAGGGGGTAACGCGCAAGCGAGCGAGCGA<br>CCGAGCAAACCCCCCACCGTCGAGTTTCTCGA<br>CGGTCTGCTGCCGGGAGACCGGCAGCGGGGGG<br>GTTTGCTCGGTCGCTCGCTCGCTTGCGCGTTAC<br>CCCTCTC |
| SEQ ID No: 298 | AAV5_Nb.BssSI_BL | GAGTGCTCGGACAGCGCAAGCGAGCGAGCGAC<br>CGAGCAAACCCCCCACCGTCGAGTTTCTCGAC<br>GGTCTGCTGCCGGGAGACCGGCAGCGGGGGGG<br>TTTGCTCGGTCGCTCGCTCGCTTGCGCTGTCCG<br>AGCACTC |
| SEQ ID No: 299 | AAV5_Nb.BssSI_TL | GAGAGGGAGCACAGCGCAAGCGAGCGAGCGA<br>CCGAGCAAACCCCCCACCGTCGAGTTTCTCGA<br>CGGTCTGCTGCCGGGAGACCGGCAGCGGGGGG<br>GTTTGCTCGGTCGCTCGCTCGCTTGCGCTGTGC<br>TCCCTCTC |
| SEQ ID No: 300 | AAV5_Nb.BtsI_BL | GAGAGGCGTCACAGCGCAAGCGAGCGAGCGAC<br>CGAGCAAACCCCCCACCGTCGAGTTTCTCGAC<br>GGTCTGCTGCCGGGAGACCGGCAGCGGGGGGG<br>TTTGCTCGGTCGCTCGCTCGCTTGCGCTGTGAC<br>GCCTCTC |
| SEQ ID No: 301 | AAV5_Nb.BtsI_TL | GAGAGGGGTGACGCGCAAGCGAGCGAGCGA<br>CCGAGCAAACCCCCCACCGTCGAGTTTCTCGA<br>CGGTCTGCTGCCGGGAGACCGGCAGCGGGGGG<br>GTTTGCTCGGTCGCTCGCTCGCTTGCGCCGTCA<br>CCCCTCTC |

TABLE 17-continued

Reverse Complement of Nicking Enzyme Targets

| SEQ ID: | Name | Sequence |
|---|---|---|
| SEQ ID No: 302 | AAV5_Nt.AlwI_BL | GAGAGGGGGACAGCGCTAGGGAGCGAGCGA CCGAGCAAACCCCCCCACCGTCGAGTTTCTCGA CGGTCTGCTGCCGGGAGACCGGCAGCGGGGGG GTTTGCTCGGTCGCTCGCTCCCTAGCGCTGTCC CCCTCTC |
| SEQ ID No: 303 | AAV5_Nt.AlwI_BL | GAGAGGGGGCCTAGCGCAAGCGAGCGAGCGAC CGAGCAAACCCCCCCACCGTCGAGTTTCTCGAC GGTCTGCTGCCGGGAGACCGGCAGCGGGGGGG TTTGCTCGGTCGCTCGCTCGCTTGCGCTAGGCC CCCTCTC |
| SEQ ID No: 304 | AAV5_Nt.BbvCI_TL | GAGAGGGGCGACTCCGCAAGCGAGCGAGCGAC CGAGCAAACCCCCCCACCGTCGAGTTTCTCGAC GGTCTGCTGCCGGGAGACCGGCAGCGGGGGGG TTTGCTCGGTCGCTCGCTCGCTTGCGGAGTCGC CCCTCTC |
| SEQ ID No: 305 | AAV5_Nt.BbvCI_BL | GAGAGGGGAGTCGGCGCAAGCGAGCGAGCGA CCGAGCAAACCCCCCCACCGTCGAGTTTCTCGA CGGTCTGCTGCCGGGAGACCGGCAGCGGGGGG GTTTGCTCGGTCGCTCGCTCGCTTGCGCCGACT CCCCTCTC |
| SEQ ID No: 306 | AAV5_Nt.BsmAI_TL | GAGAGGGGGCTCTGCGCAAGCGAGCGAGCGAC CGAGCAAACCCCCCCACCGTCGAGTTTCTCGAC GGTCTGCTGCCGGGAGACCGGCAGCGGGGGGG TTTGCTCGGTCGCTCGCTCGCTTGCGCAGAGCC CCCTCTC |
| SEQ ID No: 307 | AAV5_Nt.BsmAI_BL | GAGAGGGGGCAGAGCGCAAGCGAGCGAGCGA CCGAGCAAACCCCCCCACCGTCGAGTTTCTCGA CGGTCTGCTGCCGGGAGACCGGCAGCGGGGGG GTTTGCTCGGTCGCTCGCTCGCTTGCGCTCTGC CCCCTCTC |
| SEQ ID No: 308 | AAV5_Nt.BspQI_TL | GAGAGGGCTTCTCGCGCAAGCGAGCGAGCGAC CGAGCAAACCCCCCCACCGTCGAGTTTCTCGAC GGTCTGCTGCCGGGAGACCGGCAGCGGGGGGG TTTGCTCGGTCGCTCGCTCGCTTGCGCGAGAAG CCCTCTC |
| SEQ ID No: 309 | AAV5_Nt.BspQI_BL | GAGAGGGCGAGAAGCGCAAGCGAGCGAGCGA CCGAGCAAACCCCCCCACCGTCGAGTTTCTCGA CGGTCTGCTGCCGGGAGACCGGCAGCGGGGGG GTTTGCTCGGTCGCTCGCTCGCTTGCGCTTCTCG CCCTCTC |
| SEQ ID No: 310 | AAV5_Nt.BstNBI_TL | GAGAGGGGGGACAGCGCTGAGCGAGCGAGCG ACCGAGCAAACCCCCCCACCGTCGAGTTTCTCG ACGGTCTGCTGCCGGGAGACCGGCAGCGGGGG GGTTTGCTCGGTCGCTCGCTCGCTCAGCGCTGT CCCCCCTCTC |
| SEQ ID No: 311 | AAV5_Nt.BstNBI_BL | GAGAGGGGGCTCAGCGCAAGCGAGCGAGCGAC CGAGCAAACCCCCCCACCGTCGAGTTTCTCGAC GGTCTGCTGCCGGGAGACCGGCAGCGGGGGGG TTTGCTCGGTCGCTCGCTCGCTTGCGCTGAGCC CCCTCTC |
| SEQ ID No: 312 | wt_AAV7 | AACCGGTGAGGGAGATACGCGCGAGCGAGCGA GCCACCCCGGACGCCTGGTTTCCAGGCGTCTGC CGTCTCGAGACGAGACGGCCGGGGTGGCTCGC TCGCTCGCGCGTATCTCCCTCACCGGTT |
| SEQ ID No: 313 | AAV7_Nb.BbvCI_BL | AACCGGTGAGGGGAGTCGCGCGAGCGAGCGA GCCACCCCGGACGCCTGGTTTCCAGGCGTCTGC CGTCTCGAGACGAGACGGCCGGGGTGGCTCGC TCGCTCGCGCGACTCCCCCTCACCGGTT |
| SEQ ID No: 314 | AAV7_Nb.BbvCI_TL | AACCGGTGAGGGCGACTCCCGCGAGCGAGCGA GCCACCCCGGACGCCTGGTTTCCAGGCGTCTGC CGTCTCGAGACGAGACGGCCGGGGTGGCTCGC TCGCTCGCGGGAGTCGCCCTCACCGGTT |

TABLE 17-continued

Reverse Complement of Nicking Enzyme Targets

| SEQ ID: | Name | Sequence |
| --- | --- | --- |
| SEQ ID No: 315 | AAV7_Nb.BsmI_BL | AACCGGTGAGGGACTTACGCGCGAGCGAGCGAGCCACCCCGGACGCCTGGTTTCCAGGCGTCTGCCGTCTCGAGACGAGACGGCCGGGGTGGCTCGCTCGCTCGCGCGTAAGTCCCTCACCGGTT |
| SEQ ID No: 316 | AAV7_Nb.BsmI_TL | AACCGGTGAGGGAGATACGCGTAAGCGAGCGAGCCACCCCGGACGCCTGGTTTCCAGGCGTCTGCCGTCTCGAGACGAGACGGCCGGGGTGGCTCGCTCGCTTACGCGTATCTCCCTCACCGGTT |
| SEQ ID No: 317 | AAV7_Nb.BsrDI_BL | AACCGGTGAGGGCGTTACGCGCGAGCGAGCGAGCCACCCCGGACGCCTGGTTTCCAGGCGTCTGCCGTCTCGAGACGAGACGGCCGGGGTGGCTCGCTCGCTCGCGCGTAACGCCCTCACCGGTT |
| SEQ ID No: 318 | AAV7Nb.BsrDI_TL | AACCGGTGAGGGAGTAACGCGCGAGCGAGCGAGCCACCCCGGACGCCTGGTTTCCAGGCGTCTGCCGTCTCGAGACGAGACGGCCGGGGTGGCTCGCTCGCTCGCGCGTTACTCCCTCACCGGTT |
| SEQ ID No: 319 | AAV7_Nb.BssSI_BL | AACCGGTGCTCGAGATACGCGCGAGCGAGCGAGCCACCCCGGACGCCTGGTTTCCAGGCGTCTGCCGTCTCGAGACGAGACGGCCGGGGTGGCTCGCTCGCTCGCGCGTATCTCGAGCACCGGTT |
| SEQ ID No: 320 | AAV7_Nb.BssSI_TL | AACCGGTGAGGGAGCACCGCGCGAGCGAGCGAGCCACCCCGGACGCCTGGTTTCCAGGCGTCTGCCGTCTCGAGACGAGACGGCCGGGGTGGCTCGCTCGCTCGCGCGGTGCTCCCTCACCGGTT |
| SEQ ID No: 321 | AAV7_Nb.BtsI_BL | AACCGGTGAGGGCGTCACGCGCGAGCGAGCGAGCCACCCCGGACGCCTGGTTTCCAGGCGTCTGCCGTCTCGAGACGAGACGGCCGGGGTGGCTCGCTCGCTCGCGCGTGACGCCCTCACCGGTT |
| SEQ ID No: 322 | AAV7_Nb.BtsI_TL | AACCGGTGAGGGAGTGACGCGCGAGCGAGCGAGCCACCCCGGACGCCTGGTTTCCAGGCGTCTGCCGTCTCGAGACGAGACGGCCGGGGTGGCTCGCTCGCTCGCGCGTCACTCCCTCACCGGTT |
| SEQ ID No: 323 | AAV7_Nt.AlwI_BL | AACCGGTGAGGGAGCTAGGCGCGAGCGAGCGAGCCACCCCGGACGCCTGGTTTCCAGGCGTCTGCCGTCTCGAGACGAGACGGCCGGGGTGGCTCGCTCGCTCGCGCCTAGCTCCCTCACCGGTT |
| SEQ ID No: 324 | AAV7_Nt.AlwI_BL | AACCGGTGACCTAGATACGCGCGAGCGAGCGAGCCACCCCGGACGCCTGGTTTCCAGGCGTCTGCCGTCTCGAGACGAGACGGCCGGGGTGGCTCGCTCGCTCGCGCGTATCTAGGTCACCGGTT |
| SEQ ID No: 325 | AAV7_Nt.BbvCI_TL | AACCGGTGAGGGCGACTCCCGCGAGCGAGCGAGCCACCCCGGACGCCTGGTTTCCAGGCGTCTGCCGTCTCGAGACGAGACGGCCGGGGTGGCTCGCTCGCTCGCGGGAGTCGCCCTCACCGGTT |
| SEQ ID No: 326 | AAV7_Nt.BbvCI_BL | AACCGGTGAGGGGGAGTCGCGCGAGCGAGCGAGCCACCCCGGACGCCTGGTTTCCAGGCGTCTGCCGTCTCGAGACGAGACGGCCGGGGTGGCTCGCTCGCTCGCGCGACTCCCCCTCACCGGTT |
| SEQ ID No: 327 | AAV7_Nt.BsmAI_TL | AACCGGTGACTCTGATACGCGCGAGCGAGCGAGCCACCCCGGACGCCTGGTTTCCAGGCGTCTGCCGTCTCGAGACGAGACGGCCGGGGTGGCTCGCTCGCTCGCGCGTATCAGAGTCACCGGTT |
| SEQ ID No: 328 | AAV7_Nt.BsmAI_BL | AACCGGTGAGGCAGAGACGCGCGAGCGAGCGAGCCACCCCGGACGCCTGGTTTCCAGGCGTCTGCCGTCTCGAGACGAGACGGCCGGGGTGGCTCGCTCGCTCGCGCGTCTCTGCCTCACCGGTT |
| SEQ ID No: 329 | AAV7_Nt.BspQI_TL | AACCGGTGAGGGCTTCTCGCGCGAGCGAGCGAGCCACCCCGGACGCCTGGTTTCCAGGCGTCTGCCGTCTCGAGACGAGACGGCCGGGGTGGCTCGCTCGCTCGCGCGAGAAGCCCTCACCGGTT |

TABLE 17-continued

Reverse Complement of Nicking Enzyme Targets

| SEQ ID: | Name | Sequence |
|---|---|---|
| SEQ ID No: 330 | AAV7_Nt.BspQI_BL | AACCGGTGAGGGCGAGAAGCGCGAGCGAGCG<br>AGCCACCCCGGACGCCTGGTTTCCAGGCGTCTG<br>CCGTCTCGAGACGAGACGGCCGGGGTGGCTCG<br>CTCGCTCGCGCTTCTCGCCCTCACCGGTT |
| SEQ ID No: 331 | AAV7_Nt.BstNBI_TL | AACCGGTGAGGGAGATACGCGCTGAGCGAGCG<br>AGCCACCCCGGACGCCTGGTTTCCAGGCGTCTG<br>CCGTCTCGAGACGAGACGGCCGGGGTGGCTCG<br>CTCGCTCAGCGCGTATCTCCCTCACCGGTT |
| SEQ ID No: 332 | AAV7_Nt.BstNBI_BL | AACCGCTCAGGGAGATACGCGCGAGCGAGCGA<br>GCCACCCCGGACGCCTGGTTTCCAGGCGTCTGC<br>CGTCTCGAGACGAGACGGCCGGGGTGGCTCGC<br>TCGCTCGCGCGTATCTCCCTGAGCGGTT |

The first, second, third, and fourth restriction sites for nicking endonuclease can be arranged in various configurations. In some embodiments, the first and the second restriction sites for nicking endonuclease are at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, or at least 200 nucleotides apart. In other embodiments, the first and the second restriction sites for nicking endonuclease are about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 105, about 110, about 115, about 120, about 125, about 130, about 135, about 140, about 145, about 150, about 155, about 160, about 165, about 170, about 175, about 180, about 185, about 190, about 195, or about 200 nucleotides apart.

Similarly, in certain embodiments, the third and the fourth restriction sites for nicking endonuclease are at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, or at least 200 nucleotides apart. In further embodiments, the third and the fourth restriction sites for nicking endonuclease are about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 105, about 110, about 115, about 120, about 125, about 130, about 135, about 140, about 145, about 150, about 155, about 160, about 165, about 170, about 175, about 180, about 185, about 190, about 195, or about 200 nucleotides apart.

The disclosure provides that the overhang described in Sections 3, 5.2 (including 5.2.3), and 5.3 (including 5.3.1) can be the result of the nicking at the first and second restriction sites by nicking endonucleases and denaturing as described in Sections 3 and 5.2 (including 5.2.3). Thus, in some embodiments, the overhang resulted from the nicking at the first and second restriction sites can be the same length as the first and second restriction sites are apart (in number of nucleotides) as described in the preceding paragraphs of this Section (Section 5.3.2). As the nicking endonucleases can cut the DNA within or outside the restriction sites for the nicking endonucleases, in certain embodiments, the overhang resulted from the nicking at the first and second restriction sites can be longer or shorter than the first and second restriction sites are apart by at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 nucleotides. In other embodiments, the overhang resulted from the nicking at the first and second restriction sites can be longer or shorter than the first and second restriction sites are apart by about 10, about 11, about 12, about 13, about 14, about 15, about 16, about 17, about 18, about 19, about 20, about 21, about 22, about 23, about 24, about 25, about 26, about 27, about 28, about 29, or about 30 nucleotides.

Similarly, the disclosure provides that the overhang described in Sections 3, 5.2 (including 5.2.3), and 5.3 (including 5.3.1) can be the result of the nicking at the third and fourth restriction sites by nicking endonucleases and denaturing as described in Sections 3 and 5.2 (including 5.2.3). Thus, in some embodiments, the overhang resulted from the nicking at the third and fourth restriction sites can be the same length as the third and fourth restriction sites are apart (in number of nucleotides) as described in the preceding paragraphs of this Section (Section 5.3.2). As the nicking endonucleases can cut the DNA within or outside the restriction sites for the nicking endonucleases, in certain embodiments, the overhang resulted from the nicking at the third and fourth restriction sites can be longer or shorter than the third and fourth restriction sites are apart by at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 nucleotides. In other embodiments, the overhang resulted from the nicking at the third and fourth restriction sites can be longer or shorter than the third and fourth restriction sites are apart by about 10, about 11, about 12, about 13, about 14, about 15, about 16, about 17, about 18, about 19, about 20, about 21, about 22, about 23, about 24, about 25, about 26, about 27, about 28, about 29, or about 30 nucleotides.

As is clear from the description in Sections 3 and 5.4 and this Section (Section 5.3), the DNA molecules provided herein comprise an expression cassette. In some embodiments, the expression cassette is located between the first and second restriction sites for nicking endonuclease(s) at one end and the third and fourth restriction sites for nicking endonuclease(s) at the other end. In other embodiments, the expression cassette is located within the dsDNA segment of the DNA molecules produced by performing the method steps a to d as described in Sections 3 and 5.2, including the denaturing step described in Section 5.2.3 to provide two ssDNA overhangs. In certain embodiments, the first, second, third, and fourth restriction sites for the nicking endonucleases are arranged such that the length of the dsDNA segment described in this paragraph is at least 0.2 kb, at least 0.3 kb, at least 0.4 kb, at least 0.5 kb, at least 0.6, at least kb, at least 0.7 kb, at least 0.8 kb, at least 0.9 kb, at least 1 kb, at least 1.5 kb, at least 2 kb, at least 2.5 kb, at least 3 kb, at least 3.5 kb, at least 4 kb, at least 4.5 kb, at least 5 kb, at least 5.5 kb, at least 6 kb, at least 6.5 kb, at least 7 kb, at least 7.5 kb, at least 8 kb, at least 8.5 kb, at least 9 kb, at least 9.5 kb, or at least 10 kb. In other embodiments, the first, second, third, and fourth restriction sites for the nicking endonucleases are arranged such that the length of the dsDNA segment described in this paragraph is about 0.2 kb, about 0.3 kb, about 0.4 kb, about 0.5 kb, about 0.6, about kb, about 0.7 kb, about 0.8 kb, about 0.9 kb, about 1 kb, about 1.5 kb, about 2 kb, about 2.5 kb, about 3 kb, about 3.5 kb, about 4 kb, about 4.5 kb, about 5 kb, about 5.5 kb, about 6 kb, about 6.5 kb, about 7 kb, about 7.5 kb, about 8 kb, about 8.5 kb, about 9 kb, about 9.5 kb, or about 10 kb.

As described in Section 5.2.4, incubation with nicking endonucleases will result in a first nick corresponding to the first restriction site for the nicking endonuclease, a second nick corresponding to the second restriction site for the nicking endonuclease, a third nick corresponding to the third restriction site for the nicking endonuclease, and/or a fourth nick corresponding to the fourth restriction site for the nicking endonuclease. The disclosure provides that the first, second, third, and/or fourth nicks can be at various positions relative to the inverted repeat. In one embodiment, the first nick is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the 5' nucleotide of the ITR closing base pair of the first inverted repeat. In another embodiment, the first nick is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the 3' nucleotide of the ITR closing base pair of the first inverted repeat. In yet another embodiment, the second nick is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the 5' nucleotide of the ITR closing base pair of the first inverted repeat. In a further embodiment, the second nick is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the 3' nucleotide of the ITR closing base pair of the first inverted repeat. In one embodiment, the third nick is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the 5' nucleotide of the ITR closing base pair of the second inverted repeat. In another embodiment, the third nick is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the 3' nucleotide of the ITR closing base pair of the second inverted repeat. In yet another embodiment, the fourth nick is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the 5' nucleotide of the ITR closing base pair of the second inverted repeat. In a further embodiment, the fourth nick is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the 3' nucleotide of the ITR closing base pair of the second inverted repeat. In some embodiments, any or any combinations of the first, second, third, and fourth nicks are inside the inverted repeat. In certain embodiments, any or any combinations of the first, second, third, and fourth nicks are outside the inverted repeat. In some additional embodiments, the first, second, third, and fourth nicks can have any relative positions amongst themselves, between any of them and the inverted repeat, and/or between any of them and the expression cassette as described in this Section (Section 5.3.2), in any combination or permutation. In some further embodiments, the first, second, third, and fourth restriction sites for nicking endonucleases can have any relative positions amongst themselves, between any of them and the inverted repeat, and/or between any of them and the expression cassette as described in this Section (Section 5.3.2), in any combination or permutation.

5.3.3 Expression Cassette

As is clear from the description in Sections 3 and 5.4 and this Section (Section 5.3), the DNA molecules provided herein comprise an expression cassette An "expression cassette" is a nucleic acid molecule or a part of nucleic acid molecule containing sequences or other information that directs the cellular machinery to make RNA and protein. In some embodiments, an expression cassette comprises a promoter sequence. In certain embodiments, an expression cassette comprises a transcription unit. In yet some other embodiments, an expression cassette comprises a promoter operatively linked to a transcription unit. In one embodiment, the transcription unit comprises an open reading frame (ORF). Embodiments for ORFs for use with the methods and compositions provided herein are further described in the last paragraph of this Section (Section 5.3.3). The expression cassette can further comprise features to direct the cellular machinery to make RNA and protein. In one embodiment, the expression cassette comprises a posttranscriptional regulatory element. In another embodiment, the expression cassette further comprises a polyadenylation and/or termination signal. In yet another embodiment, the expression cassette comprises regulatory elements known and used in the art to regulate (promote, inhibit and/or turn on/off the expression of the ORF). Such regulatory elements include, for example, 5'-untranslated region (UTR), 3'-UTR, or both the 5'UTR and the 3'UTR. In some further embodiments, the expression cassette comprises any one or more features provided in this Section (Section 5.3.3) in any combination or permutation.

The expression cassette can comprise a protein coding sequence in its ORF (sense strand). Alternatively, the expression cassette can comprise the complementary sequence of the protein coding ORF (anti-sense strand) and the regulatory components and/or other signals for the cellular machinery to produce a sense strand DNA/RNA and the corresponding protein. In some embodiments, the expression cassette comprises a protein sequence without intron. In other embodiments, the expression cassette comprises a protein sequence with intron, which is removed upon transcription and splicing. The expression cassette can also comprise various numbers of ORFs or transcription units. In one embodiment, the expression cassette comprises 1, 2, 3, 4, 5, 6, 7, 8, 9, 10, 11, 12, 13, 14, 15, 16, 17, 18, 19, or 20 ORFs. In another embodiment, the expression cassette comprises 1, 2, 3, 4, 5, 6, 7, 8, 9, 10, 11, 12, 13, 14, 15, 16, 17, 18, 19, or 20 transcription units.

The expression cassettes can also comprise one or more transcriptional regulatory element, one or more posttranscriptional regulatory elements, or both one or more transcriptional regulatory element and one or more posttranscriptional regulatory elements. Such regulatory elements are any sequences that allow, contribute or modulate the functional regulation of the nucleic acid molecule, including replication, duplication, transcription, splicing, translation, stability and/or transport of the nucleic acid or one of its derivative (e.g. mRNA) into the host cell or organism. Such regulatory elements include, but are not limited to, a promoter, an enhancer, a polyadenylation signal, translation stop codon, a ribosome binding element, a transcription terminator, selection markers, origin of replication, etc.

In some embodiments, the expression cassette comprises an enhancer. Any enhancer sequence known to those skilled in the art in view of the present disclosure can be used. In some embodiments, an enhancer sequence can be human actin, human myosin, human hemoglobin, human muscle creatine, or a viral enhancer, such as one from CMV, HA, RSV, or EBV. In certain specific embodiments, the enhance can be Woodchuck HBV Posttranscriptional regulatory element (WPRE), intron/exon sequence derived from human apolipoprotein A1 precursor (ApoAI), untranslated R-U5 domain of the human T-cell leukemia virus type 1 (HTLV-1) long terminal repeat (LTR), a splicing enhancer, a synthetic rabbit β-globin intron, a P5 promoter of an AAV, or any combination thereof.

As described above, the expression cassette can comprise a promoter to control expression of a protein of interest. Promoters include any nucleotide sequence that initiates the transcription of an operably linked nucleotide sequence. Promoters can be a constitutive, inducible, or repressible. A promoter can be derived from sources including viral, bacterial, fungal, plants, insects, and animals. A promoter can be a homologous promoter (e.g., derived from the same genetic source) or a heterologous promoter (e.g., derived from a different genetic source). In some embodiments, a promoters can be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter (CMV-IE), Epstein Barr virus (EBV) promoter, or a Rous sarcoma virus (RSV) promoter. In other embodiments, a promoter can be a promoter from a human gene such as human actin, human myosin, human hemoglobin, human muscle creatine, or human metalothionein. In further embodiments, a promoter can also be a tissue specific promoter, such as a muscle or skin specific promoter, natural or synthetic.

As described above, the expression cassette can comprise a polyadenylation, termination signal, or both a polyadenylation and termination signal. Any polyadenylation signal known to those skilled in the art in view of the present disclosure can be used. In some embodiments, the polyadenylation signal can be a SV40 polyadenylation signal, AAV2 polyadenylation signal (bp 4411-4466, NC 001401), a polyadenylation signal from the Herpes Simplex Virus Thymidine Kinase Gene, LTR polyadenylation signal, bovine growth hormone (bGH) polyadenylation signal, human growth hormone (hGH) polyadenylation signal, or human β-globin polyadenylation signal.

The expression cassette can have various sizes to accommodate one or more ORFs of various lengths. In certain embodiments, the size of expression cassette is at least 0.2 kb, at least 0.3 kb, at least 0.4 kb, at least 0.5 kb, at least 0.6, at least kb, at least 0.7 kb, at least 0.8 kb, at least 0.9 kb, at least 1 kb, at least 1.5 kb, at least 2 kb, at least 2.5 kb, at least 3 kb, at least 3.5 kb, at least 4 kb, at least 4.5 kb, at least 5 kb, at least 5.5 kb, at least 6 kb, at least 6.5 kb, at least 7 kb, at least 7.5 kb, at least 8 kb, at least 8.5 kb, at least 9 kb, at least 9.5 kb, at least 10 kb, at least 15 kb, at least 20 kb, at least 25 kb, at least 30 kb, at least 35 kb, at least 40 kb, at least 45 kb, at least 50 kb, at least 55 kb, at least 60 kb, at least 65 kb, at least 70 kb, at least 75 kb, or at least 80 kb. In one specific embodiment, the expression cassette is at least 4.5 kb. In another specific embodiment, the expression cassette is at least 4.6 kb. In yet another specific embodiment, the expression cassette is at least 4.7 kb. In a further specific embodiment, the expression cassette is at least 4.8 kb. In one specific embodiment, the expression cassette is at least 4.9 kb. In another specific embodiment, the expression cassette is at least 5 kb. In other embodiments, the size of the expression cassette is about 0.2 kb, about 0.3 kb, about 0.4 kb, about 0.5 kb, about 0.6, about kb, about 0.7 kb, about 0.8 kb, about 0.9 kb, about 1 kb, about 1.5 kb, about 2 kb, about 2.5 kb, about 3 kb, about 3.5 kb, about 4 kb, about 4.5 kb, about 5 kb, about 5.5 kb, about 6 kb, about 6.5 kb, about 7 kb, about 7.5 kb, about 8 kb, about 8.5 kb, about 9 kb, about 9.5 kb, about 10 kb, about 15 kb, about 20 kb, about 25 kb, about 30 kb, about 35 kb, about 40 kb, about 45 kb, about 50 kb, about 55 kb, about 60 kb, about 65 kb, about 70 kb, about 75 kb, or about 80 kb. In one specific embodiment, the expression cassette is about 4.5 kb. In another specific embodiment, the expression cassette is about 4.6 kb. In yet another specific embodiment, the expression cassette is about 4.7 kb. In a further specific embodiment, the expression cassette is about 4.8 kb. In one specific embodiment, the expression cassette is about 4.9 kb. In another specific embodiment, the expression cassette is about 5 kb. The expression cassette can also comprise various numbers of genes of interest ("transgenes"). In one embodiment, the expression cassette comprises 1, 2, 3, 4, 5, 6, 7, 8, 9, 10, 11, 12, 13, 14, 15, 16, 17, 18, 19, or 20 transgenes. In some specific embodiment, the expression cassette comprise one transgene. In some embodiments, the transgenes are recombinant genes. In some further embodiments, the transgenes comprise cDNA sequences (e.g. no introns in the transgenes).

In some embodiment, the DNA molecules provided herein do not have the size limitations of encapsidated AAV vectors, thus enabling delivery of a large-size expression cassette to provide efficient transgene. In certain embodiments, the DNA molecules provided herein comprise an expression cassette equal to or larger than the size of any natural AAV genome.

The expression cassette can have various positions relative to the inverted repeat. In some embodiments, the expression cassette is at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, or at least 100 nucleotides apart from the inverted repeat. In certain embodiments, the expression cassette is at least 0.2 kb, at least 0.3 kb, at least 0.4 kb, at least 0.5 kb, at least 0.6, at least 0.7 kb, at least 0.8 kb, at least 0.9 kb, at least 1 kb, at least 1.5 kb, or at least 2 kb apart from the inverted repeat. In other embodiments, the expression cassette is about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, or about 100 nucleotides apart from the inverted repeat. In further embodiments, the expression cassette is about 0.2 kb, about 0.3 kb, about 0.4 kb, about 0.5 kb, about 0.6, about 0.7 kb, about 0.8 kb, about 0.9 kb, about 1 kb, about 1.5 kb, or about 2 kb apart from the inverted repeat. In one embodiment, the inverted repeat in this paragraph is the first inverted repeat as described in Sections 3 and 5.3 (including 5.3.1). In another embodiment, the inverted repeat in this paragraph is the second inverted repeat as described in Sections 3 and 5.3 (including 5.3.1) In yet another embodiment, the inverted repeat in this paragraph is both the first and the second inverted repeat as described in Sections 3 and 5.3 (including 5.3.1)

In one aspect, provided herein is a double-stranded DNA molecule comprising in 5' to 3' direction of the sense strand: i) a first inverted repeat (e.g. as described in Section 5.3.1), wherein a first and a second restriction site for nicking endonuclease are arranged on opposite strands in proximity of the first inverted repeat such that nicking results in a sense strand 5' overhang comprising the first inverted repeat upon separation of the sense from the antisense strand of the first inverted repeat (e.g. as described in Sections 5.2.3, 5.2.4 and 5.3.2); ii) a sense expression cassette; and iii) a second inverted repeat (e.g. as described in Section 5.3.1), wherein a third and a fourth restriction site for nicking endonuclease are arranged on opposite strands in proximity of the second inverted repeat such that nicking results in a sense strand 3' overhang comprising the second inverted repeat upon separation of the top from the antisense strand of the second inverted repeat (e.g. as described in Sections 5.2.3, 5.2.4 and 5.3.2)

In another aspect, provided herein is a double strand DNA molecule comprising in the 5' to 3' direction of the sense strand: i) a first inverted repeat (e.g. as described in Section 5.3.1), wherein a first and a second restriction site for nicking endonuclease are arranged on opposite strands in proximity of the first inverted repeat such that nicking results in an antisense strand 3' overhang comprising the first inverted repeat upon separation of the sense from the antisense strand of the first inverted repeat (e.g. as described in Sections 5.2.3, 5.2.4 and 5.3.2); ii) a sense expression cassette; and iii) a second inverted repeat (e.g. as described in Section 5.3.1), wherein a third and a fourth restriction site for nicking endonuclease are arranged on opposite strands in proximity of the second inverted repeat such that nicking results in an antisense strand 5' overhang comprising the second inverted repeat upon separation of the sense from the antisense of the second inverted repeat In yet another aspect, provided herein is a double-stranded DNA molecule comprising in 5' to 3' direction of the sense strand: i) a first inverted repeat (e.g. as described in Section 5.3.1), wherein a first and a second restriction site for nicking endonuclease are arranged on opposite strands in proximity of the first inverted repeat such that nicking results in a sense strand 5' overhang comprising the first inverted repeat upon separation of the sense from the antisense strand of the first inverted repeat (e.g. as described in Sections 5.2.3, 5.2.4 and 5.3.2); ii) a sense expression cassette; and iii) a second inverted repeat (e.g. as described in Section 5.3.1), wherein a third and a fourth restriction site for nicking endonuclease are arranged on opposite strands in proximity of the second inverted repeat such that nicking results in an antisense strand 5' overhang comprising the second inverted repeat upon separation of the sense from the antisense strand of the second inverted repeat (e.g. as described in Sections 5.2.3, 5.2.4 and 5.3.2).

In a further aspect, provide herein is a double stranded DNA molecule comprising in the 5' to 3' direction of the sense strand: i) a first inverted repeat (e.g. as described in Section 5.3.1), wherein a first and a second restriction site for nicking endonuclease are arranged on opposite strands in proximity of the first inverted repeat such that nicking results in an antisense strand 3' overhang comprising the first inverted repeat upon separation of the sense from the antisense strand of the first inverted repeat (e.g. as described in Sections 5.2.3, 5.2.4 and 5.3.2); ii) a sense expression cassette; and iii) a second inverted repeat (e.g. as described in Section 5.3.1), wherein a third and a fourth restriction site for nicking endonuclease are arranged on opposite strands in proximity of the second inverted repeat such that nicking results in a sense strand 3' overhang comprising the second inverted repeat upon separation of the sense from the antisense strand of the second inverted repeat (e.g. as described in Sections 5.2.3, 5.2.4 and 5.3.2 or depicted in FIGS. 2B and 2C).

In one aspect, provided herein is a double-stranded DNA molecule comprising in the 5' to 3' direction of the sense strand: i) a first inverted repeat (e.g. as described in Section 5.3.1), wherein a first and a second target site for the guide nucleic acids for programmable nicking enzyme are arranged on opposite strands in proximity of the first inverted repeat such that nicking by programmable nicking enzyme results in a sense strand 5' overhang comprising the first inverted repeat upon separation of the sense from the antisense strand of the first inverted repeat (e.g. as described in Sections 5.2.3, 5.2.4 and 5.3.2); ii) a sense expression cassette; and iii) a second inverted repeat (e.g. as described in Section 5.3.1), wherein a third and a fourth target site for the guide nucleic acids for programmable nicking enzyme are arranged on opposite strands in proximity of the second inverted repeat such that nicking by programmable nicking enzyme results in a sense strand 3' overhang comprising the second inverted repeat upon separation of the sense from the antisense of the second inverted repeat (e.g. as described in Sections 5.2.3, 5.2.4 and 5.3.2).

In another aspect, provided herein is a double strand DNA molecule comprising in the 5' to 3' direction of the sense strand: i) a first inverted repeat (e.g. as described in Section 5.3.1), wherein a first and a second target site for the guide nucleic acids for programmable nicking enzyme are arranged on opposite strands in proximity of the first inverted repeat such that nicking by programmable nicking enzyme results in an antisense strand 3' overhang comprising the first inverted repeat upon separation of the sense from the antisense strand of the first inverted repeat (e.g. as described in Sections 5.2.3, 5.2.4 and 5.3.2); ii) a sense expression cassette; and iii) a second inverted repeat (e.g. as described in Section 5.3.1), wherein a third and a fourth target site for the guide nucleic acids for programmable nicking enzyme are arranged on opposite strands in proximity of the second inverted repeat such that nicking by programmable nicking enzyme results in an antisense strand 5' overhang comprising the second inverted repeat upon separation of the sense from the antisense strand of the second inverted repeat (e.g. as described in Sections 5.2.3, 5.2.4 and 5.3.2).

In yet another aspect, provided herein is a double-stranded DNA molecule comprising in the 5' to 3' direction of the sense strand: i) a first inverted repeat (e.g. as described in Section 5.3.1), wherein a first and a second target site for the guide nucleic acids for programmable nicking enzyme are arranged on opposite strands in proximity of the first inverted repeat such that nicking by programmable nicking enzyme results in a sense strand 5' overhang comprising the first inverted repeat upon separation of the sense from the antisense strand of the first inverted repeat (e.g. as described in Sections 5.2.3, 5.2.4 and 5.3.2); ii) a sense expression cassette; and iii) a second inverted repeat (e.g. as described in Section 5.3.1), wherein a third and a fourth target site for the guide nucleic acids for programmable nicking enzyme are arranged on opposite strands in proximity of the second inverted repeat such that nicking by programmable nicking enzyme results in an antisense strand 5' overhang comprising the second inverted repeat upon separation of the sense from the antisense strand of the second inverted repeat (e.g. as described in Sections 5.2.3, 5.2.4 and 5.3.2).

In a further aspect, provide herein is a double strand DNA molecule comprising in the 5' to 3' direction of the sense strand: i) a first inverted repeat (e.g. as described in Section 5.3.1), wherein a first and a second target site for the guide nucleic acids for programmable nicking enzyme are arranged on opposite strands in proximity of the first inverted repeat such that nicking by programmable nicking enzyme results in an antisense strand 3' overhang comprising the first inverted repeat upon separation of the sense from the antisense strand of the first inverted repeat (e.g. as described in Sections 5.2.3, 5.2.4 and 5.3.2); ii) a sense expression cassette; and iii) a second inverted repeat (e.g. as described in Section 5.3.1), wherein a third and a fourth target site for the guide nucleic acids for programmable nicking enzyme are arranged on opposite strands in proximity of the second inverted repeat such that nicking by programmable nicking enzyme results in a sense strand 3' overhang comprising the second inverted repeat upon separation of the sense from the antisense strand of the second inverted repeat (e.g. as described in Sections 5.2.3, 5.2.4 and 5.3.2 or depicted in FIGS. 2B and 2C).

The expression cassettes can also comprise one or more transcriptional regulatory element(s), one or more posttranscriptional regulatory element(s), or both one or more transcriptional regulatory element(s) and one or more posttranscriptional regulatory element(s). Such regulatory elements are any sequences that allow, contribute or modulate the functional regulation of the nucleic acid molecule, including replication, duplication, transcription, splicing, translation, stability and/or transport of the nucleic acid or one of its derivative (e.g. mRNA) into the host cell or organism. Such regulatory elements include, but are not limited to, a promoter, an enhancer, a polyadenylation signal, translation stop codon, a ribosome binding element, a transcription terminator, selection markers, and/or origin of replication.

The expression cassette can have various sizes to accommodate one or more ORFs of various lengths. In certain embodiments, the size of expression cassette is at least at least 2 kb, at least 2.5 kb, at least 3 kb, at least 3.5 kb, at least 4 kb, at least 4.5 kb, at least 5 kb, at least 5.5 kb, at least 6 kb, at least 6.5 kb, at least 7 kb, at least 7.5 kb, at least 8 kb, at least 8.5 kb, at least 9 kb, at least 9.5 kb, at least 10 kb, at least 15 kb, at least 20 kb, at least 25 kb, at least 30 kb, at least 35 kb, at least 40 kb, at least 45 kb, at least 50 kb, at least 55 kb, at least 60 kb, at least 65 kb, at least 70 kb, at least 75 kb, or at least 80 kb. In one specific embodiment, the expression cassette is at least 7.5 kb. In another specific embodiment, the expression cassette is at least 7.6 kb. In yet another specific embodiment, the expression cassette is at least 7.7 kb. In a further specific embodiment, the expression cassette is at least 7.8 kb. In one specific embodiment, the expression cassette is at least 7.9 kb. In another specific embodiment, the expression cassette is at least 8 kb. In other embodiments, the size of the expression cassette is about 2 kb, about 2.5 kb, about 3 kb, about 3.5 kb, about 4 kb, about 4.5 kb, about 5 kb, about 5.5 kb, about 6 kb, about 6.5 kb, about 7 kb, about 7.5 kb, about 8 kb, about 8.5 kb, about 9 kb, about 9.5 kb, about 10 kb, about 15 kb, about 20 kb, about 25 kb, about 30 kb, about 35 kb, about 40 kb, about 45 kb, about 50 kb, about 55 kb, about 60 kb, about 65 kb, about 70 kb, about 75 kb, or about 80 kb. In one specific embodiment, the expression cassette is about 7.5 kb. In another specific embodiment, the expression cassette is about 7.6 kb. In yet another specific embodiment, the expression cassette is about 7.7 kb. In a further specific embodiment, the expression cassette is about 7.8 kb. In one specific embodiment, the expression cassette is about 7.9 kb. In another specific embodiment, the expression cassette is about 8 kb. The expression cassette can also comprise various numbers of genes of interest ("transgenes"). In one embodiment, the expression cassette comprises 1, 2, 3, 4, 5, 6, 7, 8, 9, 10, 11, 12, 13, 14, 15, 16, 17, 18, 19, or 20 transgenes. In some specific embodiment, the expression cassette comprise one transgene. In some embodiments, the transgenes are recombinant genes. In some further embodiments, the transgenes comprise cDNA sequences (e.g. no introns in the transgenes).

Additionally, the expression cassette can comprise at least 4000 nucleotides, at least 5000 nucleotides, at least 10,000 nucleotides, at least 20,000 nucleotides, at least 30,000 nucleotides, at least 40,000 nucleotides, or at least 50,000 nucleotides. In some embodiments, the expression cassette can comprise any range of from about 4000 to about 10,000 nucleotides from about 10,000 to about 50,000 nucleotides, or more than 50,000 nucleotides. In some embodiments, the expression cassette can comprise a transgene in the range of from about 500 to about 50,000 nucleotides in length. In some embodiments, the expression cassette can comprise a transgene in the range of from about 500 to about 75,000 nucleotides in length. In some embodiments, the expression cassette can comprise a transgene that is in the range of from about 500 to about 10,000 nucleotides in length. In some embodiments, the expression cassette can comprise a transgene that is in the range of from about 1000 to about 10,000 nucleotides in length. In some embodiments, the expression cassette can comprise a transgene that is in the range of from about 500 to about 5,000 nucleotides in length. In some embodiment, the DNA molecules provided herein do not have the size limitations of encapsidated AAV vectors, thus enabling delivery of a large-size expression cassette to provide efficient transgene. In certain embodiments, the DNA molecules provided herein comprise expression cassette equal to or larger than the size of any natural AAV genome.

The expression cassette can have various positions relative to the inverted repeat. In some embodiments, the expression cassette is at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, or at least 100 nucleotides apart from the inverted repeat. In certain embodiments, the expression cassette is at least 0.2 kb, at least 0.3 kb, at least 0.4 kb, at least 0.5 kb, at least 0.6, at least kb, at least 0.7 kb, at least 0.8 kb, at least 0.9 kb, at least 1 kb, at least 1.5 kb, or at least 2 kb apart from the inverted repeat. In other embodiments, the expression cassette is about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, or about 100 nucleotides apart from the inverted repeat. In further embodiments, the expression cassette is about 0.2 kb, about 0.3 kb, about 0.4 kb, about 0.5 kb, about 0.6, about kb, about 0.7 kb, about 0.8 kb, about 0.9 kb, about 1 kb, about 1.5 kb, or about 2 kb apart from the inverted repeat. In one embodiment, the inverted repeat in this paragraph is the first inverted repeat as described in Sections 3 and 5.3 (including 5.3.1). In another embodiment, the inverted repeat in this paragraph is the second inverted repeat as described in Sections 3 and 5.3 (including 5.3.1) In yet another embodiment, the inverted repeat in this paragraph is both the first and the second inverted repeat as described in Sections 3 and 5.3 (including 5.3.1)

As described above this Section (Section 5.3.3), the expression cassette can comprise one or more ORFs. In one embodiment, the ORF is an ORF of a human gene wherein genetic mutations in the human gene are known to cause a disease. In another embodiment, the ORF is an ORF of a human gene wherein genetic mutations in the human gene are known to cause a hereditary disease. In yet another embodiment, the ORF encodes a therapeutic protein. In a further embodiment, the ORF encodes an enzyme. In certain embodiments, the ORF encodes a metabolic enzyme. In some embodiments, the ORF encodes an enzyme, wherein the enzyme replaces or supplements the function of a defective enzyme in human. In one embodiment, the ORF encodes an antibody. In another embodiment, the ORF encodes a therapeutic antibody. In a further embodiment, the ORF encodes a cytokine. In yet another embodiment, the ORF encodes a RNA. In one embodiment, the ORF encodes a regulatory RNA. In another embodiment, the ORF encodes an anti-sense RNA. In yet another embodiment, the ORF encodes a siRNA. In a further embodiment, the ORF encodes a shRNA. In one embodiment, the ORF encodes a miRNA. In another embodiment, the ORF encodes a piRNA (PIWI-interacting RNA). In some embodiments, the expression cassette comprises any one or more features described in this Section (Section 5.3.3), in various permutations and combinations.

The various embodiments described in this Section (Section 5.3.3) with nicking endonucleases and/or restriction sites for nicking endonucleases are additionally provided with nicking endonucleases replaced by programmable nicking enzyme and restriction sites replaced by targeting sites for programmable nicking enzyme. The programmable nicking enzymes and their targeting sites for this paragraph and this Section (Section 5.3.3) have been provided in Section 5.2.4.

5.3.4 Viral DNA Sequence Features Absent in the DNA Molecules Provided Herein As further described in Sections 3, 5.2, 5.3.1, 5.3.2, 5.3.3, 5.3.5, 5.3.6 and 5.4, the DNA molecules provided can be produced either synthetically or recombinantly with or without certain sequence elements or features. As such, certain suitable and desired sequence features or elements can be included in the DNA molecules provided herein or excluded from the DNA molecules provided herein. The corresponding methods for making such DNA molecules including or excluding the sequence features or elements are also provided herein as described by applying the methods of 5.2 with the DNA molecules of 5.3, which can produce various DNA molecules described in 5.4.

As described in Sections 3, 5.3.1, 5.5, and 6, such DNA sequence elements or features that can be excluded from the DNA molecules provided herein can be a viral replication-associated protein binding sequence ("RABS"), which refers to a DNA sequence to which a viral DNA replication-associated protein ("RAP") or an isoform thereof, encoded by the Parvoviridae gene Rep or NS1 can bind. In some embodiments, the RABS is a Rep binding sequence ("RBS"). Rep can bind to two elements within the ITR. It can bind to a nucleotide sequence in the stem structure of the ITR (i.e., the nucleotide sequence recognized by a Rep protein for replication of viral nucleic acid molecules). Such a RBS is also referred to as RBE (Rep-binding element). Rep can also bind to a nucleotide sequence which forms a small palindrome comprising a single tip of an internal hairpin within the ITR, thereby stabilizing the association between Rep and the ITR. Such a RBS is also referred to as RBE'. In other embodiments, the RABS is an NS1-binding element ("NSBE") to which replication-associated viral protein NS1 can bind. In some embodiments, Rep can bind to a nucleotide sequence in the stem structure of the ITR (i.e., the nucleotide sequence recognized by a Rep or NS1 protein (for replication of viral nucleic acid molecules) and/or the site of specific interaction between the Rep and/or NS1 protein and the nucleotide sequence. A RABS can be a sequence of 5 nucleotides to 300 nucleotides. In some embodiments of the DNA molecules provided herein including those provided in this Section 5.3.4, the RABS can be a sequence of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210, at least 215, at least 220, at least 225, at least 230, at least 235, at least 240, at least 245, at least 250, at least 255, at least 260, at least 265, at least 270, at least 275, at least 280, at least 285, at least 290, at least 295, at least 300, at least 305, at least 310, at least 315, at least 320, at least 325, at least 330, at least 335, at least 340, at least 345, at least 350, at least 355, at least 360, at least 365, at least 370, at least 375, at least 380, at least 385, at least 390, at least 395, or at least 400 nucleotides. In some other embodiments, the RABS can be a sequence of about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, or about 400 nucleotides. In some further embodiments, any embodiment of the DNA molecules lacking an RABS described in this paragraph can be combined with any methods or DNA molecules provided herein including those provided in Sections 3, 5.2, 5.3, 5.4, and 6.

Alternatively, the DNA molecules provided herein, including those in Sections 3, 5.2, 5.3, 5.4, and 6, can lack a functional RABS by functionally inactivating the RABS sequence present in the DNA molecules with mutations, insertions, and/or deletions (including partial deletions or truncations), such that the RABS can no longer serve as a recognition and/or binding site for the Rep protein or NS1 protein. As such, in some embodiments of the DNA molecules provided herein, including those in Sections 3, 5.2, 5.3, 5.4, and 6, the DNA molecule comprise a functionally inactivated RABS. Such functional inactivation can be assess by measuring and comparing the binding between the Rep or NS1 protein and the DNA molecules comprising the functionally inactivated RABS with that between the Rep or NS1 proteins and a reference molecule comprising the wild type (wt) RBS or NSBE sequences (e.g. the same DNA molecule but with wt RBS or wt NSBE sequences). Such binding can be determined by any binding measurements known and used in the field of molecular biology, for example, chromatin immunoprecipitation (ChIP) assays, DNA electrophoretic mobility shift assay (EMSA), DNA pull-down assays, or Microplate capture and detection assays, as further described in Matthew J. Guille & G. Geoff Kneale, *Molecular Biotechnology* 8:35-52 (1997); Bipasha Dey et al., Mol Cell Biochem. 2012 June; 365(1-2):279-99, both of which are hereby incorporated in their entireties by reference. In one embodiment, the binding between the RAPs and the functionally inactivated RABS in the DNA molecule is at most 0.001%, at most 0.01%, at most 0.1%, at most 1%, at most 1.5%, at most 2%, at most 2.5%, at most 3%, at most 3.5, at most 4%, at most 4.5%, at most 5%, at most 5.5%, at most 6%, at most 6.5%, at most 7%, at most 7.5%, at most 8%, at most 8.5%, at most 9%, at most 9.5%, or at most 10%, compared to the binding between the RAPs and the wild type RBS or NSBE in a reference DNA molecule (e.g. the same DNA molecule but with a wild type RBS or NSBE sequence). In another embodiment, the binding between the RAPs and the functionally inactivated RABS in the DNA molecule is about 0.001%, about 0.01%, about 0.1%, about 1%, about 1.5%, about 2%, about 2.5%, about 3%, about 3.5, about 4%, about 4.5%, about 5%, about 5.5%, about 6%, about 6.5%, about 7%, about 7.5%, about 8%, about 8.5%, about 9%, about 9.5%, or about 10%, compared to the binding between the RAPs and the wild type RABS in a reference DNA molecule (e.g. the same DNA molecule but with a wt RBS or NSBE sequence). In yet another embodiment, the binding between the RAPs and the functionally inactivated RABS in the DNA molecule is 0.001%, 0.01%, 0.1%, 1%, 1.5%, 2%, 2.5%, 3%, 3.5, 4%, 4.5%, 5%, 5.5%, 6%, 6.5%, 7%, 7.5%, 8%, 8.5%, 9%, 9.5%, or 10%, compared to the binding between the RAPs and the wild type RABS in a reference DNA molecule (e.g. the same DNA molecule but with a wt RBS or NSBE sequence).

Furthermore, the DNA molecules provided herein, including those in Sections 3, 5.2, 5.3, 5.4, and 6, can lack a functional RAPs or viral capsid encoding sequence by functionally inactivating the Rep protein, NS1 or viral capsid encoding sequence present in the DNA molecules with mutations, insertions, and/or deletions (including partial deletions or truncations), such that the RAPs or viral capsid encoding sequence can no longer functionally express the Rep protein, NS1 protein or viral capsid protein. Such functional inactivating mutations, insertions, or deletions can be achieved, for example, by using mutations, insertions, and/or deletions to shift the open reading frame of Rep protein, NS1 protein or viral capsid encoding sequence, by using mutations, insertions, and/or deletions to remove the start codon, by using mutations, insertions, and/or deletions to remove the promoter or transcription initiation site, by using mutations, insertions, and/or deletions to remove the RNA polymerase binding sites, by using mutations, insertions, and/or deletions to remove the ribosome recognition or binding sites, or other means known and used in the field.

In one embodiment, the DNA molecule comprise an RBS inactivated by mutation. In one embodiment, the DNA molecule comprise an RBS inactivated by a mutation of 1, 2, 3, 4, 5, 6, 7, 8, 9, 10, 11, 12, 13, 14, 15, 16, 17, 18, 19, 20, 20, 21, 22, 23, 24, 25, 26, 27, 28, 29, 10, 31, 32, 33, 34, 35, 36, 37, 38, 39, or 40 nucleotides in the RBS. In another embodiment, the DNA molecule comprise an RBS inactivated by a mutation of 1%, 2%, 3%, 4%, 5%, 6%, 7%, 8%, 9%, 10%, 11%, 12%, 13%, 14%, 15%, 16%, 17%, 18%, 19%, 20%, 20%, 21%, 22%, 23%, 24%, 25%, 26%, 27%, 28%, 29%, 10%, 31%, 32%, 33%, 34%, 35%, 36%, 37%, 38%, 39%, or 40% of the nucleotides in the RBS. In a further embodiment, the DNA molecule comprise an RBS inactivated by a deletion of 1, 2, 3, 4, 5, 6, 7, 8, 9, 10, 11, 12, 13, 14, 15, 16, 17, 18, 19, 20, 20, 21, 22, 23, 24, 25, 26, 27, 28, 29, 10, 31, 32, 33, 34, 35, 36, 37, 38, 39, or 40 nucleotides in the RBS. In yet another embodiment, the DNA molecule comprise an RBS inactivated by a deletion of 1%, 2%, 3%, 4%, 5%, 6%, 7%, 8%, 9%, 10%, 11%, 12%, 13%, 14%, 15%, 16%, 17%, 18%, 19%, 20%, 20%, 21%, 22%, 23%, 24%, 25%, 26%, 27%, 28%, 29%, 10%, 31%, 32%, 33%, 34%, 35%, 36%, 37%, 38%, 39%, or 40% of the nucleotides in the RBS. In some embodiments, the deletion of the preceding sentence is an internal deletion, a deletion from the 5' end, or a deletion from the 3' end. In some embodiments, the deletion of this paragraph can be any combination of internal deletions, deletion from the 5' end, and/or deletions from the 3' end. In certain embodiments, the DNA molecule comprise an RBS inactivated by a deletion of the entire RBS sequences. In some additional embodiments, the DNA molecule comprise an RBS inactivated by a partial deletion of the RBS sequences.

In one embodiment, the DNA molecule comprise an NBSE inactivated by mutation. In one embodiment, the DNA molecule comprise an NSBE inactivated by a mutation of 1, 2, 3, 4, 5, 6, 7, 8, 9, 10, 11, 12, 13, 14, 15, 16, 17, 18, 19, 20, 20, 21, 22, 23, 24, 25, 26, 27, 28, 29, 10, 31, 32, 33, 34, 35, 36, 37, 38, 39, or 40 nucleotides in the NSBE. In another embodiment, the DNA molecule comprise an NSBE inactivated by a mutation of 1%, 2%, 3%, 4%, 5%, 6%, 7%, 8%, 9%, 10%, 11%, 12%, 13%, 14%, 15%, 16%, 17%, 18%, 19%, 20%, 20%, 21%, 22%, 23%, 24%, 25%, 26%, 27%, 28%, 29%, 10%, 31%, 32%, 33%, 34%, 35%, 36%, 37%, 38%, 39%, or 40% of the nucleotides in the NSBE. In a further embodiment, the DNA molecule comprise an NSBE inactivated by a deletion of 1, 2, 3, 4, 5, 6, 7, 8, 9, 10, 11, 12, 13, 14, 15, 16, 17, 18, 19, 20, 20, 21, 22, 23, 24, 25, 26, 27, 28, 29, 10, 31, 32, 33, 34, 35, 36, 37, 38, 39, or 40 nucleotides in the NSBE. In yet another embodiment, the DNA molecule comprise an NSBE inactivated by a deletion of 1%, 2%, 3%, 4%, 5%, 6%, 7%, 8%, 9%, 10%, 11%, 12%, 13%, 14%, 15%, 16%, 17%, 18%, 19%, 20%, 20%, 21%, 22%, 23%, 24%, 25%, 26%, 27%, 28%, 29%, 10%, 31%, 32%, 33%, 34%, 35%, 36%, 37%, 38%, 39%, or 40% of the nucleotides in the NSBE. In some embodiments, the deletion of the preceding sentence is an internal deletion, a deletion from the 5' end, or a deletion from the 3' end. In some embodiments, the deletion of this paragraph can be any combination of internal deletions, deletion from the 5' end, and/or deletions from the 3' end. In certain embodiments, the DNA molecule comprise an NSBE inactivated by a deletion of the entire NSBE sequences. In some additional embodiments, the DNA molecule comprise an NSBE inactivated by a partial deletion of the NSBE sequences.

Similarly, DNA sequence elements or features can be included or excluded from any specific regions of the DNA molecules provided herein (including Sections 5.3 and 5.4) or any specific regions of the DNA molecules used in the methods provided herein (including Section 5.2). In one embodiment, the DNA molecule lacks a Rep protein encoding sequence. In one embodiment, the DNA molecule lacks a NS1 protein encoding sequence. In another embodiment, the DNA molecule lacks a viral capsid protein encoding sequence. In some embodiments, the expression cassette lacks a Rep protein encoding sequence. In some embodiments, the expression cassette lacks a NS1 protein encoding sequence. In certain embodiments, the expression cassette lacks a viral capsid protein encoding sequence. In a further embodiment, the DNA molecule lacks an RABS. In yet another embodiment, the first inverted repeat lacks an RABS. In one embodiment, the second inverted repeat lacks an RABS. In another embodiment, the DNA sequence between the ITR closing base pair of the first inverted repeat and the ITR closing base pair of the second inverted repeat lacks an RABS. The lack of an RABS can be the lack of one RABS, the lack of two RABSs, the lack of more than two RABs, or the lack of any RABS. In one embodiment, the DNA molecule comprises a functionally inactivated Rep protein encoding sequence. In one embodiment, the DNA molecule comprises a functionally inactivated Rep protein encoding sequence. In one embodiment, the DNA molecule comprises a functionally inactivated NS1 protein recognition sequence. In one embodiment, the DNA molecule comprises a functionally inactivated NS1 protein encoding sequence. In another embodiment, the DNA molecule comprises a functionally inactivated viral capsid protein encoding sequence. In some embodiments, the expression cassette comprises a functionally inactivated Rep protein encoding sequence. In some embodiments, the expression cassette comprises a functionally inactivated NS1 protein encoding sequence. In certain embodiments, the expression cassette comprises a functionally inactivated viral capsid protein encoding sequence. In a further embodiment, the DNA molecule comprises a functionally inactivated RABS. In yet another embodiment, the first inverted repeat comprises a functionally inactivated RABS. In one embodiment, the second inverted repeat comprises a functionally inactivated RABS. In another embodiment, the DNA sequence between the ITR closing base pair of the first inverted repeat and the ITR closing base pair of the second inverted repeat comprises a functionally inactivated RABS. It is contemplated that one, two, or more RABS or all RABSs can be functionally inactivated.

Additionally, DNA sequence elements or features can be functionally inactivated from any combination of any specific regions of the DNA molecules provided herein (including Sections 5.3 and 5.4) or any specific regions of the DNA molecules used in the methods provided herein (including Section 5.2). In one embodiment, the first inverted repeat comprises a functionally inactivated RABS and the second inverted repeat comprises a functionally inactivated RABS. In another embodiment, the first inverted repeat comprises a functionally inactivated RABS and the DNA sequence between the ITR closing base pair of the first inverted repeat and the ITR closing base pair of the second inverted repeat comprises a functionally inactivated RABS. In a further embodiment, the second inverted repeat comprises a functionally inactivated RABS and the DNA sequence between the ITR closing base pair of the first inverted repeat and the ITR closing base pair of the second inverted repeat comprises a functionally inactivated RABS. In yet another embodiment, the first inverted repeat comprises a functionally inactivated RABS, the second inverted repeat comprises a functionally inactivated RABS and the DNA sequence between the ITR closing base pair of the first inverted repeat and the ITR closing base pair of the second inverted repeat comprises a functionally inactivated RABS. It is contemplated that one, two, or more RABS or all RABSs can be functionally inactivated.

As described in Sections 3, 5.3.1, 5.5, and 6, such DNA sequence elements or features that can be excluded from the DNA molecules provided herein can be a terminal resolution site ('TRS"). A TRS refers to a nucleotide sequence in the inverted repeat of the DNA molecules that is recognized by a RAP (for replication of viral nucleic acid molecules), and is the site of strand-specific cleavage by the endonuclease activity of the RAP protein. The TRS is also the site of specific interaction between the RAP and the nucleotide sequence. Nucleotide sequences of the conserved sites of specific cleavage by the endonuclease activity of the RAP proteins can be determined by DNA nicking assay known and used in the field of molecular biology, for example, gel electrophoresis, fluorophore-based in vitro nicking assays, radioactive in vitro nicking assay, as further described in Xu P, et al 2019. Antimicrob Agents Chemother 63:e01879-18; US20190203229A; both of which are hereby incorporated in their entireties by reference. In some embodiments a TRS can be a nucleotide sequence in the inverted repeat of the DNA molecules that is recognized by a Rep protein (for replication of viral nucleic acid molecules), and is the site of strand specific nicking by the endonuclease activity of the Rep protein. The TRS can also be the site of specific cleavage by the endonuclease activity of the Rep protein. In one embodiment a TRS can be a nucleotide sequence in the inverted repeat of the DNA molecules that is recognized by a NS1 protein (for replication of viral nucleic acid molecules), and is the site of strand specific nicking by the endonuclease activity of the NS1 protein. In another embodiment, the TRS can also include the site of specific interaction between the NS1 protein and the nucleotide sequence. A TRS can be a sequence of 5 nucleotides to 300 nucleotides. In some embodiments of the methods provided herein including those provided in this Section 5.3.4, the TRS can be a sequence of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, at least 200, at least 205, at least 210, at least 215, at least 220, at least 225, at least 230, at least 235, at least 240, at least 245, at least 250, at least 255, at least 260, at least 265, at least 270, at least 275, at least 280, at least 285, at least 290, at least 295, at least 300, at least 305, at least 310, at least 315, at least 320, at least 325, at least 330, at least 335, at least 340, at least 345, at least 350, at least 355, at least 360, at least 365, at least 370, at least 375, at least 380, at least 385, at least 390, at least 395, or at least 400 nucleotides. In some other embodiments, the TRS can be a sequence of about 5, about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, about 180, about 185, about 190, about 195, about 200, about 205, about 210, about 215, about 220, about 225, about 230, about 235, about 240, about 245, about 250, about 255, about 260, about 265, about 270, about 275, about 280, about 285, about 290, about 295, about 300, about 305, about 310, about 315, about 320, about 325, about 330, about 335, about 340, about 345, about 350, about 355, about 360, about 365, about 370, about 375, about 380, about 385, about 390, about 395, or about 400 nucleotides. In some further embodiments, any embodiment of the TRS described in this paragraph can be combined with any methods or DNA molecules provided herein including those provided in Sections 3, 5.2, 5.3, 5.4, and 6.

Alternatively, the DNA molecules provided herein, including those in Sections 3, 5.2, 5.3, 5.4, and 6, can lack a functional TRS by functionally inactivating the TRS sequence present in the DNA molecules with mutations, insertions, and/or deletions (including partial deletions or truncations), such that the TRS can no longer serve as a recognition and/or binding site for the RAP (i.e. Rep and NS1). As such, in some embodiments of the DNA molecules provided herein, including those in Sections 3, 5.2, 5.3, 5.4, and 6, the DNA molecule comprise a functionally inactivated TRS. Such functional inactivation can be assess by measuring and comparing the binding between the RAP (i.e. Rep and NS1) and the DNA molecules comprising the functionally inactivated TRS with that between the RAP and a reference molecule comprising the wild type (wt) TRS sequences (e.g. the same DNA molecule but with a wt TRS sequence). Such binding can be determined by any binding measurements known and used in the field of molecular biology, for example, chromatin immunoprecipitation (ChIP) assays, DNA electrophoretic mobility shift assay (EMSA), DNA pull-down assays, or Microplate capture and detection assays, as further described in Matthew J. Guille & G. Geoff Kneale, *Molecular Biotechnology* 8:35-52 (1997); Bipasha Dey et al., Mol Cell Biochem. 2012 June; 365(1-2):279-99, both of which are hereby incorporated in their entireties by reference. In one embodiment, the binding between the RAP (i.e. Rep and NS1) and the functionally inactivated TRS in the DNA molecule is at most 0.001%, at most 0.01%, at most 0.1%, at most 1%, at most 1.5%, at most 2%, at most 2.5%, at most 3%, at most 3.5, at most 4%, at most 4.5%, at most 5%, at most 5.5%, at most 6%, at most 6.5%, at most 7%, at most 7.5%, at most 8%, at most 8.5%, at most 9%, at most 9.5%, or at most 10%, compared to the binding between the RAP (i.e. Rep and NS1) and the wild type TRS in a reference DNA molecule (e.g. the same DNA molecule but with a wt TRS sequence). In another embodiment, the binding between the RAP (i.e. Rep and NS1) and the functionally inactivated TRS in the DNA molecule is about 0.001%, about 0.01%, about 0.1%, about 1%, about 1.5%, about 2%, about 2.5%, about 3%, about 3.5, about 4%, about 4.5%, about 5%, about 5.5%, about 6%, about 6.5%, about 7%, about 7.5%, about 8%, about 8.5%, about 9%, about 9.5%, or about 10%, compared to the binding between the RAP (i.e. Rep and NS1) and the wild type TRS in a reference DNA molecule (e.g. the same DNA molecule but with a wt TRS sequence). In yet another embodiment, the binding between the RAP (i.e. Rep and NS1) and the functionally inactivated TRS in the DNA molecule is 0.001%, 0.01%, 0.1%, 1%, 1.5%, 2%, 2.5%, 3%, 3.5, 4%, 4.5%, 5%, 5.5%, 6%, 6.5%, 7%, 7.5%, 8%, 8.5%, 9%, 9.5%, or 10%, compared to the binding between the RAP (i.e. Rep and NS1) and the wild type TRS in a reference DNA molecule (e.g. the same DNA molecule but with a wt TRS sequence).

In one embodiment, the DNA molecule comprise a TRS inactivated by mutation. In one embodiment, the DNA molecule comprise a TRS inactivated by a mutation of 1, 2, 3, 4, 5, 6, 7, 8, 9, 10, 11, 12, 13, 14, 15, 16, 17, 18, 19, 20, 20, 21, 22, 23, 24, 25, 26, 27, 28, 29, 10, 31, 32, 33, 34, 35, 36, 37, 38, 39, or 40 nucleotides in the TRS. In another embodiment, the DNA molecule comprise a TRS inactivated by a mutation of 1%, 2%, 3%, 4%, 5%, 6%, 7%, 8%, 9%, 10%, 11%, 12%, 13%, 14%, 15%, 16%, 17%, 18%, 19%, 20%, 20%, 21%, 22%, 23%, 24%, 25%, 26%, 27%, 28%, 29%, 10%, 31%, 32%, 33%, 34%, 35%, 36%, 37%, 38%, 39%, or 40% of the nucleotides in the TRS. In a further embodiment, the DNA molecule comprise a TRS inactivated by a deletion of 1, 2, 3, 4, 5, 6, 7, 8, 9, 10, 11, 12, 13, 14, 15, 16, 17, 18, 19, 20, 20, 21, 22, 23, 24, 25, 26, 27, 28, 29, 10, 31, 32, 33, 34, 35, 36, 37, 38, 39, or 40 nucleotides in the TRS. In yet another embodiment, the DNA molecule comprise a TRS inactivated by a deletion of 1%, 2%, 3%, 4%, 5%, 6%, 7%, 8%, 9%, 10%, 11%, 12%, 13%, 14%, 15%, 16%, 17%, 18%, 19%, 20%, 20%, 21%, 22%, 23%, 24%, 25%, 26%, 27%, 28%, 29%, 10%, 31%, 32%, 33%, 34%, 35%, 36%, 37%, 38%, 39%, or 40% of the nucleotides in the TRS. In some embodiments, the deletion of the preceding sentence is an internal deletion, a deletion from the 5' end, or a deletion from the 3' end. In some embodiments, the deletion of this paragraph can be any combination of internal deletions, deletion from the 5' end, and/or deletions from the 3' end. In certain embodiments, the DNA molecule comprise a TRS inactivated by a deletion of the entire TRS sequences. In some additional embodiments, the DNA molecule comprise a TRS inactivated by a partial deletion of the TRS sequences.

Similarly, DNA sequence elements or features can be included or excluded from any specific regions of the DNA molecules provided herein (including Sections 5.3 and 5.4) or any specific regions of the DNA molecules used in the methods provided herein (including Section 5.2). In one embodiment, the DNA molecule lacks a TRS. In yet another embodiment, the first inverted repeat lacks a TRS. In another embodiment, the second inverted repeat lacks a TRS. In a further embodiment, the first inverted repeat lacks a TRS and the second inverted repeat lacks a TRS.

Alternatively, TRS sequence elements or features can be functionally inactivated from any specific regions of the DNA molecules provided herein (including Sections 5.3 and 5.4) or any specific regions of the DNA molecules used in the methods provided herein (including Section 5.2). In one embodiment, the DNA molecule comprises a functionally inactivated TRS. In yet another embodiment, the first inverted repeat comprises a functionally inactivated TRS. In another embodiment, the second inverted repeat comprises a functionally inactivated TRS. In a further embodiment, the first inverted repeat comprises a functionally inactivated TRS and the second inverted repeat comprises a functionally inactivated TRS.

In some specific embodiments, the RABS excluded or functionally inactivated in the DNA molecules provided herein can be any, or any combination of any number, or all of the RABS sequences listed in the following table.

TABLE 18

Exemplary RAPs

| RAPs | Corresponding RABS sequences | SEQ ID NO |
|---|---|---|
| Rep (AAV1,2,7) | GCGCGCTCGCTCGCTC | 178 |
| Rep (AAV3) | TGCGCACTCGCTCGCTC | 179 |
| Rep (AAV4) | GCGCGCTCGCTCACTC | 180 |
| Rep (AAV5) | GTTCGCTCGCTCGCTGGCTC | 181 |
| NS1-NSBE1 (B19V) | GCCGCCGG | |
| NS1-NSBE2 (B19V) | GGCGGGAC | |
| NS1-NSBE3 (B19V) | TTCCGGTACA | 182 |

Further non-limiting examples of terminal repeats for DNA molecules lacking RBS sequences are exemplified in FIG. 3 as well as corresponding SEQ ID NOs: 3, 4, 5, 8, 9 and 10. In some specific embodiments, the RABS excluded or functionally inactivated in the DNA molecules provided herein can be any, or any combination of any number, or all of the RABS sequences listed in the following table.

| RAPs | Corresponding RABS sequences | Reverse Complement RABS |
|---|---|---|
| Rep (AAV1,2,7) | GCTCGCTCGCTC | GAGCGAGCGAGC |
| Rep (AAV3) | GATCGCTCGCTC | GAGCGAGCGATC |
| Rep (AAV4) | GCTCGCTCACTCACTC | GAGTGAGTGAGCGAGC |
| Rep (AAV5) | GCTCGCTCGCTGGCTC | GAGCCAGCGAGCGAGC |
| NS1-NSBE1 (B19V) | GCCGCCGG | CCGGCGGC |
| NS1-NSBE2 (B19V) | GGCGGGAC | GTCCCGCC |
| NS1-NSBE3 (B19V) | TTCCGGTACA | TGTACCGGAA |

In one specific embodiment, the DNA molecules lack encoding sequences for any one, or any combination of any number, or all of the RAPs described in the Table of the preceding paragraph. In another specific embodiment, the DNA molecules comprises functionally inactivated sequences encoding for any one, or any combination of any number, or all of the RAPs described in the Table of the preceding paragraph. In another specific embodiment, the DNA molecules comprises functionally inactivated sequences encoding for any one, or any combination of any number, or all of the RAPs described in the Table of the preceding paragraph.

In another specific embodiment, the DNA molecule comprises functionally inactivated recognition sequences for any one, or any combination of any number, or all of the RAPs described in the Table of the preceding paragraph. In one specific embodiment, one or both hairpinned inverted repeats lack the RAPS recognition sequence:

(SEQ ID NO: 333)
GGCCACTCCCGAAGAGCGCGCTCGCTATCTCACTGAGGCCGGGCGACCA
AAGGTCGCCCGACGCCCGGGCTTTGCCCGGGCGGCCTCAGTGAGATAGC
GAGCGCGCTCTTCGGGAGTGGCC

Further non-exhaustive examples of hairpinned inverted repeats that may be included in DNA molecules lacking at least one, or any, RBS sequences are exemplified in Example 10.

In other specific embodiments, the TRS excluded or functionally inactivated in the DNA molecules provided herein can be any, or any combination of any number, or all of the TRS sequences listed in the following table.

TABLE 19

| Exemplary RAPs | |
|---|---|
| RAP (Virus) | Corresponding TRS sequences |
| Rep (AAV2, AAV3, AAV4) | AGTTGG |
| Rep (AAV1, AAV6) | AGTTGC |
| Rep (AAV5) | AGTGTGGC |
| NS1 (B19) | GACACC |
| NS1 (HBOV) | CTATATCT |
| NS1 (MVM) | CTWW/TCA (W = A/T) |

As the methods provided herein do not need a viral replication step and the DNA molecules provide herein do not need to be produced or replicated in a virus life cycle, the disclosure provides and a person reading the disclosure would understand that the DNA molecules provide herein can lack various DNA sequences or features, including those sequences or features provided in this Section (Section 5.3.4). DNA molecules lacking RABS and/or TRS and DNA molecules comprising functionally inactivated RABS and/or functionally inactivated TRS as provided in this Section 5.3.4 provide at least a major advantage in that the DNA molecules would have no or significantly lower risk of mobilization or replication once administered to a patient when compared with DNA molecules including such RABS and/or TRS sequences. Risk of mobilization or mobilization risk refers to the risk of the replication defective DNA molecules reverting to replication or production of viral particles in the host that has been administered the DNA molecules. Such mobilization risk can result from the presence of viral proteins (e.g. Rep proteins, NS1 proteins or viral capsid proteins) expressed by viruses that have infected the same host that has been administered the DNA molecules. Mobilization risk poses a significant safety concern for using the replication defective viral genome as gene therapy vectors, as described for example in Liujiang Song, Hum Gene Ther, 2020 October; 31(19-20):1054-1067 (incorporated herein in its entirety by reference). Such DNA molecules lacking RABS and/or TRS would have no binding site for viral RAP to initiate the replication even if other helper viruses are present in the same host to provide RAPs. Without being bound by theory, it is thought that presence replication initiation may require helper factors, which are provided by coinfections of the host by auxiliary viruses, referred to "helper viruses" which can including viruses from the herpesvirus family, adenoviruses, and papillomaviruses.

Accordingly, in some embodiments of the DNA molecules provided herein including those in this Section 5.3.4, the DNA molecules without RABS and/or without TRS have less mobilization risk after administered to a subject or a patient when compared with DNA molecules with RABS and/or with TRS. In certain embodiments of the DNA molecules provided herein including those in this Section 5.3.4, the DNA molecules comprising functionally inactivated RABS and/or functionally inactivated TRS have less mobilization risk after administered to a subject or a patient when compared with DNA molecules with RABS and/or with TRS. Such reduction of mobilization risk can be determined as (Pm−Po)/Pm, wherein Pm is the number of viral particles produced from the control DNA molecules with RABS when RAPs are present (e.g. due to the infection of any virus comprising RAPs or engineered expression of RAPs in the same host); Po is the number of viral particles produced from DNA molecules lacking RABS or comprising functionally inactivated as provided herein under comparable conditions in the same host used for the control DNA molecules. Alternatively, such reduction of mobilization risk can be determined as (Pm−Po)/Pm, wherein Pm is the number of viral particles produced from the control DNA molecules with TRS when RAPs are present (e.g. due to the infection of any virus comprising RAPs or engineered expression of RAPs in the same host); Po is the number of viral particles produced from DNA molecules lacking TRS or comprising functionally inactivated TRS as provided herein under comparable conditions in the same host used for the control DNA molecules. Additionally, such reduction of mobilization risk can be determined as (Pm−Po)/Pm, wherein Pm is the number of viral particles produced from the control DNA molecules with RABS and with TRS when RAPs are present (e.g. due to the infection of any virus comprising Rep proteins or NS1 proteins or engineered expression of Rep proteins or NS1 proteins in the same host); Po is the number of viral particles produced from DNA molecules (i) lacking RABS or comprising functionally inactivated RABS and (ii) lacking TRS or comprising functionally inactivated TRS as provided herein under comparable conditions in the same host used for the control DNA molecules. As described in Liujiang Song, Hum Gene Ther, 2020 October; 31(19-20):1054-1067 (incorporated herein in its entirety by reference), the host used for determining the particle numbers produced can be cells, animals (e.g. mouse, hamster, rate, dog, rabbit, guinea pig, and other suitable mammals), or human. The disclosure further provides and a person of ordinary skill in the art reading the disclosure would understand that Pm and Po, each as described in this paragraph, can be used also to determine the absolute or relative levels of mobilization. Briefly, in such an assay, the DNA molecules are transfected into the host cells (e.g. HEK293 cells) or transduced into the host cells by infecting with a viral particle comprising DNA molecules. The host cells are further transfected with Rep protein, NS1 protein or co-infected with another virus expressing the Rep protein or NS1 protein (for example wild type viruses). The host cells are then cultured to produce and release viral particles. Virions are then harvested by collecting both the host cell and the culture media after culturing 48 to 72 hours (e.g. 65 hours). The titer for the viral particles (proxy for Pm and Po) can be determined by a probe-based quantitative PCR (qPCR) analysis following Benzonase treatment to eliminate nonencapsidated DNA, as described in Song et al., Cytotherapy 2013; 15:986-998, which is incorporated in its entirety by reference. An exemplary implementation of such assay is provided in Liujiang Song, Hum Gene Ther, 2020 October; 31(19-20):1054-1067, which is incorporated herein in its entirety by reference.

Based on the determination of the reduction of mobilization risk and the mobilization risk levels, in some embodiments of the DNA molecules provided herein including in this Section 5.3.4, the mobilization risk of the DNA molecules when administered to a host is lower than control DNA molecules with RABS and/or with TRS by 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, or 20%. In certain embodiments, the mobilization risk of the DNA molecules when administered to a host is lower than control DNA molecules with RABS and/or with TRS by at least 99%, at least 98%, at least 97%, at least 96%, at least 95%, at least 94%, at least 93%, at least 92%, at least 91%, at least 90%, at least 89%, at least 88%, at least 87%, at least 86%, at least 85%, at least 84%, at least 83%, at least 82%, at least 81%, at least 80%, at least 79%, at least 78%, at least 77%, at least 76%, at least 75%, at least 74%, at least 73%, at least 72%, at least 71%, at least 70%, at least 69%, at least 68%, at least 67%, at least 66%, at least 65%, at least 64%, at least 63%, at least 62%, at least 61%, at least 60%, at least 59%, at least 58%, at least 57%, at least 56%, at least 55%, at least 54%, at least 53%, at least 52%, at least 51%, at least 50%, at least 49%, at least 48%, at least 47%, at least 46%, at least 45%, at least 44%, at least 43%, at least 42%, at least 41%, at least 40%, at least 39%, at least 38%, at least 37%, at least 36%, at least 35%, at least 34%, at least 33%, at least 32%, at least 31%, at least 30%, at least 29%, at least 28%, at least 27%, at least 26%, at least 25%, at least 24%, at least 23%, at least 22%, at least 21%, or at least 20. In other embodiments, the mobilization risk of the DNA molecules when administered to a host is lower than control DNA molecules with RABS and/or with TRS by about 100%, about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 74%, about 73%, about 72%, about 71%, about 70%, about 69%, about 68%, about 67%, about 66%, about 65%, about 64%, about 63%, about 62%, about 61%, about 60%, about 59%, about 58%, about 57%, about 56%, about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, or about 20%.

Alternatively, in one embodiment, the DNA molecules provided herein including in this Section 5.3.4, result in no detectable mobilization (e.g. based on the measurement of Po provided in this Section 5.3.4). In another embodiment, the DNA molecules provided herein including in this Section 5.3.4 result in mobilization of no more than 0.0001%, no more than 0.001%, no more than 0.01%, no more than 0.1%, no more than 1%, no more than 1.5%, no more than 2%, no more than 2.5%, no more than 3%, no more than 3.5, no more than 4%, no more than 4.5%, no more than 5%, no more than 5.5%, no more than 6%, no more than 6.5%, no more than 7%, no more than 7.5%, no more than 8%, no more than 8.5%, no more than 9%, no more than 9.5%, or no more than 10%, of the mobilization resulted from a reference DNA molecule (e.g. the same DNA molecule but with a wild type RABS and/or with wild type TRS sequence). In a further embodiment, the DNA molecules provided herein including in this Section 5.3.4 result in mobilization of about 0.0001%, about 0.001%, about 0.01%, about 0.1%, about 1%, about 1.5%, about 2%, about 2.5%, about 3%, about 3.5, about 4%, about 4.5%, about 5%, about 5.5%, about 6%, about 6.5%, about 7%, about 7.5%, about 8%, about 8.5%, about 9%, about 9.5%, or about 10%, of the mobilization resulted from a reference DNA molecule (e.g. the same DNA molecule but with a wild type RABS and/or with wild type TRS sequence). In a yet another embodiment, the DNA molecules provided herein including in this Section 5.3.4 result in mobilization of 0.0001%, 0.001%, 0.01%, 0.1%, 1%, 1.5%, 2%, 2.5%, 3%, 3.5, 4%, 4.5%, 5%, 5.5%, 6%, 6.5%, 7%, 7.5%, 8%, 8.5%, 9%, 9.5%, or 10%, of the mobilization resulted from a reference DNA molecule (e.g. the same DNA molecule but with a wild type RABS and/or with wild type TRS sequence). Such percentage of mobilization can be determined by using the Pm and Po determined as further described in the preceding paragraphs (including the preceding 2 paragraphs).

In certain embodiments, the DNA molecules provided herein (for example, as in this Section 5.3.4) comprise ITRs that have functionally inactivated RABS and/or functionally inactivated TRS. In certain embodiments, the DNA molecules provided herein comprise ITRs that lack an RABS and/or a TRS. In certain embodiments, the DNA molecules provided herein have less mobilization risk after being administered to a subject or a patient when compared with DNA molecules comprising a functional RABS and/or functional TRS. ITRs that have functionally inactivated RABS and/or functionally inactivated TRS are referred to as "viral replication deficient inverted repeats" or "viral replication deficient inverted terminal repeats", interchangeably.

In certain embodiments, the methods provided herein do not require any RABS. In certain embodiments, the DNA molecules provided herein do not need to be produced and/or replicated in a virus life cycle. The person of skill in the art would understand that the DNA molecules provided herein can lack additional features traditionally associated with RABS and/or viral production or replication, including those sequences or features discussed, for example, in this Section 5.3.4. In certain embodiments, the DNA molecules lacking RBS and/or DNA molecules comprising functionally inactivated RBS provided herein (for example, as in Section 5.3.4) provide at least a further advantage in that the terminal repeat sequences of DNA molecules may have no or diminished endogenous promoter and/or transcriptional activity (e.g. the P5 AAV promoter, which shares a homolog sequence with the RBS) once in a host cell when compared with DNA molecules with wild type viral ITR sequences. Transcriptional activity or endogenous promoter activity refers to the ability of hairpin ended DNA molecules to promote transgene expression starting from the folded hairpin overhang sequence (e.g. when these sequences contain one or more transcription start sites (TSSs)). Such transcriptional activity can result from the presence of viral proteins (e.g. Rep proteins or NS1 proteins) expressed by viruses that have infected the same host that has been administered the DNA molecules or from binding of endogenous transcription factors expressed in the host cell. The presence of TSSs and promoter sequences or fragments there of (e.g. the P5 promoter) may confound intended transgene expression in therapeutic applications or influence on transgene expression cassettes independent of promoter selection, wherein tight control of (e.g. tissue specific) transgene expression by appropriate control elements (e.g. tissue specific promoters) is highly desirable. In some embodiments, the presence or level of transcriptional activity and/or endogenous promoter activity arising from the folded hairpin overhang DNA sequence of hairpin ended DNA molecules (referred to as "ITR transcriptional activity") can be determined by measuring the ability of such sequences to promote transgene expression in a host cell (e.g. by detecting report gene expression, qPCR of mRNA transcripts, western blot, etc) by hairpin ended DNA molecules provided herein that lack a cis-regulatory element (e.g. promoter as described in section in 5.3.3) upstream of the ORF (e.g. by deleting or inactivating the promoter sequence of an expression cassette as described in 5.3.3).

In further embodiments, ITR transcriptional activity can be determined by measuring the residual ability of hairpin ended DNA molecules comprising an expression cassette comprising a tissue specific cis-regulatory element (e.g. tissue specific promoter as described in section in 5.3.3), to promote transgene expression in a host cell not derived from said tissue (e.g. by detecting report genes expression, qPCR of mRNA transcripts, western blot, etc).

Based on the determination of the reduction ITR transcriptional activity and the ITR transcriptional activity levels, in some embodiments of the DNA molecules provided herein including in this Section 5.3.4, the ITR transcriptional activity of the DNA molecules when administered to a host is lower than control DNA molecules with wild type viral ITRs and/or RABS by 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, or 20%. In certain embodiments, the ITR transcriptional activity of the DNA molecules when administered to a host is lower than control DNA molecules with RABS and/or with wild type viral ITRs by at least 99%, at least 98%, at least 97%, at least 96%, at least 95%, at least 94%, at least 93%, at least 92%, at least 91%, at least 90%, at least 89%, at least 88%, at least 87%, at least 86%, at least 85%, at least 84%, at least 83%, at least 82%, at least 81%, at least 80%, at least 79%, at least 78%, at least 77%, at least 76%, at least 75%, at least 74%, at least 73%, at least 72%, at least 71%, at least 70%, at least 69%, at least 68%, at least 67%, at least 66%, at least 65%, at least 64%, at least 63%, at least 62%, at least 61%, at least 60%, at least 59%, at least 58%, at least 57%, at least 56%, at least 55%, at least 54%, at least 53%, at least 52%, at least 51%, at least 50%, at least 49%, at least 48%, at least 47%, at least 46%, at least 45%, at least 44%, at least 43%, at least 42%, at least 41%, at least 40%, at least 39%, at least 38%, at least 37%, at least 36%, at least 35%, at least 34%, at least 33%, at least 32%, at least 31%, at least 30%, at least 29%, at least 28%, at least 27%, at least 26%, at least 25%, at least 24%, at least 23%, at least 22%, at least 21%, or at least 20. In other embodiments, the ITR transcriptional activity of the DNA molecules when administered to a host is lower than control DNA molecules with RABS and/or with wild type viral ITRs by about 100%, about 99%, about 98%, about 97%, about 96%, about 95%, about 94%, about 93%, about 92%, about 91%, about 90%, about 89%, about 88%, about 87%, about 86%, about 85%, about 84%, about 83%, about 82%, about 81%, about 80%, about 79%, about 78%, about 77%, about 76%, about 75%, about 74%, about 73%, about 72%, about 71%, about 70%, about 69%, about 68%, about 67%, about 66%, about 65%, about 64%, about 63%, about 62%, about 61%, about 60%, about 59%, about 58%, about 57%, about 56%, about 55%, about 54%, about 53%, about 52%, about 51%, about 50%, about 49%, about 48%, about 47%, about 46%, about 45%, about 44%, about 43%, about 42%, about 41%, about 40%, about 39%, about 38%, about 37%, about 36%, about 35%, about 34%, about 33%, about 32%, about 31%, about 30%, about 29%, about 28%, about 27%, about 26%, about 25%, about 24%, about 23%, about 22%, about 21%, or about 20%.

In a certain embodiment, the DNA molecules provided herein including in this Section 5.3.4, result in no detectable ITR transcriptional activity (e.g. based on the measurement of transgene expression method in this Section 5.3.4). In another embodiment, the DNA molecules provided herein including in this Section 5.3.4 result in ITR transcriptional activity of no more than 0.0001%, no more than 0.001%, no more than 0.01%, no more than 0.1%, no more than 1%, no more than 1.5%, no more than 2%, no more than 2.5%, no more than 3%, no more than 3.5, no more than 4%, no more than 4.5%, no more than 5%, no more than 5.5%, no more than 6%, no more than 6.5%, no more than 7%, no more than 7.5%, no more than 8%, no more than 8.5%, no more than 9%, no more than 9.5%, or no more than 10%, of the ITR transcriptional activity resulted from a reference DNA molecule (e.g. the same DNA molecule but with a wild type RABS and/or with wild type ITR sequence). In a further embodiment, the DNA molecules provided herein including in this Section 5.3.4 result in ITR transcriptional activity of about 0.0001%, about 0.001%, about 0.01%, about 0.1%, about 1%, about 1.5%, about 2%, about 2.5%, about 3%, about 3.5, about 4%, about 4.5%, about 5%, about 5.5%, about 6%, about 6.5%, about 7%, about 7.5%, about 8%, about 8.5%, about 9%, about 9.5%, or about 10%, of the ITR transcriptional activity resulted from a reference DNA molecule (e.g. the same DNA molecule but with a wild type RABS and/or with wild type ITR sequence). In a yet another embodiment, the DNA molecules provided herein including in this Section 5.3.4 result in ITR transcriptional activity of 0.0001%, 0.001%, 0.01%, 0.1%, 1%, 1.5%, 2%, 2.5%, 3%, 3.5, 4%, 4.5%, 5%, 5.5%, 6%, 6.5%, 7%, 7.5%, 8%, 8.5%, 9%, 9.5%, or 10%, of the mobilization ITR transcriptional activity from a reference DNA molecule (e.g. the same DNA molecule but with a wild type RABS and/or with wild type ITR sequence). Such percentage of ITR transcriptional activity can be determined by using the transgene expression determined as further described in the preceding paragraphs (including the preceding 2 paragraphs).

As is clear from the descriptions in this Section 5.3.4, the DNA sequences or features excluded in the DNA molecules provided herein can be combined in any way with any of the methods provided herein (including in Sections 3, 5.2, and 6), any of the DNA molecules provided herein (including Sections 3, 5.3, and 6), and any of the hairpin-ended DNA molecules provided herein (including Sections 3, 5.4, and 6), and contribute to the functional properties of the DNA molecules as provided herein (including Sections 3, 5.5, and 6).

5.3.5 Vectors Such as Plasmids

The disclosure provides that the DNA molecules can be of various forms. In one embodiment, the DNA molecule provided for the methods and composition herein is a vector. A vector is a nucleic acid molecule that can be replicated and/or expressed in a host cell. Any vectors known to those skilled in the art are provided herein. In some embodiments, the vector can be plasmids, viral vectors, cosmids, and artificial chromosomes (e.g., bacterial artificial chromosomes or yeast artificial chromosomes). In one specific embodiment, the vector is a plasmid. As is clear from the description, when the DNA molecules are in the form of a vector (including a plasmid), the vector would comprise all the features described herein for the DNA molecules, including those described in Section 3 and this Section (Section 5.3).

In some embodiments, the vector provided in this Section (Section 5.3.5) can be used for the production of DNA molecules provided in Sections 3 and 5.4, for example by performing the method steps provided in Section 5.2. As such, the vector provided in this Section (Section 5.3.5) (1) comprises the features of the DNA molecules provided in Sections 3 and 5.4, including IRs or ITRs that can form hairpins as described in Sections 5.3.1 and 5.4, expression cassette as described in 5.3.3, and restriction sites for nicking endonucleases or restriction enzymes as described in Sections 5.3.2, 5.2.4, and 5.3.6, and/or (2) lacks the RABS and/or TRS sequences as described in Section 5.3.4. Therefore, the disclosure provides that the vector provided in this Section (Section 5.3.5) can (1) comprise any combination of embodiments of IRs or ITRs that can form hairpins as described in Sections 5.3.1 and 5.4, expression cassette as described in 5.3.3, restriction sites for nicking endonucleases or restriction enzymes as described in Sections 5.3.2 5.2.4, and 5.3.6, and additional features for the vectors provided in this Section (Section 5.3.5), and/or (2) lacks the RABS and/or TRS sequences as described in Section 5.3.4.

In some embodiments, a vector can be constructed using known techniques to provide at least the following as operatively linked components in the direction of transcription: (1) a 5' ITR sequence; (2) an expression cassette comprising a cis-regulatory element, for example, a promoter, inducible promoter, regulatory switch, enhancers and the like; and (3) a 3' IR sequence. In some embodiments, the expression cassette is flanked by the ITRs comprises a cloning site for introducing an exogenous sequence.

Specifically, in one embodiment, the DNA molecule is a plasmid. Plasmid is widely known and used in the art as a vector to replicate or express the DNA molecules in the plasmid. Plasmid often refers to a double-stranded and/or circular DNA molecule that is capable of autonomous replication in a suitable host cell. In certain embodiments, plasmids provided for the methods described in Section 5.2 can be linearized by restriction enzyme digest and/or present in a linear form. Plasmids provided for the methods and compositions described herein include commercially available plasmids for use in well-known host cells (including both prokaryotic and eukaryotic host cells), as available from various vendors and/or described in Molecular Cloning: A Laboratory Manual, 4th Edition, by Michael Green and Joseph Sambrook, ISBN 978-1-936113-42-2 (2012), which is incorporated herein in its entirety by reference. In certain embodiments, the plasmids further comprise a multiple cloning site. In some embodiments, the plasmids further comprise a selection marker, which for example, can be an antibiotic resistance gene. In some embodiments, the plasmids further comprise an origin of replication (ORI). An ORI is a sequence at which replication is initiated, enabling a plasmid to reproduce within the host cells. In certain embodiments, the ORI provided for the methods and compositions described herein can be a bacterial origin of replication. In certain embodiments, the ORI provided for the methods and compositions described herein can be a eukaryotic origin of replication. In certain embodiments, the ORI provided for the methods and compositions described herein can be a viral origin of replication. In some specific embodiments, the ORI can be pBR322, F1, ColE1, pMB1, pUC, pSC101, R6K, 15A, EBV ORI, or SV40 ORI.

The plasmids described in this Section (Section 5.3.5) can further comprise other features. In some embodiments, the plasmid further comprises a restriction enzyme site (e.g. restriction enzyme site as described in Sections 5.2.4 and 5.3.2) in the region 5' to the first inverted repeat and 3' to the second inverted repeat wherein the restriction enzyme site is not present in any of the first inverted repeat, second inverted repeat, and the region between the first and second inverted repeats. In certain embodiments, the cleavage with the restriction enzyme at the restriction site described in this paragraph results in single strand overhangs that do not anneal at detectable levels under conditions that favor annealing of the first and/or second inverted repeat (e.g. conditions as described in Section 5.2.5). In some other embodiments, the plasmid further comprises an open reading frame encoding the restriction enzyme recognizing and cleaving the restriction site describe in this paragraph. In certain embodiments, the restriction enzyme site and the corresponding restriction enzyme can be any one of the restriction enzyme site and its corresponding restriction enzyme described in Sections 5.2.4 and 5.3.2. In further embodiment, the expression of the restriction enzyme described in this paragraph is under the control of a promoter. In some embodiments, the promoter described in this paragraph can be any promoter described above in Section 5.3.3. In other embodiment, the promoter described is an inducible promoter. In certain embodiment, the inducible promoter is a chemically inducible promoter. In further embodiments, the inducible promoter is any one selected from the group consisting of: tetracycline ON (Tet-On) promoter, negative inducible pLac promoter, alcA, amyB, bli-3, bphA, catR, cbhl, cre1, exylA, gas, glaA, gla1, mir1, niiA, qa-2, Smxyl, tcu-1, thiA, vvd, xyl1, xyl1, xylP, xyn1, and ZeaR, as described in Janina Kluge et al., *Applied Microbiology and Biotechnology* 102: 6357-6372 (2018), which is incorporated herein in its entirety by reference.

Similarly, in certain embodiments, the plasmid can further comprise a fifth and a sixth restriction site for nicking endonuclease (e.g. restriction site for nicking endonuclease as described in Sections 5.2.4 and 5.3.2) in the region 5' to the first inverted repeat and 3' to the second inverted repeat, wherein the fifth and sixth restriction sites for nicking endonuclease are: a.) on opposite strands; and b.) create a break in the double stranded DNA molecule such that the single strand overhangs of the break do not anneal at detectable levels inter- or intra-molecularly under conditions that favor annealing of the first and/or second inverted repeat (e.g. conditions as described in Section 5.2.5). As is clear from the description of Section 5.2.4, incubation with nicking endonucleases will result in a fifth nick corresponding to the fifth restriction site for the nicking endonuclease and a sixth nick corresponding to the sixth restriction site for the nicking endonuclease. The disclosure provides that the fifth and sixth nick can have various relative positions between them. In one embodiment, the fifth and the sixth nick are 1, 2, 3, 4, 5, 6, 7, 8, 9, 10, 11, 12, 13, 14, 15, 16, 17, 18, 19, or 20 nucleotides apart. In some embodiments, as the ssDNA overhang between fifth and sixth nick does not anneal at detectable levels inter- or intra-molecularly under conditions that favor annealing of the first and/or second inverted repeat, the ssDNA overhang resulted from fifth and sixth nick has a lower melting temperature than the ssDNA overhangs described in Sections 5.2.3 and 5.3.2. In certain embodiments, the ssDNA overhang resulted from fifth and sixth nick is shorter than the ssDNA overhangs described in Sections 5.2.3 and 5.3.2. In other embodiments, the ssDNA overhang resulted from fifth and sixth nick has a lower percentage of G-C content than the ssDNA overhangs described in Sections 5.2.3 and 5.3.2. In some specific embodiments, the ssDNA overhang resulted from fifth and sixth nick is 0, 1, 2, 3, 4, 5, 6, 7, 8, 9, 10, 11, 12, 13, 14, 15, 16, 17, 18, 19, or 20 nucleotides in length. In other specific embodiments, the ssDNA overhang resulted from fifth and sixth nick is shorter than the ssDNA overhangs described in Sections 5.2.3 and 5.3.2 by at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, at least 175, or at least 180 nucleotides. In some specific embodiments, the ssDNA overhang resulted from fifth and sixth nick is shorter than the ssDNA overhangs described in Sections 5.2.3 and 5.3.2 by about 10, about 15, about 20, about 25, about 30, about 35, about 40, about 45, about 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, about 175, or about 180 nucleotides.

In certain embodiments, the plasmid can further comprise 7, 8, 9, 10, 11, 12, 13, 14, 15, 16, 17, 18, 19 or more restriction sites for nicking endonuclease (e.g. restriction site for nicking endonuclease as described in Sections 5.2.4 and 5.3.2) in the region 5' to the first inverted repeat and 3' to the second inverted repeat, wherein the additional restriction sites for nicking endonuclease may be: a.) on opposite strands; and b.) create a break in the double stranded DNA molecule such that the single strand overhangs of the break do not anneal at detectable levels inter- or intra-molecularly under conditions that favor annealing of the first and/or second inverted repeat (e.g. conditions as described in Section 5.2.5). In certain embodiments, the nicks in the region 5' to the first inverted repeat and 3' to the second inverted repeat, can have various relative positions between them. In one embodiment, the nicks in the region 5' to the first inverted repeat and 3' to the second inverted repeat, are 1, 2, 3, 4, 5, 6, 7, 8, 9, 10, 11, 12, 13, 14, 15, 16, 17, 18, 19, or 20 nucleotides apart. In some embodiments, as the ssDNA overhang between the nicks in the region 5' to the first inverted repeat and 3' to the second inverted repeat does not anneal at detectable levels inter- or intra-molecularly under conditions that favor annealing of the first and/or second inverted repeat, the ssDNA overhang resulting from the nicks in the region 5' to the first inverted repeat and 3' to the second inverted repeat has a lower melting temperature than the ssDNA overhangs described in Sections 5.2.3 and 5.3.2. In certain embodiments, the ssDNA overhang resulting from the nicks in the region 5' to the first inverted repeat and 3' to the second inverted repeat is shorter than the ssDNA overhangs described in Sections 5.2.3 and 5.3.2. In other embodiments, the ssDNA overhang resulting from the nicks in the region 5' to the first inverted repeat and 3' to the second inverted repeat has a lower percentage of G-C content than the ssDNA overhangs described in Sections 5.2.3 and 5.3.2. In some specific embodiments, the ssDNA overhang resulting from the nicks in the region 5' to the first inverted repeat and 3' to the second inverted repeat is 0, 1, 2, 3, 4, 5, 6, 7, 8, 9, 10, 11, 12, 13, 14, 15, 16, 17, 18, 19, or 20 nucleotides in length.

As described above in Sections 5.2.4 and 5.3.2, in various embodiments, the first, second, third, and fourth restriction sites for nicking endonuclease can be the target sequences for the same or different nicking endonucleases. Similar, in certain embodiments, the fifth and sixth restriction sites for nicking endonuclease can be target sequences for the same or different nicking endonucleases. In some embodiments, the first, second, third, fourth, fifth, and sixth restriction sites for nicking endonuclease provided for the DNA molecules as described in Sections 3 and 5.2.4 and this Section 5.3 can be all for target sequences for the same nicking endonuclease. Alternatively, in other embodiments, the first, second, third, fourth, fifth, and sixth restriction sites for nicking endonucleases are target sequences for two different nicking endonucleases, including all possible combinations of arranging the six sites for two different nicking endonuclease target sequences (e.g. the first restriction site for the first nicking endonuclease and the rest for the second nicking endonuclease, the first and second restriction sites for the first nicking endonuclease and the rest for the second nicking endonuclease, etc). Additionally, in certain embodiments, the first, second, third, fourth, fifth, and sixth restriction sites for nicking endonucleases are target sequences for three different nicking endonucleases, including all possible combinations of arranging the six sites for three different nicking endonuclease target sequences. Furthermore, in some embodiments, the first, second, third, fourth, fifth, and sixth restriction sites for nicking endonuclease are target sequences for four different nicking endonucleases, including all possible combinations of arranging the six sites for four different nicking endonuclease target sequences. Additionally, in some embodiments, the first, second, third, fourth, fifth, and sixth restriction sites for nicking endonuclease are target sequences for five different nicking endonucleases, including all possible combinations of arranging the six sites for five different nicking endonuclease target sequences. Furthermore, in some embodiments, the first, second, third, fourth, fifth, and sixth restriction sites for nicking endonuclease are target sequences for six different nicking endonucleases.

In some embodiments, the one or more of the nicking endonuclease sites described in the preceding paragraph are a target sequence of an endogenous nicking endonuclease. In some specific embodiments, the plasmid further comprises an ORF encoding a nicking endonuclease that recognizes one or more of the first, second, third, fourth, fifth, and sixth restriction sites for nicking endonuclease described in this Section (Section 5.3.5) including the preceding paragraph. In one specific embodiment, the plasmid further comprises two ORFs encoding two nicking endonucleases that recognize two or more of the first, second, third, fourth, fifth, and sixth restriction sites for nicking endonuclease described in this Section (Section 5.3.5) including the preceding paragraph. In another specific embodiment, the plasmid further comprises three ORFs encoding three nicking endonucleases that recognize three or more of the first, second, third, fourth, fifth, and sixth restriction sites for nicking endonuclease described in this Section (Section 5.3.5) including the preceding paragraph. In yet another specific embodiment, the plasmid further comprises four ORFs encoding four nicking endonucleases that recognize four or more of the first, second, third, fourth, fifth, and sixth restriction sites for nicking endonuclease described in this Section (Section 5.3.5) including the preceding paragraph. In yet another specific embodiment, the plasmid further comprises four ORFs encoding four nicking endonucleases that recognize four or more of the first, second, third, fourth, fifth, and sixth restriction sites for nicking endonuclease described in this Section (Section 5.3.5) including the preceding paragraph. In a further specific embodiment, the plasmid further comprises five ORFs encoding five nicking endonucleases that recognize five or more of the first, second, third, fourth, fifth, and sixth restriction sites for nicking endonuclease described in this Section (Section 5.3.5) including the preceding paragraph. In one specific embodiment, the plasmid further comprises six ORFs encoding six nicking endonucleases that each recognizes the first, second, third, fourth, fifth, and sixth restriction sites for nicking endonuclease described in this Section (Section 5.3.5) including the preceding paragraph. In certain embodiments, the expression of the one or more nicking endonucleases described in this paragraph is under the control of a promoter. In some embodiments, the expression of the one or more nicking endonucleases described in this paragraph is under the control of a promoter. In some embodiments, the expression of the one or more nicking endonucleases described in this paragraph is under the control of an inducible promoter. In some specific embodiments, the inducible promoter can be any inducible promoter described above in this Section (Section 5.3.5).

In some embodiments, the nicking endonuclease that recognizes the first, second, third, and/or fourth restriction site for nicking endonuclease can be any one described in Sections 3, 5.2.4 and 5.3.2. In certain specific embodiment, the nicking endonuclease that recognizes the first, second, third, and/or fourth restriction site for nicking endonuclease is Nt. BsmAI; Nt. BtsCI; N. ALwI; N. BstNBI; N. BspD6I; Nb. Mva1269I; Nb. BsrDI; Nt. BtsI; Nt. BsaI; Nt. Bpu10I; Nt. BsmBI; Nb. BbvCI; Nt. BbvCI; or Nt. BspQI. In some embodiments, the nicking endonuclease that recognizes the fifth and sixth restriction site for nicking endonuclease can be any one described in Sections 3, 5.2.4 and 5.3.2. In certain specific embodiment, the nicking endonuclease that recognizes the fifth and sixth restriction site for nicking endonuclease is Nt. BsmAI; Nt. BtsCI; N. ALwI; N. BstNBI; N. BspD6I; Nb. Mva1269I; Nb. BsrDI; Nt. BtsI; Nt. BsaI; Nt. Bpu10I; Nt. BsmBI; Nb. BbvCI; Nt. BbvCI; or Nt. BspQI.

Additionally, in some embodiments, a plasmid provided in this Section (Section 5.3.5) can comprise a selectable or selection marker for use in the production of the plasmid in bacterial cultures. In one embodiment, the selection marker can be inserted downstream (e.g. 3') of the 3' ITR sequence. In another embodiment, the selection marker can be inserted upstream (e.g., 5') of the 5' IR sequence. A plasmid provided in this Section (Section 5.3.5) can also comprise a selectable or selection marker in between the IRs for use in the production of stable expressing cell line. In one embodiment, the selection marker can be inserted upstream (e.g. 5') of the 3' ITR sequence. In another embodiment, the selection marker can be inserted downstream (e.g. 3') of the 5' ITR sequence. Embodiments of appropriate selection markers include those that confer drug resistance. In certain embodiments, selection markers can be a blasticidin S-resistance gene, kanamycin, geneticin, and the like. In a specific embodiment, the drug selection marker is a chloramphenicol-resistance gene. In some embodiments, the plasmid can further comprise an ORF encoding a selection marker. In certain embodiments, the selection marker is an antibiotics resistant gene. In some specific embodiments, the selection marker is one providing resistance against selection agent selected from the group consisting of: kanamycin, spectinomycin, streptomycin, ampicillin, carbenicillin, bleomycin, erythromycin, polymyxin b, tetracycline, chloramphenicol, blasticidin, g418/geneticin, hygromycin B, puromycin, and zeocin.

In further embodiments, the plasmid of this Section (Section 5.3.5) can comprise one or more copies of the DNA molecules described in the paragraphs between the headings of Sections 5.3 and 5.3.1. In one specific embodiment, the plasmid of this Section (Section 5.3.5) can comprise one copy of the DNA molecules described in the paragraphs between the headings of Sections 5.3 and 5.3.1. In another specific embodiment, the plasmid of this Section (Section 5.3.5) can comprise two copy of the DNA molecules described in the paragraphs between the headings of Sections 5.3 and 5.3.1. In yet another specific embodiment, the plasmid of this Section (Section 5.3.5) can comprise 1, 2, 3, 4, 5, 6, 7, 8, 9, or 10 copies of the DNA molecules described in the paragraphs between the headings of Sections 5.3 and 5.3.1.

In some embodiments, the DNA molecules for the methods and composition provided herein (e.g. as provided in Section 3 and this Section (Section 5.3)) can be linear, non-circular DNA molecules.

In some embodiments, a vector for the methods and composition provided herein comprises any one or more features described in this Section (Section 5.3.5), in various permutations and combinations. In certain embodiments, a plasmid for the methods and composition provided herein comprises any one or more features described in this Section (Section 5.3.5). In certain embodiments, a plasmid for the methods and composition provided herein comprises any one or more features described in this Section (Section 5.3.5), in various permutations and combinations.

The various embodiments described in this Section (Section 5.3.5) with nicking endonucleases and/or restriction sites for nicking endonucleases are additionally provided with nicking endonucleases replaced by programmable nicking enzyme and restriction sites replaced by targeting sites for programmable nicking enzyme. The programmable nicking enzymes and their targeting sites for this paragraph and this Section (Section 5.3.3) have been provided in Section 5.2.4.

5.3.6 DNA Molecules with Less than 4 Rstriction Sites for Nicking Endonucleases and DNA Molecules with Less than 4 Target Sites for Programmable Nicking Enzymes In one additional aspect, provided herein is a double-stranded DNA molecule comprising in 5' to 3' direction of the top strand: i) a first inverted repeat (e.g. as described in Section 5.3.1), wherein a first restriction site for nicking endonuclease and a first restriction site for restriction enzyme are arranged in the opposite ends and in proximity of the first inverted repeat such that nicking and restriction enzyme cleavage result in a top strand 5' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a second restriction site for nicking endonuclease and a second restriction site for restriction enzyme are arranged in the opposite ends and in proximity of the second inverted repeat such that nicking and restriction enzyme cleavage result in a top strand 3' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the first restriction site for nicking endonuclease and the second restriction site for restriction enzyme is more distal to expression cassette than the second restriction site for nicking endonuclease. In certain embodiments, the top strand 5' overhang comprises the first inverted repeat. In certain embodiments, the top strand 3' overhang comprises the second inverted repeat. In certain embodiments, the top strand 5' overhang comprises the first inverted repeat and the top strand 3' overhang comprises the second inverted repeat.

In another aspect, provided herein is a double strand DNA molecule comprising in 5' to 3' direction of the top strand: i) a first inverted repeat (e.g. as described in Section 5.3.1), wherein a first restriction site for nicking endonuclease and a first restriction site for restriction enzyme are arranged in the opposite ends and in proximity of the first inverted repeat such that nicking and restriction enzyme cleavage result in a bottom strand 3' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a second restriction site for nicking endonuclease and a second restriction site for restriction enzyme are arranged in the opposite ends and in proximity of the second inverted repeat such that nicking and restriction enzyme cleavage result in a bottom strand 5' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the first restriction site for nicking endonuclease and the second restriction site for restriction enzyme is more distal to expression cassette than the second restriction site for nicking endonuclease. In certain embodiments, the bottom strand 3' overhang comprises the first inverted repeat. In certain embodiments, the bottom strand 5' overhang comprises the second inverted repeat. In certain embodiments, the bottom strand 3' overhang comprises the first inverted repeat and the bottom strand 5' overhang comprises the second inverted repeat.

In yet another aspect, provided herein is a double-stranded DNA molecule comprising in 5' to 3' direction of the top strand: i) a first inverted repeat (e.g. as described in Section 5.3.1), wherein a first restriction site for nicking endonuclease and a first restriction site for restriction enzyme are arranged in the opposite ends and in proximity of the first inverted repeat such that nicking and restriction enzyme cleavage result in a top strand 5' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a second restriction site for nicking endonuclease and a second restriction site for restriction enzyme are arranged in the opposite ends and in proximity of the second inverted repeat such that nicking and restriction enzyme cleavage result in a bottom strand 5' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the first restriction site for nicking endonuclease and the second restriction site for restriction enzyme is more distal to expression cassette than the second restriction site for nicking endonuclease. In certain embodiments, the top strand 5' overhang comprises the first inverted repeat. In certain embodiments, the bottom strand 5' overhang comprises the second inverted repeat. In certain embodiments, the top strand 5' overhang comprises the first inverted repeat and the bottom strand 5' overhang comprises the second inverted repeat.

In a further aspect, provide herein is a double strand DNA molecule comprising in 5' to 3' direction of the top strand: i) a first inverted repeat (e.g. as described in Section 5.3.1), wherein a first restriction site for nicking endonuclease and a first restriction site for restriction enzyme are arranged in the opposite ends and in proximity of the first inverted repeat such that nicking and restriction enzyme cleavage result in a bottom strand 3' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a second restriction site for nicking endonuclease and a second restriction site for restriction enzyme are arranged in the opposite ends and in proximity of the second inverted repeat such that nicking and restriction enzyme cleavage result in a top strand 3' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the first restriction site for nicking endonuclease and the second restriction site for restriction enzyme is more distal to expression cassette than the second restriction site for nicking endonuclease. In certain embodiments, the bottom strand 3' overhang comprises the first inverted repeat. In certain embodiments, the top strand 3' overhang comprises the second inverted repeat. In certain embodiments, the bottom strand 3' overhang comprises the first inverted repeat and the top strand 3' overhang comprises the second inverted repeat.

Additionally, in one aspect, provided herein is a double-stranded DNA molecule comprising in 5' to 3' direction of the top strand: i) a first inverted repeat (e.g. as described in Section 5.3.1), wherein a first and a second restriction site for nicking endonuclease are arranged on opposite strands in proximity of the first inverted repeat such that nicking results in a top strand 5' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a third restriction site for nicking endonuclease and a first restriction site for restriction enzyme are arranged in the opposite ends and in proximity of the second inverted repeat such that nicking and restriction enzyme cleavage result in a top strand 3' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the third restriction site for nicking endonuclease. In certain embodiments, the top strand 5' overhang comprises the first inverted repeat. In certain embodiments, the top strand 3' overhang comprises the second inverted repeat. In certain embodiments, the top strand 5' overhang comprises the first inverted repeat and the top strand 3' overhang comprises the second inverted repeat.

In another aspect, provided herein is a double strand DNA molecule comprising in 5' to 3' direction of the top strand: i) a first inverted repeat (e.g. as described in Section 5.3.1), wherein a first and a second restriction site for nicking endonuclease are arranged on opposite strands in proximity of the first inverted repeat such that nicking results in a bottom strand 3' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a third restriction site for nicking endonuclease and a first restriction site for restriction enzyme are arranged in the opposite ends and in proximity of the second inverted repeat such that nicking and restriction enzyme cleavage result in a bottom strand 5' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the third restriction site for nicking endonuclease. In certain embodiments, the bottom strand 3' overhang comprises the first inverted repeat. In certain embodiments, the bottom strand 5' overhang comprises the second inverted repeat. In certain embodiments, the bottom strand 3' overhang comprises the first inverted repeat and the bottom strand 5' overhang comprises the second inverted repeat.

In yet another aspect, provided herein is a double-stranded DNA molecule comprising in 5' to 3' direction of the top strand: i) a first inverted repeat (e.g. as described in Section 5.3.1), wherein a first and a second restriction site for nicking endonuclease are arranged on opposite strands in proximity of the first inverted repeat such that nicking results in a top strand 5' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a third restriction site for nicking endonuclease and a first restriction site for restriction enzyme are arranged in the opposite ends and in proximity of the second inverted repeat such that nicking and restriction enzyme cleavage result in a bottom strand 5' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the third restriction site for nicking endonuclease. In certain embodiments, the top strand 5' overhang comprises the first inverted repeat. In certain embodiments, the bottom strand 5' overhang comprises the second inverted repeat. In certain embodiments, the top strand 5' overhang comprises the first inverted repeat and the bottom strand 5' overhang comprises the second inverted repeat.

In a further aspect, provide herein is a double strand DNA molecule comprising in 5' to 3' direction of the top strand: i) a first inverted repeat (e.g. as described in Section 5.3.1), wherein a first and a second restriction site for nicking endonuclease are arranged on opposite strands in proximity of the first inverted repeat such that nicking results in a bottom strand 3' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a third restriction site for nicking endonuclease and a first restriction site for restriction enzyme are arranged in the opposite ends and in proximity of the second inverted repeat such that nicking and restriction enzyme cleavage result in a top strand 3' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the third restriction site for nicking endonuclease. In certain embodiments, the bottom strand 3' overhang comprises the first inverted repeat. In certain embodiments, the top strand 3' overhang comprises the second inverted repeat. In certain embodiments, the bottom strand 3' overhang comprises the first inverted repeat and the top strand 3' overhang comprises the second inverted repeat.

Additionally, in one aspect, provided herein is a double-stranded DNA molecule comprising in 5' to 3' direction of the top strand: i) a first inverted repeat (e.g. as described in Section 5.3.1), wherein a first restriction site for nicking endonuclease and a first restriction site for restriction enzyme are arranged in the opposite ends and in proximity of the first inverted repeat such that nicking and restriction enzyme cleavage result in a top strand 5' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a second and a third restriction site for nicking endonuclease are arranged on opposite strands in proximity of the second inverted repeat such that nicking results in a top strand 3' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the first restriction site for nicking endonuclease. In certain embodiments, the top strand 5' overhang comprises the first inverted repeat. In certain embodiments, the top strand 3' overhang comprises the second inverted repeat. In certain embodiments, the top strand 5' overhang comprises the first inverted repeat and the top strand 3' overhang comprises the second inverted repeat.

In another aspect, provided herein is a double strand DNA molecule comprising in 5' to 3' direction of the top strand: i) a first inverted repeat (e.g. as described in Section 5.3.1), wherein a first restriction site for nicking endonuclease and a first restriction site for restriction enzyme are arranged in the opposite ends and in proximity of the first inverted repeat such that nicking and restriction enzyme cleavage result in a bottom strand 3' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a second and a third restriction site for nicking endonuclease are arranged on opposite strands in proximity of the second inverted repeat such that nicking results in a bottom strand 5' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the first restriction site for nicking endonuclease. In certain embodiments, the bottom strand 3' overhang comprises the first inverted repeat. In certain embodiments, the bottom strand 5' overhang comprises the second inverted repeat. In certain embodiments, the bottom strand 3' overhang comprises the first inverted repeat and the bottom strand 5' overhang comprises the second inverted repeat.

In yet another aspect, provided herein is a double-stranded DNA molecule comprising in 5' to 3' direction of the top strand: i) a first inverted repeat (e.g. as described in Section 5.3.1), wherein a first restriction site for nicking endonuclease and a first restriction site for restriction enzyme are arranged in the opposite ends and in proximity of the first inverted repeat such that nicking and restriction enzyme cleavage result in a top strand 5' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a second and a third restriction site for nicking endonuclease are arranged on opposite strands in proximity of the second inverted repeat such that nicking results in a bottom strand 5' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the first restriction site for nicking endonuclease. In certain embodiments, the top strand 5' overhang comprises the first inverted repeat. In certain embodiments, the bottom strand 5' overhang comprises the second inverted repeat. In certain embodiments, the top strand 5' overhang comprises the first inverted repeat and the bottom strand 5' overhang comprises the second inverted repeat.

In a further aspect, provide herein is a double strand DNA molecule comprising in 5' to 3' direction of the top strand: i) a first inverted repeat (e.g. as described in Section 5.3.1), wherein a first restriction site for nicking endonuclease and a first restriction site for restriction enzyme are arranged in the opposite ends and in proximity of the first inverted repeat such that nicking and restriction enzyme cleavage result in a bottom strand 3' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a second and a third restriction site for nicking endonuclease are arranged on opposite strands in proximity of the second inverted repeat such that nicking results in a top strand 3' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the first restriction site for nicking endonuclease. In certain embodiments, the bottom strand 3' overhang comprises the first inverted repeat. In certain embodiments, the top strand 3' overhang comprises the second inverted repeat. In certain embodiments, the bottom strand 3' overhang comprises the first inverted repeat and the top strand 3' overhang comprises the second inverted repeat.

In one additional aspect, provided herein is a double-stranded DNA molecule comprising in 5' to 3' direction of the top strand: i) a first inverted repeat (e.g. as described in Section 5.3.1), wherein a first target site for the guide nucleic acid for programmable nicking enzyme and a first restriction site for restriction enzyme are arranged in the opposite ends and in proximity of the first inverted repeat such that nicking by the programmable nicking enzyme and restriction enzyme cleavage result in a top strand 5' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a second target site for the guide nucleic acid for programmable nicking enzyme and a second restriction site for restriction enzyme are arranged in the opposite ends and in proximity of the second inverted repeat such that nicking by the programmable nicking enzyme and restriction enzyme cleavage result in a top strand 3' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the first target site for the guide nucleic acid for programmable nicking enzyme and the second restriction site for restriction enzyme is more distal to expression cassette than the second target site for the guide nucleic acid for programmable nicking enzyme. In certain embodiments, the top strand 5' overhang comprises the first inverted repeat. In certain embodiments, the top strand 3' overhang comprises the second inverted repeat. In certain embodiments, the top strand 5' overhang comprises the first inverted repeat and the top strand 3' overhang comprises the second inverted repeat.

In another aspect, provided herein is a double strand DNA molecule comprising in 5' to 3' direction of the top strand: i) a first inverted repeat (e.g. as described in Section 5.3.1), wherein a first target site for the guide nucleic acid for programmable nicking enzyme and a first restriction site for restriction enzyme are arranged in the opposite ends and in proximity of the first inverted repeat such that nicking by programmable nicking enzyme and restriction enzyme cleavage result in a bottom strand 3' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a second target site for the guide nucleic acid for programmable nicking enzyme and a second restriction site for restriction enzyme are arranged in the opposite ends and in proximity of the second inverted repeat such that nicking by programmable nicking enzyme and restriction enzyme cleavage result in a bottom strand 5' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the first target site for the guide nucleic acid for programmable nicking enzyme and the second restriction site for restriction enzyme is more distal to expression cassette than the second target site for the guide nucleic acid for programmable nicking enzyme. In certain embodiments, the bottom strand 3' overhang comprises the first inverted repeat. In certain embodiments, the bottom strand 5' overhang comprises the second inverted repeat. In certain embodiments, the bottom strand 3' overhang comprises the first inverted repeat and the bottom strand 5' overhang comprises the second inverted repeat.

In yet another aspect, provided herein is a double-stranded DNA molecule comprising in 5' to 3' direction of the top strand: i) a first inverted repeat (e.g. as described in Section 5.3.1), wherein a first target site for the guide nucleic acid for programmable nicking enzyme and a first restriction site for restriction enzyme are arranged in the opposite ends and in proximity of the first inverted repeat such that nicking by programmable nicking enzyme and restriction enzyme cleavage result in a top strand 5' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a second target site for the guide nucleic acid for programmable nicking enzyme and a second restriction site for restriction enzyme are arranged in the opposite ends and in proximity of the second inverted repeat such that nicking by programmable nicking enzyme and restriction enzyme cleavage result in a bottom strand 5' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the first target site for the guide nucleic acid for programmable nicking enzyme and the second restriction site for restriction enzyme is more distal to expression cassette than the second target site for the guide nucleic acid for programmable nicking enzyme. In certain embodiments, the top strand 5' overhang comprises the first inverted repeat. In certain embodiments, the bottom strand 5' overhang comprises the second inverted repeat. In certain embodiments, the top strand 5' overhang comprises the first inverted repeat and the bottom strand 5' overhang comprises the second inverted repeat.

In a further aspect, provide herein is a double strand DNA molecule comprising in 5' to 3' direction of the top strand: i) a first inverted repeat (e.g. as described in Section 5.3.1), wherein a first target site for the guide nucleic acid for programmable nicking enzyme and a first restriction site for restriction enzyme are arranged in the opposite ends and in proximity of the first inverted repeat such that nicking by programmable nicking enzyme and restriction enzyme cleavage result in a bottom strand 3' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a second target site for the guide nucleic acid for programmable nicking enzyme and a second restriction site for restriction enzyme are arranged in the opposite ends and in proximity of the second inverted repeat such that nicking by programmable nicking enzyme and restriction enzyme cleavage result in a top strand 3' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the first target site for the guide nucleic acid for programmable nicking enzyme and the second restriction site for restriction enzyme is more distal to expression cassette than the second target site for the guide nucleic acid for programmable nicking enzyme. In certain embodiments, the bottom strand 3' overhang comprises the first inverted repeat. In certain embodiments, the top strand 3' overhang comprises the second inverted repeat. In certain embodiments, the bottom strand 3' overhang comprises the first inverted repeat and the top strand 3' overhang comprises the second inverted repeat.

Additionally, in one aspect, provided herein is a double-stranded DNA molecule comprising in 5' to 3' direction of the top strand: i) a first inverted repeat (e.g. as described in Section 5.3.1), wherein a first and a second target site for the guide nucleic acids for programmable nicking enzyme are arranged on opposite strands in proximity of the first inverted repeat such that nicking by programmable nicking enzyme results in a top strand 5' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a third target site for the guide nucleic acid for programmable nicking enzyme and a first restriction site for restriction enzyme are arranged in the opposite ends and in proximity of the second inverted repeat such that nicking by programmable nicking enzyme and restriction enzyme cleavage result in a top strand 3' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the third target site for the guide nucleic acid for programmable nicking enzyme. In certain embodiments, the top strand 5' overhang comprises the first inverted repeat. In certain embodiments, the top strand 3' overhang comprises the second inverted repeat. In certain embodiments, the top 5' overhang comprises the first inverted repeat and the top strand 3' overhang comprises the second inverted repeat.

In another aspect, provided herein is a double strand DNA molecule comprising in 5' to 3' direction of the top strand: i) a first inverted repeat (e.g. as described in Section 5.3.1), wherein a first and a second target site for the guide nucleic acids for programmable nicking enzyme are arranged on opposite strands in proximity of the first inverted repeat such that nicking by programmable nicking enzyme results in a bottom strand 3' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a third target site for the guide nucleic acid for programmable nicking enzyme and a first restriction site for restriction enzyme are arranged in the opposite ends and in proximity of the second inverted repeat such that nicking by programmable nicking enzyme and restriction enzyme cleavage result in a bottom strand 5' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the third target site for the guide nucleic acid for programmable nicking enzyme. In certain embodiments, the bottom strand 3' overhang comprises the first inverted repeat. In certain embodiments, the bottom strand 5' overhang comprises the second inverted repeat. In certain embodiments, the bottom strand 3' overhang comprises the first inverted repeat and the bottom strand 5' overhang comprises the second inverted repeat.

In yet another aspect, provided herein is a double-stranded DNA molecule comprising in 5' to 3' direction of the top strand: i) a first inverted repeat (e.g. as described in Section 5.3.1), wherein a first and a second target site for the guide nucleic acids for programmable nicking enzyme are arranged on opposite strands in proximity of the first inverted repeat such that nicking by programmable nicking enzyme results in a top strand 5' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a third target site for the guide nucleic acid for programmable nicking enzyme and a first restriction site for restriction enzyme are arranged in the opposite ends and in proximity of the second inverted repeat such that nicking by programmable nicking enzyme and restriction enzyme cleavage result in a bottom strand 5' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the third target site for the guide nucleic acid for programmable nicking enzyme. In certain embodiments, the top strand 5' overhang comprises the first inverted repeat. In certain embodiments, the bottom strand 5' overhang comprises the second inverted repeat. In certain embodiments, the top strand 5' overhang comprises the first inverted repeat and the bottom strand 5' overhang comprises the second inverted repeat.

In a further aspect, provide herein is a double strand DNA molecule comprising in 5' to 3' direction of the top strand: i) a first inverted repeat (e.g. as described in Section 5.3.1), wherein a first and a second target site for the guide nucleic acids for programmable nicking enzyme are arranged on opposite strands in proximity of the first inverted repeat such that nicking by programmable nicking enzyme results in a bottom strand 3' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a third target site for the guide nucleic acid for programmable nicking enzyme and a first restriction site for restriction enzyme are arranged in the opposite ends and in proximity of the second inverted repeat such that nicking by programmable nicking enzyme and restriction enzyme cleavage result in a top strand 3' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the third target site for the guide nucleic acid for programmable nicking enzyme. In certain embodiments, the bottom strand 3' overhang comprises the first inverted repeat. In certain embodiments, the top strand 3' overhang comprises the second inverted repeat. In certain embodiments, the bottom strand 3' overhang comprises the first inverted repeat and the top strand 3' overhang comprises the second inverted repeat.

Additionally, in one aspect, provided herein is a double-stranded DNA molecule comprising in 5' to 3' direction of the top strand: i) a first inverted repeat (e.g. as described in Section 5.3.1), wherein a first target site for the guide nucleic acid for programmable nicking enzyme and a first restriction site for restriction enzyme are arranged in the opposite ends and in proximity of the first inverted repeat such that nicking by programmable nicking enzyme and restriction enzyme cleavage result in a top strand 5' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a second and a third target site for the guide nucleic acids for programmable nicking enzyme are arranged on opposite strands in proximity of the second inverted repeat such that nicking by programmable nicking enzyme results in a top strand 3' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the first target site for the guide nucleic acid for programmable nicking enzyme. In certain embodiments, the top strand 5' overhang comprises the first inverted repeat. In certain embodiments, the top strand 3' overhang comprises the second inverted repeat. In certain embodiments, the top strand 5' overhang comprises the first inverted repeat and the top strand 3' overhang comprises the second inverted repeat.

In another aspect, provided herein is a double strand DNA molecule comprising in 5' to 3' direction of the top strand: i) a first inverted repeat (e.g. as described in Section 5.3.1), wherein a first target site for the guide nucleic acid for programmable nicking enzyme and a first restriction site for restriction enzyme are arranged in the opposite ends and in proximity of the first inverted repeat such that nicking by programmable nicking enzyme and restriction enzyme cleavage result in a bottom strand 3' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a second and a third target site for the guide nucleic acids for programmable nicking enzyme are arranged on opposite strands in proximity of the second inverted repeat such that nicking by programmable nicking enzyme results in a bottom strand 5' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the first target site for the guide nucleic acid for programmable nicking enzyme. In certain embodiments, the bottom strand 3' overhang comprises the first inverted repeat. In certain embodiments, the bottom strand 5' overhang comprises the second inverted repeat. In certain embodiments, the bottom strand 3' overhang comprises the first inverted repeat and the bottom strand 5' overhang comprises the second inverted repeat.

In yet another aspect, provided herein is a double-stranded DNA molecule comprising in 5' to 3' direction of the top strand: i) a first inverted repeat (e.g. as described in Section 5.3.1), wherein a first target site for the guide nucleic acid for programmable nicking enzyme and a first restriction site for restriction enzyme are arranged in the opposite ends and in proximity of the first inverted repeat such that nicking by programmable nicking enzyme and restriction enzyme cleavage result in a top strand 5' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a second and a third target site for the guide nucleic acids for programmable nicking enzyme are arranged on opposite strands in proximity of the second inverted repeat such that nicking by programmable nicking enzyme results in a bottom strand 5' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the first target site for the guide nucleic acid for programmable nicking enzyme. In certain embodiments, the top strand 5' overhang comprises the first inverted repeat. In certain embodiments, the bottom strand 5' overhang comprises the second inverted repeat. In certain embodiments, the top strand 5' overhang comprises the first inverted repeat and the bottom strand 5' overhang comprises the second inverted repeat.

In a further aspect, provide herein is a double strand DNA molecule comprising in 5' to 3' direction of the top strand: i) a first inverted repeat (e.g. as described in Section 5.3.1), wherein a first target site for the guide nucleic acid for programmable nicking enzyme and a first restriction site for restriction enzyme are arranged in the opposite ends and in proximity of the first inverted repeat such that nicking by programmable nicking enzyme and restriction enzyme cleavage result in a bottom strand 3' overhang comprising the first inverted repeat or a fragment thereof (e.g., at least 50%, 60%, 70%, 75%, 80%, 85%, 90%, 95%, or 99% of the first inverted repeat) upon separation of the top from the bottom strand of the first inverted repeat (e.g. as described in Sections 5.2.3, 5.2.4 and 5.3.2); ii) an expression cassette (e.g. as described in Section 5.3.3); and iii) a second inverted repeat (e.g. as described in Section 5.3.1), wherein a second and a third target site for the guide nucleic acids for programmable nicking enzyme are arranged on opposite strands in proximity of the second inverted repeat such that nicking by programmable nicking enzyme results in a top strand 3' overhang comprising the second inverted repeat or a fragment thereof (e.g., at least 50%, 60%, 70%, 75%, 80%, 85%, 90%, 95%, or 99% of the second inverted repeat) upon separation of the top from the bottom strand of the second inverted repeat (e.g. as described in Sections 5.2.3, 5.2.4 and 5.3.2), wherein the first restriction site for restriction enzyme is more distal to expression cassette than the first target site for the guide nucleic acid for programmable nicking enzyme. In certain embodiments, the bottom strand 3' overhang comprises the first inverted repeat. In certain embodiments, the top strand 3' overhang comprises the second inverted repeat. In certain embodiments, the bottom strand 3' overhang comprises the first inverted repeat and the top strand 3' overhang comprises the second inverted repeat.

The DNA molecules provided in this Section (Section 5.3.6) comprise various features or have various embodiments as described in this Section (Section 5.3.6), which features and embodiments are further described in the various subsections below: the embodiments for the inverted repeats, including the first inverted repeat and/or the second inverted repeat, are described in Section 5.3.1, the embodiments for the restriction enzymes, nicking endonucleases, and their respective restriction sites are described in Section 5.3.2, the embodiments for the programmable nicking enzymes and their target sites are described in Section 5.2.4, the embodiments for the expression cassette are described in Section 5.3.3, and the embodiments for plasmids and vectors are described in Section 5.3.5. As such, the disclosure provides DNA molecules comprising any permutations and combinations of the various embodiments of DNA molecules and embodiments of features of the DNA molecules described herein.

The various embodiments described in this Section (Section 5.3.6) with nicking endonucleases are interchangeable with programmable nicking enzyme and restriction sites for nicking endonucleases are interchangeable with the target sites for programmable nicking enzyme. As such, additional embodiments of any combination resulted by replacing one or more elements of nicking endonucleases with programmable nicking enzyme and/or replacing one or more elements of restriction sites for nicking endonucleases with the target sites for programmable nicking enzyme are provided herein in this Section (Section 5.3.6). The programmable nicking enzymes and their targeting sites for this paragraph and this Section (Section 5.3.3) have been provided in Section 5.2.4.

5.3.7 Isolated DNA Molecules

One of the advantages of the methods and DNA molecules provided herein is the purity of the isolated DNA molecules produced in the methods and provided herein, because the DNA molecules provided herein are resistant to exonuclease or other DNA digestion enzymes and thus can be treated, as described in Section 5.2.6, with such exonuclease or DNA digestion enzymes to remove the DNA contaminants that are susceptible to such treatment. As already described in the paragraphs between the heading of Section 5.3 and the heading of Section 5.3.1, the DNA molecules provided herein including in Sections 3, 5.2, 5.3, 5.4, and 6 can be isolated DNA molecules of various purity. Furthermore, the disclosure provides and a person of ordinary skill in the art would understand that the DNA molecules provided herein including in Sections 3, 5.2, 5.3, 5.4, and 6 can be free of certain general DNA contaminants, free of certain specific DNA contaminants, or both free of certain general DNA contaminants and free of certain specific DNA contaminants.

Accordingly, in one embodiment, the isolated DNA molecules are free of fragments of the DNA molecules. In another embodiment, the isolated DNA molecules are free of nucleic acid contaminants that are not fragments of the DNA molecules. In a further embodiment, the isolated DNA molecules are free of baculoviral DNA. In one embodiment, the isolated DNA molecules are free of fragments of the DNA molecules and free of nucleic acid contaminants that are not fragments of the DNA molecules. In another embodiment, the isolated DNA molecules are free of fragments of the DNA molecules and free of baculoviral DNA. In a further embodiment, the isolated DNA molecules are free of baculoviral DNA and free of nucleic acid contaminants that are not fragments of the DNA molecules. In yet another embodiment, the isolated DNA molecules are free of fragments of the DNA molecules, free of baculoviral DNA, and free of nucleic acid contaminants that are not fragments of the DNA molecules.

Specifically, in one embodiment, the fragments of the DNA molecules are no more than 1%, no more than 2%, no more than 3%, no more than 4%, no more than 5%, no more than 6%, no more than 7%, no more than 8%, no more than 9%, no more than 10%, no more than 11%, no more than 12%, no more than 13%, no more than 14%, no more than 15%, no more than 16%, no more than 17%, no more than 18%, no more than 19%, no more than 20%, no more than 21%, no more than 22%, no more than 23%, no more than 24%, no more than 25%, no more than 26%, no more than 27%, no more than 28%, no more than 29%, no more than 30%, no more than 31%, no more than 32%, no more than 33%, no more than 34%, no more than 35%, no more than 36%, no more than 37%, no more than 38%, no more than 39%, no more than 40%, no more than 41%, no more than 42%, no more than 43%, no more than 44%, no more than 45%, no more than 46%, no more than 47%, no more than 48%, no more than 49%, or no more than 50% of the isolated DNA molecules. In another embodiment, the fragments of the DNA molecules are less than 1%, less than 2%, less than 3%, less than 4%, less than 5%, less than 6%, less than 7%, less than 8%, less than 9%, less than 10%, less than 11%, less than 12%, less than 13%, less than 14%, less than 15%, less than 16%, less than 17%, less than 18%, less than 19%, less than 20%, less than 21%, less than 22%, less than 23%, less than 24%, less than 25%, less than 26%, less than 27%, less than 28%, less than 29%, less than 30%, less than 31%, less than 32%, less than 33%, less than 34%, less than 35%, less than 36%, less than 37%, less than 38%, less than 39%, less than 40%, less than 41%, less than 42%, less than 43%, less than 44%, less than 45%, less than 46%, less than 47%, less than 48%, less than 49%, or less than 50% of the isolated DNA molecules. In yet another embodiment, the fragments of the DNA molecules are about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50% of the isolated DNA molecules.

Additionally, in one embodiment, the nucleic acid contaminants that are not fragments of the DNA molecules are no more than 1%, no more than 2%, no more than 3%, no more than 4%, no more than 5%, no more than 6%, no more than 7%, no more than 8%, no more than 9%, no more than 10%, no more than 11%, no more than 12%, no more than 13%, no more than 14%, no more than 15%, no more than 16%, no more than 17%, no more than 18%, no more than 19%, no more than 20%, no more than 21%, no more than 22%, no more than 23%, no more than 24%, no more than 25%, no more than 26%, no more than 27%, no more than 28%, no more than 29%, no more than 30%, no more than 31%, no more than 32%, no more than 33%, no more than 34%, no more than 35%, no more than 36%, no more than 37%, no more than 38%, no more than 39%, no more than 40%, no more than 41%, no more than 42%, no more than 43%, no more than 44%, no more than 45%, no more than 46%, no more than 47%, no more than 48%, no more than 49%, or no more than 50% of the isolated DNA molecules. In another embodiment, the nucleic acid contaminants that are not fragments of the DNA molecules are less than 1%, less than 2%, less than 3%, less than 4%, less than 5%, less than 6%, less than 7%, less than 8%, less than 9%, less than 10%, less than 11%, less than 12%, less than 13%, less than 14%, less than 15%, less than 16%, less than 17%, less than 18%, less than 19%, less than 20%, less than 21%, less than 22%, less than 23%, less than 24%, less than 25%, less than 26%, less than 27%, less than 28%, less than 29%, less than 30%, less than 31%, less than 32%, less than 33%, less than 34%, less than 35%, less than 36%, less than 37%, less than 38%, less than 39%, less than 40%, less than 41%, less than 42%, less than 43%, less than 44%, less than 45%, less than 46%, less than 47%, less than 48%, less than 49%, or less than 50% of the isolated DNA molecules. In yet another embodiment, the nucleic acid contaminants that are not fragments of the DNA molecules are about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50% of the isolated DNA molecules.

In addition, in one embodiment, the baculoviral DNA are no more than 1%, no more than 2%, no more than 3%, no more than 4%, no more than 5%, no more than 6%, no more than 7%, no more than 8%, no more than 9%, no more than 10%, no more than 11%, no more than 12%, no more than 13%, no more than 14%, no more than 15%, no more than 16%, no more than 17%, no more than 18%, no more than 19%, no more than 20%, no more than 21%, no more than 22%, no more than 23%, no more than 24%, no more than 25%, no more than 26%, no more than 27%, no more than 28%, no more than 29%, no more than 30%, no more than 31%, no more than 32%, no more than 33%, no more than 34%, no more than 35%, no more than 36%, no more than 37%, no more than 38%, no more than 39%, no more than 40%, no more than 41%, no more than 42%, no more than 43%, no more than 44%, no more than 45%, no more than 46%, no more than 47%, no more than 48%, no more than 49%, or no more than 50% of the isolated DNA molecules. In another embodiment, the baculoviral DNA are less than 1%, less than 2%, less than 3%, less than 4%, less than 5%, less than 6%, less than 7%, less than 8%, less than 9%, less than 10%, less than 11%, less than 12%, less than 13%, less than 14%, less than 15%, less than 16%, less than 17%, less than 18%, less than 19%, less than 20%, less than 21%, less than 22%, less than 23%, less than 24%, less than 25%, less than 26%, less than 27%, less than 28%, less than 29%, less than 30%, less than 31%, less than 32%, less than 33%, less than 34%, less than 35%, less than 36%, less than 37%, less than 38%, less than 39%, less than 40%, less than 41%, less than 42%, less than 43%, less than 44%, less than 45%, less than 46%, less than 47%, less than 48%, less than 49%, or less than 50% of the isolated DNA molecules. In yet another embodiment, the baculoviral DNA are about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50% of the isolated DNA molecules.

The various embodiments the isolated DNA molecules provided herein of various purities with respect to the specific contaminants as described in the preceding paragraphs (e.g. fragments of the DNA molecules, nucleic acid contaminants that are not fragments of the DNA molecules, and/or baculoviral DNA) of this Section 5.3.7 are not mutually exclusive and thus can be combined in various combinations by selecting and combining any embodiments provided in the list of the preceding paragraphs of this Section 5.3.7. Furthermore, the isolated DNA molecules provided in this Section 5.3.7 and those in the paragraphs between the heading of Section 5.3 and the heading of Section 5.3.1 can also be combined in various combinations by selecting and combining any suitable embodiments provided in the list described therein.

5.3.8 DNA Molecules Packaged in Viral Particles

The DNA molecules provided herein, including those in Sections 3, 5.2, 5.3, 5.4, and 6, can be packaged in viral particles. Such viral particle can be packaged by transfecting the DNA molecules into a suitable host cell (e.g. HEK 293) and co-transfecting the host cells with other molecules necessary for viral packaging (e.g. viral capsid (Cap) protein), as described in Grieger J C, et al., Nat Protoc 2006; 1:1412-1428; and Liujiang Song, Hum Gene Ther, 2020 October; 31(19-20):1054-1067, both of which are incorporated herein in their entireties by reference. One of the advantages of the methods and DNA molecules provided herein is the purity of the DNA molecules provided herein when produced and packaged in viral particles, because the isolated DNA molecules of various purity as provided in Section 5.3.7 can be transfected into host cells and/or packaged in viral particles, thereby providing DNA molecules having various purity in packaged viral particles. Accordingly, the disclosure provides and a person of ordinary skill in the art would understand that the DNA molecules provided herein including in Sections 3, 5.2, 5.3, 5.4, and 6 can be free of certain general DNA contaminants, free of certain specific DNA contaminants, or both free of certain general DNA contaminants and free of certain specific DNA contaminants, when such DNA molecules are packaged in viral particles.

Accordingly, in one embodiment, the DNA molecules packaged in viral particles are free of fragments of the DNA molecules. In another embodiment, the DNA molecules packaged in viral particles are free of nucleic acid contaminants that are not fragments of the DNA molecules. In a further embodiment, the DNA molecules packaged in viral particles are free of baculoviral DNA. In one embodiment, the DNA molecules packaged in viral particles are free of fragments of the DNA molecules and free of nucleic acid contaminants that are not fragments of the DNA molecules. In another embodiment, the DNA molecules packaged in viral particles are free of fragments of the DNA molecules and free of baculoviral DNA. In a further embodiment, the DNA molecules packaged in viral particles are free of baculoviral DNA and free of nucleic acid contaminants that are not fragments of the DNA molecules. In yet another embodiment, the DNA molecules packaged in viral particles are free of fragments of the DNA molecules, free of baculoviral DNA, and free of nucleic acid contaminants that are not fragments of the DNA molecules.

Specifically, in one embodiment, the fragments of the DNA molecules are no more than 1%, no more than 2%, no more than 3%, no more than 4%, no more than 5%, no more than 6%, no more than 7%, no more than 8%, no more than 9%, no more than 10%, no more than 11%, no more than 12%, no more than 13%, no more than 14%, no more than 15%, no more than 16%, no more than 17%, no more than 18%, no more than 19%, no more than 20%, no more than 21%, no more than 22%, no more than 23%, no more than 24%, no more than 25%, no more than 26%, no more than 27%, no more than 28%, no more than 29%, no more than 30%, no more than 31%, no more than 32%, no more than 33%, no more than 34%, no more than 35%, no more than 36%, no more than 37%, no more than 38%, no more than 39%, no more than 40%, no more than 41%, no more than 42%, no more than 43%, no more than 44%, no more than 45%, no more than 46%, no more than 47%, no more than 48%, no more than 49%, or no more than 50% of the DNA molecules packaged in viral particles. In another embodiment, the fragments of the DNA molecules are less than 1%, less than 2%, less than 3%, less than 4%, less than 5%, less than 6%, less than 7%, less than 8%, less than 9%, less than 10%, less than 11%, less than 12%, less than 13%, less than 14%, less than 15%, less than 16%, less than 17%, less than 18%, less than 19%, less than 20%, less than 21%, less than 22%, less than 23%, less than 24%, less than 25%, less than 26%, less than 27%, less than 28%, less than 29%, less than 30%, less than 31%, less than 32%, less than 33%, less than 34%, less than 35%, less than 36%, less than 37%, less than 38%, less than 39%, less than 40%, less than 41%, less than 42%, less than 43%, less than 44%, less than 45%, less than 46%, less than 47%, less than 48%, less than 49%, or less than 50% of the DNA molecules packaged in viral particles. In yet another embodiment, the fragments of the DNA molecules are about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50% of the DNA molecules packaged in viral particles.

Additionally, in one embodiment, the nucleic acid contaminants that are not fragments of the DNA molecules are no more than 1%, no more than 2%, no more than 3%, no more than 4%, no more than 5%, no more than 6%, no more than 7%, no more than 8%, no more than 9%, no more than 10%, no more than 11%, no more than 12%, no more than 13%, no more than 14%, no more than 15%, no more than 16%, no more than 17%, no more than 18%, no more than 19%, no more than 20%, no more than 21%, no more than 22%, no more than 23%, no more than 24%, no more than 25%, no more than 26%, no more than 27%, no more than 28%, no more than 29%, no more than 30%, no more than 31%, no more than 32%, no more than 33%, no more than 34%, no more than 35%, no more than 36%, no more than 37%, no more than 38%, no more than 39%, no more than 40%, no more than 41%, no more than 42%, no more than 43%, no more than 44%, no more than 45%, no more than 46%, no more than 47%, no more than 48%, no more than 49%, or no more than 50% of the DNA molecules packaged in viral particles. In another embodiment, the nucleic acid contaminants that are not fragments of the DNA molecules are less than 1%, less than 2%, less than 3%, less than 4%, less than 5%, less than 6%, less than 7%, less than 8%, less than 9%, less than 10%, less than 11%, less than 12%, less than 13%, less than 14%, less than 15%, less than 16%, less than 17%, less than 18%, less than 19%, less than 20%, less than 21%, less than 22%, less than 23%, less than 24%, less than 25%, less than 26%, less than 27%, less than 28%, less than 29%, less than 30%, less than 31%, less than 32%, less than 33%, less than 34%, less than 35%, less than 36%, less than 37%, less than 38%, less than 39%, less than 40%, less than 41%, less than 42%, less than 43%, less than 44%, less than 45%, less than 46%, less than 47%, less than 48%, less than 49%, or less than 50% of the DNA molecules packaged in viral particles. In yet another embodiment, the nucleic acid contaminants that are not fragments of the DNA molecules are about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50% of the DNA molecules packaged in viral particles.

In addition, in one embodiment, the baculoviral DNA are no more than 1%, no more than 2%, no more than 3%, no more than 4%, no more than 5%, no more than 6%, no more than 7%, no more than 8%, no more than 9%, no more than 10%, no more than 11%, no more than 12%, no more than 13%, no more than 14%, no more than 15%, no more than 16%, no more than 17%, no more than 18%, no more than 19%, no more than 20%, no more than 21%, no more than 22%, no more than 23%, no more than 24%, no more than 25%, no more than 26%, no more than 27%, no more than 28%, no more than 29%, no more than 30%, no more than 31%, no more than 32%, no more than 33%, no more than 34%, no more than 35%, no more than 36%, no more than 37%, no more than 38%, no more than 39%, no more than 40%, no more than 41%, no more than 42%, no more than 43%, no more than 44%, no more than 45%, no more than 46%, no more than 47%, no more than 48%, no more than 49%, or no more than 50% of the DNA molecules packaged in viral particles. In another embodiment, the baculoviral DNA are less than 1%, less than 2%, less than 3%, less than 4%, less than 5%, less than 6%, less than 7%, less than 8%, less than 9%, less than 10%, less than 11%, less than 12%, less than 13%, less than 14%, less than 15%, less than 16%, less than 17%, less than 18%, less than 19%, less than 20%, less than 21%, less than 22%, less than 23%, less than 24%, less than 25%, less than 26%, less than 27%, less than 28%, less than 29%, less than 30%, less than 31%, less than 32%, less than 33%, less than 34%, less than 35%, less than 36%, less than 37%, less than 38%, less than 39%, less than 40%, less than 41%, less than 42%, less than 43%, less than 44%, less than 45%, less than 46%, less than 47%, less than 48%, less than 49%, or less than 50% of the DNA molecules packaged in viral particles. In yet another embodiment, the baculoviral DNA are about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50% of the DNA molecules packaged in viral particles.

The disclosure provides that the various contaminants described in this Section 5.3.8 can be detected and determined by various methods known and practiced in the field, for example, by Next-generation sequencing (NGS) or by PCR.

The various embodiments the DNA molecules packaged in viral particles provided herein of various purities with respect to the specific contaminants as described in the preceding paragraphs (e.g. fragments of the DNA molecules, nucleic acid contaminants that are not fragments of the DNA molecules, and/or baculoviral DNA) of this Section 5.3.8 are not mutually exclusive and thus can be combined in various combinations by selecting and combining any embodiments provided in the list of the preceding paragraphs of this Section 5.3.8. Furthermore, the DNA molecules packaged in viral particles provided in this Section 5.3.8 and those in the paragraphs between the heading of Section 5.3 and the heading of Section 5.3.1 can also be combined in various combinations by selecting and combining any suitable embodiments provided in the list described therein.

5.4 Hairpin-Ended DNA Molecules

The disclosure provides that the hairpin-ended DNA molecules of this Section (Section 5.4) can be produced by performing the method steps described in Section 5.2 (including Sections 5.2.3, 5.2.4, and 5.2.5) on DNA molecules provided in Section 5.3. As such, the hairpin-ended DNA molecules of this Section (Section 5.4) can (1) comprise the various features of the DNA molecules provided in Sections 3 and 5.3, including IRs or ITRs that can form hairpins as described in Section 5.3.1 and this Section (Section 5.4), specific sequences, origins, and identities of IRs or ITRs as described in Section 5.3.1 and this Section (Section 5.4), expression cassette as described in 5.3.3, restriction sites for nicking endonucleases or restriction enzymes as described in Sections 5.3.2, 5.2.4, and 5.3.6, and the targeting sites for programmable nicking enzymes as described in Section 5.2.4, and/or (2) lacks the RABS and/or TRS sequences as described in Section 5.3.4. Therefore, the disclosure provides that the hairpin-ended DNA molecules of this Section (Section 5.4) can (1) comprise any combination of embodiments of IRs or ITRs that can form hairpins as described in Sections 5.3.1 and this Section (Section 5.4), expression cassette as described in 5.3.3, restriction sites for nicking endonucleases or restriction enzymes as described in Sections 5.3.2, 5.2.4, and 5.3.6, the targeting sites for programmable nicking enzymes as described in Section 5.2.4, and additional features for the vectors provided in this Section (Section 5.4), and/or (2) lacks the RABS and/or TRS sequences as described in Section 5.3.4.

As is clear from the descriptions, the ITRs or the hairpinned ITRs in the hairpin-ended DNA molecules provided in this Section (Section 5.4) can be formed from the ITRs or IRs provided above in Sections 3 and 5.3.1, for example upon performing the method steps described in Sections 3, 5.2.3, 5.2.4, and 5.2.5. Accordingly, in some embodiments, the two ITRs or the two hairpinned ITRs in the hairpin-ended DNA molecules provided in this Section (Section 5.4) can comprise any embodiments of the IRs or ITRs provided in Sections 3 and 5.3.1 and additional embodiments provided in this Section (Section 5.4), in any combination.

In one aspect, provided herein is a double strand DNA molecule comprising in 5' to 3' direction of the top strand:

a.) a first hairpinned inverted repeat (e.g. as described in Section 5.3.1 and this Section (Section 5.4)); b.) a nick of the bottom strand (e.g. as described in Sections 5.2.4 and 5.3.2, and this Section (Section 5.4)); c.) an expression cassette (e.g. as described 5.3.3 and this Section (Section 5.4)); d.) a nick of the bottom strand (e.g. as described in Sections 5.2.4 and 5.3.2, and this Section (Section 5.4)); and e.) a second hairpinned inverted repeat (e.g. as described in Section 5.3.1 and this Section (Section 5.4)).

In another aspect, provided herein is a double strand DNA molecule comprising in 5' to 3' direction of the top strand: a.) a first hairpinned inverted repeat (e.g. as described in Section 5.3.1 and this Section (Section 5.4)); b.) a nick of the top strand (e.g. as described in Sections 5.2.4 and 5.3.2, and this Section (Section 5.4)); c.) an expression cassette (e.g. as described 5.3.3 and this Section (Section 5.4)); d.) a nick of the top strand (e.g. as described in Sections 5.2.4 and 5.3.2, and this Section (Section 5.4)); and e.) a second hairpinned inverted repeat (e.g. as described in Section 5.3.1 and this Section (Section 5.4)).

In yet another aspect, provided herein is a double strand DNA molecule comprising in 5' to 3' direction of the top strand: a.) a first hairpinned inverted repeat (e.g. as described in Section 5.3.1 and this Section (Section 5.4)); b.) a nick of the bottom strand (e.g. as described in Sections 5.2.4 and 5.3.2, and this Section (Section 5.4)); c.) an expression cassette (e.g. as described 5.3.3 and this Section (Section 5.4)); d.) a nick of the top strand (e.g. as described in Sections 5.2.4 and 5.3.2, and this Section (Section 5.4)); and e.) a second hairpinned inverted repeat (e.g. as described in Section 5.3.1 and this Section (Section 5.4)).

In a further aspect, provided herein is a double strand DNA molecule comprising in 5' to 3' direction of the top strand: a.) a first hairpinned inverted repeat (e.g. as described in Section 5.3.1 and this Section (Section 5.4)); b.) a nick of the top strand (e.g. as described in Sections 5.2.4 and 5.3.2, and this Section (Section 5.4)); c.) an expression cassette (e.g. as described 5.3.3 and this Section (Section 5.4)); d.) a nick of the bottom strand (e.g. as described in Sections 5.2.4 and 5.3.2, and this Section (Section 5.4)); and e.) a second hairpinned inverted repeat (e.g. as described in Section 5.3.1 and this Section (Section 5.4)).

The secondary structure is formed based on conformations (e.g. domains) that include base pair stacking, stems, hairpins, bulges, internal loops and multi-branch loops. A domain-level description of IRs represents the strand and formed complexes in terms of domains rather than specific nucleotide sequences. At the sequence level, each domain is assigned a particular nucleotide sequence or motif, and its complement's sequence is determined by Watson-Crick base pairing. This spans the full range of binding between any pair of complementary nucleotides, including G-T wobble base pairs. The overall set of bound (e.g. base paired) and unbound domains form a unimolecular complex and exhibit various secondary structure. In some embodiments, hairpins can have a base-paired stem and a small loop of unpaired bases. In certain embodiments, the presence of interweaved non-palindromic polynucleotides sections in the polynucleotide sequence can lead to unpaired nucleotides known as bulges. Bulges can have one or more nucleotides and are classified in different types depending on their location: in the top strand (bulge), in both strands (internal loop) or at a junction. The collection of these base pairs constitutes the secondary structure of DNA, which occur in its three-dimensional structure.

A domain-level description for the DNA molecules provided herein are also provided to represent multiple strands and their complexes in terms of domains rather than specific nucleotide sequences. In some embodiments, domains (e.g. sequences motifs) of interacting single stranded DNA strands can exhibit particular secondary structures on a single strand level that can interact with other DNA strands and in some cases take on a hybridized structure when a first strand is bound to a complementary domain on a second strand to form a duplex. Interactions of different DNA strands that generate new complexes or changes in secondary structure can be viewed as "reactions." Additional unimolecular and bimolecular reactions are also possible at the sequence level. Poor sequence design can lead to sequence-level structures or interactions (e.g. multiple domains of complimentary in the expression cassette) that interfere with the intended reactions of a system comprising one or more DNA molecules provided herein. Undesired interactions can be avoided by design, resulting in reliable and predictable secondary structure formation.

The disclosure provides that the underlying forces leading to the secondary structure of DNA are governed by hydrophobic interactions that underlie thermodynamic laws and the overall conformation may be influenced by physico-chemical conditions. An exemplary list of factors determining equilibrium state include the type of solvent, chemical agents crowding, salt concentrations, pH and temperature. While free energy change parameters and enthalpy change parameters derived from experimental literature allow for a prediction of conformation stability, the overall three-dimensional structures of the hairpin formed from the IR sequences, as usual in statistical mechanics, corresponds to an ensemble of molecular conformations, not just one conformation. Predominant conformations cam transition as the physical or chemical conditions (e.g. salts, pH or temperature) are permutated.

"Stem domain" or "stem" refers to a self-complementary nucleotide sequence of the overhang strand that will form Watson-Crick base pairs. The stem comprises primarily Watson-Crick base pairs formed between the two antiparallel stretches of DNA pairs and can be a right-handed helix. In one embodiment, the stem comprise the stretch of self-complimentary DNA sequence in a palindromic sequence.

"Primary stem domain" or "primary stem" refers to the part of self-complementary or reverse complement nucleotide sequences of the ITR that is most proximal to the expression cassette or the non-ITR sequences of the DNA molecule. In one embodiment, the primary stem domain is the self-complimentary stretch of a palindromic sequence that forms the termini of the DNA molecules provided herein and is covalently linked to the non-ITR sequences flanked by the ITRs. The primary stem encompasses both the start as well as the end of an IR sequence. In certain embodiments, the primary stems range in length from 1 to 100 or more bp. The lengths of primary stem region have an effect on denature/renature kinetics. In some specific embodiments, the primary stem region have at least approximately 4 and 25 nucleotides to ensure thermal stability. In other specific embodiments, the primary stem region have about 4 and 25 nucleotides to ensure thermal stability. On the other hand, the inverted repeat domains may be of any length sufficient to maintain an approximate three dimensional structure at physiological conditions.

"Loop" or "loop domain" refers to the region of unpaired nucleotides in an IR or ITR that is not a turning point and not in a stem. In some embodiments, a loop domain is found at the apex of the IR structure. The loop domain can serve as the region in which the local directionality of the DNA strand is reversed to afford the two antiparallel strands of the originating stem. Because of steric repulsion, in certain embodiments, a loop comprises a minimum of two nucleotides to make a turn in a DNA hairpin. In other embodiments, a loop comprises four nucleotides or more. In yet other embodiments, a loop comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 nucleotides. In some further embodiments, a loop comprises about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 nucleotides. The loop follows a self-complementary sequence of a stem and serves to connect the further nucleotides to the stem domain. In some embodiments, a loop comprise a sequence of oligonucleotides that does not form contiguous duplex structure with other nucleotides in the loop sequence or other elements of the ITR (e.g., the loop remains in flexible, single-stranded form). In one embodiment, the loop sequence that does not form a duplex with other nucleotides in the loop sequence is a series of identical bases (e.g. AAAAAAAA, CCCCCCCC, GGGGGGG or TTTTTTTT). In one embodiment, the loop contains between 2 and 30 nucleotides. In a further embodiment, the loop domain contains between 2 and 15 nucleotides. In yet a further embodiment, the loop comprises a mixture of nucleotides.

As used herein, the term "hairpin" refers to any DNA structure as well as the overall DNA structure, including secondary or tertiary structure, formed from an IR or ITR sequence. As used herein, a "hairpinned" DNA molecule refers to a DNA molecule wherein one or more hairpins has formed in the DNA molecule. In one embodiment, a hairpin comprises a complementary stem and a loop. A hairpin in its simplest form consists of a complementary stem and a loop. A structure encompassing stems and loops are referred to as "stem-loop," "stem loop," or "SL." In another embodiment, a hairpin consists of a complementary stem and a loop. "Branched hairpin" refers to a subset of hairpin that has multiple stem-loops that form branch structures (e.g. as depicted in FIG. 1). An IR or ITR after forming hairpin can be referred to as hairpinned ITR or IR. A "hairpin-ended" DNA molecule refers to a DNA molecule wherein a hairpin has formed at one end of the DNA molecule or a hairpin has formed at each of the 2 end of the DNA molecule.

"Turning point" or "apex" refers to the region of unpaired nucleotides at the spatial end of the ITR. The turning point serves as the region in which the global directionality of the DNA strand is reversed to afford the two antiparallel strands of the originating stem. The turning point also marks the point at which the IR or ITR sequence becomes inverted or the reverse compliment.

In some embodiments, the part of ITR following the primary stem domain, can encode a nucleotide sequence, which in contrast to regular double-stranded DNA, can form non-Watson-Crick-based structural elements when folding on itself, including wobbles and mismatches, and structural defects or imperfections, such as bulges and internal loops (see e.g. FIG. 1). A "bulge" contains one or more unpaired nucleotides on one strand, whereas "internal loops" contain one or more unpaired nucleotides on both top and bottom strands. Symmetric internal loops tend to distort the helix less than bulges and asymmetric internal loops, which can kink or bend the helix. In some embodiments, the unpaired nucleotides in a stem can engage in diverse structural interactions, such as noncanonical hydrogen bonding and stacking, which lend themselves to additional thermodynamic stability and functional diversity. Without being bound by theory, it is thought that the structural diversity of IR stems and loops leads to complex secondary structures, and functional diversity.

In some embodiment, a hairpin for the hairpin-ended DNA molecule comprises a primary stem. In one embodiment, a hairpin for the hairpin-ended DNA molecule comprises 1, 2, 3, 4, 5, 6, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 stems. In another embodiment, a hairpin for the hairpin-ended DNA molecule comprises 1, 2, 3, 4, 5, 6, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 loops. In yet another embodiment, a hairpin for the hairpin-ended DNA molecule comprises 1, 2, 3, 4, 5, 6, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 internal loops. In a further embodiment, a hairpin for the hairpin-ended DNA molecule comprises 1, 2, 3, 4, 5, 6, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 bulges. In one embodiment, a hairpin for the hairpin-ended DNA molecule comprises 1, 2, 3, 4, 5, 6, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 branched hairpins. In another embodiment, a hairpin for the hairpin-ended DNA molecule comprises 1, 2, 3, 4, 5, 6, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 apexes. In a further embodiments, a hairpin for the hairpin-ended DNA molecule comprise any number of stems, branched hairpins, loops, bulges, apexes, and/or internal loops, in any combination.

In some embodiments, the hairpin structure in the DNA molecules provided herein is formed by a symmetrical overhang. In order to obtain a symmetrical overhang, the modification in the 5' stem region will require a cognate 3' modification at the corresponding position in the stem region so that the modified 5' position(s) can form base pair(s) with the modified 3' position(s). Such modification to form a symmetrical overhang can be performed as described in the present disclosure in combination with the state of the art at the time of filing. For example, by generating a BstNBI restriction site for nicking endonuclease by an insertion of an A at position 23 will require an insertion of T at position 105 with respect to the wt AAV2 ITR (e.g., SEQ ID NO:162).

In some embodiments, the 5' and 3' hairpinned ITRs from a hairpinned ITR pair can have different reverse complement nucleotide sequences to harbor the antiparallel restriction sites for nicking endonuclease (e.g. 5' ITR such that nicking results in a bottom strand 5' overhang and the 3' ITR such that nicking results in a bottom strand 3' overhang) but still have the same three-dimensional spatial organization such that both ITRs have mutations that result in the same overall 3D shape.

In some embodiments, hairpinned ITRs for use herein can comprise a modification (e.g., deletion, substitution or addition) of at least 1, 2, 3, 4, 5, 6, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in any one or more of the regions selected from: the primary stem domain, a stem, a branched hairpin, a loop, a bulge or an internal loop. In one specific embodiment, the nucleotide in a right hairpinned ITR can be substituted from an A to a G, C or T or deleted or one or more nucleotides added; a nucleotide in a left hairpinned ITR can be changed from a T to a G, C or A, or deleted or one or more nucleotides added.

In some embodiments, hairpinned ITRs for use herein can comprise a modification (e.g., deletion, substitution or addition) of at least 1, 2, 3, 4, 5, 6, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in any one or more of the regions selected from: the primary stem domain, a stem, a branched hairpin, a loop, a bulge or an internal loop, in order to replace or deplete the occurrence of CpG motifs, thereby; (i) reducing or eliminating the binding of such modified hairpinned ITRs to toll like family of receptors (TLRs) (e.g. TLR9) compared to viral wild type ITRs and/or (ii) reduce or diminish ITR transcriptional activity by removing transcriptionally active CpG islands. Transcriptionally active CpG islands are commonly defined as sequences with a C+G ratio of greater than 50% and observed-to-expected CpG dinucleotides at 60% or higher as described in Gardiner-Garden M, Frommer M. CpG Islands in vertebrate genomes. J Mol Biol 1987; 196:261-282. In one specific embodiment, the nucleotide in a right hairpinned ITR can be substituted from an G or C to a A or T or deleted or one or more nucleotides added between a C and G or a G and C; a nucleotide in a left hairpinned ITR can be changed from a C or G to a T or A, or deleted or one or more nucleotides added between a C and G or a G and C. In one specific embodiment the hairpinned ITRs comprise a CpG depleted sequence of (SEQ ID NO 336):
TTGGTCACTCCCTCTCTGTACACTCACTCACTCACTGATCCCTGGATAC
CAAAGGTATCCAGACACCCAGTCTTTGACTGGGTGGGATCAGTGAGTGA
GTGAGTGTACAGAGAGGGAGTGACCAA In some embodiments, the hairpinned ITR of the DNA molecules provided herein can comprise primary stem wherein 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more complementary base pairs are removed from each of the primary stem domains such that the primary stem domain is shorter and has a lower free energy of folding. Briefly, in such embodiments, if a base is removed in the portion of the primary stem domain, the complementary base pair in primary stem domain is also removed, thereby shortening the overall primary stem domain.

In some embodiments, the hairpinned ITR of the DNA molecules provided herein can comprise primary stem wherein 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more complementary base pairs are introduced from each of the primary stem domains such that the primary stem domain is longer and has a higher free energy of folding. Briefly, in such embodiments, if a base is introduced in the portion of the primary stem domain, the complementary base pair in primary stem domain is also introduced, thereby lengthening the overall primary stem domain.

In some embodiments, the hairpinned ITR of the DNA molecules provided herein can comprise primary stem wherein 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more complementary base pairs are substituted from A or T to G or C from each of the primary stem domains such that the primary stem domain is more G/C rich and has a higher free energy of folding. Briefly, in such embodiments, if a base is substitute (e.g. T to G) in the portion of the primary stem domain, the complementary base pair in primary stem domain is also substituted (e.g. A to C, thereby increasing the G/C content the overall primary stem domain.

In further embodiments, the hairpinned ITR of the DNA molecules provided herein can comprise a primary stem wherein 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more complementary base pairs are substituted from G or C to A or T, or deleted or one or more nucleotides added between a C and G or a G and C; from each of the primary stem domains such that the primary stem domain contains less or no CpG motifs and has a lower TLR9 binding propensity than a viral ITR and/or fewer transcriptionally active CpG islands compared to a reference DNA (e.g. the same DNA molecule but with a unmodified primary stem sequence comprising CpG motifs).

In yet another embodiment, the hairpinned ITR of the DNA molecules provided herein can comprise a primary stem wherein 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more complementary base pairs are substituted from G or C to A or T from each of the primary stem domains such that RAPs (e.g. Rep) can no longer efficiently bind to the primary stem domain.

In yet another embodiment, the hairpinned ITR of the DNA molecules provided herein can comprise a primary stem wherein 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more complementary base pairs are substituted from A or T to G or C from each of the primary stem domains such that the primary stem domain is more G/C rich and has a higher free energy of folding such that RAPs (e.g. Rep or NS1) can no longer efficiently bind to the primary stem domain.

In some embodiments, a hairpinned ITR sequence in the DNA molecules provide herein can have between 1 and 40 nucleotide deletions relative to a full-length WT viral ITR sequence while the whole wt ITR sequence is still present in the vector. For example, in a symmetric ITR such as the AAV2 ITR, if restriction sites for nicking endonuclease are each 25 bases away from the Apex, the portion after the restriction site for nicking endonuclease of the overhang does not need to be the wt IR sequence as it will be removed from the DNA molecules after incubation with nicking endonuclease (or nicking endonuclease and restriction enzymes) and denaturing as described in Sections 5.2.3 and 5.2.4. In certain embodiments, a hairpinned ITR sequence in the DNA molecules provide herein can have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotide deletions relative to a full-length WT viral ITR sequence while the whole wt ITR sequence is still present in the vector.

In some embodiments, the restriction site for nicking endonuclease is chosen based on the predicted melting temperature of the isolated nucleotide sequence present in the ITR stem region. In some embodiments, the predicted melting temperature is between 40-95° C. Further embodiments are for the restriction site for nicking endonuclease and the embodiments factoring in melting temperature are described in Sections 5.2.3, 5.2.4, 5.2.5 and 5.3.2 above.

In one embodiment, the length and GC content of the nucleotide sequence encompassing stem region of a hairpinned ITR in a DNA molecule provided herein is further modified by a deletion, insertion, and/or substitution so that a hairpin forms when the temperature is maintained at approximately 4° C. For example, the nucleotide sequence of the structural element can be modified as compared to the wild-type sequence of a viral ITR. In one embodiment, the length and GC content of the stem is designed so that a hairpin forms when the temperature is maintained at approximately 10° C. or more below the melting temperature of the total ITR. The hairpin's melting temperature can be designed by changing the GC content, distance between restriction sites for nicking endonuclease and the junction closest to the primary stem (e.g. number 4 in FIG. 1), or sequence mismatch or loop, so that the melting temperature is high enough to allow the hairpinned ITR to remain folded above 50° C. to ensure stable storage. The actual optimal length of the stem can vary with sequence of ITR and micro domains such as branches, loops and arms of the ITR, which can be determined according to the present disclosure in combination of the state of the art.

In some embodiments, the stem region of the hairpinned ITR encode a restriction site for Class II nicking endonuclease (e.g. NNNN downstream of 5'). In some embodiments, the stem region does not contain a restriction site for Class II nicking endonuclease.

In some embodiments, the stem region of the hairpinned ITR encode a restriction site for Class I nicking endonuclease. In some embodiments, the stem region of the hairpinned ITR encode a restriction site for Class III, IV or V nicking endonuclease. FIG. 4 depicts various exemplary arrangements of the restriction sites for endo nuclease in the primary stem of a hairpin.

In some embodiments, the expression cassette in the hairpin-ended DNA molecules can be any embodiments of the expression cassette described in Section 5.3.3. In certain embodiments, the ITRs in the hairpin-ended DNA molecules can be any embodiments of the IR or ITR described in Section 5.3.1. In further embodiments, the arrangement among the ITR, the expression cassette, and the restriction sites for nicking endonuclease or restriction enzymes can be any arrangement as described in Sections 5.2.3, 5.2.4, 5.2.5, 5.3.1, 5.3.2, 5.3.3 and 5.3.6.

In some embodiments, the hairpin-ended DNA comprises a top strand that is covalently linked to the 3' ITR as well as 5' ITR and once the ITR is folded, the bottom strand is flanked by two nicks (a first and a second nick) at either end of the bottom strand such that the expression cassette is in between the first nick and the second nick, wherein the first nick is formed between the 3' end of the bottom strand and the juxtaposed 5' end of the top strand as a result of top strand 5' ITR hairpin and the second nick is formed between the 5' end of the bottom strand and the juxtaposed 3' end of the top strand as a result of top strand 3' ITR hairpin.

In some embodiments, the hairpin-ended DNA comprises a bottom strand that is covalently linked to the 3' ITR as well as 5' ITR and once the ITR is folded, the top strand is flanked by two nicks (a first nick and a second nick) at either end of the top strand such that the expression cassette is in between the first nick and the second nick, wherein the first nick is formed between the 5' end of the top strand and the juxtaposed 3' end of the bottom strand as a result of bottom strand 3' ITR hairpin and the second nick is formed between the 3' end of the top strand and the juxtaposed 5' end of the bottom strand as a result of bottom strand 3' ITR hairpin.

In some embodiments, the hairpin-ended DNA comprises a top strand that is covalently linked to the 5' ITR and the bottom strand is covalently linked to the 5' ITR so that when the ITRs are folded, the first nick is formed adjacent to the bottom strand between the 3' end of the bottom strand and the juxtaposed 5' end of the top strand as a result of top strand 5' ITR hairpin and the second nick is formed adjacent to the top strand between the 3' end of the top strand and the juxtaposed 5' end of the bottom strand as a result of bottom strand 5' ITR hairpin, with the expression cassette being flanked by the first and second nicks.

In some embodiments, the hairpin-ended DNA comprises a top strand that is covalently linked to the 3' ITR and the bottom strand is covalently linked to the 3' ITR so that when the ITRs are folded, the first nick is formed adjacent to the top strand between the 5' end of the top strand and the juxtaposed 3' end of the bottom strand as a result of bottom strand 3' ITR hairpin and the second nick is formed adjacent to the bottom strand between the 5' end of the bottom strand and the juxtaposed 3' end of the top strand as a result of top strand 3' ITR hairpin, with the expression cassette being flanked by the first and second nicks.

In some embodiments, the hairpin-ended DNA comprising the two nicks as described in this Section (Section 5.4) and the preceding 4 paragraphs can be ligated to repair the nicks by forming a covalent bond between the two nucleotides flanking the nick. In some embodiments, one of the two nicks described in this Section (Section 5.45.4) and the preceding 4 paragraphs can be ligated and repaired such that when denatured, the DNA molecule becomes a linear single stranded DNA molecule. In some embodiments, the two nicks described in this Section (Section 5.4) and the preceding 4 paragraphs can be ligated and repaired such that when denatured, the DNA molecule becomes a circular single stranded DNA molecule.

In some embodiments, the two flanking ITR pairs in the hairpin-ended DNA molecule comprise identical DNA sequence. In some embodiments, the two flanking ITR pairs in the hairpin-ended DNA molecule comprise different DNA sequences. In some embodiments, one of the ITRs in the hairpin-ended DNA molecule is modified by deletion, insertion, and/or substitution as compared to the other ITR in the same hairpin-ended DNA molecule. In another embodiment, the first ITR and the second ITR in the hairpin-ended DNA molecule are both modified, e.g. by deletion, insertion, and/or substitution. In yet another embodiment, the first ITR and the second ITR in the hairpin-ended DNA molecule comprise different DNA sequences and are both modified. In a further embodiment, the first ITR and the second ITR in the hairpin-ended DNA molecule comprise different DNA sequences and are both modified, wherein the modifications for the two ITRs are different. In yet a further embodiment, the first ITR and the second ITR in the hairpin-ended DNA molecule comprise different DNA sequences and are both modified, wherein the modifications for the two ITRs are identical. In one embodiment, the first ITR and the second ITR in the hairpin-ended DNA molecule comprise identical DNA sequence and are both modified, wherein the modifications for the two ITRs are different. In one embodiment, the first ITR and the second ITR in the hairpin-ended DNA molecule comprise identical DNA sequence and are both modified, wherein the modifications for the two ITRs are identical. In one embodiment, the first ITR and the second ITR in the hairpin-ended DNA are both modified ITRs and the two modified ITRs are not identical. In some embodiments, the hairpin-ended DNA molecules comprise two ITRs that are asymmetric, wherein the asymmetry can be a result of any changes in one ITR that are not reflected in the other ITR. In certain embodiments, the hairpin-ended DNA molecules comprise two ITRs that are asymmetric, wherein the ITRs are different with respect to each other in any way. In certain embodiments, the modifications provided in this paragraph, including deletion, insertion, and/or substitution, can be any such modifications described above in this Section (Section 5.4).

In one aspect, a hairpin-ended DNA molecule provided herein comprises, in the 5' to 3' direction: a first IR, a nucleotide sequence of interest and a second IR. In one embodiment, the nucleotide sequence of interest comprises an expression cassette as described herein, e.g. in Sections 5.3.3. In certain embodiments, the hairpin-ended DNA molecules provided herein including in Section 3 and this Section (Section 5.4) comprise an expression cassette, wherein the expression cassette can be any embodiments described in Sections 3 and 5.3.3.

The hairpin-ended DNA molecules can comprise a combination of dsDNA and ssDNA. In some embodiments, certain portion of the hairpin-ended DNA molecules provided in this Section (Section 5.4) is dsDNA. In some embodiments, the dsDNA portion of the hairpin-ended DNA molecules provided in this Section (Section 5.4) comprises the expression cassette, a stem region of the ITR, or both. In some embodiments, certain portion of the hairpin-ended DNA molecules provided in this Section (Section 5.4) is ssDNA. In further embodiments, the dsDNA portion of the hairpin-ended DNA molecules provided in this Section (Section 5.4) In one embodiment, the dsDNA portion of the hairpin-ended DNA molecules provided in this Section (Section 5.4) accounts for over 90% of the hairpin-ended DNA molecules. In another embodiment, the dsDNA portion of the hairpin-ended DNA molecules provided in this Section (Section 5.4) accounts for at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% of the hairpin-ended DNA molecules. In another embodiment, the dsDNA portion of the hairpin-ended DNA molecules provided in this Section (Section 5.4) accounts for about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% of the hairpin-ended DNA molecules.

In some embodiments, the hairpin-ended DNA molecule provided herein can be efficiently targeted or transported to the nucleus of a cell. In one embodiment, the hairpin-ended DNA molecule provided herein can be efficiently targeted or transported to the nucleus of a cell by the binding between the aptamer formed at the ITR and a nucleus protein. In another embodiment, the hairpin-ended DNA molecule provided herein can be efficiently targeted or transported to the nucleus of a cell, such that the abundance of the hairpin-ended DNA molecules in the nucleus is 10%, 20%, 30%, 40%, 50%, 60%, 70%, 80%, 90%, or 100% higher than that in the cytoplasm. In yet another embodiment, the hairpin-ended DNA molecule provided herein can be efficiently targeted or transported to the nucleus of a cell, such that the abundance of the hairpin-ended DNA molecules in the nucleus is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 fold higher than that in the cytoplasm.

In various embodiments of the hairpin-ended DNA molecule provided herein including in Section (Section 5.4), the hairpin-ended DNA molecule lacks the RABS and/or TRS sequences as described in Section 5.3.4. In others embodiments of the hairpin-ended DNA molecule provided herein including in Section (Section 5.4), the hairpin-ended DNA molecule lacks any or any combination of the DNA sequences, elements, or features as described in Section 5.3.4.

In some additional embodiments, embodiments of the hairpin-ended DNA molecule provided herein including in Section (Section 5.4), the hairpin-ended DNA molecule can be an isolated hairpin-ended DNA molecules in any embodiment with respect to purity as described in Section 5.3.7.

5.5 Functional Properties of the Hairpin-Ended DNA Molecules

In some embodiments, the ITR promotes the long-term survival of the nucleic acid molecule in the nucleus of a cell. In some embodiments, the ITR promotes the permanent survival of the nucleic acid molecule in the nucleus of a cell (e.g., for the entire life-span of the cell). In some embodiments, the ITR promotes the stability of the nucleic acid molecule in the nucleus of a cell. In some embodiments, the ITR inhibits or prevents the degradation of the nucleic acid molecule in the nucleus of a cell.

In some embodiments, when the ITR assumes its folded state, it is resistant to exonuclease digestion (e.g. exonuclease V), e.g. for over an hour at 37° C. In one embodiment, the hairpin-ended DNA molecule is resistant to exonuclease digestion (e.g. digestion by exonuclease V). In another embodiment, the hairpin-ended DNA molecule is resistant to exonuclease digestion (e.g. digestion by exonuclease V) for at least 1, at least 2, at least 3, at least 4, at least 5, at least 6, at least 7, at least 8, at least 9, at least 10 or more hours. In yet another embodiment, the hairpin-ended DNA molecule is resistant to exonuclease digestion (e.g. digestion by exonuclease V) for about 1, about 2, about 3, about 4, about 5, about 6, about 7, about 8, about 9, or about 10 hours.

As unexpectedly found by the inventors and provided herein, duplex linear DNA vectors with ITRs similar to viral ITRs can be produced without the need for RAPs and consequently independent of the RABS or TRS sequence for genome replication. Accordingly, the RABS and TRS can optionally be encoded in the nucleotide sequence disclosed herein but are not required and offer flexibility with regard to designing the ITRs. In one embodiment, the DNA molecules provided herein comprise ITRs that do not comprise RABS. In another embodiment, the DNA molecules provided herein comprise ITRs that do not comprise TRS. In yet another embodiment, the DNA molecules provided herein comprise ITRs that do not comprise either RABS or TRS. In a further embodiment, the DNA molecules provided herein comprise ITRs that comprise RABS, TRS, or both RABS and TRS.

In some embodiments, the hairpin-ended DNA molecules provided herein are stable in the host cell. In some embodiments, the hairpin-ended DNA molecules provided herein are stable in the host cell for long term culture.

In certain embodiments, the hairpin-ended DNA molecules provided herein can be efficiently delivered to a host cell.

The DNA molecules provided herein have superior stability not just for their resistance to exonuclease digestion described above, but also with respect to their structure. In one embodiment, the structure of the DNA molecules remains the same after storage at room temperature for 1 days, 2 days, 3 days, 4 days, 5 days, 6 days, 7 days, 2 weeks, 3 weeks, 4 weeks, 5 weeks, 6 weeks, 7 weeks, 8 weeks, 3 months, 4 months, 5 months, 6 months, 7 months, 8 months, 9 months, 10 months, 11 months, or 12 months. In another embodiment, the ensemble structure of the DNA molecules remains the same after storage at room temperature for 1 days, 2 days, 3 days, 4 days, 5 days, 6 days, 7 days, 2 weeks, 3 weeks, 4 weeks, 5 weeks, 6 weeks, 7 weeks, 8 weeks, 3 months, 4 months, 5 months, 6 months, 7 months, 8 months, 9 months, 10 months, 11 months, or 12 months. In some embodiments, the structure of the DNA molecules provided herein is the same after 2, 3, 4, 5, 10 or 20 cycles of denaturing/renaturing (e.g. denaturing as described in Section 5.2.3 and re-annealing as described in Section 5.2.5). DNA structures can be described by an ensemble of structures at or around the energy minimum. In certain embodiments, the ensemble DNA structure is the same after 2, 3, 4, 5, 10 or 20 cycles of denaturing/renaturing. In one embodiment, the folded hairpin structure formed from the ITR or IR provided herein is the same after 2, 3, 4, 5, 10 or 20 cycles of denaturing/renaturing. In another embodiment, the ensemble structure of the folded hairpin is the same after 2, 3, 4, 5, 10 or 20 cycles of denaturing/renaturing.

5.6 Delivery Vehicles Comprising the Hairpin-Ended DNA Molecules

In some embodiments, the hairpin-ended DNA molecules provided herein can be delivered via a hybridosome as described in U.S. Pat. No. 10,561,610, which is herein incorporated in its entirety by reference. In other embodiments, the DNA molecules provided herein can be delivered via a hybridosome.

In certain embodiments, the DNA molecules provided herein can be delivered via lipid particles including lipid nanoparticles. In other embodiments, the hairpin-ended DNA molecules provided herein can be delivered via lipid nanoparticles. In some embodiments, the lipid nanoparticle comprises any one or more lipids selected from ionizable lipid, non-cationic lipid (e.g. phospholipid), a sterol (e.g., cholesterol) and a PEGylated lipid. In one embodiment, the lipid particle comprises any one or more lipids selected from ionizable lipid, non-cationic lipid (e.g. phospholipid), a sterol (e.g., cholesterol) and a PEGylated lipid, where the molar ratio of lipids ranges from 20 to 70 mole percent or 40 to 60 mole percent for the ionizable lipid, the mole percent of non-cationic lipid ranges from 0 to 30 or 0 to 15, the mole percent of sterol ranges from 20 to 70 or 30 to 50, and the mole percent of PEGylated lipid ranges from 1 to 6 or 2 to 5. In another embodiment, the lipid particle comprises any one or more lipids selected from ionizable lipid, non-cationic lipid (e.g. phospholipid), a sterol (e.g., cholesterol) and a PEGylated lipid, where the molar ratio of lipids ranges from 40 to 60 mole percent for the ionizable lipid, the mole percent of non-cationic lipid ranges from 0 to 15, the mole percent of sterol ranges from 30 to 50, and the mole percent of PEGylated lipid ranges from 2 to 5. In yet another embodiment, the lipid particle comprises any one or more lipids selected from ionizable lipid, non-cationic lipid (e.g. phospholipid), a sterol (e.g., cholesterol) and a PEGylated lipid, where the molar ratio of lipids ranges from 20 to 70 mole percent for the ionizable lipid, the mole percent of non-cationic lipid ranges from 0 to 30, the mole percent of sterol ranges from 20 to 70, and the mole percent of PEGylated lipid ranges from 1 to 6.

The disclosure provides that ionizable lipids can be used employed to condense the nucleic acid cargo, at low pH and to drive membrane association and fusogenicity. Such ionizable lipids can be used as part of the delivery vehicle for the compositions of and methods for the DNA molecules provided herein. In some embodiments, ionizable lipids are lipids comprising at least one amino group that is positively charged or becomes protonated under acidic conditions, for example at pH of 6.5 or lower. In some embodiments, ionizable lipids have at least one protonatable or deprotonatable group, such that the lipid is positively charged at a pH at or below physiological pH (e.g., pH 7.4), and neutral at a second pH, for example at or above physiological pH. It will be understood by one of ordinary skill in the art that the addition or removal of protons as a function of pH is an equilibrium process, and that the reference to a charged or a neutral lipid refers to the nature of the predominant species and does not require that all of the lipid be present in the charged or neutral form. Generally, ionizable lipids have a $pK_a$ of the protonatable group in the range of about 4 to about 7.

Further exemplary ionizable lipids are described in PCT patent publications WO2015/095340, WO2015/199952, WO2018/011633, WO2017/049245, WO2015/061467, WO2012/040184, WO2012/000104, WO2015/074085, WO2016/081029, WO2017/004143, WO2017/075531, WO2017/117528, WO2011/022460, WO2013/148541, WO2013/116126, WO2011/153120, WO2012/044638, WO2012/054365, WO2011/090965, WO2013/016058, WO2012/162210, WO2008/042973, WO2010/129709, WO2010/144740, WO2012/099755, WO2013/049328, WO2013/086322, WO2013/086373, WO2011/071860, WO2009/132131, WO2010/048536, WO2010/088537, WO2010/054401, WO2010/054406, WO2010/054405, WO2010/054384, WO2012/016184, WO2009/086558, WO2010/042877, WO2011/000106, WO2011/000107, WO2005/120152, WO2011/141705, WO2013/126803, WO2006/007712, WO2011/038160, WO2005/121348, WO2011/066651, WO2009/127060, WO2011/141704, WO2006/069782, WO2012/031043, WO2013/006825, WO2013/033563, WO2013/089151, WO2017/099823, WO2015/095346, and WO2013/086354, all of which are herein incorporated in their entirety by reference.

In some specific embodiments, the ionizable lipid is MC3 (6Z,9Z,28Z,31Z)-heptatriaconta-6,9,28,31-tetraen-19-yl-4-(dimethylamino) butanoate (DLin-MC3-DMA or MC3).

In some specific embodiments, the ionizable lipid is MC3 (6Z,9Z,28Z,31Z)-heptatriaconta-6,9,28,31-tetraen-19-yl-4-(dimethylamino) butanoate (DLin-MC3-DMA or MC3).

In some specific embodiments, the ionizable lipid is (((4-hydroxybutyl)azanediyl) bis(hexane-6,1-diyl)bis(2-hexyldecanoate).

In some specific embodiments, the ionizable lipid is 9-Heptadecanyl 8-{(2-hydroxyethyl)[6-oxo-6-(undecyloxy) hexyl]amino}octanoate.

In some embodiments, the lipid nanoparticles encapsulation the DNA molecule of provided herein include one or more lipids selected from the group consisting of distearoyl-phosphatidylcholine (DSPC), dioleoyl-phosphatidylcholine (DOPC), dipalmitoyl-phosphatidylcholine (DPPC), dioleoyl-phosphatidylglycerol (DOPG), dipalmitoyl-phosphatidylglycerol (DPPG), dioleoyl-phosphatidylethanolamine (DOPE), palmitoyloleoyl-phosphatidylcholine (POPC), palmitoyloleoyl-phosphatidylethanolamine (POPE) and dioleoyl-phosphatidy-lethanolamine, dipalmitoyl-phosphatidyl-ethanolamine (DPPE), dimyristoylphospho-ethanolamine (DMPE), distearoyl-phosphatidyl-ethanolamine (DSPE), 16-O-monomethyl PE, 16-O-dimethyl PE, 18-1-trans PE, 1-stearioyl-2-oleoyl-phosphatidyethanol amine (SOPE), and 1,2-dielaidoyl-sn-glycero-3-phophoethanolamine (transDOPE).

Delivery vehicles provided herein include those for delivering the DNA molecules provided herein to cells, which sometime are referred to as transfection. Further useful transfection methods include, but are not limited to, lipid-mediated transfection, cationic polymer-mediated transfection, or calcium phosphate precipitation. Transfection reagents well known in the art are provided herein and include, but are not limited to, TurboFect Transfection Reagent (Thermo Fisher Scientific), Pro-Ject Reagent (Thermo Fisher Scientific), TRANSPASS™ P Protein Transfection Reagent (New England Biolabs), CHARIOT™ Protein Delivery Reagent (Active Motif), PROTEO-JUICE™ Protein Transfection Reagent (EMD Millipore), 293fectin, LIPOFECT AMINE™ 2000, LIPOFECT AMINE™ 3000 (Thermo Fisher Scientific), LIPOFECT AMINE™ (Thermo Fisher Scientific), LIPOFECTIN™ (Thermo Fisher Scientific), DMRIE-C, CELLFECTIN™ (Thermo Fisher Scientific), OLIGOFECT AMINE™ (Thermo Fisher Scientific), LIPOFECT ACE™, FUGENE™ (Roche, Basel, Switzerland), FUGENE™ HD (Roche), TRANSFECT AM™ (Transfectam, Promega, Madison, Wis.), TFX-10™ (Promega), TFX-20™ (Promega), TFX-50™ (Promega), TRANSFECTIN™ (BioRad, Hercules, Calif.), SILENTFECT™ (Bio-Rad), Effectene™ (Qiagen, Valencia, Calif.), DC-chol (Avanti Polar Lipids), GENEPORTER™ (Gene Therapy Systems, San Diego, Calif.), DHARMAFECT 1™ (Dharmacon, Lafayette, Colo.), DHARMAFECT 2™ (Dharmacon), DHARMAFECT 3™ (Dharmacon), DHARMAFECT 4™ (Dharmacon), ESCORT™ III (Sigma, St. Louis, Mo.), and ESCORT™ IV (Sigma Chemical Co.)

In some cases, chemical delivery systems can be used to deliver the DNA molecules provided herein, for example, by using cationic transfection reagents, which include compaction of negatively charged nucleic acid by polycationic chemicals to form cationic liposome/micelle or cationic polymers. Cationic lipids used for the delivery method include, but not limited to monovalent cationic lipids, polyvalent cationic lipids, guanidine containing compounds, cholesterol derivative compounds, cationic polymers, (e.g., poly(ethylenimine), poly-L-lysine, protamine, other cationic polymers), and lipid-polymer hybrids.

In some embodiments, DNA molecules provided herein are delivered by making transient penetration in cell membrane by applying mechanical, electrical, ultrasonic, hydrodynamic, or laser-based energy so that DNA entrance into the targeted cells is facilitated. For example, a DNA molecule provided herein can be delivered by transiently disrupting cell membrane by squeezing the cell through a size-restricted channel or by other means known in the art.

The disclosure provides that the DNA molecules provided herein can be prepared as pharmaceutical compositions. It will be understood that such compositions necessarily comprise one or more active ingredients and, most often, a pharmaceutically acceptable excipient.

Relative amounts of the active ingredient (e.g. DNA molecules provided herein or cells comprising DNA molecules provided herein for transfer or transplantation into a subject), a pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

Formulations of the present disclosure can include, without limitation, saline, liposomes, lipid nanoparticles, polymers, peptides, proteins, cells comprising DNA molecules provided herein (e.g., for transfer or transplantation into a subject) and combinations thereof. In some embodiments, formulations can include exosomes, extracellular vesicles, hybridosomes and fusosomes.

In the case of viral particles, exosomes or hybridosomes, which may contain endogenous nucleic acids, quantification of DNA molecules may be used as the measure of the dose contained in the formulation. Any method known in the art can be used to determine the DNA molecule number of a composition provided herein. One method for performing DNA molecule number titration is as follows: samples of viral particles, exosomes or hybridosomes compositions comprising hairpin-ended DNA are first treated with DNase to eliminate contaminating host DNA from the production process. The DNase resistant particles are then subjected to heat treatment to release the genome from the capsid. The released genomes are then quantitated by real-time PCR using primer/probe sets targeting specific region of the viral genome (for example poly A signal). Another suitable method for determining genome copies is quantitative-PCR (qPCR), particularly the optimized qPCR or digital droplet PCR.

Formulations of the pharmaceutical compositions described herein may be prepared by any method known or hereafter developed in the art of pharmacology. As used herein the term "pharmaceutical composition" refers to compositions comprising at least one active ingredient and optionally one or more pharmaceutically acceptable excipients.

In general, such preparatory methods include the step of associating the active ingredient with an excipient and/or one or more other accessory ingredients. As used herein, the phrase "active ingredient" generally refers to either DNA molecules provided herein or cells or substance comprising the DNA molecules provided herein.

Formulations of the DNA molecules and pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

In some embodiments, the formulations described herein may contain sufficient DNA molecules or active ingredients for expression of the ORFs in the expression cassette for the treatment of a disease.

In some embodiments, DNA molecules of the present disclosure are substantially free of any viral proteins such as AAV Rep78. In some embodiments, the isolated DNA molecules of the disclosure are 100% free, 99% free, 98% free, 97% free, 96% free, 95% free, 94% free, 93% free, 92% free, 91% free, or 90% free of viral proteins.

The DNA molecules of the present disclosure can be formulated using one or more excipients or diluents to (1) increase stability; (2) increase cell transfection or transduction; (3) permit the sustained or delayed release of the active ingredients; (4) alter the biodistribution (e.g., target the DNA molecules or active ingredients comprising the DNA molecules to specific tissues or cell types); (5) increase the translation of ORFs in the expression cassette; (6) alter the release profile of the protein encoded by the ORFs of the expression cassette and/or (7) allow for regulatable expression of the ORFs of the expression cassette.

In some embodiments, a pharmaceutically acceptable excipient may be at least 95%, at least 96%, at least 97%, at least 98%, at least 99%, or 100% pure. In some embodiments, an excipient is approved for use for humans and for veterinary use. In some embodiments, an excipient may be approved by United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Excipients, as used herein, include, but are not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, Md., 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Exemplary diluents include those known and used in the art (see Remington: The Science and Practice of Pharmacy, 21st Edition, A. R. Gennaro, Lippincott, Williams & Wilkins, Baltimore, Md., 2006.)

In some embodiments, the pharmaceutical composition for the DNA molecules provided herein can comprise at least one inactive ingredient. As used herein, the term "inactive ingredient" refers to one or more agents that do not contribute to the activity of the active ingredient of the pharmaceutical composition included in formulations. In some embodiments, all, none or some of the inactive ingredients used in the formulations of the present disclosure can be any one of such approved by the US Food and Drug Administration (FDA) and used in the art.

5.7 Method of Using

The disclosure provides that the DNA molecules provided herein can be used to deliver the ORFs or transgenes in the expression cassette to a cell for expression. ORFs or transgenes as described in Section 5.3.3 can be efficiently delivered. The disclosure provides that the DNA molecules provided herein can be used to deliver the ORFs or transgenes in the expression cassette to a human subject. Any ORFs or transgenes as described in Section 5.3.3 can be efficiently delivered.

In one specific embodiment, the method of delivering a gene of interest to a cell for expression comprises: transfecting the DNA molecules provided herein into the cell. In certain embodiments, the cell is a human cell. In another embodiment, the cell is a human primary cell. In yet another embodiment, the cell is a primary human blood cell. In one embodiment, the DNA molecules can be transfected into the cell via any delivery vehicles described in Section 5.6.

In another specific embodiment, the method of delivering a gene of interest to a human subject for expression comprises: transfecting the DNA molecules provided herein into a cell and administering the cell to a human subject. In certain embodiments, the cell is a human cell. In another embodiment, the cell is a human primary cell. In yet another embodiment, the cell is a primary human blood cell. In one embodiment, the DNA molecules can be transfected into the cell via any delivery vehicles described in Section 5.6.

In some embodiments, the DNA molecules provided herein can be used in gene therapy by delivering a disease correcting genes in the expression cassette into a cell or a human subject as described in the preceding 3 paragraphs.

In certain embodiments, the DNA molecules provided herein can be used to transfect cells that are difficult to transfect as known in the art. Such cells known to be difficult to transfect include cells that are not actively dividing. In some embodiments, such cells can be human primary cells, including, for example, human primary blood cells, human primary hepatocyte, human primary neurons, human primary muscle cells, human primary cardiomyocyte.

5.7.1 Host Cell

As used herein, the term "host cell", includes any cell type that is susceptible to transformation, transfection, transduction, and the like with a nucleic acid construct or hairpin ended expression vector of the present disclosure.

In some embodiments, a hairpin ended vector as disclosed herein delivers the expression cassette into a subject host cell. In some embodiments, the subject host cell is a human host cell, including, for example blood cells, stem cells, hematopoietic cells, CD34+ cells, liver cells, cancer cells, vascular cells, muscle cells, pancreatic cells, neural cells, ocular or retinal cells, epithelial or endothelial cells, dendritic cells, fibroblasts, or any other cell of mammalian origin, including, without limitation, hepatic (i.e., liver) cells, lung cells, cardiac cells, pancreatic cells, intestinal cells, diaphragmatic cells, renal (i.e., kidney) cells, neural cells, blood cells, bone marrow cells, or any one or more selected tissues of a subject for which gene therapy is contemplated. In one aspect, the subject host cell is a human host cell.

The present disclosure also relates to host cells as mentioned above, including a hairpin ended vector as disclosed herein. Thus, one can use multiple host cells depending on the purpose as is obvious to the skilled artisan. A hairpin ended vector for expression comprising an expression cassette as disclosed herein can be introduced into a host cell so that the donor sequence is maintained as a chromosomal integrant. The term host cell encompasses any progeny of a parent cell that is not identical to the parent cell due to mutations that occur during replication. The choice of a host cell may to a large extent depend upon the donor sequence and its source.

The host cell may also be a eukaryote, such as a mammalian, insect, plant, or fungal cell. In one embodiment, the host cell is a human cell (e.g., a primary cell, a stem cell, or an immortalized cell line). In some embodiments, the host cell can be administered a hairpin ended vector for expression of an expression cassette as disclosed herein ex vivo and then delivered to the subject after the gene therapy event. A host cell can be any cell type, e.g., a somatic cell or a stem cell, an induced pluripotent stem cell, or a blood cell, e.g., T-cell or B-cell, or bone marrow cell. In certain embodiments, the host cell is an allogenic cell. In some embodiments, gene modifed host cells, e.g., bone marrow stem cells, e.g., CD34+ cells, or induced pluripotent stem cells can be transplanted back into a patient for expression of a therapeutic protein.

5.7.2 Testing for Successful Gene Expression Using a Hairpin-Ended DNA Molecule Assays well known in the art can be used to test the efficiency of gene delivery of an expression cassette by a hairpin-ended DNA molecule in both in vitro and in vivo models. In some embodiments, levels of the expression of a protein encoded by the hairpin-ended DNA can be assessed by one skilled in the art by measuring mRNA and protein levels of the protein (e.g., reverse transcription PCR, western blot analysis, and enzyme-linked immunosorbent assay (ELISA)). In one embodiment, the DNA comprises a reporter protein that can be used to assess the expression of the expression cassette, for example by examining the expression of the reporter protein by fluorescence microscopy or a luminescence plate reader. For in vivo applications, protein function assays can be used to test the functionality of a given transcript to determine if gene expression has successfully occurred. One skilled in the art will be able to determine the best test for measuring functionality of a transcript by the hairpin-ended DNA molecule in vitro or in vivo.

It is contemplated herein that the effects of gene expression from the hairpin-ended DNA in a cell or subject can last for at least 0.5 month, at least 1 month, at least 2 months, at least 3 months, at least four months, at least 5 months, at least six months, at least 10 months, at least 12 months, at least 18 months, at least 2 years, at least 5 years, at least 10 years, at least 20 years, or can be permanent.

In some embodiments, the hairpin-ended DNA molecules described herein can be codon optimized for the host cell. As used herein, the term "codon optimized" or "codon optimization" refers to the process of modifying a nucleic acid sequence for enhanced expression in the cells of the vertebrate of interest, e.g., mouse or human (e.g., humanized), by replacing at least one, more than one, or a significant number of codons of the native sequence (e.g., a prokaryotic sequence) with codons that are more frequently or most frequently used in the genes of that vertebrate. Various species exhibit particular bias for certain codons of a particular amino acid. Typically, codon optimization does not alter the amino acid sequence of the original translated protein. Optimized codons can be determined using e.g., Aptagen's Gene Forge® codon optimization and custom gene synthesis platform (Aptagen, Inc.) or another publicly available database.

All patent applications, publications (patents and patent applications, scientific literature, or any other publications), patents, GenBank citations and other database citations, webpage disclosures, commercial catalogs, and other references cited herein are incorporated by reference in their entirety.

6. EXAMPLES

A number of embodiments have been described. Nevertheless, it will be understood that various examples in this Section (i.e., Section 6) describes specific embodiments herein solely for the purpose of illustration and do not limit the scope as described in the claims or the disclosure. Various modifications can be made without departing from the spirit and scope of what is provided herein.

6.1 Example 1—Production of Plasmids Encoding the Vector

The nucleic acid sequences encoding the vectors were designed in silico. Construct 1 encodes for a left inverted repeat, a mini human PGK promoter, a turboluc ORF, SV40 poly (a) and a right inverted repeat

```
(TGCGCGACTCGCTCGCTCACTGAGGCCGGGCGACCAAAGGTCGCCCGA
CGCCCGGGCTTTGCCCGGGCGGCCTCAGTGAGCGAGCGAGTCGCGCAGA
GAGGTTAAAACCAACTAGACAACTTTGTATATCTAGAGTTGGGGTTGCG
CCTTTTCCAAGGCAGCCCTGGGTTTGCGCAGGGACGCGGCTGCTCTGGG
CGTGGTTCCGGGAAACGCAGCGGCGCCGACCCTGGGTCTCGCACATTCT
TCACGTCCGTTCGCAGCGTCACCCGGATCTTCGCCGCTACCCTTGTGGG
CCCCCCGGCGACGCTTCCTGCTCCGCCCCTAAGTCGGGAAGGTTCCTTG
CGGTTCGCGGCGTGCCGGACGTGACAAACGGAAGCCGCACGTCTCACTA
GTACCCTCGCAGACGGACAGCGCCAGGGAGCAATGGCAGCGCGCCGACC
GCGATGGGCTGTGGCCAATAGCGGCTGCTCAGCAGGGCGCGCCGAGAGC
AGCGGCCGGGAAGGGCGGTGCGGGAGGCGGGGTGTGGGCGGTAGTGT
GGGCCCTGTTCCTGCCCGCGCGGTGTTCCGCATTCTGCAAGCCTCCGGA
GCGCACGTCGGCAGTCGGCTCCCTCGTTGACCGAATCACCGACCTCTCT
CCCCAGGCAAGTTTGTACAAAAAAGCGCGGCCGCGGCAGGCTGCCACCA
TGGAAACCGATACACTGCTGCTTTGGGTACTTTTGCTGTGGGTGCCCGG
CAGTACGGGCGACGCCGCACAACCAGCTAGGAGAGCAGTCCGGAGCCTG
GTCCCCTCTTCCgAGGCCGAGGCTGAACGGGGAAAGCTGCCAGGCAAGA
AACTCCCCTTAGAGGTTCTCATCGAGCTGGAAGCAAACGCACGCAAGGC
CGGTTGCACTAGGGGCTGCCTCATCTGCCTCAGCAAGATCAAATGTACA
GCAAAGATGAAGAAGTATATTCCTGGCCGCTGTGCAGACTACGGAGGCG
ACAAAAAAACAGGACAAGCTGGTATAGTTGGCGCCATCGTAGATATCCC
CGAGATTAGTGGGTTCAAGGAAATGGAGCCAATGGAGCAATTCATTGCA
CAGGTTGATAGATGTGCGGATTGCACTACTGGTTGCCTTAAGGGCTTGG
CGAATGTCAAGTGTAGTGATCTTCTGAAAAAGTGGCTACCCGGCCGGTG
TGCCACCTTCGCTGACAAAATACAGAGCGAAGTCGACAATATTAAAGGA
CTTGCCGGGGACTAATGATAGTGACACAAAGTGACGCGTCCTAGAGCTC
GCACTGTGCCTTCTAGTTGCCAGCCATCTGTTGTTTGCCCCTCCCCCGT
GCCTTCCTTGACCCTGGAAGGTGCCACTCCCACTGTCCTTTCCTAATAA
AATGAGGAAATTGCATCGCATTGTCTGAGTAGGTGTCATTCTATTCTGG
GGGGTGGGGTGGGCAGGACAGCAAGGGGGAGGATTGGGAAGAGAATAG
CAGGCATGCTGGGGAGGGCGCTAGCGCAGGAACCCCTTTTAATGGAGTT
GGCGAGTCCCTCTCTGCGCGCTCGCTCGCTCACTGAGGCCGGGCGACCA
AAGGTCGCCCGACGCCCGGGCTTTGCCCGGGCGGCCTCAGTGAGCGAGC
GAGCGCGCAGAGATCGACTC SEQ ID NO: 174)
``` with the four restriction sites for nicking endonuclease arranged to lead to ITR overhangs on the 5' top strand and 3' bottom strand. Construct 2 encodes for a modified left ITR, a human PGK promoter, a secreted turboluc ORF, SV40 poly (a), a right ITR and a double restriction sites for nicking endonuclease 115 base pairs downstream of the right ITR (TGCGCGACTCGCTCGCTCACTGAGGCCGGGCGACCAAAGGTCGCCCGA

CGCCCGGGCTTTGCCCGGGCGGCCTCAGTGAGCGAGCGAGTCGCGCAGA

GAGGTTAAAACCAACTAGACAACTTTGTATATCTAGAGTTGGGGTTGCG

CCTTTTCCAAGGCAGCCCTGGGTTTGCGCAGGGACGCGGCTGCTCTGGG

CGTGGTTCCGGGAAACGCAGCGGCGCCGACCCTGGGTCTCGCACATTCT

TCACGTCCGTTCGCAGCGTCACCCGGATCTTCGCCGCTACCCTTGTGGG

CCCCCCGGCGACGCTTCCTGCTCCGCCCCTAAGTCGGGAAGGTTCCTTG

CGGTTCGCGGCGTGCCGGACGTGACAAACGGAAGCCGCACGTCTCACTA

GTACCCTCGCAGACGGACAGCGCCAGGGAGCAATGGCAGCGCGCCGACC

GCGATGGGCTGTGGCCAATAGCGGCTGCTCAGCAGGGCGCGCCGAGAGC

AGCGGCCGGGAAGGGCGGTGCGGGAGGCGGGGTGTGGGCGGTAGTGT

GGGCCCTGTTCCTGCCCGCGCGGTGTTCCGCATTCTGCAAGCCTCCGGA

GCGCACGTCGGCAGTCGGCTCCCTCGTTGACCGAATCACCGACCTCTCT

CCCCAGGCAAGTTTGTACAAAAAAGCGCGGCCGCGGCAGGCTGCCACCA

TGGAAACCGATACACTGCTGCTTTGGGTACTTTTGCTGTGGGTGCCCGG

CAGTACGGGCGACGCCGCACAACCAGCTAGGAGAGCAGTCCGGAGCCTG

GTCCCCTCTTCCgAGGCCGAGGCTGAACGGGAAAGCTGCCAGGCAAGA

AACTCCCCTTAGAGGTTCTCATCGAGCTGGAAGCAAACGCACGCAAGGC

CGGTTGCACTAGGGGCTGCCTCATCTGCCTCAGCAAGATCAAATGTACA

GCAAAGATGAAGAAGTATATTCCTGGCCGCTGTGCAGACTACGGAGGCG

ACAAAAAAACAGGACAAGCTGGTATAGTTGGCGCCATCGTAGATATCCC

CGAGATTAGTGGGTTCAAGGAAATGGAGCCAATGGAGCAATTCATTGCA

CAGGTTGATAGATGTGCGGATTGCACTACTGGTTGCCTTAAGGGCTTGG

CGAATGTCAAGTGTAGTGATCTTCTGAAAAAGTGGCTACCCGGCCGGTG

TGCCACCTTCGCTGACAAAATACAGAGCGAAGTCGACAATATTAAAGGA

CTTGCCGGGACTAATGATAGTGACACAAAGTGACGCGTCCTAGAGCTC

GCACTGTGCCTTCTAGTTGCCAGCCATCTGTTGTTTGCCCCTCCCCCGT

GCCTTCCTTGACCCTGGAAGGTGCCACTCCCACTGTCCTTTCCTAATAA

AATGAGGAAATTGCATCGCATTGTCTGAGTAGGTGTCATTCTATTCTGG

GGGGTGGGGTGGGGCAGGACAGCAAGGGGGAGGATTGGGAAGAGAATAG

CAGGCATGCTGGGGAGGGCGCTAGCGCAGGAACCCCTTTTAATGGAGTT

GGCGAGTCCCTCTCTGCGCGCTCGCTCGCTCACTGAGGCCGGGCGACCA

AAGGTCGCCCGACGCCCGGGCTTTGCCCGGGCGGCCTCAGTGAGCGAGC

GAGCGCGCAGAGATCGACTCCTCGGCCACTTGGAGGGGCCGGGGGGACG

ACGCAATCTGGAGTGGAAAGAACCCCCGTCTATGCGGCTTAAAGCACGG

CCAGGGAATAGTGGATCAAGTGTACTGACATGTGCCGGAGTCCCTCCAT

GCCCAGATCGACTCCCTCGAGATATATGGATCC

SEQ ID NO: 175).

Construct 1 and 2 were synthetized and cloned into a pUC57 backbone (plasmid 1 and plasmid 2, respectively) by a commercial DNA synthesis vendor.

Plasmids 1 & 2 were transformed and then amplified overnight in the NEB stable or MDS-42 strain followed by plasmid isolation using commercial plasmid isolation kit (Nucleobond Xtra Maxi Plus EF (Macherey Nagel)) and dissolved in nuclease free water.

For construct 1: To induce nicks on construct 1, the nicking endonuclease Nt.BstNBI (6.2 U/µg DNA) was added to the isolated construct 1 in 1× Neb3.1 Buffer and incubated at 55° C. for one hour. The reaction mix containing the nicked plasmid was then heated to 90° C. on a thermo shaker for 10 min, in order to dissociate the ITR flanked transgene from the plasmid back bone and the mix was then left to cool to room temperature for 30 min to allow for ITR folding at the single stranded overhangs ends. The reaction mix was then supplemented with both the restriction enzyme PvuII and RecBCD Exonuclease V (0.157 U and 0.625 U per µg of nicked plasmid, respectively) as well as adenosine triphosphate (final concentration of 1 mM). The reaction mix was then placed on a shaker at 37° C. for 120 min to allow for the restriction enzyme to cleave the backbone fragment and the exonuclease to digest backbone fragments. The exonuclease generally does not digest linear fragments protected by hairpin ends. Finally, the reaction mix was purified using Takara NucleoSpin Gel and PCR clean-up kit and remaining ITR flanked vector was eluted according to the manufacturer's instructions.

For construct 2: To induce nicks and linearize construct 2, the nicking endonuclease Nt.BstNBI (0.62 U/µg DNA) was added to the isolated construct 2 in 1× Neb3.1 Buffer and incubated at 55° C. for 120 min. The reaction mix containing the nicked construct 2 was then heated to 95° C. on a thermocycler for 3 min in order to dissociate the ITR flanked transgene from the plasmid back bone and subsequently cooled down to 40° C. in the thermocycler with a slope of 0.05° C./s. The reaction mix was then supplemented with Exonuclease V (2.5 U/µg of DNA) as well as adenosine triphosphate (final concentration of 1 mM). The reaction mix was then placed on a shaker at 37° C. for 120 min to allow for the restriction enzyme to cleave the backbone fragment and the exonuclease to digest backbone fragments. The exonuclease generally does not digest linear fragments protected by hairpin ends. Finally, the reaction mix was purified using a Takara NucleoSpin Gel and PCR clean-up kit and remaining ITR flanked vector was eluted according to the manufacturer's instructions.

Nicked, de/renatured and digestion resistant DNA products were visualized by native agarose gel electrophoresis.

Figure 6:
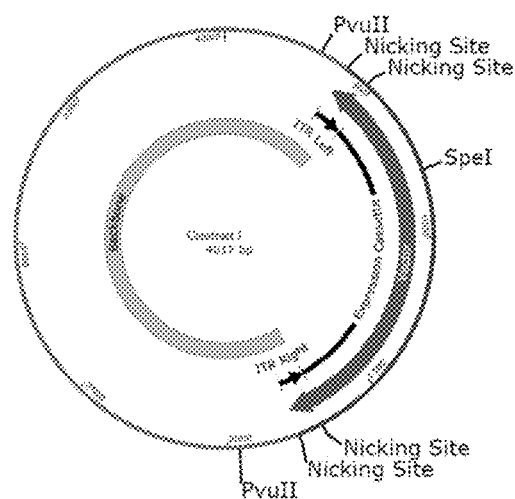
FIG. 6 depicts construct 1 and visualization of DNA products from construct 1 after performing method steps as described in Example 1.
Figure 6:
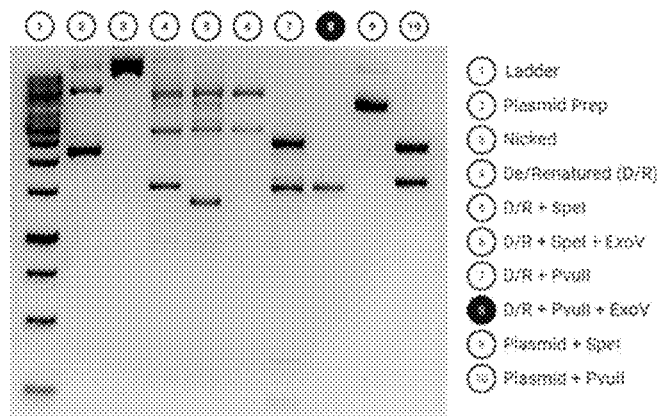

For construct 1, the agarose gel (FIG. 6) shows the nicked plasmid in lane 3, the de/renatured DNA products in lane 4 and the single band of digestion resistant vector in lane 8. To further validate the formation of folded ITRs, the plasmid as well as de/renatured DNA products were digested with the restriction enzyme SpeI, which has a single cut site in the mini PGK promoter region of the vector. As seen in FIG. 6, SpeI digestion cleaves the vector, causing a shift of the lower band in lane 5 and upon treatment with the exonuclease V, the vector fragment is digested while the backbone, which is protected from digestion by the folded anti-sense ITRs, remain. The opposite is true when the de/renatured DNA is digested with the restriction enzyme PvuII, which has two cut sites in the backbone, and following exonuclease V treatment, only the desired product remains (lane 8). Additionally, the construct 1 starting material linearized with SpeI or PvuII, releasing a linear DNA strand in the case of SpeI and two fragments with PvuII. Overall, this demonstrated that a double stranded DNA molecule comprising an expression cassette flanked by two inverted repeats, further each comprising a first and a second restriction site for nicking endonuclease arranged on opposite strands is formed by nicking followed by de/renaturing of the DNA. The formation of such a hairpin ended DNA molecule was further shown to be resistant to exonuclease V digestion.

Figure 7:
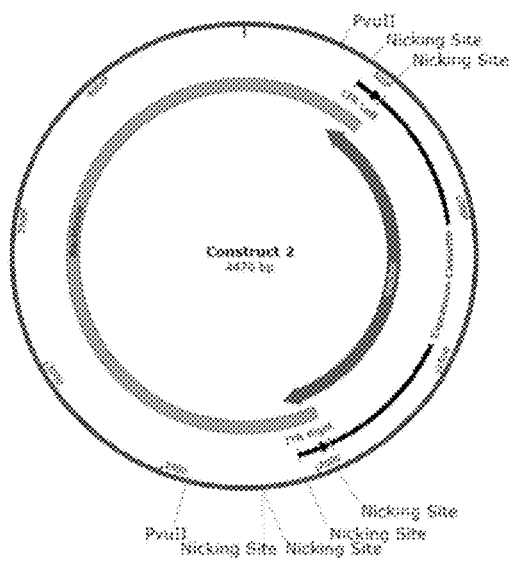
FIG. 7 depicts construct 2 and visualization of DNA products from construct 1 after performing method steps as described in Example 1.
Figure 7:
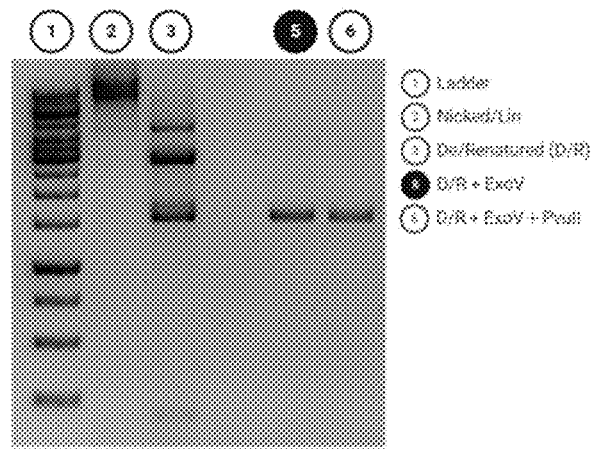

For construct 2, which contains a close proximity double restriction sites for nicking endonuclease downstream of the 3' ITR, the treatment with the nicking endonuclease BstNBI leads to a linearization of the circular plasmid. As seen in FIG. 7, the agarose gels shows the linearized DNA in lane 2. After de/renaturing, the DNA products are visible in lane 3 and following digestion with RecBCD Exonuclease V a single band of digestion resistant vector is visible in lane 5. To further validate the formation of folded ITRs and the linearization of the plasmid, the re/denatured DNA products were digested with PvuII which has two cut sites in the backbone. Following Exonuclease V digestion, no additional bands were detected. This shows that by incorporating a close proximity double restriction sites for nicking endonuclease upstream of the 5' ITR or downstream of the 3' ITR, the backbone can by fragmented simultaneously while the inverted repeat section is nicked, making a further digestion of the backbone by a restriction site obsolete.

6.2 Example 2 Repeated de-/Renaturing of DNA Constructs

To assess the stability of folding of the DNA constructs, the nicked construct 1 and the corresponding hairpinned vector were subject to multiple cycles of denaturing and annealing. In a first step, 100 ng total DNA was incubated in NEB buffer 3.1 with 1 µM Sybr Green I dye and transferred into a 384 well PCR plate. The plate was sealed and Sybr Green fluorescence was continuously monitored over several 70-98° C. heating cycles performed on a Quantstudio 5 real time PCR machine. Following three heating cycles for the vector (in addition to the heating cycle during production) and 4 cycles for the nicked construct, the samples were visualized by native agarose gel electrophoresis. As seen in FIG. 8A, one band was present for the vector in lane 2 as well as bands corresponding to the vector and back bone were visible in line 3. In addition, the melting curves in FIG. 8B and FIG. 8C show distinct melting fingerprints that remain very similar throughout every cycle.

6.3 Example 3 Isothermal Formation of Vector

Aside from dissociating the vector from the nicked plasmid by thermal energy, the possibility of isothermal denaturing using a chemical denaturing agent was tested. Specifically, the capacity of NaOH to act as a denaturing agent to dissociate the nicked construct of example 1 was tested. First the nicked construct (100 ng total DNA) was mixed with 0.2 µM SYBR green I dye in NEB buffer 3.1 that was previously adjusted for corresponding pH values with 1M NaOH. Fluorescence signal was detected at corresponding pH values using a plate reader. As seen in FIG. 9B, as the pH is increased, the background adjusted fluorescence decreases, indicating an increased fraction of denatured DNA. The pH of the denatured DNA was then reverted to pH 7.9 with HCl and the samples were loaded on to an agarose electrophoresis gel. As seen FIG. 9A, at a pH over 10.3 the DNA construct dissociated and formed the expected bands including a band for the corresponding vector. The same band is visible after re/denatured using thermal energy.

6.4 Example 4 Transfection Of LNPs and Hybridosomes

Lipid nanoparticles were prepared on a Nanoassemblr™ microfluidic system (Precision NanoSystems) according to the manufacturer's instructions. Depending on the desired formulation, an ethanol solution similar to that of the pre-formed vesicle approach, consisting of an ionazible lipid (e.g. MC3), a zwitterionic lipid (e.g., di stearoylphosphatidylcholine (DSPC), dioleoylglycerophosphocholine (DOPC), a component to provide membrane integrity (such as a sterol, e.g., cholesterol) and a conjugated lipid molecule (such as a PEG-lipid, e.g., 1-(monomethoxy-polyethyleneglycol)-2,3-dimyristoylglycerol, with an average PEG molecular weight of 2000 ("PEG-DMG")) at the appropriate molar ratio (e.g. 40:40:18:2), was prepared at concentrations of 10 mM total lipid. Furthermore, an aqueous DNA solution with a DNA to lipid wt/wt ratio of approximately 14 was prepared in 25 mM acetate buffer at pH 4.0. Depending on the total volume of production 1 and 3 ml syringes where used to create the inlet stream with a total flow rate of 12 ml/min. For each formulation the aqueous DNA solution was mixed with the ethanol-lipid solution with a flow rate ratio of 3:1 (Aq:Et) at room temperature. The product was then dialyzed against PBS to remove the residual ethanol as well as to raise the pH to 7.4.

For exosome production, cells were grown in stirred bioreactors in perfusion mode and exosome isolation was performed by tangential flow filtration followed by Captocore 700 liquid chromatography as described in Nordin et al Methods in Molecular Biology, vol 1953. Humana Press, New York, N.Y. (2019), which is herein incorporated in its entirety by reference.

Human embryonic kidney cells (HEK-293T) were cultured in DMEM supplemented with 10% FCS. The cells were grown at 37° C. in a 5% $CO_2$-humified incubator. For testing the Luciferase expression, cells ($2\times10^4$/well) were seeded in a 96-well plate and transfected for 48 h with 100 ng, 10 ng and 1 ng (0.37 pmol, 0.031 pmol, 0.001 pmol and 0.001 pmol) of DNA vector coding for Turboluc. Transfection was mediated using Hybridosomes generated by fusing exosomes with lipid nanoparticles as outlined in U.S. Ser. No. 15/112,180. As a comparison, cells additionally were transfected with lipid nanoparticles.

Luciferase expression level was determined 48 h after transfection using the Gluc Glow Assay kit from NanoLight Technology. 150 µl of medium in wells containing transfected cells was removed (50 µl of medium left in wells) and 50 µl Coelenterazine in cell lysis buffer (NanoLight Technology) was added at a final concentration of 50 µM Coelenterazine. The cells then were incubated at room temperature for 5 min. while being shaken in the dark. The cell lysis containing the luciferase substrate was transferred into a white 96-well plate (BRAND). Luciferase activity was determined by measuring the luminescence using a SynergyMX plate reader (BioTek) and shown in FIG. 10.

6.5 Example 5 Expression in Dividing and Non-Dividing Cells

Constructs were generated to include an open reading frame encoding the Turboluc reporter gene into the expression cassette flanked by two ITRs. Expression of Turboluc from the vectors over time was determined based on Luciferase activity in each cell culture, confirming that the Luciferase activity resulted from gene expression from the vector.

In detail, human embryonic kidney cells (HEK-293T) were cultured in DMEM (10% FCS, 1% pen/strep) and 2 mM stable Glutamine. Irradiated mouse embryonic fibroblasts (C57BL/6, Thermo Fisher) were cultured in DMEM (10% FCS, 1% pen/strep), 2 mM stable Glutamine and 1 mM Sodium Pyruvate. The cells were grown at 37° C. in a 5% $CO_2$-humified incubator. Cells ($6 \times 10^4$/well) were seeded in a 96-well plate coated with 0.1% Gelatine solution and transfected with 100 ng (0.13 pmol) of folded ITR DNA vector 1 of example 1. Transfections were done using JetPrime (PolyPlus) transfection reagent according to the manufacturer's instructions. Culture medium was changed 3 days post transfection. Luciferase expression level was determined at different days after transfection, starting with day 1 post transfection using the Gluc Glow Assay kit (NanoLight Technology). The medium in wells containing transfected cells was replaced with phosphate-buffered saline (50 μl) and 50 μl Coelenterazine in cell lysis buffer (NanoLight Technology) was added at a final concentration of 50 μM Coelenterazine. The cells then were incubated at room temperature for 5 min, while being shaken in the dark. The cell lysis containing the luciferase substrate was transferred into a white 96-well plate. For construct 2, which encodes for a secreted Turboluc, a 50 ul sample supernatant was removed at on different days and the complete medium was exchanged. The supernatant sample was incubated for 2 minutes with Coelenterazine at a final concentration of 50 μM. Luciferase activity was determined by measuring the luminescence using a SynergyMX plate reader (BioTek). For the analysis of background, bioluminescence from untreated cells was measured following the protocol mentioned above. As seen in FIG. 11A and FIG. 11B, for construct 1, expressing non-secreted Turboluc, luciferase activity peaks in dividing cells on day 2, while in non-dividing cells the expression continues to increase. As seen in FIG. 11C and FIG. 11D, for construct 2 encoding secreted Turboluc, luciferase activity peaks in dividing cells on day 2, while in non-dividing cells the expression increases and then remains stable over 9 days. As a direct comparison, equimolar amounts of full circular plasmids encoding construct 2 were also transfected and as seen in FIG. 11C and FIG. 11D, generally a lower luciferase activity was recorded, indicating improved nuclear delivery of the purified construct 2 with folded ITRs.

6.6 Example 6 Construction of DNA Plasmids Containing ITRs

De novo cell-free synthesis of oligonucleotides as routinely provided by commercial DNA synthesis vendors allows for fast and economic production of bespoke vectors and vector libraries, however de novo synthesis of sequences containing long inverted repeats can pose a challenge, especially if multiple sections of similar inverted repeats are present (as in the left ITRs and right ITRs flanking an expression cassette). Accordingly, a strategy was devised that allows for the assembly of ITR containing plasmids. Many viral ITRs contain restriction enzyme sites approximately at in the middle of their respective ITRs (i.e. BssHII in B19V ITRs or BsaHI in AAV2 ITRs) and artificial ITRs can be designed to entail a central restriction site. To increase manufacturability of the constructs, the ITR sequences are split close to the ITR specific restriction enzyme site (i.e. the left ITR is split L1 and split L2, the right ITR split into R1 and R2) and separately manufactured. As depicted in FIG. 12 by generating two first gene fragments, one encoding split ITR R2 and the other encoding split ITR L2 along with have a multiple cloning site and either an antibiotic resistance cassette or a origin of replication, the de novo gene fragments are be assembled and ligated to make a circular plasmid which is transformed for amplification. A third gene fragment is synthesized containing the remaining halves of the split ITRs (R1 and L1, respectively) as well as an antibiotic resistance cassette and an origin of replication. Both the plasmid resulting from step 1, encoding the split ITRs R2 and L2 as well as the joined multiple cloning site, as well as the third fragment can then be digested by the ITR specific restriction enzyme (i.e. BssHII in HBoV ITRs or BsaHI in AAV2 ITRs) and then scarlessly circularized to form a plasmid containing both ITRs as well as a multiple cloning site. Bespoke expression cassettes can then be cloned into the vector at the multiple cloning site.

6.7 Example 7 Long Term Expression of Ligated and Non-Ligated Constructs

Construct 3 is a construct with the four restriction sites for nicking endonuclease arranged to lead to ITR overhangs on the 5' top strand and 3' bottom strand. Construct 3 encodes for a modified left ITR, a truncated SFFV promoter, a mouse kappa IgG leader, a turboluc ORF, bGH poly(A) signal (a), a right ITR and a double restriction sites for nicking endonuclease 115 base pairs downstream of the right ITR

```
(TGCGCGACTCGCTCGCTCACTGAGGCCGGGCGACCAAAGGTCGCCCGA

CGCCCGGGCTTTGCCCGGGCGGCCTCAGTGAGCGAGCGAGTCGCGCAGA

GAGGTTAAAACCAACTAGACAACTTTGTATATCTAGAGTAACGCCATTT

TGCAAGGCATGGAAAATACCAAACCAAGAATAGAGAAGTTCAGATCAA

GGGCGGGTACATGAAAATAGCTAACGTTGGGCCAAACAGGATATCTGCG

GTGAGCAGTTTCGGCCCCGGCCCGGGGCCAAGAACAGATGGTCACCGCA

GTTTCGGCCCCGGCCCGAGGCCAAGAACAGATGGTCCCCAGATATGGCC

CAACCCTCAGCAGTTTCTTAAGACCCATCAGATGTTTCCAGGCTCCCCC

AAGGACCTGAAATGACCCTGCGCCTTATTTGAATTAACCAATCAGCCTG

CTTCTCGCTTCTGTTCGCGCGCTTCTGCTTCCCGAGCTCTATAAAAGAG

CTCACAACCCCTCACTCGGCGCGCCAGTCCTCCGATTGACTGAGTGCGG

CCGCGGCAGGCTGCCACCATGGAAACCGATACACTGCTGCTTTGGGTAC

TTTTGCTGTGGGTGCCCGGCAGTACGGGCGACGCCGCACAACCAGCTAG

GAGAGCAGTCCGGAGCCTGGTCCCCTCTTCCGAGGCCGAGGCTGAACGG

GGAAAGCTGCCAGGCAAGAAACTCCCCTTAGAGGTTCTCATCGAGCTGG

AAGCAAACGCACGCAAGGCCGGTTGCACTAGGGGCTGCCTCATCTGCCT

CAGCAAGATCAAATGTACAGCAAAGATGAAGAAGTATATTCCTGGCCGC

TGTGCAGACTACGGAGGCGACAAAAAAACAGGACAAGCTGGTATAGTTG

GCGCCATCGTAGATATCCCCGAGATTAGTGGGTTCAAGGAAATGGAGCC

AATGGAGCAATTCATTGCACAGGTTGATAGATGTGCGGATTGCACTACT

GGTTGCCTTAAGGGCTTGGCGAATGTCAAGTGTAGTGATCTTCTGAAAA
```

-continued
```
AGTGGCTACCCGGCCGGTGTGCCACCTTCGCTGACAAAATACAGAGCGA

AGTCGACAATATTAAAGGACTTGCCGGGGACTAATGATAGTGACACAAA

GTGACGCGTCCTAGAGCTCGCACTGTGCCTTCTAGTTGCCAGCCATCTG

TTGTTTGCCCCTCCCCCGTGCCTTCCTTGACCCTGGAAGGTGCCACTCC

CACTGTCCTTTCCTAATAAAATGAGGAAATTGCATCGCATTGTCTGAGT

AGGTGTCATTCTATTCTGGGGGTGGGGTGGGGCAGGACAGCAAGGGGG

AGGATTGGGAAGAGAATAGCAGGCATGCTGGGGAGGGCGCTAGCGCAGG

AACCCCTTTTAATGGAGTTGGCGAGTCCCTCTCTGCGCGCTCGCTCGCT

CACTGAGGCCGGGCGACCAAAGGTCGCCCGACGCCCGGGCTTTGCCCGG

GCGGCCTCAGTGAGCGAGCGAGCGCGCAGAGATCGACTCCTCGGCCACT

TGGAGGGGCCGGGGGACGACGCAATCTGGAGTGGAAAGAACCCCCGTC

TATGCGGCTTAAAGCACGGCCAGGGAATAGTGGATCAAGTGTACTGACA

TGTGCCGGAGTCCCTCCATGCCCAGATCGACTCCCTCGAG SEQ ID

NO: 334).
```

Construct 3 was produced by the same method as for construct 2 in Example 1. Following purification by a Gel and PCR clean-up kit, the purified vector was mixed with T4 ligase and T4 ligation buffer according to the manufacturer instructions and was incubated at 25° C. for 2 h. To confirm complete ligation, the pH of samples of the ligated construct was adjusted with 100 mM Tris-HCl (pH 8.8), T5 exonuclease was added to the mix which was then incubated for 1 h at 37° C. Ligation was further confirmed by dilution of a sample of the ligated construct in water followed by the addition of formamide and loading dye. This mix was incubated at 65° C. for 5 mins and then kept on ice until loading in onto the agarose gel. After the ligation step, the ligated construct was re-purified using a Gel and PCR clean-up kit.

To confirm ligation, results were analyzed using an agarose gel. The agarose gel (FIG. 20A) shows the purified construct in lane 2, the ligase & construct mix after ligation in lane 3, the T5 exonuclease treated, previously ligated construct in lane 4, the formamide denatured, previously ligated construct in lane 5 and the resulting re-purified ligated construct in lane 6. The second half of the agarose gel shows the non-ligated construct in ligation buffer (lane 7), T5 exonuclease treated (lane 8), formamide denatured (lane 9) and re-purified (lane 10).

The purified ligated construct, non-ligated construct and circular parent plasmid were subsequently loaded into LNPs, as well as Hybridosomes as outlined in Example 4. Expression of secreted turboluc following transfection of non-dividing HepRG cells with hybridosome encapsulating ligated construct, non-ligated construct or parent circular plasmid was monitored over time (FIG. 20B). While the expression from the transfection with the circular plasmid quickly diminished, the ligated construct and the non-ligated construct remained stable over time. Surprisingly, expression from the non-ligated construct was observed at levels that are higher than the levels seen in transfection with the ligated construct.

6.8 Example 8 Long Term Expression after Transfection with LNPs and Hybridosomes Constructs were generated to include an open reading frame encoding the Turboluc reporter gene into the expression cassette flanked by two ITRs. Expression of secreted Turboluc from the vectors over time was determined based on luciferase activity.

In detail, differentiated non-dividing HepRG cells were maintained in HepaRG™ Maintenance/Metabolism media and transfected with LNPs and Hybridosomes, previously prepared as outlined in example 7. To analyze duration of expression luciferase expression level was determined at different time points for non-dividing cells (FIG. 21A) as described in example 7. Luciferase activity was determined by measuring the luminescence using a SynergyMX plate reader (BioTek). For the analysis of background, bioluminescence from untreated cells was measured following the protocol described in Example 1 above. As seen in FIG. 21A, for non-dividing cells transfected with a construct encoding secreted Turboluc, luciferase activity remains stable over two months.

6.9 Example 9 Transfection with Cre Encoding Hairpin Ended DNA

A construct was designed in silico encoding a left ITR, a EF1a promoter modified to remove nicking sites, a Cre-recombinase ORF, bGH poly(A) signal (a), a right ITR and a double restriction sites for nicking endonuclease 115 base pairs downstream of the right ITR. The construct was ordered to be synthesized and cloned into a pUC mini backbone. The hairpin-ended DNA was produced from circular plasmids as in example 1 and the purified DNA molecules were subsequently loaded into LNPs, as well as Hybridosomes as outlined in Example 4. The percentage of cells transfected was monitored using a monoclonally expanded HEK293-loxP-GFP-RFP (GenTarget) stable cell line. Upon successful transfection Cre recombinase protein is expressed in the cells, enters the nuclease and excises the foxed GFP-stop, to switch the cells from GFP positive to RFP positive. The vector transfected with JetPrime acted as a positive control. The HEK293-loxP-GFP-RFP cells were plated in 96 well plates and transfected with four different doses of DNA. After 72 h the cells were trypsinated and analyzed by flow cytometry for RFP expression. As seen in FIG. 22, at the highest dose, Hybridosomes successfully transfected >85% of the cells while LNPs and positive control JetPrime showed limited transfection efficiency of the cell population.

6.10 Example 10 RABS Substitutions

In order to investigate the effect of an AAV RBE on the process and transfection efficiency, de novo DNA backbones encoding a right ITR, a pUC ori, Ampicilin resistance and a left ITR were designed and synthesized as well as cloned into a kanamycin resistance vector by a commercial vendor. The vectors were digested and the synthesized fragment excised from the kanamycin backbone and isolated by gel extraction. The synthesized backbone fragment was then purified and the expression cassette of example 7 encoding for secreted turboluc was ligated with synthesized backbones, to circularize the plasmids. Five backbones encoding the left and right ITRs shown below between the expression cassette were produced and amplified in Stabl3 bacteria. The plasmids were then nicked with Nt.BstNBI and hairpin ended DNA was produced as described in Example 1. The production of the hairpin ended DNA was confirmed by running an agarose gel as shown in FIG. 23. The gel shows no pronounced differences in products nor yield. Next, HepRG cells were transfected with 50 ng of the purified hairpin ended DNAs using JetPrime according to the manufacturer instructions and levels of secreted turboluc were monitored on several days as described in Example 7. turer instructions. After 48 hours, luciferase expression was recorded using the Steady-Glo luminescence assay on a SynergyMX plate reader (BioTek) and shown in FIG. 25B.

|  | Left ITR | Right ITR |
|---|---|---|
| Plasmid 1<br>AAV2 RBE | GAGTCCCTCTCTGCGCGCTCGC<br>TCGCTCACTGAGGCCGGGCGA<br>CCAAAGGTCGCCCGACGCCCG<br>GGCTTTGCCCGGGCGGCCTCAG<br>TGAGCGAGCGAGCGCGCAGAG<br>AGGGACTCGCCAA | TTGGCGAGTCCCTCTCTGCGCGCT<br>CGCTCGCTCACTGAGGCCGGGCG<br>ACCAAAGGTCGCCCGACGCCCGG<br>GCTTTGCCCGGGCGGCCTCAGTG<br>AGCGAGCGAGCGCGCAGAGAGG<br>GACTC |
| Plasmid 2<br>ITR1 | GAGTCCCTCTCTGCGC<u>GGTCCT</u><br><u>TCGCTC</u>ACTGAGGCCGGGCGA<br>CCAAAGGTCGCCCGACGCCCG<br>GGCTTTGCCCGGGCGGCCTCAG<br><u>TGAGCGAAGGACC</u>GCGCAGAG<br>AGGGACTCGCCAA | TTGGCGAGTCCCTCTCTGCGC<u>GG</u><br><u>TCCTTCGCTC</u>ACTGAGGCCGGGC<br>GACCAAAGGTCGCCCGACGCCCG<br>GGCTTTGCCCGGGCGGCCTCAGT<br><u>GAGCGAAGGACC</u>GCGCAGAGAG<br>GGACTC |
| Plasmid 3<br>ITR2 | GAGTCCCTCTCTGCGCGCTCCT<br>TCGGTCACTGAGGCCGGGCGA<br>CCAAAGGTCGCCCGACGCCCG<br>GGCTTTGCCCGGGCGGCCTCAG<br>TGACCGAAGGAGCGCGCAGAG<br>AGGGACTCGCCAA | TTGGCGAGTCCCTCTCTGCGCGCT<br>CCTTCGGTCACTGAGGCCGGGCG<br>ACCAAAGGTCGCCCGACGCCCGG<br>GCTTTGCCCGGGCGGCCTCAGTG<br>ACCGAAGGAGCGCGCAGAGAGG<br>GACTC |
| Plasmid 4<br>ITR3 | GAGTCCCTCTCTGCGCGATCAC<br>TCACTCACTGAGGCCGGGCGA<br>CCAAAGGTCGCCCGACGCCCG<br>GGCTTTGCCCGGGCGGCCTCAG<br><u>TGAGTGAGTGATC</u>GCGCAGAG<br>AGGGACTCGCCAA | TTGGCGAGTCCCTCTCTGCGCGA<br>TCACTCACTCACTGAGGCCGGGC<br>GACCAAAGGTCGCCCGACGCCCG<br>GGCTTTGCCCGGGCGGCCTCAGT<br><u>GAGTGAGTGATC</u>GCGCAGAGAG<br>GGACTC |
| Plasmid 5<br>ITR4 | GAGTCCCTCTCTGCGC<u>GCCCGA</u><br><u>ACGCAC</u>ACTGAGGCCGGGCGA<br>CCAAAGGTCGCCCGACGCCCG<br>GGCTTTGCCCGGGCGGCCTCAG<br><u>TGTGCGTTCGGGC</u>GCGCAGAG<br>AGGGACTCGCCAA | TTGGCGAGTCCCTCTCTGCGC<u>GC</u><br><u>CCGAACGCAC</u>ACTGAGGCCGGGC<br>GACCAAAGGTCGCCCGACGCCCG<br>GGCTTTGCCCGGGCGGCCTCAGT<br><u>GTGCGTTCGGGC</u>GCGCAGAGAGG<br>GACTC |

6.11 Example 11 Production of Hairpin Ended DNA with Double Nicking Sites

A DNA fragment was de novo designed to contain double nicking sites (i) between the right ITR, the pUC ori, (ii) between the pUC ori and the ampicillin resistance, as well as (iii) between the ampicillin resistance and the left ITR and synthesized as well as cloned into a kanamycin resistance vector by a commercial vendor. Analogous to Example 10, the ITR and backbone fragment was then excised, and gel purified to be ligated with a firefly luciferase expression cassette as depicted in FIG. 24B (corresponding sequence below). The plasmid was amplified, 0.5 mg of plasmid nicked with Nt.BspQI enzyme NEB (40 ul) at 500 ng/ul in nicking buffer and incubated for 1 h at 37 deg. The nicked plasmid was then denatured by addition of 33 mM of NaOH followed by annealing with 41.6 mM Tris pH 7.2. Then the annealed DNA fragments were digested with exonuclease V. Samples of each step were loaded onto an agarose gel and as seen in FIG. 25A, after nicking, the plasmid is split into the 3 expected fragments (A, B & C), all of which have double stranded ends. Upon denaturing and annealing, the A band is further fragmented into a slightly lower A1 band as well as a new faint band labeled A2/A3. This corresponds to the release of the overhangs from the product as depicted in FIG. 25A. After digestion only band A1 is resistant to digestion. The digestion resistant hairpin ended DNA was then purified as described in Example 1 and HEK293T cells were transfected using JetPrime according to the manufac-

SEQ ID NO.: 335
(GTTCGAGATCGCTCTTCAGAAGAGCGCGGAGTCACATTCGCGACTCGC

AATGCATTGCAGGGCGAGGGCGAGGGCCGCCCCTACGAGGGCCACAACA

CCGTGAAGCTGAAGGTGACCAAGGGCGGCCCCCTGCCCTTCGCCTGGGA

CATCCTGTCCCCCCAGTTCCAGTACGGCTCCAAGGTGTACGTGAAGCAC

CCCGCCGACATCCCAGCTCGGTAGCCACCTGACGTCGCTCTTCGCGCTC

GCTCGCTCACTGAGGCCGGGCGACCAAAGGTCGCCCGACGCCCGGGCTT

TGCCCGGGCGGCCTCAGTGAGCGAGCGAGCGCGAAGAGCGGGAGTGAGT

GGCCAAAAAGTACCCGGCCAGAAAGGAACCGTAAAACCAACTAGACAGC

CGGTGACTTTGTTCCCCAGCTCGGTTCATTCTCAAGCCTCAGACAGGAG

AACCGGGACTAGTATATGAGCTCCGGTGCCCGTCAGTGGGCAGAGCGCA

CATCGCCCACAGTCCCCGAGAAGTTGGGGGAGGGGTCGGCAATTGAAC

CGGTGCCTAGAGAAGGTGGCGCGGGGTAAACTGGGAAAGTGATGTCGTG

TACTGGCTCCGCCTTTTTCCCGAGGGTGGGGGAGAACCGTATATAAGTG

CAGTAGTCGCCGTGAACGTTCTTTTTCGCAACGGGTTTGCCGCCAGAAC

ACAGGTAAGTGCCGTGTGTGGTTCCCGCGGGCCTGGCCTCTTTACGGGT

TATGGCCCTTGCGTGCCTTGAATTACTTCCACGCCCCTGGCTGCAGTAC

GTGATTCTTGATCCCGAGCTTCGGGTTGGAAGTGGGTGGGAGAGTTCGA

GGCCTTGCGCTTAAGGAGCCCCTTCGCCTCGTGCTTGAGTTGAGGCCTG

```
GCCTGGGCGCTGGGGCCGCCGCGTGCGAATCTGGTGGCACCTTCGCGCC
TGTCTCGCTGCTTTCGATAAGTCTCTAGCCATTTAAAATTTTTGATGAC
CTGCTGCGACGCTTTTTTTCTGGCAAGATAGTCTTGTAAATGCGGGCCA
AGATCGATCTGCACACTGGTATTTCGGTTTTTGGGGCCGCGGGCGGCGA
CGGGGCCCGTGCGTCCCAGCGCACATGTTCGGCGAGGCGGGGCCTGCGA
GCGCGGCCACCGAGAATCGGACGGGGGTAGTCTCAAGCTGGCCGGCCTG
CTCTGGTGCCTGGCCTCGCGCCGCCGTGTATCGCCCCGCCCTGGGCGGC
AAGGCTGGCCCGGTCGGCACCAGTTGCGTGAGCGGAAAGATGGCCGCTT
CCCGGCCCTGCTGCAGGGAGCTCAAAATGGAGGACGCGGCGCTCGGGAG
AGCGGGCGGGTGAGACACCCACACAAAGGAAAAGGGCCTTTCCGTCCTC
AGCCGTCGCTTCATGTGACACCACGGAGTACCGGGCGCCGTCCAGGCAC
CTCGATTAGTTCTCGATCGAGCTTTTGGAGTACGTCGTCTTTAGGTTGG
GGGGAGGGGTTTTATGCGATGGAGTTTCCCCACACTGAGTGGGTGGAGA
CTGAAGTTAGGCCAGCTTGGCACTTGATGTAATTCTCCTTGGAATTTGC
CCTTTTTGAGTTTGGATCTTGGTTCATTCTCAAGCCTCAGACAGTGGTT
CAAAGTTTTTTTCTTCCATTTCAGGTGTCGTGAGCGGCCGCGGCAGGCT
GCCACCATGGAGGATGCCAAGAATATTAAGAAAGGCCCTGCCCCATTCT
ACCCTCTGGAAGATGGCACTGCTGGTGAGCAACTGCACAAGGCCATGAA
GAGGTATGCCCTGGTCCCTGGCACAATTGCCTTCACTGATGCTCACATT
GAGGTGGACATCACCTATGCTGAATACTTTGAGATGTCTGTGAGGCTGG
CAGAAGCCATGAAAAGATATGGACTGAACACCAACCACAGGATTGTGGT
GTGCTCTGAGAACTCTCTCCAGTTCTTCATGCCTGTGTTGGGAGCCCTG
TTCATTGGAGTGGCTGTGGCCCCTGCCAATGACATCTACAATGAGAGAG
AGCTCCTGAACAGCATGGGCATCAGCCAGCCAACTGTGGTCTTTGTGAG
CAAGAAGGGCCTGCAAAAGATCCTGAATGTGCAGAAGAAGCTGCCCATC
ATCCAGAAGATCATCATCATGGACAGCAAGACTGACTACCAGGGCTTCC
AGAGCATGTATACCTTTGTGACCAGCCACCTCCCCCCTGGCTTCAATGA
GTATGACTTTGTGCCTGAGAGCTTTGACAGGGACAAGACAATTGCTCTG
ATTATGAACAGCTCTGGCTCCACTGGACTGCCCAAAGGTGTGGCTCTGC
CCCACAGAACTGCTTGTGTGAGATTCAGCCATGCCAGAGACCCCATCTT
TGGCAACCAGATCATCCCTGACACTGCCATCCTGTCTGTGGTTCCATTC
CATCATGGCTTTGGCATGTTCACAACACTGGGGTACCTGATCTGTGGCT
TCAGAGTGGTGCTGATGTATAGGTTTGAGGAGGAGCTGTTTCTGAGGAG
CTTGCAAGACTACAAGATCCAGTCTGCCCTGCTGGTGCCCACTCTGTTC
AGCTTCTTTGCCAAGAGCACCCTCATTGACAAGTATGACCTGAGCAACC
TGCATGAGATTGCCTCTGGAGGAGCACCCCTGAGCAAGGAGGTGGGTGA
GGCTGTGGCAAAGAGGTTCCATCTCCCAGGAATCAGACAGGGCTATGGC
CTGACTGAGACCACCTCTGCCATCCTCATCACCCCTGAAGGAGATGACA
AGCCTGGTGCTGTGGGCAAGGTGGTTCCCTTTTTTGAGGCCAAGGTGGT
GGACCTGGACACTGGCAAGACCCTGGGAGTGAACCAGAGGGGTGAGCTG

TGTGTGAGGGGTCCCATGATCATGTCTGGCTATGTGAACAACCCTGAGG
CCACCAATGCCCTGATTGACAAGGATGGCTGGCTGCACTCTGGTGATAT
TGCCTACTGGGATGAGGATGAGCACTTTTTCATTGTGGACAGGCTGAAG
AGTCTCATCAAGTACAAAGGCTACCAAGTGGCACCTGCTGAGCTTGAGA
GCATCCTGCTCCAGCACCCCAACATCTTTGATGCTGGTGTGGCTGGCCT
GCCTGATGATGATGCTGGAGAGCTGCCTGCTGCTGTTGTGGTTCTGGAG
CATGGAAAGACCATGACTGAGAAGGAGATTGTGGACTATGTGGCCAGTC
AGGTGACCACTGCCAAGAAGCTGAGGGGAGGTGTGGTGTTTGTGGATGA
GGTGCCAAAGGGTCTGACTGGCAAGCTGGATGCCAGAAAGATCAGAGAG
ATCCTGATCAAGGCCAAGAAGGGAGGAAAGATTGCAGTTTAAGGATCCT
GACACAAAGTGACGCGTAATCAACCTCTGGATTACAAAATTTGTGAAAG
ATTGACTGGTATTCTTAACTATGTTGCTCCTTTTACGCTATGTGGATAC
GCTGCTTTAATGCCTTTGTATCATGCTATTGCTTCCCGTATGGCTTTCA
TTTTCTCCTCCTTGTATAAATCCTGGTTGCTGTCTCTTTATGAGGAGTT
GTGGCCCGTTGTCAGGCAACGTGGCGTGGTGTGCACTGTGTTTGCTGAC
GCAACCCCCACTGGTTGGGGCATTGCCACCACCTGTCAGCTCCTTTCCG
GGACTTTCGCTTTCCCCCTCCCTATTGCCACGGCGGAACTCATCGCCGC
CTGCCTTGCCCGCTGCTGGACAGGGGCTCGGCTGTTGGGCACTGACAAT
TCCGTGGTGTTGTCGGGGAAATCATCGTCCTTTCCTTGGCTGCTCGCCT
GTGTTGCCACCTGGATTCTGCGCGGGACGTCCTTCTGCTACGTCCCTTC
GGCCCTCAATCCAGCGGACCTTCCTTCCCGCGGCCTGCTGCCGGCTCTG
CGGCCTCTTCCGCGTCTTCGCCTTCGCCCTCAGACGAGTCGGATCTCCC
TTTGGGCCGCCTCCCCGCACGCGTCCTAGAGCTCGCACTGTGCCTTCTA
GTTGCCAGCCATCTGTTGTTTGCCCCTCCCCCGTGCCTTCCTTGACCCT
GGAAGGTGCCACTCCCACTGTCCTTTCCTAATAAAATGAGGAAATTGCA
TCGCATTGTCTGAGTAGGTGTCATTCTATTCTGGGGGGTGGGGTGGGGC
AGGACAGCAAGGGGGAGGATTGGGAAGAGAATAGCAGGCATGCTGGGGA
GGGCGCTAGCGCAGGGGGACCCCAAGTGACGATTGAACCCCGATTCAGG
TACCCATTGGAAATTTTAATGGAGTAACATAACTGCTGGAGTAGATGAA
GAACCTCTTGGCCACTCCGCTCCCGAAGAGCGCACTCGCTCGCTCGGTG
GGGCCTGGCGACCAAAGGTCGCCAGACGGACGTGCTTTGCACGTCCGGC
CCCACCGAGCGAGCGAGTGCGCTCTTCGGGCCACTTGGAGGGGCCGGGG
GGACGACGCAATCTGGAGTGGAAAGAACCCCCGTCTATGCGGCTTAAAG
CACGGCCAGGGAATAGTGGATCAAGTGTACTGACATGTGCCGGCAATGC
ATTGCGTCCCGAGTCACATTCGCGACTCTCGACGCTCTTCAGAAGAGCA
GCTTAGCTTCAATAGCTCAATGATATCGGAAAGAACATGTGAGCAAAAG
GCCAGCAAAAGGCCAGGAACCGTAAAAAGGCCGCGTTGCTGGCGTTTTT
CCATAGGCTCCGCCCCCCTGACGAGCATCACAAAAATCGACGCTCAAGT
CAGAGGTGGCGAAACCCGACAGGACTATAAAGATACCAGGCGTTTCCCC
CTGGAAGCTCCCTCGTGCGCTCTCCTGTTCCGACCCTGCCGCTTACCGG
ATACCTGTCCGCCTTTCTCCCTTCGGGAAGCGTGGCGCTTTCTCATAGC
```

-continued

```
TCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGG
TAACTATCGTCTTGAGTCCAACCCGGTAAGACACGACTTATCGCCACTG
GCAGCAGCCACTGGTAACAGGATTAGCAGAGCGAGGTATGTAGGCGGTG
CTACAGAGTTCTTGAAGTGGTGGCCTAACTACGGCTACACTAGAAGAAC
AGTATTTGGTATCTGCGCTCTGCTGAAGCCAGTTACCTTCGGAAAAAGA
GTTGGTAGCTCTTGATCCGGCAAACAAACCACCGCTGGTAGCGGTGGTT
TTTTTGTTTGCAAGCAGCAGATTACGCGCAGAAAAAAAGGATCTCAAGA
AGATCCTTTGATCTTTTCTACGGGGTCTGACGCTCAGTGGAACGAAAAC
TCACGTTAAGGGGCTCTTCAGAAGAGCGAGTCACATTCGCGACTCTGCA
ATGCATTGCCATGAGATTATCAAAAAGGATCTTCACCTAGATCCTTTTA
AATTAAAAATGAAGTTTTAAATCAATCTAAAGTATATATGAGTAAACTT
GGTCTGACAGTTACCAATGCTTAATCAGTGAGGCACCTATCTCAGCGAT
CTGTCTATTTCGTTCATCCATAGTTGCCTGACTCCCCGTCGTGTAGATA
ACTACGATACGGGAGGGCTTACCATCTGGCCCCAGTGCTGCAATGATAC
CGCGAGACCCACGCTCACCGGCTCCAGATTTATCAGCAATAAACCAGCC
AGCCGGAAGGGCCGAGCGCAGAAGTGGTCCTGCAACTTTATCCGCCTCC
ATCCAGTCTATTAATTGTTGCCGGGAAGCTAGAGTAAGTAGTTCGCCAG
TTAATAGTTTGCGCAACGTTGTTGCCATTGCTACAGGCATCGTGGTGTC
ACGCTCGTCGTTTGGTATGGCTTCATTCAGCTCCGGTTCCCAACGATCA
AGGCGAGTTACATGATCCCCCATGTTGTGCAAAAAAGCGGTTAGCTCCT
TCGGTCCTCCGATCGTTGTCAGAAGTAAGTTGGCCGCAGTGTTATCACT
CATGGTTATGGCAGCACTGCATAATTCTCTTACTGTCATGCCATCCGTA
AGATGCTTTTCTGTGACTGGTGAGTACTCAACCAAGTCATTCTGAGAAT
AGTGTATGCGGCGACCGAGTTGCTCTTGCCCGGCGTCAATACGGGATAA
TACCGCGCCACATAGCAGAACTTTAAAAGTGCTCATCATTGGAAAACGT
TCTTCGGGGCGAAAACTCTCAAGGATCTTACCGCTGTTGAGATCCAGTT
CGATGTAACCCACTCGTGCACCCAACTGATCTTCAGCATCTTTTACTTT
CACCAGCGTTTCTGGGTGAGCAAAAACAGGAAGGCAAAATGCCGCAAAA
AAGGGAATAAGGGCGACACGGAAATGTTGAATACTCATACTCTTCCTTT
TTCAATATTATTGAAGCATTTATCAGGGTTATTGTCTCATGAGCGGATA
CATATTTGAATGTATTTAGAAAAATAAACAAATAGGGGTTCCGCGCACA
TTTCCCCGAAAAGTA)
```

6.12 Example 12 Hairpinned Inverted Repeat DNA with Hetero-Telomeric HBOV Derived ITRs A DNA fragment was de novo designed to contain double nicking sites (i) between the right HBOV-derived ITR, the pUC ori, (ii) between the pUC ori and the ampicillin resistance, as well as (iii) between the ampicillin resistance and the left HBOV-derived ITR and synthesized as well as cloned into a kanamycin resistance vector by a commercial vendor. Analogous to Example 10, the ITR and backbone fragment was then excised, and gel purified to be ligated with a firefly luciferase expression cassette fragment and circularized as described in the previous example. The plasmid is amplified, and 0.5 mg of plasmid are nicked with Nt.BspQI enzyme NEB (40 ul) at 500 ng/ul in nicking buffer and incubated for 1 h at 37 deg. The nicked plasmid is then denatured by addition of 33 mM of NaOH to release the overhangs, followed by annealing of the overhangs with 41.6 mM Tris pH 7.2. Then the annealed DNA fragments are digested with RecBDC. Samples of each step care visualized an agarose gel to confirm the production of the vector.

(SEQ ID NO 337)
```
GTTCGAGATCGCTCTTCAGAAGAGCGCGGAGTCACATTCGCGACTCGC
AATGCATTGCAGGGCGAGGGCGAGGGCCGCCCCTACGAGGGCCACAACA
CCGTGAAGCTGAAGGTGACCAAGGGCGGCCCCCTGCCCTTCGCCTGGGA
CATCCTGTCCCCCCAGTTCCAGTACGGCTCCAAGGTGTACGTGAAGCAC
CCCGCCGACATCCCAGCTCGGTAGCCACCTGACGTCGCTCTTCGGTGGT
TGTACAGACGCCATCTTGGAATCCAATATGTCTGCCGGCTCAGTCATGC
CTGCGCTGCGCGCAGCGCGCTGCGCGCGCATGATCTAATCGCCGGCA
GACATATTGGATTCCAAGATGGCGTCTGTACAACCACCGAAGAGCGGAG
TGGCCAAAAAGTACCCGGCCAGAAAGGAACCGTAAAACCAACTAGACAG
CCGGTGACTTTGTTCCCCAGCTCGGTTCATTCTCAAGCCTCAGACAGGA
GAACCGGGACTAGTATATGAGCTCCGGTGCCCGTCAGTGGGCAGAGCGC
ACATCGCCCACAGTCCCCGAGAAGTTGGGGGAGGGGTCGGCAATTGAA
CCGGTGCCTAGAGAAGGTGGCGCGGGGTAAACTGGGAAAGTGATGTCGT
GTACTGGCTCCGCCTTTTTCCCGAGGGTGGGGGAGAACCGTATATAAGT
GCAGTAGTCGCCGTGAACGTTCTTTTTCGCAACGGGTTTGCCGCCAGAA
CACAGGTAAGTGCCGTGTGTGGTTCCCGCGGGCCTGGCCTCTTTACGGG
TTATGGCCCTTGCGTGCCTTGAATTACTTCCACGCCCCTGGCTGCAGTA
CGTGATTCTTGATCCCGAGCTTCGGGTTGGAAGTGGGTGGGAGAGTTCG
AGGCCTTGCGCTTAAGGAGCCCCTTCGCCTCGTGCTTGAGTTGAGGCCT
GGCCTGGGCGCTGGGGCCGCCGCGTGCGAATCTGGTGGCACCTTCGCGC
CTGTCTCGCTGCTTTCGATAAGTCTCTAGCCATTTAAAATTTTTGATGA
CCTGCTGCGACGCTTTTTTTCTGGCAAGATAGTCTTGTAAATGCGGGCC
AAGATCGATCTGCACACTGGTATTTCGGTTTTTGGGGCCGCGGGCGGCG
ACGGGCCCGTGCGTCCCAGCGCACATGTTCGGCGAGGCGGGGCCTGCG
AGCGCGGCCACCGAGAATCGGACGGGGGTAGTCTCAAGCTGGCCGGCCT
GCTCTGGTGCCTGGCCTCGCGCCGCCGTGTATCGCCCCGCCCTGGGCGG
CAAGGCTGGCCCGGTCGGCACCAGTTGCGTGAGCGGAAAGATGGCCGCT
TCCCGGCCCTGCTGCAGGGAGCTCAAAATGGAGGACGCGGCGCTCGGGA
GAGCGGGCGGGTGAGACACCCACACAAAGGAAAAGGGCCTTTCCGTCCT
CAGCCGTCGCTTCATGTGACACCACGGAGTACCGGGCGCCGTCCAGGCA
CCTCGATTAGTTCTCGATCGAGCTTTTGGAGTACGTCGTCTTTAGGTTG
GGGGGAGGGGTTTTATGCGATGGAGTTTCCCCACACTGAGTGGGTGGAG
ACTGAAGTTAGGCCAGCTTGGCACTTGATGTAATTCTCCTTGGAATTTG
CCCTTTTTGAGTTTGGATCTTGGTTCATTCTCAAGCCTCAGACAGTGGT
```

-continued

TCAAAGTTTTTTTCTTCCATTTCAGGTGTCGTGAGCGGCCGCGGCAGGC
TGCCACCATGGAGGATGCCAAGAATATTAAGAAAGGCCCTGCCCCATTC
TACCCTCTGGAAGATGGCACTGCTGGTGAGCAACTGCACAAGGCCATGA
AGAGGTATGCCCTGGTCCCTGGCACAATTGCCTTCACTGATGCTCACAT
TGAGGTGGACATCACCTATGCTGAATACTTTGAGATGTCTGTGAGGCTG
GCAGAAGCCATGAAAAGATATGGACTGAACACCAACCACAGGATTGTGG
TGTGCTCTGAGAACTCTCTCCAGTTCTTCATGCCTGTGTTGGGAGCCCT
GTTCATTGGAGTGGCTGTGGCCCCTGCCAATGACATCTACAATGAGAGA
GAGCTCCTGAACAGCATGGGCATCAGCCAGCCAACTGTGGTCTTTGTGA
GCAAGAAGGGCCTGCAAAAGATCCTGAATGTGCAGAAGAAGCTGCCCAT
CATCCAGAAGATCATCATCATGGACAGCAAGACTGACTACCAGGGCTTC
CAGAGCATGTATACCTTTGTGACCAGCCACCTCCCCCCTGGCTTCAATG
AGTATGACTTTGTGCCTGAGAGCTTTGACAGGGACAAGACAATTGCTCT
GATTATGAACAGCTCTGGCTCCACTGGACTGCCCAAAGGTGTGGCTCTG
CCCCACAGAACTGCTTGTGTGAGATTCAGCCATGCCAGAGACCCCATCT
TTGGCAACCAGATCATCCCTGACACTGCCATCCTGTCTGTGGTTCCATT
CCATCATGGCTTTGGCATGTTCACAACACTGGGGTACCTGATCTGTGGC
TTCAGAGTGGTGCTGATGTATAGGTTTGAGGAGGAGCTGTTTCTGAGGA
GCTTGCAAGACTACAAGATCCAGTCTGCCCTGCTGGTGCCCACTCTGTT
CAGCTTCTTTGCCAAGAGCACCCTCATTGACAAGTATGACCTGAGCAAC
CTGCATGAGATTGCCTCTGGAGGAGCACCCCTGAGCAAGGAGGTGGGTG
AGGCTGTGGCAAAGAGGTTCCATCTCCCAGGAATCAGACAGGGCTATGG
CCTGACTGAGACCACCTCTGCCATCCTCATCACCCCTGAAGGAGATGAC
AAGCCTGGTGCTGTGGGCAAGGTGGTTCCCTTTTTTGAGGCCAAGGTGG
TGGACCTGGACACTGGCAAGACCCTGGGAGTGAACCAGAGGGGTGAGCT
GTGTGTGAGGGGTCCCATGATCATGTCTGGCTATGTGAACAACCCTGAG
GCCACCAATGCCCTGATTGACAAGGATGGCTGGCTGCACTCTGGTGATA
TTGCCTACTGGGATGAGGATGAGCACTTTTTCATTGTGGACAGGCTGAA
GAGTCTCATCAAGTACAAAGGCTACCAAGTGGCACCTGCTGAGCTTGAG
AGCATCCTGCTCCAGCACCCCAACATCTTTGATGCTGGTGTGGCTGGCC
TGCCTGATGATGATGCTGGAGAGCTGCCTGCTGCTGTTGTGGTTCTGGA
GCATGGAAAGACCATGACTGAGAAGGAGATTGTGGACTATGTGGCCAGT
CAGGTGACCACTGCCAAGAAGCTGAGGGGAGGTGTGGTGTTTGTGGATG
AGGTGCCAAAGGGTCTGACTGGCAAGCTGGATGCCAGAAAGATCAGAGA
GATCCTGATCAAGGCCAAGAAGGGAGGAAAGATTGCAGTTTAAGGATCC
TGACACAAAGTGACGCGTAATCAACCTCTGGATTACAAAATTTGTGAAA
GATTGACTGGTATTCTTAACTATGTTGCTCCTTTTACGCTATGTGGATA
CGCTGCTTTAATGCCTTTGTATCATGCTATTGCTTCCCGTATGGCTTTC
ATTTTCTCCTCCTTGTATAAATCCTGGTTGCTGTCTCTTTATGAGGAGT
TGTGGCCCGTTGTCAGGCAACGTGGCGTGGTGTGCACTGTGTTTGCTGA
CGCAACCCCCACTGGTTGGGGCTTTGCCACCACCTGTCAGCTCCTTTCC

-continued

GGGACTTTCGCTTTCCCCCTCCCTATTGCCACGGCGGAACTCATCGCCG
CCTGCCTTGCCCGCTGCTGGACAGGGGCTCGGCTGTTGGGCACTGACAA
TTCCGTGGTGTTGTCGGGGAAATCATCGTCCTTTCCTTGGCTGCTCGCC
TGTGTTGCCACCTGGATTCTGCGCGGGACGTCCTTCTGCTACGTCCCTT
CGGCCCTCAATCCAGCGGACCTTCCTTCCCGCGGCCTGCTGCCGGCTCT
GCGGCCTCTTCCGCGTCTTCGCCTTCGCCCTCAGACGAGTCGGATCTCC
CTTTGGGCCGCCTCCCCGCACGCGTCCTAGAGCTCGCACTGTGCCTTCT
AGTTGCCAGCCATCTGTTGTTTGCCCCTCCCCCGTGCCTTCCTTGACCC
TGGAAGGTGCCACTCCCACTGTCCTTTCCTAATAAAATGAGGAAATTGC
ATCGCATTGTCTGAGTAGGTGTCATTCTATTCTGGGGGGTGGGGTGGGG
CAGGACAGCAAGGGGGAGGATTGGGAAGAGAATAGCAGGCATGCTGGGG
AGGGCGCTAGCGCAGGGGGACCCCAAGTGACGATTGAACCCCGATTCAG
GTACCCATTGGAAATTTTAATGGAGTAACATAACTGCTGGAGTAGATGA
AGAACCTCTTGGCCACTCCGTTGCTTATGCAATCGCGAAACTCTATATC
TTGCTCTTCTTAATGTGTTGTTGTTGTACATGCGCCATCTTAGTTTTAT
ATCAGCTGGCGCCTTAGTTATATAACATGCATGTTATATAACTAAGGCG
CCAGCTGATATAAAACTAAGATGGCGCATGTACAACAACAACACATTAA
GAAGAGCGCCGGGGGGACGACGCAATCTGGAGTGGAAAGAACCCCCGTC
TATGCGGCTTAAAGCACGGCCAGGGAATAGTGGATCAAGTGTACTGACA
TGTGCCGGCAATGCATTGCGTCCCGAGTCACATTCGCGACTCTCGACGC
TCTTCAGAAGAGCAGCTTAGCTTCAATAGCTCAATGATATCGGAAAGAA
CATGTGAGCAAAAGGCCAGCAAAAGGCCAGGAACCGTAAAAAGGCCGCG
TTGCTGGCGTTTTTCCATAGGCTCCGCCCCCCTGACGAGCATCACAAAA
ATCGACGCTCAAGTCAGAGGTGGCGAAACCCGACAGGACTATAAAGATA
CCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGG
CGCTTTCTCATAGCTCACGCTGTAGGTATCTCAGTTCGGTGTAGGTCGT
TCGCTCCAAGCTGGGCTGTGTGCACGAACCCCCCGTTCAGCCCGACCGC
TGCGCCTTATCCGGTAACTATCGTCTTGAGTCCAACCCGGTAAGACACG
ACTTATCGCCACTGGCAGCAGCCACTGGTAACAGGATTAGCAGAGCGAG
GTATGTAGGCGGTGCTACAGAGTTCTTGAAGTGGTGGCCTAACTACGGC
TACACTAGAAGAACAGTATTTGGTATCTGCGCTCTGCTGAAGCCAGTTA
CCTTCGGAAAAAGAGTTGGTAGCTCTTGATCCGGCAAACAAACCACCGC
TGGTAGCGGTGGTTTTTTTGTTTGCAAGCAGCAGATTACGCGCAGAAAA
AAAGGATCTCAAGAAGATCCTTTGATCTTTTCTACGGGGTCTGACGCTC
AGTGGAACGAAAACTCACGTTAAGGGGCTTCAGAAGAGCGAGTCACA
TTCGCGACTCTGCAATGCATTGCCATGAGATTATCAAAAAGGATCTTCA
CCTAGATCCTTTTAAATTAAAAATGAAGTTTTAAATCAATCTAAAGTAT
ATATGAGTAAACTTGGTCTGACAGTTACCAATGCTTAATCAGTGAGGCA
CCTATCTCAGCGATCTGTCTATTTCGTTCATCCATAGTTGCCTGACTCC

-continued

```
CCGTCGTGTAGATAACTACGATACGGGAGGGCTTACCATCTGGCCCCAG

TGCTGCAATGATACCGCGAGACCCACGCTCACCGGCTCCAGATTTATCA

GCAATAAACCAGCCAGCCGGAAGGGCCGAGCGCAGAAGTGGTCCTGCAA

CTTTATCCGCCTCCATCCAGTCTATTAATTGTTGCCGGGAAGCTAGAGT

AAGTAGTTCGCCAGTTAATAGTTTGCGCAACGTTGTTGCCATTGCTACA

GGCATCGTGGTGTCACGCTCGTCGTTTGGTATGGCTTCATTCAGCTCCG

GTTCCCAACGATCAAGGCGAGTTACATGATCCCCCATGTTGTGCAAAAA

AGCGGTTAGCTCCTTCGGTCCTCCGATCGTTGTCAGAAGTAAGTTGGCC

GCAGTGTTATCACTCATGGTTATGGCAGCACTGCATAATTCTCTTACTG

TCATGCCATCCGTAAGATGCTTTTCTGTGACTGGTGAGTACTCAACCAA

GTCATTCTGAGAATAGTGTATGCGGCGACCGAGTTGCTCTTGCCCGGCG

TCAATACGGGATAATACCGCGCCACATAGCAGAACTTTAAAAGTGCTCA

TCATTGGAAAACGTTCTTCGGGGCGAAAACTCTCAAGGATCTTACCGCT

GTTGAGATCCAGTTCGATGTAACCCACTCGTGCACCCAACTGATCTTCA

GCATCTTTTACTTTCACCAGCGTTTCTGGGTGAGCAAAAACAGGAAGGC

AAAATGCCGCAAAAAAGGGAATAAGGGCGACACGGAAATGTTGAATACT

CATACTCTTCCTTTTTCAATATTATTGAAGCATTTATCAGGGTTATTGT

CTCATGAGCGGATACATATTTGAATGTATTTAGAAAAATAAACAAATAG

GGGTTCCGCGCACATTTCCCCGAAAAGTA
```

6.13 Example 13 Production and Transfection of OriL-Derived ITRs

A plasmid comprising a left and right inverted repeat derived from the human OriL sequence (SEQ ID No 29, and FIG. 4) each flanked Nt.BspQI nicking sites by was designed. The expression cassette comprised a mini human PGK promoter, a secreted turboluc ORF, SV40 poly (a). The plasmid was transformed and then amplified overnight in the NEBstable strain followed by plasmid isolation using commercial plasmid isolation kit (Nucleobond Xtra Maxi Plus EF (Macherey Nagel)) and dissolved in nuclease free water.

The plasmid was nicked as described in Example 1 using the nicking endonuclease Nt.BstNBI (6.2 U/μg DNA). The reaction mix containing the nicked plasmid was then heated to 92° C. on a thermo shaker for 3 min, in order to dissociate the OriL-derived ITR flanked transgene from the plasmid back bone and the mix was then left to cool to room temperature for 30 min to allow for ITR folding at the single stranded overhangs ends. The reaction mix was then digested with both the restriction enzyme PvuII and RecBCD as described in example 1. Finally, the reaction mix was purified using Takara NucleoSpin Gel and PCR clean-up kit and remaining ITR flanked vector was eluted according to the manufacturer's instructions. Samples from the different production steps were visualized on the agarose gel (FIG. 26). A single band of digestion resistant vector is present in lane 5. The third band in lane 4, indicates incomplete denaturing by the thermoshaker, leaving nicked plasmid in the reaction mix. Upon adding PvuII and RecBCD, the nicked plasmid was successfully digested away while the hairpin ended DNA remained. HEK293 cell were transfected with the purified construct using JetPrime according to the manufacturer protocol. Luciferase expression level in the supernatant was determined 48 h after transfection using the Gluc Glow Assay kit from NanoLight Technology.

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

---

What is claimed is:

1. A method for preparing a hairpin-ended DNA molecule in vitro, wherein the method comprises:
   a. providing a double-stranded DNA molecule, wherein the double-stranded DNA molecule comprises in 5' to 3' direction of the top strand:
      i. a first inverted repeat, wherein a first and a second restriction site for nicking endonuclease are arranged on opposite strands wherein nicking results in:
         (1) a top strand 5' single strand DNA overhang comprising the first inverted repeat or a fragment thereof upon separation of the top from the bottom strand of the first inverted repeat; or
         (2) a bottom strand 3' single strand DNA overhang comprising the first inverted repeat upon separation of the top from the bottom strand of the first inverted repeat; and
      ii. an expression cassette; and
      iii. a second inverted repeat, wherein a third and a fourth restriction site for nicking endonuclease are arranged on opposite strands wherein nicking results in:
         (1) a top strand 3' single strand DNA overhang comprising the second inverted repeat or a fragment thereof upon separation of the top from the bottom strand of the second inverted repeat; or
         (2) a bottom strand 5' single strand DNA overhang comprising the second inverted repeat upon separation of the top from the bottom strand of the second inverted repeat;
   b. incubating the double-stranded DNA molecule with one or more nicking endonucleases recognizing the four restriction sites, thereby creating the two single strand DNA overhangs as specified in step a upon separation of the top from the bottom strand; wherein the length of each single strand DNA overhang is independently at least 20 nucleotides in length;
   c. denaturing and thereby creating a DNA fragment that comprises the expression cassette and is flanked by the two single strand DNA overhangs; and
   d. annealing the single strand DNA overhangs and thereby creating a hairpinned inverted repeat on both ends of the DNA fragment resulting from step c.

2. The method of claim 1, wherein the double-stranded DNA molecule of step a is provided by:
   a. culturing a host cell in vitro comprising the double-stranded DNA molecule under conditions resulting in amplification of the double-stranded DNA molecule; and
   b. releasing the double-stranded DNA molecule from the host cell.

3. The method of claim 1, wherein the double-stranded DNA molecule of step a is provided by in vitro replication.

4. The method of claim 2, wherein the host cell is a bacterial host cell.

5. The double-stranded DNA molecule of claim 1, wherein the first, second, third, and fourth restriction sites for nicking endonuclease are all restriction sites for the same nicking endonuclease.

6. The method of claim 1, wherein the double-stranded DNA molecule of step a is characterized in that:
   a. the first and/or the second inverted repeat has a nucleotide sequence that is at least 50%, 60%, 70%, 80%, 90%, 95%, 98%, or at least 99% identical to the ITR of a parvovirus; and/or
   b. the first and/or the second inverted repeat is a modified ITR of a parvovirus.

7. The method of claim 6, wherein the parvovirus is a Dependoparvovirus, a Bocaparvovirus, an Erythroparvovirus, a Protoparvovirus, or a Tetraparvovirus.

8. The method of claim 1, wherein the double-stranded DNA molecule of step a is characterized in that:
   a. the first nick is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the 5' nucleotide of the ITR closing base pair of the first inverted repeat; and/or
   b. the second nick is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the 3' nucleotide of the ITR closing base pair of the first inverted repeat; and/or
c. the third nick is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the 5' nucleotide of the ITR closing base pair of the second inverted repeat, and the fourth nick is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the 3' nucleotide of the ITR closing base pair of the second inverted repeat; or
d. the third nick is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the 3' nucleotide of the ITR closing base pair of the second inverted repeat; and the fourth nick is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the 5' nucleotide of the ITR closing base pair of the second inverted repeat;
wherein the first nick and the fourth nick are two resulting nicks on the top strand, with the first nick being the one closer to the 5' end of the top strand and the fourth nick being the one closer to the 3' end of the top strand, and wherein the second nick and the third nick are two resulting nicks on the bottom strand, with the third nick being the one closer to the 5' end of the bottom strand and the second nick being the one closer to the 3' end of the bottom strand.

9. The method of claim 1, wherein the double-stranded DNA molecule of step a is characterized in that:
a. the first nick is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the 3' nucleotide of the ITR closing base pair of the first inverted repeat; and/or
b. the second nick is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the 5' nucleotide of the ITR closing base pair of the first inverted repeat; and/or
c. the third nick is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the 3' nucleotide of the ITR closing base pair of the second inverted repeat; and the fourth nick is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the 5' nucleotide of the ITR closing base pair of the second inverted repeat; or
d. the third nick is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the 5' nucleotide of the ITR closing base pair of the second inverted repeat; and the fourth nick is within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides from the 3' nucleotide of the ITR closing base pair of the second inverted repeat;
wherein the first nick and the fourth nick are two resulting nicks on the top strand, with the first nick being the one closer to the 5' end of the top strand and the fourth nick being the one closer to the 3' end of the top strand, and wherein the second nick and the third nick are two resulting nicks on the bottom strand, with the third nick being the one closer to the 5' end of the bottom strand and the second nick being the one closer to the 3' end of the bottom strand.

10. The method of claim 1, wherein the double-stranded DNA molecule of step a is a plasmid, wherein the plasmid
a. is circular; or
b. is linear.

11. The method of claim 10, wherein the plasmid further comprises a restriction enzyme site in the region 5' to the first inverted repeat and 3' to the second inverted repeat wherein the restriction enzyme site is not present in any of the first inverted repeat, second inverted repeat, and/or the region between the first and second inverted repeats; and
a. wherein cleavage with said restriction enzyme results in single strand DNA overhangs that do not anneal under annealing conditions of the first and/or second inverted repeat.

12. The method of claim 1, wherein the size of the expression cassette of the double-stranded DNA molecule in step a is at least 4 kb, at least 4.5 kb, at least 5 kb, at least 5.5 kb, at least 6 kb, at least 6.5 kb, at least 7 kb, at least 7.5 kb, at least 8 kb, at least 8.5 kb, at least 9 kb, at least 9.5 kb, or at least 10 kb.

13. The method of claim 1, wherein the expression cassette of the DNA fragment created in step c comprises a transgene in the range of from about 500 to about 50,000 nucleotides in length, from about 500 to about 75,000 nucleotides in length, from about 500 to about 10,000 nucleotides in length, from about 1000 to about 10,000 nucleotides in length, or from about 500 to about 5,000 nucleotides in length.

14. The method of claim 1, wherein the first and second inverted repeat of the double-stranded DNA molecule of step a each lack a functional RABS and a functional TRS.

15. The method of claim 11 further comprising,
e. incubating the double-stranded DNA molecule of step a or step b, or the fragments resulting from step d, with one or more restriction enzymes resulting in the break in the double stranded DNA molecule; and
f. incubating the fragments of the double-stranded DNA molecule with an exonuclease thereby digesting the fragments of the double-stranded DNA molecule except the fragment resulting from step d.

16. The method of claim 1 further comprising ligating the nicks of the fragment resulting from step d with a ligase to form a circular DNA.

17. The method of claim 15 further comprising after step f, repairing the nicks of the fragment resulting from step d with a ligase to form a circular DNA.

18. The method of claim 1, wherein
a. the bottom strand is in anti-sense orientation with respect to an open reading frame in the expression cassette; or
b. the top strand is in anti-sense orientation with respect to an open reading frame in the expression cassette.

19. The method of claim 1, wherein the double-stranded DNA molecule of step a is characterized in that the first inverted repeat and the second inverted repeat each comprise a palindromic sequence that is 78%, 79%, 80%, 81%, 82%, 83%, 84%, 85%, 86%, 87%, 88%, 89%, 90% 91%, 92%, 93%, 94%, 95%, 96%, 97%, 98%, or 99% identical when read forwards as when read backwards on the complementary strand, and wherein
  a. the first and the second restriction site for nicking endonuclease are at least 19, at least 20, at least 25, at least 30, at least 35, at least 40, at least 50, at least 60, at least 70, at least 80, at least 90, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, or at least 200 nucleotides apart; and/or
  b. the third and the fourth restriction sites for nicking endonuclease at least 19, at least 20, at least 25, at least 30, at least 35, at least 40, at least 50, at least 60, at least 70, at least 80, at least 90, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, or at least 200 nucleotides apart.

20. The method of claim 1, wherein either or both of said hairpinned inverted repeats of step d comprise a primary stem and an apex.

21. The method of claim 20, wherein either or both of said hairpinned inverted repeats of step d further comprise one or more
  a. branched hairpin;
  b. bulge; and/or
  c. internal loop.

22. The method of claim 1, wherein the first and second inverted repeat of the double-stranded DNA molecule of step a each further comprise a modification (e.g., deletion, substitution or addition) of at least one nucleotide in order to replace or deplete the occurrence of CpG motifs.

23. The method of claim 1, wherein the first and second inverted repeat of the double-stranded DNA molecule of step d comprises the following: The sequence from one nucleotide of the ITR closing base pair to the other nucleotide of the ITR closing base pair has a Gibbs free energy of unfolding under physiological conditions of no more than −10 kcal/mol.

24. The method of claim 1, wherein the length of each single strand DNA overhang is independently at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, or at least 100 nucleotides in length.

* * * * *

SEQUENCE LISTING

```
<160> NUMBER OF SEQ ID NOS: 338

<210> SEQ ID NO 1
<211> LENGTH: 125
<212> TYPE: DNA
<213> ORGANISM: Artificial Sequence
<220> FEATURE:
<223> OTHER INFORMATION: source: AAV1; Recogn.Site: Nb.BbvCI; Format: bl

<400> SEQUENCE: 1
ttgcccactc ccctcagcg cgctcgctcg ctcggtgggg cctgcggacc aaaggtccgc      60
agacggcaga gctctgctct gccggcccca ccgagcgagc gagcgcgctg aggggagtg     120 ggcaa                                                                125

<210> SEQ ID NO 2
<211> LENGTH: 125
<212> TYPE: DNA
<213> ORGANISM: Artificial Sequence
<220> FEATURE:
<223> OTHER INFORMATION: source: AAV1; Recogn. Site: Nb.BbvCI; Format:
      tl

<400> SEQUENCE: 2
ttgcccactc ccgctgaggg cgctcgctcg ctcggtgggg cctgcggacc aaaggtccgc      60
```
agacggcaga gctctgctct gccggcccca ccgagcgagc gagcgccctc agcgggagtg    120
ggcaa                                                                125

<210> SEQ ID NO 3
<211> LENGTH: 85
<212> TYPE: DNA
<213> ORGANISM: Artificial Sequence
<220> FEATURE:
<223> OTHER INFORMATION: exemplary ITR - ssDNA overhang

<400> SEQUENCE: 3
gctcgactcg ctcactgagg ccgggcgacc aaaggtcgcc cgacgccgg gctttgcccg    60 ggcggcctca gtgagcgagt cgagc                                          85

<210> SEQ ID NO 4
<211> LENGTH: 77
<212> TYPE: DNA
<213> ORGANISM: Artificial Sequence
<220> FEATURE:
<223> OTHER INFORMATION: exemplary ITR - ssDNA overhang

<400> SEQUENCE: 4
gctcgactca ctgaggccgg gcgaccaaag gtcgcccgac gcccgggctt tgcccgggcg    60
gcctcagtga gtcgagc                                                   77

<210> SEQ ID NO 5
<211> LENGTH: 69
<212> TYPE: DNA
<213> ORGANISM: Artificial Sequence
<220> FEATURE:
<223> OTHER INFORMATION: exemplary ITR - ssDNA overhang

<400> SEQUENCE: 5
cgctgactca ggccgggcga ccaaaggtcg cccgacgccc gggctttgcc cgggcggcct    60
gagtcagcg                                                            69

<210> SEQ ID NO 6
<211> LENGTH: 125
<212> TYPE: DNA
<213> ORGANISM: AAV serotype 4 (AAV4)
<220> FEATURE:
<223> OTHER INFORMATION: AAV4 right wt

<400> SEQUENCE: 6
ttggccacat tagctatgcg cgctcgctca ctcactcggc cctggagacc aaaggtctcc    60
agactgccgg cctctggccg gcagggccga gtgagtgagc gagcgcgcat agagggagtg    120
gccaa                                                                125

<210> SEQ ID NO 7
<211> LENGTH: 89
<212> TYPE: DNA
<213> ORGANISM: Artificial Sequence
<220> FEATURE:
<223> OTHER INFORMATION: exemplary ITR - ssDNA overhang

<400> SEQUENCE: 7
cgcgctcgct cgctcactga ggccgggcga ccaaaggtcg cccgacgccc gggctttgcc    60
cgggcggcct cagtgagcga gcgagcgcg                                      89

<210> SEQ ID NO 8
<211> LENGTH: 71

```
<212> TYPE: DNA
<213> ORGANISM: Artificial Sequence
<220> FEATURE:
<223> OTHER INFORMATION: exemplary ITR - ssDNA overhang

<400> SEQUENCE: 8
tcgctcactg aggccgggcg accaaaggtc gcccgacgcc cgggctttgc ccgggcggcc      60
tcagtgagcg a                                                          71

<210> SEQ ID NO 9
<211> LENGTH: 59
<212> TYPE: DNA
<213> ORGANISM: Artificial Sequence
<220> FEATURE:
<223> OTHER INFORMATION: exemplary ITR - ssDNA overhang

<400> SEQUENCE: 9
actgaggccg gcgaccaaa ggtcgcccga cgcccgggct tgcccgggc ggcctcagt        59

<210> SEQ ID NO 10
<211> LENGTH: 51
<212> TYPE: DNA
<213> ORGANISM: Artificial Sequence
<220> FEATURE:
<223> OTHER INFORMATION: exemplary ITR - ssDNA overhang

<400> SEQUENCE: 10
aggccgggcg accaaaggtc gcccgacgcc cgggctttgc ccgggcggcc t               51

<210> SEQ ID NO 11
<211> LENGTH: 125
<212> TYPE: DNA
<213> ORGANISM: Artificial Sequence
<220> FEATURE:
<223> OTHER INFORMATION: AAV1 Left ITR

<400> SEQUENCE: 11
ttgcccactc cctctctgcg cgctcgctcg ctcggtgggg cctgcggacc aaaggtccgc      60
agacggcaga gctctgctct gccggcccca ccgagcgagc gagcgcgcag agagggagtg     120
ggcaa                                                                 125

<210> SEQ ID NO 12
<211> LENGTH: 125
<212> TYPE: DNA
<213> ORGANISM: Artificial Sequence
<220> FEATURE:
<223> OTHER INFORMATION: AAV1 Right ITR

<400> SEQUENCE: 12
ttgcccactc cctctctgcg cgctcgctcg ctcggtgggg cctgcggacc aaaggtccgc      60
agacggcaga gctctgctct gccggcccca ccgagcgagc gagcgcgcag agagggagtg     120
ggcaa                                                                 125

<210> SEQ ID NO 13
<211> LENGTH: 125
<212> TYPE: DNA
<213> ORGANISM: Artificial Sequence
<220> FEATURE:
<223> OTHER INFORMATION: AAV2 Left ITR

<400> SEQUENCE: 13
ttggccactc cctctctgcg cgctcgctcg ctcactgagg ccgggcgacc aaaggtcgcc      60
```

```
cgacgcccgg gctttgcccg ggcggcctca gtgagcgagc gagcgcgcag agagggagtg    120
gccaa                                                                125

<210> SEQ ID NO 14
<211> LENGTH: 125
<212> TYPE: DNA
<213> ORGANISM: Artificial Sequence
<220> FEATURE:
<223> OTHER INFORMATION: AAV2 Right ITR

<400> SEQUENCE: 14
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg    120
gccaa                                                                125

<210> SEQ ID NO 15
<211> LENGTH: 125
<212> TYPE: DNA
<213> ORGANISM: Artificial Sequence
<220> FEATURE:
<223> OTHER INFORMATION: AAV3 Left ITR

<400> SEQUENCE: 15
ttggccactc cctctatgcg cactcgctcg ctcggtgggg cctggcgacc aaaggtcgcc    60
agacggacgt gctttgcacg tccggcccca ccgagcgagc gagtgcgcat agagggagtg    120
gccaa                                                                125

<210> SEQ ID NO 16
<211> LENGTH: 125
<212> TYPE: DNA
<213> ORGANISM: Artificial Sequence
<220> FEATURE:
<223> OTHER INFORMATION: AAV3 Right ITR

<400> SEQUENCE: 16
ttggccactc cctctatgcg cactcgctcg ctcggtgggg cctggcgacc aaaggtcgcc    60
agacggacgt gctttgcacg tccggcccca ccgagcgagc gagtgcgcat agagggagtg    120
gccaa                                                                125

<210> SEQ ID NO 17
<211> LENGTH: 125
<212> TYPE: DNA
<213> ORGANISM: Artificial Sequence
<220> FEATURE:
<223> OTHER INFORMATION: AAV4 Left ITR

<400> SEQUENCE: 17
ttggccactc cctctatgcg cgctcgctca ctcactcggc cctggagacc aaaggtctcc    60
agactgccgg cctctggccg gcagggccga gtgagtgagc gagcgcgcat agagggagtg    120
gccaa                                                                125

<210> SEQ ID NO 18
<211> LENGTH: 112
<212> TYPE: DNA
<213> ORGANISM: Artificial Sequence
<220> FEATURE:
<223> OTHER INFORMATION: AAV4 Right ITR

<400> SEQUENCE: 18
ctatgcgcgc tcgctcactc actcggccct ggagaccaaa ggtctccaga ctgccggcct    60
```

-continued ctggccggca gggccgagtg agtgagcgag cgcgcataga gggagtggcc aa         112

<210> SEQ ID NO 19
<211> LENGTH: 137
<212> TYPE: DNA
<213> ORGANISM: Artificial Sequence
<220> FEATURE:
<223> OTHER INFORMATION: AAV5 (accession No. NC_006152) Left ITR

<400> SEQUENCE: 19 ctctccccc tgtcgcgttc gctcgctcgc tggctcgttt gggggggtgg cagctcaaag   60
agctgccaga cgacggccct ctggccgtcg cccccccaaa cgagccagcg agcgagcgaa  120
cgcgacaggg gggagag                                                137

<210> SEQ ID NO 20
<211> LENGTH: 137
<212> TYPE: DNA
<213> ORGANISM: Artificial Sequence
<220> FEATURE:
<223> OTHER INFORMATION: AAV5 (accession No. NC_006152) Right ITR

<400> SEQUENCE: 20 ctctccccc tgtcgcgttc gctcgctcgc tggctcgttt gggggggtgg cagctcaaag   60
agctgccaga cgacggccct ctggccgtcg cccccccaaa cgagccagcg agcgagcgaa  120
cgcgacaggg gggagag                                                137

<210> SEQ ID NO 21
<211> LENGTH: 125
<212> TYPE: DNA
<213> ORGANISM: Artificial Sequence
<220> FEATURE:
<223> OTHER INFORMATION: AAV7 (accession No. NC_006260) Left ITR

<400> SEQUENCE: 21
ttggccactc cctctatgcg cgctcgctcg ctcggtgggg cctgcggacc aaaggtccgc   60
agacggcaga gctctgctct gccggcccca ccgagcgagc gagcgcgcat agagggagtg  120
gccaa                                                              125

<210> SEQ ID NO 22
<211> LENGTH: 125
<212> TYPE: DNA
<213> ORGANISM: Artificial Sequence
<220> FEATURE:
<223> OTHER INFORMATION: AAV7 (accession No. NC_006260) Right ITR

<400> SEQUENCE: 22
ttggccactc cctctatgcg cgctcgctcg ctcggtgggg cctgcggacc aaaggtccgc   60
agacggcaga gctctgctct gccggcccca ccgagcgagc gagcgcgcat agagggagtg  120
gccaa                                                              125

<210> SEQ ID NO 23
<211> LENGTH: 140
<212> TYPE: DNA
<213> ORGANISM: Artificial Sequence
<220> FEATURE:
<223> OTHER INFORMATION: HBOV (accession No. JQ923422) Left ITR

<400> SEQUENCE: 23
gtggttgtac agacgccatc ttggaatcca atatgtctgc cggctcagtc atgcctgcgc   60
tgcgcgcagc gcgctgcgcg cgcgcatgat ctaatcgccg gcagacatat tggattccaa    120
gatggcgtct gtacaaccac                                                140

<210> SEQ ID NO 24
<211> LENGTH: 200
<212> TYPE: DNA
<213> ORGANISM: Artificial Sequence
<220> FEATURE:
<223> OTHER INFORMATION: HBOV (accession No. JQ923422) Right ITR

<400> SEQUENCE: 24
ttgcttatgc aatcgcgaaa ctctatatct tttaatgtgt tgttgttgta catgcgccat    60
cttagtttta tatcagctgg cgccttagtt atataacatg catgttatat aactaaggcg    120
ccagctgata taaaactaag atggcgcatg tacaacaaca acacattaaa agatatagag    180
tttcgcgatt gcataagcaa                                                200

<210> SEQ ID NO 25
<211> LENGTH: 89
<212> TYPE: DNA
<213> ORGANISM: Artificial Sequence
<220> FEATURE:
<223> OTHER INFORMATION: hB19 (accession No. AY386330) Left ITR

<400> SEQUENCE: 25
tgggccagct tgcttggggt tgccttgaca ctaagacaag cggcgcgccg cttgatctta    60
gtggcacgtc aaccccaagc gctggccca                                      89

<210> SEQ ID NO 26
<211> LENGTH: 89
<212> TYPE: DNA
<213> ORGANISM: Artificial Sequence
<220> FEATURE:
<223> OTHER INFORMATION: hB19 (accession No. AY386330) Right ITR

<400> SEQUENCE: 26
tgggccagcg cttggggttg acgtgccact aagatcaagc ggcgcgccgc ttgtcttagt    60
gtcaaggcaa ccccaagcaa gctggccca                                      89

<210> SEQ ID NO 27
<211> LENGTH: 70
<212> TYPE: DNA
<213> ORGANISM: Artificial Sequence
<220> FEATURE:
<223> OTHER INFORMATION: exemplary ITR - ssDNA overhang

<400> SEQUENCE: 27
ccatgcatcc ggctttaaac gggcaactgc gtctcattca cgttagagac tacaaccgtc    60
ggatgcatgg                                                           70

<210> SEQ ID NO 28
<211> LENGTH: 102
<212> TYPE: DNA
<213> ORGANISM: Artificial Sequence
<220> FEATURE:
<223> OTHER INFORMATION: exemplary ITR - ssDNA overhang

<400> SEQUENCE: 28
ttcaaacctg ccgggggaga agcggcgttt tttcccggcc gccgcttctc ttcttctccc    60
gccgccggga aaaaggcgg gagaagcccc ggcaggtttg aa                        102

```
<210> SEQ ID NO 29
<211> LENGTH: 92
<212> TYPE: DNA
<213> ORGANISM: Artificial Sequence
<220> FEATURE:
<223> OTHER INFORMATION: exemplary ITR - ssDNA overhang

<400> SEQUENCE: 29
gtccgggcca tgcttcaaac ctgccggggc ttctcccgcc ttttttcccg gcggcgggag      60
aagtagattt ctcgtacctg catggcccgg ac                                   92

<210> SEQ ID NO 30
<211> LENGTH: 50
<212> TYPE: DNA
<213> ORGANISM: Artificial Sequence
<220> FEATURE:
<223> OTHER INFORMATION: AAV2 Right ITR

<400> SEQUENCE: 30
cttctcccgc cgccgggaaa aaaggcggga gaagccccgg caggtttgaa                 50

<210> SEQ ID NO 31
<211> LENGTH: 87
<212> TYPE: DNA
<213> ORGANISM: Artificial Sequence
<220> FEATURE:
<223> OTHER INFORMATION: exemplary ITR - ssDNA overhang

<400> SEQUENCE: 31
ccagcgcttg gggttgacgt gccactaaga tcaagcggcg cgcgcgcgcc gcttgtctta     60
gtgtcaaggc aaccccaagc aagctgg                                         87

<210> SEQ ID NO 32
<211> LENGTH: 113
<212> TYPE: DNA
<213> ORGANISM: Artificial Sequence
<220> FEATURE:
<223> OTHER INFORMATION: exemplary ITR - ssDNA overhang

<400> SEQUENCE: 32
ggttgactct gggccagctt gcttggggtt gccttgacac taagacaagc ggcgcgcgcg     60
cgccgcttga tcttagtggc acgtcaaccc caagcgctgg cccagagtca acc           113

<210> SEQ ID NO 33
<211> LENGTH: 83
<212> TYPE: DNA
<213> ORGANISM: Artificial Sequence
<220> FEATURE:
<223> OTHER INFORMATION: exemplary ITR - ssDNA overhang

<400> SEQUENCE: 33
cgcgctcgct cgctcactga ggccgggcca aggcccgac gcccgggctt tgcccgggcg      60
gcctcagtga gcgagcgagc gcg                                             83

<210> SEQ ID NO 34
<211> LENGTH: 83
<212> TYPE: DNA
<213> ORGANISM: Artificial Sequence
<220> FEATURE:
<223> OTHER INFORMATION: exemplary ITR - ssDNA overhang

<400> SEQUENCE: 34
cgcgctcgct cgctcactga ggccgggcga ccaaaggtcg cccgacgccc gtttcgggcg     60
```
gcctcagtga gcgagcgagc gcg          83

<210> SEQ ID NO 35
<211> LENGTH: 67
<212> TYPE: DNA
<213> ORGANISM: Artificial Sequence
<220> FEATURE:
<223> OTHER INFORMATION: exemplary ITR - ssDNA overhang

<400> SEQUENCE: 35
cgcgctcgct cgctcactga ggccgcccgg gctttgcccg ggcggcctca gtgagcgagc   60
gagcgcg                                                            67

<210> SEQ ID NO 36
<211> LENGTH: 125
<212> TYPE: DNA
<213> ORGANISM: Artificial Sequence
<220> FEATURE:
<223> OTHER INFORMATION: source: AAV2; Recogn.Site: Nb.BbvCI; Format: bl

<400> SEQUENCE: 36
ttggccactc ccctcagcg cgctcgctcg ctcactgagg ccgggcgacc aaaggtcgcc   60
cgacgcccgg gctttgcccg ggcggcctca gtgagcgagc gagcgcgctg agggggagtg  120
gccaa                                                              125

<210> SEQ ID NO 37
<211> LENGTH: 125
<212> TYPE: DNA
<213> ORGANISM: Artificial Sequence
<220> FEATURE:
<223> OTHER INFORMATION: source: AAV2; Recogn.Site: Nb.BbvCI; Format: tl

<400> SEQUENCE: 37
ttggccactc ccgctgaggg cgctcgctcg ctcactgagg ccgggcgacc aaaggtcgcc   60
cgacgcccgg gctttgcccg ggcggcctca gtgagcgagc gagcgccctc agcgggagtg  120
gccaa                                                              125

<210> SEQ ID NO 38
<211> LENGTH: 125
<212> TYPE: DNA
<213> ORGANISM: Artificial Sequence
<220> FEATURE:
<223> OTHER INFORMATION: source: AAV3; Recogn.Site: Nb.BbvCI; Format: bl

<400> SEQUENCE: 38
ttggccactc ccctcagcg cactcgctcg ctcggtgggg cctggcgacc aaaggtcgcc   60
agacggacgt gctttgcacg tccggcccca ccgagcgagc gagtgcgctg agggggagtg  120
gccaa                                                              125

<210> SEQ ID NO 39
<211> LENGTH: 125
<212> TYPE: DNA
<213> ORGANISM: Artificial Sequence
<220> FEATURE:
<223> OTHER INFORMATION: source: AAV3; Recogn.Site: Nb.BbvCI; Format: tl

<400> SEQUENCE: 39
ttggccactc ccgctgaggg cactcgctcg ctcggtgggg cctggcgacc aaaggtcgcc   60
agacggacgt gctttgcacg tccggcccca ccgagcgagc gagtgccctc agcgggagtg  120
gccaa                                                              125

<210> SEQ ID NO 40
<211> LENGTH: 125
<212> TYPE: DNA
<213> ORGANISM: Artificial Sequence
<220> FEATURE:
<223> OTHER INFORMATION: source: AAV4 left; Recogn.Site: Nb.BbvCI;
      Format: bl

<400> SEQUENCE: 40
ttggccactc cccctcagcg cgctcgctca ctcactcggc cctggagacc aaaggtctcc    60
agactgccgg cctctggccg gcagggccga gtgagtgagc gagcgcgctg aggggagtg    120 gccaa                                                               125

<210> SEQ ID NO 41
<211> LENGTH: 125
<212> TYPE: DNA
<213> ORGANISM: Artificial Sequence
<220> FEATURE:
<223> OTHER INFORMATION: source: AAV4 left; Recogn.Site: Nb.BbvCI;
      Format: tl

<400> SEQUENCE: 41
ttggccactc ccgctgaggg cgctcgctca ctcactcggc cctggagacc aaaggtctcc    60
agactgccgg cctctggccg gcagggccga gtgagtgagc gagcgccctc agcgggagtg    120
gccaa                                                               125

<210> SEQ ID NO 42
<211> LENGTH: 125
<212> TYPE: DNA
<213> ORGANISM: Artificial Sequence
<220> FEATURE:
<223> OTHER INFORMATION: source: AAV4 right; Recogn.Site: Nb.BbvCI;
      Format: bl

<400> SEQUENCE: 42
ttggccacat tacctcagcg cgctcgctca ctcactcggc cctggagacc aaaggtctcc    60
agactgccgg cctctggccg gcagggccga gtgagtgagc gagcgcgctg aggggagtg    120 gccaa                                                               125

<210> SEQ ID NO 43
<211> LENGTH: 125
<212> TYPE: DNA
<213> ORGANISM: Artificial Sequence
<220> FEATURE:
<223> OTHER INFORMATION: source: AAV4 right; Recogn.Site: Nb.BbvCI;
      Format: tl

<400> SEQUENCE: 43
ttggccacat tagctgaggg cgctcgctca ctcactcggc cctggagacc aaaggtctcc    60
agactgccgg cctctggccg gcagggccga gtgagtgagc gagcgccctc agcgggagtg    120
gccaa                                                               125

<210> SEQ ID NO 44
<211> LENGTH: 137
<212> TYPE: DNA
<213> ORGANISM: Artificial Sequence
<220> FEATURE:
<223> OTHER INFORMATION: source: AAV5; Recogn.Site: Nb.BbvCI; Format: bl

<400> SEQUENCE: 44
ctctcccctc agccgcgttc gctcgctcgc tggctcgttt ggggggggtgg cagctcaaag    60 agctgccaga cgacggccct ctggccgtcg cccccccaaa cgagccagcg agcgagcgaa   120
cgcggctgag gggagag                                                  137

<210> SEQ ID NO 45
<211> LENGTH: 137
<212> TYPE: DNA
<213> ORGANISM: Artificial Sequence
<220> FEATURE:
<223> OTHER INFORMATION: source: AAV5; Recogn.Site: Nb.BbvCI; Format: tl

<400> SEQUENCE: 45
ctctccccgc tgaggcgttc gctcgctcgc tggctcgttt ggggggggtgg cagctcaaag    60 agctgccaga cgacggccct ctggccgtcg cccccccaaa cgagccagcg agcgagcgaa   120
cgcctcagcg gggagag                                                  137

<210> SEQ ID NO 46
<211> LENGTH: 125
<212> TYPE: DNA
<213> ORGANISM: Artificial Sequence
<220> FEATURE:
<223> OTHER INFORMATION: source: AAV7; Recogn.Site: Nb.BbvCI; Format: bl

<400> SEQUENCE: 46
ttggccactc ccctcagcg cgctcgctcg ctcggtgggg cctgcggacc aaaggtccgc    60
agacggcaga gctctgctct gccggcccca ccgagcgagc gagcgcgctg aggggagtg   120 gccaa                                                               125

<210> SEQ ID NO 47
<211> LENGTH: 125
<212> TYPE: DNA
<213> ORGANISM: Artificial Sequence
<220> FEATURE:
<223> OTHER INFORMATION: source: AAV7; Recogn.Site: Nb.BbvCI; Format: tl

<400> SEQUENCE: 47
ttggccactc ccgctgaggg cgctcgctcg ctcggtgggg cctgcggacc aaaggtccgc    60
agacggcaga gctctgctct gccggcccca ccgagcgagc gagcgccctc agcgggagtg   120
gccaa                                                               125

<210> SEQ ID NO 48
<211> LENGTH: 125
<212> TYPE: DNA
<213> ORGANISM: Artificial Sequence
<220> FEATURE:
<223> OTHER INFORMATION: source: AAV1; Recogn.Site: Nb.BsmI; Format: bl

<400> SEQUENCE: 48
ttgcccactc cctgaatgcg cgctcgctcg ctcggtgggg cctgcggacc aaaggtccgc    60
agacggcaga gctctgctct gccggcccca ccgagcgagc gagcgcgcat tcagggagtg   120
ggcaa                                                               125

<210> SEQ ID NO 49
<211> LENGTH: 125
<212> TYPE: DNA
<213> ORGANISM: Artificial Sequence
<220> FEATURE:
<223> OTHER INFORMATION: source: AAV1; Recogn.Site: Nb.BsmI; Format: tl

<400> SEQUENCE: 49

```
ttgcccactc cctctctgcg cattcgctcg ctcggtgggg cctgcggacc aaaggtccgc    60
agacggcaga gctctgctct gccggcccca ccgagcgagc gaatgcgcag agagggagtg   120
ggcaa                                                              125

<210> SEQ ID NO 50
<211> LENGTH: 125
<212> TYPE: DNA
<213> ORGANISM: Artificial Sequence
<220> FEATURE:
<223> OTHER INFORMATION: source: AAV2; Recogn.Site: Nb.BsmI; Format: bl

<400> SEQUENCE: 50
ttggccactc cctgaatgcg cgctcgctcg ctcactgagg ccgggcgacc aaaggtcgcc    60
cgacgcccgg gctttgcccg ggcggcctca gtgagcgagc gagcgcgcat tcagggagtg   120
gccaa                                                              125

<210> SEQ ID NO 51
<211> LENGTH: 125
<212> TYPE: DNA
<213> ORGANISM: Artificial Sequence
<220> FEATURE:
<223> OTHER INFORMATION: source: AAV2; Recogn.Site: Nb.BsmI; Format: tl

<400> SEQUENCE: 51
ttggccactc cctctctgcg cattcgctcg ctcactgagg ccgggcgacc aaaggtcgcc    60
cgacgcccgg gctttgcccg ggcggcctca gtgagcgagc gaatgcgcag agagggagtg   120
gccaa                                                              125

<210> SEQ ID NO 52
<211> LENGTH: 125
<212> TYPE: DNA
<213> ORGANISM: Artificial Sequence
<220> FEATURE:
<223> OTHER INFORMATION: source: AAV3; Recogn.Site: Nb.BsmI; Format: bl

<400> SEQUENCE: 52
ttggccactc cctgaatgcg cactcgctcg ctcggtgggg cctggcgacc aaaggtcgcc    60
agacggacgt gctttgcacg tccggcccca ccgagcgagc gagtgcgcat tcagggagtg   120
gccaa                                                              125

<210> SEQ ID NO 53
<211> LENGTH: 125
<212> TYPE: DNA
<213> ORGANISM: Artificial Sequence
<220> FEATURE:
<223> OTHER INFORMATION: source: AAV3; Recogn.Site: Nb.BsmI; Format: tl

<400> SEQUENCE: 53
ttggccactc cctctatgcg cattcgctcg ctcggtgggg cctggcgacc aaaggtcgcc    60
agacggacgt gctttgcacg tccggcccca ccgagcgagc gaatgcgcat agagggagtg   120
gccaa                                                              125

<210> SEQ ID NO 54
<211> LENGTH: 125
<212> TYPE: DNA
<213> ORGANISM: Artificial Sequence
<220> FEATURE:
<223> OTHER INFORMATION: source: AAV4 left; Recogn.Site: Nb.BsmI;
      Format: bl
```

```
<400> SEQUENCE: 54
ttggccactc cctgaatgcg cgctcgctca ctcactcggc cctggagacc aaaggtctcc      60
agactgccgg cctctggccg gcagggccga gtgagtgagc gagcgcgcat tcagggagtg     120
gccaa                                                                 125

<210> SEQ ID NO 55
<211> LENGTH: 125
<212> TYPE: DNA
<213> ORGANISM: Artificial Sequence
<220> FEATURE:
<223> OTHER INFORMATION: source: AAV4 left; Recogn.Site: Nb.BsmI;
      Format: tl

<400> SEQUENCE: 55
ttggccactc cctctatgcg cattcgctca ctcactcggc cctggagacc aaaggtctcc      60
agactgccgg cctctggccg gcagggccga gtgagtgagc gaatgcgcat agagggagtg     120
gccaa                                                                 125

<210> SEQ ID NO 56
<211> LENGTH: 125
<212> TYPE: DNA
<213> ORGANISM: Artificial Sequence
<220> FEATURE:
<223> OTHER INFORMATION: source: AAV4 right; Recogn.Site: Nb.BsmI;
      Format: bl

<400> SEQUENCE: 56
ttggccacat taggaatgcg cgctcgctca ctcactcggc cctggagacc aaaggtctcc      60
agactgccgg cctctggccg gcagggccga gtgagtgagc gagcgcgcat tcagggagtg     120
gccaa                                                                 125

<210> SEQ ID NO 57
<211> LENGTH: 125
<212> TYPE: DNA
<213> ORGANISM: Artificial Sequence
<220> FEATURE:
<223> OTHER INFORMATION: source: AAV4 right; Recogn.Site: Nb.BsmI;
      Format: tl

<400> SEQUENCE: 57
ttggccacat tagctatgcg cattcgctca ctcactcggc cctggagacc aaaggtctcc      60
agactgccgg cctctggccg gcagggccga gtgagtgagc gaatgcgcat agagggagtg     120
gccaa                                                                 125

<210> SEQ ID NO 58
<211> LENGTH: 137
<212> TYPE: DNA
<213> ORGANISM: Artificial Sequence
<220> FEATURE:
<223> OTHER INFORMATION: source: AAV5; Recogn.Site: Nb.BsmI; Format: bl

<400> SEQUENCE: 58
ctctccccga atgcgcgttc gctcgctcgc tggctcgttt gggggggtgg cagctcaaag      60
agctgccaga cgacggccct ctggccgtcg ccccccaaa cgagccagcg agcgagcgaa     120
cgcgcattcg gggagag                                                    137

<210> SEQ ID NO 59
<211> LENGTH: 137
```

<212> TYPE: DNA
<213> ORGANISM: Artificial Sequence
<220> FEATURE:
<223> OTHER INFORMATION: source: AAV5; Recogn.Site: Nb.BsmI; Format: tl

<400> SEQUENCE: 59
ctctcccccc tgtcgcattc gctcgctcgc tggctcgttt ggggggggtgg cagctcaaag    60 agctgccaga cgacggccct ctggccgtcg ccccccaaa cgagccagcg agcgagcgaa    120
tgcgacaggg gggagag                                                   137

<210> SEQ ID NO 60
<211> LENGTH: 125
<212> TYPE: DNA
<213> ORGANISM: Artificial Sequence
<220> FEATURE:
<223> OTHER INFORMATION: source: AAV7; Recogn.Site: Nb.BsmI; Format: bl

<400> SEQUENCE: 60
ttggccactc cctgaatgcg cgctcgctcg ctcggtgggg cctgcggacc aaaggtccgc    60
agacggcaga gctctgctct gccggcccca ccgagcgagc gagcgcgcat tcagggagtg    120
gccaa                                                                125

<210> SEQ ID NO 61
<211> LENGTH: 125
<212> TYPE: DNA
<213> ORGANISM: Artificial Sequence
<220> FEATURE:
<223> OTHER INFORMATION: source: AAV7; Recogn.Site: Nb.BsmI; Format: tl

<400> SEQUENCE: 61
ttggccactc cctctatgcg cattcgctcg ctcggtgggg cctgcggacc aaaggtccgc    60
agacggcaga gctctgctct gccggcccca ccgagcgagc gaatgcgcat agagggagtg    120
gccaa                                                                125

<210> SEQ ID NO 62
<211> LENGTH: 125
<212> TYPE: DNA
<213> ORGANISM: Artificial Sequence
<220> FEATURE:
<223> OTHER INFORMATION: source: AAV1; Recogn.Site: Nb.BsrDI; Format: bl

<400> SEQUENCE: 62
ttgcccactc ccgcaatgcg cgctcgctcg ctcggtgggg cctgcggacc aaaggtccgc    60
agacggcaga gctctgctct gccggcccca ccgagcgagc gagcgcgcat tgcgggagtg    120
ggcaa                                                                125

<210> SEQ ID NO 63
<211> LENGTH: 125
<212> TYPE: DNA
<213> ORGANISM: Artificial Sequence
<220> FEATURE:
<223> OTHER INFORMATION: source: AAV1; Recogn.Site: Nb.BsrDI; Format: tl

<400> SEQUENCE: 63
ttgcccactc cctcattgcg cgctcgctcg ctcggtgggg cctgcggacc aaaggtccgc    60
agacggcaga gctctgctct gccggcccca ccgagcgagc gagcgcgcaa tgagggagtg    120
ggcaa                                                                125

<210> SEQ ID NO 64

```
<211> LENGTH: 125
<212> TYPE: DNA
<213> ORGANISM: Artificial Sequence
<220> FEATURE:
<223> OTHER INFORMATION: source: AAV2; Recogn.Site: Nb.BsrDI; Format: bl

<400> SEQUENCE: 64
ttggccactc ccgcaatgcg cgctcgctcg ctcactgagg ccgggcgacc aaaggtcgcc      60
cgacgcccgg gctttgcccg ggcggcctca gtgagcgagc gagcgcgcat tgcgggagtg     120
gccaa                                                                 125

<210> SEQ ID NO 65
<211> LENGTH: 125
<212> TYPE: DNA
<213> ORGANISM: Artificial Sequence
<220> FEATURE:
<223> OTHER INFORMATION: source: AAV2; Recogn.Site: Nb.BsrDI; Format: tl

<400> SEQUENCE: 65
ttggccactc cctcattgcg cgctcgctcg ctcactgagg ccgggcgacc aaaggtcgcc      60
cgacgcccgg gctttgcccg ggcggcctca gtgagcgagc gagcgcgcaa tgagggagtg     120
gccaa                                                                 125

<210> SEQ ID NO 66
<211> LENGTH: 125
<212> TYPE: DNA
<213> ORGANISM: Artificial Sequence
<220> FEATURE:
<223> OTHER INFORMATION: source: AAV3; Recogn.Site: Nb.BsrDI; Format: bl

<400> SEQUENCE: 66
ttggccactc ccgcaatgcg cactcgctcg ctcggtgggg cctggcgacc aaaggtcgcc      60
agacggacgt gctttgcacg tccggcccca ccgagcgagc gagtgcgcat tgcgggagtg     120
gccaa                                                                 125

<210> SEQ ID NO 67
<211> LENGTH: 125
<212> TYPE: DNA
<213> ORGANISM: Artificial Sequence
<220> FEATURE:
<223> OTHER INFORMATION: source: AAV3; Recogn.Site: Nb.BsrDI; Format: tl

<400> SEQUENCE: 67
ttggccactc cctcattgcg cactcgctcg ctcggtgggg cctggcgacc aaaggtcgcc      60
agacggacgt gctttgcacg tccggcccca ccgagcgagc gagtgcgcaa tgagggagtg     120
gccaa                                                                 125

<210> SEQ ID NO 68
<211> LENGTH: 125
<212> TYPE: DNA
<213> ORGANISM: Artificial Sequence
<220> FEATURE:
<223> OTHER INFORMATION: source: AAV4 left; Recogn.Site: Nb.BsrDI;
      Format: bl

<400> SEQUENCE: 68
ttggccactc ccgcaatgcg cgctcgctca ctcactcggc cctggagacc aaaggtctcc      60
agactgccgg cctctggccg gcagggccga gtgagtgagc gagcgcgcat tgcgggagtg     120
gccaa                                                                 125
```

<210> SEQ ID NO 69
<211> LENGTH: 125
<212> TYPE: DNA
<213> ORGANISM: Artificial Sequence
<220> FEATURE:
<223> OTHER INFORMATION: source: AAV4 left; Recogn.Site: Nb.BsrDI;
      Format: tl

<400> SEQUENCE: 69
ttggccactc cctcattgcg cgctcgctca ctcactcggc cctggagacc aaaggtctcc    60
agactgccgg cctctggccg gcagggccga gtgagtgagc gagcgcgcaa tgagggagtg   120
gccaa                                                               125

<210> SEQ ID NO 70
<211> LENGTH: 125
<212> TYPE: DNA
<213> ORGANISM: Artificial Sequence
<220> FEATURE:
<223> OTHER INFORMATION: source: AAV4 right; Recogn.Site: Nb.BsrDI;
      Format: bl

<400> SEQUENCE: 70
ttggccacat tagcaatgcg cgctcgctca ctcactcggc cctggagacc aaaggtctcc    60
agactgccgg cctctggccg gcagggccga gtgagtgagc gagcgcgcat tgcgggagtg   120
gccaa                                                               125

<210> SEQ ID NO 71
<211> LENGTH: 125
<212> TYPE: DNA
<213> ORGANISM: Artificial Sequence
<220> FEATURE:
<223> OTHER INFORMATION: source: AAV4 right; Recogn.Site: Nb.BsrDI;
      Format: tl

<400> SEQUENCE: 71
ttggccacat tagcattgcg cgctcgctca ctcactcggc cctggagacc aaaggtctcc    60
agactgccgg cctctggccg gcagggccga gtgagtgagc gagcgcgcaa tgagggagtg   120
gccaa                                                               125

<210> SEQ ID NO 72
<211> LENGTH: 137
<212> TYPE: DNA
<213> ORGANISM: Artificial Sequence
<220> FEATURE:
<223> OTHER INFORMATION: source: AAV5; Recogn.Site: Nb.BsrDI; Format: bl

<400> SEQUENCE: 72
ctctccgcaa tgtcgcgttc gctcgctcgc tggctcgttt ggggggggtgg cagctcaaag    60 agctgccaga cgacggccct ctggccgtcg ccccccaaa cgagccagcg agcgagcgaa   120
cgcgacattg cggagag                                                  137

<210> SEQ ID NO 73
<211> LENGTH: 137
<212> TYPE: DNA
<213> ORGANISM: Artificial Sequence
<220> FEATURE:
<223> OTHER INFORMATION: source: AAV5; Recogn.Site: Nb.BsrDI; Format: tl

<400> SEQUENCE: 73
ctctccccca ttgcgcgttc gctcgctcgc tggctcgttt ggggggggtgg cagctcaaag    60 agctgccaga cgacggcccct ctggccgtcg ccccccaaa cgagccagcg agcgagcgaa    120
cgcgcaatgg gggagag                                                    137

<210> SEQ ID NO 74
<211> LENGTH: 125
<212> TYPE: DNA
<213> ORGANISM: Artificial Sequence
<220> FEATURE:
<223> OTHER INFORMATION: source: AAV7; Recogn.Site: Nb.BsrDI; Format: bl

<400> SEQUENCE: 74
ttggccactc ccgcaatgcg cgctcgctcg ctcggtgggg cctgcggacc aaaggtccgc    60
agacggcaga gctctgctct gccggcccca ccgagcgagc gagcgcgcat tgcgggagtg    120
gccaa                                                                125

<210> SEQ ID NO 75
<211> LENGTH: 125
<212> TYPE: DNA
<213> ORGANISM: Artificial Sequence
<220> FEATURE:
<223> OTHER INFORMATION: source: AAV7; Recogn.Site: Nb.BsrDI; Format: tl

<400> SEQUENCE: 75
ttggccactc cctcattgcg cgctcgctcg ctcggtgggg cctgcggacc aaaggtccgc    60
agacggcaga gctctgctct gccggcccca ccgagcgagc gagcgcgcaa tgagggagtg    120
gccaa                                                                125

<210> SEQ ID NO 76
<211> LENGTH: 125
<212> TYPE: DNA
<213> ORGANISM: Artificial Sequence
<220> FEATURE:
<223> OTHER INFORMATION: source: AAV1; Recogn.Site: Nb.BssSI; Format: bl

<400> SEQUENCE: 76
ttgcccacga gctctctgcg cgctcgctcg ctcggtgggg cctgcggacc aaaggtccgc    60
agacggcaga gctctgctct gccggcccca ccgagcgagc gagcgcgcag agagctcgtg    120
ggcaa                                                                125

<210> SEQ ID NO 77
<211> LENGTH: 125
<212> TYPE: DNA
<213> ORGANISM: Artificial Sequence
<220> FEATURE:
<223> OTHER INFORMATION: source: AAV1; Recogn.Site: Nb.BssSI; Format: tl

<400> SEQUENCE: 77
ttgcccactc cctcgtggcg cgctcgctcg ctcggtgggg cctgcggacc aaaggtccgc    60
agacggcaga gctctgctct gccggcccca ccgagcgagc gagcgcgcca cgagggagtg    120
ggcaa                                                                125

<210> SEQ ID NO 78
<211> LENGTH: 125
<212> TYPE: DNA
<213> ORGANISM: Artificial Sequence
<220> FEATURE:
<223> OTHER INFORMATION: source: AAV2; Recogn.Site: Nb.BssSI; Format: bl

<400> SEQUENCE: 78
ttggccacga gctctctgcg cgctcgctcg ctcactgagg ccgggcgacc aaaggtcgcc    60

```
cgacgcccgg gctttgcccg ggcggcctca gtgagcgagc gagcgcgcag agagctcgtg    120
gccaa                                                              125

<210> SEQ ID NO 79
<211> LENGTH: 125
<212> TYPE: DNA
<213> ORGANISM: Artificial Sequence
<220> FEATURE:
<223> OTHER INFORMATION: source: AAV2; Recogn.Site: Nb.BssSI; Format: tl

<400> SEQUENCE: 79
ttggccactc cctcgtggcg cgctcgctcg ctcactgagg ccgggcgacc aaaggtcgcc    60
cgacgcccgg gctttgcccg ggcggcctca gtgagcgagc gagcgcgcca cgagggagtg    120
gccaa                                                              125

<210> SEQ ID NO 80
<211> LENGTH: 125
<212> TYPE: DNA
<213> ORGANISM: Artificial Sequence
<220> FEATURE:
<223> OTHER INFORMATION: source: AAV3; Recogn.Site: Nb.BssSI; Format: bl

<400> SEQUENCE: 80
ttggccacga gctctatgcg cactcgctcg ctcggtgggg cctggcgacc aaaggtcgcc    60
agacggacgt gctttgcacg tccggcccca ccgagcgagc gagtgcgcat agagctcgtg    120
gccaa                                                              125

<210> SEQ ID NO 81
<211> LENGTH: 125
<212> TYPE: DNA
<213> ORGANISM: Artificial Sequence
<220> FEATURE:
<223> OTHER INFORMATION: source: AAV3; Recogn.Site: Nb.BssSI; Format: tl

<400> SEQUENCE: 81
ttggccactc cctcgtggcg cactcgctcg ctcggtgggg cctggcgacc aaaggtcgcc    60
agacggacgt gctttgcacg tccggcccca ccgagcgagc gagtgcgcca cgagggagtg    120
gccaa                                                              125

<210> SEQ ID NO 82
<211> LENGTH: 125
<212> TYPE: DNA
<213> ORGANISM: Artificial Sequence
<220> FEATURE:
<223> OTHER INFORMATION: source: AAV4 left; Recogn.Site: Nb.BssSI;
      Format: bl

<400> SEQUENCE: 82
ttggccacga gctctatgcg cgctcgctca ctcactcggc cctggagacc aaaggtctcc    60
agactgccgg cctctggccg gcagggccga gtgagtgagc gagcgcgcat agagctcgtg    120
gccaa                                                              125

<210> SEQ ID NO 83
<211> LENGTH: 125
<212> TYPE: DNA
<213> ORGANISM: Artificial Sequence
<220> FEATURE:
<223> OTHER INFORMATION: source: AAV4 left; Recogn.Site: Nb.BssSI;
      Format: tl
```

-continued

<400> SEQUENCE: 83
ttggccactc cctcgtggcg cgctcgctca ctcactcggc cctggagacc aaaggtctcc    60
agactgccgg cctctggccg gcagggccga gtgagtgagc gagcgcgcca cgagggagtg   120
gccaa                                                              125

<210> SEQ ID NO 84
<211> LENGTH: 125
<212> TYPE: DNA
<213> ORGANISM: Artificial Sequence
<220> FEATURE:
<223> OTHER INFORMATION: source: AAV4 right; Recogn.Site: Nb.BssSI;
      Format: bl

<400> SEQUENCE: 84
ttggccacga gagctatgcg cgctcgctca ctcactcggc cctggagacc aaaggtctcc    60
agactgccgg cctctggccg gcagggccga gtgagtgagc gagcgcgcat agagctcgtg   120
gccaa                                                              125

<210> SEQ ID NO 85
<211> LENGTH: 125
<212> TYPE: DNA
<213> ORGANISM: Artificial Sequence
<220> FEATURE:
<223> OTHER INFORMATION: source: AAV4 right; Recogn.Site: Nb.BssSI;
      Format: tl

<400> SEQUENCE: 85
ttggccacat tctcgtggcg cgctcgctca ctcactcggc cctggagacc aaaggtctcc    60
agactgccgg cctctggccg gcagggccga gtgagtgagc gagcgcgcca cgagggagtg   120
gccaa                                                              125

<210> SEQ ID NO 86
<211> LENGTH: 137
<212> TYPE: DNA
<213> ORGANISM: Artificial Sequence
<220> FEATURE:
<223> OTHER INFORMATION: source: AAV5; Recogn.Site: Nb.BssSI; Format: bl

<400> SEQUENCE: 86
ctcacgagcc tgtcgcgttc gctcgctcgc tggctcgttt gggggggtgg cagctcaaag    60
agctgccaga cgacggccct ctggccgtcg ccccccaaa cgagccagcg agcgagcgaa   120
cgcgacaggc tcgtgag                                                 137

<210> SEQ ID NO 87
<211> LENGTH: 137
<212> TYPE: DNA
<213> ORGANISM: Artificial Sequence
<220> FEATURE:
<223> OTHER INFORMATION: source: AAV5; Recogn.Site: Nb.BssSI; Format: tl

<400> SEQUENCE: 87
ctctccctcg tgtcgcgttc gctcgctcgc tggctcgttt gggggggtgg cagctcaaag    60
agctgccaga cgacggccct ctggccgtcg ccccccaaa cgagccagcg agcgagcgaa   120
cgcgacacga gggagag                                                 137

<210> SEQ ID NO 88
<211> LENGTH: 125
<212> TYPE: DNA
<213> ORGANISM: Artificial Sequence
<220> FEATURE:
<223> OTHER INFORMATION: source: AAV7; Recogn.Site: Nb.BssSI; Format: bl

<400> SEQUENCE: 88
ttggccacga gctctatgcg cgctcgctcg ctcggtgggg cctgcggacc aaaggtccgc    60
agacggcaga gctctgctct gccggcccca ccgagcgagc gagcgcgcat agagctcgtg   120
gccaa                                                              125

<210> SEQ ID NO 89
<211> LENGTH: 125
<212> TYPE: DNA
<213> ORGANISM: Artificial Sequence
<220> FEATURE:
<223> OTHER INFORMATION: source: AAV7; Recogn.Site: Nb.BssSI; Format: tl

<400> SEQUENCE: 89
ttggccactc cctcgtggcg cgctcgctcg ctcggtgggg cctgcggacc aaaggtccgc    60
agacggcaga gctctgctct gccggcccca ccgagcgagc gagcgcgcca cgagggagtg   120
gccaa                                                              125

<210> SEQ ID NO 90
<211> LENGTH: 125
<212> TYPE: DNA
<213> ORGANISM: Artificial Sequence
<220> FEATURE:
<223> OTHER INFORMATION: source: AAV1; Recogn.Site: Nb.BtsI; Format: bl

<400> SEQUENCE: 90
ttgcccactc ccgcagtgcg cgctcgctcg ctcggtgggg cctgcggacc aaaggtccgc    60
agacggcaga gctctgctct gccggcccca ccgagcgagc gagcgcgcac tgcgggagtg   120
ggcaa                                                              125

<210> SEQ ID NO 91
<211> LENGTH: 125
<212> TYPE: DNA
<213> ORGANISM: Artificial Sequence
<220> FEATURE:
<223> OTHER INFORMATION: source: AAV1; Recogn.Site: Nb.BtsI; Format: tl

<400> SEQUENCE: 91
ttgcccactc cctcactgcg cgctcgctcg ctcggtgggg cctgcggacc aaaggtccgc    60
agacggcaga gctctgctct gccggcccca ccgagcgagc gagcgcgcag tgagggagtg   120
ggcaa                                                              125

<210> SEQ ID NO 92
<211> LENGTH: 125
<212> TYPE: DNA
<213> ORGANISM: Artificial Sequence
<220> FEATURE:
<223> OTHER INFORMATION: source: AAV2; Recogn.Site: Nb.BtsI; Format: bl

<400> SEQUENCE: 92
ttggccactc ccgcagtgcg cgctcgctcg ctcactgagg ccgggcgacc aaaggtcgcc    60
cgacgcccgg gctttgcccg ggcggcctca gtgagcgagc gagcgcgcac tgcgggagtg   120
gccaa                                                              125

<210> SEQ ID NO 93
<211> LENGTH: 125
<212> TYPE: DNA

<213> ORGANISM: Artificial Sequence
<220> FEATURE:
<223> OTHER INFORMATION: source: AAV2; Recogn.Site: Nb.BtsI; Format: tl

<400> SEQUENCE: 93
ttggccactc cctcactgcg cgctcgctcg ctcactgagg ccgggcgacc aaaggtcgcc    60
cgacgcccgg gctttgcccg ggcggcctca gtgagcgagc gagcgcgcag tgagggagtg   120
gccaa                                                              125

<210> SEQ ID NO 94
<211> LENGTH: 125
<212> TYPE: DNA
<213> ORGANISM: Artificial Sequence
<220> FEATURE:
<223> OTHER INFORMATION: source: AAV3; Recogn.Site: Nb.BtsI; Format: bl

<400> SEQUENCE: 94
ttggccactc ccgcagtgcg cactcgctcg ctcggtgggg cctggcgacc aaaggtcgcc    60
agacggacgt gctttgcacg tccggcccca ccgagcgagc gagtgcgcac tgcgggagtg   120
gccaa                                                              125

<210> SEQ ID NO 95
<211> LENGTH: 125
<212> TYPE: DNA
<213> ORGANISM: Artificial Sequence
<220> FEATURE:
<223> OTHER INFORMATION: source: AAV3; Recogn.Site: Nb.BtsI; Format: tl

<400> SEQUENCE: 95
ttggccactc cctcactgcg cactcgctcg ctcggtgggg cctggcgacc aaaggtcgcc    60
agacggacgt gctttgcacg tccggcccca ccgagcgagc gagtgcgcag tgagggagtg   120
gccaa                                                              125

<210> SEQ ID NO 96
<211> LENGTH: 125
<212> TYPE: DNA
<213> ORGANISM: Artificial Sequence
<220> FEATURE:
<223> OTHER INFORMATION: source: AAV4 left; Recogn.Site: Nb.BtsI;
    Format: bl

<400> SEQUENCE: 96
ttggccactc ccgcagtgcg cgctcgctca ctcactcggc cctggagacc aaaggtctcc    60
agactgccgg cctctggccg gcagggccga gtgagtgagc gagcgcgcac tgcgggagtg   120
gccaa                                                              125

<210> SEQ ID NO 97
<211> LENGTH: 125
<212> TYPE: DNA
<213> ORGANISM: Artificial Sequence
<220> FEATURE:
<223> OTHER INFORMATION: source: AAV4 left; Recogn.Site: Nb.BtsI;
    Format: tl

<400> SEQUENCE: 97
ttggccactc cctcactgcg cgctcgctca ctcactcggc cctggagacc aaaggtctcc    60
agactgccgg cctctggccg gcagggccga gtgagtgagc gagcgcgcag tgagggagtg   120
gccaa                                                              125

```
<210> SEQ ID NO 98
<211> LENGTH: 125
<212> TYPE: DNA
<213> ORGANISM: Artificial Sequence
<220> FEATURE:
<223> OTHER INFORMATION: source: AAV4 right; Recogn.Site: Nb.BtsI;
      Format: bl

<400> SEQUENCE: 98
ttggccacat tagcagtgcg cgctcgctca ctcactcggc cctggagacc aaaggtctcc      60
agactgccgg cctctggccg gcagggccga gtgagtgagc gagcgcgcac tgcgggagtg     120
gccaa                                                                 125

<210> SEQ ID NO 99
<211> LENGTH: 125
<212> TYPE: DNA
<213> ORGANISM: Artificial Sequence
<220> FEATURE:
<223> OTHER INFORMATION: source: AAV4 right; Recogn.Site: Nb.BtsI;
      Format: tl

<400> SEQUENCE: 99
ttggccacat tagcactgcg cgctcgctca ctcactcggc cctggagacc aaaggtctcc      60
agactgccgg cctctggccg gcagggccga gtgagtgagc gagcgcgcag tgagggagtg     120
gccaa                                                                 125

<210> SEQ ID NO 100
<211> LENGTH: 137
<212> TYPE: DNA
<213> ORGANISM: Artificial Sequence
<220> FEATURE:
<223> OTHER INFORMATION: source: AAV5; Recogn.Site: Nb.BtsI; Format: bl

<400> SEQUENCE: 100
ctctccgcag tgtcgcgttc gctcgctcgc tggctcgttt ggggggggtgg cagctcaaag     60 agctgccaga cgacggccct ctggccgtcg ccccccaaa cgagccagcg agcgagcgaa      120
cgcgacactg cggagag                                                    137

<210> SEQ ID NO 101
<211> LENGTH: 137
<212> TYPE: DNA
<213> ORGANISM: Artificial Sequence
<220> FEATURE:
<223> OTHER INFORMATION: source: AAV5; Recogn.Site: Nb.BtsI; Format: tl

<400> SEQUENCE: 101
ctctccccac tgccgcgttc gctcgctcgc tggctcgttt ggggggggtgg cagctcaaag     60 agctgccaga cgacggccct ctggccgtcg ccccccaaa cgagccagcg agcgagcgaa      120
cgcggcagtg gggagag                                                    137

<210> SEQ ID NO 102
<211> LENGTH: 125
<212> TYPE: DNA
<213> ORGANISM: Artificial Sequence
<220> FEATURE:
<223> OTHER INFORMATION: source: AAV7; Recogn.Site: Nb.BtsI; Format: bl

<400> SEQUENCE: 102
ttggccactc ccgcagtgcg cgctcgctcg ctcggtgggg cctgcggacc aaaggtccgc      60
agacggcaga gctctgctct gccggcccca ccgagcgagc gagcgcgcac tgcgggagtg     120
```

```
gccaa                                                                    125

<210> SEQ ID NO 103
<211> LENGTH: 125
<212> TYPE: DNA
<213> ORGANISM: Artificial Sequence
<220> FEATURE:
<223> OTHER INFORMATION: source: AAV7; Recogn.Site: Nb.BtsI; Format: tl

<400> SEQUENCE: 103
ttggccactc cctcactgcg cgctcgctcg ctcggtgggg cctgcggacc aaaggtccgc      60
agacggcaga gctctgctct gccggcccca ccgagcgagc gagcgcgcag tgagggagtg     120
gccaa                                                                    125

<210> SEQ ID NO 104
<211> LENGTH: 125
<212> TYPE: DNA
<213> ORGANISM: Artificial Sequence
<220> FEATURE:
<223> OTHER INFORMATION: source: AAV1; Recogn.Site: Nt.AlwI; Format: bl

<400> SEQUENCE: 104
ttgcccactc cctcgatccg cgctcgctcg ctcggtgggg cctgcggacc aaaggtccgc      60
agacggcaga gctctgctct gccggcccca ccgagcgagc gagcgcggat cgagggagtg     120
ggcaa                                                                    125

<210> SEQ ID NO 105
<211> LENGTH: 125
<212> TYPE: DNA
<213> ORGANISM: Artificial Sequence
<220> FEATURE:
<223> OTHER INFORMATION: source: AAV1; Recogn.Site: Nt.AlwI; Format: tl

<400> SEQUENCE: 105
ttgcccactg gatctctgcg cgctcgctcg ctcggtgggg cctgcggacc aaaggtccgc      60
agacggcaga gctctgctct gccggcccca ccgagcgagc gagcgcgcag agatccagtg     120
ggcaa                                                                    125

<210> SEQ ID NO 106
<211> LENGTH: 125
<212> TYPE: DNA
<213> ORGANISM: Artificial Sequence
<220> FEATURE:
<223> OTHER INFORMATION: source: AAV2; Recogn.Site: Nt.AlwI; Format: bl

<400> SEQUENCE: 106
ttggccactc cctcgatccg cgctcgctcg ctcactgagg ccgggcgacc aaaggtcgcc      60
cgacgcccgg gctttgcccg gcggcctca gtgagcgagc gagcgcggat cgagggagtg      120
gccaa                                                                    125

<210> SEQ ID NO 107
<211> LENGTH: 125
<212> TYPE: DNA
<213> ORGANISM: Artificial Sequence
<220> FEATURE:
<223> OTHER INFORMATION: source: AAV2; Recogn.Site: Nt.AlwI; Format: tl

<400> SEQUENCE: 107
ttggccactg gatctctgcg cgctcgctcg ctcactgagg ccgggcgacc aaaggtcgcc      60
cgacgcccgg gctttgcccg gcggcctca gtgagcgagc gagcgcgcag agatccagtg      120
```

```
gccaa                                                          125

<210> SEQ ID NO 108
<211> LENGTH: 125
<212> TYPE: DNA
<213> ORGANISM: Artificial Sequence
<220> FEATURE:
<223> OTHER INFORMATION: source: AAV3; Recogn.Site: Nt.AlwI; Format: bl

<400> SEQUENCE: 108
ttggccactc cctcgatccg cactcgctcg ctcggtgggg cctggcgacc aaaggtcgcc    60
agacggacgt gctttgcacg tccggcccca ccgagcgagc gagtgcggat cgagggagtg   120
gccaa                                                              125

<210> SEQ ID NO 109
<211> LENGTH: 125
<212> TYPE: DNA
<213> ORGANISM: Artificial Sequence
<220> FEATURE:
<223> OTHER INFORMATION: source: AAV3; Recogn.Site: Nt.AlwI; Format: tl

<400> SEQUENCE: 109
ttggccactg gatctatgcg cactcgctcg ctcggtgggg cctggcgacc aaaggtcgcc    60
agacggacgt gctttgcacg tccggcccca ccgagcgagc gagtgcgcat agatccagtg   120
gccaa                                                              125

<210> SEQ ID NO 110
<211> LENGTH: 125
<212> TYPE: DNA
<213> ORGANISM: Artificial Sequence
<220> FEATURE:
<223> OTHER INFORMATION: source: AAV4 left; Recogn.Site: Nt.AlwI;
      Format: bl

<400> SEQUENCE: 110
ttggccactc cctcgatccg cgctcgctca ctcactcggc cctggagacc aaaggtctcc    60
agactgccgg cctctggccg gcagggccga gtgagtgagc gagcgcggat cgagggagtg   120
gccaa                                                              125

<210> SEQ ID NO 111
<211> LENGTH: 125
<212> TYPE: DNA
<213> ORGANISM: Artificial Sequence
<220> FEATURE:
<223> OTHER INFORMATION: source: AAV4 left; Recogn.Site: Nt.AlwI;
      Format: tl

<400> SEQUENCE: 111
ttggccactg gatctatgcg cgctcgctca ctcactcggc cctggagacc aaaggtctcc    60
agactgccgg cctctggccg gcagggccga gtgagtgagc gagcgcgcat agatccagtg   120
gccaa                                                              125

<210> SEQ ID NO 112
<211> LENGTH: 125
<212> TYPE: DNA
<213> ORGANISM: Artificial Sequence
<220> FEATURE:
<223> OTHER INFORMATION: source: AAV4 right; Recogn.Site: Nt.AlwI;
      Format: bl

<400> SEQUENCE: 112
```

-continued ttggccacat tagcgatccg cgctcgctca ctcactcggc cctggagacc aaaggtctcc    60
agactgccgg cctctggccg gcagggccga gtgagtgagc gagcgcggat cgagggagtg   120
gccaa                                                              125

<210> SEQ ID NO 113
<211> LENGTH: 125
<212> TYPE: DNA
<213> ORGANISM: Artificial Sequence
<220> FEATURE:
<223> OTHER INFORMATION: source: AAV4 right; Recogn.Site: Nt.AlwI;
      Format: tl

<400> SEQUENCE: 113
ttggccacag gatctatgcg cgctcgctca ctcactcggc cctggagacc aaaggtctcc    60
agactgccgg cctctggccg gcagggccga gtgagtgagc gagcgcgcat agatccagtg   120
gccaa                                                              125

<210> SEQ ID NO 114
<211> LENGTH: 137
<212> TYPE: DNA
<213> ORGANISM: Artificial Sequence
<220> FEATURE:
<223> OTHER INFORMATION: source: AAV5; Recogn.Site: Nt.AlwI; Format: bl

<400> SEQUENCE: 114
ctctcccccc tgtcgcgatc cctcgctcgc tggctcgttt ggggggggtgg cagctcaaag    60 agctgcaga cgacggccct ctggccgtcg ccccccaaa cgagccagcg agcgagggat   120
cgcgacaggg gggagag                                                 137

<210> SEQ ID NO 115
<211> LENGTH: 137
<212> TYPE: DNA
<213> ORGANISM: Artificial Sequence
<220> FEATURE:
<223> OTHER INFORMATION: source: AAV5; Recogn.Site: Nt.AlwI; Format: tl

<400> SEQUENCE: 115
ctctcccccg gatcgcgttc gctcgctcgc tggctcgttt ggggggggtgg cagctcaaag    60 agctgcaga cgacggccct ctggccgtcg ccccccaaa cgagccagcg agcgagcgaa   120
cgcgatccgg gggagag                                                 137

<210> SEQ ID NO 116
<211> LENGTH: 125
<212> TYPE: DNA
<213> ORGANISM: Artificial Sequence
<220> FEATURE:
<223> OTHER INFORMATION: source: AAV7; Recogn.Site: Nt.AlwI; Format: bl

<400> SEQUENCE: 116
ttggccactc cctcgatccg cgctcgctcg ctcggtgggg cctgcggacc aaaggtccgc    60
agacggcaga gctctgctct gccggcccca ccgagcgagc gagcgcggat cgagggagtg   120
gccaa                                                              125

<210> SEQ ID NO 117
<211> LENGTH: 125
<212> TYPE: DNA
<213> ORGANISM: Artificial Sequence
<220> FEATURE:
<223> OTHER INFORMATION: source: AAV7; Recogn.Site: Nt.AlwI; Format: tl

<400> SEQUENCE: 117
ttggccactg atctatgcgc cgctcgctcg ctcggtgggg cctgcggacc aaaggtccgc    60
agacggcaga gctctgctct gccggcccca ccgagcgagc gagcgcgcat agatccagtg   120
gccaa                                                              125

<210> SEQ ID NO 118
<211> LENGTH: 125
<212> TYPE: DNA
<213> ORGANISM: Artificial Sequence
<220> FEATURE:
<223> OTHER INFORMATION: source: AAV1; Recogn.Site: Nt.BbvCI; Format: bl

<400> SEQUENCE: 118
ttgcccactc ccgctgaggg cgctcgctcg ctcggtgggg cctgcggacc aaaggtccgc    60
agacggcaga gctctgctct gccggcccca ccgagcgagc gagcgccctc agcgggagtg   120
ggcaa                                                              125

<210> SEQ ID NO 119
<211> LENGTH: 125
<212> TYPE: DNA
<213> ORGANISM: Artificial Sequence
<220> FEATURE:
<223> OTHER INFORMATION: source: AAV1; Recogn.Site: Nt.BbvCI; Format: tl

<400> SEQUENCE: 119
ttgcccactc ccctcagcg cgctcgctcg ctcggtgggg cctgcggacc aaaggtccgc     60
agacggcaga gctctgctct gccggcccca ccgagcgagc gagcgcgctg aggggagtg    120 ggcaa                                                              125

<210> SEQ ID NO 120
<211> LENGTH: 125
<212> TYPE: DNA
<213> ORGANISM: Artificial Sequence
<220> FEATURE:
<223> OTHER INFORMATION: source: AAV2; Recogn.Site: Nt.BbvCI; Format: bl

<400> SEQUENCE: 120
ttggccactc ccgctgaggg cgctcgctcg ctcactgagg ccgggcgacc aaaggtcgcc    60
cgacgcccgg gctttgcccg ggcggcctca gtgagcgagc gagcgccctc agcgggagtg   120
gccaa                                                              125

<210> SEQ ID NO 121
<211> LENGTH: 125
<212> TYPE: DNA
<213> ORGANISM: Artificial Sequence
<220> FEATURE:
<223> OTHER INFORMATION: source: AAV2; Recogn.Site: Nt.BbvCI; Format: tl

<400> SEQUENCE: 121
ttggccactc ccctcagcg cgctcgctcg ctcactgagg ccgggcgacc aaaggtcgcc     60
cgacgcccgg gctttgcccg ggcggcctca gtgagcgagc gagcgcgctg aggggagtg   120 gccaa                                                              125

<210> SEQ ID NO 122
<211> LENGTH: 125
<212> TYPE: DNA
<213> ORGANISM: Artificial Sequence
<220> FEATURE:

<223> OTHER INFORMATION: source: AAV3; Recogn.Site: Nt.BbvCI; Format: bl

<400> SEQUENCE: 122
ttggccactc ccgctgaggg cactcgctcg ctcggtgggg cctggcgacc aaaggtcgcc    60
agacggacgt gctttgcacg tccggcccca ccgagcgagc gagtgccctc agcgggagtg    120
gccaa    125

<210> SEQ ID NO 123
<211> LENGTH: 125
<212> TYPE: DNA
<213> ORGANISM: Artificial Sequence
<220> FEATURE:
<223> OTHER INFORMATION: source: AAV3; Recogn.Site: Nt.BbvCI; Format: tl

<400> SEQUENCE: 123
ttggccactc ccctcagcg cactcgctcg ctcggtgggg cctggcgacc aaaggtcgcc     60
agacggacgt gctttgcacg tccggcccca ccgagcgagc gagtgcgctg aggggagtg    120 gccaa    125

<210> SEQ ID NO 124
<211> LENGTH: 125
<212> TYPE: DNA
<213> ORGANISM: Artificial Sequence
<220> FEATURE:
<223> OTHER INFORMATION: source: AAV4 left; Recogn.Site: Nt.BbvCI;
      Format: bl

<400> SEQUENCE: 124
ttggccactc ccgctgaggg cgctcgctca ctcactcggc cctggagacc aaaggtctcc    60
agactgccgg cctctggccg gcagggccga gtgagtgagc gagcgccctc agcgggagtg    120
gccaa    125

<210> SEQ ID NO 125
<211> LENGTH: 125
<212> TYPE: DNA
<213> ORGANISM: Artificial Sequence
<220> FEATURE:
<223> OTHER INFORMATION: source: AAV4 left; Recogn.Site: Nt.BbvCI;
      Format: tl

<400> SEQUENCE: 125
ttggccactc ccctcagcg cgctcgctca ctcactcggc cctggagacc aaaggtctcc     60
agactgccgg cctctggccg gcagggccga gtgagtgagc gagcgcgctg aggggagtg    120 gccaa    125

<210> SEQ ID NO 126
<211> LENGTH: 125
<212> TYPE: DNA
<213> ORGANISM: Artificial Sequence
<220> FEATURE:
<223> OTHER INFORMATION: source: AAV4 right; Recogn.Site: Nt.BbvCI;
      Format: bl

<400> SEQUENCE: 126
ttggccacat tagctgaggg cgctcgctca ctcactcggc cctggagacc aaaggtctcc    60
agactgccgg cctctggccg gcagggccga gtgagtgagc gagcgccctc agcgggagtg    120
gccaa    125

<210> SEQ ID NO 127

```
<211> LENGTH: 125
<212> TYPE: DNA
<213> ORGANISM: Artificial Sequence
<220> FEATURE:
<223> OTHER INFORMATION: source: AAV4 right; Recogn.Site: Nt.BbvCI;
      Format: tl

<400> SEQUENCE: 127
ttggccacat tacctcagcg cgctcgctca ctcactcggc cctggagacc aaaggtctcc      60
agactgccgg cctctggccg gcagggccga gtgagtgagc gagcgcgctg aggggggagtg   120 gccaa                                                                125

<210> SEQ ID NO 128
<211> LENGTH: 137
<212> TYPE: DNA
<213> ORGANISM: Artificial Sequence
<220> FEATURE:
<223> OTHER INFORMATION: source: AAV5; Recogn.Site: Nt.BbvCI; Format: bl

<400> SEQUENCE: 128
ctctccccgc tgaggcgttc gctcgctcgc tggctcgttt ggggggtgg cagctcaaag       60 agctgccaga cgacggccct ctggccgtcg cccccccaaa cgagccagcg agcgagcgaa    120
cgcctcagcg gggagag                                                   137

<210> SEQ ID NO 129
<211> LENGTH: 137
<212> TYPE: DNA
<213> ORGANISM: Artificial Sequence
<220> FEATURE:
<223> OTHER INFORMATION: source: AAV5; Recogn.Site: Nt.BbvCI; Format: tl

<400> SEQUENCE: 129
ctctcccctc agccgcgttc gctcgctcgc tggctcgttt ggggggtgg cagctcaaag       60 agctgccaga cgacggccct ctggccgtcg cccccccaaa cgagccagcg agcgagcgaa    120
cgcggctgag gggagag                                                   137

<210> SEQ ID NO 130
<211> LENGTH: 125
<212> TYPE: DNA
<213> ORGANISM: Artificial Sequence
<220> FEATURE:
<223> OTHER INFORMATION: source: AAV7; Recogn.Site: Nt.BbvCI; Format: bl

<400> SEQUENCE: 130
ttggccactc ccgctgaggg cgctcgctcg ctcggtgggg cctgcggacc aaaggtccgc      60
agacggcaga gctctgctct gccggcccca ccgagcgagc gagcgccctc agcgggagtg    120
gccaa                                                                125

<210> SEQ ID NO 131
<211> LENGTH: 125
<212> TYPE: DNA
<213> ORGANISM: Artificial Sequence
<220> FEATURE:
<223> OTHER INFORMATION: source: AAV7; Recogn.Site: Nt.BbvCI; Format: tl

<400> SEQUENCE: 131
ttggccactc ccctcagcg cgctcgctcg ctcggtgggg cctgcggacc aaaggtccgc       60
agacggcaga gctctgctct gccggcccca ccgagcgagc gagcgcgctg aggggggagtg   120 gccaa                                                                125
```

<210> SEQ ID NO 132
<211> LENGTH: 125
<212> TYPE: DNA
<213> ORGANISM: Artificial Sequence
<220> FEATURE:
<223> OTHER INFORMATION: source: AAV1; Recogn.Site: Nt.BsmAI; Format: bl

<400> SEQUENCE: 132
ttgcccactg agactctgcg cgctcgctcg ctcggtgggg cctgcggacc aaaggtccgc    60
agacggcaga gctctgctct gccggcccca ccgagcgagc gagcgcgcag agtctcagtg   120
ggcaa                                                              125

<210> SEQ ID NO 133
<211> LENGTH: 125
<212> TYPE: DNA
<213> ORGANISM: Artificial Sequence
<220> FEATURE:
<223> OTHER INFORMATION: source: AAV1; Recogn.Site: Nt.BsmAI; Format: tl

<400> SEQUENCE: 133
ttgcccactc cgtctctgcg cgctcgctcg ctcggtgggg cctgcggacc aaaggtccgc    60
agacggcaga gctctgctct gccggcccca ccgagcgagc gagcgcgcag agacggagtg   120
ggcaa                                                              125

<210> SEQ ID NO 134
<211> LENGTH: 125
<212> TYPE: DNA
<213> ORGANISM: Artificial Sequence
<220> FEATURE:
<223> OTHER INFORMATION: source: AAV2; Recogn.Site: Nt.BsmAI; Format: bl

<400> SEQUENCE: 134
ttggccactg agactctgcg cgctcgctcg ctcactgagg ccgggcgacc aaaggtcgcc    60
cgacgcccgg gctttgcccg ggcggcctca gtgagcgagc gagcgcgcag agtctcagtg   120
gccaa                                                              125

<210> SEQ ID NO 135
<211> LENGTH: 125
<212> TYPE: DNA
<213> ORGANISM: Artificial Sequence
<220> FEATURE:
<223> OTHER INFORMATION: source: AAV2; Recogn.Site: Nt.BsmAI; Format: tl

<400> SEQUENCE: 135
ttggccactc cgtctctgcg cgctcgctcg ctcactgagg ccgggcgacc aaaggtcgcc    60
cgacgcccgg gctttgcccg ggcggcctca gtgagcgagc gagcgcgcag agacggagtg   120
gccaa                                                              125

<210> SEQ ID NO 136
<211> LENGTH: 125
<212> TYPE: DNA
<213> ORGANISM: Artificial Sequence
<220> FEATURE:
<223> OTHER INFORMATION: source: AAV3; Recogn.Site: Nt.BsmAI; Format: bl

<400> SEQUENCE: 136
ttggccactg agactatgcg cactcgctcg ctcggtgggg cctggcgacc aaaggtcgcc    60
agacggacgt gctttgcacg tccggcccca ccgagcgagc gagtgcgcat agtctcagtg   120
gccaa                                                              125

<210> SEQ ID NO 137
<211> LENGTH: 125
<212> TYPE: DNA
<213> ORGANISM: Artificial Sequence
<220> FEATURE:
<223> OTHER INFORMATION: source: AAV3; Recogn.Site: Nt.BsmAI; Format: tl

<400> SEQUENCE: 137
ttggccactc cgtctctgcg cactcgctcg ctcggtgggg cctggcgacc aaaggtcgcc    60
agacggacgt gctttgcacg tccggcccca ccgagcgagc gagtgcgcag agacggagtg   120
gccaa                                                              125

<210> SEQ ID NO 138
<211> LENGTH: 125
<212> TYPE: DNA
<213> ORGANISM: Artificial Sequence
<220> FEATURE:
<223> OTHER INFORMATION: source: AAV4 left; Recogn.Site: Nt.BsmAI;
      Format: bl

<400> SEQUENCE: 138
ttggccactg agactatgcg cgctcgctca ctcactcggc cctggagacc aaaggtctcc    60
agactgccgg cctctggccg gcagggccga gtgagtgagc gagcgcgcat agtctcagtg   120
gccaa                                                              125

<210> SEQ ID NO 139
<211> LENGTH: 125
<212> TYPE: DNA
<213> ORGANISM: Artificial Sequence
<220> FEATURE:
<223> OTHER INFORMATION: source: AAV4 left; Recogn.Site: Nt.BsmAI;
      Format: tl

<400> SEQUENCE: 139
ttggccactc cgtctctgcg cgctcgctca ctcactcggc cctggagacc aaaggtctcc    60
agactgccgg cctctggccg gcagggccga gtgagtgagc gagcgcgcag agacggagtg   120
gccaa                                                              125

<210> SEQ ID NO 140
<211> LENGTH: 125
<212> TYPE: DNA
<213> ORGANISM: Artificial Sequence
<220> FEATURE:
<223> OTHER INFORMATION: source: AAV4 right; Recogn.Site: Nt.BsmAI;
      Format: bl

<400> SEQUENCE: 140
ttggccacag agactatgcg cgctcgctca ctcactcggc cctggagacc aaaggtctcc    60
agactgccgg cctctggccg gcagggccga gtgagtgagc gagcgcgcat agtctcagtg   120
gccaa                                                              125

<210> SEQ ID NO 141
<211> LENGTH: 125
<212> TYPE: DNA
<213> ORGANISM: Artificial Sequence
<220> FEATURE:
<223> OTHER INFORMATION: source: AAV4 right; Recogn.Site: Nt.BsmAI;
      Format: tl

<400> SEQUENCE: 141

```
ttggccacat tgtctctgcg cgctcgctca ctcactcggc cctggagacc aaaggtctcc      60
agactgccgg cctctggccg gcagggccga gtgagtgagc gagcgcgcag agacggagtg     120
gccaa                                                                 125

<210> SEQ ID NO 142
<211> LENGTH: 137
<212> TYPE: DNA
<213> ORGANISM: Artificial Sequence
<220> FEATURE:
<223> OTHER INFORMATION: source: AAV5; Recogn.Site: Nt.BsmAI; Format: bl

<400> SEQUENCE: 142
ctctcccccg agacgcgttc gctcgctcgc tggctcgttt gggggggtgg cagctcaaag      60
agctgccaga cgacggccct ctggccgtcg cccccccaaa cgagccagcg agcgagcgaa     120
cgcgtctcgg gggagag                                                    137

<210> SEQ ID NO 143
<211> LENGTH: 137
<212> TYPE: DNA
<213> ORGANISM: Artificial Sequence
<220> FEATURE:
<223> OTHER INFORMATION: source: AAV5; Recogn.Site: Nt.BsmAI; Format: tl

<400> SEQUENCE: 143
ctctcccccg tctcgcgttc gctcgctcgc tggctcgttt gggggggtgg cagctcaaag      60
agctgccaga cgacggccct ctggccgtcg cccccccaaa cgagccagcg agcgagcgaa     120
cgcgagacgg gggagag                                                    137

<210> SEQ ID NO 144
<211> LENGTH: 125
<212> TYPE: DNA
<213> ORGANISM: Artificial Sequence
<220> FEATURE:
<223> OTHER INFORMATION: source: AAV7; Recogn.Site: Nt.BsmAI; Format: bl

<400> SEQUENCE: 144
ttggccactg agactatgcg cgctcgctcg ctcggtgggg cctgcggacc aaaggtccgc      60
agacggcaga gctctgctct gccggcccca ccgagcgagc gagcgcgcat agtctcagtg     120
gccaa                                                                 125

<210> SEQ ID NO 145
<211> LENGTH: 125
<212> TYPE: DNA
<213> ORGANISM: Artificial Sequence
<220> FEATURE:
<223> OTHER INFORMATION: source: AAV7; Recogn.Site: Nt.BsmAI; Format: tl

<400> SEQUENCE: 145
ttggccactc cgtctctgcg cgctcgctcg ctcggtgggg cctgcggacc aaaggtccgc      60
agacggcaga gctctgctct gccggcccca ccgagcgagc gagcgcgcag agacggagtg     120
gccaa                                                                 125

<210> SEQ ID NO 146
<211> LENGTH: 125
<212> TYPE: DNA
<213> ORGANISM: Artificial Sequence
<220> FEATURE:
<223> OTHER INFORMATION: source: AAV1; Recogn.Site: Nt.BspQI; Format: bl

<400> SEQUENCE: 146
```
ttgcccactc ccgaagagcg cgctcgctcg ctcggtgggg cctgcggacc aaaggtccgc    60
agacggcaga gctctgctct gccggcccca ccgagcgagc gagcgcgctc ttcgggagtg   120
ggcaa                                                              125

<210> SEQ ID NO 147
<211> LENGTH: 125
<212> TYPE: DNA
<213> ORGANISM: Artificial Sequence
<220> FEATURE:
<223> OTHER INFORMATION: source: AAV1; Recogn.Site: Nt.BspQI; Format: tl

<400> SEQUENCE: 147
ttgcccactc ccgctcttcg cgctcgctcg ctcggtgggg cctgcggacc aaaggtccgc    60
agacggcaga gctctgctct gccggcccca ccgagcgagc gagcgcgaag agcgggagtg   120
ggcaa                                                              125

<210> SEQ ID NO 148
<211> LENGTH: 125
<212> TYPE: DNA
<213> ORGANISM: Artificial Sequence
<220> FEATURE:
<223> OTHER INFORMATION: source: AAV2; Recogn.Site: Nt.BspQI; Format: bl

<400> SEQUENCE: 148
ttggccactc ccgaagagcg cgctcgctcg ctcactgagg ccgggcgacc aaaggtcgcc    60
cgacgcccgg gctttgcccg ggcggcctca gtgagcgagc gagcgcgctc ttcgggagtg   120
gccaa                                                              125

<210> SEQ ID NO 149
<211> LENGTH: 125
<212> TYPE: DNA
<213> ORGANISM: Artificial Sequence
<220> FEATURE:
<223> OTHER INFORMATION: source: AAV2; Recogn.Site: Nt.BspQI; Format: tl

<400> SEQUENCE: 149
ttggccactc ccgctcttcg cgctcgctcg ctcactgagg ccgggcgacc aaaggtcgcc    60
cgacgcccgg gctttgcccg ggcggcctca gtgagcgagc gagcgcgaag agcgggagtg   120
gccaa                                                              125

<210> SEQ ID NO 150
<211> LENGTH: 125
<212> TYPE: DNA
<213> ORGANISM: Artificial Sequence
<220> FEATURE:
<223> OTHER INFORMATION: source: AAV3; Recogn.Site: Nt.BspQI; Format: bl

<400> SEQUENCE: 150
ttggccactc ccgaagagcg cactcgctcg ctcggtgggg cctggcgacc aaaggtcgcc    60
agacggacgt gctttgcacg tccggcccca ccgagcgagc gagtgcgctc ttcgggagtg   120
gccaa                                                              125

<210> SEQ ID NO 151
<211> LENGTH: 125
<212> TYPE: DNA
<213> ORGANISM: Artificial Sequence
<220> FEATURE:
<223> OTHER INFORMATION: source: AAV3; Recogn.Site: Nt.BspQI; Format: tl

```
<400> SEQUENCE: 151
ttggccactc ccgctcttcg cactcgctcg ctcggtgggg cctggcgacc aaaggtcgcc      60
agacggacgt gctttgcacg tccggcccca ccgagcgagc gagtgcgaag agcgggagtg     120
gccaa                                                                125

<210> SEQ ID NO 152
<211> LENGTH: 125
<212> TYPE: DNA
<213> ORGANISM: Artificial Sequence
<220> FEATURE:
<223> OTHER INFORMATION: source: AAV4 left; Recogn.Site: Nt.BspQI;
      Format: bl

<400> SEQUENCE: 152
ttggccactc ccgaagagcg cgctcgctca ctcactcggc cctggagacc aaaggtctcc      60
agactgccgg cctctggccg gcagggccga gtgagtgagc gagcgcgctc ttcgggagtg     120
gccaa                                                                125

<210> SEQ ID NO 153
<211> LENGTH: 125
<212> TYPE: DNA
<213> ORGANISM: Artificial Sequence
<220> FEATURE:
<223> OTHER INFORMATION: source: AAV4 left; Recogn.Site: Nt.BspQI;
      Format: tl

<400> SEQUENCE: 153
ttggccactc ccgctcttcg cgctcgctca ctcactcggc cctggagacc aaaggtctcc      60
agactgccgg cctctggccg gcagggccga gtgagtgagc gagcgcgaag agcgggagtg     120
gccaa                                                                125

<210> SEQ ID NO 154
<211> LENGTH: 125
<212> TYPE: DNA
<213> ORGANISM: Artificial Sequence
<220> FEATURE:
<223> OTHER INFORMATION: source: AAV4 right; Recogn.Site: Nt.BspQI;
      Format: bl

<400> SEQUENCE: 154
ttggccacat agaagagcg cgctcgctca ctcactcggc cctggagacc aaaggtctcc       60
agactgccgg cctctggccg gcagggccga gtgagtgagc gagcgcgctc ttcgggagtg     120
gccaa                                                                125

<210> SEQ ID NO 155
<211> LENGTH: 125
<212> TYPE: DNA
<213> ORGANISM: Artificial Sequence
<220> FEATURE:
<223> OTHER INFORMATION: source: AAV4 right; Recogn.Site: Nt.BspQI;
      Format: tl

<400> SEQUENCE: 155
ttggccacat agctcttcg cgctcgctca ctcactcggc cctggagacc aaaggtctcc       60
agactgccgg cctctggccg gcagggccga gtgagtgagc gagcgcgaag agcgggagtg     120
gccaa                                                                125

<210> SEQ ID NO 156
<211> LENGTH: 137
```

```
<212> TYPE: DNA
<213> ORGANISM: Artificial Sequence
<220> FEATURE:
<223> OTHER INFORMATION: source: AAV5; Recogn.Site: Nt.BspQI; Format: b1

<400> SEQUENCE: 156
ctctcccgaa gagcgcgttc gctcgctcgc tggctcgttt ggggggtgg cagctcaaag     60 agctgccaga cgacggccct ctggccgtcg ccccccaaa cgagccagcg agcgagcgaa    120
cgcgctcttc gggagag                                                  137

<210> SEQ ID NO 157
<211> LENGTH: 137
<212> TYPE: DNA
<213> ORGANISM: Artificial Sequence
<220> FEATURE:
<223> OTHER INFORMATION: source: AAV5; Recogn.Site: Nt.BspQI; Format: t1

<400> SEQUENCE: 157
ctctcccgct cttcgcgttc gctcgctcgc tggctcgttt ggggggtgg cagctcaaag     60 agctgccaga cgacggccct ctggccgtcg ccccccaaa cgagccagcg agcgagcgaa    120
cgcgaagagc gggagag                                                  137

<210> SEQ ID NO 158
<211> LENGTH: 125
<212> TYPE: DNA
<213> ORGANISM: Artificial Sequence
<220> FEATURE:
<223> OTHER INFORMATION: source: AAV7; Recogn.Site: Nt.BspQI; Format: b1

<400> SEQUENCE: 158
ttggccactc ccgaagagcg cgctcgctcg ctcggtgggg cctgcggacc aaaggtccgc     60
agacggcaga gctctgctct gccggcccca ccgagcgagc gagcgcgctc ttcgggagtg    120
gccaa                                                                125

<210> SEQ ID NO 159
<211> LENGTH: 125
<212> TYPE: DNA
<213> ORGANISM: Artificial Sequence
<220> FEATURE:
<223> OTHER INFORMATION: source: AAV7; Recogn.Site: Nt.BspQI; Format: t1

<400> SEQUENCE: 159
ttggccactc ccgctcttcg cgctcgctcg ctcggtgggg cctgcggacc aaaggtccgc     60
agacggcaga gctctgctct gccggcccca ccgagcgagc gagcgcgaag agcgggagtg    120
gccaa                                                                125

<210> SEQ ID NO 160
<211> LENGTH: 127
<212> TYPE: DNA
<213> ORGANISM: Artificial Sequence
<220> FEATURE:
<223> OTHER INFORMATION: source: AAV1; Recogn.Site: Nt.BstNBI; Format:
      b1

<400> SEQUENCE: 160
ttgcccactc cctctctgcg cgactcgctc gctcggtggg gcctgcggac caaaggtccg     60
cagacggcag agctctgctc tgccggcccc accgagcgag cgagtcgcgc agagagggag    120
tgggcaa                                                              127
```

<210> SEQ ID NO 161
<211> LENGTH: 125
<212> TYPE: DNA
<213> ORGANISM: Artificial Sequence
<220> FEATURE:
<223> OTHER INFORMATION: source: AAV1; Recogn.Site: Nt.BstNBI; Format:
      t1

<400> SEQUENCE: 161
ttgccgagtc cctctctgcg cgctcgctcg ctcggtgggg cctgcggacc aaaggtccgc     60
agacggcaga gctctgctct gccggcccca ccgagcgagc gagcgcgcag agagggactc    120
ggcaa                                                                125

<210> SEQ ID NO 162
<211> LENGTH: 127
<212> TYPE: DNA
<213> ORGANISM: Artificial Sequence
<220> FEATURE:
<223> OTHER INFORMATION: source: AAV2; Recogn.Site: Nt.BstNBI; Format:
      b1

<400> SEQUENCE: 162
ttggccactc cctctctgcg cgactcgctc gctcactgag gccgggcgac caaaggtcgc     60
ccgacgcccg ggctttgccc gggcggcctc agtgagcgag cgagtcgcgc agagagggag    120
tggccaa                                                              127

<210> SEQ ID NO 163
<211> LENGTH: 125
<212> TYPE: DNA
<213> ORGANISM: Artificial Sequence
<220> FEATURE:
<223> OTHER INFORMATION: source: AAV2; Recogn.Site: Nt.BstNBI; Format:
      t1

<400> SEQUENCE: 163
ttggcgagtc cctctctgcg cgctcgctcg ctcactgagg ccgggcgacc aaaggtcgcc     60
cgacgcccgg gctttgcccg gcggcctca gtgagcgagc gagcgcgcag agagggactc    120
gccaa                                                                125

<210> SEQ ID NO 164
<211> LENGTH: 127
<212> TYPE: DNA
<213> ORGANISM: Artificial Sequence
<220> FEATURE:
<223> OTHER INFORMATION: source: AAV3; Recogn.Site: Nt.BstNBI; Format:
      b1

<400> SEQUENCE: 164
ttggccactc cctctatgcg cgactcgctc gctcggtggg gcctggcgac caaaggtcgc     60
cagacggacg tgctttgcac gtccggcccc accgagcgag cgagtcgcgc atagagggag    120
tggccaa                                                              127

<210> SEQ ID NO 165
<211> LENGTH: 125
<212> TYPE: DNA
<213> ORGANISM: Artificial Sequence
<220> FEATURE:
<223> OTHER INFORMATION: source: AAV3; Recogn.Site: Nt.BstNBI; Format:
      t1

<400> SEQUENCE: 165
ttggcgagtc cctctatgcg cactcgctcg ctcggtgggg cctggcgacc aaaggtcgcc     60

```
agacggacgt gctttgcacg tccggcccca ccgagcgagc gagtgcgcat agagggactc    120
gccaa                                                                125

<210> SEQ ID NO 166
<211> LENGTH: 127
<212> TYPE: DNA
<213> ORGANISM: Artificial Sequence
<220> FEATURE:
<223> OTHER INFORMATION: source: AAV4 left; Recogn.Site: Nt.BstNBI;
      Format: bl

<400> SEQUENCE: 166
ttggccactc cctctatgcg cgactcgctc actcactcgg ccctggagac caaaggtctc    60
cagactgccg gcctctggcc ggcagggccg agtgagtgag cgagtcgcgc atagagggag    120
tggccaa                                                              127

<210> SEQ ID NO 167
<211> LENGTH: 125
<212> TYPE: DNA
<213> ORGANISM: Artificial Sequence
<220> FEATURE:
<223> OTHER INFORMATION: source: AAV4 left; Recogn.Site: Nt.BstNBI;
      Format: tl

<400> SEQUENCE: 167
ttggcgagtc cctctatgcg cgctcgctca ctcactcggc cctggagacc aaaggtctcc    60
agactgccgg cctctggccg gcagggccga gtgagtgagc gagcgcgcat agagggactc    120
gccaa                                                                125

<210> SEQ ID NO 168
<211> LENGTH: 127
<212> TYPE: DNA
<213> ORGANISM: Artificial Sequence
<220> FEATURE:
<223> OTHER INFORMATION: source: AAV4 right; Recogn.Site: Nt.BstNBI;
      Format: bl

<400> SEQUENCE: 168
ttggccacat tagctatgcg cgactcgctc actcactcgg ccctggagac caaaggtctc    60
cagactgccg gcctctggcc ggcagggccg agtgagtgag cgagtcgcgc atagagggag    120
tggccaa                                                              127

<210> SEQ ID NO 169
<211> LENGTH: 125
<212> TYPE: DNA
<213> ORGANISM: Artificial Sequence
<220> FEATURE:
<223> OTHER INFORMATION: source: AAV4 right; Recogn.Site: Nt.BstNBI;
      Format: tl

<400> SEQUENCE: 169
ttggccagag tcgctatgcg cgctcgctca ctcactcggc cctggagacc aaaggtctcc    60
agactgccgg cctctggccg gcagggccga gtgagtgagc gagcgcgcat agagactctg    120
gccaa                                                                125

<210> SEQ ID NO 170
<211> LENGTH: 139
<212> TYPE: DNA
<213> ORGANISM: Artificial Sequence
<220> FEATURE:
```

<223> OTHER INFORMATION: source: AAV5; Recogn.Site: Nt.BstNBI; Format:
    bl

<400> SEQUENCE: 170
ctctcccccc tgtcgcgact cgctcgctcg ctggctcgtt tggggggtg gcagctcaaa     60 gagctgccag acgacggccc tctggccgtc gcccccccaa acgagccagc gagcgagcga    120
gtcgcgacag gggggagag                                                139

<210> SEQ ID NO 171
<211> LENGTH: 137
<212> TYPE: DNA
<213> ORGANISM: Artificial Sequence
<220> FEATURE:
<223> OTHER INFORMATION: source: AAV5; Recogn.Site: Nt.BstNBI; Format:
    tl

<400> SEQUENCE: 171 ctctccccccg agtcgcgttc gctcgctcgc tggctcgttt gggggggtgg cagctcaaag    60
agctgccaga cgacggccct ctggccgtcg cccccccaaa cgagccagcg agcgagcgaa   120
cgcgactcgg gggagag                                                  137

<210> SEQ ID NO 172
<211> LENGTH: 127
<212> TYPE: DNA
<213> ORGANISM: Artificial Sequence
<220> FEATURE:
<223> OTHER INFORMATION: source: AAV7; Recogn.Site: Nt.BstNBI; Format:
    bl

<400> SEQUENCE: 172
ttggccactc cctctatgcg cgactcgctc gctcggtggg gcctgcggac caaaggtccg    60
cagacggcag agctctgctc tgccggcccc accgagcgag cgagtcgcgc atagagggag   120
tggccaa                                                            127

<210> SEQ ID NO 173
<211> LENGTH: 125
<212> TYPE: DNA
<213> ORGANISM: Artificial Sequence
<220> FEATURE:
<223> OTHER INFORMATION: source: AAV7; Recogn.Site: Nt.BstNBI; Format:
    tl

<400> SEQUENCE: 173
ttggcgagtc cctctatgcg cgctcgctcg ctcggtgggg cctgcggacc aaaggtccgc    60
agacggcaga gctctgctct gccggcccca ccgagcgagc gagcgcgcat agagggactc   120
gccaa                                                              125

<210> SEQ ID NO 174
<211> LENGTH: 1636
<212> TYPE: DNA
<213> ORGANISM: Artificial Sequence
<220> FEATURE:
<223> OTHER INFORMATION: Construct 1 encodes for a left inverted repeat,
    a mini human PGK promoter, a turboluc ORF, SV40 poly a and
    a right inverted repeat

<400> SEQUENCE: 174
tgcgcgactc gctcgctcac tgaggccggg cgaccaaagg tcgcccgacg cccgggcttt    60
gcccgggcgg cctcagtgag cgagcgagtc gcgcagagag gttaaaacca actagacaac   120
tttgtatatc tagagttggg gttgcgcctt ttccaaggca gccctgggtt tgcgcaggga   180

```
cgcggctgct ctgggcgtgg ttccgggaaa cgcagcggcg ccgaccctgg gtctcgcaca      240
ttcttcacgt ccgttcgcag cgtcacccgg atcttcgccg ctacccttgt gggcccccccg     300 gcgacgcttc ctgctccgcc cctaagtcgg gaaggttcct tgcggttcgc ggcgtgccgg      360
acgtgacaaa cggaagccgc acgtctcact agtaccctcg cagacggaca gcgccaggga     420
gcaatggcag cgcgccgacc gcgatgggct gtggccaata gcggctgctc agcagggcgc     480
gccgagagca gcgccggga aggggcggtg cgggaggcgg ggtgtggggc ggtagtgtgg      540
gccctgttcc tgcccgcgcg cgtgttccgca ttctgcaagc ctccggagcg cacgtcggca    600
gtcggctccc tcgttgaccg aatcaccgac ctctctcccc aggcaagttt gtacaaaaaa    660
gcgcggccgc ggcaggctgc caccatggaa accgatacac tgctgctttg ggtacttttg     720
ctgtgggtgc ccggcagtac gggcgacgcc gcacaaccag ctaggagagc agtccggagc     780
ctggtcccct cttccgaggc cgaggctgaa cggggaaagc tgccaggcaa gaaactcccc     840
ttagaggttc tcatcgagct ggaagcaaac gcacgcaagg ccggttgcac tagggggctgc   900 ctcatctgcc tcagcaagat caaatgtaca gcaaagatga agaagtatat tcctggccgc    960
tgtgcagact acgaggcga caaaaaaaca ggacaagctg gtatagttgg cgccatcgta    1020
gatatccccg agattagtgg gttcaaggaa atggagccaa tggagcaatt cattgcacag   1080
gttgatagat gtcggattg cactactggt tgccttaagg gcttggcgaa tgtcaagtgt     1140
agtgatcttc tgaaaaagtg gctacccggc cggtgtgcca ccttcgctga caaaatacag   1200
agcgaagtcg acaatattaa aggacttgcc ggggactaat gatagtgaca caaagtgacg    1260
cgtcctagag ctcgcactgt gccttctagt tgccagccat ctgttgtttg cccctccccc    1320
gtgccttcct tgaccctgga aggtgccact cccactgtcc tttcctaata aaatgaggaa    1380
attgcatcgc attgtctgag taggtgtcat tctattctgg ggggtggggt ggggcaggac    1440
agcaaggggg aggattggga agagaatagc aggcatgctg ggggagggcgc tagcgcagga    1500 acccctttta atggagttgg cgagtccctc tctgcgcgct cgctcgctca ctgaggccgg    1560
gcgaccaaag gtcgcccgac gcccgggctt tgcccgggcg gcctcagtga gcgagcgagc   1620
gcgcagagat cgactc                                                   1636
```

<210> SEQ ID NO 175
<211> LENGTH: 1796
<212> TYPE: DNA
<213> ORGANISM: Artificial Sequence
<220> FEATURE:
<223> OTHER INFORMATION: Construct 2 encodes for a modified left ITR, a human PGK promoter, a secreted turboluc ORF, SV40 poly-A, a right ITR and a double restriction sites for nicking endonuclease 115 base pairs downstream of the right ITR

<400> SEQUENCE: 175

```
tgcgcgactc gctcgctcac tgaggccggg cgaccaaagg tcgcccgacg cccgggcttt      60 gccccgggcgg cctcagtgag cgagcgagtc gcgcagagag gttaaaacca actagacaac   120
tttgtatatc tagagttggg gttgcgcctt ttccaaggca gccctgggtt tgcgcaggga    180
cgcggctgct ctgggcgtgg ttccgggaaa cgcagcggcg ccgaccctgg gtctcgcaca    240
ttcttcacgt ccgttcgcag cgtcacccgg atcttcgccg ctacccttgt gggcccccccg   300 gcgacgcttc ctgctccgcc cctaagtcgg gaaggttcct tgcggttcgc ggcgtgccgg    360
acgtgacaaa cggaagccgc acgtctcact agtaccctcg cagacggaca gcgccaggga   420
gcaatggcag cgcgccgacc gcgatgggct gtggccaata gcggctgctc agcagggcgc    480
```

```
gccgagagca gcggccggga aggggcggtg cgggaggcgg ggtgtggggc ggtagtgtgg    540
gccctgttcc tgcccgcgcg gtgttccgca ttctgcaagc ctccggagcg cacgtcggca    600
gtcggctccc tcgttgaccg aatcaccgac ctctctcccc aggcaagttt gtacaaaaaa    660
gcgcggccgc ggcaggctgc caccatggaa accgatacac tgctgctttg gtacttttg     720 ctgtgggtgc ccggcagtac gggcgacgcc gcacaaccag ctaggagagc agtccggagc    780
ctggtcccct cttccgaggc cgaggctgaa cggggaaagc tgccaggcaa gaaactcccc    840
ttagaggttc tcatcgagct ggaagcaaac gcacgcaagg ccggttgcac tagggggctgc    900 ctcatctgcc tcagcaagat caaatgtaca gcaaagatga agaagtatat tcctggccgc    960
tgtgcagact acggaggcga caaaaaaaca ggacaagctg gtatagttgg cgccatcgta   1020
gatatccccg agattagtgg gttcaaggaa atggagccaa tggagcaatt cattgcacag   1080
gttgatagat gtgcggattg cactactggt tgccttaagg gcttggcgaa tgtcaagtgt   1140
agtgatcttc tgaaaaagtg gctacccggc cggtgtgcca ccttcgctga caaaatacag   1200
agcgaagtcg acaatattaa aggacttgcc ggggactaat gatagtgaca caaagtgacg   1260
cgtcctagag ctcgcactgt gccttctagt tgccagccat ctgttgtttg ccctccccc    1320 gtgccttcct tgaccctgga aggtgccact cccactgtcc tttcctaata aaatgaggaa   1380
attgcatcgc attgtctgag taggtgtcat tctattctgg ggggtggggt ggggcaggac   1440 agcaagggg aggattggga agagaatagc aggcatgctg gggagggcgc tagcgcagga    1500 accccttta atggagttgg cgagtccctc tctgcgcgct cgctcgctca ctgaggccgg    1560
gcgaccaaag gtcgcccgac gcccgggctt tgcccgggcg gcctcagtga gcgagcgagc   1620
gcgcagagat cgactcctcg gccacttgga ggggccgggg ggacgacgca atctggagtg   1680
gaaagaaccc ccgtctatgc ggcttaaagc acggccaggg aatagtggat caagtgtact   1740
gacatgtgcc ggagtccctc catgcccaga tcgactccct cgagatatat ggatcc       1796
```

<210> SEQ ID NO 176
<211> LENGTH: 23
<212> TYPE: DNA
<213> ORGANISM: AAV serotype 2 (AAV2)
<220> FEATURE:
<223> OTHER INFORMATION: AAV2 wt gRNA for Nicking Cas9

<400> SEQUENCE: 176

```
agcgagcgag cgcgcagaga ggg                                            23
```

<210> SEQ ID NO 177
<211> LENGTH: 16
<212> TYPE: DNA
<213> ORGANISM: AAV serotype 2 (AAV2)
<220> FEATURE:
<223> OTHER INFORMATION: AAV2 wt gDNA for PfAgo

<400> SEQUENCE: 177

```
gctcgctcgc tcggtg                                                    16
```

<210> SEQ ID NO 178
<211> LENGTH: 16
<212> TYPE: DNA
<213> ORGANISM: Artificial Sequence
<220> FEATURE:
<223> OTHER INFORMATION: Rep AAV1,2,7

<400> SEQUENCE: 178

```
gcgcgctcgc tcgctc                                                         16
```

<210> SEQ ID NO 179
<211> LENGTH: 17
<212> TYPE: DNA
<213> ORGANISM: Artificial Sequence
<220> FEATURE:
<223> OTHER INFORMATION: Rep AAV3

<400> SEQUENCE: 179

```
tgcgcactcg ctcgctc                                                        17
```

<210> SEQ ID NO 180
<211> LENGTH: 16
<212> TYPE: DNA
<213> ORGANISM: Artificial Sequence
<220> FEATURE:
<223> OTHER INFORMATION: Rep AAV4

<400> SEQUENCE: 180

```
gcgcgctcgc tcactc                                                         16
```

<210> SEQ ID NO 181
<211> LENGTH: 20
<212> TYPE: DNA
<213> ORGANISM: Artificial Sequence
<220> FEATURE:
<223> OTHER INFORMATION: Rep AAV5

<400> SEQUENCE: 181

```
gttcgctcgc tcgctggctc                                                     20
```

<210> SEQ ID NO 182
<211> LENGTH: 10
<212> TYPE: DNA
<213> ORGANISM: Artificial Sequence
<220> FEATURE:
<223> OTHER INFORMATION: NS1-NSBE3 B19V

<400> SEQUENCE: 182

```
ttccggtaca                                                                10
```

<210> SEQ ID NO 183
<211> LENGTH: 104
<212> TYPE: DNA
<213> ORGANISM: Human bocavirus (HBoV)
<220> FEATURE:
<223> OTHER INFORMATION: HBoV (nucleotides 129-237 of wt genome) (Fig.
      1)

<400> SEQUENCE: 183

```
tcttggaatc caatatgtct gccggctcag tcatgcctgc gctgcgcgca gcgcgctgcg         60
cgcgcgcatg atctaatcgc cggcagacat attggattcc aaga                         104
```

<210> SEQ ID NO 184
<211> LENGTH: 109
<212> TYPE: DNA
<213> ORGANISM: B19 parvovirus
<220> FEATURE:
<223> OTHER INFORMATION: B19 (nucleotides 139-227 on wt genome) (Fig. 1)

<400> SEQUENCE: 184

```
gggttggctc tgggccagct tgcttggggt tgccttgaca ctaagacaag cggcgcgccg         60
cttgatctta gtggcacgtc aaccccaagc gctggcccag agccaaccc                   109
```

```
<210> SEQ ID NO 185
<211> LENGTH: 50
<212> TYPE: DNA
<213> ORGANISM: Artificial Sequence
<220> FEATURE:
<223> OTHER INFORMATION: mtDNA OriL (Fig.4)

<400> SEQUENCE: 185
ttcaaacctg ccggggcttc tcccgccttt tttcccggcg gcgggagaag         50

<210> SEQ ID NO 186
<211> LENGTH: 99
<212> TYPE: DNA
<213> ORGANISM: Adeno-Associated Virus-1 (AAV1)

<400> SEQUENCE: 186
aacgggtgag ggagagacgc gcgagcgagc gagccacccc ggacgcctgg tttccaggcg     60
tctgccgtct cgagacgaga cggccggggt ggctcgctc                            99

<210> SEQ ID NO 187
<211> LENGTH: 99
<212> TYPE: DNA
<213> ORGANISM: Artificial Sequence
<220> FEATURE:
<223> OTHER INFORMATION: AAV1_Nb.BbvCI_BL

<400> SEQUENCE: 187
aacgggtgag ggggagtcgc gcgagcgagc gagccacccc ggacgcctgg tttccaggcg     60
tctgccgtct cgagacgaga cggccggggt ggctcgctc                            99

<210> SEQ ID NO 188
<211> LENGTH: 99
<212> TYPE: DNA
<213> ORGANISM: Artificial Sequence
<220> FEATURE:
<223> OTHER INFORMATION: AAV1_Nb.BbvCI_TL

<400> SEQUENCE: 188
aacgggtgag ggcgactccc gcgagcgagc gagccacccc ggacgcctgg tttccaggcg     60
tctgccgtct cgagacgaga cggccggggt ggctcgctc                            99

<210> SEQ ID NO 189
<211> LENGTH: 99
<212> TYPE: DNA
<213> ORGANISM: Artificial Sequence
<220> FEATURE:
<223> OTHER INFORMATION: AAV1_Nb.BsmI_BL

<400> SEQUENCE: 189
aacgggtgag ggacttacgc gcgagcgagc gagccacccc ggacgcctgg tttccaggcg     60
tctgccgtct cgagacgaga cggccggggt ggctcgctc                            99

<210> SEQ ID NO 190
<211> LENGTH: 99
<212> TYPE: DNA
<213> ORGANISM: Artificial Sequence
<220> FEATURE:
<223> OTHER INFORMATION: AAV1_Nb.BsmI_TL

<400> SEQUENCE: 190
aacgggtgag ggagagacgc gtaagcgagc gagccacccc ggacgcctgg tttccaggcg     60
tctgccgtct cgagacgaga cggccggggt ggctcgctc                            99
```

<210> SEQ ID NO 191
<211> LENGTH: 99
<212> TYPE: DNA
<213> ORGANISM: Artificial Sequence
<220> FEATURE:
<223> OTHER INFORMATION: AAV1_Nb.BsrDI_BL

<400> SEQUENCE: 191
aacgggtgag ggcgttacgc gcgagcgagc gagccacccc ggacgcctgg tttccaggcg    60
tctgccgtct cgagacgaga cggccggggt ggctcgctc                          99

<210> SEQ ID NO 192
<211> LENGTH: 99
<212> TYPE: DNA
<213> ORGANISM: Artificial Sequence
<220> FEATURE:
<223> OTHER INFORMATION: AAV1_Nb.BsrDI_TL

<400> SEQUENCE: 192
aacgggtgag ggagtaacgc gcgagcgagc gagccacccc ggacgcctgg tttccaggcg    60
tctgccgtct cgagacgaga cggccggggt ggctcgctc                          99

<210> SEQ ID NO 193
<211> LENGTH: 99
<212> TYPE: DNA
<213> ORGANISM: Artificial Sequence
<220> FEATURE:
<223> OTHER INFORMATION: AAV1_Nb.BssSI_BL

<400> SEQUENCE: 193
aacgggtgct cgagagacgc gcgagcgagc gagccacccc ggacgcctgg tttccaggcg    60
tctgccgtct cgagacgaga cggccggggt ggctcgctc                          99

<210> SEQ ID NO 194
<211> LENGTH: 99
<212> TYPE: DNA
<213> ORGANISM: Artificial Sequence
<220> FEATURE:
<223> OTHER INFORMATION: AAV1_Nb.BssSI_TL

<400> SEQUENCE: 194
aacgggtgag ggagcaccgc gcgagcgagc gagccacccc ggacgcctgg tttccaggcg    60
tctgccgtct cgagacgaga cggccggggt ggctcgctc                          99

<210> SEQ ID NO 195
<211> LENGTH: 99
<212> TYPE: DNA
<213> ORGANISM: Artificial Sequence
<220> FEATURE:
<223> OTHER INFORMATION: AAV1_Nb.BtsI_BL

<400> SEQUENCE: 195
aacgggtgag ggcgtcacgc gcgagcgagc gagccacccc ggacgcctgg tttccaggcg    60
tctgccgtct cgagacgaga cggccggggt ggctcgctc                          99

<210> SEQ ID NO 196
<211> LENGTH: 99
<212> TYPE: DNA
<213> ORGANISM: Artificial Sequence
<220> FEATURE:
<223> OTHER INFORMATION: AAV1_Nb.BtsI_TL

<400> SEQUENCE: 196
aacgggtgag ggagtgacgc gcgagcgagc gagccacccc ggacgcctgg tttccaggcg    60
tctgccgtct cgagacgaga cggccggggt ggctcgctc    99

<210> SEQ ID NO 197
<211> LENGTH: 99
<212> TYPE: DNA
<213> ORGANISM: Artificial Sequence
<220> FEATURE:
<223> OTHER INFORMATION: AAV1_Nt.AlwI_BL

<400> SEQUENCE: 197
aacgggtgag ggagctaggc gcgagcgagc gagccacccc ggacgcctgg tttccaggcg    60
tctgccgtct cgagacgaga cggccggggt ggctcgctc    99

<210> SEQ ID NO 198
<211> LENGTH: 99
<212> TYPE: DNA
<213> ORGANISM: Artificial Sequence
<220> FEATURE:
<223> OTHER INFORMATION: AAV1_Nt.AlwI_BL

<400> SEQUENCE: 198
aacgggtgac ctagagacgc gcgagcgagc gagccacccc ggacgcctgg tttccaggcg    60
tctgccgtct cgagacgaga cggccggggt ggctcgctc    99

<210> SEQ ID NO 199
<211> LENGTH: 99
<212> TYPE: DNA
<213> ORGANISM: Artificial Sequence
<220> FEATURE:
<223> OTHER INFORMATION: AAV1_Nt.BbvCI_TL

<400> SEQUENCE: 199
aacgggtgag ggcgactccc gcgagcgagc gagccacccc ggacgcctgg tttccaggcg    60
tctgccgtct cgagacgaga cggccggggt ggctcgctc    99

<210> SEQ ID NO 200
<211> LENGTH: 99
<212> TYPE: DNA
<213> ORGANISM: Artificial Sequence
<220> FEATURE:
<223> OTHER INFORMATION: AAV1_Nt.BbvCI_BL

<400> SEQUENCE: 200
aacgggtgag ggggagtcgc gcgagcgagc gagccacccc ggacgcctgg tttccaggcg    60
tctgccgtct cgagacgaga cggccggggt ggctcgctc    99

<210> SEQ ID NO 201
<211> LENGTH: 99
<212> TYPE: DNA
<213> ORGANISM: Artificial Sequence
<220> FEATURE:
<223> OTHER INFORMATION: AAV1_Nt.BsmAI_TL

<400> SEQUENCE: 201
aacgggtgac tctgagacgc gcgagcgagc gagccacccc ggacgcctgg tttccaggcg    60
tctgccgtct cgagacgaga cggccggggt ggctcgctc    99

<210> SEQ ID NO 202
<211> LENGTH: 99

```
<212> TYPE: DNA
<213> ORGANISM: Artificial Sequence
<220> FEATURE:
<223> OTHER INFORMATION: AAV1_Nt.BsmAI_BL

<400> SEQUENCE: 202
aacgggtgag gcagagacgc gcgagcgagc gagccacccc ggacgcctgg tttccaggcg      60
tctgccgtct cgagacgaga cggccggggt ggctcgctc                            99

<210> SEQ ID NO 203
<211> LENGTH: 99
<212> TYPE: DNA
<213> ORGANISM: Artificial Sequence
<220> FEATURE:
<223> OTHER INFORMATION: AAV1_Nt.BspQI_TL

<400> SEQUENCE: 203
aacgggtgag ggcttctcgc gcgagcgagc gagccacccc ggacgcctgg tttccaggcg      60
tctgccgtct cgagacgaga cggccggggt ggctcgctc                            99

<210> SEQ ID NO 204
<211> LENGTH: 99
<212> TYPE: DNA
<213> ORGANISM: Artificial Sequence
<220> FEATURE:
<223> OTHER INFORMATION: AAV1_Nt.BspQI_BL

<400> SEQUENCE: 204
aacgggtgag ggcgagaagc gcgagcgagc gagccacccc ggacgcctgg tttccaggcg      60
tctgccgtct cgagacgaga cggccggggt ggctcgctc                            99

<210> SEQ ID NO 205
<211> LENGTH: 100
<212> TYPE: DNA
<213> ORGANISM: Artificial Sequence
<220> FEATURE:
<223> OTHER INFORMATION: AAV1_Nt.BstNBI_TL

<400> SEQUENCE: 205
aacgggtgag ggagagacgc gctgagcgag cgagccaccc cggacgcctg gtttccaggc      60
gtctgccgtc tcgagacgag acggccgggg tggctcgctc                          100

<210> SEQ ID NO 206
<211> LENGTH: 99
<212> TYPE: DNA
<213> ORGANISM: Artificial Sequence
<220> FEATURE:
<223> OTHER INFORMATION: AAV1_Nt.BstNBI_BL

<400> SEQUENCE: 206
aacggctcag ggagagacgc gcgagcgagc gagccacccc ggacgcctgg tttccaggcg      60
tctgccgtct cgagacgaga cggccggggt ggctcgctc                            99

<210> SEQ ID NO 207
<211> LENGTH: 99
<212> TYPE: DNA
<213> ORGANISM: Adeno-Associated Virus -2 (AAV2)

<400> SEQUENCE: 207
aaccggtgag ggagagacgc gcgagcgagc gagtgactcc ggcccgctgg tttccagcgg      60
gctgcgggcc cgaaacgggc cgccggagt cactcgctc                             99
```

<210> SEQ ID NO 208
<211> LENGTH: 99
<212> TYPE: DNA
<213> ORGANISM: Artificial Sequence
<220> FEATURE:
<223> OTHER INFORMATION: AAV2_Nb.BbvCI_BL

<400> SEQUENCE: 208

```
aaccggtgag ggggagtcgc gcgagcgagc gagtgactcc ggcccgctgg tttccagcgg      60
gctgcgggcc cgaaacgggc ccgccggagt cactcgctc                             99
```

<210> SEQ ID NO 209
<211> LENGTH: 99
<212> TYPE: DNA
<213> ORGANISM: Artificial Sequence
<220> FEATURE:
<223> OTHER INFORMATION: AAV2_Nb.BbvCI_TL

<400> SEQUENCE: 209

```
aaccggtgag ggcgactccc gcgagcgagc gagtgactcc ggcccgctgg tttccagcgg      60
gctgcgggcc cgaaacgggc ccgccggagt cactcgctc                             99
```

<210> SEQ ID NO 210
<211> LENGTH: 99
<212> TYPE: DNA
<213> ORGANISM: Artificial Sequence
<220> FEATURE:
<223> OTHER INFORMATION: AAV2_Nb.BsmI_BL

<400> SEQUENCE: 210

```
aaccggtgag ggacttacgc gcgagcgagc gagtgactcc ggcccgctgg tttccagcgg      60
gctgcgggcc cgaaacgggc ccgccggagt cactcgctc                             99
```

<210> SEQ ID NO 211
<211> LENGTH: 99
<212> TYPE: DNA
<213> ORGANISM: Artificial Sequence
<220> FEATURE:
<223> OTHER INFORMATION: AAV2_Nb.BsmI_TL

<400> SEQUENCE: 211

```
aaccggtgag ggagagacgc gtaagcgagc gagtgactcc ggcccgctgg tttccagcgg      60
gctgcgggcc cgaaacgggc ccgccggagt cactcgctc                             99
```

<210> SEQ ID NO 212
<211> LENGTH: 99
<212> TYPE: DNA
<213> ORGANISM: Artificial Sequence
<220> FEATURE:
<223> OTHER INFORMATION: AAV2_Nb.BsrDI_BL

<400> SEQUENCE: 212

```
aaccggtgag ggcgttacgc gcgagcgagc gagtgactcc ggcccgctgg tttccagcgg      60
gctgcgggcc cgaaacgggc ccgccggagt cactcgctc                             99
```

<210> SEQ ID NO 213
<211> LENGTH: 99
<212> TYPE: DNA
<213> ORGANISM: Artificial Sequence
<220> FEATURE:
<223> OTHER INFORMATION: AAV2_Nb.BsrDI_TL

<400> SEQUENCE: 213

```
aaccggtgag ggagtaacgc gcgagcgagc gagtgactcc ggcccgctgg tttccagcgg      60
gctgcgggcc cgaaacgggc ccgccggagt cactcgctc                             99

<210> SEQ ID NO 214
<211> LENGTH: 99
<212> TYPE: DNA
<213> ORGANISM: Artificial Sequence
<220> FEATURE:
<223> OTHER INFORMATION: AAV2_Nb.BssSI_BL

<400> SEQUENCE: 214
aaccggtgct cgagagacgc gcgagcgagc gagtgactcc ggcccgctgg tttccagcgg      60
gctgcgggcc cgaaacgggc ccgccggagt cactcgctc                             99

<210> SEQ ID NO 215
<211> LENGTH: 99
<212> TYPE: DNA
<213> ORGANISM: Artificial Sequence
<220> FEATURE:
<223> OTHER INFORMATION: AAV2_Nb.BssSI_TL

<400> SEQUENCE: 215
aaccggtgag ggagcaccgc gcgagcgagc gagtgactcc ggcccgctgg tttccagcgg      60
gctgcgggcc cgaaacgggc ccgccggagt cactcgctc                             99

<210> SEQ ID NO 216
<211> LENGTH: 99
<212> TYPE: DNA
<213> ORGANISM: Artificial Sequence
<220> FEATURE:
<223> OTHER INFORMATION: AAV2_Nb.BtsI_BL

<400> SEQUENCE: 216
aaccggtgag ggcgtcacgc gcgagcgagc gagtgactcc ggcccgctgg tttccagcgg      60
gctgcgggcc cgaaacgggc ccgccggagt cactcgctc                             99

<210> SEQ ID NO 217
<211> LENGTH: 99
<212> TYPE: DNA
<213> ORGANISM: Artificial Sequence
<220> FEATURE:
<223> OTHER INFORMATION: AAV2_Nb.BtsI_TL

<400> SEQUENCE: 217
aaccggtgag ggagtgacgc gcgagcgagc gagtgactcc ggcccgctgg tttccagcgg      60
gctgcgggcc cgaaacgggc ccgccggagt cactcgctc                             99

<210> SEQ ID NO 218
<211> LENGTH: 99
<212> TYPE: DNA
<213> ORGANISM: Artificial Sequence
<220> FEATURE:
<223> OTHER INFORMATION: AAV2_Nt.AlwI_BL

<400> SEQUENCE: 218
aaccggtgag ggagctaggc gcgagcgagc gagtgactcc ggcccgctgg tttccagcgg      60
gctgcgggcc cgaaacgggc ccgccggagt cactcgctc                             99

<210> SEQ ID NO 219
<211> LENGTH: 99
<212> TYPE: DNA
```

```
<213> ORGANISM: Artificial Sequence
<220> FEATURE:
<223> OTHER INFORMATION: AAV2_Nt.AlwI_BL

<400> SEQUENCE: 219
aaccggtgac ctagagacgc gcgagcgagc gagtgactcc ggcccgctgg tttccagcgg      60
gctgcgggcc cgaaacgggc cgccggagt cactcgctc                              99

<210> SEQ ID NO 220
<211> LENGTH: 99
<212> TYPE: DNA
<213> ORGANISM: Artificial Sequence
<220> FEATURE:
<223> OTHER INFORMATION: AAV2_Nt.BbvCI_TL

<400> SEQUENCE: 220
aaccggtgag ggcgactccc gcgagcgagc gagtgactcc ggcccgctgg tttccagcgg      60
gctgcgggcc cgaaacgggc cgccggagt cactcgctc                              99

<210> SEQ ID NO 221
<211> LENGTH: 99
<212> TYPE: DNA
<213> ORGANISM: Artificial Sequence
<220> FEATURE:
<223> OTHER INFORMATION: AAV2_Nt.BbvCI_BL

<400> SEQUENCE: 221
aaccggtgag ggggagtcgc gcgagcgagc gagtgactcc ggcccgctgg tttccagcgg      60
gctgcgggcc cgaaacgggc cgccggagt cactcgctc                              99

<210> SEQ ID NO 222
<211> LENGTH: 99
<212> TYPE: DNA
<213> ORGANISM: Artificial Sequence
<220> FEATURE:
<223> OTHER INFORMATION: AAV2_Nt.BsmAI_TL

<400> SEQUENCE: 222
aaccggtgac tctgagacgc gcgagcgagc gagtgactcc ggcccgctgg tttccagcgg      60
gctgcgggcc cgaaacgggc cgccggagt cactcgctc                              99

<210> SEQ ID NO 223
<211> LENGTH: 99
<212> TYPE: DNA
<213> ORGANISM: Artificial Sequence
<220> FEATURE:
<223> OTHER INFORMATION: AAV2_Nt.BsmAI_BL

<400> SEQUENCE: 223
aaccggtgag gcagagacgc gcgagcgagc gagtgactcc ggcccgctgg tttccagcgg      60
gctgcgggcc cgaaacgggc cgccggagt cactcgctc                              99

<210> SEQ ID NO 224
<211> LENGTH: 99
<212> TYPE: DNA
<213> ORGANISM: Artificial Sequence
<220> FEATURE:
<223> OTHER INFORMATION: AAV2_Nt.BspQI_TL

<400> SEQUENCE: 224
aaccggtgag ggcttctcgc gcgagcgagc gagtgactcc ggcccgctgg tttccagcgg      60
gctgcgggcc cgaaacgggc cgccggagt cactcgctc                              99
```

<210> SEQ ID NO 225
<211> LENGTH: 99
<212> TYPE: DNA
<213> ORGANISM: Artificial Sequence
<220> FEATURE:
<223> OTHER INFORMATION: AAV2_Nt.BspQI_BL

<400> SEQUENCE: 225
aaccggtgag ggcgagaagc gcgagcgagc gagtgactcc ggcccgctgg tttccagcgg    60
gctgcgggcc cgaaacgggc cgccggagt cactcgctc                           99

<210> SEQ ID NO 226
<211> LENGTH: 100
<212> TYPE: DNA
<213> ORGANISM: Artificial Sequence
<220> FEATURE:
<223> OTHER INFORMATION: AAV2_Nt.BstNBI_TL

<400> SEQUENCE: 226
aaccggtgag ggagagacgc gctgagcgag cgagtgactc cggcccgctg gtttccagcg    60
ggctgcgggc ccgaaacggg cccgccggag tcactcgctc                          100

<210> SEQ ID NO 227
<211> LENGTH: 99
<212> TYPE: DNA
<213> ORGANISM: Artificial Sequence
<220> FEATURE:
<223> OTHER INFORMATION: AAV2_Nt.BstNBI_BL

<400> SEQUENCE: 227
aaccgctcag ggagagacgc gcgagcgagc gagtgactcc ggcccgctgg tttccagcgg    60
gctgcgggcc cgaaacgggc cgccggagt cactcgctc                           99

<210> SEQ ID NO 228
<211> LENGTH: 99
<212> TYPE: DNA
<213> ORGANISM: Adeno-Associated Virus-3 (AAV3)

<400> SEQUENCE: 228
aaccggtgag ggagatacgc gtgagcgagc gagccacccc ggaccgctgg tttccagcgg    60
tctgcctgca cgaaacgtgc aggccggggt ggctcgctc                          99

<210> SEQ ID NO 229
<211> LENGTH: 99
<212> TYPE: DNA
<213> ORGANISM: Artificial Sequence
<220> FEATURE:
<223> OTHER INFORMATION: AAV3_Nb.BbvCI_BL

<400> SEQUENCE: 229
aaccggtgag ggggagtcgc gtgagcgagc gagccacccc ggaccgctgg tttccagcgg    60
tctgcctgca cgaaacgtgc aggccggggt ggctcgctc                          99

<210> SEQ ID NO 230
<211> LENGTH: 99
<212> TYPE: DNA
<213> ORGANISM: Artificial Sequence
<220> FEATURE:
<223> OTHER INFORMATION: AAV3_Nb.BbvCI_TL

<400> SEQUENCE: 230
aaccggtgag ggcgactccc gtgagcgagc gagccacccc ggaccgctgg tttccagcgg    60
tctgcctgca cgaaacgtgc aggccggggt ggctcgctc    99

<210> SEQ ID NO 231
<211> LENGTH: 99
<212> TYPE: DNA
<213> ORGANISM: Artificial Sequence
<220> FEATURE:
<223> OTHER INFORMATION: AAV3_Nb.BsmI_BL

<400> SEQUENCE: 231
aaccggtgag ggacttacgc gtgagcgagc gagccacccc ggaccgctgg tttccagcgg    60
tctgcctgca cgaaacgtgc aggccggggt ggctcgctc    99

<210> SEQ ID NO 232
<211> LENGTH: 99
<212> TYPE: DNA
<213> ORGANISM: Artificial Sequence
<220> FEATURE:
<223> OTHER INFORMATION: AAV3_Nb.BsmI_TL

<400> SEQUENCE: 232
aaccggtgag ggagatacgc gtaagcgagc gagccacccc ggaccgctgg tttccagcgg    60
tctgcctgca cgaaacgtgc aggccggggt ggctcgctc    99

<210> SEQ ID NO 233
<211> LENGTH: 99
<212> TYPE: DNA
<213> ORGANISM: Artificial Sequence
<220> FEATURE:
<223> OTHER INFORMATION: AAV3_Nb.BsrDI_BL

<400> SEQUENCE: 233
aaccggtgag ggcgttacgc gtgagcgagc gagccacccc ggaccgctgg tttccagcgg    60
tctgcctgca cgaaacgtgc aggccggggt ggctcgctc    99

<210> SEQ ID NO 234
<211> LENGTH: 99
<212> TYPE: DNA
<213> ORGANISM: Artificial Sequence
<220> FEATURE:
<223> OTHER INFORMATION: AAV3_Nb.BsrDI_TL

<400> SEQUENCE: 234
aaccggtgag ggagtaacgc gtgagcgagc gagccacccc ggaccgctgg tttccagcgg    60
tctgcctgca cgaaacgtgc aggccggggt ggctcgctc    99

<210> SEQ ID NO 235
<211> LENGTH: 99
<212> TYPE: DNA
<213> ORGANISM: Artificial Sequence
<220> FEATURE:
<223> OTHER INFORMATION: AAV3_Nb.BssSI_BL

<400> SEQUENCE: 235
aaccggtgct cgagatacgc gtgagcgagc gagccacccc ggaccgctgg tttccagcgg    60
tctgcctgca cgaaacgtgc aggccggggt ggctcgctc    99

<210> SEQ ID NO 236
<211> LENGTH: 99
<212> TYPE: DNA
<213> ORGANISM: Artificial Sequence

```
<220> FEATURE:
<223> OTHER INFORMATION: AAV3_Nb.BssSI_TL

<400> SEQUENCE: 236
aaccggtgag ggagcaccgc gtgagcgagc gagccacccc ggaccgctgg tttccagcgg    60
tctgcctgca cgaaacgtgc aggccggggt ggctcgctc                           99

<210> SEQ ID NO 237
<211> LENGTH: 99
<212> TYPE: DNA
<213> ORGANISM: Artificial Sequence
<220> FEATURE:
<223> OTHER INFORMATION: AAV3_Nb.BtsI_BL

<400> SEQUENCE: 237
aaccggtgag ggcgtcacgc gtgagcgagc gagccacccc ggaccgctgg tttccagcgg    60
tctgcctgca cgaaacgtgc aggccggggt ggctcgctc                           99

<210> SEQ ID NO 238
<211> LENGTH: 99
<212> TYPE: DNA
<213> ORGANISM: Artificial Sequence
<220> FEATURE:
<223> OTHER INFORMATION: AAV3_Nb.BtsI_TL

<400> SEQUENCE: 238
aaccggtgag ggagtgacgc gtgagcgagc gagccacccc ggaccgctgg tttccagcgg    60
tctgcctgca cgaaacgtgc aggccggggt ggctcgctc                           99

<210> SEQ ID NO 239
<211> LENGTH: 99
<212> TYPE: DNA
<213> ORGANISM: Artificial Sequence
<220> FEATURE:
<223> OTHER INFORMATION: AAV3_Nt.AlwI_BL

<400> SEQUENCE: 239
aaccggtgag ggagctaggc gtgagcgagc gagccacccc ggaccgctgg tttccagcgg    60
tctgcctgca cgaaacgtgc aggccggggt ggctcgctc                           99

<210> SEQ ID NO 240
<211> LENGTH: 99
<212> TYPE: DNA
<213> ORGANISM: Artificial Sequence
<220> FEATURE:
<223> OTHER INFORMATION: AAV3_Nt.AlwI_BL

<400> SEQUENCE: 240
aaccggtgac ctagatacgc gtgagcgagc gagccacccc ggaccgctgg tttccagcgg    60
tctgcctgca cgaaacgtgc aggccggggt ggctcgctc                           99

<210> SEQ ID NO 241
<211> LENGTH: 99
<212> TYPE: DNA
<213> ORGANISM: Artificial Sequence
<220> FEATURE:
<223> OTHER INFORMATION: AAV3_Nt.BbvCI_TL

<400> SEQUENCE: 241
aaccggtgag ggcgactccc gtgagcgagc gagccacccc ggaccgctgg tttccagcgg    60
tctgcctgca cgaaacgtgc aggccggggt ggctcgctc                           99
```

-continued

<210> SEQ ID NO 242
<211> LENGTH: 99
<212> TYPE: DNA
<213> ORGANISM: Artificial Sequence
<220> FEATURE:
<223> OTHER INFORMATION: AAV3_Nt.BbvCI_BL

<400> SEQUENCE: 242
aaccggtgag ggggagtcgc gtgagcgagc gagccacccc ggaccgctgg tttccagcgg    60
tctgcctgca cgaaacgtgc aggccggggt ggctcgctc                          99

<210> SEQ ID NO 243
<211> LENGTH: 99
<212> TYPE: DNA
<213> ORGANISM: Artificial Sequence
<220> FEATURE:
<223> OTHER INFORMATION: AAV3_Nt.BsmAI_TL

<400> SEQUENCE: 243
aaccggtgac tctgatacgc gtgagcgagc gagccacccc ggaccgctgg tttccagcgg    60
tctgcctgca cgaaacgtgc aggccggggt ggctcgctc                          99

<210> SEQ ID NO 244
<211> LENGTH: 99
<212> TYPE: DNA
<213> ORGANISM: Artificial Sequence
<220> FEATURE:
<223> OTHER INFORMATION: AAV3_Nt.BsmAI_BL

<400> SEQUENCE: 244
aaccggtgag gcagagacgc gtgagcgagc gagccacccc ggaccgctgg tttccagcgg    60
tctgcctgca cgaaacgtgc aggccggggt ggctcgctc                          99

<210> SEQ ID NO 245
<211> LENGTH: 99
<212> TYPE: DNA
<213> ORGANISM: Artificial Sequence
<220> FEATURE:
<223> OTHER INFORMATION: AAV3_Nt.BspQI_TL

<400> SEQUENCE: 245
aaccggtgag ggcttctcgc gtgagcgagc gagccacccc ggaccgctgg tttccagcgg    60
tctgcctgca cgaaacgtgc aggccggggt ggctcgctc                          99

<210> SEQ ID NO 246
<211> LENGTH: 99
<212> TYPE: DNA
<213> ORGANISM: Artificial Sequence
<220> FEATURE:
<223> OTHER INFORMATION: AAV3_Nt.BspQI_BL

<400> SEQUENCE: 246
aaccggtgag ggcgagaagc gtgagcgagc gagccacccc ggaccgctgg tttccagcgg    60
tctgcctgca cgaaacgtgc aggccggggt ggctcgctc                          99

<210> SEQ ID NO 247
<211> LENGTH: 100
<212> TYPE: DNA
<213> ORGANISM: Artificial Sequence
<220> FEATURE:
<223> OTHER INFORMATION: AAV3_Nt.BstNBI_TL

<400> SEQUENCE: 247

```
aaccggtgag ggagatacgc gctgagcgag cgagccaccc cggaccgctg gtttccagcg      60
gtctgcctgc acgaaacgtg caggccgggg tggctcgctc                           100
```

<210> SEQ ID NO 248
<211> LENGTH: 99
<212> TYPE: DNA
<213> ORGANISM: Artificial Sequence
<220> FEATURE:
<223> OTHER INFORMATION: AAV3_Nt.BstNBI_BL

<400> SEQUENCE: 248

```
aaccgctcag ggagatacgc gtgagcgagc gagccacccc ggaccgctgg tttccagcgg      60
tctgcctgca cgaaacgtgc aggccggggt ggctcgctc                            99
```

<210> SEQ ID NO 249
<211> LENGTH: 125
<212> TYPE: DNA
<213> ORGANISM: Adeno-Associated Virus-4 (AAV)
<220> FEATURE:
<223> OTHER INFORMATION: AAV4_left

<400> SEQUENCE: 249

```
aaccggtgag ggagatacgc gcgagcgagt gagtgagccg ggacctctgg tttccagagg      60
tctgacggcc ggagaccggc cgtcccggct cactcactcg ctcgcgcgta tctccctcac     120
cggtt                                                                 125
```

<210> SEQ ID NO 250
<211> LENGTH: 125
<212> TYPE: DNA
<213> ORGANISM: Artificial Sequence
<220> FEATURE:
<223> OTHER INFORMATION: AAV4_left_Nb.BbvCI_BL

<400> SEQUENCE: 250

```
aaccggtgag ggggagtcgc gcgagcgagt gagtgagccg ggacctctgg tttccagagg      60
tctgacggcc ggagaccggc cgtcccggct cactcactcg ctcgcgcgac tcccccctcac    120 cggtt                                                                 125
```

<210> SEQ ID NO 251
<211> LENGTH: 125
<212> TYPE: DNA
<213> ORGANISM: Artificial Sequence
<220> FEATURE:
<223> OTHER INFORMATION: AAV4_left_Nb.BbvCI_TL

<400> SEQUENCE: 251

```
aaccggtgag ggcgactccc gcgagcgagt gagtgagccg ggacctctgg tttccagagg      60
tctgacggcc ggagaccggc cgtcccggct cactcactcg ctcgcgggag tcgccctcac     120
cggtt                                                                 125
```

<210> SEQ ID NO 252
<211> LENGTH: 125
<212> TYPE: DNA
<213> ORGANISM: Artificial Sequence
<220> FEATURE:
<223> OTHER INFORMATION: AAV4_left_Nb.BsmI_BL

<400> SEQUENCE: 252

```
aaccggtgag ggacttacgc gcgagcgagt gagtgagccg ggacctctgg tttccagagg      60
```

```
tctgacggcc ggagaccggc cgtcccggct cactcactcg ctcgcgcgta agtccctcac    120
cggtt                                                               125

<210> SEQ ID NO 253
<211> LENGTH: 125
<212> TYPE: DNA
<213> ORGANISM: Artificial Sequence
<220> FEATURE:
<223> OTHER INFORMATION: AAV4_left_Nb.BsmI_TL

<400> SEQUENCE: 253
aaccggtgag ggagatacgc gtaagcgagt gagtgagccg ggacctctgg tttccagagg    60
tctgacggcc ggagaccggc cgtcccggct cactcactcg cttacgcgta tctccctcac    120
cggtt                                                               125

<210> SEQ ID NO 254
<211> LENGTH: 125
<212> TYPE: DNA
<213> ORGANISM: Artificial Sequence
<220> FEATURE:
<223> OTHER INFORMATION: AAV4_left_Nb.BsrDI_BL

<400> SEQUENCE: 254
aaccggtgag ggcgttacgc gcgagcgagt gagtgagccg ggacctctgg tttccagagg    60
tctgacggcc ggagaccggc cgtcccggct cactcactcg ctcgcgcgta acgccctcac    120
cggtt                                                               125

<210> SEQ ID NO 255
<211> LENGTH: 125
<212> TYPE: DNA
<213> ORGANISM: Artificial Sequence
<220> FEATURE:
<223> OTHER INFORMATION: AAV4_left_Nb.BsrDI_TL

<400> SEQUENCE: 255
aaccggtgag ggagtaacgc gcgagcgagt gagtgagccg ggacctctgg tttccagagg    60
tctgacggcc ggagaccggc cgtcccggct cactcactcg ctcgcgcgtt actccctcac    120
cggtt                                                               125

<210> SEQ ID NO 256
<211> LENGTH: 125
<212> TYPE: DNA
<213> ORGANISM: Artificial Sequence
<220> FEATURE:
<223> OTHER INFORMATION: AAV4_left_Nb.BssSI_BL

<400> SEQUENCE: 256
aaccggtgct cgagatacgc gcgagcgagt gagtgagccg ggacctctgg tttccagagg    60
tctgacggcc ggagaccggc cgtcccggct cactcactcg ctcgcgcgta tctcgagcac    120
cggtt                                                               125

<210> SEQ ID NO 257
<211> LENGTH: 125
<212> TYPE: DNA
<213> ORGANISM: Artificial Sequence
<220> FEATURE:
<223> OTHER INFORMATION: AAV4_left_Nb.BssSI_TL

<400> SEQUENCE: 257
aaccggtgag ggagcaccgc gcgagcgagt gagtgagccg ggacctctgg tttccagagg    60
```
tctgacggcc ggagaccggc cgtcccggct cactcactcg ctcgcgcggt gctccctcac    120
cggtt                                                                125

<210> SEQ ID NO 258
<211> LENGTH: 125
<212> TYPE: DNA
<213> ORGANISM: Artificial Sequence
<220> FEATURE:
<223> OTHER INFORMATION: AAV4_left_Nb.BtsI_BL

<400> SEQUENCE: 258
aaccggtgag ggcgtcacgc gcgagcgagt gagtgagccg ggacctctgg tttccagagg     60
tctgacggcc ggagaccggc cgtcccggct cactcactcg ctcgcgcgtg acgccctcac    120
cggtt                                                                125

<210> SEQ ID NO 259
<211> LENGTH: 125
<212> TYPE: DNA
<213> ORGANISM: Artificial Sequence
<220> FEATURE:
<223> OTHER INFORMATION: AAV4_left_Nb.BtsI_TL

<400> SEQUENCE: 259
aaccggtgag ggagtgacgc gcgagcgagt gagtgagccg ggacctctgg tttccagagg     60
tctgacggcc ggagaccggc cgtcccggct cactcactcg ctcgcgcgtc actccctcac    120
cggtt                                                                125

<210> SEQ ID NO 260
<211> LENGTH: 125
<212> TYPE: DNA
<213> ORGANISM: Artificial Sequence
<220> FEATURE:
<223> OTHER INFORMATION: AAV4_left_Nt.AlwI_BL

<400> SEQUENCE: 260
aaccggtgag ggagctaggc gcgagcgagt gagtgagccg ggacctctgg tttccagagg     60
tctgacggcc ggagaccggc cgtcccggct cactcactcg ctcgcgccta gctccctcac    120
cggtt                                                                125

<210> SEQ ID NO 261
<211> LENGTH: 125
<212> TYPE: DNA
<213> ORGANISM: Artificial Sequence
<220> FEATURE:
<223> OTHER INFORMATION: AAV4_left_Nt.AlwI_BL

<400> SEQUENCE: 261
aaccggtgac ctagatacgc gcgagcgagt gagtgagccg ggacctctgg tttccagagg     60
tctgacggcc ggagaccggc cgtcccggct cactcactcg ctcgcgcgta tctaggtcac    120
cggtt                                                                125

<210> SEQ ID NO 262
<211> LENGTH: 125
<212> TYPE: DNA
<213> ORGANISM: Artificial Sequence
<220> FEATURE:
<223> OTHER INFORMATION: AAV4_left_Nt.BbvCI_TL

<400> SEQUENCE: 262
aaccggtgag ggcgactccc gcgagcgagt gagtgagccg ggacctctgg tttccagagg    60
tctgacggcc ggagaccggc cgtcccggct cactcactcg ctcgcgggag tcgccctcac   120
cggtt                                                              125

<210> SEQ ID NO 263
<211> LENGTH: 125
<212> TYPE: DNA
<213> ORGANISM: Artificial Sequence
<220> FEATURE:
<223> OTHER INFORMATION: AAV4_left_Nt.BbvCI_BL

<400> SEQUENCE: 263
aaccggtgag ggggagtcgc gcgagcgagt gagtgagccg ggacctctgg tttccagagg    60
tctgacggcc ggagaccggc cgtcccggct cactcactcg ctcgcgcgac tcccccctcac  120 cggtt                                                              125

<210> SEQ ID NO 264
<211> LENGTH: 125
<212> TYPE: DNA
<213> ORGANISM: Artificial Sequence
<220> FEATURE:
<223> OTHER INFORMATION: AAV4_left_Nt.BsmAI_TL

<400> SEQUENCE: 264
aaccggtgac tctgatacgc gcgagcgagt gagtgagccg ggacctctgg tttccagagg    60
tctgacggcc ggagaccggc cgtcccggct cactcactcg ctcgcgcgta tcagagtcac   120
cggtt                                                              125

<210> SEQ ID NO 265
<211> LENGTH: 125
<212> TYPE: DNA
<213> ORGANISM: Artificial Sequence
<220> FEATURE:
<223> OTHER INFORMATION: AAV4_left_Nt.BsmAI_BL

<400> SEQUENCE: 265
aaccggtgag gcagagacgc gcgagcgagt gagtgagccg ggacctctgg tttccagagg    60
tctgacggcc ggagaccggc cgtcccggct cactcactcg ctcgcgcgtc tctgcctcac   120
cggtt                                                              125

<210> SEQ ID NO 266
<211> LENGTH: 125
<212> TYPE: DNA
<213> ORGANISM: Artificial Sequence
<220> FEATURE:
<223> OTHER INFORMATION: AAV4_left_Nt.BspQI_TL

<400> SEQUENCE: 266
aaccggtgag ggcttctcgc gcgagcgagt gagtgagccg ggacctctgg tttccagagg    60
tctgacggcc ggagaccggc cgtcccggct cactcactcg ctcgcgcgag aagccctcac   120
cggtt                                                              125

<210> SEQ ID NO 267
<211> LENGTH: 125
<212> TYPE: DNA
<213> ORGANISM: Artificial Sequence
<220> FEATURE:
<223> OTHER INFORMATION: AAV4_left_Nt.BspQI_BL

<400> SEQUENCE: 267

```
aaccggtgag ggcgagaagc gcgagcgagt gagtgagccg ggacctctgg tttccagagg        60
tctgacggcc ggagaccggc cgtcccggct cactcactcg ctcgcgcttc tcgccctcac       120
cggtt                                                                   125

<210> SEQ ID NO 268
<211> LENGTH: 127
<212> TYPE: DNA
<213> ORGANISM: Artificial Sequence
<220> FEATURE:
<223> OTHER INFORMATION: AAV4_left_Nt.BstNBI_TL

<400> SEQUENCE: 268
aaccggtgag ggagatacgc gctgagcgag tgagtgagcc gggacctctg gtttccagag        60
gtctgacggc cggagaccgg ccgtcccggc tcactcactc gctcagcgcg tatctccctc       120
accggtt                                                                 127

<210> SEQ ID NO 269
<211> LENGTH: 125
<212> TYPE: DNA
<213> ORGANISM: Artificial Sequence
<220> FEATURE:
<223> OTHER INFORMATION: AAV4_left_Nt.BstNBI_BL

<400> SEQUENCE: 269
aaccgctcag ggagatacgc gcgagcgagt gagtgagccg ggacctctgg tttccagagg        60
tctgacggcc ggagaccggc cgtcccggct cactcactcg ctcgcgcgta tctccctgag       120
cggtt                                                                   125

<210> SEQ ID NO 270
<211> LENGTH: 125
<212> TYPE: DNA
<213> ORGANISM: Adeno-Associated Virus-4 (AAV)
<220> FEATURE:
<223> OTHER INFORMATION: AAV4_Right

<400> SEQUENCE: 270
aaccggtgta atcgatacgc gcgagcgagt gagtgagccg ggacctctgg tttccagagg        60
tctgacggcc ggagaccggc cgtcccggct cactcactcg ctcgcgcgta tctccctcac       120
cggtt                                                                   125

<210> SEQ ID NO 271
<211> LENGTH: 125
<212> TYPE: DNA
<213> ORGANISM: Artificial Sequence
<220> FEATURE:
<223> OTHER INFORMATION: AAV4_Right_Nb.BbvCI_BL

<400> SEQUENCE: 271
aaccggtgta atggagtcgc gcgagcgagt gagtgagccg ggacctctgg tttccagagg        60
tctgacggcc ggagaccggc cgtcccggct cactcactcg ctcgcgcgac tcccctcac       120 cggtt                                                                   125

<210> SEQ ID NO 272
<211> LENGTH: 125
<212> TYPE: DNA
<213> ORGANISM: Artificial Sequence
<220> FEATURE:
<223> OTHER INFORMATION: AAV4_Right_Nb.BbvCI_TL
```

<400> SEQUENCE: 272
aaccggtgta atcgactccc gcgagcgagt gagtgagccg ggacctctgg tttccagagg    60
tctgacggcc ggagaccggc cgtcccggct cactcactcg ctcgcgggag tcgccctcac   120
cggtt                                                              125

<210> SEQ ID NO 273
<211> LENGTH: 125
<212> TYPE: DNA
<213> ORGANISM: Artificial Sequence
<220> FEATURE:
<223> OTHER INFORMATION: AAV4_Right_Nb.BsmI_BL

<400> SEQUENCE: 273
aaccggtgta atccttacgc gcgagcgagt gagtgagccg ggacctctgg tttccagagg    60
tctgacggcc ggagaccggc cgtcccggct cactcactcg ctcgcgcgta agtccctcac   120
cggtt                                                              125

<210> SEQ ID NO 274
<211> LENGTH: 125
<212> TYPE: DNA
<213> ORGANISM: Artificial Sequence
<220> FEATURE:
<223> OTHER INFORMATION: AAV4_Right_Nb.BsmI_TL

<400> SEQUENCE: 274
aaccggtgta atcgatacgc gtaagcgagt gagtgagccg ggacctctgg tttccagagg    60
tctgacggcc ggagaccggc cgtcccggct cactcactcg cttacgcgta tctccctcac   120
cggtt                                                              125

<210> SEQ ID NO 275
<211> LENGTH: 125
<212> TYPE: DNA
<213> ORGANISM: Artificial Sequence
<220> FEATURE:
<223> OTHER INFORMATION: AAV4_Right_Nb.BsrDI_BL

<400> SEQUENCE: 275
aaccggtgta atcgttacgc gcgagcgagt gagtgagccg ggacctctgg tttccagagg    60
tctgacggcc ggagaccggc cgtcccggct cactcactcg ctcgcgcgta acgccctcac   120
cggtt                                                              125

<210> SEQ ID NO 276
<211> LENGTH: 125
<212> TYPE: DNA
<213> ORGANISM: Artificial Sequence
<220> FEATURE:
<223> OTHER INFORMATION: AAV4_Right_Nb.BsrDI_TL

<400> SEQUENCE: 276
aaccggtgta atcgtaacgc gcgagcgagt gagtgagccg ggacctctgg tttccagagg    60
tctgacggcc ggagaccggc cgtcccggct cactcactcg ctcgcgcgtt actccctcac   120
cggtt                                                              125

<210> SEQ ID NO 277
<211> LENGTH: 125
<212> TYPE: DNA
<213> ORGANISM: Artificial Sequence
<220> FEATURE:
<223> OTHER INFORMATION: AAV4_Right_Nb.BssSI_BL

<400> SEQUENCE: 277
aaccggtgct ctcgatacgc gcgagcgagt gagtgagccg ggacctctgg tttccagagg    60
tctgacggcc ggagaccggc cgtcccggct cactcactcg ctcgcgcgta tctcgagcac   120
cggtt                                                              125

<210> SEQ ID NO 278
<211> LENGTH: 125
<212> TYPE: DNA
<213> ORGANISM: Artificial Sequence
<220> FEATURE:
<223> OTHER INFORMATION: AAV4_Right_Nb.BssSI_TL

<400> SEQUENCE: 278
aaccggtgta agagcaccgc gcgagcgagt gagtgagccg ggacctctgg tttccagagg    60
tctgacggcc ggagaccggc cgtcccggct cactcactcg ctcgcgcggt gctccctcac   120
cggtt                                                              125

<210> SEQ ID NO 279
<211> LENGTH: 125
<212> TYPE: DNA
<213> ORGANISM: Artificial Sequence
<220> FEATURE:
<223> OTHER INFORMATION: AAV4_Right_Nb.BtsI_BL

<400> SEQUENCE: 279
aaccggtgta atcgtcacgc gcgagcgagt gagtgagccg ggacctctgg tttccagagg    60
tctgacggcc ggagaccggc cgtcccggct cactcactcg ctcgcgcgtg acgccctcac   120
cggtt                                                              125

<210> SEQ ID NO 280
<211> LENGTH: 125
<212> TYPE: DNA
<213> ORGANISM: Artificial Sequence
<220> FEATURE:
<223> OTHER INFORMATION: AAV4_Right_Nb.BtsI_TL

<400> SEQUENCE: 280
aaccggtgta atcgtgacgc gcgagcgagt gagtgagccg ggacctctgg tttccagagg    60
tctgacggcc ggagaccggc cgtcccggct cactcactcg ctcgcgcgtc actccctcac   120
cggtt                                                              125

<210> SEQ ID NO 281
<211> LENGTH: 125
<212> TYPE: DNA
<213> ORGANISM: Artificial Sequence
<220> FEATURE:
<223> OTHER INFORMATION: AAV4_Right_Nt.AlwI_BL

<400> SEQUENCE: 281
aaccggtgta atcgctaggc gcgagcgagt gagtgagccg ggacctctgg tttccagagg    60
tctgacggcc ggagaccggc cgtcccggct cactcactcg ctcgcgccta gctccctcac   120
cggtt                                                              125

<210> SEQ ID NO 282
<211> LENGTH: 125
<212> TYPE: DNA
<213> ORGANISM: Artificial Sequence
<220> FEATURE:

<223> OTHER INFORMATION: AAV4_Right_Nt.AlwI_BL

<400> SEQUENCE: 282
aaccggtgtc ctagatacgc gcgagcgagt gagtgagccg ggacctctgg tttccagagg    60
tctgacggcc ggagaccggc cgtcccggct cactcactcg ctcgcgcgta tctaggtcac   120
cggtt                                                              125

<210> SEQ ID NO 283
<211> LENGTH: 125
<212> TYPE: DNA
<213> ORGANISM: Artificial Sequence
<220> FEATURE:
<223> OTHER INFORMATION: AAV4_Right_Nt.BbvCI_TL

<400> SEQUENCE: 283
aaccggtgta atcgactccc gcgagcgagt gagtgagccg ggacctctgg tttccagagg    60
tctgacggcc ggagaccggc cgtcccggct cactcactcg ctcgcgggag tcgccctcac   120
cggtt                                                              125

<210> SEQ ID NO 284
<211> LENGTH: 125
<212> TYPE: DNA
<213> ORGANISM: Artificial Sequence
<220> FEATURE:
<223> OTHER INFORMATION: AAV4_Right_Nt.BbvCI_BL

<400> SEQUENCE: 284
aaccggtgta atggagtcgc gcgagcgagt gagtgagccg ggacctctgg tttccagagg    60
tctgacggcc ggagaccggc cgtcccggct cactcactcg ctcgcgcgac tccccctcac   120
cggtt                                                              125

<210> SEQ ID NO 285
<211> LENGTH: 125
<212> TYPE: DNA
<213> ORGANISM: Artificial Sequence
<220> FEATURE:
<223> OTHER INFORMATION: AAV4_Right_Nt.BsmAI_TL

<400> SEQUENCE: 285
aaccggtgtc tctgatacgc gcgagcgagt gagtgagccg ggacctctgg tttccagagg    60
tctgacggcc ggagaccggc cgtcccggct cactcactcg ctcgcgcgta tcagagtcac   120
cggtt                                                              125

<210> SEQ ID NO 286
<211> LENGTH: 125
<212> TYPE: DNA
<213> ORGANISM: Artificial Sequence
<220> FEATURE:
<223> OTHER INFORMATION: AAV4_Right_Nt.BsmAI_BL

<400> SEQUENCE: 286
aaccggtgta acagagacgc gcgagcgagt gagtgagccg ggacctctgg tttccagagg    60
tctgacggcc ggagaccggc cgtcccggct cactcactcg ctcgcgcgtc tctgcctcac   120
cggtt                                                              125

<210> SEQ ID NO 287
<211> LENGTH: 125
<212> TYPE: DNA
<213> ORGANISM: Artificial Sequence
<220> FEATURE:
<223> OTHER INFORMATION: AAV4_Right_Nt.BspQI_TL

<400> SEQUENCE: 287
aaccggtgta atcttctcgc gcgagcgagt gagtgagccg ggacctctgg tttccagagg    60
tctgacggcc ggagaccggc cgtcccggct cactcactcg ctcgcgcgag aagccctcac   120
cggtt                                                               125

<210> SEQ ID NO 288
<211> LENGTH: 125
<212> TYPE: DNA
<213> ORGANISM: Artificial Sequence
<220> FEATURE:
<223> OTHER INFORMATION: AAV4_Right_Nt.BspQI_BL

<400> SEQUENCE: 288
aaccggtgta atcgagaagc gcgagcgagt gagtgagccg ggacctctgg tttccagagg    60
tctgacggcc ggagaccggc cgtcccggct cactcactcg ctcgcgcttc tcgccctcac   120
cggtt                                                               125

<210> SEQ ID NO 289
<211> LENGTH: 127
<212> TYPE: DNA
<213> ORGANISM: Artificial Sequence
<220> FEATURE:
<223> OTHER INFORMATION: AAV4_Right_Nt.BstNBI_TL

<400> SEQUENCE: 289
aaccggtgta atcgatacgc gctgagcgag tgagtgagcc gggacctctg gtttccagag    60
gtctgacggc cggagaccgg ccgtcccggc tcactcactc gctcagcgcg tatctccctc   120
accggtt                                                             127

<210> SEQ ID NO 290
<211> LENGTH: 125
<212> TYPE: DNA
<213> ORGANISM: Artificial Sequence
<220> FEATURE:
<223> OTHER INFORMATION: AAV4_Right_Nt.BstNBI_BL

<400> SEQUENCE: 290
aaccggtctc agcgatacgc gcgagcgagt gagtgagccg ggacctctgg tttccagagg    60
tctgacggcc ggagaccggc cgtcccggct cactcactcg ctcgcgcgta tctctgagac   120
cggtt                                                               125

<210> SEQ ID NO 291
<211> LENGTH: 137
<212> TYPE: DNA
<213> ORGANISM: Adeno-Associated Virus-5 (AAV5)

<400> SEQUENCE: 291 gagaggggggg acagcgcaag cgagcgagcg accgagcaaa ccccccccacc gtcgagtttc    60
tcgacggtct gctgccggga gaccggcagc gggggggttt gctcggtcgc tcgctcgctt   120
gcgctgtccc ccctctc                                                  137

<210> SEQ ID NO 292
<211> LENGTH: 137
<212> TYPE: DNA
<213> ORGANISM: Artificial Sequence
<220> FEATURE:

<223> OTHER INFORMATION: AAV5_Nb.BbvCI_BL

<400> SEQUENCE: 292
gagaggggag tcggcgcaag cgagcgagcg accgagcaaa ccccccacc gtcgagtttc    60 tcgacggtct gctgccggga daccggcagc ggggggtt gctcggtcgc tcgctcgctt    120
gcgccgactc ccctctc                                                  137

<210> SEQ ID NO 293
<211> LENGTH: 137
<212> TYPE: DNA
<213> ORGANISM: Artificial Sequence
<220> FEATURE:
<223> OTHER INFORMATION: AAV5_Nb.BbvCI_TL

<400> SEQUENCE: 293
gagaggggcg actccgcaag cgagcgagcg accgagcaaa ccccccacc gtcgagtttc    60 tcgacggtct gctgccggga daccggcagc ggggggtt gctcggtcgc tcgctcgctt    120
gcggagtcgc ccctctc                                                  137

<210> SEQ ID NO 294
<211> LENGTH: 137
<212> TYPE: DNA
<213> ORGANISM: Artificial Sequence
<220> FEATURE:
<223> OTHER INFORMATION: AAV5_Nb.BsmI_BL

<400> SEQUENCE: 294
gagaggggct tacgcgcaag cgagcgagcg accgagcaaa ccccccacc gtcgagtttc    60 tcgacggtct gctgccggga daccggcagc ggggggtt gctcggtcgc tcgctcgctt    120
gcgcgtaagc ccctctc                                                  137

<210> SEQ ID NO 295
<211> LENGTH: 137
<212> TYPE: DNA
<213> ORGANISM: Artificial Sequence
<220> FEATURE:
<223> OTHER INFORMATION: AAV5_Nb.BsmI_TL

<400> SEQUENCE: 295
gagagggggg acagcgtaag cgagcgagcg accgagcaaa ccccccacc gtcgagtttc    60 tcgacggtct gctgccggga daccggcagc ggggggtt gctcggtcgc tcgctcgctt    120
acgctgtccc ccctctc                                                  137

<210> SEQ ID NO 296
<211> LENGTH: 137
<212> TYPE: DNA
<213> ORGANISM: Artificial Sequence
<220> FEATURE:
<223> OTHER INFORMATION: AAV5_Nb.BsrDI_BL

<400> SEQUENCE: 296
gagaggcgtt acagcgcaag cgagcgagcg accgagcaaa ccccccacc gtcgagtttc    60 tcgacggtct gctgccggga daccggcagc ggggggtt gctcggtcgc tcgctcgctt    120
gcgctgtaac gcctctc                                                  137

<210> SEQ ID NO 297
<211> LENGTH: 137
<212> TYPE: DNA
<213> ORGANISM: Artificial Sequence

```
<220> FEATURE:
<223> OTHER INFORMATION: AAV5_Nb.BsrDI_TL

<400> SEQUENCE: 297 gagaggggt aacgcgcaag cgagcgagcg accgagcaaa ccccccacc gtcgagtttc      60 tcgacggtct gctgccggga gaccggcagc gggggggttt gctcggtcgc tcgctcgctt    120
gcgcgttacc ccctctc                                                  137

<210> SEQ ID NO 298
<211> LENGTH: 137
<212> TYPE: DNA
<213> ORGANISM: Artificial Sequence
<220> FEATURE:
<223> OTHER INFORMATION: AAV5_Nb.BssSI_BL

<400> SEQUENCE: 298
gagtgctcgg acagcgcaag cgagcgagcg accgagcaaa ccccccacc gtcgagtttc     60 tcgacggtct gctgccggga gaccggcagc gggggggttt gctcggtcgc tcgctcgctt    120
gcgctgtccg agcactc                                                  137

<210> SEQ ID NO 299
<211> LENGTH: 137
<212> TYPE: DNA
<213> ORGANISM: Artificial Sequence
<220> FEATURE:
<223> OTHER INFORMATION: AAV5_Nb.BssSI_TL

<400> SEQUENCE: 299
gagagggagc acagcgcaag cgagcgagcg accgagcaaa ccccccacc gtcgagtttc     60 tcgacggtct gctgccggga gaccggcagc gggggggttt gctcggtcgc tcgctcgctt    120
gcgctgtgct ccctctc                                                  137

<210> SEQ ID NO 300
<211> LENGTH: 137
<212> TYPE: DNA
<213> ORGANISM: Artificial Sequence
<220> FEATURE:
<223> OTHER INFORMATION: AAV5_Nb.BtsI_BL

<400> SEQUENCE: 300
gagaggcgtc acagcgcaag cgagcgagcg accgagcaaa ccccccacc gtcgagtttc     60 tcgacggtct gctgccggga gaccggcagc gggggggttt gctcggtcgc tcgctcgctt    120
gcgctgtgac gcctctc                                                  137

<210> SEQ ID NO 301
<211> LENGTH: 137
<212> TYPE: DNA
<213> ORGANISM: Artificial Sequence
<220> FEATURE:
<223> OTHER INFORMATION: AAV5_Nb.BtsI_TL

<400> SEQUENCE: 301 gagagggtg acggcgcaag cgagcgagcg accgagcaaa ccccccacc gtcgagtttc      60 tcgacggtct gctgccggga gaccggcagc gggggggttt gctcggtcgc tcgctcgctt    120
gcgccgtcac ccctctc                                                  137

<210> SEQ ID NO 302
<211> LENGTH: 137
<212> TYPE: DNA
```

<213> ORGANISM: Artificial Sequence
<220> FEATURE:
<223> OTHER INFORMATION: AAV5_Nt.AlwI_BL

<400> SEQUENCE: 302 gagaggggggg acagcgctag ggagcgagcg accgagcaaa ccccccacc gtcgagtttc     60 tcgacggtct gctgccggga gaccggcagc ggggggtttt gctcggtcgc tcgctcccta    120
gcgctgtccc ccctctc                                                   137

<210> SEQ ID NO 303
<211> LENGTH: 137
<212> TYPE: DNA
<213> ORGANISM: Artificial Sequence
<220> FEATURE:
<223> OTHER INFORMATION: AAV5_Nt.AlwI_BL

<400> SEQUENCE: 303
gagagggggc ctagcgcaag cgagcgagcg accgagcaaa ccccccacc gtcgagtttc     60 tcgacggtct gctgccggga gaccggcagc ggggggtttt gctcggtcgc tcgctcgctt    120
gcgctaggcc ccctctc                                                   137

<210> SEQ ID NO 304
<211> LENGTH: 137
<212> TYPE: DNA
<213> ORGANISM: Artificial Sequence
<220> FEATURE:
<223> OTHER INFORMATION: AAV5_Nt.BbvCI_TL

<400> SEQUENCE: 304
gagaggggcg actccgcaag cgagcgagcg accgagcaaa ccccccacc gtcgagtttc     60 tcgacggtct gctgccggga gaccggcagc ggggggtttt gctcggtcgc tcgctcgctt    120
gcggagtcgc ccctctc                                                   137

<210> SEQ ID NO 305
<211> LENGTH: 137
<212> TYPE: DNA
<213> ORGANISM: Artificial Sequence
<220> FEATURE:
<223> OTHER INFORMATION: AAV5_Nt.BbvCI_BL

<400> SEQUENCE: 305
gagaggggag tcggcgcaag cgagcgagcg accgagcaaa ccccccacc gtcgagtttc     60 tcgacggtct gctgccggga gaccggcagc ggggggtttt gctcggtcgc tcgctcgctt    120
gcgccgactc ccctctc                                                   137

<210> SEQ ID NO 306
<211> LENGTH: 137
<212> TYPE: DNA
<213> ORGANISM: Artificial Sequence
<220> FEATURE:
<223> OTHER INFORMATION: AAV5_Nt.BsmAI_TL

<400> SEQUENCE: 306 gagaggggggc tctgcgcaag cgagcgagcg accgagcaaa ccccccacc gtcgagtttc    60 tcgacggtct gctgccggga gaccggcagc ggggggtttt gctcggtcgc tcgctcgctt   120
gcgcagagcc ccctctc                                                  137

<210> SEQ ID NO 307
<211> LENGTH: 137

```
<212> TYPE: DNA
<213> ORGANISM: Artificial Sequence
<220> FEATURE:
<223> OTHER INFORMATION: AAV5_Nt.BsmAI_BL

<400> SEQUENCE: 307 gagaggggc agagcgcaag cgagcgagcg accgagcaaa ccccccacc gtcgagtttc    60 tcgacggtct gctgccggga gaccggcagc ggggggtttt gctcggtcgc tcgctcgctt   120
gcgctctgcc ccctctc                                                 137

<210> SEQ ID NO 308
<211> LENGTH: 137
<212> TYPE: DNA
<213> ORGANISM: Artificial Sequence
<220> FEATURE:
<223> OTHER INFORMATION: AAV5_Nt.BspQI_TL

<400> SEQUENCE: 308
gagagggctt ctcgcgcaag cgagcgagcg accgagcaaa ccccccacc gtcgagtttc    60 tcgacggtct gctgccggga gaccggcagc ggggggtttt gctcggtcgc tcgctcgctt   120
gcgcgagaag ccctctc                                                 137

<210> SEQ ID NO 309
<211> LENGTH: 137
<212> TYPE: DNA
<213> ORGANISM: Artificial Sequence
<220> FEATURE:
<223> OTHER INFORMATION: AAV5_Nt.BspQI_BL

<400> SEQUENCE: 309
gagagggcga gaagcgcaag cgagcgagcg accgagcaaa ccccccacc gtcgagtttc    60 tcgacggtct gctgccggga gaccggcagc ggggggtttt gctcggtcgc tcgctcgctt   120
gcgcttctcg ccctctc                                                 137

<210> SEQ ID NO 310
<211> LENGTH: 139
<212> TYPE: DNA
<213> ORGANISM: Artificial Sequence
<220> FEATURE:
<223> OTHER INFORMATION: AAV5_Nt.BstNBI_TL

<400> SEQUENCE: 310 gagaggggg acagcgctga gcgagcgagc gaccgagcaa accccccac cgtcgagttt    60 ctcgacggtc tgctgccggg agaccggcag cggggggtt tgctcggtcg ctcgctcgct   120
cagcgctgtc ccccctctc                                               139

<210> SEQ ID NO 311
<211> LENGTH: 137
<212> TYPE: DNA
<213> ORGANISM: Artificial Sequence
<220> FEATURE:
<223> OTHER INFORMATION: AAV5_Nt.BstNBI_BL

<400> SEQUENCE: 311 gagaggggc tcagcgcaag cgagcgagcg accgagcaaa ccccccacc gtcgagtttc    60 tcgacggtct gctgccggga gaccggcagc ggggggtttt gctcggtcgc tcgctcgctt   120
gcgctgagcc ccctctc                                                 137

<210> SEQ ID NO 312
```

<211> LENGTH: 125
<212> TYPE: DNA
<213> ORGANISM: Adeno-Associated Virus-7 (AAV7)

<400> SEQUENCE: 312
aaccggtgag ggagatacgc gcgagcgagc gagccacccc ggacgcctgg tttccaggcg    60
tctgccgtct cgagacgaga cggccggggt ggctcgctcg ctcgcgcgta tctccctcac   120
cggtt                                                              125

<210> SEQ ID NO 313
<211> LENGTH: 125
<212> TYPE: DNA
<213> ORGANISM: Artificial Sequence
<220> FEATURE:
<223> OTHER INFORMATION: AAV7_Nb.BbvCI_BL

<400> SEQUENCE: 313
aaccggtgag ggggagtcgc gcgagcgagc gagccacccc ggacgcctgg tttccaggcg    60
tctgccgtct cgagacgaga cggccggggt ggctcgctcg ctcgcgcgac tccccctcac   120
cggtt                                                              125

<210> SEQ ID NO 314
<211> LENGTH: 125
<212> TYPE: DNA
<213> ORGANISM: Artificial Sequence
<220> FEATURE:
<223> OTHER INFORMATION: AAV7_Nb.BbvCI_TL

<400> SEQUENCE: 314
aaccggtgag ggcgactccc gcgagcgagc gagccacccc ggacgcctgg tttccaggcg    60
tctgccgtct cgagacgaga cggccggggt ggctcgctcg ctcgcgggag tcgccctcac   120
cggtt                                                              125

<210> SEQ ID NO 315
<211> LENGTH: 125
<212> TYPE: DNA
<213> ORGANISM: Artificial Sequence
<220> FEATURE:
<223> OTHER INFORMATION: AAV7_Nb.BsmI_BL

<400> SEQUENCE: 315
aaccggtgag ggacttacgc gcgagcgagc gagccacccc ggacgcctgg tttccaggcg    60
tctgccgtct cgagacgaga cggccggggt ggctcgctcg ctcgcgcgta agtccctcac   120
cggtt                                                              125

<210> SEQ ID NO 316
<211> LENGTH: 125
<212> TYPE: DNA
<213> ORGANISM: Artificial Sequence
<220> FEATURE:
<223> OTHER INFORMATION: AAV7_Nb.BsmI_TL

<400> SEQUENCE: 316
aaccggtgag ggagatacgc gtaagcgagc gagccacccc ggacgcctgg tttccaggcg    60
tctgccgtct cgagacgaga cggccggggt ggctcgctcg cttacgcgta tctccctcac   120
cggtt                                                              125

<210> SEQ ID NO 317
<211> LENGTH: 125

```
<212> TYPE: DNA
<213> ORGANISM: Artificial Sequence
<220> FEATURE:
<223> OTHER INFORMATION: AAV7_Nb.BsrDI_BL

<400> SEQUENCE: 317
aaccggtgag ggcgttacgc gcgagcgagc gagccacccc ggacgcctgg tttccaggcg      60
tctgccgtct cgagacgaga cggccggggt ggctcgctcg ctcgcgcgta acgccctcac     120
cggtt                                                                125

<210> SEQ ID NO 318
<211> LENGTH: 125
<212> TYPE: DNA
<213> ORGANISM: Artificial Sequence
<220> FEATURE:
<223> OTHER INFORMATION: AAV7_Nb.BsrDI_TL

<400> SEQUENCE: 318
aaccggtgag ggagtaacgc gcgagcgagc gagccacccc ggacgcctgg tttccaggcg      60
tctgccgtct cgagacgaga cggccggggt ggctcgctcg ctcgcgcgtt actccctcac     120
cggtt                                                                125

<210> SEQ ID NO 319
<211> LENGTH: 125
<212> TYPE: DNA
<213> ORGANISM: Artificial Sequence
<220> FEATURE:
<223> OTHER INFORMATION: AAV7_Nb.BssSI_BL

<400> SEQUENCE: 319
aaccggtgct cgagatacgc gcgagcgagc gagccacccc ggacgcctgg tttccaggcg      60
tctgccgtct cgagacgaga cggccggggt ggctcgctcg ctcgcgcgta tctcgagcac     120
cggtt                                                                125

<210> SEQ ID NO 320
<211> LENGTH: 125
<212> TYPE: DNA
<213> ORGANISM: Artificial Sequence
<220> FEATURE:
<223> OTHER INFORMATION: AAV7_Nb.BssSI_TL

<400> SEQUENCE: 320
aaccggtgag ggagcaccgc gcgagcgagc gagccacccc ggacgcctgg tttccaggcg      60
tctgccgtct cgagacgaga cggccggggt ggctcgctcg ctcgcgcggt gctccctcac     120
cggtt                                                                125

<210> SEQ ID NO 321
<211> LENGTH: 125
<212> TYPE: DNA
<213> ORGANISM: Artificial Sequence
<220> FEATURE:
<223> OTHER INFORMATION: AAV7_Nb.BtsI_BL

<400> SEQUENCE: 321
aaccggtgag ggcgtcacgc gcgagcgagc gagccacccc ggacgcctgg tttccaggcg      60
tctgccgtct cgagacgaga cggccggggt ggctcgctcg ctcgcgcgtg acgccctcac     120
cggtt                                                                125

<210> SEQ ID NO 322
```

```
<211> LENGTH: 125
<212> TYPE: DNA
<213> ORGANISM: Artificial Sequence
<220> FEATURE:
<223> OTHER INFORMATION: AAV7_Nb.BtsI_TL

<400> SEQUENCE: 322
aaccggtgag ggagtgacgc gcgagcgagc gagccacccc ggacgcctgg tttccaggcg      60
tctgccgtct cgagacgaga cggccggggt ggctcgctcg ctcgcgcgtc actccctcac     120
cggtt                                                                 125

<210> SEQ ID NO 323
<211> LENGTH: 125
<212> TYPE: DNA
<213> ORGANISM: Artificial Sequence
<220> FEATURE:
<223> OTHER INFORMATION: AAV7_Nt.AlwI_BL

<400> SEQUENCE: 323
aaccggtgag ggagctaggc gcgagcgagc gagccacccc ggacgcctgg tttccaggcg      60
tctgccgtct cgagacgaga cggccggggt ggctcgctcg ctcgcgccta gctccctcac     120
cggtt                                                                 125

<210> SEQ ID NO 324
<211> LENGTH: 125
<212> TYPE: DNA
<213> ORGANISM: Artificial Sequence
<220> FEATURE:
<223> OTHER INFORMATION: AAV7_Nt.AlwI_BL

<400> SEQUENCE: 324
aaccggtgac ctagatacgc gcgagcgagc gagccacccc ggacgcctgg tttccaggcg      60
tctgccgtct cgagacgaga cggccggggt ggctcgctcg ctcgcgcgta tctaggtcac     120
cggtt                                                                 125

<210> SEQ ID NO 325
<211> LENGTH: 125
<212> TYPE: DNA
<213> ORGANISM: Artificial Sequence
<220> FEATURE:
<223> OTHER INFORMATION: AAV7_Nt.BbvCI_TL

<400> SEQUENCE: 325
aaccggtgag ggcgactccc gcgagcgagc gagccacccc ggacgcctgg tttccaggcg      60
tctgccgtct cgagacgaga cggccggggt ggctcgctcg ctcgcgggag tcgccctcac     120
cggtt                                                                 125

<210> SEQ ID NO 326
<211> LENGTH: 125
<212> TYPE: DNA
<213> ORGANISM: Artificial Sequence
<220> FEATURE:
<223> OTHER INFORMATION: AAV7_Nt.BbvCI_BL

<400> SEQUENCE: 326
aaccggtgag ggggagtcgc gcgagcgagc gagccacccc ggacgcctgg tttccaggcg      60
tctgccgtct cgagacgaga cggccggggt ggctcgctcg ctcgcgcgac tcccctcac      120
cggtt                                                                 125
```

<210> SEQ ID NO 327
<211> LENGTH: 125
<212> TYPE: DNA
<213> ORGANISM: Artificial Sequence
<220> FEATURE:
<223> OTHER INFORMATION: AAV7_Nt.BsmAI_TL

<400> SEQUENCE: 327

```
aaccggtgac tctgatacgc gcgagcgagc gagccacccc ggacgcctgg tttccaggcg    60
tctgccgtct cgagacgaga cggccggggt ggctcgctcg ctcgcgcgta tcagagtcac   120
cggtt                                                              125
```

<210> SEQ ID NO 328
<211> LENGTH: 125
<212> TYPE: DNA
<213> ORGANISM: Artificial Sequence
<220> FEATURE:
<223> OTHER INFORMATION: AAV7_Nt.BsmAI_BL

<400> SEQUENCE: 328

```
aaccggtgag gcagagacgc gcgagcgagc gagccacccc ggacgcctgg tttccaggcg    60
tctgccgtct cgagacgaga cggccggggt ggctcgctcg ctcgcgcgtc tctgcctcac   120
cggtt                                                              125
```

<210> SEQ ID NO 329
<211> LENGTH: 125
<212> TYPE: DNA
<213> ORGANISM: Artificial Sequence
<220> FEATURE:
<223> OTHER INFORMATION: AAV7_Nt.BspQI_TL

<400> SEQUENCE: 329

```
aaccggtgag ggcttctcgc gcgagcgagc gagccacccc ggacgcctgg tttccaggcg    60
tctgccgtct cgagacgaga cggccggggt ggctcgctcg ctcgcgcgag aagccctcac   120
cggtt                                                              125
```

<210> SEQ ID NO 330
<211> LENGTH: 125
<212> TYPE: DNA
<213> ORGANISM: Artificial Sequence
<220> FEATURE:
<223> OTHER INFORMATION: AAV7_Nt.BspQI_BL

<400> SEQUENCE: 330

```
aaccggtgag ggcgagaagc gcgagcgagc gagccacccc ggacgcctgg tttccaggcg    60
tctgccgtct cgagacgaga cggccggggt ggctcgctcg ctcgcgcttc tcgccctcac   120
cggtt                                                              125
```

<210> SEQ ID NO 331
<211> LENGTH: 127
<212> TYPE: DNA
<213> ORGANISM: Artificial Sequence
<220> FEATURE:
<223> OTHER INFORMATION: AAV7_Nt.BstNBI_TL

<400> SEQUENCE: 331

```
aaccggtgag ggagatacgc gctgagcgag cgagccaccc cggacgcctg gtttccaggc    60
gtctgccgtc tcgagacgag acggccgggg tggctcgctc gctcagcgcg tatctccctc   120
accggtt                                                            127
```

<210> SEQ ID NO 332
<211> LENGTH: 125
<212> TYPE: DNA
<213> ORGANISM: Artificial Sequence
<220> FEATURE:
<223> OTHER INFORMATION: AAV7_Nt.BstNBI_BL

<400> SEQUENCE: 332

```
aaccgctcag ggagatacgc gcgagcgagc gagccacccc ggacgcctgg tttccaggcg    60
tctgccgtct cgagacgaga cggccggggt ggctcgctcg ctcgcgcgta tctccctgag   120
cggtt                                                               125
```

<210> SEQ ID NO 333
<211> LENGTH: 121
<212> TYPE: DNA
<213> ORGANISM: Artificial Sequence
<220> FEATURE:
<223> OTHER INFORMATION: Artificial ITR 333

<400> SEQUENCE: 333

```
ggccactccc gaagagcgcg ctcgctatct cactgaggcc gggcgaccaa aggtcgcccg    60
acgcccgggc tttgcccggg cggcctcagt gagatagcga gcgcgctctt cgggagtggc   120
c                                                                   121
```

<210> SEQ ID NO 334
<211> LENGTH: 1656
<212> TYPE: DNA
<213> ORGANISM: Artificial Sequence
<220> FEATURE:
<223> OTHER INFORMATION: Construct 3

<400> SEQUENCE: 334

```
tgcgcgactc gctcgctcac tgaggccggg cgaccaaagg tcgcccgacg cccgggcttt    60
gcccgggcgg cctcagtgag cgagcgagtc gcgcagagag gttaaaacca actagacaac   120
tttgtatatc tagagtaacg ccattttgca aggcatggaa aaataccaaa ccaagaatag   180
agaagttcag atcaagggcg ggtacatgaa aatagctaac gttgggccaa acaggatatc   240
tgcggtgagc agtttcggcc ccggcccggg gccaagaaca gatggtcacc gcagtttcgg   300
ccccggcccg aggccaagaa cagatggtcc ccagatatgg cccaaccctc agcagtttct   360
taagacccat cagatgtttc caggctcccc caaggacctg aaatgaccct gcgccttatt   420
tgaattaacc aatcagcctg cttctcgctt ctgttcgcgc gcttctgctt cccgagctct   480
ataaaagagc tcacaaccccc tcactcggcg cgccagtcct ccgattgact gagtgcggcc   540
gcggcaggct gccaccatgg aaaccgatac actgctgctt tgggtacttt tgctgtgggt   600
gcccggcagt acgggcgacg ccgcacaacc agctaggaga gcagtccgga gcctggtccc   660
ctcttccgag gccgaggctg aacggggaaa gctgccaggc aagaaactcc ccttagaggt   720
tctcatcgag ctggaagcaa acgcacgcaa ggccggttgc actaggggct gcctcatctg   780
cctcagcaag atcaaatgta cagcaaagat gaagaagtat attcctggcc gctgtgcaga   840
ctacggaggc gacaaaaaaa caggacaagc tggtatagtt ggcgccatcg tagatatccc   900
cgagattagt gggttcaagg aaatggagcc aatggagcaa ttcattgcac aggttgatag   960
atgtgcggat tgcactactg gttgccttaa gggcttggcg aatgtcaagt gtagtgatct  1020
tctgaaaaag tggctacccg gccggtgtgc caccttcgct gacaaaatac agagcgaagt  1080
cgacaatatt aaaggacttg ccggggacta atgatagtga cacaaagtga cgcgtcctag  1140
```

```
agctcgcact gtgccttcta gttgccagcc atctgttgtt tgcccctccc ccgtgccttc    1200
cttgaccctg gaaggtgcca ctcccactgt cctttcctaa taaaatgagg aaattgcatc    1260
gcattgtctg agtaggtgtc attctattct gggggtgggg gtggggcagg acagcaaggg    1320
ggaggattgg gaagagaata gcaggcatgc tggggagggc gctagcgcag gaaccccttt    1380
taatggagtt ggcgagtccc tctctgcgcg ctcgctcgct cactgaggcc gggcgaccaa    1440
aggtcgcccg acgcccgggc tttgcccggg cggcctcagt gagcgagcga gcgcgcagag    1500
atcgactcct cggccacttg gaggggccgg gggacgacg caatctggag tggaaagaac     1560
ccccgtctat gcggcttaaa gcacggccag ggaatagtgg atcaagtgta ctgacatgtg    1620
ccggagtccc tccatgccca gatcgactcc ctcgag                              1656
```

<210> SEQ ID NO 335
<211> LENGTH: 6433
<212> TYPE: DNA
<213> ORGANISM: Artificial Sequence
<220> FEATURE:
<223> OTHER INFORMATION: DNA Construct 335

<400> SEQUENCE: 335

```
gttcgagatc gctcttcaga agagcgcgga gtcacattcg cgactcgcaa tgcattgcag      60
ggcgagggcg agggccgccc ctacgagggc cacaacaccg tgaagctgaa ggtgaccaag     120
ggcggccccc tgcccttcgc ctgggacatc ctgtccccc agttccagta cggctccaag     180
gtgtacgtga agcaccccgc cgacatccca gctcggtagc cacctgacgt cgctcttcgc    240
gctcgctcgc tcactgaggc cgggcgacca aaggtcgccc gacgcccggg cttttgcccgg   300 gcggcctcag tgagcgagcg agcgcgaaga gcgggagtga gtggccaaaa agtacccggc    360
cagaaaggaa ccgtaaaacc aactagacag ccggtgactt tgttccccag ctcggttcat    420
tctcaagcct cagacaggag aaccgggact agtatatgag ctccggtgcc cgtcagtggg    480
cagagcgcac atcgcccaca gtccccgaga agttgggggg aggggtcggc aattgaaccg    540
gtgcctagag aaggtggcgc gggtaaact gggaaagtga tgtcgtgtac tggctccgcc     600 ttttttcccga gggtggggga gaaccgtata taagtgcagt agtcgccgtg aacgttcttt    660
ttcgcaacgg gtttgccgcc agaacacagg taagtgccgt gtgtggttcc cgcgggcctg    720
gcctctttac gggttatggc ccttgcgtgc cttgaattac ttccacgccc ctggctgcag    780
tacgtgattc ttgatcccga gcttcgggtt ggaagtgggt gggagagttc gaggccttgc    840
gcttaaggag cccctttcgcc tcgtgcttga gttgaggcct ggcctgggcg ctggggccgc    900
cgcgtgcgaa tctggtggca ccttcgcgcc tgtctcgctg ctttcgataa gtctctagcc    960
atttaaaatt tttgatgacc tgctgcgacg ctttttttct ggcaagatag tcttgtaaat   1020
gcgggccaag atcgatctgc acactggtat ttcggttttt gggccgcgcg gcggcgacgg   1080
ggcccgtgcg tccagcgca catgttcggc gaggcgggcc tgcgagcgc ggccaccgag     1140 aatcggacgg gggtagtctc aagctggccg gcctgctctg gtgcctggcc tcgcgccgcc    1200
gtgtatcgcc ccgccctggg cggcaaggct ggcccggtcg gcaccagttg cgtgagcgga   1260
aagatggccg cttcccggcc ctgctgcagg gagctcaaaa tggaggacgc ggcgctcggg   1320
agagcgggcg ggtgagacac ccacacaaag gaaaagggcc tttccgtcct cagccgtcgc   1380
ttcatgtgac accacggagt accgggcgcc gtccaggcac ctcgattagt tctcgatcga   1440
gcttttggag tacgtcgtct ttaggttggg gggagggggtt ttatgcgatg gagtttcccc   1500
```

-continued

```
acactgagtg ggtggagact gaagttaggc cagcttggca cttgatgtaa ttctccttgg    1560
aatttgccct ttttgagttt ggatcttggt tcattctcaa gcctcagaca gtggttcaaa    1620 gttttttct tccatttcag gtgtcgtgag cggccgcggc aggctgccac catggaggat     1680
gccaagaata ttaagaaagg ccctgcccca ttctaccctc tggaagatgg cactgctggt    1740
gagcaactgc acaaggccat gaagaggtat gccctggtcc ctggcacaat tgccttcact    1800
gatgctcaca ttgaggtgga catcacctat gctgaatact ttgagatgtc tgtgaggctg    1860
gcagaagcca tgaaaagata tggactgaac accaaccaca ggattgtggt gtgctctgag    1920
aactctctcc agttcttcat gcctgtgttg ggagccctgt tcattggagt ggctgtggcc    1980
cctgccaatg acatctacaa tgagagagag ctcctgaaca gcatgggcat cagccagcca    2040
actgtggtct ttgtgagcaa gaagggcctg caaaagatcc tgaatgtgca gaagaagctg    2100
cccatcatcc agaagatcat catcatggac agcaagactg actaccaggg cttccagagc    2160
atgtatacct ttgtgaccag ccacctcccc cctggcttca atgagtatga ctttgtgcct    2220
gagagctttg acagggacaa gacaattgct ctgattatga cagctctgg ctccactgga    2280 ctgcccaaag gtgtggctct gccccacaga actgcttgtg tgagattcag ccatgccaga    2340
gaccccatct ttggcaacca gatcatccct gacactgcca tcctgtctgt ggttccattc    2400
catcatggct ttggcatgtt cacaacactg gggtacctga tctgtggctt cagagtggtg    2460
ctgatgtata ggtttgagga ggagctgttt ctgaggagct gcaagacta caagatccag    2520 tctgccctgc tggtgcccac tctgttcagc ttctttgcca agagcaccct cattgacaag    2580
tatgacctga gcaacctgca tgagattgcc tctggaggag cacccctgag caaggaggtg    2640
ggtgaggctg tggcaaagag gttccatctc ccaggaatca gacagggcta tggcctgact    2700
gagaccacct ctgccatcct catcacccct gaaggagatg acaagcctgg tgctgtgggc    2760
aaggtggttc cctttttga ggccaaggtg gtggacctgg acactggcaa gaccctggga    2820
gtgaaccaga ggggtgagct gtgtgtgagg ggtcccatga tcatgtctgg ctatgtgaac    2880
aaccctgagg ccaccaatgc cctgattgac aaggatggct ggctgcactc tggtgatatt    2940
gcctactggg atgaggatga gcacttttc attgtggaca ggctgaagag tctcatcaag    3000
tacaaaggct accaagtggc acctgctgag cttgagagca tcctgctcca gcaccccaac    3060
atctttgatg ctggtgtggc tggcctgcct gatgatgatg ctggagagct gcctgctgct    3120
gttgtggttc tggagcatgg aaagaccatg actgagaagg agattgtgga ctatgtggcc    3180
agtcaggtga ccactgccaa gaagctgagg ggaggtgtgg tgtttgtgga tgaggtgcca    3240
aagggtctga ctggcaagct ggatgccaga aagatcagag agatcctgat caaggccaag    3300
aagggaggaa agattgcagt ttaaggatcc tgacacaaag tgacgcgtaa tcaacctctg    3360
gattacaaaa tttgtgaaag attgactggt attcttaact atgttgctcc ttttacgcta    3420
tgtggatacg ctgctttaat gcctttgtat catgctattg cttcccgtat ggctttcatt    3480
ttctcctcct tgtataaatc ctggttgctg tctctttatg aggagttgtg gcccgttgtc    3540
aggcaacgtg gcgtggtgtg cactgtgttt gctgacgcaa cccccactgg ttggggcttt    3600
gccaccacct gtcagctcct ttccgggact ttcgctttcc cctcccctat gccacggcg    3660 gaactcatcg ccgcctgcct tgcccgctgc tggacagggg ctcggctgtt gggcactgac    3720
aattccgtgg tgttgtcggg gaaatcatcg tcctttcctt ggctgctcgc ctgtgttgcc    3780
acctggattc tgcgcgggac gtccttctgc tacgtccctt cggccctcaa tccagcggac    3840
cttccttccc gcggcctgct gccggctctg cggcctcttc cgcgtcttcg ccttcgccct    3900
```

```
cagacgagtc ggatctccct ttgggccgcc tccccgcacg cgtcctagag ctcgcactgt   3960
gccttctagt tgccagccat ctgttgtttg ccctccccc gtgccttcct tgaccctgga    4020
aggtgccact cccactgtcc tttcctaata aatgaggaa attgcatcgc attgtctgag    4080
taggtgtcat tctattctgg ggggtggggt gggcaggac agcaaggggg aggattggga    4140
agagaatagc aggcatgctg gggagggcgc tagcgcaggg ggaccccaag tgacgattga   4200
accccgattc aggtacccat tggaaatttt aatggagtaa cataactgct ggagtagatg    4260
aagaacctct tggccactcc gctcccgaag agcgcactcg ctcgctcggt ggggcctggc    4320
gaccaaaggt cgccagacgg acgtgctttg cacgtccggc cccaccgagc gagcgagtgc    4380
gctcttcggg ccacttggag gggccggggg gacgacgcaa tctggagtgg aaagaacccc    4440
cgtctatgcg gcttaaagca cggccaggga atagtggatc aagtgtactg acatgtgccg    4500
gcaatgcatt gcgtcccgag tcacattcgc gactctcgac gctcttcaga agagcagctt    4560
agcttcaata gctcaatgat atcggaaaga acatgtgagc aaaaggccag caaaaggcca    4620
ggaaccgtaa aaaggccgcg ttgctggcgt ttttccatag gctccgcccc cctgacgagc    4680
atcacaaaaa tcgacgctca agtcagaggt ggcgaaaccc gacaggacta taaagatacc    4740
aggcgtttcc ccctggaagc tccctcgtgc gctctcctgt tccgaccctg ccgcttaccg    4800
gatacctgtc cgcctttctc ccttcgggaa gcgtggcgct ttctcatagc tcacgctgta    4860
ggtatctcag ttcggtgtag gtcgttcgct ccaagctggg ctgtgtgcac gaaccccccg    4920
ttcagcccga ccgctgcgcc ttatccggta actatcgtct tgagtccaac ccggtaagac    4980
acgacttatc gccactggca gcagccactg gtaacaggat tagcagagcg aggtatgtag    5040
gcggtgctac agagttcttg aagtggtggc ctaactacgg ctacactaga agaacagtat    5100
ttggtatctg cgctctgctg aagccagtta ccttcggaaa aagagttggt agctcttgat    5160
ccggcaaaca aaccaccgct ggtagcggtg gtttttttgt ttgcaagcag cagattacgc    5220
gcagaaaaaa aggatctcaa gaagatcctt tgatctttc tacggggtct gacgctcagt    5280
ggaacgaaaa ctcacgttaa ggggctcttc agaagagcga gtcacattcg cgactctgca    5340
atgcattgcc atgagattat caaaaaggat cttcacctag atcctttaa attaaaaatg    5400 aagttttaaa tcaatctaaa gtatatatga gtaaacttgg tctgacagtt accaatgctt    5460
aatcagtgag gcacctatct cagcgatctg tctatttcgt tcatccatag ttgcctgact    5520
ccccgtcgtg tagataacta cgatacggga gggcttacca tctggcccca gtgctgcaat    5580
gataccgcga gacccacgct caccggctcc agatttatca gcaataaacc agccagccgg    5640
aagggccgag cgcagaagtg gtcctgcaac tttatccgcc tccatccagt ctattaattg    5700
ttgccgggaa gctagagtaa gtagttcgcc agttaatagt ttgcgcaacg ttgttgccat    5760
tgctacaggc atcgtggtgt cacgctcgtc gtttggtatg gcttcattca gctccggttc    5820
ccaacgatca aggcgagtta catgatcccc catgttgtgc aaaaaagcgg ttagctcctt    5880
cggtcctccg atcgttgtca gaagtaagtt ggccgcagtg ttatcactca tggttatggc    5940
agcactgcat aattctctta ctgtcatgcc atccgtaaga tgcttttctg tgactggtga    6000
gtactcaacc aagtcattct gagaatagtg tatgcggcga ccgagttgct cttgcccggc    6060
gtcaatacgg gataataccg cgccacatag cagaacttta aaagtgctca tcattggaaa    6120
acgttcttcg gggcgaaaac tctcaaggat cttaccgctg ttgagatcca gttcgatgta    6180
acccactcgt gcacccaact gatcttcagc atcttttact ttcaccagcg tttctgggtg    6240
```

| | |
|---|---:|
| agcaaaaaca ggaaggcaaa atgccgcaaa aaagggaata agggcgacac ggaaatgttg | 6300 |
| aatactcata ctcttccttt ttcaatatta ttgaagcatt tatcagggtt attgtctcat | 6360 |
| gagcggatac atatttgaat gtatttagaa aaataaacaa atagggg ttc cgcgcacatt | 6420 |
| tccccgaaaa gta | 6433 |

<210> SEQ ID NO 336
<211> LENGTH: 125
<212> TYPE: DNA
<213> ORGANISM: Artificial Sequence
<220> FEATURE:
<223> OTHER INFORMATION: CpG depleted sequence

<400> SEQUENCE: 336

| | |
|---|---:|
| ttggtcactc cctctctgta cactcactca ctcactgatc cctggatacc aaaggtatcc | 60 |
| agacacccag tctttgactg ggtgggatca gtgagtgagt gagtgtacag agagggagtg | 120 |
| accaa | 125 |

<210> SEQ ID NO 337
<211> LENGTH: 6545
<212> TYPE: DNA
<213> ORGANISM: Artificial Sequence
<220> FEATURE:
<223> OTHER INFORMATION: Construct 337

<400> SEQUENCE: 337

| | |
|---|---:|
| gttcgagatc gctcttcaga agagcgcgga gtcacattcg cgactcgcaa tgcattgcag | 60 |
| ggcgagggcg agggccgccc ctacgagggc cacaacaccg tgaagctgaa ggtgaccaag | 120 |
| ggcggccccc tgcccttcgc ctgggacatc ctgtccccc c agttccagta cggctccaag | 180 |
| gtgtacgtga agcaccccgc cgacatccca gctcggtagc cacctgacgt cgctcttcgg | 240 |
| tggttgtaca gacgccatct tggaatccaa tatgtctgcc ggctcagtca tgcctgcgct | 300 |
| gcgcgcagcg cgctgcgcgc gcgcatgatc taatcgccgg cagacatatt ggattccaag | 360 |
| atggcgtctg tacaaccacc gaagagcgga gtggccaaaa agtacccggc cagaaaggaa | 420 |
| ccgtaaaacc aactagacag ccggtgactt tgttccccag ctcggttcat tctcaagcct | 480 |
| cagacaggag aaccgggact agtatatgag ctccggtgcc cgtcagtggg cagagcgcac | 540 |
| atcgcccaca gtccccgaga agttgggggg aggggtcggc aattgaaccg gtgcctagag | 600 |
| aaggtggcgc ggggtaaact gggaaagtga tgtcgtgtac tggctccgcc ttttttcccga | 660 |
| gggtggggga gaaccgtata taagtgcagt agtcgccgtg aacgttcttt ttcgcaacgg | 720 |
| gtttgccgcc agaacacagg taagtgccgt gtgtggttcc cgcgggcctg gcctctttac | 780 |
| gggttatggc ccttgcgtgc cttgaattac ttccacgccc ctggctgcag tacgtgattc | 840 |
| ttgatcccga gcttcgggtt ggaagtgggt gggagagttc gaggccttgc gcttaaggag | 900 |
| ccccttcgcc tcgtgcttga gttgaggcct ggcctgggcg ctgggccgc cgcgtgcgaa | 960 |
| tctggtggca ccttcgcgcc tgtctcgctg ctttcgataa gtctctagcc atttaaaatt | 1020 |
| tttgatgacc tgctgcgacg cttttttttct ggcaagatag tcttgtaaat gcgggccaag | 1080 |
| atcgatctgc acactggtat ttcggttttt ggggccgcgg gcggcgacgg ggcccgtgcg | 1140 |
| tcccagcgca catgttcggc gaggcgggc ctgcgagcgc ggccaccgag aatcggacgg | 1200 |
| gggtagtctc aagctggccg gcctgctctg tgcctggcc tcgcgccgcc gtgtatcgcc | 1260 |
| ccgcctggg cggcaaggct ggcccggtcg gcaccagttg cgtgagcgga agatggccg | 1320 |
| cttcccggcc ctgctgcagg gagctcaaaa tggaggacgc ggcgctcggg agagcgggcg | 1380 |

```
ggtgagacac ccacacaaag gaaaagggcc tttccgtcct cagccgtcgc ttcatgtgac    1440
accacggagt accgggcgcc gtccaggcac ctcgattagt tctcgatcga gcttttggag    1500
tacgtcgtct ttaggttggg gggaggggtt ttatgcgatg gagtttcccc acactgagtg    1560
ggtggagact gaagttaggc cagcttggca cttgatgtaa ttctccttgg aatttgccct    1620
ttttgagttt ggatcttggt tcattctcaa gcctcagaca gtggttcaaa gttttttctt    1680
tccatttcag gtgtcgtgag cggccgcggc aggctgccac catggaggat gccaagaata    1740
ttaagaaagg ccctgcccca ttctaccctc tggaagatgg cactgctggt gagcaactgc    1800
acaaggccat gaagaggtat gccctggtcc ctggcacaat tgccttcact gatgctcaca    1860
ttgaggtgga catcacctat gctgaatact ttgagatgtc tgtgaggctg cagaagcca     1920 tgaaaagata tggactgaac accaaccaca ggattgtggt gtgctctgag aactctctcc    1980
agttcttcat gcctgtgttg ggagccctgt tcattggagt ggctgtggcc cctgccaatg    2040
acatctacaa tgagagagag ctcctgaaca gcatgggcat cagccagcca actgtggtct    2100
ttgtgagcaa gaagggcctg caaaagatcc tgaatgtgca gaagaagctg cccatcatcc    2160
agaagatcat catcatggac agcaagactg actaccaggg cttccagagc atgtataccc    2220
ttgtgaccag ccacctcccc cctggcttca atgagtatga ctttgtgcct gagagctttg    2280
acagggacaa gacaattgct ctgattatga acagctctgg ctccactgga ctgcccaaag    2340
gtgtggctct gccccacaga actgcttgtg tgagattcag ccatgccaga gaccccatct    2400
ttggcaacca gatcatccct gacactgcca tcctgtctgt ggttccattc catcatggct    2460
ttggcatgtt cacaacactg gggtacctga tctgtggctt cagagtggtg ctgatgtata    2520
ggtttgagga ggagctgttt ctgaggagct tgcaagacta caagatccag tctgccctgc    2580
tggtgcccac tctgttcagc ttcttttgcca agagcaccct cattgacaag tatgacctga    2640
gcaacctgca tgagattgcc tctggaggag caccctgag caaggaggtg ggtgaggctg    2700
tggcaaagag gttccatctc ccaggaatca gacagggcta tggcctgact gagaccacct    2760
ctgccatcct catcacccct gaaggagatg acaagcctgg tgctgtgggc aaggtggttc    2820 cctttttga ggccaaggtg gtggacctgg acactggcaa gaccctggga gtgaaccaga    2880
ggggtgagct gtgtgtgagg ggtcccatga tcatgtctgg ctatgtgaac aaccctgagg    2940
ccaccaatgc cctgattgac aaggatggct ggctgcactc tggtgatatt gcctactggg    3000
atgaggatga gcactttttc attgtggaca ggctgaagag tctcatcaag tacaaaggct    3060
accaagtggc cctgctgag cttgagcaga tcctgctcca gcaccccaac atctttgatg    3120
ctggtgtggc tggcctgcct gatgatgatg ctggagagct gcctgctgct gttgtggttc    3180
tggagcatgg aaagaccatg actgagaagg agattgtgga ctatgtggcc agtcaggtga    3240
ccactgccaa gaagctgagg ggaggtgtgg tgtttgtgga tgaggtgcca aagggtctga    3300
ctggcaagct ggatgccaga aagatcagag agatcctgat caaggccaag aagggaggaa    3360
agattgcagt ttaaggatcc tgacacaaag tgacgcgtaa tcaacctctg gattacaaaa    3420
tttgtgaaag attgactggt attcttaact atgttgctcc ttttacgcta tgtggatacg    3480
ctgctttaat gcctttgtat catgctattg cttcccgtat ggctttcatt ttctcctcct    3540
tgtataaatc ctggttgctg tctctttatg aggagttgtg gcccgttgtc aggcaacgtg    3600
gcgtggtgtg cactgtgttt gctgacgcaa ccccactggt tggggctttg ccaccaccct    3660
gtcagctcct ttccgggact ttcgctttcc ccctccctat tgccacggcg gaactcatcg    3720
```

```
ccgcctgcct tgcccgctgc tggacagggg ctcggctgtt gggcactgac aattccgtgg   3780
tgttgtcggg gaaatcatcg tcctttcctt ggctgctcgc ctgtgttgcc acctggattc   3840
tgcgcgggac gtccttctgc tacgtccctt cggccctcaa tccagcggac cttccttccc   3900
gcggcctgct gccggctctg cggcctcttc cgcgtcttcg ccttcgccct cagacgagtc   3960
ggatctccct ttgggccgcc tccccgcacg cgtcctagag ctcgcactgt gccttctagt   4020
tgccagccat ctgttgtttg cccctccccc gtgccttcct tgaccctgga aggtgccact   4080
cccactgtcc tttcctaata aaatgaggaa attgcatcgc attgtctgag taggtgtcat   4140
tctattctgg ggggtggggt ggggcaggac agcaaggggg aggattggga agagaatagc   4200
aggcatgctg gggagggcgc tagcgcaggg ggaccccaag tgacgattga accccgattc   4260
aggtacccat tggaaatttt aatggagtaa cataactgct ggagtagatg aagaacctct   4320
tggccactcc gttgcttatg caatcgcgaa actctatatc ttgctcttct taatgtgttg   4380
ttgttgtaca tgcgccatct tagttttata tcagctggcg ccttagttat ataacatgca   4440
tgttatataa ctaaggcgcc agctgatata aaactaagat ggcgcatgta caacaacaac   4500
acattaagaa gagcgccggg gggacgacgc aatctggagt ggaagaacc cccgtctatg    4560 cggcttaaag cacggccagg gaatagtgga tcaagtgtac tgacatgtgc cggcaatgca   4620
ttgcgtcccg agtcacattc gcgactctcg acgctcttca gaagagcagc ttagcttcaa   4680
tagctcaatg atatcggaaa gaacatgtga gcaaaaggcc agcaaaggcc caggaaccgt   4740
aaaaaggccg cgttgctggc gttttttccat aggctccgcc cccctgacga gcatcacaaa   4800
aatcgacgct caagtcagag gtggcgaaac ccgacaggac tataaagata ccaggcgttt   4860 cccccctggaa gctccctcgt gcgctctcct gttccgaccc tgccgcttac cggatacctg   4920
tccgcctttc tcccttcggg aagcgtggcg ctttctcata gctcacgctg taggtatctc   4980
agttcggtgt aggtcgttcg ctccaagctg ggctgtgtgc acgaaccccc cgttcagccc   5040
gaccgctgcg ccttatccgg taactatcgt cttgagtcca acccggtaag acacgactta   5100
tcgccactgg cagcagccac tggtaacagg attagcagag cgaggtatgt aggcggtgct   5160
acagagttct tgaagtggtg gcctaactac ggctacacta agaacagt atttggtatc     5220 tgcgctctgc tgaagccagt taccttcgga aaaagagttg gtagctcttg atccggcaaa   5280
caaaccaccg ctggtagcgg tggttttttt gtttgcaagc agcagattac gcgcagaaaa   5340
aaaggatctc aagaagatcc tttgatcttt tctacggggt ctgacgctca gtggaacgaa   5400
aactcacgtt aaggggctct tcagaagagc gagtcacatt cgcgactctg caatgcattg   5460
ccatgagatt atcaaaaagg atcttcacct agatcctttt aaattaaaaa tgaagtttta   5520
aatcaatcta agtatatat gagtaaactt ggtctgacag ttaccaatgc ttaatcagtg    5580
aggcacctat ctcagcgatc tgtctatttc gttcatccat agttgcctga ctccccgtcg   5640
tgtagataac tacgatacgg gagggcttac catctggccc cagtgctgca atgataccgc   5700
gagacccacg ctcaccggct ccagatttat cagcaataaa ccagccagcc ggaagggccg   5760
agcgcagaag tggtcctgca actttatccg cctccatcca gtctattaat tgttgccggg   5820
aagctagagt aagtagttcg ccagttaata gtttgcgcaa cgttgttgcc attgctacag   5880
gcatcgtggt gtcacgctcg tcgtttggta tggcttcatt cagctccggt tcccaacgat   5940
caaggcgagt tacatgatcc cccatgttgt gcaaaaaagc ggttagctcc ttcggtcctc   6000
cgatcgttgt cagaagtaag ttggccgcag tgttatcact catggttatg gcagcactgc   6060
ataattctct tactgtcatg ccatccgtaa gatgcttttc tgtgactggt gagtactcaa   6120
```

```
ccaagtcatt ctgagaatag tgtatgcggc gaccgagttg ctcttgcccg gcgtcaatac      6180
gggataatac cgcgccacat agcagaactt taaaagtgct catcattgga aaacgttctt      6240
cggggcgaaa actctcaagg atcttaccgc tgttgagatc cagttcgatg taacccactc      6300
gtgcacccaa ctgatcttca gcatcttttt ctttcaccag cgtttctggg tgagcaaaaa      6360
caggaaggca aaatgccgca aaaagggaa taagggcgac acggaaatgt tgaatactca       6420
tactcttcct ttttcaatat tattgaagca tttatcaggg ttattgtctc atgagcggat      6480
acatatttga atgtatttag aaaaataaac aatagggggt tccgcgcaca tttccccgaa      6540
aagta                                                                 6545

<210> SEQ ID NO 338
<211> LENGTH: 58
<212> TYPE: DNA
<213> ORGANISM: Artificial Sequence
<220> FEATURE:
<223> OTHER INFORMATION: Aptamer (Fig. 5)

<400> SEQUENCE: 338
atccggcttt aaacgggcaa ctgcgtctca ttcacgttag agactacaac cgtcggat         58
```